United States Patent
Yam et al.

(10) Patent No.: US 11,744,876 B2
(45) Date of Patent: Sep. 5, 2023

(54) IMMUNOMODULATOR ANTIBODY DRUG CONJUGATES AND USES THEREOF

(71) Applicant: Sutro Biopharma, Inc., South San Francisco, CA (US)

(72) Inventors: Alice Yam, Tiburon, CA (US); Andreas Maderna, Escondido, CA (US); Cristina Abrahams, Burlingame, CA (US); Willy Solis, San Mateo, CA (US); Xiaofan Li, Fremont, CA (US); Ryan Stafford, Emeryville, CA (US); Gang Yin, South San Francisco, CA (US); Venita De Almeida, San Carlos, CA (US); Krishna Bajjuri, Union City, CA (US); Adam A. Galan, Alameda, CA (US)

(73) Assignee: SUTRO BIOPHARMA, INC., South San Francisco, CA (US)

( * ) Notice: Subject to any disclaimer, the term of this patent is extended or adjusted under 35 U.S.C. 154(b) by 0 days.

(21) Appl. No.: 16/898,233

(22) Filed: Jun. 10, 2020

(65) Prior Publication Data

US 2020/0405813 A1 Dec. 31, 2020

Related U.S. Application Data

(60) Provisional application No. 62/859,629, filed on Jun. 10, 2019, provisional application No. 62/984,758, filed on Mar. 3, 2020.

(51) Int. Cl.
| | |
|---|---|
| *A61K 47/64* | (2017.01) |
| *A61K 47/68* | (2017.01) |
| *A61K 38/18* | (2006.01) |
| *A61K 47/65* | (2017.01) |
| *A61P 35/00* | (2006.01) |
| *A61K 39/00* | (2006.01) |

(52) U.S. Cl.
CPC .......... *A61K 38/1866* (2013.01); *A61K 47/65* (2017.08); *A61K 47/6803* (2017.08); *A61K 47/6835* (2017.08); *A61K 47/6889* (2017.08); *A61P 35/00* (2018.01); *A61K 2039/572* (2013.01)

(58) Field of Classification Search
CPC .. A61K 31/4745; A61K 38/06; A61K 47/545; A61K 47/6803; A61K 47/6811; A61K 47/6835; A61K 47/6889; C07K 5/0205; C07D 471/04
See application file for complete search history.

(56) References Cited

U.S. PATENT DOCUMENTS

| | | | |
|---|---|---|---|
| 9,676,871 B2 * | 6/2017 | Strop | A61K 47/6803 |
| 2010/0034837 A1 * | 2/2010 | Beria | A61P 35/00 |
| | | | 530/395 |
| 2015/0017187 A1 * | 1/2015 | Thanos | A61K 47/6869 |
| | | | 530/387.3 |
| 2015/0105540 A1 | 4/2015 | Miao et al. | |
| 2015/0376161 A1 * | 12/2015 | Johansen | A61P 35/02 |
| | | | 548/200 |
| 2016/0039920 A1 | 2/2016 | Casi et al. | |
| 2016/0257709 A1 * | 9/2016 | Kline | C07K 16/30 |
| 2017/0158772 A1 * | 6/2017 | Thompson | A61K 47/6803 |
| 2018/0140700 A1 * | 5/2018 | Phillips | A61K 47/6851 |
| 2019/0083641 A1 * | 3/2019 | Stafford | A61K 47/6425 |
| 2019/0144546 A1 * | 5/2019 | Stafford | A61K 47/6803 |
| | | | 424/181.1 |
| 2022/0133904 A1 * | 5/2022 | Schibli | A61K 49/0058 |
| | | | 424/179.1 |

FOREIGN PATENT DOCUMENTS

| | | | | |
|---|---|---|---|---|
| WO | WO 2012/000632 A1 | 1/2012 | | |
| WO | WO 2015/168279 A1 | 11/2015 | | |
| WO | WO 2017/072662 A1 | 5/2017 | | |
| WO | WO-2018112027 A1 * | 6/2018 | .......... | A61K 31/553 |
| WO | WO 2019/099412 A1 | 5/2019 | | |
| WO | WO-2020168017 A1 * | 8/2020 | ......... | A61K 47/6803 |
| WO | WO 2020/252043 A1 | 12/2020 | | |
| WO | WO-2020257235 A1 * | 12/2020 | | |

OTHER PUBLICATIONS

T. List et al., "A Chemically Defined Trifunctional Antibody-Cytokine-Drug Conjugate with Potent Antitumor Activity", Molecular Cancer Therapeutics, vol. 13, No. 11, Sep. 9, 2014, pp. 2641-2652.

* cited by examiner

*Primary Examiner* — Jeffrey E. Russel
(74) *Attorney, Agent, or Firm* — Squire Patton Boggs (US)

(57) ABSTRACT

Provided herein are compounds, trifunctional antibody products thereof, and methods and pharmaceutical compositions for use in treatment of inflammatory and/or proliferative diseases.

47 Claims, 22 Drawing Sheets
Specification includes a Sequence Listing.

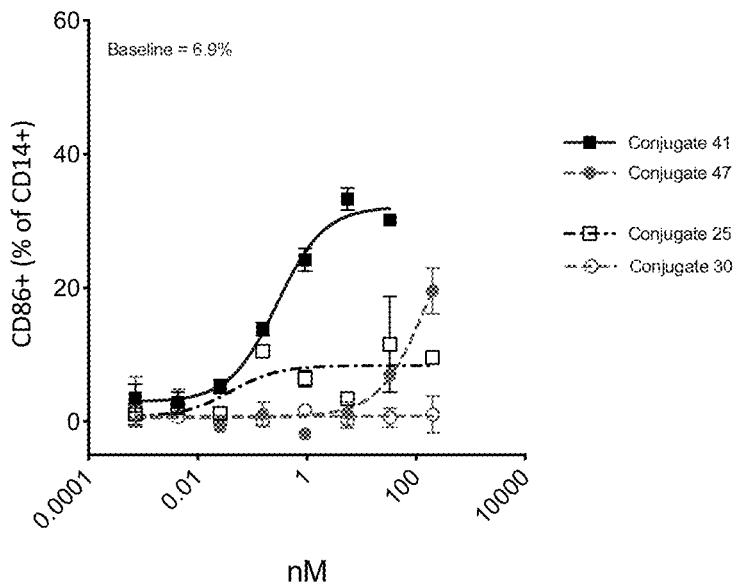
FIG. 4E
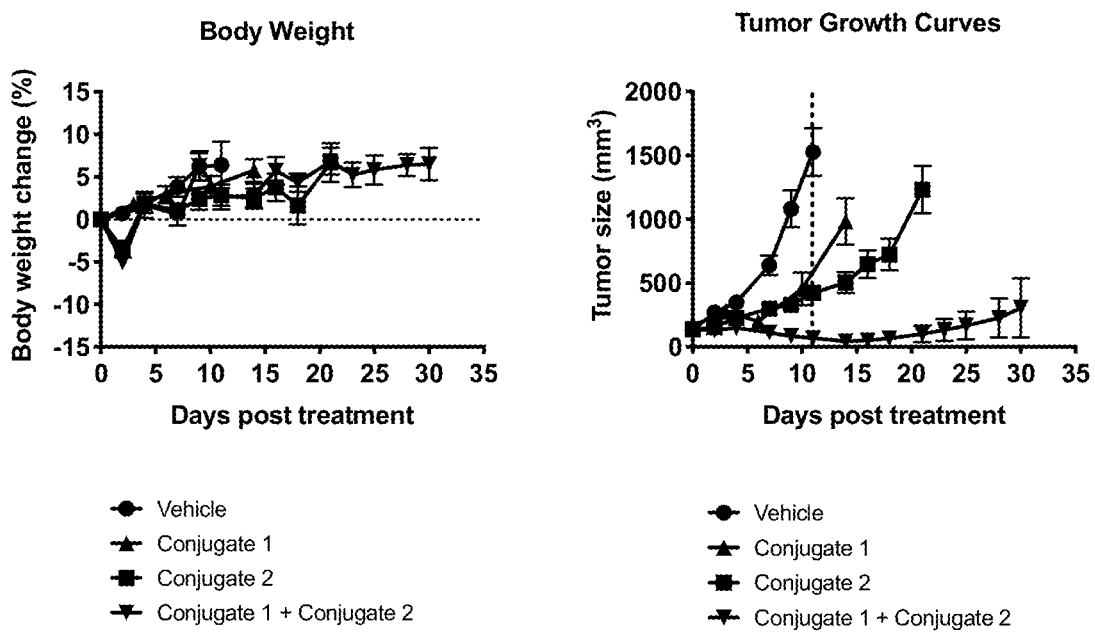
FIG. 5A
FIG. 5B

SEQUENCE LISTING

```
<160> NUMBER OF SEQ ID NOS: 77

<210> SEQ ID NO 1
<211> LENGTH: 455
<212> TYPE: PRT
<213> ORGANISM: Artificial Sequence
<220> FEATURE:
<223> OTHER INFORMATION: Synthetic: 1848-H01 HC Y180/F404TAG
<220> FEATURE:
<221> NAME/KEY: MOD_RES
<222> LOCATION: (188)..(188)
<223> OTHER INFORMATION: para-azidomethylphenylalanine
<220> FEATURE:
<221> NAME/KEY: MOD_RES
<222> LOCATION: (412)..(412)
<223> OTHER INFORMATION: para-azidomethylphenylalanine

<400> SEQUENCE: 1

Met Glu Val Gln Leu Val Glu Ser Gly Gly Leu Val Gln Pro Gly
1               5                   10                  15

Gly Ser Leu Arg Leu Ser Cys Ala Ala Ser Gly Phe Asn Ile Arg Thr
                20                  25                  30

Gln Ser Ile His Trp Val Arg Gln Ala Pro Gly Lys Gly Leu Glu Trp
            35                  40                  45

Ile Gly Asp Ile Phe Pro Ile Asp Gly Ile Thr Asp Tyr Ala Asp Ser
        50                  55                  60

Val Lys Gly Arg Phe Thr Ile Ser Ala Asp Thr Ser Lys Asn Thr Ala
65                  70                  75                  80

Tyr Leu Gln Met Asn Ser Leu Arg Ala Glu Asp Thr Ala Val Tyr Tyr
                85                  90                  95

Cys Ala Arg Gly Ser Trp Ser Trp Pro Ser Gly Met Asp Tyr Tyr Leu
                100                 105                 110

Asp Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
        130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Xaa Ser Leu Ser Ser
                180                 185                 190
```

Val Val Thr Val Pro Ser Ser Ser Leu Gly Thr Gln Thr Tyr Ile Cys
            195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
            275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
            355                 360                 365

Asn Gln Val Ser Leu Thr Cys Leu Val Lys Gly Phe Tyr Pro Ser Asp
            370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Xaa Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
            435                 440                 445

Leu Ser Leu Ser Pro Gly Lys
    450                 455

<210> SEQ ID NO 2
<211> LENGTH: 215
<212> TYPE: PRT
<213> ORGANISM: Artificial Sequence
<220> FEATURE:
<223> OTHER INFORMATION: Synthetic: Trastuzumab LC

<400> SEQUENCE: 2

Met Asp Ile Gln Met Thr Gln Ser Pro Ser Ser Leu Ser Ala Ser Val
1               5                   10                  15

Gly Asp Arg Val Thr Ile Thr Cys Arg Ala Ser Gln Asp Val Asn Thr
            20                  25                  30

Ala Val Ala Trp Tyr Gln Gln Lys Pro Gly Lys Ala Pro Lys Leu Leu
        35                  40                  45

Ile Tyr Ser Ala Ser Phe Leu Tyr Ser Gly Val Pro Ser Arg Phe Ser
    50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Gln Gln His Tyr Thr Thr Pro
                85                  90                  95

```
Pro Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
    115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 3
<211> LENGTH: 451
<212> TYPE: PRT
<213> ORGANISM: Artificial Sequence
<220> FEATURE:
<223> OTHER INFORMATION: Synthetic: Trastuzumab-Hc Y180/F404
<220> FEATURE:
<221> NAME/KEY: MOD_RES
<222> LOCATION: (184)..(184)
<223> OTHER INFORMATION: para-azidomethylphenylalanine
<220> FEATURE:
<221> NAME/KEY: MOD_RES
<222> LOCATION: (408)..(408)
<223> OTHER INFORMATION: para-azidomethylphenylalanine

<400> SEQUENCE: 3

Met Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Asn Ile Lys Asp
            20                  25                  30

Thr Tyr Ile His Trp Val Arg Gln Ala Pro Lys Gly Leu Glu Trp
            35                  40                  45

Val Ala Arg Ile Tyr Pro Thr Asn Gly Tyr Thr Arg Tyr Ala Asp Ser
    50                  55                  60

Val Lys Gly Arg Phe Thr Ile Ser Ala Asp Thr Ser Lys Asn Thr Ala
65                  70                  75                  80

Tyr Leu Gln Met Asn Ser Leu Arg Ala Glu Asp Thr Ala Val Tyr Tyr
                85                  90                  95

Cys Ser Arg Trp Gly Gly Asp Gly Phe Tyr Ala Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Xaa Ser Leu Ser Ser Val Val Thr Val
            180                 185                 190

Pro Ser Ser Ser Leu Gly Thr Gln Thr Tyr Ile Cys Asn Val Asn His
```

```
                195                 200                 205
Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Xaa Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 4
<211> LENGTH: 447
<212> TYPE: PRT
<213> ORGANISM: Artificial Sequence
<220> FEATURE:
<223> OTHER INFORMATION: Synthetic: aMUC16-sofituzumab_HC-Y180/F404TAG
<220> FEATURE:
<221> NAME/KEY: MOD_RES
<222> LOCATION: (180)..(180)
<223> OTHER INFORMATION: para-azidomethylphenylalanine
<220> FEATURE:
<221> NAME/KEY: MOD_RES
<222> LOCATION: (404)..(404)
<223> OTHER INFORMATION: para-azidomethylphenylalanine

<400> SEQUENCE: 4

Met Glu Val Gln Leu Val Glu Ser Gly Gly Gly Leu Val Gln Pro Gly
1               5                   10                  15

Gly Ser Leu Arg Leu Ser Cys Ala Ala Ser Gly Tyr Ser Ile Thr Asn
            20                  25                  30

Asp Tyr Ala Trp Asn Trp Val Arg Gln Ala Pro Gly Lys Gly Leu Glu
        35                  40                  45

Trp Val Gly Tyr Ile Ser Tyr Ser Gly Tyr Thr Thr Tyr Asn Pro Ser
    50                  55                  60
```

Leu Lys Ser Arg Phe Thr Ile Ser Arg Asp Thr Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Trp Thr Ser Gly Leu Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Xaa Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Xaa Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 5
<211> LENGTH: 215
<212> TYPE: PRT
<213> ORGANISM: Artificial Sequence
<220> FEATURE:

<223> OTHER INFORMATION: Synthetic: aMUC16-sofituzumab_LC

<400> SEQUENCE: 5

Met Asp Ile Gln Met Thr Gln Ser Pro Ser Ser Leu Ser Ala Ser Val
1               5                   10                  15

Gly Asp Arg Val Thr Ile Thr Cys Lys Ala Ser Asp Leu Ile His Asn
            20                  25                  30

Trp Leu Ala Trp Tyr Gln Gln Lys Pro Gly Lys Ala Pro Lys Leu Leu
        35                  40                  45

Ile Tyr Gly Ala Thr Ser Leu Glu Thr Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gln Gln Tyr Trp Thr Thr Pro
                85                  90                  95

Phe Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 6
<211> LENGTH: 455
<212> TYPE: PRT
<213> ORGANISM: Artificial Sequence
<220> FEATURE:
<223> OTHER INFORMATION: Synthetic: 1848-B10_Y180TAG_Q295A
<220> FEATURE:
<221> NAME/KEY: MOD_RES
<222> LOCATION: (188)..(188)
<223> OTHER INFORMATION: para-azidomethylphenylalanine

<400> SEQUENCE: 6

Met Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Asn Thr Thr Thr
            20                  25                  30

Lys Ser Ile His Trp Val Arg Gln Ala Pro Gly Lys Gly Leu Glu Trp
        35                  40                  45

Val Gly Glu Ile Tyr Pro Arg Asp Gly Ile Thr Asp Tyr Ala Asp Ser
    50                  55                  60

Val Lys Gly Arg Phe Thr Ile Ser Ala Asp Thr Ser Lys Asn Thr Ala
65                  70                  75                  80

Tyr Leu Gln Met Asn Ser Leu Arg Ala Glu Asp Thr Ala Val Tyr Tyr
                85                  90                  95

Cys Ala Arg Gly Gly Trp His Trp Arg Ser Gly Tyr Ser Tyr Tyr Leu

```
                    100                 105                 110
Asp Tyr Trp Gly Gln Gly Thr Leu Val Thr Val Ser Ser Ala Ser Thr
                    115                 120                 125

Lys Gly Pro Ser Val Phe Pro Leu Ala Pro Ser Ser Lys Ser Thr Ser
            130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Xaa Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Lys Val Glu
            210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Ala Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 7
<211> LENGTH: 222
<212> TYPE: PRT
<213> ORGANISM: Artificial Sequence
<220> FEATURE:
<223> OTHER INFORMATION: Synthetic: trastuzumab-LC-Qtag1

<400> SEQUENCE: 7

Met Asp Ile Gln Met Thr Gln Ser Pro Ser Ser Leu Ser Ala Ser Val
```

-continued

```
                1               5                      10                      15
            Gly Asp Arg Val Thr Ile Thr Cys Arg Ala Ser Gln Asp Val Asn Thr
                            20                      25                      30

Ala Val Ala Trp Tyr Gln Gln Lys Pro Gly Lys Ala Pro Lys Leu Leu
                            35                      40                      45

Ile Tyr Ser Ala Ser Phe Leu Tyr Ser Gly Val Pro Ser Arg Phe Ser
                50                      55                      60

Gly Ser Arg Ser Gly Thr Asp Phe Thr Leu Thr Ile Ser Ser Leu Gln
             65                     70                      75                      80

Pro Glu Asp Phe Ala Thr Tyr Tyr Cys Gln Gln His Tyr Thr Thr Pro
                            85                      90                      95

Pro Thr Phe Gly Gln Gly Thr Lys Val Glu Ile Lys Arg Thr Val Ala
                            100                     105                     110

Ala Pro Ser Val Phe Ile Phe Pro Pro Ser Asp Glu Gln Leu Lys Ser
                            115                     120                     125

Gly Thr Ala Ser Val Val Cys Leu Leu Asn Asn Phe Tyr Pro Arg Glu
                            130                     135                     140

Ala Lys Val Gln Trp Lys Val Asp Asn Ala Leu Gln Ser Gly Asn Ser
            145                     150                     155                     160

Gln Glu Ser Val Thr Glu Gln Asp Ser Lys Asp Ser Thr Tyr Ser Leu
                            165                     170                     175

Ser Ser Thr Leu Thr Leu Ser Lys Ala Asp Tyr Glu Lys His Lys Val
                            180                     185                     190

Tyr Ala Cys Glu Val Thr His Gln Gly Leu Ser Ser Pro Val Thr Lys
                            195                     200                     205

Ser Phe Asn Arg Gly Glu Cys Gly Gly Leu Leu Gln Gly Ala
                            210                     215                     220

<210> SEQ ID NO 8
<211> LENGTH: 455
<212> TYPE: PRT
<213> ORGANISM: Artificial Sequence
<220> FEATURE:
<223> OTHER INFORMATION: Synthetic: 1848-B10 HC Y180/F404TAG
<220> FEATURE:
<221> NAME/KEY: MOD_RES
<222> LOCATION: (188)..(188)
<223> OTHER INFORMATION: para-azidomethylphenylalanine
<220> FEATURE:
<221> NAME/KEY: MOD_RES
<222> LOCATION: (412)..(412)
<223> OTHER INFORMATION: para-azidomethylphenylalanine

<400> SEQUENCE: 8

Met Glu Val Gln Leu Val Glu Ser Gly Gly Gly Leu Val Gln Pro Gly
            1               5                       10                      15

Gly Ser Leu Arg Leu Ser Cys Ala Ala Ser Gly Phe Asn Thr Thr
                            20                      25                      30

Lys Ser Ile His Trp Val Arg Gln Ala Pro Gly Lys Gly Leu Glu Trp
                            35                      40                      45

Val Gly Glu Ile Tyr Pro Arg Asp Gly Ile Thr Asp Tyr Ala Asp Ser
                50                      55                      60

Val Lys Gly Arg Phe Thr Ile Ser Ala Asp Thr Ser Lys Asn Thr Ala
             65                     70                      75                      80

Tyr Leu Gln Met Asn Ser Leu Arg Ala Glu Asp Thr Ala Val Tyr Tyr
                            85                      90                      95

Cys Ala Arg Gly Gly Trp His Trp Arg Ser Gly Tyr Ser Tyr Tyr Leu
                            100                     105                     110
```

Asp Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
        130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Xaa Ser Leu Ser Ser
            180                 185                 190

Val Val Thr Val Pro Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Xaa Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 9
<211> LENGTH: 455
<212> TYPE: PRT
<213> ORGANISM: Artificial Sequence
<220> FEATURE:
<223> OTHER INFORMATION: Synthetic: 1848-B10_F404TAG_Q295A
<220> FEATURE:
<221> NAME/KEY: MOD_RES
<222> LOCATION: (412)..(412)
<223> OTHER INFORMATION: para-azidomethylphenylalanine

```
<400> SEQUENCE: 9

Met Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Asn Thr Thr Thr
            20                  25                  30

Lys Ser Ile His Trp Val Arg Gln Ala Pro Gly Lys Gly Leu Glu Trp
        35                  40                  45

Val Gly Glu Ile Tyr Pro Arg Asp Gly Ile Thr Asp Tyr Ala Asp Ser
    50                  55                  60

Val Lys Gly Arg Phe Thr Ile Ser Ala Asp Thr Ser Lys Asn Thr Ala
65                  70                  75                  80

Tyr Leu Gln Met Asn Ser Leu Arg Ala Glu Asp Thr Ala Val Tyr Tyr
                85                  90                  95

Cys Ala Arg Gly Gly Trp His Trp Arg Ser Gly Tyr Ser Tyr Tyr Leu
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Ala Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Xaa Phe Leu Tyr Ser
                405                 410                 415
```

```
Lys Leu Thr Val Asp Lys Ser Arg Trp Gln Gln Gly Asn Val Phe Ser
                420                 425                 430

Cys Ser Val Met His Glu Ala Leu His Asn His Tyr Thr Gln Lys Ser
            435                 440                 445

Leu Ser Leu Ser Pro Gly Lys
    450                 455

<210> SEQ ID NO 10
<211> LENGTH: 5
<212> TYPE: PRT
<213> ORGANISM: Artificial Sequence
<220> FEATURE:
<223> OTHER INFORMATION: Synthetic

<400> SEQUENCE: 10

Leu Leu Gln Gly Ala
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic

<400> SEQUENCE: 11

Tyr Ala His Gln Ala His Tyr
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic

<400> SEQUENCE: 12

Tyr Arg Tyr Arg Gln
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic

<400> SEQUENCE: 13

Pro Asn Pro Gln Leu Pro Phe
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic

<400> SEQUENCE: 14

Pro Lys Pro Gln Gln Phe Met
1               5

<210> SEQ ID NO 15
<211> LENGTH: 6
<212> TYPE: PRT
```

```
<213> ORGANISM: Artificial Sequence
<220> FEATURE:
<223> OTHER INFORMATION: Synthetic

<400> SEQUENCE: 15

Gly Gln Gln Gln Leu Gly
1               5

<210> SEQ ID NO 16
<211> LENGTH: 7
<212> TYPE: PRT
<213> ORGANISM: Artificial Sequence
<220> FEATURE:
<223> OTHER INFORMATION: Synthetic

<400> SEQUENCE: 16

Trp Ala Leu Gln Arg Pro His
1               5

<210> SEQ ID NO 17
<211> LENGTH: 7
<212> TYPE: PRT
<213> ORGANISM: Artificial Sequence
<220> FEATURE:
<223> OTHER INFORMATION: Synthetic

<400> SEQUENCE: 17

Trp Glu Leu Gln Arg Pro Tyr
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic

<400> SEQUENCE: 18

Tyr Pro Met Gln Gly Trp Phe
1               5

<210> SEQ ID NO 19
<211> LENGTH: 6
<212> TYPE: PRT
<213> ORGANISM: Artificial Sequence
<220> FEATURE:
<223> OTHER INFORMATION: Synthetic

<400> SEQUENCE: 19

Leu Ser Leu Ser Gln Gly
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

Gly Gly Gly Leu Leu Gln Gly Gly
1               5

<210> SEQ ID NO 21
<211> LENGTH: 5
<212> TYPE: PRT
<213> ORGANISM: Artificial Sequence
```

```
<220> FEATURE:
<223> OTHER INFORMATION: Synthetic

<400> SEQUENCE: 21

Gly Leu Leu Gln Gly
1               5

<210> SEQ ID NO 22
<211> LENGTH: 10
<212> TYPE: PRT
<213> ORGANISM: Artificial Sequence
<220> FEATURE:
<223> OTHER INFORMATION: Synthetic

<400> SEQUENCE: 22

Gly Ser Pro Leu Ala Gln Ser His Gly Gly
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Synthetic

<400> SEQUENCE: 23

Gly Leu Leu Gln Gly Gly Gly
1               5

<210> SEQ ID NO 24
<211> LENGTH: 6
<212> TYPE: PRT
<213> ORGANISM: Artificial Sequence
<220> FEATURE:
<223> OTHER INFORMATION: Synthetic

<400> SEQUENCE: 24

Gly Leu Leu Gln Gly Gly
1               5

<210> SEQ ID NO 25
<211> LENGTH: 4
<212> TYPE: PRT
<213> ORGANISM: Artificial Sequence
<220> FEATURE:
<223> OTHER INFORMATION: Synthetic

<400> SEQUENCE: 25

Gly Leu Leu Gln
1

<210> SEQ ID NO 26
<211> LENGTH: 8
<212> TYPE: PRT
<213> ORGANISM: Artificial Sequence
<220> FEATURE:
<223> OTHER INFORMATION: Synthetic

<400> SEQUENCE: 26

Leu Leu Gln Leu Leu Gln Gly Ala
1               5

<210> SEQ ID NO 27
<211> LENGTH: 7
<212> TYPE: PRT
<213> ORGANISM: Artificial Sequence
<220> FEATURE:
```

<223> OTHER INFORMATION: Synthetic

<400> SEQUENCE: 27

Leu Leu Gln Tyr Gln Gly Ala
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic

<400> SEQUENCE: 28

Leu Leu Gln Gly Ser Gly
1               5

<210> SEQ ID NO 29
<211> LENGTH: 6
<212> TYPE: PRT
<213> ORGANISM: Artificial Sequence
<220> FEATURE:
<223> OTHER INFORMATION: Synthetic

<400> SEQUENCE: 29

Leu Leu Gln Tyr Gln Gly
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic

<400> SEQUENCE: 30

Leu Leu Gln Leu Leu Gln Gly
1               5

<210> SEQ ID NO 31
<211> LENGTH: 5
<212> TYPE: PRT
<213> ORGANISM: Artificial Sequence
<220> FEATURE:
<223> OTHER INFORMATION: Synthetic

<400> SEQUENCE: 31

Ser Leu Leu Gln Gly
1               5

<210> SEQ ID NO 32
<211> LENGTH: 5
<212> TYPE: PRT
<213> ORGANISM: Artificial Sequence
<220> FEATURE:
<223> OTHER INFORMATION: Synthetic

<400> SEQUENCE: 32

Leu Leu Gln Leu Gln
1               5

<210> SEQ ID NO 33
<211> LENGTH: 6
<212> TYPE: PRT
<213> ORGANISM: Artificial Sequence
<220> FEATURE:
<223> OTHER INFORMATION: Synthetic

```
<400> SEQUENCE: 33

Leu Leu Gln Leu Leu Gln
1               5

<210> SEQ ID NO 34
<211> LENGTH: 5
<212> TYPE: PRT
<213> ORGANISM: Artificial Sequence
<220> FEATURE:
<223> OTHER INFORMATION: Synthetic

<400> SEQUENCE: 34

Leu Leu Gln Gly Arg
1               5

<210> SEQ ID NO 35
<211> LENGTH: 6
<212> TYPE: PRT
<213> ORGANISM: Artificial Sequence
<220> FEATURE:
<223> OTHER INFORMATION: Synthetic

<400> SEQUENCE: 35

Leu Leu Gln Gly Pro Ala
1               5

<210> SEQ ID NO 36
<211> LENGTH: 6
<212> TYPE: PRT
<213> ORGANISM: Artificial Sequence
<220> FEATURE:
<223> OTHER INFORMATION: Synthetic

<400> SEQUENCE: 36

Leu Leu Gln Gly Pro Pro
1               5

<210> SEQ ID NO 37
<211> LENGTH: 8
<212> TYPE: PRT
<213> ORGANISM: Artificial Sequence
<220> FEATURE:
<223> OTHER INFORMATION: Synthetic

<400> SEQUENCE: 37

Gly Gly Leu Leu Gln Gly Pro Pro
1               5

<210> SEQ ID NO 38
<211> LENGTH: 5
<212> TYPE: PRT
<213> ORGANISM: Artificial Sequence
<220> FEATURE:
<223> OTHER INFORMATION: Synthetic

<400> SEQUENCE: 38

Leu Leu Gln Gly Gly
1               5

<210> SEQ ID NO 39
<211> LENGTH: 4
<212> TYPE: PRT
<213> ORGANISM: Artificial Sequence
<220> FEATURE:
<223> OTHER INFORMATION: Synthetic
```

<400> SEQUENCE: 39

Leu Leu Gln Gly
1

<210> SEQ ID NO 40
<211> LENGTH: 15
<212> TYPE: PRT
<213> ORGANISM: Artificial Sequence
<220> FEATURE:
<223> OTHER INFORMATION: Synthetic

<400> SEQUENCE: 40

Gly Gly Gly Gly Ser Gly Gly Gly Gly Ser Gly Gly Gly Gly Ser
1               5                   10                  15

<210> SEQ ID NO 41
<211> LENGTH: 330
<212> TYPE: PRT
<213> ORGANISM: Artificial Sequence
<220> FEATURE:
<223> OTHER INFORMATION: Synthetic: IgG1 Constant Region

<400> SEQUENCE: 41

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

```
Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 42
<211> LENGTH: 456
<212> TYPE: PRT
<213> ORGANISM: Artificial Sequence
<220> FEATURE:
<223> OTHER INFORMATION: Synthetic: 1848-H01 HC Y180/F404TAG
<220> FEATURE:
<221> NAME/KEY: MOD_RES
<222> LOCATION: (188)..(188)
<223> OTHER INFORMATION: para-azidomethylphenylalanine
<220> FEATURE:
<221> NAME/KEY: MOD_RES
<222> LOCATION: (412)..(412)
<223> OTHER INFORMATION: para-azidomethylphenylalanine

<400> SEQUENCE: 42

Met Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Asn Ile Arg Thr
            20                  25                  30

Gln Ser Ile His Trp Val Arg Gln Ala Pro Gly Lys Gly Leu Glu Trp
        35                  40                  45

Ile Gly Asp Ile Phe Pro Ile Asp Gly Ile Thr Asp Tyr Ala Asp Ser
    50                  55                  60

Val Lys Gly Arg Phe Thr Ile Ser Ala Asp Thr Ser Lys Asn Thr Ala
65                  70                  75                  80

Tyr Leu Gln Met Asn Ser Leu Arg Ala Glu Asp Thr Ala Val Tyr Tyr
                85                  90                  95

Cys Ala Arg Gly Ser Trp Ser Trp Pro Ser Gly Met Asp Tyr Tyr Leu
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Xaa Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
```

```
                260                 265                 270
Asp Val Ser His Glu Asp Pro Glu Val Lys Phe Asn Trp Tyr Val Asp
        275                 280                 285
Gly Val Glu Val His Asn Ala Lys Thr Lys Pro Arg Glu Glu Gln Tyr
    290                 295                 300
Asn Ser Thr Tyr Arg Val Val Ser Val Leu Thr Val Leu His Gln Asp
305                 310                 315                 320
Trp Leu Asn Gly Lys Glu Tyr Lys Cys Lys Val Ser Asn Lys Ala Leu
                325                 330                 335
Pro Ala Pro Ile Glu Lys Thr Ile Ser Lys Ala Lys Gly Gln Pro Arg
            340                 345                 350
Glu Pro Gln Val Tyr Thr Leu Pro Pro Ser Arg Glu Glu Met Thr Lys
        355                 360                 365
Asn Gln Val Ser Leu Thr Cys Leu Val Lys Gly Phe Tyr Pro Ser Asp
    370                 375                 380
Ile Ala Val Glu Trp Glu Ser Asn Gly Gln Pro Glu Asn Asn Tyr Lys
385                 390                 395                 400
Thr Thr Pro Pro Val Leu Asp Ser Asp Gly Ser Xaa Phe Phe Leu Tyr
                405                 410                 415
Ser Lys Leu Thr Val Asp Lys Ser Arg Trp Gln Gln Gly Asn Val Phe
            420                 425                 430
Ser Cys Ser Val Met His Glu Ala Leu His Asn His Tyr Thr Gln Lys
        435                 440                 445
Ser Leu Ser Leu Ser Pro Gly Lys
    450                 455

<210> SEQ ID NO 43
<211> LENGTH: 448
<212> TYPE: PRT
<213> ORGANISM: Artificial Sequence
<220> FEATURE:
<223> OTHER INFORMATION: Synthetic: aGFP IgG HC Y180F/404TAG
<220> FEATURE:
<221> NAME/KEY: MOD_RES
<222> LOCATION: (181)..(181)
<223> OTHER INFORMATION: para-azidomethylphenylalanine
<220> FEATURE:
<221> NAME/KEY: MOD_RES
<222> LOCATION: (405)..(405)
<223> OTHER INFORMATION: para-azidomethylphenylalanine

<400> SEQUENCE: 43

Met Gln Val Gln Leu Val Glu Ser Gly Gly Gly Leu Val Gln Pro Gly
1               5                   10                  15
Gly Ser Leu Arg Leu Ser Cys Ala Ala Ser Gly Phe Thr Phe Ser Arg
            20                  25                  30
Tyr Gly Met His Trp Val Arg Gln Ala Pro Gly Lys Gly Leu Glu Trp
        35                  40                  45
Val Ser Gly Ile Ser Ser Ile Gly Ser Asn Thr Tyr Tyr Ala Asp Ser
    50                  55                  60
Val Lys Gly Arg Phe Thr Ile Ser Arg Asp Asn Ser Lys Asn Thr Leu
65                  70                  75                  80
Tyr Leu Gln Met Asn Ser Leu Arg Ala Glu Asp Thr Ala Val Tyr Tyr
                85                  90                  95
Cys Ala Arg Trp Tyr Lys Thr Tyr Ile Asp Val Trp Gly Gln Gly Thr
            100                 105                 110
Leu Val Thr Val Ser Ser Ala Ser Thr Lys Gly Pro Ser Val Phe Pro
        115                 120                 125
```

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Xaa Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Xaa Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 44
<211> LENGTH: 5
<212> TYPE: PRT
<213> ORGANISM: Artificial Sequence
<220> FEATURE:
<223> OTHER INFORMATION: Synthetic

<400> SEQUENCE: 44

Leu Leu Gln Gly Ala
1               5

<210> SEQ ID NO 45
<211> LENGTH: 7
<212> TYPE: PRT
<213> ORGANISM: Artificial Sequence

```
<220> FEATURE:
<223> OTHER INFORMATION: Synthetic

<400> SEQUENCE: 45

Tyr Ala His Gln Ala His Tyr
1               5

<210> SEQ ID NO 46
<211> LENGTH: 5
<212> TYPE: PRT
<213> ORGANISM: Artificial Sequence
<220> FEATURE:
<223> OTHER INFORMATION: Synthetic

<400> SEQUENCE: 46

Tyr Arg Tyr Arg Gln
1               5

<210> SEQ ID NO 47
<211> LENGTH: 7
<212> TYPE: PRT
<213> ORGANISM: Artificial Sequence
<220> FEATURE:
<223> OTHER INFORMATION: Synthetic

<400> SEQUENCE: 47

Pro Asn Pro Gln Leu Pro Phe
1               5

<210> SEQ ID NO 48
<211> LENGTH: 7
<212> TYPE: PRT
<213> ORGANISM: Artificial Sequence
<220> FEATURE:
<223> OTHER INFORMATION: Synthetic

<400> SEQUENCE: 48

Pro Lys Pro Gln Gln Phe Met
1               5

<210> SEQ ID NO 49
<211> LENGTH: 6
<212> TYPE: PRT
<213> ORGANISM: Artificial Sequence
<220> FEATURE:
<223> OTHER INFORMATION: Synthetic

<400> SEQUENCE: 49

Gly Gln Gln Gln Leu Gly
1               5

<210> SEQ ID NO 50
<211> LENGTH: 7
<212> TYPE: PRT
<213> ORGANISM: Artificial Sequence
<220> FEATURE:
<223> OTHER INFORMATION: Synthetic

<400> SEQUENCE: 50

Trp Ala Leu Gln Arg Pro His
1               5

<210> SEQ ID NO 51
<211> LENGTH: 7
<212> TYPE: PRT
<213> ORGANISM: Artificial Sequence
<220> FEATURE:
```

```
<223> OTHER INFORMATION: Synthetic

<400> SEQUENCE: 51

Trp Glu Leu Gln Arg Pro Tyr
1               5

<210> SEQ ID NO 52
<211> LENGTH: 7
<212> TYPE: PRT
<213> ORGANISM: Artificial Sequence
<220> FEATURE:
<223> OTHER INFORMATION: Synthetic

<400> SEQUENCE: 52

Tyr Pro Met Gln Gly Trp Phe
1               5

<210> SEQ ID NO 53
<211> LENGTH: 6
<212> TYPE: PRT
<213> ORGANISM: Artificial Sequence
<220> FEATURE:
<223> OTHER INFORMATION: Synthetic

<400> SEQUENCE: 53

Leu Ser Leu Ser Gln Gly
1               5

<210> SEQ ID NO 54
<211> LENGTH: 8
<212> TYPE: PRT
<213> ORGANISM: Artificial Sequence
<220> FEATURE:
<223> OTHER INFORMATION: Synthetic

<400> SEQUENCE: 54

Gly Gly Gly Leu Leu Gln Gly Gly
1               5

<210> SEQ ID NO 55
<211> LENGTH: 5
<212> TYPE: PRT
<213> ORGANISM: Artificial Sequence
<220> FEATURE:
<223> OTHER INFORMATION: Synthetic

<400> SEQUENCE: 55

Gly Leu Leu Gln Gly
1               5

<210> SEQ ID NO 56
<211> LENGTH: 10
<212> TYPE: PRT
<213> ORGANISM: Artificial Sequence
<220> FEATURE:
<223> OTHER INFORMATION: Synthetic

<400> SEQUENCE: 56

Gly Ser Pro Leu Ala Gln Ser His Gly Gly
1               5                   10

<210> SEQ ID NO 57
<211> LENGTH: 7
<212> TYPE: PRT
<213> ORGANISM: Artificial Sequence
<220> FEATURE:
<223> OTHER INFORMATION: Synthetic
```

```
<400> SEQUENCE: 57

Gly Leu Leu Gln Gly Gly Gly
1               5

<210> SEQ ID NO 58
<211> LENGTH: 6
<212> TYPE: PRT
<213> ORGANISM: Artificial Sequence
<220> FEATURE:
<223> OTHER INFORMATION: Synthetic

<400> SEQUENCE: 58

Gly Leu Leu Gln Gly Gly
1               5

<210> SEQ ID NO 59
<211> LENGTH: 4
<212> TYPE: PRT
<213> ORGANISM: Artificial Sequence
<220> FEATURE:
<223> OTHER INFORMATION: Synthetic

<400> SEQUENCE: 59

Gly Leu Leu Gln
1

<210> SEQ ID NO 60
<211> LENGTH: 8
<212> TYPE: PRT
<213> ORGANISM: Artificial Sequence
<220> FEATURE:
<223> OTHER INFORMATION: Synthetic

<400> SEQUENCE: 60

Leu Leu Gln Leu Leu Gln Gly Ala
1               5

<210> SEQ ID NO 61
<211> LENGTH: 5
<212> TYPE: PRT
<213> ORGANISM: Artificial Sequence
<220> FEATURE:
<223> OTHER INFORMATION: Synthetic

<400> SEQUENCE: 61

Leu Leu Gln Gly Ala
1               5

<210> SEQ ID NO 62
<211> LENGTH: 7
<212> TYPE: PRT
<213> ORGANISM: Artificial Sequence
<220> FEATURE:
<223> OTHER INFORMATION: Synthetic

<400> SEQUENCE: 62

Leu Leu Gln Tyr Gln Gly Ala
1               5

<210> SEQ ID NO 63
<211> LENGTH: 6
<212> TYPE: PRT
<213> ORGANISM: Artificial Sequence
<220> FEATURE:
<223> OTHER INFORMATION: Synthetic
```

```
<400> SEQUENCE: 63

Leu Leu Gln Gly Ser Gly
1               5

<210> SEQ ID NO 64
<211> LENGTH: 6
<212> TYPE: PRT
<213> ORGANISM: Artificial Sequence
<220> FEATURE:
<223> OTHER INFORMATION: Synthetic

<400> SEQUENCE: 64

Leu Leu Gln Tyr Gln Gly
1               5

<210> SEQ ID NO 65
<211> LENGTH: 7
<212> TYPE: PRT
<213> ORGANISM: Artificial Sequence
<220> FEATURE:
<223> OTHER INFORMATION: Synthetic

<400> SEQUENCE: 65

Leu Leu Gln Leu Leu Gln Gly
1               5

<210> SEQ ID NO 66
<211> LENGTH: 5
<212> TYPE: PRT
<213> ORGANISM: Artificial Sequence
<220> FEATURE:
<223> OTHER INFORMATION: Synthetic

<400> SEQUENCE: 66

Ser Leu Leu Gln Gly
1               5

<210> SEQ ID NO 67
<211> LENGTH: 5
<212> TYPE: PRT
<213> ORGANISM: Artificial Sequence
<220> FEATURE:
<223> OTHER INFORMATION: Synthetic

<400> SEQUENCE: 67

Leu Leu Gln Leu Gln
1               5

<210> SEQ ID NO 68
<211> LENGTH: 6
<212> TYPE: PRT
<213> ORGANISM: Artificial Sequence
<220> FEATURE:
<223> OTHER INFORMATION: Synthetic

<400> SEQUENCE: 68

Leu Leu Gln Leu Leu Gln
1               5

<210> SEQ ID NO 69
<211> LENGTH: 5
<212> TYPE: PRT
<213> ORGANISM: Artificial Sequence
<220> FEATURE:
<223> OTHER INFORMATION: Synthetic

<400> SEQUENCE: 69
```

```
Leu Leu Gln Gly Arg
1               5

<210> SEQ ID NO 70
<211> LENGTH: 6
<212> TYPE: PRT
<213> ORGANISM: Artificial Sequence
<220> FEATURE:
<223> OTHER INFORMATION: Synthetic

<400> SEQUENCE: 70

Leu Leu Gln Gly Pro Ala
1               5

<210> SEQ ID NO 71
<211> LENGTH: 6
<212> TYPE: PRT
<213> ORGANISM: Artificial Sequence
<220> FEATURE:
<223> OTHER INFORMATION: Synthetic

<400> SEQUENCE: 71

Leu Leu Gln Gly Pro Pro
1               5

<210> SEQ ID NO 72
<211> LENGTH: 8
<212> TYPE: PRT
<213> ORGANISM: Artificial Sequence
<220> FEATURE:
<223> OTHER INFORMATION: Synthetic

<400> SEQUENCE: 72

Gly Gly Leu Leu Gln Gly Pro Pro
1               5

<210> SEQ ID NO 73
<211> LENGTH: 5
<212> TYPE: PRT
<213> ORGANISM: Artificial Sequence
<220> FEATURE:
<223> OTHER INFORMATION: Synthetic

<400> SEQUENCE: 73

Leu Leu Gln Gly Gly
1               5

<210> SEQ ID NO 74
<211> LENGTH: 4
<212> TYPE: PRT
<213> ORGANISM: Artificial Sequence
<220> FEATURE:
<223> OTHER INFORMATION: Synthetic

<400> SEQUENCE: 74

Leu Leu Gln Gly
1

<210> SEQ ID NO 75
<211> LENGTH: 15
<212> TYPE: PRT
<213> ORGANISM: Artificial Sequence
<220> FEATURE:
<223> OTHER INFORMATION: Synthetic

<400> SEQUENCE: 75
```

```
Gly Gly Gly Gly Ser Gly Gly Gly Ser Gly Gly Gly Ser
1               5                  10                 15
```

<210> SEQ ID NO 76
<211> LENGTH: 11
<212> TYPE: PRT
<213> ORGANISM: Artificial Sequence
<220> FEATURE:
<223> OTHER INFORMATION: Synthetic

<400> SEQUENCE: 76

```
Ala Ala Gly Ser Asp Gln Glu Pro Lys Ser Ser
1               5                  10
```

<210> SEQ ID NO 77
<211> LENGTH: 238
<212> TYPE: PRT
<213> ORGANISM: Artificial Sequence
<220> FEATURE:
<223> OTHER INFORMATION: Synthetic

<400> SEQUENCE: 77

```
Ala Ala Gly Ser Asp Gln Glu Pro Lys Ser Ser Asp Lys Thr His Thr
1               5                  10                  15

Cys Pro Pro Cys Ser Ala Pro Glu Leu Leu Gly Gly Ser Ser Val Phe
            20                  25                  30

Leu Phe Pro Pro Lys Pro Lys Asp Thr Leu Met Ile Ser Arg Thr Pro
        35                  40                  45

Glu Val Thr Cys Val Val Val Asp Val Ser His Glu Asp Pro Glu Val
    50                  55                  60

Lys Phe Asn Trp Tyr Val Asp Gly Val Glu Val His Asn Ala Lys Thr
65                  70                  75                  80

Lys Pro Arg Glu Glu Gln Tyr Asn Ser Thr Tyr Arg Val Val Ser Val
                85                  90                  95

Leu Thr Val Leu His Gln Asp Trp Leu Asn Gly Lys Glu Tyr Lys Cys
            100                 105                 110

Lys Val Ser Asn Lys Ala Leu Pro Ala Pro Ile Glu Lys Thr Ile Ser
        115                 120                 125

Lys Ala Lys Gly Gln Pro Arg Glu Pro Gln Val Tyr Thr Leu Pro Pro
    130                 135                 140

Ser Arg Asp Glu Leu Thr Lys Asn Gln Val Ser Leu Thr Cys Leu Val
145                 150                 155                 160

Lys Gly Phe Tyr Pro Ser Asp Ile Ala Val Glu Trp Glu Ser Asn Gly
                165                 170                 175

Gln Pro Glu Asn Asn Tyr Lys Thr Thr Pro Pro Val Leu Asp Ser Asp
            180                 185                 190

Gly Ser Phe Phe Leu Tyr Ser Lys Leu Thr Val Asp Lys Ser Arg Trp
        195                 200                 205

Gln Gln Gly Asn Val Phe Ser Cys Ser Val Met His Glu Ala Leu His
    210                 215                 220

Asn His Tyr Thr Gln Lys Ser Leu Ser Leu Ser Pro Gly Lys
225                 230                 235
```

IMMUNOMODULATOR ANTIBODY DRUG CONJUGATES AND USES THEREOF

CROSS REFERENCE TO RELATED APPLICATIONS

This application claims the benefit of U.S. Provisional Application No. U.S. 62/859,629, filed Jun. 10, 2019, and U.S. Provisional Application No. U.S. 62/984,758, filed Mar. 3, 2020, the contents of which are hereby incorporated by reference in their entireties.

This application incorporates by reference the computer readable sequence listing entitled "108843.00293 SEQ LIST," created Aug. 19, 2020, having 54 KB.

FIELD

This disclosure is related to compounds, trifunctional antibody products thereof, and methods and pharmaceutical compositions for use in treatment of inflammatory and/or proliferative diseases.

BACKGROUND OF THE INVENTION

A number of currently used cancer treatment regimens employ combinations of drugs which may display therapeutic activity in vivo, by acting through complementary mechanisms of action. For instance, cytotoxic drugs are employed in combination with adjuvants and/or immune system modulators. However, cytotoxic drugs are not tumor specific and conventional cancer chemotherapy is associated with side effects.

Tumor cells express specific antigens which can be targeted, e.g., by use of antibodies. If the antibodies are conjugated to cytotoxic drugs i.e, if antibody drug conjugates are employed, targeted delivery of cytotoxic drugs to the tumor site can reduce side effects associated with the non-specific cytotoxic drugs. If an immune response can be induced at the same time, the immune system can recruit immune cells to target tumors expressing specific antigens, thereby boosting the therapeutic efficacy of the antibody-drug conjugate cancer treatment. Further, the immune response may not be limited to targeting only tumor cells that express those tumor antigens. Tumor cells in the periphery may also be targeted via antigen spreading and/or through less specific mechanisms of tumor cell killing (e.g. cytokine release)

Therapeutic induction of tumor-cell apoptosis combined with dendritic cell (DC) activation and maturation by certain currently used standard of care chemotherapies represents an attractive combination approach for immune-oncology (IO) compounds (G. Kroemer et al., *Annu. Rev. Immunol.* 31 (2013) 51-72). Due to their highly sophisticated antigen-presenting machinery, DCs are central to the initiation and regulation of anti-cancer immunity (R. M. Steinman, J. Banchereau, *Nature* 449 (2007) 419-426). However, tumors have evolved several mechanisms to interfere with the maturation and antigen processing capacity of tumor residing DCs (J. Idoyaga, et al., *Cancer Immunol. Immunother.* 56 (2007) 1237-1250; B. Almand, et al., *J. Immunol.* 166 (2001) 678-689; F. Ghiringhelli, et al., *J. Exp. Med.* 202 (2005) 919-929).

In contrast to mature DCs, which efficiently promote tumor immune responses, immature or dysfunctional DCs can induce immuno-suppressive effects. Tumors exploit these properties by suppressing DC maturation or inducing a dysfunctional state, allowing tumors to avoid immune recognition (W. Zou, Nat. Rev. Cancer 5 (2005) 263-274; R. L. Sabado, et al., *Immunotherapy* 2 (2010) 37-56). Therefore, therapeutic approaches that activate tumor resident DCs and promote the priming of tumor antigen-specific T cells may address the limitations of current anti-cancer therapeutics and increase cancer immunity. However, only a few studies have investigated the capacity of cytotoxic cancer therapeutics, as employed by antibody drug conjugate (ADCs), to improve DC functions.

One of the earliest reports identifying cytotoxic compounds with immune stimulatory functions triggering immune surveillance included the mitotic spindle inhibitor vinblastine, targeting the beta subunit of tubulin. Vinblastine was identified as a potent and direct inducer of DC maturation, which is different from its antimitotic activities on tumor cells (N. Mizumoto, et al., *Blood* 106 (2005) 3082-3089; H. Tanaka, et al., *Cancer Res.* 69 (2009) 6978-6986; H. Tanaka, et al., H. *Cancer Res.* 69 (2009) 6987-6994). In an extension of this work, a large variety of tubulin poisons were shown to induce DC activation and maturation, when exposed to mouse or human dendritic cells, indicative of a class effect. When tested in vitro, colchicine, vinblastine, vindesine, vincristine, combretastatin-A4, dolastatin 10, dolastatin 15, monomethylauristatin E (MMAE), ansamitocin P3 and DM1 induced phenotypic and functional dendritic cell (DC) maturation and activation (P. Muller, et al., *Oncoimmunology* 3 (2014) e954460). The experimental endpoints used to study DC activation and maturation included expression of the co-stimulatory molecules and the maturation marker CD80 and CD86 and production of the pro-inflammatory cytokines IL-1b, IL-6, and IL-12. Studies testing dolastatin 10 and the synthetic analog MMAE as well as the maytansinoid, ansamitocin P3 (K. Martin, et al., *Cancer Immunol. Immunother.* 63 (2014) 925-938; P. Muller, et al., Cancer Immunol. Res. 2 (2014) 741-755) were conducted in preclinical tumor growth studies in mice. These three cytotoxics are commonly used as payloads for ADCs and stimulated CD8+ effector cell migration to experimental tumors grown in mice. When tested in vitro, an increase in cytolytic activities and presentation of major histocompatibility complex I as well as upregulation of the differentiation markers CD80 and CD86 on dendritic cells, were reported. Importantly, when ADCs employing tubulin inhibitors were administered in combination with immune-checkpoint inhibitors such as anti-PD-L1- and anti-CTLA-4 antibodies, more than additive anti-tumor effects were observed in syngeneic tumor models in mice. In these experiments, dolastatins efficiently promoted antigen uptake and migration of tumor-resident DCs to tumor draining lymph nodes and significantly increased their capacity to prime T-cells (S. J. Gardai, et al., *Cancer Res.* 75 (2015) Abstract No. 2469; P. Mueller, et al., *Sci. Trans. Med.* 7 (2015) 188-202; S. I. Rothschild, et al., *Swiss Med Wkly.* 145 (2015) w14066). These findings revealed a novel mechanism of action of tubulin inhibitors when tested in vivo, and provided a rationale for combination treatment of tubulin inhibitor based ADCs with immune based therapies.

Immuno-histochemical analysis of tumor samples from patients treated with an ADC, SGN-35, comprised of an anti-CD30 antibody conjugated to vcMMAE (H. P. Gerber, *Biochem. Pharmacol.* 79 (2010) 1544-1552) revealed significant changes in the population of inflammatory cells (P. Muller, et al., *Cancer Immunol. Res.* 2 (2014) 741-755). In SGN-35 treated Hodgkin's lymphoma tumors, a 2-3 fold increase in the number of intra-tumoral CD8+ effector T-cells was observed (P. Muller, et al., *Cancer Immunol. Res.* 2 (2014) 741-755; S. J. Gardai, et al., *Cancer Res.* 75 (2015)

Abstract No. 2469; P. Mueller et al., *Sci. Trans. Med.* 7 (2015) 188-202). These studies provided evidence for tubulin destabilizing poisons to stimulate the cancer immunity cycle. However, additional studies are required to identify the molecular pathways engaged by tubulin inhibitors leading to activation and maturation of tumor resident DCs. A deeper understanding of the molecular events triggered by tubulin inhibitors leading to DC activation is lacking in the field. While increased numbers of CD8+ effector T-cells in preclinical and clinical tumors following treatment with cytotoxic compounds were reported, it is not clear how broadly these observations apply for ADC development. There is a need in the field for identification of optimal combination regimens between ADCs and immune-oncology compounds that can overcome the limitations of current immune checkpoint inhibitors by increasing the recruitment and infiltration of antigen specific CD8+ effector T-cells to the tumor.

There is a continuing need for effective treatments of inflammatory and/or proliferative diseases.

SUMMARY OF THE INVENTION

Provided herein are compounds useful, for example, for the treatment of cancer. The compounds are trifunctional antibody conjugates, such as immunomodulator-antibody-drug-conjugates, in particular immunostimulatory-antibody-drug-conjugates (iADCs), and provide targeted delivery of two therapeutic agents (e.g., a cytotoxic agent and an immunomodulatory agent) In certain embodiments, the iADCs display remarkable efficacy or bioavailability, or both, for the treatment of, for example, cancer in a human. In certain embodiments, the iADCs allow for targeted delivery of cytotoxic drugs to tumor sites while also boosting the immune system response. Provided herein are compounds of Formula (I), and subformulae thereof.

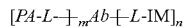        Formula (I)

wherein
Ab is an antibody, or an antigen-binding fragment thereof;
each L is independently an optional linker;
each PA is independently a drug payload;
each IM is independently an immunomodulatory payload;
subscript n is an integer selected from 1 to 8;
subscript m is an integer selected from 1 to 8; and
each bracketed group is covalently linked to Ab.

The iADCs of Formula (I) and subformulae thereof are useful in methods of treatment and prevention of cell proliferation and cancer, methods of detection of cell proliferation and cancer, and methods of diagnosis of cell proliferation and cancer. The conjugates are useful in methods of treatment and prevention of inflammatory diseases and conditions.

In another aspect, provided are compositions comprising the iADCs of Formula (I) and subformulae thereof. In some embodiments, the compositions are pharmaceutical compositions. Any suitable pharmaceutical composition may be used. In a further aspect, provided herein are kits comprising the iADCs or pharmaceutical compositions.

In another aspect, provided herein are methods of using the iADCs described herein. In some embodiments, the methods are methods of delivering one or more payload moieties to a target cell or tissue. In some embodiments, the methods are methods of treatment. In some embodiments, the methods are diagnostic methods. In some embodiments, the methods are analytical methods. In some embodiments, the iADCs are used to treat a disease or condition. In some aspects, the disease or condition is selected from a cancer, and/or an inflammatory disease or condition.

Also provided herein is the use of the iADCs described herein, and pharmaceutical compositions thereof, for the treatment of cancer, and/or an inflammatory disease or condition.

In a further aspect, provided herein are linker payloads comprising cytotoxic compounds and linker payloads comprising immunomodulatory compounds which are useful for the preparation of iADCs described herein.

BRIEF DESCRIPTION OF THE FIGURES

FIG. 3C and FIG. 3D illustrate monocyte activation in isolated PBMCs in the presence of Anti-FolR1-immunostimulatory/cytotoxin-antibody drug conjugates (iADCs), anti-FolR1-cytotoxin-ADC and anti-FolR1-ISAC (two donors, FIG. 3C and FIG. 3D)

FIGS. 4A-4E, respectively, illustrate monocyte activation in isolated PBMCs in the presence of anti-FolR1-iADCs comprising conjugated TLR7/8 agonists and cytotoxic drugs. No monocyte activation was observed for the anti-GFP-iADC conjugated to the same TLR7/8 agonist and cytotoxic drugs.

FIGS. 5A-5B illustrate mean percent body weight change and tumor response for animals bearing established MC38-hFolRα tumors treated with Conjugate 1 (ADC), Conjugate 2 (ISAC), or the combination of Conjugate 1+Conjugate 2. FIG. 5A shows the effects of treatment on body weight and FIG. 5B shows the effects on tumor growth.

FIG. 6A shows the effects of treatment on body weight and FIG. 6B shows the effect on tumor growth.

DETAILED DESCRIPTION

Figure 1A:
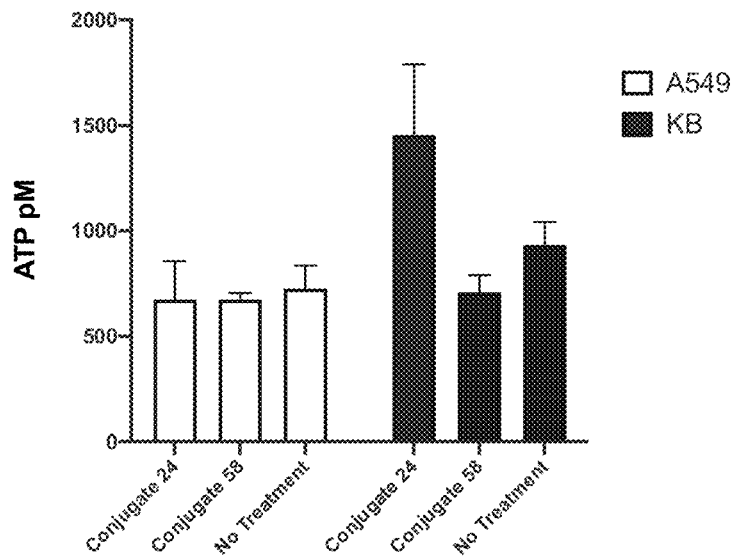
FIGS. 1A and 1B, respectively, illustrate induced immunogenic cell death (ICD) in the presence of certain anti-FolR1-ADCs described herein as measured by ATP release in the cell culture medium (FIG. 1A), and Calreticulin expression on the cell surface (FIG. 1B), of the FolRα (also known as FolR1 or FolRα) positive KB cells but not on FolRa-negative A549 cells after ADC treatment for 48 hours.

Cytotoxic compounds can induce anti-tumor immunity via two mechanisms: direct activation and maturation of dendritic cells (DCs) and by inducing immunogenic cell death (ICD). Both mechanisms have been shown to engage the adaptive immune response through improved cross presentation of tumor derived antigens and priming of specific CD8+ effector T-cells, thereby triggering an immune response towards the tumor. Described herein are therapeutics that utilize both mechanisms, thereby addressing some of the current limitations of single agent immuno-oncology treatments such as a lack of specificity and side effects.

Described herein are trifunctional armed antibody conjugates, such as immunomodulator-antibody-drug-conjugates (iADCs), that (i) provide targeted delivery of therapeutic agents (e.g., by targeting a tumor specific antigen), (ii) deliver cytotoxic payloads at the targeted site; and (iii) deliver immunomodulatory agents at the targeted site. Cytotoxin-mediated cell death can also contribute to the mobilization of immune system. Advantageously, the iADCs mobilize the immune system for simultaneous stimulation of several cell types, resulting in a mix of activated immune cells, cytokines and chemokines at the tumor site, while also delivering therapeutic drugs, thereby improving and/or prolonging the anti-cancer effect of the treatment, and/or reducing side effects.

1. Definitions

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a difference over what is generally understood in the art. The techniques and procedures described or referenced herein are generally well understood and commonly employed using conventional methodologies by those skilled in the art, such as, for example, the widely utilized molecular cloning methodologies described in Green & Sambrook, *Molecular Cloning: A Laboratory Manual* $4^{th}$ ed. (2012), Cold Spring Harbor Laboratory Press, Cold Spring Harbor, N.Y.; and Ausubel et al., *Current Protocols in Molecular Biology*, John Wiley & Sons. As appropriate, procedures involving the use of commercially available kits and reagents are generally carried out in accordance with manufacturer-defined protocols and conditions unless otherwise noted.

As used herein, the singular forms "a," "an," and "the" include the plural referents unless the context clearly indicates otherwise.

The term "about" indicates and encompasses an indicated value and a range above and below that value. In certain embodiments, the term "about" indicates the designated value ±10%, ±5%, or ±1%. In certain embodiments, the term "about" indicates the designated value ±one standard deviation of that value. In certain embodiments, e.g., for logarithmic scales (e.g., pH), the term "about" indicates the designated value ±0.3, +0.2, or 0.1.

The term "immunoglobulin" refers to a class of structurally related proteins generally comprising two pairs of polypeptide chains: one pair of light (L) chains and one pair of heavy (H) chains. In an "intact immunoglobulin," all four of these chains are interconnected by disulfide bonds. The structure of immunoglobulins has been well characterized. See, e.g., Paul, Fundamental Immunology 7th ed., Ch. 5 (2013) Lippincott Williams & Wilkins, Philadelphia, Pa. Briefly, each heavy chain typically comprises a heavy chain variable region ($V_H$ or VH) and a heavy chain constant region ($C_H$ or CH). The heavy chain constant region typically comprises three domains, abbreviated $C_H1$ (or CH1), $C_H2$ (or CH2), and $C_H3$ (or CH3). Each light chain typically comprises a light chain variable region ($V_L$ or VL) and a light chain constant region. The light chain constant region typically comprises one domain, abbreviated $C_L$ or CL.

The term "antibody" is used herein in its broadest sense. An antibody includes intact antibodies (e.g., intact immunoglobulins), and antibody fragments (e.g., antigen binding fragments of antibodies). Antibodies comprise at least one antigen-binding domain. One example of an antigen-binding domain is an antigen binding domain formed by a $V_H$-$V_L$ dimer.

The $V_H$ and $V_L$ regions may be further subdivided into regions of hypervariability ("hypervariable regions (HVRs)"; also called "complementarity determining regions" (CDRs)) interspersed with regions that are more conserved. The more conserved regions are called framework regions (FRs). Each $V_H$ and $V_L$ generally comprises three CDRs and four FRs, arranged in the following order (from N-terminus to C-terminus): FR1-CDR1-FR2-CDR2-FR3-CDR3-FR4. The CDRs are involved in antigen binding, and influence antigen specificity and binding affinity of the antibody. See Kabat et al., *Sequences of Proteins of Immunological Interest* 5th ed. (1991) Public Health Service, National Institutes of Health, Bethesda, Md., incorporated by reference in its entirety.

The light chain from any vertebrate species can be assigned to one of two types, called kappa and lambda, based on the sequence of the constant domain.

The heavy chain from any vertebrate species can be assigned to one of five different classes (or isotypes): IgA, IgD, IgE, IgG, and IgM. These classes are also designated α, δ, ε, γ, and μ, respectively. The IgG and IgA classes are further divided into subclasses on the basis of differences in sequence and function. Humans express the following subclasses: IgG1, IgG2, IgG3, IgG4, IgA1, and IgA2.

The amino acid sequence boundaries of a CDR can be determined by one of skill in the art using any of a number of known numbering schemes, including those described by Kabat et al., supra ("Kabat" numbering scheme); A1-Lazikani et al., 1997, *J. Mol. Biol.*, 273:927-948 ("Chothia" numbering scheme); MacCallum et al., 1996, *J. Mol. Biol.* 262:732-745 ("Contact" numbering scheme); Lefranc et al., *Dev. Comp. Immunol.*, 2003, 27:55-77 ("IMGT" numbering scheme); and Honegge and Pluckthun, *J. Mol. Biol.*, 2001, 309:657-70 ("AHo" numbering scheme), each of which is incorporated by reference in its entirety.

CDRs may be assigned, for example, using antibody numbering software, such as Abnum, available at www.bioinf.org.uk/abs/abnum/, and described in Abhinandan and Martin, *Immunology*, 2008, 45:3832-3839, incorporated by reference in its entirety.

The "EU numbering scheme" is generally used when referring to a residue in an antibody heavy chain constant region (e.g., as reported in Kabat et al., supra). Unless stated otherwise, the EU numbering scheme is used to refer to residues in antibody heavy chain constant regions described herein.

An "antibody fragment" comprises a portion of an intact antibody, such as the antigen binding or variable region of an intact antibody. Antibody fragments include, for example, Fv fragments, Fab fragments, F(ab')2 fragments, Fab' fragments, scFv (sFv) fragments, and scFv-Fc fragments.

"Fv" fragments comprise a non-covalently-linked dimer of one heavy chain variable domain and one light chain variable domain.

"Fab" fragments comprise, in addition to the heavy and light chain variable domains, the constant domain of the light chain and the first constant domain ($C_{H1}$) of the heavy chain. Fab fragments may be generated, for example, by recombinant methods or by papain digestion of a full-length antibody.

"F(ab')$_2$" fragments contain two Fab' fragments joined, near the hinge region, by disulfide bonds. F(ab')$_2$ fragments may be generated, for example, by recombinant methods or by pepsin digestion of an intact antibody. The F(ab') fragments can be dissociated, for example, by treatment with β-mercaptoethanol.

"Single-chain Fv" or "sFv" or "scFv" antibody fragments comprise a $V_H$ domain and a $V_L$ domain in a single polypeptide chain. The VH and VL are generally linked by a peptide linker. See Pluckthun A. (1994). In some embodiments, the linker is GGGGSGGGGSGGGGS (SEQ ID NO:75). In some embodiments, the linker is AAGSDQEPKSS (SEQ ID NO:76). Antibodies from *Escherichia coli*. In Rosenberg M. & Moore G. P. (Eds.), *The Pharmacology of Monoclonal Antibodies* vol. 113 (pp. 269-315). Springer-Verlag, New York, incorporated by reference in its entirety.

"scFv-Fc" fragments comprise an scFv attached to an Fc domain. For example, an Fc domain may be attached to the C-terminus of the scFv. The Fc domain may follow the $V_H$ or $V_L$, depending on the orientation of the variable domains in the scFv (i.e., $V_H$-$V_L$ or VL-VH). Any suitable Fc domain known in the art or described herein may be used. In some cases, the Fc domain comprises an IgG1 Fc domain. In some embodiments, the IgG1 Fc domain comprises SEQ ID NO:77, or a portion thereof. SEQ ID NO:77 provides the sequence of $C_H1$, $C_H2$, and $C_H3$ of the human IgG1 constant region.

The term "monoclonal antibody" refers to an antibody from a population of substantially homogeneous antibodies. A population of substantially homogeneous antibodies comprises antibodies that are substantially similar and that bind the same epitope(s), except for variants that may normally arise during production of the monoclonal antibody. Such variants are generally present in only minor amounts. A monoclonal antibody is typically obtained by a process that includes the selection of a single antibody from a plurality of antibodies. For example, the selection process can be the selection of a unique clone from a plurality of clones, such as a pool of hybridoma clones, phage clones, yeast clones, bacterial clones, or other recombinant DNA clones. The selected antibody can be further altered, for example, to improve affinity for the target ("affinity maturation"), to humanize the antibody, to improve its production in cell culture, and/or to reduce its immunogenicity in a subject.

The term "chimeric antibody" refers to an antibody in which a portion of the heavy and/or light chain is derived from a particular source or species, while the remainder of the heavy and/or light chain is derived from a different source or species.

"Humanized" forms of non-human antibodies are chimeric antibodies that contain minimal sequence derived from the non-human antibody. A humanized antibody is generally a human immunoglobulin (recipient antibody) in which residues from one or more CDRs are replaced by residues from one or more CDRs of a non-human antibody (donor antibody). The donor antibody can be any suitable non-human antibody, such as a mouse, rat, rabbit, chicken, or non-human primate antibody having a desired specificity, affinity, or biological effect. In some instances, selected framework region residues of the recipient antibody are replaced by the corresponding framework region residues from the donor antibody. Humanized antibodies may also comprise residues that are not found in either the recipient antibody or the donor antibody. Such modifications may be made to further refine antibody function. For further details, see Jones et al., *Nature*, 1986, 321:522-525; Riechmann et al., *Nature,* 1988, 332:323-329; and Presta, *Curr. Op. Struct. Biol.,* 1992, 2:593-596, each of which is incorporated by reference in its entirety.

A "human antibody" is one which possesses an amino acid sequence corresponding to that of an antibody produced by a human or a human cell, or derived from a non-human source that utilizes a human antibody repertoire or human antibody-encoding sequences (e.g., obtained from human sources or designed de novo). Human antibodies specifically exclude humanized antibodies.

An "isolated antibody" is one that has been separated and/or recovered from a component of its natural environment. Components of the natural environment may include enzymes, hormones, and other proteinaceous or nonproteinaceous materials. In some embodiments, an isolated antibody is purified to a degree sufficient to obtain at least 15 residues of N-terminal or internal amino acid sequence, for example by use of a spinning cup sequenator. In some embodiments, an isolated antibody is purified to homogeneity by gel electrophoresis (e.g., SDS-PAGE) under reducing or nonreducing conditions, with detection by Coomassie blue or silver stain. An isolated antibody includes an antibody in situ within recombinant cells, since at least one component of the antibody's natural environment is not present. In some aspects, an isolated antibody is prepared by at least one purification step.

In some embodiments, an isolated antibody is purified to at least 80%, 85%, 90%, 95%, or 99% by weight. In some embodiments, an isolated antibody is purified to at least 80%, 85%, 90%, 95%, or 99% by volume. In some embodiments, an isolated antibody is provided as a solution comprising at least 85%, 90%, 95%, 98%, 99% to 100% by weight. In some embodiments, an isolated antibody is provided as a solution comprising at least 85%, 90%, 95%, 98%, 99% to 100% by volume.

"Affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity, which reflects a 1:1 interaction between members of a binding pair (e.g., antibody and antigen). The affinity of a molecule X for its partner Y can be represented by the dissociation constant ($K_D$). Affinity can be measured by common methods known in the art, including those described herein. Affinity can be determined, for example, using surface plasmon resonance (SPR) technology, such as a Biacore® instrument. In some embodiments, the affinity is determined at 25° C.

With regard to the binding of an antibody to a target molecule, the terms "specific binding," "specifically binds to," "specific for," "selectively binds," and "selective for" a particular antigen (e.g., a polypeptide target) or an epitope on a particular antigen mean binding that is measurably different from a non-specific or non-selective interaction. Specific binding can be measured, for example, by determining binding of a molecule compared to binding of a control molecule. Specific binding can also be determined by competition with a control molecule that mimics the antibody binding site on the target. In that case, specific binding is indicated if the binding of the antibody to the target is competitively inhibited by the control molecule.

An "affinity matured" antibody is one with one or more alterations in one or more CDRs or FRs that result in an improvement in the affinity of the antibody for its antigen, compared to a parent antibody which does not possess the alteration(s). In one embodiment, an affinity matured antibody has nanomolar or picomolar affinity for the target antigen. Affinity matured antibodies may be produced using a variety of methods known in the art. For example, Marks et al. (*Bio Technology,* 1992, 10:779-783, incorporated by reference in its entirety) describes affinity maturation by $V_H$ and $V_L$ domain shuffling. Random mutagenesis of CDR and/or framework residues is described by, for example, Barbas et al. (*Proc. Nat. Acad. Sci. U.S.A.,* 1994, 91:3809-3813); Schier et al., *Gene,* 1995, 169:147-155; Yelton et al., *J. Immunol.,* 1995, 155:1994-2004; Jackson et al., *J. Immunol.,* 1995, 154:3310-33199; and Hawkins et al, *J. Mol. Biol.,* 1992, 226:889-896, each of which is incorporated by reference in its entirety.

The term "amino acid" refers to the twenty common naturally occurring amino acids. Naturally occurring amino acids include alanine (Ala; A), arginine (Arg; R), asparagine (Asn; N), aspartic acid (Asp; D), cysteine (Cys; C); glutamic acid (Glu; E), glutamine (Gln; Q), Glycine (Gly; G); histidine (His; H), isoleucine (Ile; I), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V), and the less common pyrrolysine and selenocysteine. Natural amino acids also include citrulline. Naturally encoded amino acids include post-translational variants of the 22 naturally occurring amino acids such as prenylated amino acids, isoprenylated amino acids, myrisoylated amino acids, palmitoylated amino acids, N-linked glycosylated amino acids, 0-linked glycosylated amino acids, phosphorylated amino acids, and acylated amino acids. The term "amino acid" also includes non-natural (or unnatural) or synthetic $\alpha$, $\beta$ $\gamma$ or $\delta$ amino acids, and includes but is not limited to, amino acids found in proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, arginine and histidine. In certain embodiments, the amino acid is in the L-configuration. Alternatively, the amino acid can be a derivative of alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, $\beta$-alanyl, $\beta$-valinyl, $\beta$-leucinyl, $\beta$-isoleuccinyl, $\beta$-prolinyl, $\beta$-phenylalaninyl, $\beta$-tryptophanyl, $\beta$-methioninyl, $\beta$-glycinyl, $\beta$-serinyl, $\beta$-threoninyl, $\beta$-cysteinyl, $\beta$-tyrosinyl, $\beta$-asparaginyl, $\beta$-glutaminyl, $\beta$-aspartoyl, $\beta$-glutaroyl, $\beta$-lysinyl, $\beta$-argininyl or $\beta$-histidinyl. Unnatural amino acids are not proteinogenic amino acids, or post-translationally modified variants thereof. In particular, the term unnatural amino acid refers to an amino acid that is not one of the 20 common amino acids or pyrrolysine or selenocysteine, or post-translationally modified variants thereof.

The term "conjugate" or "antibody conjugate" refers to an antibody linked to one or more payload moieties. The antibody can be any antibody described herein. The payload can be any payload described herein. The antibody can be directly linked to the payload via a covalent bond, or the antibody can be linked to the payload indirectly via a linker. Typically, the linker is covalently bonded to the antibody and also covalently bonded to the payload. The term "antibody drug conjugate" or "ADC" refers to a conjugate wherein at least one payload is a therapeutic moiety such as a drug.

"pAMF" mutation refers to a variant phenylalanine residue, i.e., para-azidomethyl-L-phenylalanine, added or substituted into a polypeptide.

The term "payload" refers to a molecular moiety that can be conjugated to an antibody. In particular embodiments, payloads are selected from the group consisting of therapeutic moieties and/or labelling moieties described herein.

The term "linker" refers to a molecular moiety that is capable of forming at least two covalent bonds. Typically, a linker is capable of forming at least one covalent bond to an antibody and at least another covalent bond to a payload. In certain embodiments, a linker can form more than one covalent bond to an antibody. In certain embodiments, a linker can form more than one covalent bond to a payload or can form covalent bonds to more than one payload. After a linker forms a bond to an antibody, or a payload, or both, the remaining structure, i.e. the residue of the linker after one or more covalent bonds are formed, may still be referred to as a "linker" herein. The term "linker precursor" refers to a linker having one or more reactive groups capable of forming a covalent bond with an antibody or payload, or both. In some embodiments, the linker is a cleavable linker. For example, a cleavable linker can be one that is released by a bio-labile function, which may or may not be engineered. In some embodiments, the linker is a non-cleavable linker. For example, a non-cleavable linker can be one that is released upon degradation of the antibody.

When referring to the compounds provided herein, the following terms have the following meanings unless indicated otherwise. Unless defined otherwise, all technical and scientific terms used herein have the same meaning as is commonly understood by one of ordinary skill in the art. In the event that there is a plurality of definitions for a term herein, those in this section prevail unless stated otherwise.

The term "alkyl," as used herein, unless otherwise specified, refers to a saturated straight or branched hydrocarbon. In certain embodiments, the alkyl group is a primary, secondary, or tertiary hydrocarbon. In certain embodiments, the alkyl group includes one to ten carbon atoms, i.e., $C_1$ to $C_{10}$ alkyl. The term includes both substituted and unsubstituted alkyl groups, including halogenated alkyl groups. In some or any embodiments, the alkyl is unsubstituted. In some or any embodiments, the alkyl is substituted. In certain embodiments, the alkyl group is a fluorinated alkyl group. Non-limiting examples of moieties with which the alkyl group can be substituted are selected from the group consisting of halogen (fluoro, chloro, bromo or iodo), hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., Protective Groups in Organic Synthesis, John Wiley and Sons, Second Edition, 1991, hereby incorporated by reference. In certain embodiments, the alkyl group is selected from the group consisting of methyl, $CF_3$, $CCl_3$, $CFCl_2$, $CF_2Cl$, ethyl, $CH_2CF_3$, $CF_2CF_3$, propyl, isopropyl, butyl, isobutyl, secbutyl, t-butyl, pentyl, isopentyl, neopentyl, hexyl, isohexyl, 3-methylpentyl, 2,2-dimethylbutyl, and 2,3-dimethylbutyl.

The term "lower alkyl," as used herein, and unless otherwise specified, refers to a saturated straight or branched hydrocarbon having one to six carbon atoms, i.e., $C_1$ to $C_6$ alkyl. In certain embodiments, the lower alkyl group is a primary, secondary, or tertiary hydrocarbon. The term includes both substituted and unsubstituted moieties.

The term "alkylene," as used herein, unless otherwise specified, refers to a divalent alkyl group, as defined herein. In some or any embodiments, alkylene is unsubstituted.

"Alkenyl" refers to an olefinically unsaturated hydrocarbon groups, in certain embodiments, having up to about 11 carbon atoms or from 2 to 6 carbon atoms which can be straight-chained or branched and having at least 1 or from 1 to 2 sites of alkenyl unsaturation.

"Alkenylene" refers to a divalent alkenyl as defined herein. Lower alkenylene is $C_2$-$C_6$-alkenylene.

"Alkynyl" refers to acetylenically unsaturated hydrocarbon groups, in certain embodiments, having up to about 11 carbon atoms or from 2 to 6 carbon atoms which can be straight-chained or branched and having at least 1 or from 1 to 2 sites of alkynyl unsaturation. Non-limiting examples of alkynyl groups include acetylenic, ethynyl (—C≡CH), propargyl(-$CH_2$C≡CH), and the like.

"Alkynylene" refers to a divalent alkynyl as defined herein. Lower alkynylene is C2-C6-alkynylene.

The term "aryl," as used herein, and unless otherwise specified, refers to phenyl, biphenyl, or naphthyl. The term includes both substituted and unsubstituted moieties. An aryl group can be substituted with any described moiety, including, but not limited to, one or more moieties selected from the group consisting of halogen (fluoro, chloro, bromo or iodo), alkyl, haloalkyl, hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., Protective Groups in Organic Synthesis, John Wiley and Sons, Second Edition, 1991.

The term "arylene," as used herein, and unless otherwise specified refers to a divalent aryl group, as defined herein.

"Alkarylene" refers to an arylene group, as defined herein wherein the aryl ring is substituted with one or two alkyl groups. "Substituted alkarylene" refers to an alkarylene, as defined herein, where the arylene group is further substituted, as defined for aryl.

"Aralkylene" refers to an —$CH_2$-arylene-, -arylene-$CH_2$—, or —$CH_2$-arylene-$CH_2$— group, where arylene is as defined herein. "Substituted aralkylene" refers to an aralkylene, as defined herein, where the aralkylene group is substituted, as defined for aryl.

"Alkoxy" and "alkoxyl," refer to the group —OR' where R' is alkyl or cycloalkyl. Alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Alkoxycarbonyl" refers to a radical —C(O)-alkoxy where alkoxy is as defined herein.

"Amino" refers to the radical —$NH_2$.

The term "alkylamino," as used herein, and unless otherwise specified, refers to the group —NHR' where R' is $C_{1-10}$alkyl, as defined herein. In some or any embodiments, the alkylamino is $C_{1-6}$alkylamino.

The term "dialkylamino," as used herein, and unless otherwise specified, refers to the group —NR'R' where each R' is independently $C_{1-10}$alkyl, as defined herein. In some or any embodiments, the dialkylamino is di-$C_{1-6}$alkylamino.

"Carboxyl" or "carboxy" refers to the radical —C(O)OH.

The term "cycloalkyl," as used herein, unless otherwise specified, refers to a saturated cyclic hydrocarbon. In certain embodiments, the cycloalkyl group may be a saturated, and/or bridged, and/or non-bridged, and/or a fused bicyclic group. In certain embodiments, the cycloalkyl group includes three to ten carbon atoms, i.e., $C_3$ to $C_{10}$ cycloalkyl. In some embodiments, the cycloalkyl has from 3 to 15 ($C_{3-15}$), from 3 to 10 ($C_{3-10}$), or from 3 to 7 ($C_{3-7}$) carbon atoms. In certain embodiments, the cycloalkyl group is cyclopropyl, cyclobutyl, cyclopentyl, cyclohexyl, cyclohexylmethyl, cycloheptyl, bicyclo[2.1.1]hexyl, bicyclo[2.2.1]heptyl, decalinyl, or adamantyl.

The term "cycloalkylene," as used herein refers to a divalent cycloalkyl group, as defined herein. Lower cycloalkylene refers to a $C_3$-$C_6$-cycloalkylene.

"Fused bicyclic aryl," as used herein, is naphthyl.

The term "heterocyclyl" and "heterocyclic" refer to a monovalent monocyclic non-aromatic ring system and/or multicyclic ring system that contains at least one non-aromatic ring, wherein one or more of the non-aromatic ring atoms are heteroatoms independently selected from O, S, and N; and the remaining ring atoms of the non-aromatic ring are carbon atoms, and wherein any aromatic ring atoms are optionally heteroatoms independently selected from O, S, and N and the remaining ring atoms of the non-aromatic ring are carbon atoms. In certain embodiments, the heterocyclyl or heterocyclic group has from 3 to 20, from 3 to 15, from 3 to 10, from 3 to 8, from 4 to 7, from 4 to 11, or from 5 to 6 ring atoms. Heterocyclyl groups are bonded to the rest of the molecule through the non-aromatic ring. In certain embodiments, the heterocyclyl is a monocyclic, bicyclic, tricyclic, or tetracyclic ring system, which may include a fused or bridged ring system and in which the nitrogen or sulfur atoms may be optionally oxidized, the nitrogen atoms may be optionally quaternized, and some rings may be partially or fully saturated, or aromatic. The heterocyclyl may be attached to the main structure at any heteroatom or carbon atom of its non-aromatic ring which results in the creation of a stable compound. Heterocycloalkyl refers to a heterocycle which is a monovalent, monocyclic or multicyclic, non-aromatic ring system. In some or any embodiments, heterocycloalkyl is a monovalent, monocyclic or multicyclic, fully-saturated ring system. Examples of such heterocyclic and/or heterocycloalkyl radicals include, but are not limited to, 2,5-diazabicyclo[2.2.2]octanyl, 3,9-diazabicyclo[3.3.2]decanyl), azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, β-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, heterocyclic may also be optionally substituted as described herein. In some or any embodiments, heterocyclic and heterocycloalkyl are substituted with 1, 2, or 3 groups independently selected from halogen (fluoro, chloro, bromo or iodo), alkyl, haloalkyl, hydroxyl, amino, alkylamino, and alkoxy. In some embodiments, a hetercycloalkyl group may comprise 1, 2, 3, or 4 heteroatoms. Those of skill in the art will recognize that a 4-membered heterocycloalkyl may generally comprise 1 or 2 heteroatoms, a 5-6 membered heterocycloalkyl may generally comprise 1 or 2 heteroatoms, and a 7-10 membered heterocycloalkyl may generally comprise 1, 2, 3, or 4 heteroatoms.

"Heterocycloalkylene" refers to a divalent heterocycloalkyl, as defined herein.

"N-linked heterocycloalkyl" or "N-linked heterocyclyl" refers to a heterocycloalkyl, as defined above, comprising at least one nitrogen and wherein the heterocycloalkyl is attached to the main structure via a nitrogen atom in a non-aromatic ring. In some or any embodiments, the N-linked heterocycloalkyl and/or N-linked heterocyclyl is fully saturated.

The term "heteroaryl" refers to refers to a monovalent monocyclic aromatic group and/or multicyclic aromatic group, wherein at least one aromatic ring contains one or more heteroatoms independently selected from O, S, and N in the ring. Each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. A heteroaryl may be attached to the rest of the molecule via a nitrogen or a carbon atom. In some embodiments, monocyclic heteroaryl groups include, but are not limited to, furanyl, imidazolyl, isothiazolyl, isoxazolyl, oxadiazolyl, oxadiazolyl, oxazolyl, pyrazinyl, pyrazolyl, pyridazinyl, pyridyl, pyrimidinyl, pyrrolyl, imidazolyl, triazolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, heteroaryl may also be optionally substituted as described herein. "Substituted heteroaryl" is heteroaryl substituted as defined for aryl.

The term "heteroarylene" refers to a divalent heteroaryl group, as defined herein. "Substituted heteroarylene" is heteroarylene substituted as defined for aryl.

"Partially saturated heteroaryl" refers to a multicyclic (e.g., bicyclic, tricyclic) fused ring system that contains at least one non-aromatic ring and at least one aromatic ring, wherein one or more of the non-aromatic ring atoms and/or one or more of the aromatic ring atoms are heteroatoms independently selected from O, S, and N; and the remaining ring atoms are carbon atoms. Partially saturated heteroaryl groups are bonded to the rest of the molecule through the aromatic ring. In certain embodiments, the partially saturated heteroaryl group has from 6 to 20, from 6 to 15, from 6 to 10, from 6 to 8, or from 8 to 11 ring atoms. In certain embodiments, the partially saturated heteroaryl group has 8, 9, 10, or 11 ring atoms (in some embodiments 9 or 10). The partially saturated heteroaryl may be attached to the main structure at any heteroatom or carbon atom of its aromatic ring which results in the creation of a stable compound. In some or any embodiments, an oxo group may be present as a substituent on one of the ring atoms. A partially saturated heteroaryl radical consists of one of the following or comprises one or more of the following: benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, tetrahydropyrazinyl, dihydropyrazinonyl, dihydropyridinyl, tetrahydropyridinyl, dihydropyrimidinyl, dihydropyrrolyl, furanonyl, imidazolinyl, indolinyl, tetrahydroindolyl, isoindolinyl, tetrahydroisoindolyl, isobenzotetrahydrofuranyl, isobenzotetrahydrothienyl, isochromanyl, isocoumarinyl, isoindolinyl, dihydroisoxazolyl, oxazinyl, dihydrooxazinyl, oxo-oxazolyl, dihydrooxazolyl, dihydropiperidonyl, dihydro-4-piperidonyl, dihydropyrazolyl, dihydropyrazolinyl, dihydropyrrolyl, azabicyclo[2.2.2]oct-2-enyl, dihydrofuryl, tetrahydroisoquinolinyl, dihydropyranyl, pyranyl, dihydrothienyl, oxathiazinyl, dihydrothiazolyl, tetrahydroquinolinyl, and 5,6,7,8-tetrahydro-[1,2,4]triazolo[4,3-a]pyrazinyl. In certain embodiments, the partially saturated heteroaryl radical is benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, chromanyl, chromonyl, coumarinyl, dihydrobenzisothiazinyl, dihydrobenzisoxazinyl, dihydroisoindolyl, indolinyl, isobenzotetrahydrofuranyl, isobenzotetrahydrothienyl, isochromanyl, isocoumarinyl, isoindolinyl, tetrahydroisoquinolinyl, tetrahydroquinolinyl, or 5,6,7,8-tetrahydro-[1,2,4]triazolo[4,3-a]pyrazinyl. In certain embodiments, partially saturated heteroaryl may also be optionally substituted as described herein.

"Spiro-heterocyclic" or "spiro-heterocycle" or "spiro-heterocycloalkyl" refers to a heterocyclic ring, as defined herein, which comprises two rings which are connected to each other via a common atom. Non-limiting examples of spiro-heterocycles include azetidinyl rings, morpholinyl rings, and/or piperidinyl rings that are attached via a common atom to another ring (e.g., ring B as shown below):

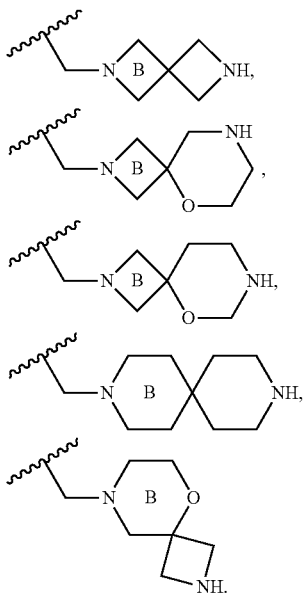

A spiro-heterocycloalkyl may be optionally substituted with, for example, 1-2 $C_{1-3}$alkyl.

The term "protecting group" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis.

"Pharmaceutically acceptable salt" refers to any salt of a compound provided herein which retains its biological properties and which is not toxic or otherwise undesirable for pharmaceutical use. Such salts may be derived from a variety of organic and inorganic counter-ions well known in the art. Such salts include, but are not limited to: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like.

Pharmaceutically acceptable salts further include, by way of example only and without limitation, sodium, potassium, calcium, magnesium, ammonium, tetraalkylammonium and the like, and when the compound contains a basic functionality, salts of non-toxic organic or inorganic acids, such as hydrohalides, e.g. hydrochloride and hydrobromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate and the like.

The term "substantially free of" or "substantially in the absence of" with respect to a composition refers to a composition that includes at least 85 or 90% by weight, in certain embodiments 95%, 98%, 99% or 100% by weight, of the designated enantiomer of that compound. In certain embodiments, in the methods and compounds provided herein, the compounds are substantially free of enantiomers.

Similarly, the term "isolated" with respect to a composition refers to a composition that includes at least 85, 90%, 95%, 98%, and 99% to 100% by weight, of the compound, the remainder comprising other chemical species or enantiomers.

"Solvate" refers to a compound provided herein or a salt thereof that further includes a stoichiometric or non-stoichiometric amount of solvent bound by non-covalent intermolecular forces. Where the solvent is water, the solvate is a hydrate.

"Isotopic composition" refers to the amount of each isotope present for a given atom, and "natural isotopic composition" refers to the naturally occurring isotopic composition or abundance for a given atom. Atoms containing their natural isotopic composition may also be referred to herein as "non-enriched" atoms. Unless otherwise designated, the atoms of the compounds recited herein are meant to represent any stable isotope of that atom. For example, unless otherwise stated, when a position is designated specifically as "H" or "hydrogen," the position is understood to have hydrogen at its natural isotopic composition.

"Isotopic enrichment" refers to the percentage of incorporation of an amount of a specific isotope at a given atom in a molecule in the place of that atom's natural isotopic abundance. For example, deuterium enrichment of 1% at a given position means that 1% of the molecules in a given sample contain deuterium at the specified position. Because the naturally occurring distribution of deuterium is about 0.0156%, deuterium enrichment at any position in a compound synthesized using non-enriched starting materials is about 0.0156%. The isotopic enrichment of the compounds provided herein can be determined using conventional analytical methods known to one of ordinary skill in the art, including mass spectrometry and nuclear magnetic resonance spectroscopy.

"Isotopically enriched" refers to an atom having an isotopic composition other than the natural isotopic composition of that atom. "Isotopically enriched" may also refer to a compound containing at least one atom having an isotopic composition other than the natural isotopic composition of that atom.

As used herein, "alkyl," "alkylene," "alkylamino," "dialkylamino," "cycloalkyl," "aryl," "arylene," "alkoxy," "alkoxycarbonyl," "amino," "carboxyl," "heterocyclyl," "heterocycloalkyl," "heteroaryl," "heteroarylene," "partially saturated heteroaryl," "spiro-heterocyclyl," "carboxyl," and "amino acid" groups optionally comprise deuterium at one or more positions where hydrogen atoms are present, and wherein the deuterium composition of the atom or atoms is other than the natural isotopic composition.

Also as used herein, "alkyl," "alkylamino," "dialkylamino," "cycloalkyl," "aryl," "alkoxy," "alkoxycarbonyl," "amino," "carboxyl," "heterocyclyl," "heteroaryl," "partially saturated heteroaryl," "spiro-heterocyclyl," "carboxyl" and "amino acid" groups optionally comprise carbon-13 at an amount other than the natural isotopic composition.

As used herein, $EC_{50}$ refers to a dosage, concentration, or amount of a particular test compound that elicits a dose-dependent response at 50% of maximal expression of a particular response that is induced, provoked, or potentiated by the particular test compound.

As used herein, the $IC_{50}$ refers to an amount, concentration, or dosage of a particular test compound that achieves a 50% inhibition of a maximal response in an assay that measures such response.

As used herein, the terms "subject" and "patient" are used interchangeably herein. The terms "subject" and "subjects" refer to an animal, such as a mammal including a non-primate (e.g., a cow, pig, horse, cat, dog, rat, and mouse) and a primate (e.g., a monkey such as a cynomolgous monkey, a chimpanzee and a human), and for example, a human. In certain embodiments, the subject is refractory or non-responsive to current treatments for hepatitis C infection. In another embodiment, the subject is a farm animal (e.g., a horse, a cow, a pig, etc.) or a pet (e.g., a dog or a cat). In certain embodiments, the subject is a human.

As used herein, the terms "therapeutic agent" and "therapeutic agents" refer to any agent(s) which can be used in the treatment or prevention of a disorder or one or more symptoms thereof. In certain embodiments, the term "therapeutic agent" includes a compound and/or an antibody conjugate provided herein. In certain embodiments, a therapeutic agent is an agent which is known to be useful for, or has been or is currently being used for the treatment or prevention of a disorder or one or more symptoms thereof.

As used herein, the term "therapeutically effective amount" or "effective amount" refers to an amount of an antibody or composition that when administered to a subject is effective to treat a disease or disorder. In some embodiments, a therapeutically effective amount or effective amount refers to an amount of an antibody or composition that when administered to a subject is effective to prevent or ameliorate a disease or the progression of the disease, or result in amelioration of symptoms. A "therapeutically effective amount" can vary depending on, inter alia, the compound, the disease and its severity, and the age, weight, etc., of the subject to be treated.

"Treating" or "treatment" of any disease or disorder refers, in certain embodiments, to ameliorating a disease or disorder that exists in a subject. In another embodiment, "treating" or "treatment" includes ameliorating at least one physical parameter, which may be indiscernible by the subject. In yet another embodiment, "treating" or "treatment" includes modulating the disease or disorder, either physically (e.g., stabilization of a discernible symptom) or physiologically (e.g., stabilization of a physical parameter) or both. In yet another embodiment, "treating" or "treatment" includes delaying or preventing the onset of the disease or disorder, or delaying or preventing recurrence of the disease or disorder. In yet another embodiment, "treating" or "treatment" includes the reduction or elimination of either the disease or disorder, or to retard the progression of the disease or disorder or of one or more symptoms of the disease or disorder, or to reduce the severity of the disease or disorder or of one or more symptoms of the disease or disorder.

As used herein, the term "inhibits growth" (e.g. referring to cells, such as tumor cells) is intended to include any measurable decrease in cell growth (e.g., tumor cell growth) when contacted with an antibody or antibody conjugate, as compared to the growth of the same cells not in contact with the antibody or antibody conjugate. In some embodiments, growth may be inhibited by at least about 10%, 20%, 30%, 40%, 50%, 60%, 70%, 80%, 90%, 99%, or 100%. The decrease in cell growth can occur by a variety of mechanisms, including but not limited to antibody internalization, apoptosis, necrosis, and/or effector function-mediated activity.

"Treating" or "treatment" of any disease or disorder refers, in certain embodiments, to ameliorating a disease or disorder that exists in a subject. In another embodiment, "treating" or "treatment" includes ameliorating at least one physical parameter, which may be indiscernible by the subject. In yet another embodiment, "treating" or "treatment" includes modulating the disease or disorder, either physically (e.g., stabilization of a discernible symptom) or physiologically (e.g., stabilization of a physical parameter) or both. In yet another embodiment, "treating" or "treatment" includes delaying the onset of the disease or disorder.

As used herein, the terms "prophylactic agent" and "prophylactic agents" as used refer to any agent(s) which can be used in the prevention of a disorder or one or more symptoms thereof. In certain embodiments, the term "prophylactic agent" includes a compound provided herein. In certain other embodiments, the term "prophylactic agent" does not refer a compound provided herein. For example, a prophylactic agent is an agent which is known to be useful for, or has been or is currently being used to prevent or impede the onset, development, progression, and/or severity of a disorder.

As used herein, the phrase "prophylactically effective amount" refers to the amount of a therapy (e.g., prophylactic agent) which is sufficient to result in the prevention or reduction of the development, recurrence or onset of one or more symptoms associated with a disorder (, or to enhance or improve the prophylactic effect(s) of another therapy (e.g., another prophylactic agent).

In some chemical structures illustrated herein, certain substituents, chemical groups, and atoms are depicted with a curvy/wavy line (e.g., ⤳⤳)

that intersects a bond or bonds to indicate the atom through which the substituents, chemical groups, and atoms are bonded. For example, in some structures, such as but not limited to, this curvy/wavy line indicates the atoms in the backbone of a conjugate or linker-payload structure to which the illustrated chemical entity is bonded. In some structures, such as but not limited to

this curvy/wavy line indicates the atoms in the antibody or antibody fragment as well as the atoms in the backbone of a conjugate or linker-payload structure to which the illustrated chemical entity is bonded.

The term "site-specific" refers to a modification of a polypeptide at a predetermined sequence location in the polypeptide. The modification is at a single, predictable residue of the polypeptide with little or no variation. In particular embodiments, a modified amino acid is introduced at that sequence location, for instance recombinantly or synthetically. Similarly, a moiety can be "site-specifically" linked to a residue at a particular sequence location in the polypeptide. In certain embodiments, a polypeptide can comprise more than one site-specific modification.

2. Conjugates

Provided herein are immunostimulatory antibody-drug conjugates (iADCs). In certain embodiments, the iADCs are dual conjugates of antibodies with TLR7 agonists and cytotoxins. The conjugates comprise an antibody recognizing a suitable antigen (e.g., a tumor antigen) covalently linked directly or indirectly, via linkers, to payloads (e.g., PA and IM described herein). In certain embodiments, the antibody is linked to one payload. In further embodiments, the antibody is linked to more than one payload. In certain embodiments, the antibody is linked to two, three, four, five, six, seven, eight, or more payloads.

The payloads can be any payloads deemed useful by the practitioner of skill. In certain embodiments, the payloads are therapeutic moieties. In certain embodiments, the payload is a diagnostic moiety, e.g. a label. Useful payloads are described in the sections and examples below.

The linkers can be any linkers capable of forming at least one bond to the antibody and at least one bond to a payload. Useful linkers are described in the sections and examples below.

The antibody is typically a protein comprising multiple polypeptide chains. In certain embodiments, the antibody is a heterotetramer comprising two identical light (L) chains and two identical heavy (H) chains. Each light chain can be linked to a heavy chain by one covalent disulfide bond. Each heavy chain can be linked to the other heavy chain by one or more covalent disulfide bonds. Each heavy chain and each light chain can also have one or more intrachain disulfide bonds. As is known to those of skill in the art, each heavy chain typically comprises a variable domain (VH) followed by a number of constant domains. Each light chain typically comprises a variable domain at one end ($V_L$) and a constant domain. As is known to those of skill in the art, antibodies typically have selective affinity for their target molecules, i.e. antigens.

The antibodies provided herein can have any antibody form known to those of skill in the art. They can be full-length, or fragments. Exemplary full length antibodies include IgA, IgA1, IgA2, IgD, IgE, IgG, IgG1, IgG2, IgG3, IgG4, IgM, etc. Exemplary fragments include Fv, Fab, Fc, scFv, scFv-Fc, etc.

In certain embodiments, the antibody of the conjugate comprises one, two, three, four, five, or six of the CDR sequences described herein. In certain embodiments, the antibody of the conjugate comprises a heavy chain variable domain ($V_H$) described herein. In certain embodiments, the antibody of the conjugate comprises a light chain variable domain ($V_L$) described herein. In certain embodiments, the antibody of the conjugate comprises a heavy chain variable domain ($V_H$) described herein and a light chain variable domain ($V_L$) described herein. In certain embodiments, the antibody of the conjugate comprises a paired heavy chain variable domain and a light chain variable domain described herein ($V_H$-$V_L$ pair). In certain embodiments, the antibody of the conjugate comprises a three heavy chain CDRs and three light chain CDRs with sequences consisting of the heavy chain and light chain CDRs of any paired heavy chain variable domain and a light chain variable domain described herein (six CDRs of any $V_H$-$V_L$ pair).

In certain embodiments, the antibody conjugate can be formed from an antibody that comprises one or more reactive groups. In certain embodiments, the antibody conjugate can be formed from an antibody comprising all naturally encoded amino acids. Those of skill in the art will recognize that several naturally encoded amino acids include reactive groups capable of conjugation to a payload or to a linker. These reactive groups include cysteine side chains, lysine side chains, and amino-terminal groups. In these embodiments, the antibody conjugate can comprise a payload or linker linked to the residue of an antibody reactive group. In these embodiments, the payload precursor or linker precursor comprises a reactive group capable of forming a bond with an antibody reactive group. Typical reactive groups include maleimide groups, activated carbonates (including but not limited to, p-nitrophenyl ester), activated esters (including but not limited to, N-hydroxysuccinimide, p-nitrophenyl ester, and aldehydes). Particularly useful reactive groups include maleimide and succinimide, for instance N-hydroxysuccinimide, for forming bonds to cysteine and lysine side chains. Further reactive groups are described in the sections and examples below.

In further embodiments, the antibody comprises one or more modified amino acids having a reactive group, as described herein. Typically, the modified amino acid is not a naturally encoded amino acid. These modified amino acids can comprise a reactive group useful for forming a covalent bond to a linker precursor or to a payload precursor. One of skill in the art can use the reactive group to link the polypeptide to any molecular entity capable of forming a covalent bond to the modified amino acid. Thus, provided herein are conjugates comprising an antibody comprising a modified amino acid residue linked to a payload directly or indirectly via a linker. Exemplary modified amino acids are described in the sections below. Generally, the modified amino acids have reactive groups capable of forming bonds to linkers or payloads with complementary reactive groups.

In certain embodiments, the non-natural amino acids are positioned at select locations in a polypeptide chain of the antibody. These locations were identified as providing optimal sites for substitution with the non-natural amino acids. Each site is capable of bearing a non-natural amino acid with optimal structure, function, and/or methods for producing the antibody.

In certain embodiments, a site-specific position for substitution provides an antibody that is stable. Stability can be measured by any technique apparent to those of skill in the art.

In certain embodiments, a site-specific position for substitution provides an antibody that has optimal functional properties. For instance, the antibody can show little or no loss of binding affinity for its target antigen compared to an antibody without the site-specific non-natural amino acid. In certain embodiments, the antibody can show enhanced binding compared to an antibody without the site-specific non-natural amino acid.

In certain embodiments, a site-specific position for substitution provides an antibody that can be made advantageously. For instance, in certain embodiments, the antibody shows advantageous properties in its methods of synthesis, discussed below. In certain embodiments, the antibody can show little or no loss in yield in production compared to an antibody without the site-specific non-natural amino acid. In certain embodiments, the antibody can show enhanced yield in production compared to an antibody without the site-specific non-natural amino acid. In certain embodiments, the antibody can show little or no loss of tRNA suppression compared to an antibody without the site-specific non-natural amino acid. In certain embodiments, the antibody can show enhanced tRNA suppression in production compared to an antibody without the site-specific non-natural amino acid.

In certain embodiments, a site-specific position for substitution provides an antibody that has advantageous solubility. In certain embodiments, the antibody can show little or no loss in solubility compared to an antibody without the site-specific non-natural amino acid. In certain embodiments, the antibody can show enhanced solubility compared to an antibody without the site-specific non-natural amino acid.

In certain embodiments, a site-specific position for substitution provides an antibody that has advantageous expression. In certain embodiments, the antibody can show little or no loss in expression compared to an antibody without the site-specific non-natural amino acid. In certain embodiments, the antibody can show enhanced expression compared to an antibody without the site-specific non-natural amino acid.

In certain embodiments, a site-specific position for substitution provides an antibody that has advantageous folding. In certain embodiments, the antibody can show little or no loss in proper folding compared to an antibody without the site-specific non-natural amino acid. In certain embodiments, the antibody can show enhanced folding compared to an antibody without the site-specific non-natural amino acid.

In certain embodiments, a site-specific position for substitution provides an antibody that is capable of advantageous conjugation. As described below, several non-natural amino acids have side chains or functional groups that facilitate conjugation of the antibody to a second agent, either directly or via a linker. In certain embodiments, the antibody can show enhanced conjugation efficiency compared to an antibody without the same or other non-natural amino acids at other positions. In certain embodiments, the antibody can show enhanced conjugation yield compared to an antibody without the same or other non-natural amino acids at other positions. In certain embodiments, the antibody can show enhanced conjugation specificity compared to an antibody without the same or other non-natural amino acids at other positions.

In some embodiments, one or more non-natural amino acids are located at selected site-specific positions in at least one polypeptide chain of the antibody. The polypeptide chain can be any polypeptide chain of the antibody without limitation, including either light chain or either heavy chain. The site-specific position can be in any domain of the antibody, including any variable domain and any constant domain.

In certain embodiments, the antibodies provided herein comprise one non-natural amino acid at a site-specific position. In certain embodiments, the antibodies provided herein comprise two non-natural amino acids at site-specific positions. In certain embodiments, the antibodies provided herein comprise three non-natural amino acids at site-specific positions. In certain embodiments, the antibodies provided herein comprise more than three non-natural amino acids at site-specific positions.

In certain embodiments, the antibodies provided herein comprise one or more non-natural amino acids each at a position independently selected from the group consisting of heavy chain or light chain residues HC-F404, HC-K121, HC-Y180, HC-F241, HC-221, LC-T22, LC-S7, LC-N152, LC-K42, LC-E161, LC-D170, HC-S136, HC-S25, HC-A40, HC-S119, HC-S190, HC-K222, HC-R19, HC-Y52, or HC-S70, according to the Kabat or Chothia or EU numbering scheme, or a post-translationally modified variant thereof. In certain embodiments, the antibodies provided herein comprise one or more non-natural amino acids each at a position independently selected from the group consisting of HC-180, HC-222, LC-7, or LC-42, according to the Kabat or Chothia or EU numbering scheme, or a post-translationally modified variant thereof. In these designations, HC indicates a heavy chain residue, and LC indicates a light chain residue. In certain embodiments, the non-natural amino acids are at HC-F404. In certain embodiments, the non-natural amino acids are at HC-Y180. In certain embodiments, the non-natural amino acids are at HC-F404 and HC-Y180. In certain embodiments, the non-natural amino acids are at HC-K222. In certain embodiments, the non-natural amino acids are at LC-S7. In certain embodiments, the non-natural amino acids are at LC-K42. In certain embodiments, the non-natural amino acids are at HC-Y180 and LC-K42. In certain embodiments, the non-natural amino acids are at HC-F404 and LC-K42. In certain embodiments, the non-natural amino acids are at HC-Y180, HC-F404, and LC-K42. In certain embodiments, the non-natural amino acids are at HC-Y180, HC-K222, LC-S7, and LC-K42. In certain embodiments, the non-natural amino acids are HC-F241, HC-K121, and/or HC-S190. In certain embodiments, the non-natural amino acids are the same. In certain embodiments, the non-natural amino acids are different. In certain embodiments, the non-natural amino acids are residues of Formula (30), herein.

In some embodiments, the antibody sequence may encompass a Q-tag sequence that is compatible with transglutaminase conjugation. In some embodiments, the one or more glutamine residues are in Q tags independently selected from those described elsewhere herein. In such embodiments, a linker-payload bearing an amino group can be conjugated to the side chain of one or more glutamine (Q) residues in the antibody in the presence of transglutaminase.

In certain embodiments, provided herein are conjugates according to Formula (C1) or (C2):

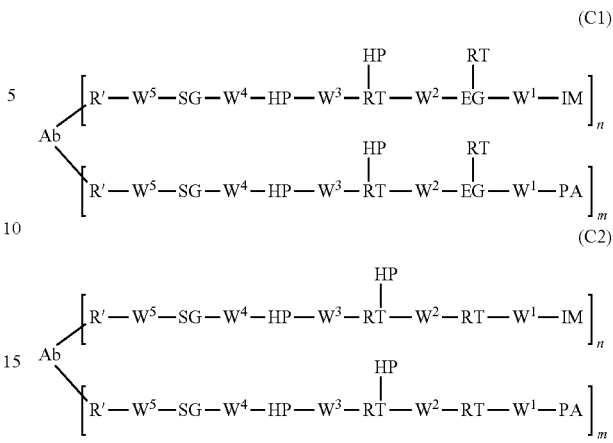

or a pharmaceutically acceptable salt, solvate, stereoisomer, regioisomer, or tautomer thereof, wherein:
Ab is a residue of an antibody or an antigen binding fragment thereof;
PA is a payload moiety;
IM is an immunostimulatory moiety
each $W^1$, $W^2$, $W^3$, $W^4$, and $W^5$ is independently, at each occurrence, a single bond, absent, or a divalent attaching group;
each EG is independently, at each occurrence, absent, or an eliminator group;
each RT is, in the backbone of Formula (C1) or (C2), is absent or is a release trigger group, or RT, when bonded to EG and EG is an eliminator group, is hydrogen or a release trigger group;
each HP is independently, at each occurrence, a single bond, absent, a monovalent hydrophilic group, or a divalent hydrophilic group;
each SG is independently, at each occurrence, a single bond, absent, or a divalent spacer group;
each R' is independently, at each occurrence, a terminal conjugating group, or a divalent residue of a terminal conjugating group;
subscript m is an integer selected from 1 to 30; and
subscript n is an integer selected from 1 to 30.
In some embodiments, n is an integer selected from 1 to 8. In some embodiments, n is 2. In some embodiments, n is 3. In some embodiments, n is 4. In some embodiments, n is 5. In some embodiments, n is 6. In some embodiments, n is 7. In some embodiments, n is 8.

In some embodiments, m is an integer from 1 to 8. In some embodiments, m is 2. In some embodiments, m is 3. In some embodiments, m is 4. In some embodiments, m is 5. In some embodiments, m is 6. In some embodiments, m is 7. In some embodiments, m is 8.

Any combination of m and n is contemplated within the scope of embodiments presented herein.

2.1 Attaching Groups

Attaching groups facilitate incorporation of eliminator groups, release trigger groups, hydrophobic groups, spacer groups, and/or conjugating groups into a compound. Useful attaching groups are known to, and are apparent to, those of skill in the art. Examples of useful attaching groups are provided herein. In certain embodiments, attaching groups are designated $W^1$, $W^2$, $W^3$, $W^4$, or $W^5$. In certain embodiments, an attaching group can comprise a divalent ketone, divalent ester, divalent ether, divalent amide, divalent amine, alkylene, arylene, sulfide, disulfide, carbonylene, or a combination thereof. In certain embodiments an attaching group can comprise —C(O)—, —O—, —C(O)NH—, —C(O)NH-alkyl-, —OC(O)NH—, —SC(O)NH—, —NH—, —NH-alkyl-, —C(O)N(CH₃)—, —C(O)N(CH₃)-alkyl-, —N(CH₃)—, —N(CH₃)-alkyl-, —N(CH₃)CH₂CH₂N(CH₃)—, —C(O)CH₂CH₂CH₂C(O)—, —S—, —S—S—, —OCH₂CH₂O—, or the reverse (e.g. —NHC(O)—) thereof, or a combination thereof.

2.2 Eliminator Groups

Eliminator groups facilitate separation of a biologically active portion of a compound or conjugate described herein from the remainder of the compound or conjugate in vivo and/or in vitro. Eliminator groups can also facilitate separation of a biologically active portion of a compound or conjugate described herein in conjunction with a release trigger group. For example, the eliminator group and the release trigger group can react in a Releasing Reaction to release a biologically active portion of a compound or conjugate described herein from the compound or conjugate in vivo and/or in vitro. Upon initiation of the Releasing Reaction by the release trigger, the eliminator group cleaves the biologically active moiety, or a prodrug form of the biologically active moiety, and forms a stable, non-toxic entity that has no further effect on the activity of the biologically active moiety.

In certain embodiments, the eliminator group is designated EG herein. Useful eliminator groups include those described herein. In certain embodiments, the eliminator group is:

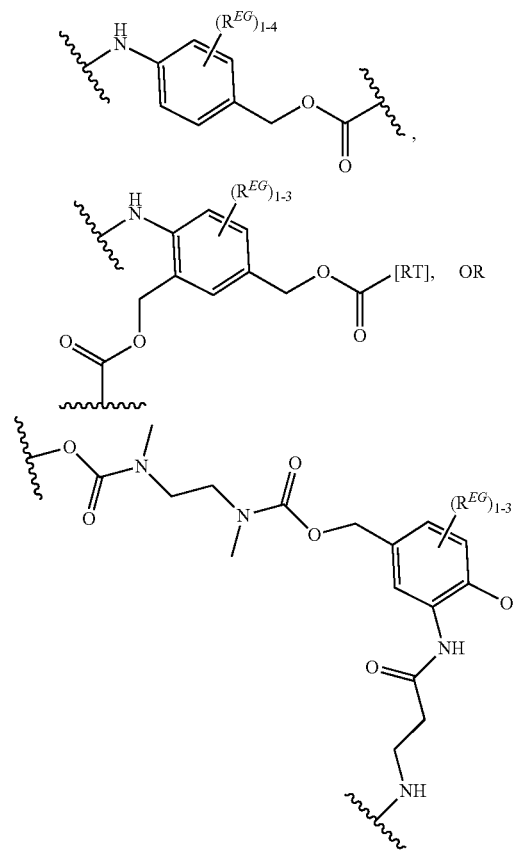

Wherein each $R^{EG}$ is independently selected from the group consisting of hydrogen, alkyl, biphenyl, —CF₃, —NO₂, —CN, fluoro, bromo, chloro, alkoxyl, alkylamino, dialkylamino, alkyl-C(O)O—, alkylamino-C(O)— and dialkylamino-C(O)—. In each structure, the phenyl ring can be bound to one, two, three, or in some cases, four $R^{EG}$ groups. In the second and third structures, those of skill will recognize that EG is bonded to an RT that is not within the backbone of formula (C1) as indicated in the above description of formula (C1). In some embodiments, each $R^{EG}$ is independently selected from the group consisting of hydrogen, alkyl, biphenyl, —CF₃, alkoxyl, alkylamino, dialkylamino, alkyl-C(O)O—, alkylamino-C(O)— and dialkylamino-C(O)—. In further embodiments, each $R^{EG}$ is independently selected from the group consisting of hydrogen, —NO₂, —CN, fluoro, bromo, and chloro. In certain embodiments, the eliminator group

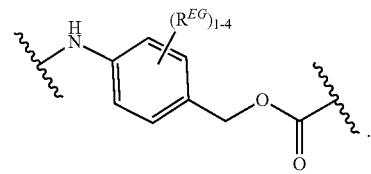

In certain embodiments, the eliminator group is

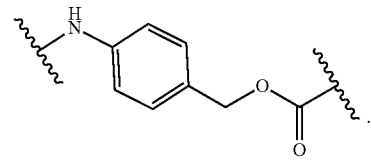 [SMILES: *Nc1ccc(COC(*)=O)cc1]

In certain embodiments, the eliminator group is

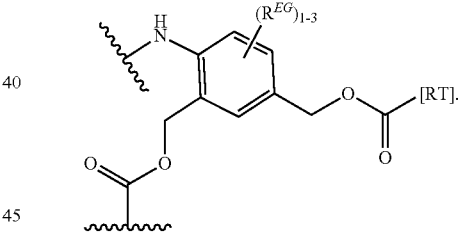

In certain embodiments, the eliminator group is

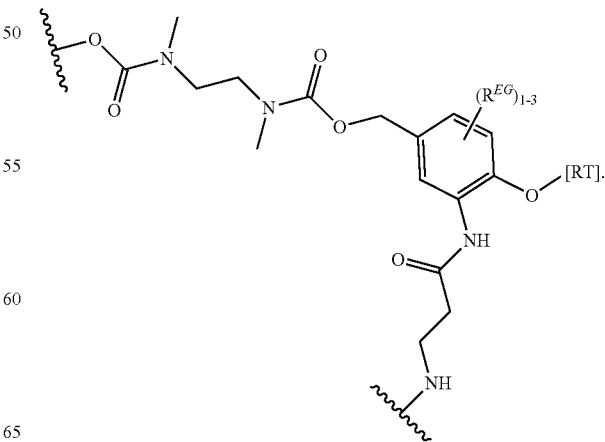

In some embodiments, the eliminator group is:

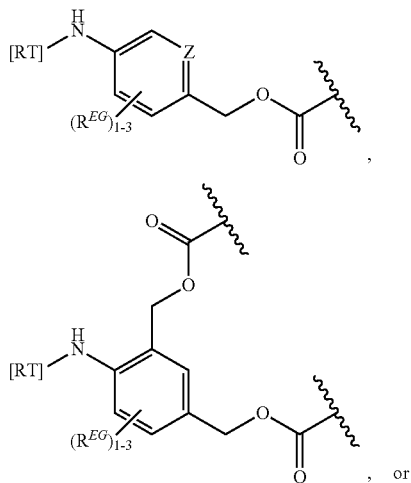

, or

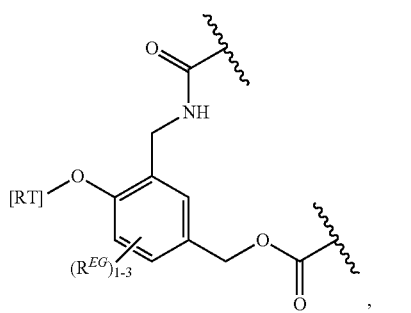

wherein Z may be CH or N, each $R^{EG}$ is independently selected from the group consisting of hydrogen, alkyl, biphenyl, —CF$_3$, —NO$_2$, —CN, fluoro, bromo, chloro, alkoxyl, alkylamino, dialkylamino, alkyl-C(O)O—, alkylamino-C(O)— and dialkylamino-C(O)—. In each structure, the phenyl ring can be bound to one, two, three, or in some cases, four $R^{EG}$ groups. In the first and second structures, those of skill will recognize that EG is bonded to an RT that is not within the backbone of formula (C1) as indicated in the above description of formula (C1). In some embodiments, each $R^{EG}$ is independently selected from the group consisting of hydrogen, alkyl, biphenyl, —CF$_3$, alkoxyl, alkylamino, dialkylamino, alkyl-C(O)O—, alkylamino-C(O)— and dialkylamino-C(O)—. In further embodiments, each $R^{EG}$ is independently selected from the group consisting of hydrogen, —NO$_2$, —CN, fluoro, bromo, and chloro. In some embodiments, each $R^{EG}$ in the EG is hydrogen. In certain embodiments, the eliminator group is

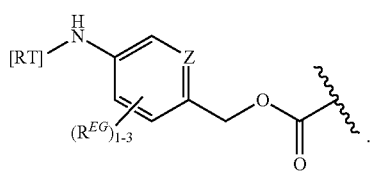

In certain embodiments, the eliminator group is

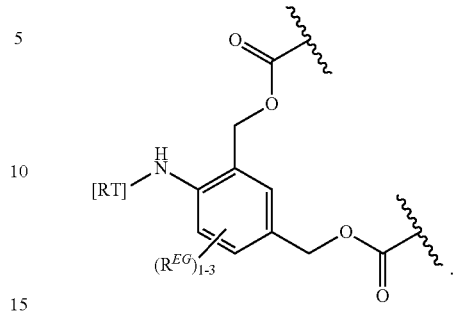

In certain embodiments, the eliminator group is

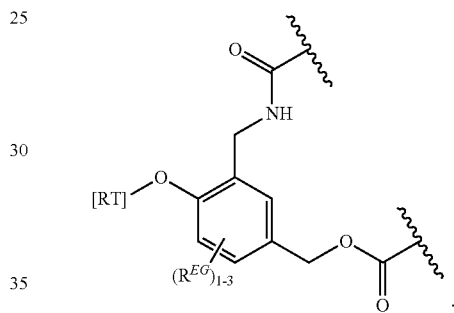

2.3 Release Trigger Groups

Release trigger groups facilitate separation of a biologically active portion of a compound or conjugate described herein from the remainder of the compound or conjugate in vivo and/or in vitro. Release trigger groups can also facilitate separation of a biologically active portion of a compound or conjugate described herein in conjunction with an eliminator group. For example, the eliminator group and the release trigger group can react in a Releasing Reaction to release a biologically active portion of a compound or conjugate described herein from the compound or conjugate in vivo and/or in vitro. In certain embodiment, the release trigger can act through a biologically-driven reaction with high tumor:nontumor specificity, such as the proteolytic action of an enzyme overexpressed in a tumor environment.

In certain embodiments, the release trigger group is designated RT herein. In certain embodiments, RT is divalent and bonded within the backbone of formula (C1). In other embodiments, RT is monovalent and bonded to EG as depicted above. Useful release trigger groups include those described herein. In certain embodiments, the release trigger group comprises a residue of a natural or non-natural amino acid or residue of a sugar ring. In certain embodiments, the release trigger group is:

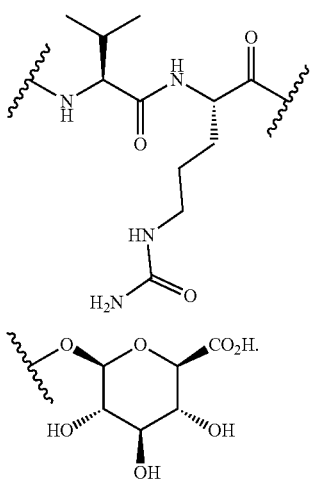

or

Those of skill will recognize that the first structure is divalent and can be bonded within the backbone of Formula (C1) or as depicted in Formula (C2), and that the second structure is monovalent and can be bonded to EG as depicted in formula (C1) above. In certain embodiments, the release trigger group is

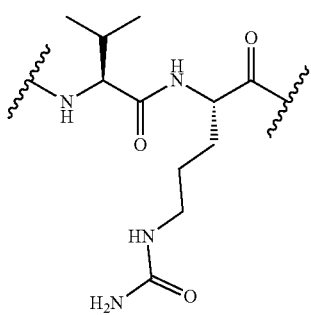

In certain embodiments, the release trigger group is

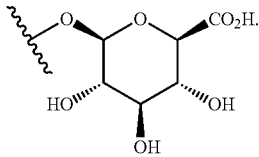 [SMILES: *O[C@H]1O[C@@H](C(=O)O)[C@H](O)[C@@H](O)[C@@H]1O]

In some embodiments, the release trigger group is a protease-cleavable $R_1$-Val-$X_1$ peptide according to the structure of:

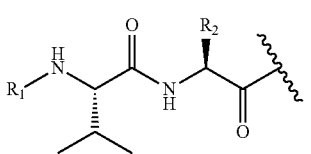

wherein $R_1$ is a bond to the rest of the compound or

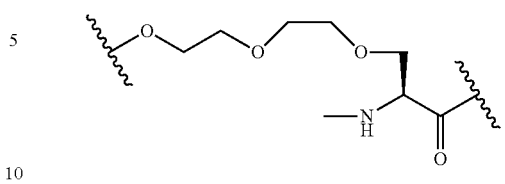

and $R_2$ is —$CH_3$, —$CH_2CH_2CO_2H$, or —$(CH_2)_3$ $NHCONH_2$; a legumain-cleavable Ala-Ala-Asn (AAN) or Ala-Ala-Asp (AAD) peptide according to the structure of:

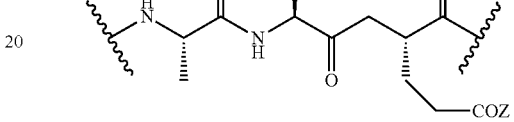

where Z is OH or $NH_2$; or a β-glucuronidase-cleavable β-glucuronide according to the structure of:

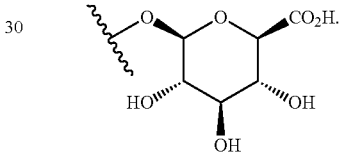

Those of skill will recognize that and

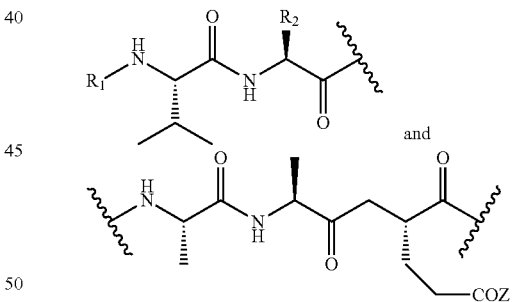

are divalent structures and can be bonded within the backbone of Formula (C1) or as depicted in Formula (C2). The structure

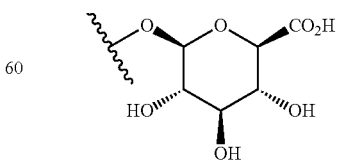

is monovalent and can be bonded to EG as depicted in formula (C1) above.

2.4 Hydrophilic Groups

Hydrophilic groups facilitate increasing the hydrophilicity of the compounds described herein. It is believed that increased hydrophilicity allows for greater solubility in aqueous solutions, such as aqueous solutions found in biological systems. Hydrophilic groups can also function as spacer groups, which are described in further detail herein.

In certain embodiments, the hydrophilic group is designated HP herein. Useful hydrophilic groups include those described herein. In certain embodiments, the hydrophilic group is a divalent poly(ethylene glycol). In certain embodiments, the hydrophilic group is a divalent poly(ethylene glycol) according to the formula:

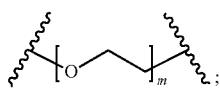

wherein m is an integer from 1 to 13, optionally 1 to 4, optionally 2 to 4, or optionally 4 to 8.

In some embodiments, the hydrophilic group is a divalent poly(ethylene glycol) according to the following formula:

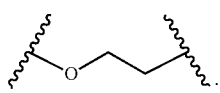 [SMILES: *CCO*]

In some other embodiments, the hydrophilic group is a divalent poly(ethylene glycol) according to the following formula:

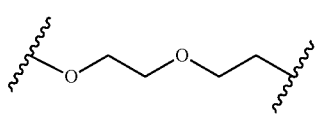

In other embodiments, the hydrophilic group is a divalent poly(ethylene glycol) according to the following formula:

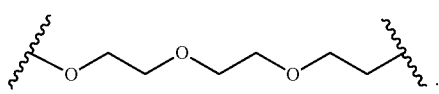

In other embodiments, the hydrophilic group is a divalent poly(ethylene glycol) according to the following formula:

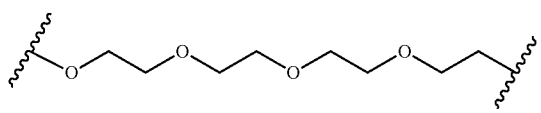

In some embodiments, the hydrophilic group can bear a chain-presented sulfonic acid according to the formula:

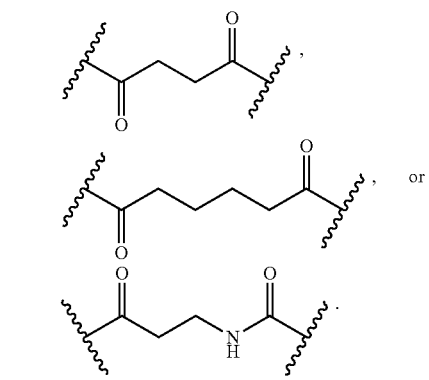

2.5 Spacer Groups

Spacer groups facilitate spacing of the conjugating group from the other groups of the compounds described herein. This spacing can lead to more efficient conjugation of the compounds described herein to a second compound as well as more efficient cleavage of the active catabolite. The spacer group can also stabilize the conjugating group and lead to improved overall antibody-drug conjugate properties.

In certain embodiments, the spacer group is designated SG herein. Useful spacer groups include those described herein. In certain embodiments, the spacer group is:

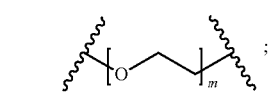

In certain embodiments, the spacer group, $W^4$, and the hydrophilic group combine to form a divalent poly(ethylene glycol) according to the formula:

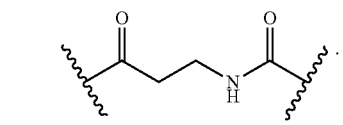

wherein m is an integer from 1 to 13, optionally 1 to 4, optionally 2 to 4, or optionally 4 to 8.

In some embodiments, the SG is

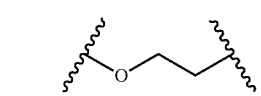

In some embodiments, the divalent poly(ethylene glycol) has the following formula:

In some other embodiments, the divalent poly(ethylene glycol) has the following formula:

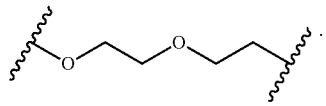 [SMILES: *CCOCCO*]

In other embodiments, the divalent poly(ethylene glycol) has the following formula:

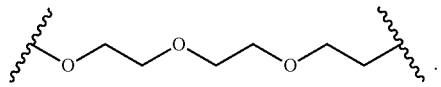 [SMILES: *CCOCCOCCO*]

In other embodiments, the divalent poly(ethylene glycol) has the following formula:

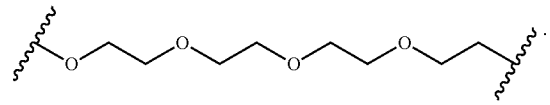 [SMILES: *CCOCCOCCOCCO*]

In some embodiments, the hydrophilic group can bear a chain-presented sulfonic acid according to the formula:

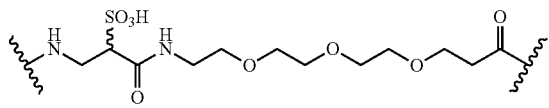

2.6 Conjugating Groups and Residues Thereof

Conjugating groups facilitate conjugation of the payloads described herein to a second compound, such as an antibody described herein. In certain embodiments, the conjugating group is designated R herein. Conjugating groups can react via any suitable reaction mechanism known to those of skill in the art. In certain embodiments, a conjugating group reacts through a [3+2] alkyne-azide cycloaddition reaction, inverse-electron demand Diels-Alder ligation reaction, thiol-electrophile reaction, or carbonyl-oxyamine reaction, as described in detail herein. In certain embodiments, the conjugating group comprises an alkyne, strained alkyne, tetrazine, thiol, para-acetyl-phenylalanine residue, oxyamine, maleimide, or azide. In certain embodiments, the conjugating group is:

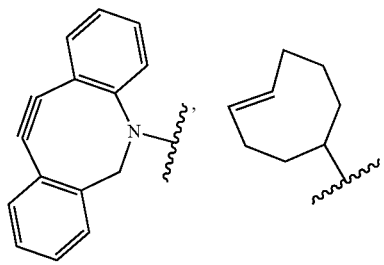

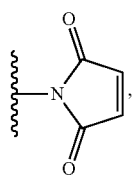
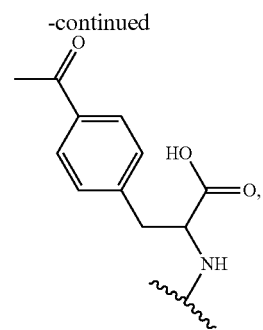

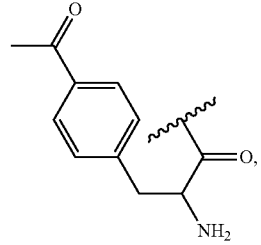
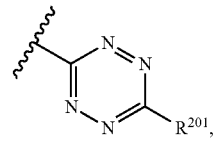

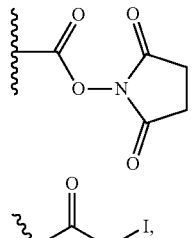
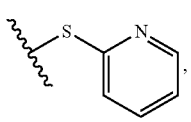

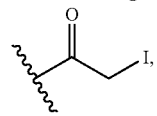 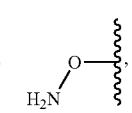 —N₃, or —SH;

wherein $R^{201}$ is lower alkyl. In an embodiment, $R^{201}$ is methyl, ethyl, or propyl. In an embodiment, $R^{201}$ is methyl. Additional conjugating groups are described in, for example, U.S. Patent Publication No. 2014/0356385, U.S. Patent Publication No. 2013/0189287, U.S. Patent Publication No. 2013/0251783, U.S. Pat. Nos. 8,703,936, 9,145,361, 9,222,940, and 8,431,558.

After conjugation, a divalent residue of the conjugating group is formed and is bonded to the residue of a second compound. The structure of the divalent residue is determined by the type of conjugation reaction employed to form the conjugate.

In certain embodiments when a conjugate is formed through a [3+2] alkyne-azide cycloaddition reaction, the divalent residue of the conjugating group comprises a triazole ring or fused cyclic group comprising a triazole ring. In certain embodiment when a conjugate is formed through a strain-promoted [3+2] alkyne-azide cycloaddition (SPAAC) reaction, the divalent residue of the conjugating group is:

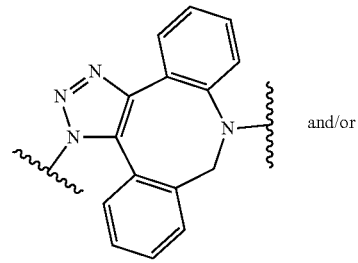 and/or

-continued

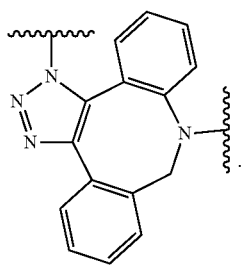

In certain embodiments when a conjugate is formed through a tetrazine inverse electron demand Diels-Alder ligation reaction, the divalent residue of the conjugating group comprises a fused bicyclic ring having at least two adjacent nitrogen atoms in the ring. In certain embodiments when a conjugate is formed through a tetrazine inverse electron demand Diels-Alder ligation reaction, the divalent residue of the conjugating group is:

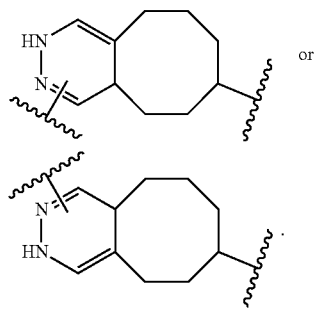

In certain embodiments when a conjugate is formed through a thiol-maleimide reaction, the divalent residue of the conjugating group comprises succinimidylene and a sulfur linkage. In certain embodiments when a conjugate is formed through a thiol-maleimide reaction, the divalent residue of the conjugating group is:

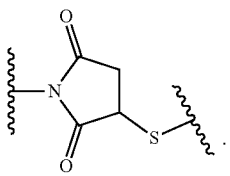 [SMILES: *SC1CC(=O)N(*)C1=O]

In certain embodiments, a conjugate is formed through a thiol-N-hydroxysuccinimide reaction using the following group:

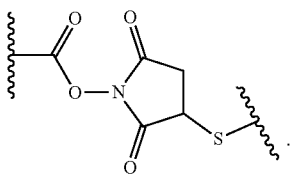 [SMILES: *SC1CC(=O)N(OC(*)=O)C1=O]

The reaction involved for formation of the conjugate comprises the following step:

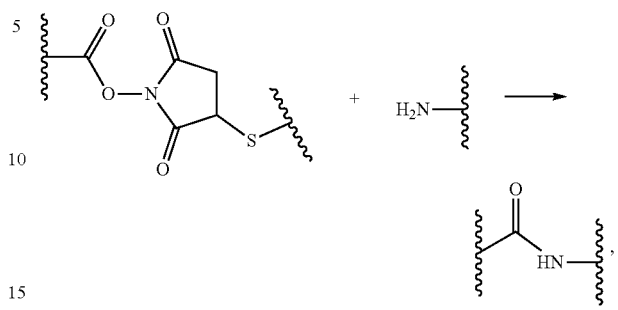

and the resulting divalent residue of the conjugating group is:

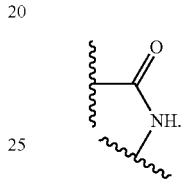

In certain embodiments when a conjugate is formed through a carbonyl-oxyamine reaction, the divalent residue of the conjugating group comprises a divalent residue of a non-natural amino acid. In certain embodiments when a conjugate is formed through a carbonyl-oxyamine reaction, the divalent residue of the conjugating group is:

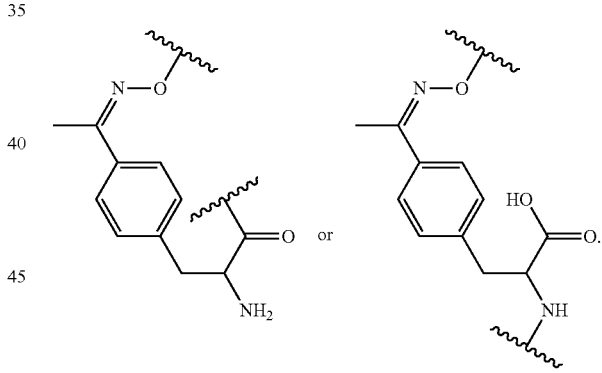

In certain embodiments when a conjugate is formed through a carbonyl-oxyamine reaction, the divalent residue of the conjugating group comprises an oxime linkage. In certain embodiments when a conjugate is formed through a carbonyl-oxyamine reaction, the divalent residue of the conjugating group is:

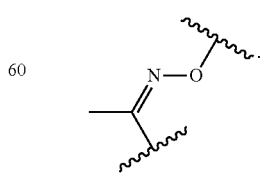

In some embodiment, provided herein is a conjugate according to Formula (C1) or (C2) or a pharmaceutically acceptable salt, solvate, stereoisomer, or tautomer thereof; wherein EG comprises phenylene, carboxylene, amine, or a combination thereof. In an embodiment, provided herein is a conjugate according to Formula (C1) or (C2), or a pharmaceutically acceptable salt, solvate, stereoisomer, or tautomer thereof; wherein EG is:

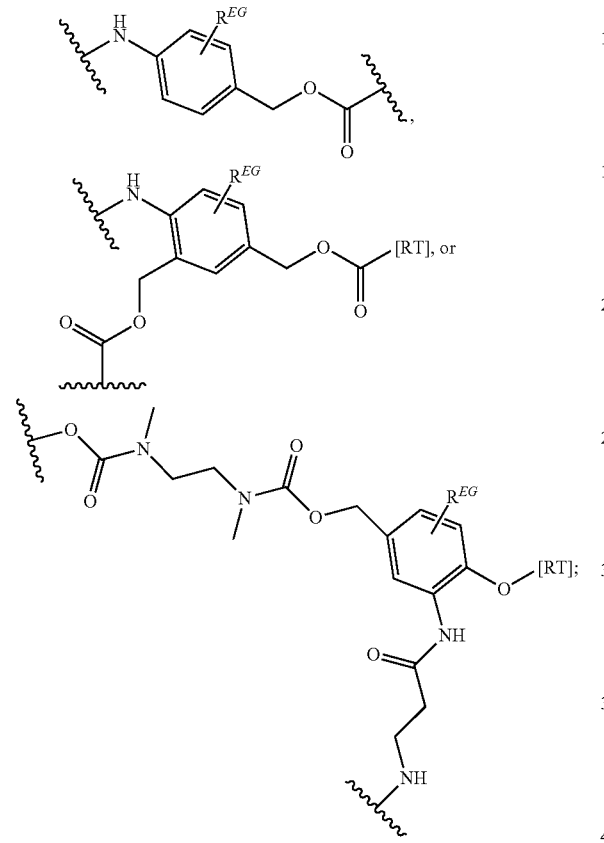

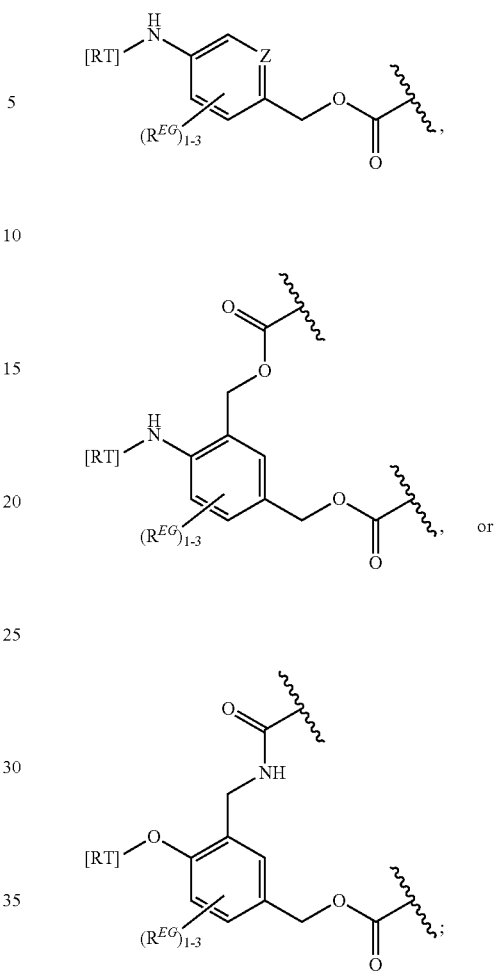

wherein each $R^{EG}$ is independently selected from the group consisting of hydrogen, alkyl, biphenyl, —CF$_3$, —NO$_2$, —CN, fluoro, bromo, chloro, alkoxyl, alkylamino, dialkylamino, alkyl-C(O)O—, alkylamino-C(O)— and dialkylamino-C(O)—. In each structure, the phenyl ring can be bound to one, two, three, or in some cases, four $R^{EG}$ groups. In the second and third structures, those of skill will recognize that EG is bonded to an RT that is not within the backbone of Formula C1 as indicated in the above description of Formula C1. In some embodiments, each $R^{EG}$ is independently selected from the group consisting of hydrogen, alkyl, biphenyl, —CF$_3$, alkoxyl, alkylamino, dialkylamino, alkyl-C(O)O—, alkylamino-C(O)— and dialkylamino-C(O)—. In further embodiments, each $R^{EG}$ is independently selected from the group consisting of hydrogen, —NO$_2$, —CN, fluoro, bromo, and chloro.

In some embodiments, provided herein is a conjugate according to Formula (C1) or (C2) or a pharmaceutically acceptable salt, solvate, stereoisomer, or tautomer thereof; wherein EG comprises phenylene, carboxylene, amine, or a combination thereof. In an embodiment, provided herein is a conjugate according to Formula (C1) or (C2), or a pharmaceutically acceptable salt, solvate, stereoisomer, or tautomer thereof; wherein EG is:

wherein Z may be CH or N, each $R^{EG}$ is independently selected from the group consisting of hydrogen, alkyl, biphenyl, —CF$_3$, —NO$_2$, —CN, fluoro, bromo, chloro, alkoxyl, alkylamino, dialkylamino, alkyl-C(O)O—, alkylamino-C(O)— and dialkylamino-C(O)—. In each structure, the phenyl ring can be bound to one, two, three, or in some cases, four $R^{EG}$ groups. In the second and third structures, those of skill will recognize that EG is bonded to an RT that is not within the backbone of Formula C1 as indicated in the above description of Formula C1. In some embodiments, each $R^{EG}$ is independently selected from the group consisting of hydrogen, alkyl, biphenyl, —CF$_3$, alkoxyl, alkylamino, dialkylamino, alkyl-C(O)O—, alkylamino-C(O)— and dialkylamino-C(O)—. In further embodiments, each $R^{EG}$ is independently selected from the group consisting of hydrogen, —NO$_2$, —CN, fluoro, bromo, and chloro. In some embodiments, each $R^{EG}$ in the EG is hydrogen.

In some embodiments, provided herein is a conjugate according to Formula (C1) or (C2), or a pharmaceutically acceptable salt, solvate, stereoisomer, or tautomer thereof, wherein RT comprises a residue of a natural or non-natural amino acid or a residue of a sugar. In an embodiment, provided herein is a conjugate according to Formula (C1) or (C2), or a pharmaceutically acceptable salt, solvate, stereoisomer, or tautomer thereof; wherein RT is:

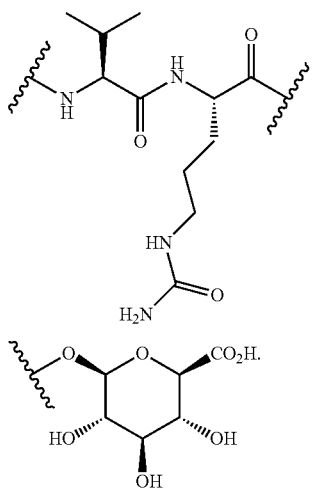

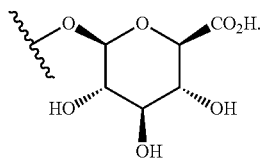

Those of skill will recognize that the first structure is divalent and can be bonded within the backbone as depicted in Formula (C2), and that the second structure is monovalent and can be bonded to EG as depicted in Formula (C1) above.

In some embodiments, provided herein is a conjugate according to Formula (C1) or (C2), or a pharmaceutically acceptable salt, solvate, stereoisomer, or tautomer thereof, wherein RT comprises a residue of a natural or non-natural amino acid or a residue of a sugar. In an embodiment, provided herein is a conjugate according to Formula (C1) or (C2), or a pharmaceutically acceptable salt, solvate, stereoisomer, or tautomer thereof; wherein RT is:

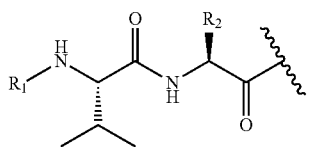

wherein $R_1$ is a bond to the rest of the compound or

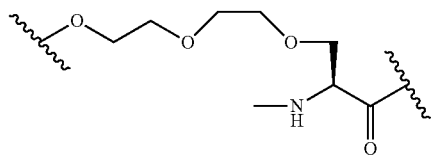 [SMILES: *OCCOCCOC[C@H](NC)C(*)=O]

and $R_2$ is —$CH_3$, —$CH_2CH_2CO_2H$, or —$(CH_2)_3$ $NHCONH_2$; a legumain-cleavable Ala-Ala-Asn (AAN) or Ala-Ala-Asp (AAD) peptide according to the structure of:

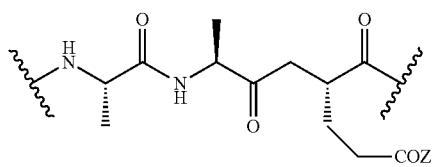

where Z is OH or $NH_2$; or a β-glucuronidase-cleavable β-glucuronide according to the structure of:

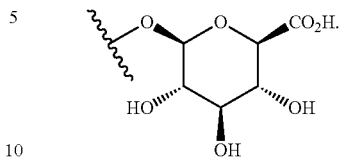

Those of skill will recognize that

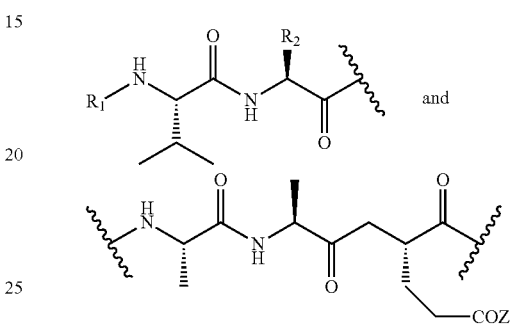

are divalent structures and can be bonded within the backbone of Formula (C1) or as depicted in Formula (C2). The structure

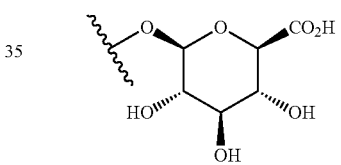

is monovalent and can be bonded to EG as depicted in formula (C1) above.

In an embodiment, provided herein is a conjugate according to Formula (C1) or (C2), or a pharmaceutically acceptable salt, solvate, stereoisomer, or tautomer thereof; wherein HP comprises poly(ethylene glycol). In an embodiment, provided herein is a conjugate according to Formula (C1) or (C2), or a pharmaceutically acceptable salt, solvate, stereoisomer, or tautomer thereof; wherein HP is:

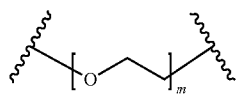

wherein m is an integer selected from 1 to 13.

In an embodiment, provided herein is a conjugate according to Formula (C1) or (C2), or a pharmaceutically acceptable salt, solvate, stereoisomer, or tautomer thereof; wherein SG comprises $C_1$-$C_{10}$ alkylene, $C_4$-$C_6$ alkylene, carbonylene, or combination thereof. In an embodiment, provided herein is a conjugate according to Formula (C1) or (C2), or a pharmaceutically acceptable salt, solvate, stereoisomer, or tautomer thereof; wherein SG is:

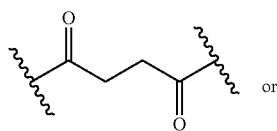 or

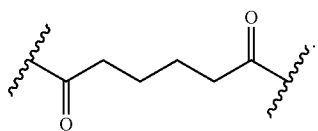

In an embodiment, provided herein is a conjugate according to Formula (C1) or (C2), or a pharmaceutically acceptable salt, solvate, stereoisomer, or tautomer thereof; wherein $W^1$, $W^2$, $W^3$, $W^4$, and $W^5$ are each independently a single bond, absent, or comprise a divalent ketone, divalent ester, divalent ether, divalent amide, divalent amine, alkylene, arylene, sulfide, disulfide, carbonylene, or a combination thereof. In an embodiment, provided herein is a conjugate according to Formula (C1) or (C2), or a pharmaceutically acceptable salt, solvate, stereoisomer, or tautomer thereof; wherein $W^1$, $W^2$, $W^3$, $W^4$, and $W^5$ are each independently a single bond, absent, or comprise —C(O)—, —O—, —C(O)NH—, —C(O)NH-alkyl-, —OC(O)NH—, —SC(O)NH—, —NH—, —NH-alkyl-, —C(O)N(CH$_3$)—, —C(O)N(CH$_3$)-alkyl-, —N(CH$_3$)—, —N(CH$_3$)-alkyl-, —N(CH$_3$)CH$_2$CH$_2$N(CH$_3$)—, —C(O)CH$_2$CH$_2$CH$_2$C(O)—, —S—, —S—S—, —OCH$_2$CH$_2$O—, or the reverse (e.g. —NHC(O)—) thereof, or a combination thereof.

In an embodiment, provided herein is a conjugate according to Formula (C1) or (C2), or a pharmaceutically acceptable salt, solvate, stereoisomer, or tautomer thereof; wherein R' comprises a triazolyl ring. In an embodiment, provided herein is a conjugate according to Formula (C1) or (C2), or a pharmaceutically acceptable salt, solvate, stereoisomer, or tautomer thereof; wherein R' is a triazolyl ring or fused cyclic group comprising a triazole ring. In an embodiment, provided herein is a conjugate according to Formula (C1) or (C2), or a pharmaceutically acceptable salt, solvate, stereoisomer, or tautomer thereof, wherein R' is:

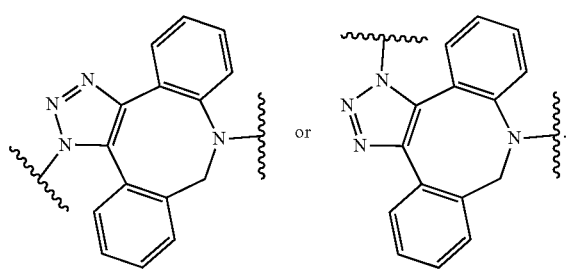 [SMILES: *N1Cc2ccccc2-c2c(nnn2*)-c2ccccc21 ; *N1Cc2ccccc2-c2nnn(*)c2-c2ccccc21]

In an embodiment, provided herein is a conjugate according to Formula (C1) or (C2), or a pharmaceutically acceptable salt, solvate, stereoisomer, or tautomer thereof; wherein R' comprises a fused bicyclic ring having at least two adjacent nitrogen atoms in the ring. In an embodiment, provided herein is a conjugate according to Formula (C1) or (C2), or a pharmaceutically acceptable salt, solvate, stereoisomer, or tautomer thereof; wherein R' is:

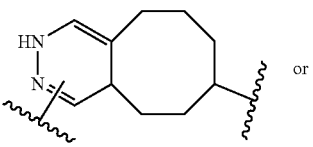 or

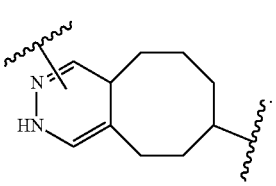

In an embodiment, provided herein is a conjugate according to Formula (C1) or (C2), or a pharmaceutically acceptable salt, solvate, stereoisomer, or tautomer thereof; wherein R' comprises a sulfur linkage. In an embodiment, provided herein is a conjugate according to Formula (C1) or (C2), or a pharmaceutically acceptable salt, solvate, stereoisomer, or tautomer thereof; wherein R' is:

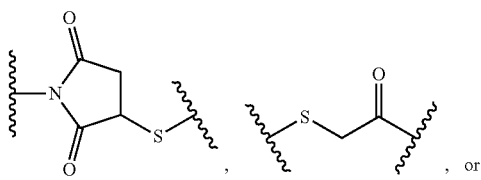, or

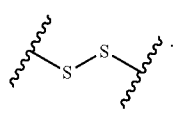.

In an embodiment, provided herein is a conjugate according to Formula (C1) or (C2), or a pharmaceutically acceptable salt, solvate, stereoisomer, or tautomer thereof; wherein R' comprises a divalent residue of a non-natural amino acid. In an embodiment, provided herein is a conjugate according to Formula (C1) or (C2), or a pharmaceutically acceptable salt, solvate, stereoisomer, or tautomer thereof; wherein R' is:

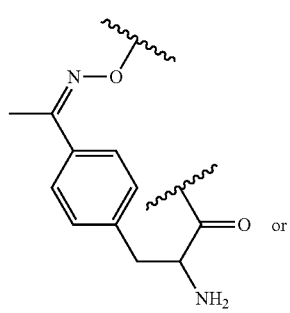 or

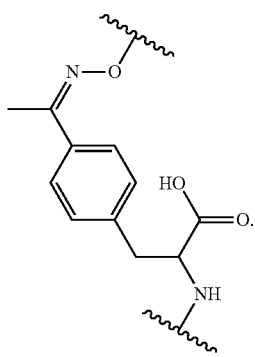

In an embodiment, provided herein is a conjugate according to Formula (C1) or (C2), or a pharmaceutically acceptable salt, solvate, stereoisomer, or tautomer thereof; wherein comprises an oxime linkage. In an embodiment, provided herein is a conjugate according to Formula (C1) or (C2), or a pharmaceutically acceptable salt, solvate, stereoisomer, or tautomer thereof; wherein R' is:

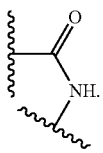

In an embodiment, provided herein is a conjugate according to Formula (C1) or (C2), or a pharmaceutically acceptable salt, solvate, stereoisomer, or tautomer thereof; wherein comprises an oxime linkage. In an embodiment, provided herein is a conjugate according to Formula (C1) or (C2), or a pharmaceutically acceptable salt, solvate, stereoisomer, or tautomer thereof; wherein R' is:

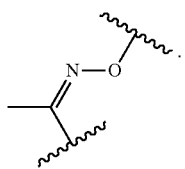 [SMILES: *O/N=C(\*)C]

In an embodiment, provided herein is a conjugate according to Formula (C1) or (C2), or a pharmaceutically acceptable salt, solvate, stereoisomer, or tautomer thereof; wherein R' is:

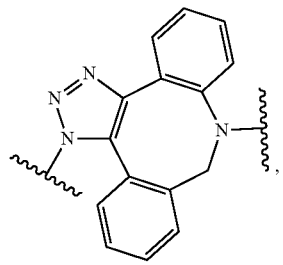

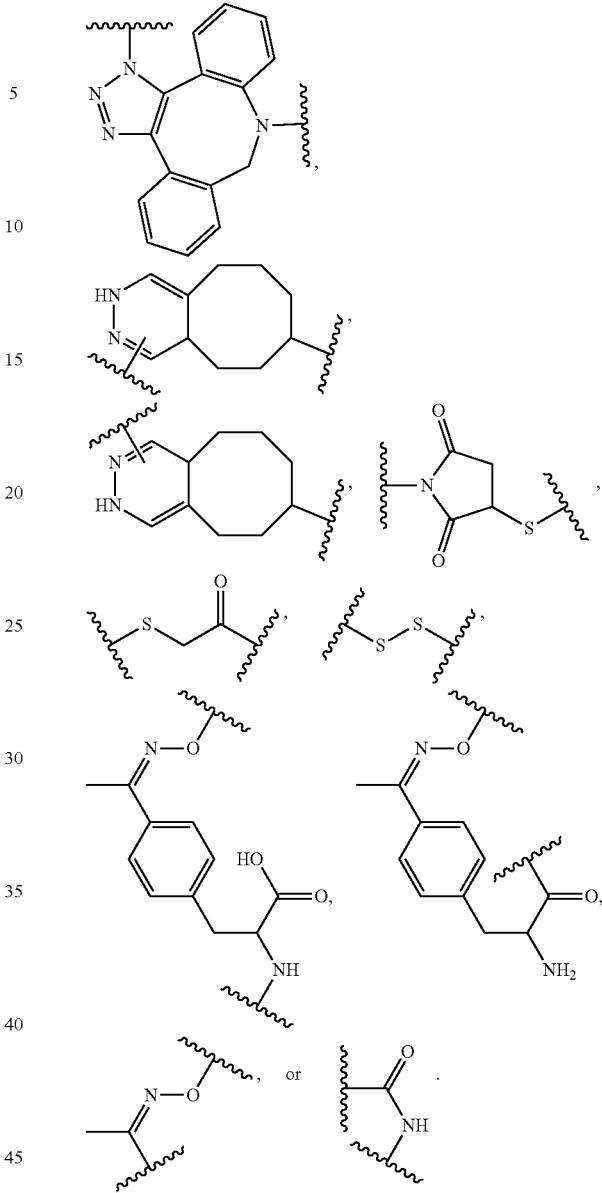

In an embodiment, provided herein is a compound according to Formula (C1) or (C2), or a pharmaceutically acceptable salt, solvate, stereoisomer, or tautomer thereof; wherein Ab is a residue of any compound known to be useful for conjugation to a payload, described herein, and an optional linker, described herein. In an embodiment, provided herein is a compound according to Formula (C1) or (C2), or a pharmaceutically acceptable salt, solvate, stereoisomer, or tautomer thereof; wherein Ab is a residue of an antibody chain, or an antigen binding fragment thereof.

In an aspect, provided herein is an antibody conjugate comprising payloads, described herein, and optional linkers, described herein, linked to an antibody, wherein Ab is a residue of the antibody. In an embodiment, provided herein is an antibody conjugate according to Formula (C1) or (C2), or a pharmaceutically acceptable salt, solvate, stereoisomer, or tautomer thereof, wherein: Ab is a residue of the antibody; and R' comprises a triazole ring or fused cyclic group comprising a triazole ring. In an embodiment, provided herein is an antibody conjugate according to Formula (C1) or (C2), or a pharmaceutically acceptable salt, solvate, stereoisomer, or tautomer thereof, wherein: Ab is a residue of the antibody; and R' is:

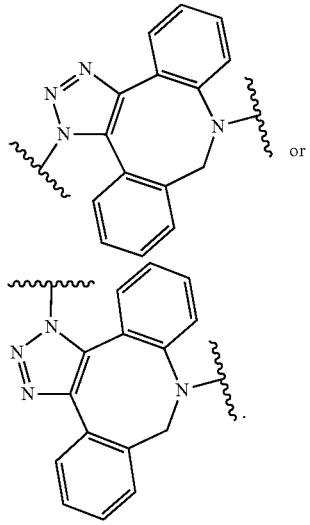

In an embodiment, provided herein is an antibody conjugate according to Formula (C1) or (C2), or a pharmaceutically acceptable salt, solvate, stereoisomer, or tautomer thereof, wherein: Ab is a residue of the antibody or an antigen binding fragment thereof; and R' comprises a fused bicyclic ring, wherein the fused bicyclic ring has at least two adjacent nitrogen atoms in the ring. In an embodiment, provided herein is an antibody conjugate according to Formula (C1) or (C2), or a pharmaceutically acceptable salt, solvate, stereoisomer, or tautomer thereof, wherein: Ab is a residue of the antibody or an antigen binding fragment thereof; and R' is:

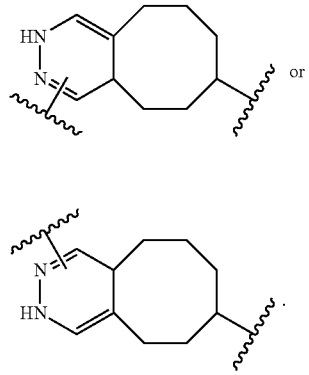

In an embodiment, provided herein is an antibody conjugate according to Formula (C1) or (C2), or a pharmaceutically acceptable salt, solvate, stereoisomer, or tautomer thereof, wherein: Ab is a residue of the polypeptide; and R' comprises a sulfur linkage. In an embodiment, provided herein is an antibody conjugate according to Formula (C1) or (C2), or a pharmaceutically acceptable salt, solvate, stereoisomer, or tautomer thereof, wherein: Ab is a residue of the polypeptide; and R' is:

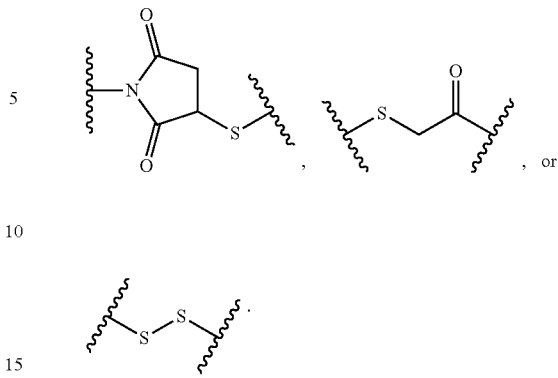

In an embodiment, provided herein is an antibody conjugate according to Formula (C1) or (C2), or a pharmaceutically acceptable salt, solvate, stereoisomer, or tautomer thereof, wherein: Ab is a residue of the polypeptide; and R' comprises a divalent residue of a non-natural amino acid. In an embodiment, provided herein is an antibody conjugate according to Formula (C1) or (C2), or a pharmaceutically acceptable salt, solvate, stereoisomer, or tautomer thereof, wherein: Ab is a residue of the polypeptide; and R' is:

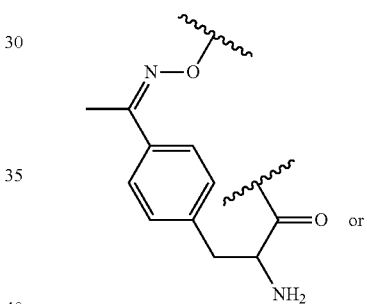

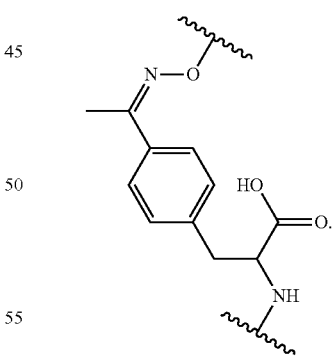

In an embodiment, provided herein is an antibody conjugate according to Formula (C1) or (C2), or a pharmaceutically acceptable salt, solvate, stereoisomer, or tautomer thereof, wherein: Ab is a residue of the polypeptide; and R' comprises an oxime linkage. In an embodiment, provided herein is an antibody conjugate according to Formula (C1) or (C2), or a pharmaceutically acceptable salt, solvate, stereoisomer, or tautomer thereof, wherein: Ab is a residue of the polypeptide; and R' is:

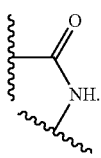

In an embodiment, provided herein is an antibody conjugate according to Formula (C1) or (C2), or a pharmaceutically acceptable salt, solvate, stereoisomer, or tautomer thereof, wherein: Ab is a residue of the polypeptide; and R' comprises an oxime linkage. In an embodiment, provided herein is an antibody conjugate according to Formula (C1) or (C2), or a pharmaceutically acceptable salt, solvate, stereoisomer, or tautomer thereof, wherein: Ab is a residue of the polypeptide; and R' is:

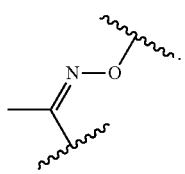 [SMILES: *O/N=C(\*)C]

A linker linked to a drug compound (e.g., cytotoxic drug) is L-PA herein. Subsequently, a L-PA is conjugated to an antibody construct, such as an antibody or an antibody chain, or an antigen binding fragment thereof, to form an antibody conjugate to PA. A linker linked to an immune-modulatory compound is L-IM herein. A L-IM is conjugated to an antibody construct, such as an antibody or an antibody chain, or an antigen binding fragment thereof, to form an antibody conjugate to IM.

In an embodiment, provided herein is a conjugate according to any of the following formulas, where Ab indicates a residue of the antibody or an antigen binding fragment thereof, PA indicates a drug payload moiety, IM indicates an immunomodulator (e.g., immunostimulator) moiety, and regioisomers thereof. Those of skill will recognize that Ab can bind at more than one position. Each regioisomer and mixtures thereof are provided in the formulae below, wherein

indicates a bond to the linker-immunomodulator. Those of skill in the art will recognize that the linkers in the formulae depicted for L-PA can also be linkers in the moiety L-IM. Those of skill in the art will recognize that the linker in L-PA may be the same or different from the linker in L-IM, and further, the moiety L-IM in each of the formulas may also comprise regioisomers.

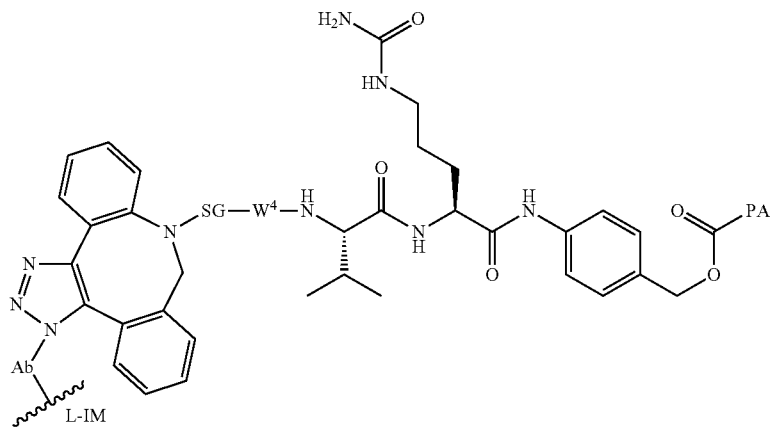

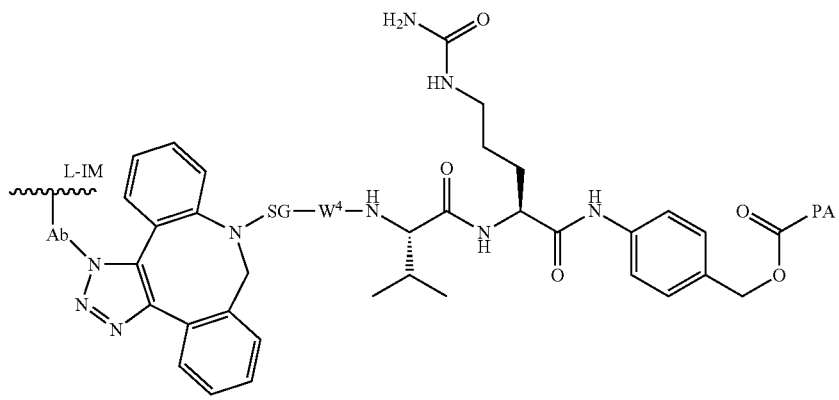

-continued
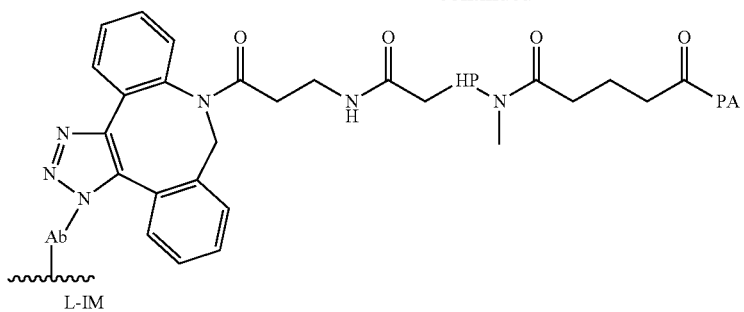
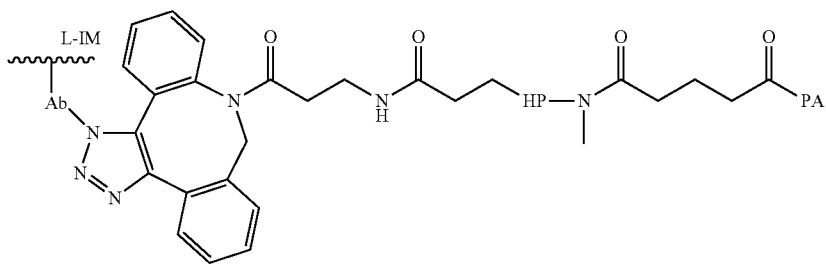
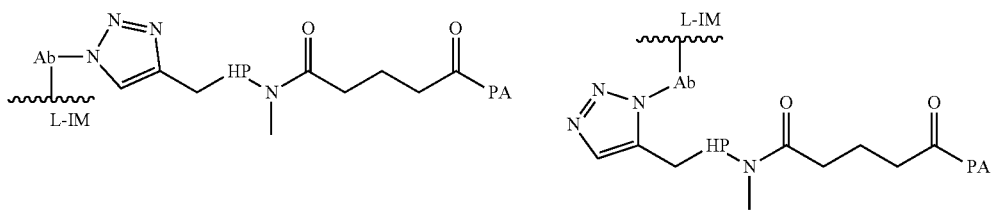
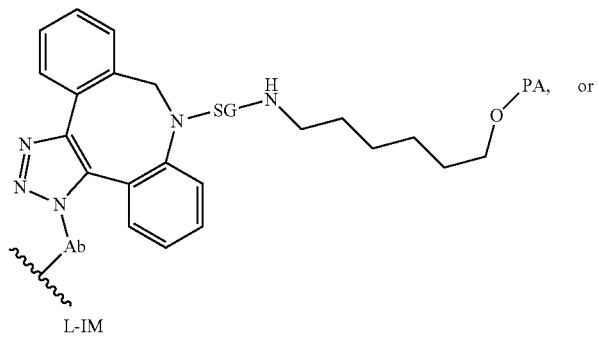
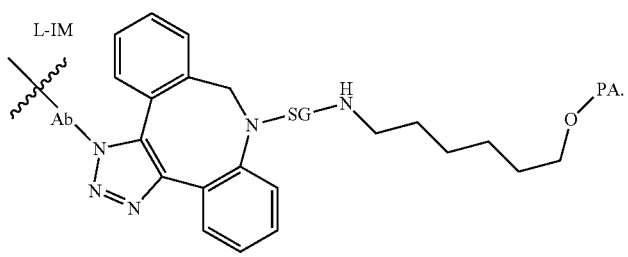

In an embodiment, provided herein is a conjugate according to any of the following formulas, where Ab indicates a residue of the antibody and PA indicates a payload moiety, IM indicates an immunomodulator moiety, and regioisomers thereof. Each

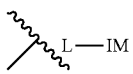

regioisomer and mixtures thereof are provided in the formulae below, wherein indicates a bond to the linker-immunomodulator. Those of skill in the art will recognize that the linkers in the formulae depicted for L-PA can also be linkers in the moiety L-IM. Those of skill in the art will recognize that the linker in L-PA may be the same or different from the linker in L-IM, and further, the moiety L-IM in each of the formulas may also comprise regioisomers.

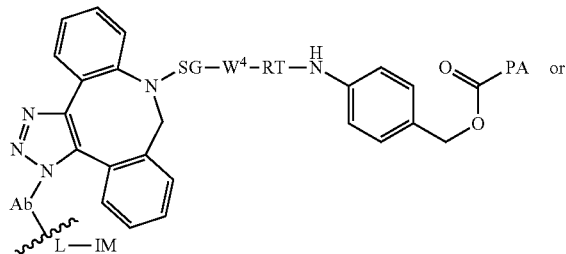

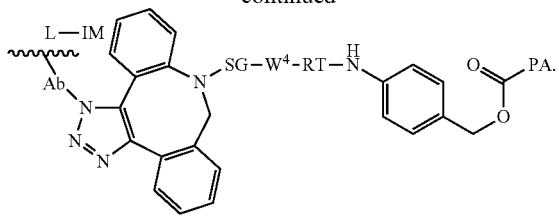

In an embodiment, provided herein is a conjugate according to any of the following formulas, where Ab indicates a residue of the antibody and PA indicates a payload moiety, IM indicates an immunomodulator moiety, and regioisomers thereof. Each

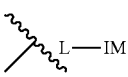

regioisomer and mixtures thereof are provided in the formulae below, wherein L indicates a bond to the linker-immunomodulator. Those of skill in the art will recognize that the linkers in the formulae depicted for L-PA can also be linkers in the moiety L-IM. Those of skill in the art will recognize that the linker in L-PA may be the same or different from the linker in L-IM, and further, the moiety L-IM in each of the formulas may also comprise regioisomers.

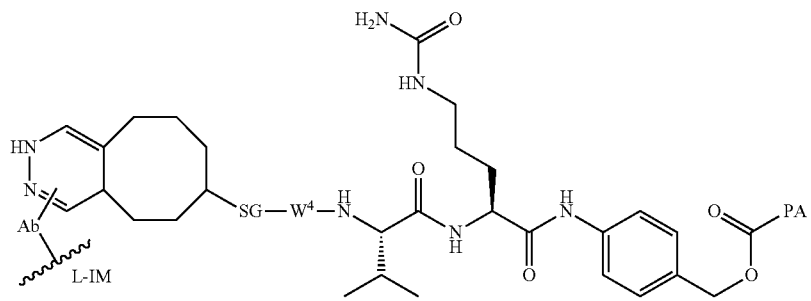

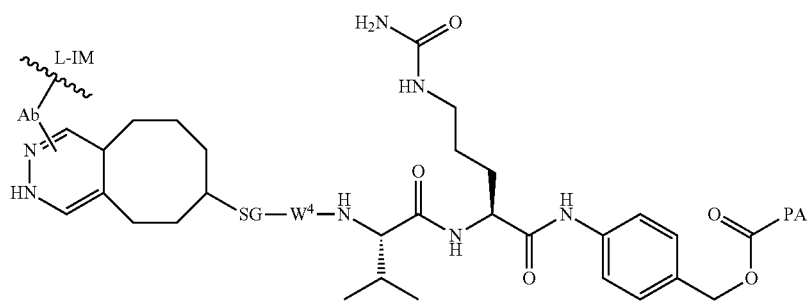

-continued
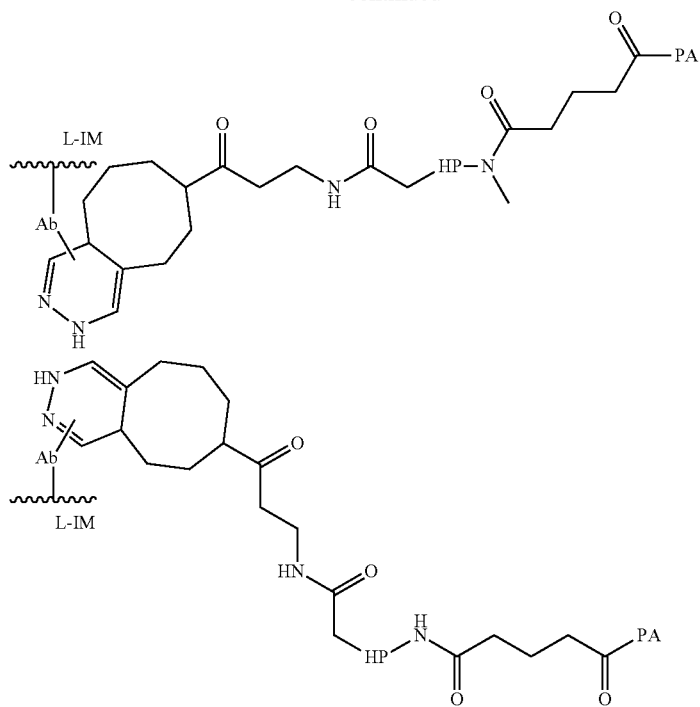
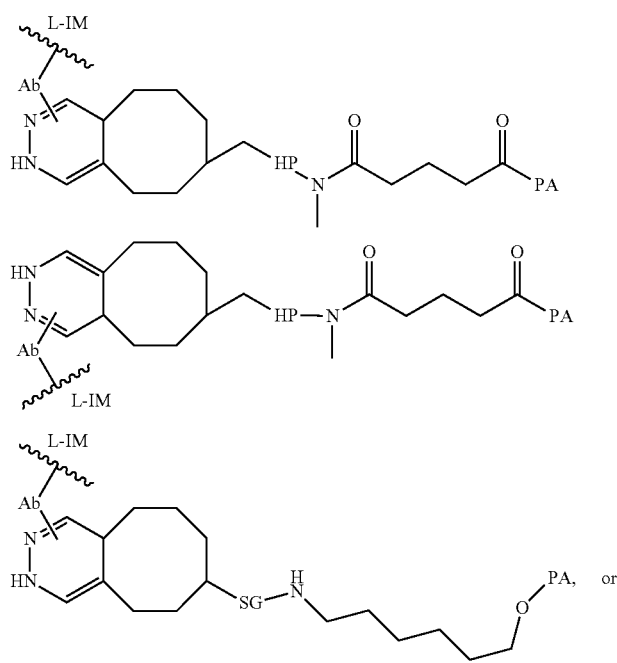
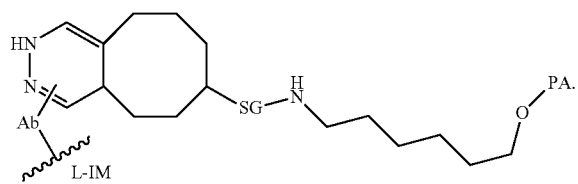

In an embodiment, provided herein is a conjugate according to any of Formulas 101a-107, where Ab indicates a residue of the antibody and PA indicates a payload moiety, IM indicates an immunomodulator moiety, and regioisomers thereof. Each regioisomer and mixtures thereof are provided in the formulae below, wherein

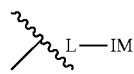

indicates a bond to the linker-immunomodulator. Those of skill in the art will recognize that the linkers in the formulae depicted for L-PA can also be linkers in the moiety L-IM. Those of skill in the art will recognize that the linker in L-PA may be the same or different from the linker in L-IM, and further, the moiety L-IM in each of the formulas above may also comprise regioisomers.

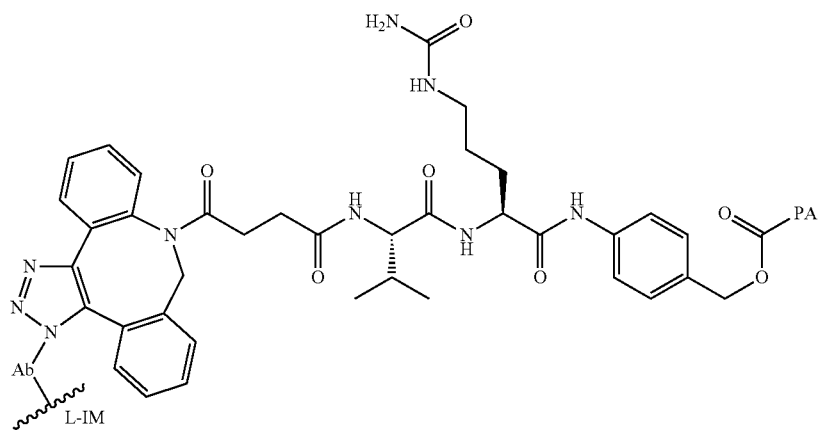

(101a)

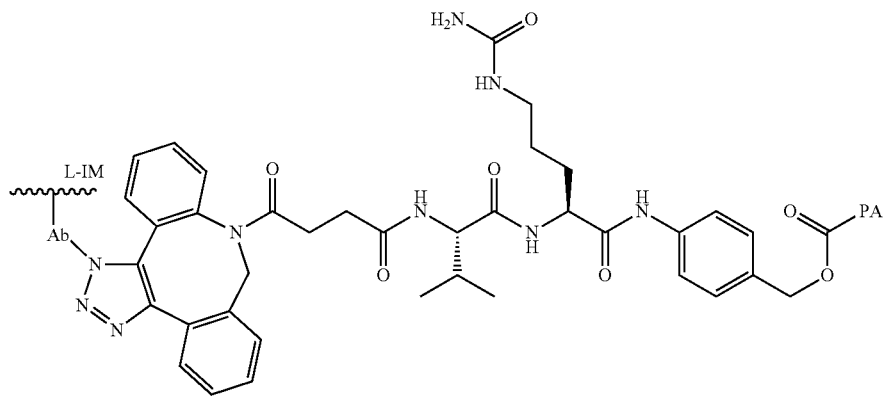

(101b)

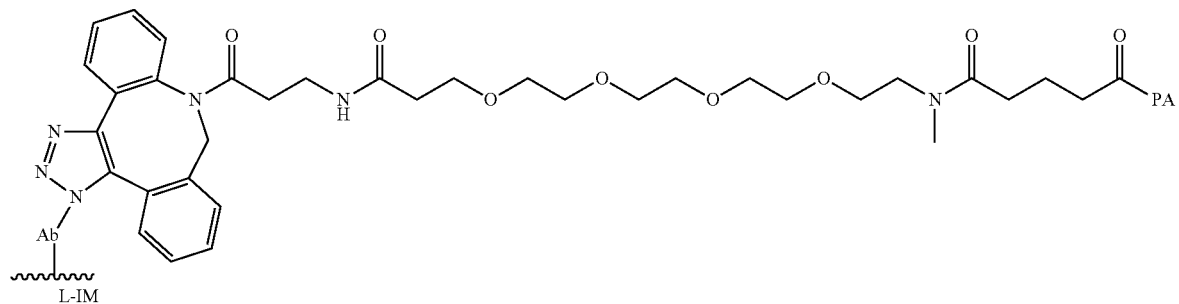

(102a)

-continued
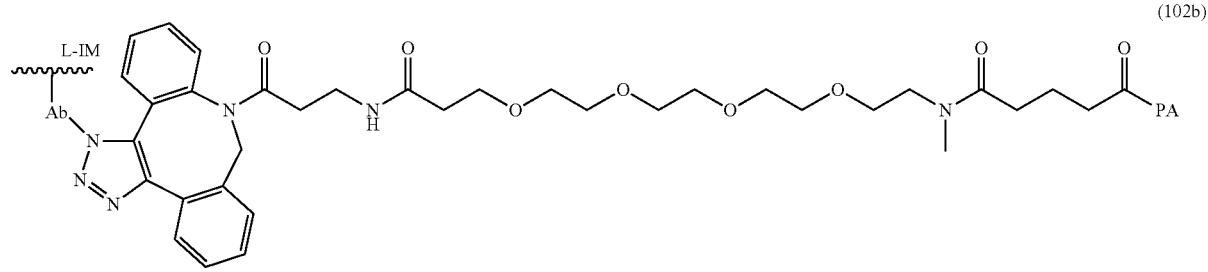
(102b)
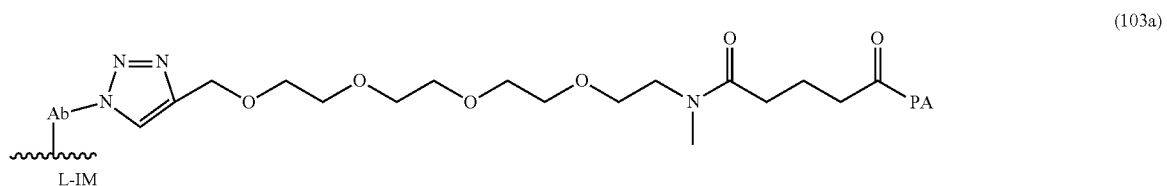
(103a)
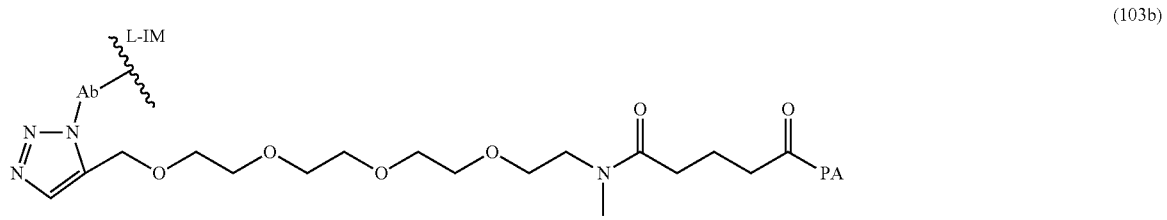
(103b)
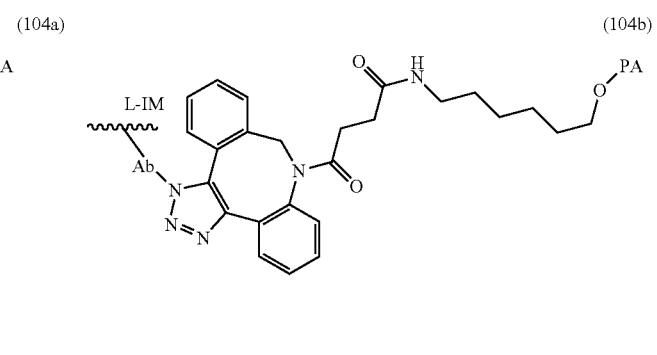
(104a) (104b)
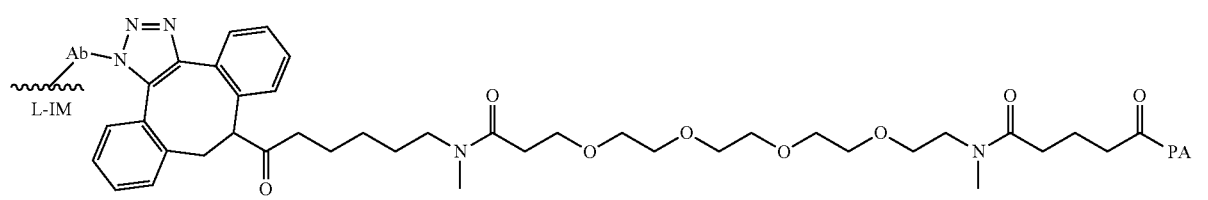
(105a)
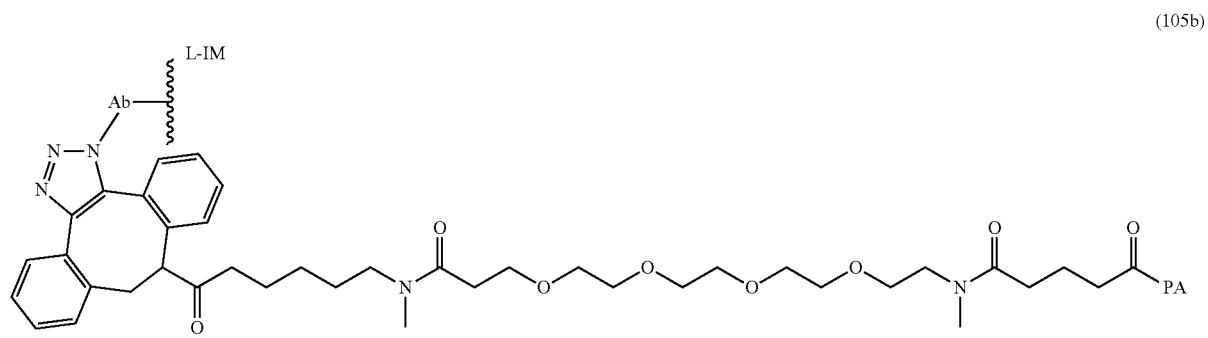
(105b)

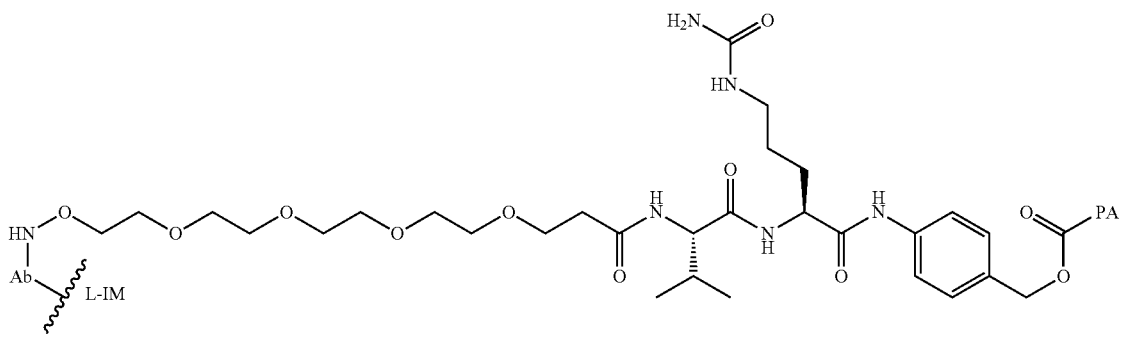

(106)

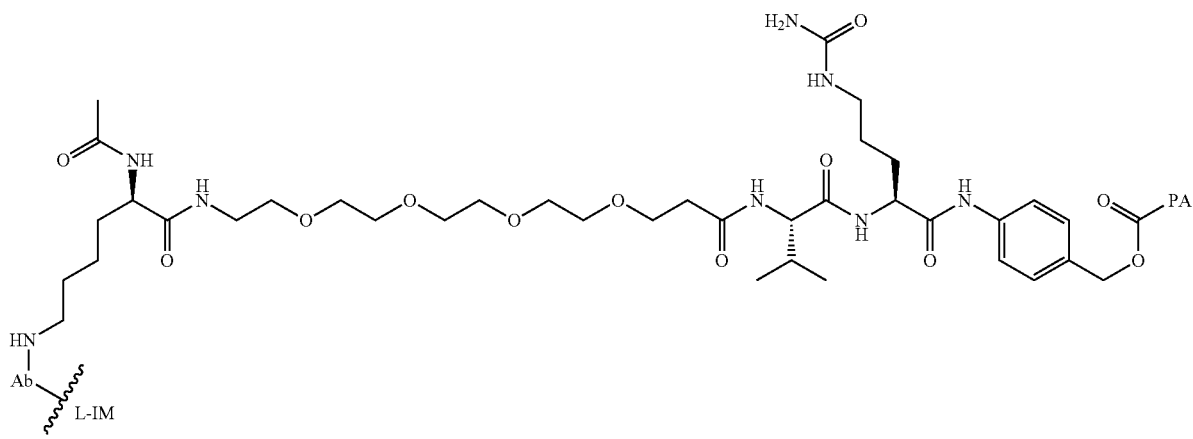

(107)

In any of the foregoing embodiments, the conjugate comprises m number of PA moieties, wherein m is an integer selected from 1 to 8. In some embodiments, m is 2. In some embodiments, m is 3. In some embodiments, m is 4. In some embodiments, m is 5. In some embodiments, m is 6. In some embodiments, m is 7. In some embodiments, m is 8. Those of skill in the art will recognize that Formulas (101a) and (101b) are regioisomers based on the nitrogen atom in the triazole to which the antibody is attached. Similarly, Formulas (102a) and (102b), (103a) and (103b), (104a) and (104b), (105a) and (105b) are pairs of regioisomers. And further, the moiety L-IM in each of the formulas above may also comprise regioisomers. In each of conjugates 101a through 107, the moiety L-IM can be according to any of formulas 201a through 207 below. In certain embodiments, provided herein are each conjugate according to any pairwise combination of one or more of 101a-107 with one or more of 201a-207.

In an embodiment, provided herein is a conjugate according to any of the following formulas, where Ab indicates a residue of the antibody or an antigen binding fragment thereof, PA indicates a drug payload moiety, IM indicates an immunomodulator (e.g., immunostimulator) moiety, and regioisomers thereof. Those of skill will recognize that Ab can bind at more than one position. Each regioisomer and mixtures thereof are provided in the formulae below, wherein

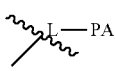

indicates a bond to the linker-payload. Those of skill in the art will recognize that the linkers in the formulae depicted for L-IM can also be linkers in the moiety L-PA. Those of skill in the art will recognize that the linker in L-PA may be the same or different from the linker in L-IM, and further, the moiety L-IM in each of the formulas may also comprise regioisomers.

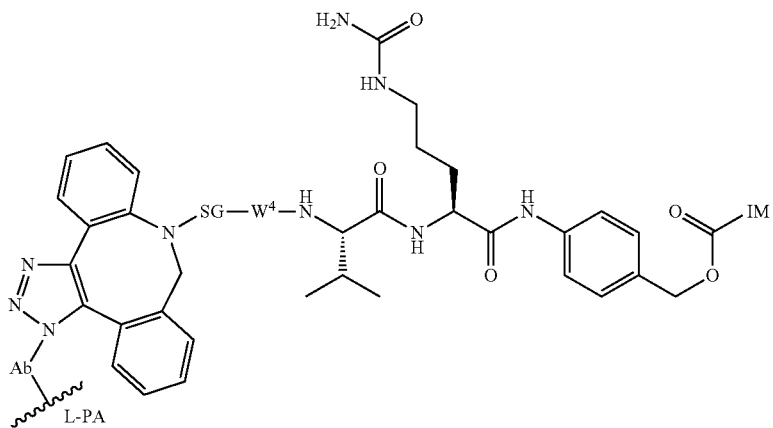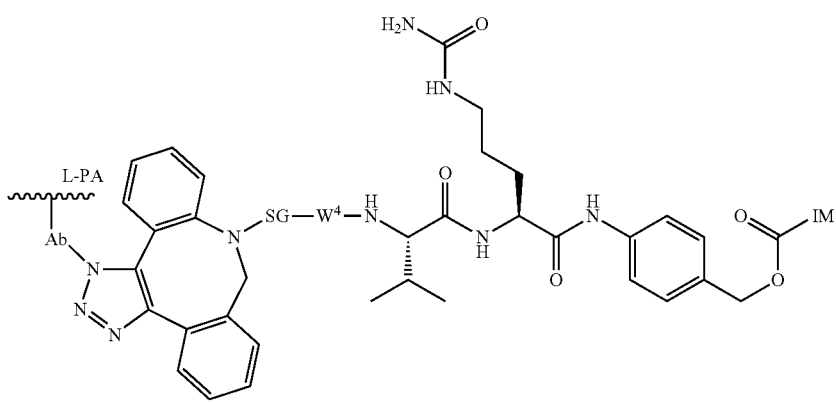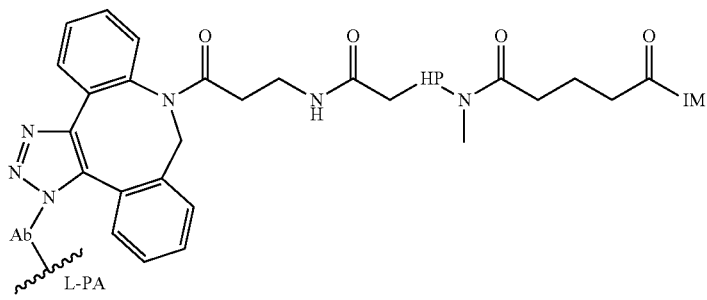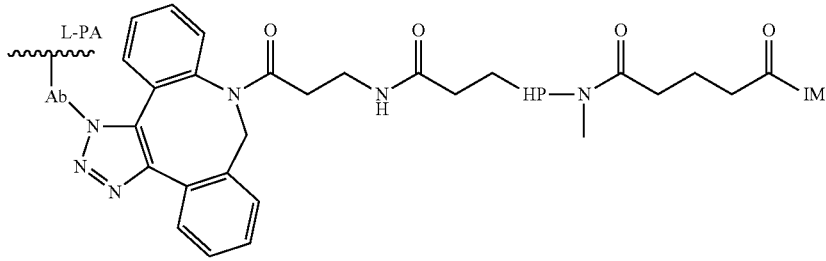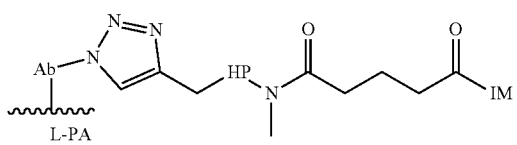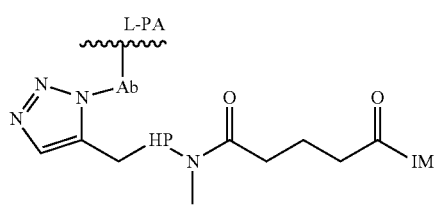

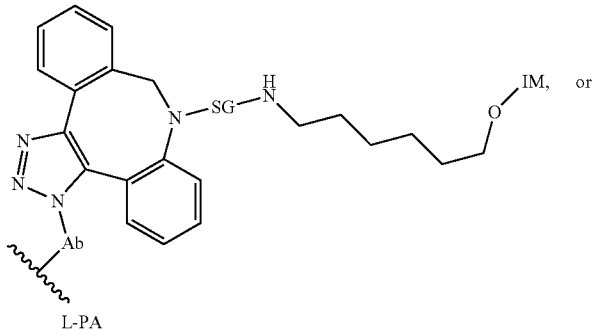

L-PA

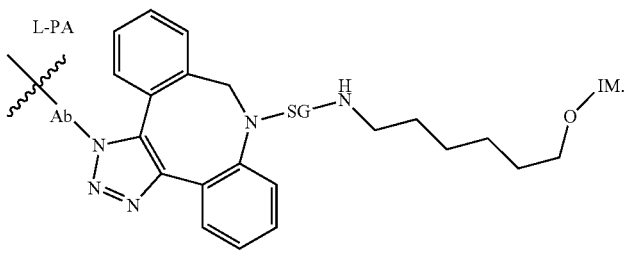

In an embodiment, provided herein is a conjugate according to any of the following formulas, where Ab indicates a residue of the antibody and PA indicates a payload moiety, IM indicates an immunomodulator moiety, and regioisomers thereof. Each regioisomer and mixtures thereof are provided in the formulae below, wherein

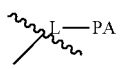

indicates a bond to the linker-immunomodulator. Those of skill in the art will recognize that the linkers in the formulae depicted for L-PA can also be linkers in the moiety L-IM. Those of skill in the art will recognize that the linker in L-PA may be the same or different from the linker in L-IM, and further, the moiety L-IM in each of the formulas may also comprise regioisomers.

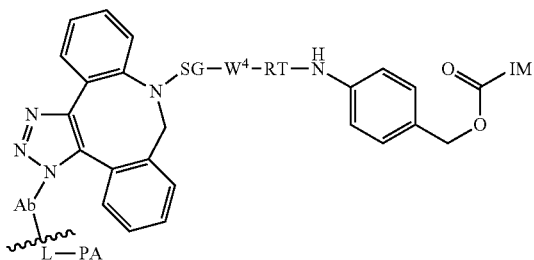

or

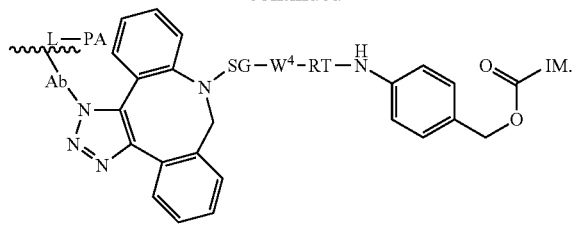

In an embodiment, provided herein is a conjugate according to any of the following formulas, where Ab indicates a residue of the antibody and PA indicates a payload moiety, IM indicates an immunomodulator moiety, and regioisomers thereof. Each regioisomer and mixtures thereof are provided in the formulae below, wherein

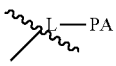

indicates a bond to the linker-immunomodulator. Those of skill in the art will recognize that the linkers in the formulae depicted for L-PA can also be linkers in the moiety L-IM. Those of skill in the art will recognize that the linker in L-PA may be the same or different from the linker in L-IM, and further, the moiety L-IM in each of the formulas may also comprise regioisomers.

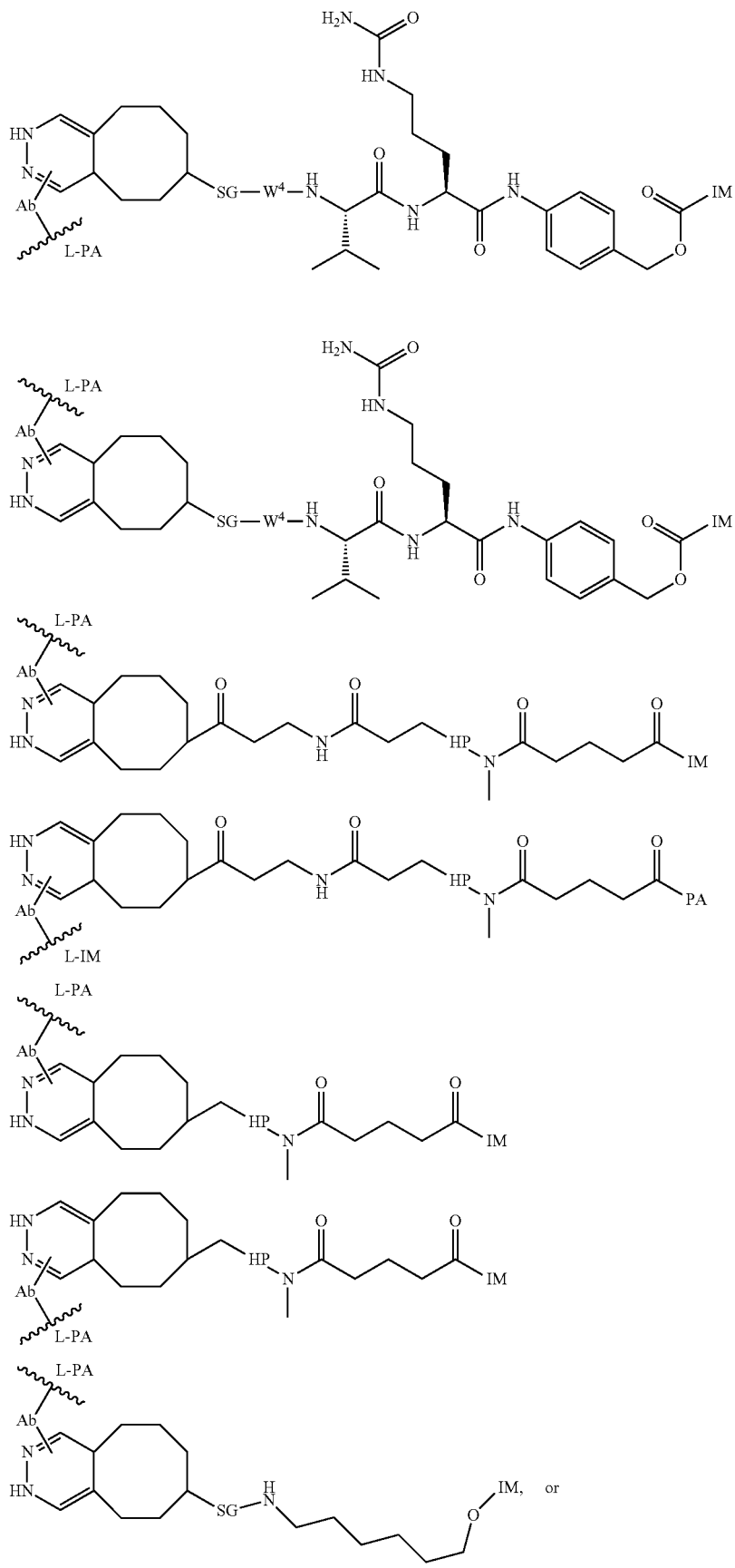

-continued

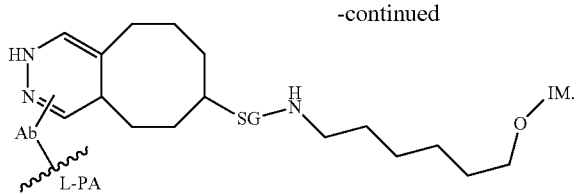

In an embodiment, provided herein is a conjugate according to any of Formulas 201a-207, where Ab indicates a residue of the antibody and PA indicates a payload moiety, IM indicates an immunomodulator moiety, and regioisomers thereof. Each regioisomer and mixtures thereof are provided in the formulae below, wherein

indicates a bond to the linker-immunomodulator. Those of skill in the art will recognize that the linkers in the formulae depicted for L-PA can also be linkers in the moiety L-IM. Those of skill in the art will recognize that the linker in L-PA may be the same or different from the linker in L-IM, and further, the moiety L-IM in each of the formulas above may also comprise regioisomers.

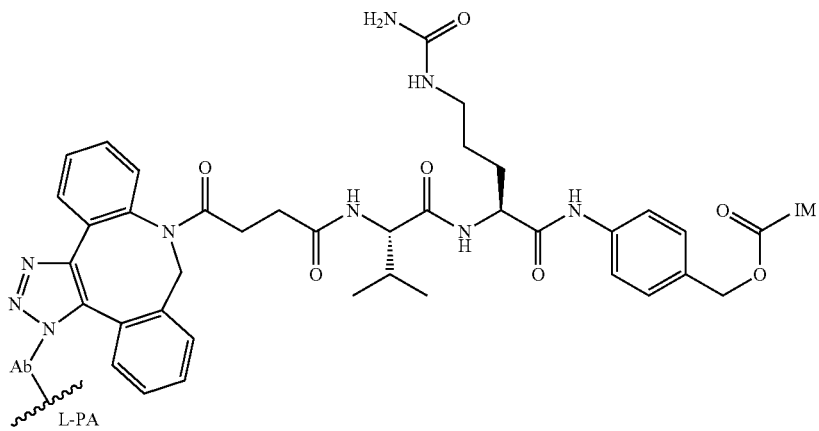

(201a)

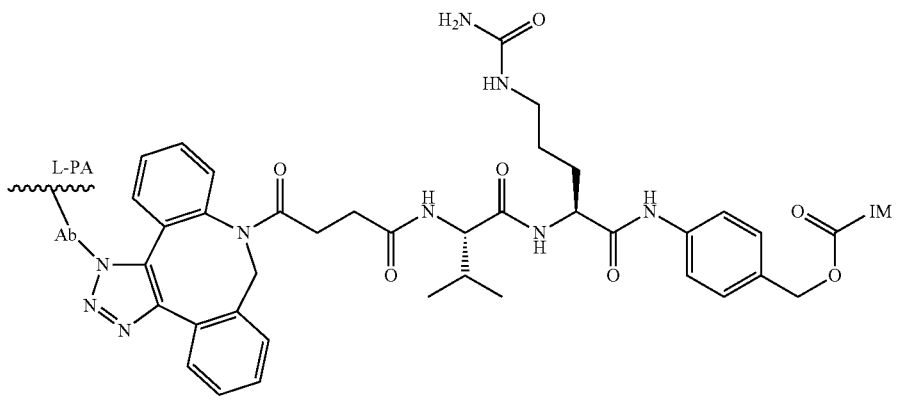

(201b)

(202a)
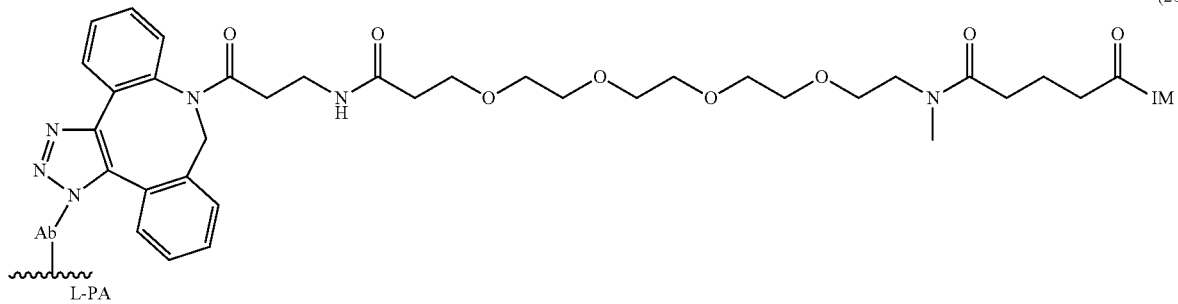
(202b)
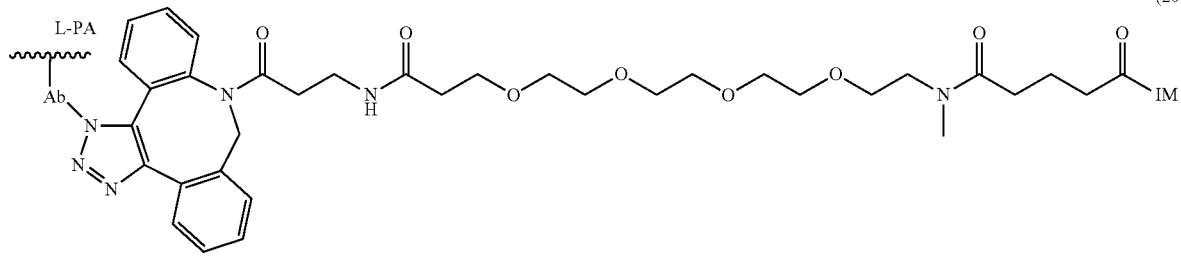
(203a)
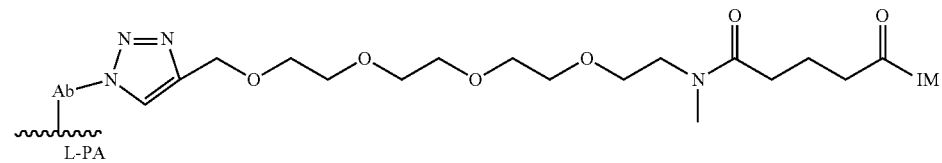
(203b)
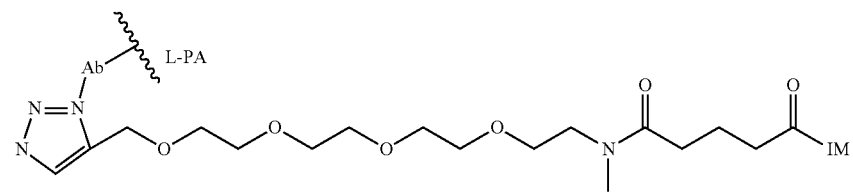
(204a)
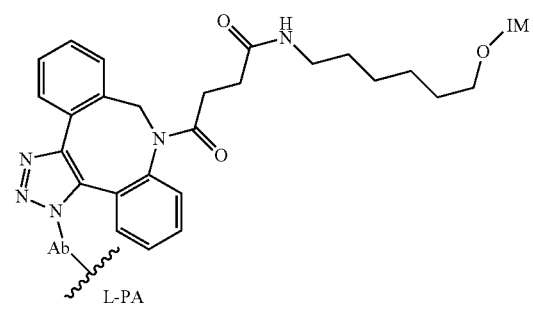
(204b)
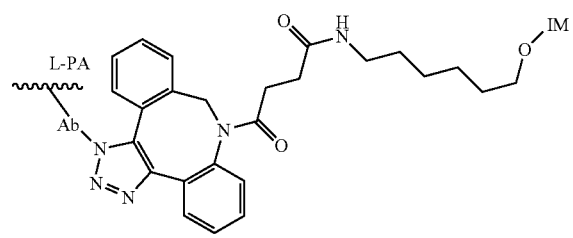
(205a)
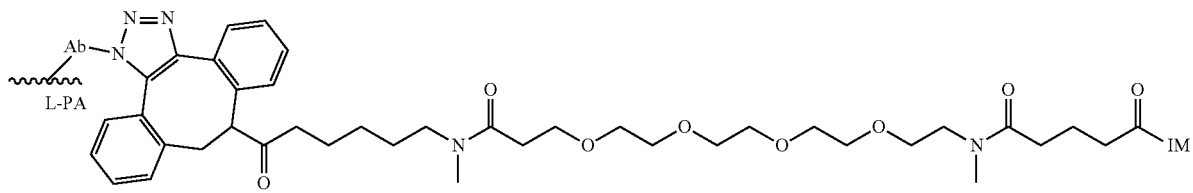

(205b)

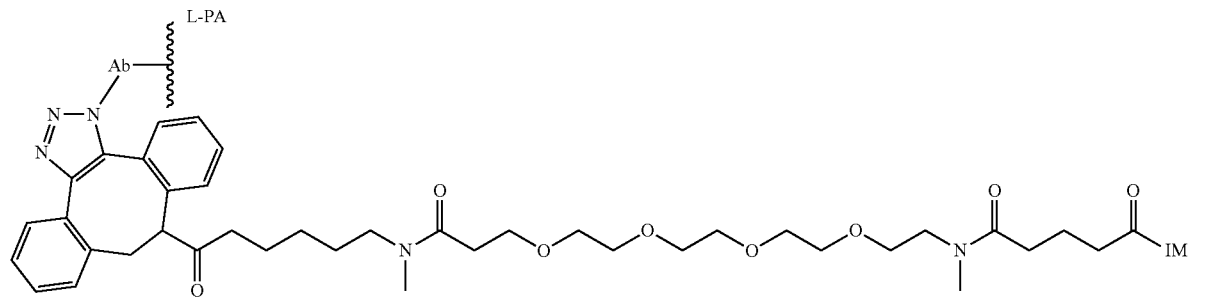

(206)

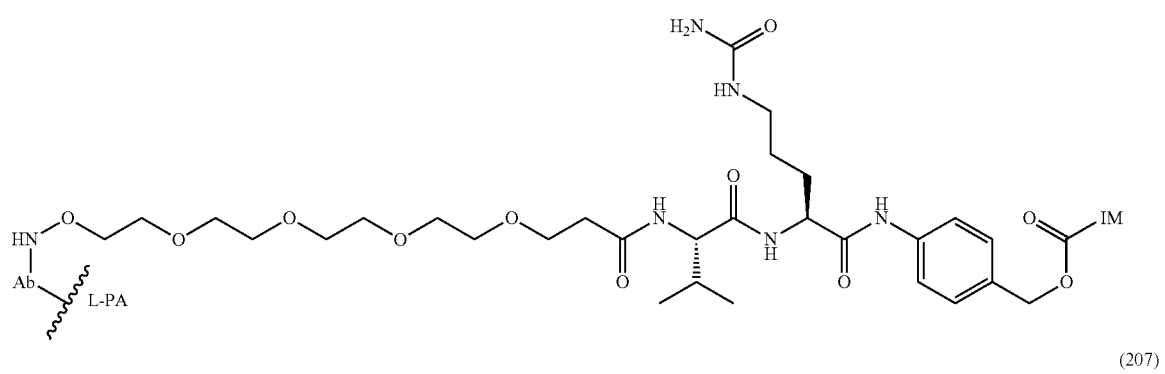

(207)

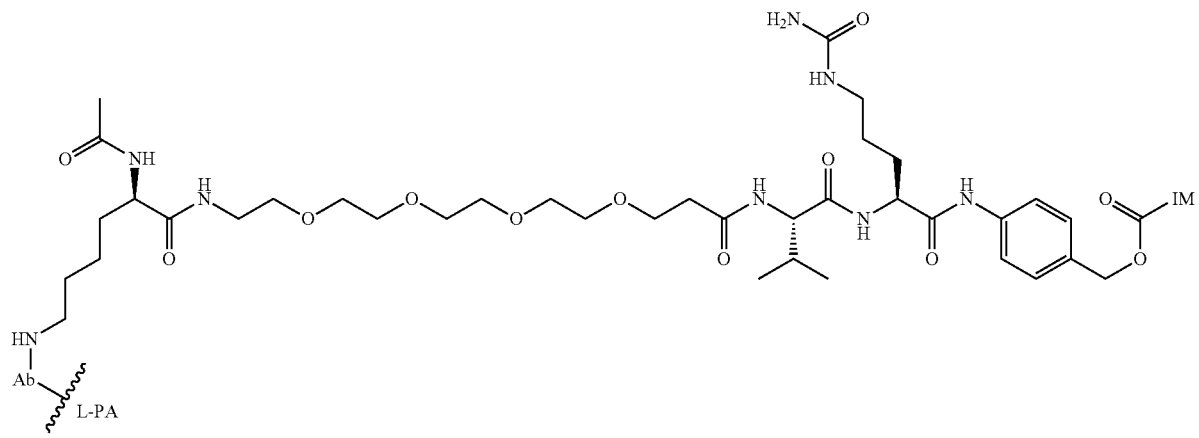

In any of the foregoing embodiments, the conjugate comprises n number of PA moieties, wherein n is an integer selected from 1 to 8. In some embodiments, n is 2. In some embodiments, n is 3. In some embodiments, n is 4. In some embodiments, n is 5. In some embodiments, n is 6. In some embodiments, n is 7. In some embodiments, n is 8. Those of skill in the art will recognize that Formulas (201a) and (201b) are regioisomers based on the nitrogen atom in the triazole to which the antibody is attached. Similarly, Formulas (202a) and (202b), (203a) and (203b), (204a) and (204b), (205a) and (205b) are pairs of regioisomers. And further, the moiety L-IM in each of the formulas above may also comprise regioisomers. In each of conjugates 201a through 207, the moiety L-PA can be according to any of formulas 101a through 107 above. In certain embodiments, provided herein are each conjugate according to any pairwise combination of one or more of 101a-107 with one or more of 201a-207.

In certain embodiments, provided herein is a conjugate according to formulas 101 and 201. In certain embodiments, provided herein is a conjugate according to formulas 101 and 202. In certain embodiments, provided herein is a conjugate according to formulas 101 and 203. In certain embodiments, provided herein is a conjugate according to formulas 101 and 204. In certain embodiments, provided herein is a conjugate according to formulas 101 and 205. In certain embodiments, provided herein is a conjugate according to formulas 101 and 206. In certain embodiments, provided herein is a conjugate according to formulas 101 and 207. In each embodiment, each of formulas 101, 102, 104, 104, 105, 201, 202, 203, 204, and 205, refer to either regioisomer or both regioisomers of each formula.

In certain embodiments, provided herein is a conjugate according to formulas 102 and 201. In certain embodiments, provided herein is a conjugate according to formulas 102 and 202. In certain embodiments, provided herein is a conjugate according to formulas 102 and 203. In certain embodiments, provided herein is a conjugate according to formulas 102 and 204. In certain embodiments, provided herein is a conjugate according to formulas 102 and 205. In certain embodiments, provided herein is a conjugate according to formulas 102 and 206. In certain embodiments, provided herein is a conjugate according to formulas 102 and 207. In each embodiment, each of formulas 101, 102, 104, 104, 105, 201, 202, 203, 204, and 205, refer to either regioisomer or both regioisomers of each formula.

In certain embodiments, provided herein is a conjugate according to formulas 103 and 201. In certain embodiments, provided herein is a conjugate according to formulas 103 and 202. In certain embodiments, provided herein is a conjugate according to formulas 103 and 203. In certain embodiments, provided herein is a conjugate according to formulas 103 and 204. In certain embodiments, provided herein is a conjugate according to formulas 103 and 205. In certain embodiments, provided herein is a conjugate according to formulas 103 and 206. In certain embodiments, provided herein is a conjugate according to formulas 103 and 207. In each embodiment, each of formulas 101, 102, 104, 104, 105, 201, 202, 203, 204, and 205, refer to either regioisomer or both regioisomers of each formula.

In certain embodiments, provided herein is a conjugate according to formulas 104 and 201. In certain embodiments, provided herein is a conjugate according to formulas 104 and 202. In certain embodiments, provided herein is a conjugate according to formulas 104 and 203. In certain embodiments, provided herein is a conjugate according to formulas 104 and 204. In certain embodiments, provided herein is a conjugate according to formulas 104 and 205. In certain embodiments, provided herein is a conjugate according to formulas 104 and 206. In certain embodiments, provided herein is a conjugate according to formulas 104 and 207. In each embodiment, each of formulas 101, 102, 104, 104, 105, 201, 202, 203, 204, and 205, refer to either regioisomer or both regioisomers of each formula.

In certain embodiments, provided herein is a conjugate according to formulas 105 and 201. In certain embodiments, provided herein is a conjugate according to formulas 105 and 202. In certain embodiments, provided herein is a conjugate according to formulas 105 and 203. In certain embodiments, provided herein is a conjugate according to formulas 105 and 204. In certain embodiments, provided herein is a conjugate according to formulas 105 and 205. In certain embodiments, provided herein is a conjugate according to formulas 105 and 206. In certain embodiments, provided herein is a conjugate according to formulas 105 and 207. In each embodiment, each of formulas 101, 102, 104, 104, 105, 201, 202, 203, 204, and 205, refer to either regioisomer or both regioisomers of each formula.

In certain embodiments, provided herein is a conjugate according to formulas 106 and 201. In certain embodiments, provided herein is a conjugate according to formulas 106 and 202. In certain embodiments, provided herein is a conjugate according to formulas 106 and 203. In certain embodiments, provided herein is a conjugate according to formulas 106 and 204. In certain embodiments, provided herein is a conjugate according to formulas 106 and 205. In certain embodiments, provided herein is a conjugate according to formulas 106 and 206. In certain embodiments, provided herein is a conjugate according to formulas 106 and 207. In each embodiment, each of formulas 101, 102, 104, 104, 105, 201, 202, 203, 204, and 205, refer to either regioisomer or both regioisomers of each formula.

In certain embodiments, provided herein is a conjugate according to formulas 107 and 201. In certain embodiments, provided herein is a conjugate according to formulas 107 and 202. In certain embodiments, provided herein is a conjugate according to formulas 107 and 203. In certain embodiments, provided herein is a conjugate according to formulas 107 and 204. In certain embodiments, provided herein is a conjugate according to formulas 107 and 205. In certain embodiments, provided herein is a conjugate according to formulas 107 and 206. In certain embodiments, provided herein is a conjugate according to formulas 107 and 207. In each embodiment, each of formulas 101, 102, 104, 104, 105, 201, 202, 203, 204, and 205, refer to either regioisomer or both regioisomers of each formula.

In particular embodiments, provided herein are antibody conjugates according to any of Formulas 101a-105b and 201a-205b wherein Ab comprises a residue of a non-natural amino acid according to Formula (30), below. In particular embodiments, provided herein are antibody conjugates according to any of Formulas 101a-105b and 201a-205b wherein Ab comprises a residue of a non-natural amino acid according to Formula (30), below, at heavy chain position 404 according to the EU numbering system. In particular embodiments, provided herein are antibody conjugates according to any of Formulas 101a-105b and 201a-205b wherein Ab comprises a residue of a non-natural amino acid according to Formula (30), below, at heavy chain position 180 according to the EU numbering system. In particular embodiments, provided herein are antibody conjugates according to any of Formulas 101a-105b and 201a-205b wherein Ab comprises a residue of a non-natural amino acid according to Formula (30), below, at heavy chain position 241 according to the EU numbering system. In particular embodiments, provided herein are antibody conjugates according to any of Formulas 101a-105b and 201a-205b wherein Ab comprises a residue of a non-natural amino acid according to Formula (30), below, at heavy chain position 222 according to the EU numbering system. In particular embodiments, provided herein are antibody conjugates according to any of Formulas 101a-105b and 201a-205b wherein Ab comprises a residue of a non-natural amino acid according to Formula (30), below, at light chain position 7 according to the Kabat or Chothia numbering system. In particular embodiments, provided herein are antibody conjugates according to any of Formulas 101a-105b and 201a-205b wherein Ab comprises a residue of the non-natural amino acid according to Formula (30), below, at light chain position 42 according to the Kabat or Chothia numbering system. In certain embodiments, PA is a cytotoxic compound described herein.

(30)

Those of skill will recognize that amino acids such as Formula (30) are incorporated into polypeptides and antibodies as residues. For instance, a residue of Formula (30) can be according to the following Formula (30'):

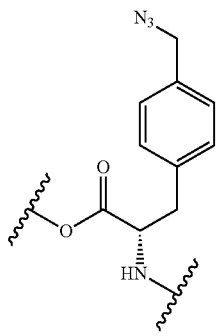

(30')

Further modification, for instance at —N₃ is also encompassed within the term residue herein.

In particular embodiments, provided herein are antibody conjugates according to any of Formulas 101a-105b and 201a-205b wherein Ab comprises a residue of the non-natural amino acid according to Formula (56), below. In particular embodiments, provided herein are antibody conjugates according to any of Formulas 101a-105b and 201a-205b wherein Ab comprises a residue of the non-natural amino acid according to Formula (56), below, at heavy chain position 404 according to the EU numbering system. In particular embodiments, provided herein are antibody conjugates according to any of Formulas 101a-105b and 201a-205b wherein Ab comprises a residue of the non-natural amino acid according to Formula (56), below, at heavy chain position 180 according to the EU numbering system. In particular embodiments, provided herein are antibody conjugates according to any of Formulas 101a-105b and 201a-205b wherein Ab comprises a residue of the non-natural amino acid according to Formula (56), below, at heavy chain position 241 according to the EU numbering system. In particular embodiments, provided herein are antibody conjugates according to any of Formulas 101a-105b and 201a-205b wherein Ab comprises a residue of the non-natural amino acid according to Formula (56), below, at heavy chain position 222 according to the EU numbering system. In particular embodiments, provided herein are antibody conjugates according to any of Formulas 101a-105b and 201a-205b wherein Ab comprises a residue of the non-natural amino acid according to Formula (56), below, at light chain position 7 according to the Kabat or Chothia numbering system. In particular embodiments, provided herein are antibody conjugates according to any of Formulas 101a-105b and 201a-205b wherein Ab comprises a residue of the non-natural amino acid according to Formula (56), below, at light chain position 42 according to the Kabat or Chothia numbering system. The non-natural amino acid according to Formula (56) is as follows:

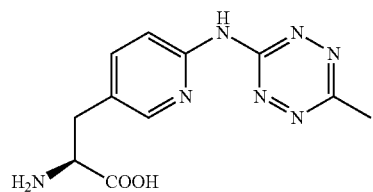

(56)

In particular embodiments, provided herein are antibody conjugates according to any of Formulas 101a-105b and 201a-205b wherein Ab comprises a non-natural amino acid residue of para-azidomethyl-L-phenylalanine. In particular embodiments, provided herein are antibody conjugates according to any of Formulas 101a-105b and 201a-205b wherein Ab comprises the non-natural amino acid residue para-azidomethyl-L-phenylalanine at heavy chain position 404 according to the EU numbering system. In particular embodiments, provided herein are antibody conjugates according to any of Formulas 101a-105b and 201a-205b wherein Ab comprises a non-natural amino acid residue of para-azidomethyl-L-phenylalanine at heavy chain position 180 according to the EU numbering system. In particular embodiments, provided herein are antibody conjugates according to any of Formulas 101a-105b and 201a-205b wherein Ab comprises a non-natural amino acid residue of para-azidomethyl-L-phenylalanine at heavy chain position 241 according to the EU numbering system. In particular embodiments, provided herein are antibody conjugates according to any of Formulas 101a-105b and 201a-205b wherein Ab comprises a non-natural amino acid residue of para-azidomethyl-L-phenylalanine at heavy chain position 222 according to the EU numbering system. In particular embodiments, provided herein are antibody conjugates according to any of Formulas 101a-105b and 201a-205b wherein Ab comprises a non-natural amino acid residue para-azidomethyl-L-phenylalanine at light chain position 7 according to the Kabat or Chothia numbering system. In particular embodiments, provided herein are antibody conjugates according to any of Formulas 101a-105b and 201a-205b wherein Ab comprises a non-natural amino acid residue para-azidomethyl-L-phenylalanine at light chain position 42 according to the Kabat or Chothia numbering system. In certain embodiments, PA is any cytotoxic payload described herein. In some embodiments, IM is a compound of Formula (III) or any other immunomodulatory compound described herein.

In particular embodiments, provided herein are antibody conjugates according to any of Formulas 101a-105b and 201a-205b wherein Ab comprises a non-natural amino acid residue of para-acetyl-L-phenylalanine. In particular embodiments, provided herein are antibody conjugates according to any of Formulas 101a-105b and 201a-205b wherein Ab comprises the non-natural amino acid residue para-acetyl-L-phenylalanine at heavy chain position 404 according to the EU numbering system. In particular embodiments, provided herein are antibody conjugates according to any of Formulas 101a-105b and 201a-205b wherein Ab comprises a non-natural amino acid residue of para-acetyl-L-phenylalanine at heavy chain position 180 according to the EU numbering system. In particular embodiments, provided herein are antibody conjugates according to any of Formulas 101a-105b and 201a-205b wherein Ab comprises a non-natural amino acid residue of para-acetyl-L-phenylalanine at heavy chain position 241 according to the EU numbering system. In particular embodiments, provided herein are antibody conjugates according to any of Formulas 101a-105b and 201a-205b wherein Ab comprises a non-natural amino acid residue of para-acetyl-L-phenylalanine at heavy chain position 222 according to the EU numbering system. In particular embodiments, provided herein are antibody conjugates according to any of Formulas 101a-105b and 201a-205b wherein Ab comprises a non-natural amino acid residue para-acetyl-L-phenylalanine at light chain position 7 according to the Kabat or Chothia numbering system. In particular embodiments, provided herein are antibody conjugates according to any of Formulas 101a-105b and 201a-205b wherein Ab comprises a non-natural amino acid residue para-acetyl-L-phenylalanine at light chain position 42 according to the Kabat or Chothia numbering system. In certain embodiments, PA is any cytotoxic payload described herein. In some embodiments, IM is a compound of Formula (III) or any other immunomodulatory compound described herein.

In particular embodiments, provided herein are antibody conjugates according to any of Formulas 106, 107, 206, and 207 wherein Ab comprises a glutamine residue. The glutamine residue can be any glutamine residue suitable for conjugation. In certain embodiments, the glutamine residue is at heavy chain position 195 according to the EU numbering system. In certain embodiments, the antibody is deglycosylated or aglycosylated. In certain embodiments, the antibody comprises a QTAG, as described herein. In certain embodiments, the QTAG is at the C-terminus of one or more polypeptide chains. In certain embodiments, the QTAG has the sequence L-Q-R, or leucine-glutamine-arginine. In certain embodiments, the antibody comprises a QTAG at any of the heavy chain positions 122, 294, 295, 296, 374, and 399 according to the EU numbering system. In certain embodiments, the antibody comprises LQR at any of the heavy chain positions 122, 294, 295, 296, 374, and 399 according to the EU numbering system. In these embodiments, the position number indicates the site of the left-most amino acid residue of the QTAG, and the other residues of the QTAG are substituted for subsequent residues in the antibody sequence. In certain embodiments, the antibody is conjugated at one or more amino termini of a heavy chain or a light chain. In certain embodiments, the antibody comprises more than one glutamine and/or amino terminus for conjugation. Conjugation at such sites can proceed with the enzyme transglutaminase according to standard techniques. Useful transglutaminase techniques are described in, for instance, Jeger et al., 2010, *Angew. Chem. Int. Ed.* 49:9995-9997, Strop et al., Chemistry & Biology 2013:161-167, and the Examples below.

In a first aspect, provided herein is an antibody conjugate comprising an antibody, or an antigen-binding fragment thereof, covalently linked to a drug payload and further covalently linked to an immunomodulatory payload, i.e., the antibody conjugate is an immunomodulatory drug antibody conjugate (iADC). In some cases, the drug payload is a cytotoxic compound. In some examples, the cytotoxic compound is selected from the group consisting of alkylating agents, DNA-crosslinking agents, anti-tumor antibiotics, anti-metabolites, anti-mitotic agents (e.g., microtubule disrupting agents), histone-deacetylase (HDAC) inhibitors, telomerase inhibitors, and immunogenic cell death agents. In some cases, the immunomodulatory payload in the antibody conjugate is an immunostimulatory payload. In some cases, the immunomodulatory payload in the antibody conjugate is selected from the group consisting of toll-like receptor agonists, kinase inhibitors, growth factor inhibitors (e.g., EGFR, PDGF, VEGF inhibitors), Calcineurin inhibitors, CRAC inhibitors, PARP1 antagonists, PPARγ agonists, Kv1.3 antagonists, PP2A agonists, MYD88 inhibitors, BCL-2 inhibitors, Adenosine A2A receptor (A2ar) agonists, Toll-like receptor 7/8 (TLR7/8) agonists, Toll-like receptor 4 (TLR4) agonists, Toll-like receptor 9 (TLR9) agonists, calcium-activated potassium channel (Kca3.1) agonists, TGF~R1 inhibitors, TGF-R2 inhibitors, GLi 1 inhibitors, tankyrase (TNKS) antagonists, Traf2 and Nck-interacting kinase (TNIK) antagonists, imides, and vitamin D receptor (VDR) agonists.

In any of the preceding embodiments, the drug payload is linked to the antibody, or antigen-binding fragment, via a linker. The antibody conjugate of any of the previous claims wherein the immunomodulatory payload is linked to the antibody, or antigen-binding fragment, via a linker.

In another aspect, provided herein is an antibody conjugate (an iADC) according to Formula (I):

$$[PA\text{-}L\text{-}]_m Ab\text{-}[\text{-}L\text{-}IM]_n \qquad \text{Formula (I)}$$

or a pharmaceutically acceptable salt, solvate, stereoisomer, tautomer or mixture of regioisomers thereof;
wherein Ab is an antibody, or an antigen-binding fragment thereof;
each L is independently an optional linker;
each PA is independently a drug payload;
each IM is independently an immunomodulatory payload;
subscript n is an integer from 1 to 8;
subscript m is an integer from 1 to 8; and
each bracketed group is covalently linked to Ab.

In some embodiments of Formula (I), L-PA is independently

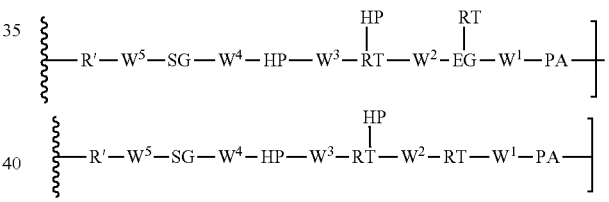

In some embodiments of Formula (I), L-IM is independently

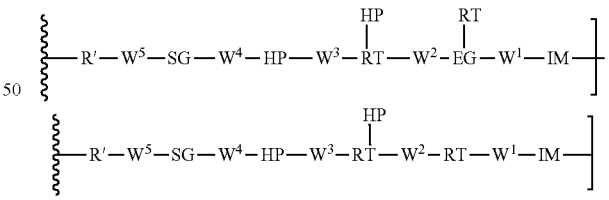

In some embodiments, the antibody conjugate of Formula (I) according to the structure of Formula (II):

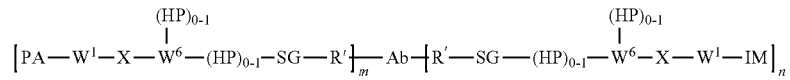

Formula (II)

or a pharmaceutically acceptable salt, solvate, stereoisomer, tautomer or mixture of regioisomers thereof, wherein:

each $W^1$ is independently, at each occurrence, a single bond, absent or a divalent spacer;

each X is independently, at each occurrence, absent,

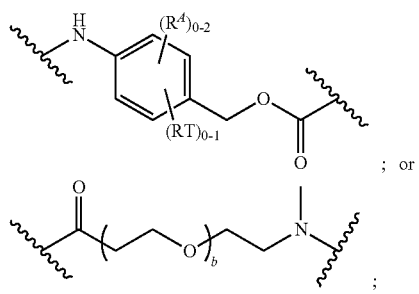

; or

;

subscript b is an integer from 1 to 10;

each $R^A$ is absent or is independently, at each occurrence, selected from $C_{1-3}$alkyl;

each RT is absent, or is independently, at each occurrence, a release trigger group;

each HP is absent or is independently, at each occurrence, a hydrophilic group;

each $W^6$ is independently, at each occurrence, a peptide, or absent;

each SG is independently, at each occurrence, absent, or a divalent spacer group;

each R' is independently, at each occurrence, a divalent residue of a conjugated group;

subscript n is an integer from 1 to 30;

subscript m is an integer from 1 to 30

Ab is an antibody or an antigen binding fragment thereof;

PA is a cytotoxic compound payload, or a residue thereof; and

IM is an immunomodulatory payload, or a residue thereof.

In some embodiments of Formula (I) and/or Formula (II), SG is independently, at each occurrence,

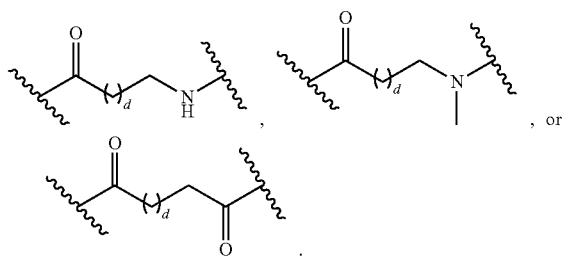

.

wherein subscript d is an integer from 1 to 10, wherein each

indicates a point of attachment to the rest of the formula.

In some embodiments of Formula (I) and/or Formula (II), SG is independently, at each occurrence,

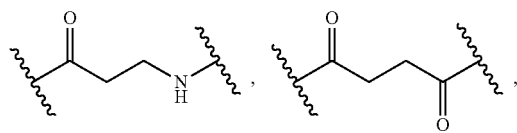

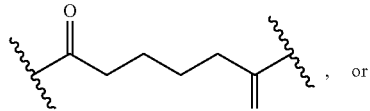

, or

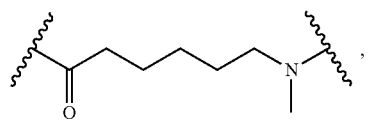

, wherein each

indicates a point of attachment to the rest of the In some embodiments of Formula (I) and/or Formula (II), antibody conjugate of any one of claims 8-10, wherein $W^1$, when present, is

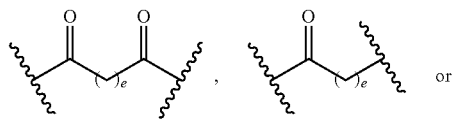

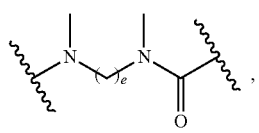

, wherein subscript e is an integer from 1 to 10, wherein each

indicates a point of attachment to the rest of the formula.

In some embodiments of Formula (I) and/or Formula (II), $W^1$, when present, is

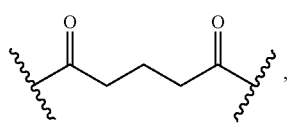

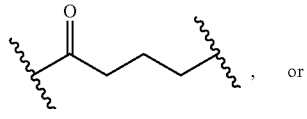

, or

-continued
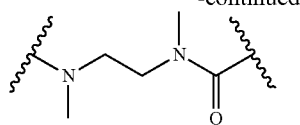
5
wherein each
10
indicates a point of attachment to the rest of the formula.
In some embodiments of Formula (I) and/or Formula (II), when $W^6$ is a peptide, the peptide may comprise natural and/or non-natural amino acid residues. In some instances of Formula (VI), $W^6$, when present, is a tripeptide residue. In some of such instances, $W^6$ is
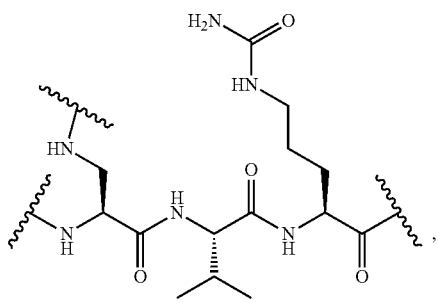
,
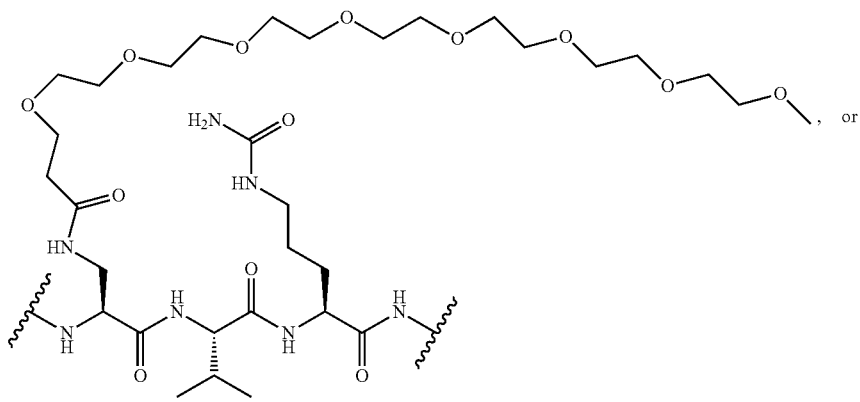
, or
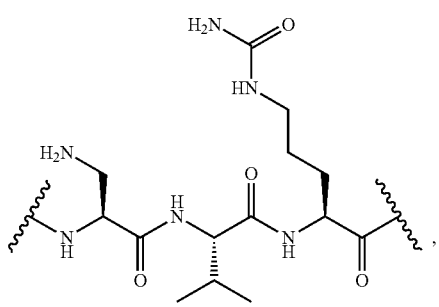
, wherein each

indicates a point of attachment to the rest of the formula. In some instances of Formula (VI), $W^6$, when present, is a dipeptide residue. In some of such instances, $W^6$, when present, is

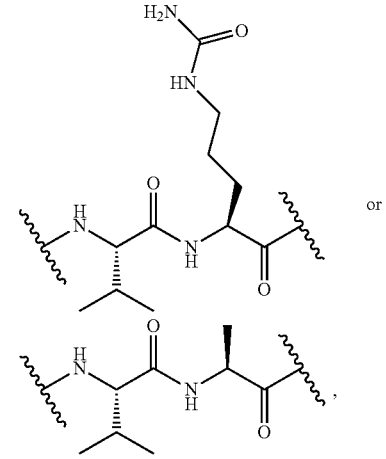

or wherein each

indicates a point of attachment to the rest of the formula.

In some embodiments of Formula (I) and/or Formula (II), RT is independently, at each occurrence,

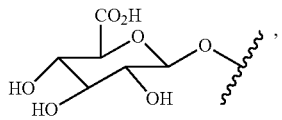

wherein

indicates a point of attachment to the rest of the formula.

In some embodiments of Formula (I) and/or Formula (II), HP, when present, is independently, at each occurrence, a PEG group. In some embodiments of Formula (I) and/or Formula (II), HP, when present, is independently, at each occurrence,

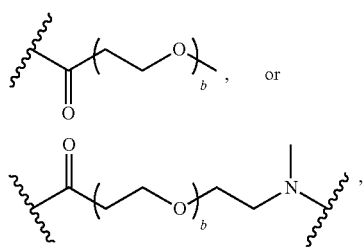

wherein subscript b is an integer from 1 to 10, and

indicates a point of attachment to the rest of the formula.

In some embodiments of Formula (I) and/or Formula (II), R' is independently, at each occurrence:

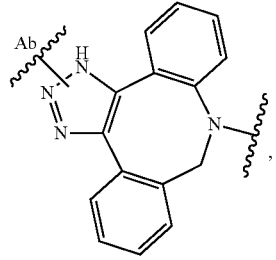

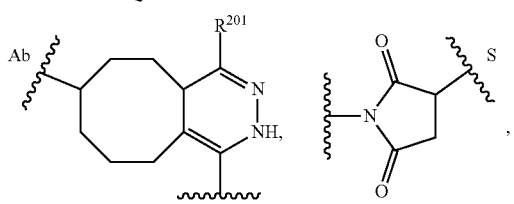

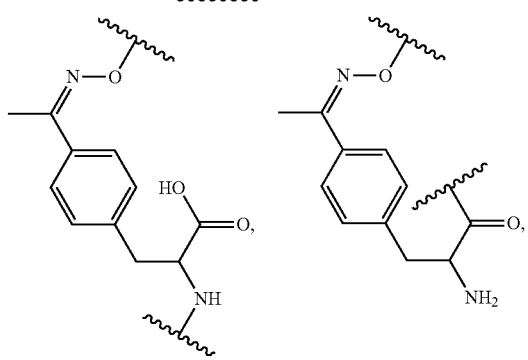

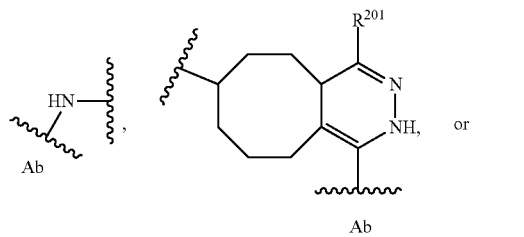

or

-continued

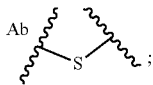

wherein $R^{201}$ is $C_{1-6}$alkyl, wherein each

indicates a point of attachment to the rest of the formula,

indicates a point of attachment to the antibody, or an antigen binding fragment thereof, and

indicates a point of attachment to the antibody, or an antigen binding fragment thereof, via a sulfur atom of a cysteine residue.

In some embodiments of Formula (I) and/or Formula (II), the antibody, or an antigen binding fragment thereof, is selected from the group consisting of: anti-BCMA, anti-Muc16, trastuzumab, sofitizumab, anti-GFP, and anti-FolRa, or an antigen binding fragment thereof.

In some embodiments of Formula (I) and/or Formula (II), the antibody, or an antigen binding fragment thereof, comprises two or more non-natural amino acids suitable for conjugation.

In some embodiments of Formula (I) and/or Formula (II), in the antibody, or antigen binding fragment thereof, at least one of the two or more non-natural amino acids residues is a pAMF residue.

In some embodiments of Formula (I) and/or Formula (II), the antibody, or an antigen binding fragment thereof, comprises a Y180 pAMF mutation, a F404 pAMF mutation, or both.

In some embodiments of Formula (I) and/or Formula (II), the antibody, or an antigen binding fragment thereof, is modified by substituting in or adding one or more glutamine (Q) residues. In some of such embodiments of Formula (I) and/or Formula (II), the one or more glutamine residues are in Q tags selected from the group consisting of LLQGA (SEQ ID NO: 44), YAHQAHY (SEQ ID NO: 45), YRYRQ (SEQ ID NO: 46), PNPQLPF (SEQ ID NO: 47), PKPQQFM (SEQ ID NO: 48), GQQQLG (SEQ ID NO: 49), WALQRPH (SEQ ID NO: 50), WELQRPY (SEQ ID NO: 51), YPMQGWF (SEQ ID NO: 52), LSLSQG (SEQ ID NO: 53), GGGLLQGG (SEQ ID NO: 54), GLLQG (SEQ ID NO: 55), GSPLAQSHGG (SEQ ID NO: 56), GLLQGGG (SEQ ID NO: 57), GLLQGG (SEQ ID NO: 58), GLLQ (SEQ ID NO: 59), LLQLLQGA (SEQ ID NO: 60), LLQGA (SEQ ID NO: 61), LLQYQGA (SEQ ID NO: 62), LLQGSG (SEQ ID NO: 63), LLQYQG (SEQ ID NO: 64), LLQLLQG (SEQ ID NO: 65), SLLQG (SEQ ID NO: 66), LLQLQ (SEQ ID NO: 67), LLQLLQ (SEQ ID NO: 68), LLQGR (SEQ ID NO: 69), LLQGPA (SEQ ID NO: 70), LLQGPP (SEQ ID NO: 71), GGLLQGPP (SEQ ID NO: 72), LLQGG (SEQ ID NO:73), LLQG (SEQ ID NO:74), and LQR. In some embodiments, the acyl donor glutamine-containing tag (Q tag) comprises an amino acid sequence selected from the group consisting of LLQGPA (SEQ ID NO: 70), LLQGPP (SEQ ID NO:71) or GGLLQGPP (SEQ ID NO:72). In some embodiments, the acyl donor glutamine-containing tag (Q tag) comprises an amino acid sequence selected from the group consisting of LLQGG (SEQ ID NO:73), and LLQGA (SEQ ID NO:44). In some embodiments, the acyl donor glutamine-containing tag (Q tag) comprises or consists of the amino acid sequence LQR. In some of such embodiments of Formula (I) and/or Formula (II), the one or more glutamine residues are in a Q tag with the sequence LQR.

In a group of embodiments, in the antibody conjugates described herein, the ratio of the cytotoxic compound: immunomodulatory compound is adjusted to provide optimal therapeutic effect. In some embodiments of Formula (I) and/or Formula (II), the ratio cytotoxic compound:immunomodulatory compound is about 1-3:1 or greater than 3:1. In some embodiments of Formula (I) and/or Formula (II), the ratio PA:IM is about 1:1, 2:1, 3:1, or greater than 3:1.

Embodiments of PA and IM are described in more detail in the sections below. In some embodiments of Formula (I) and/or Formula (II), PA and IM are as described in the payloads section below and herein.

In some embodiments of Formula (I) and/or Formula (II),

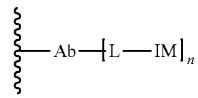

has a structure selected from the group consisting of:

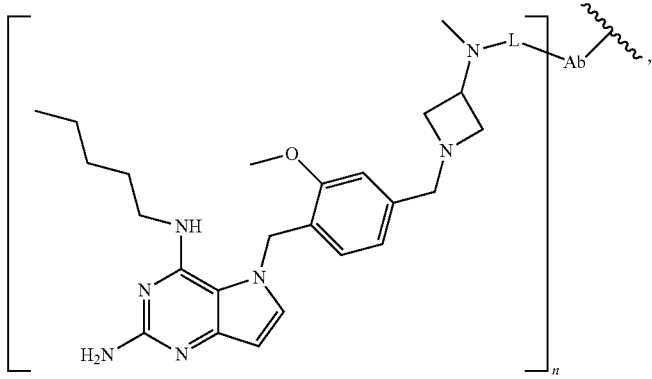

-continued
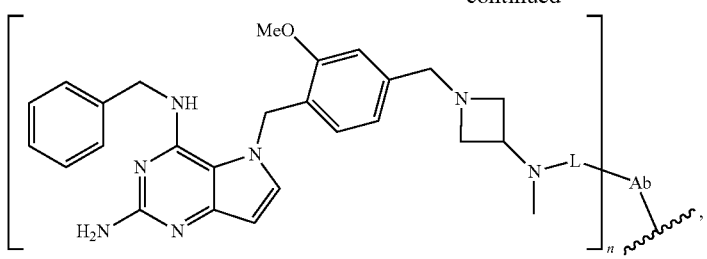
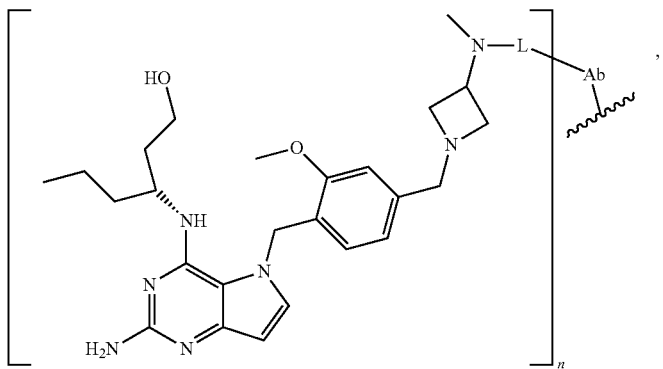
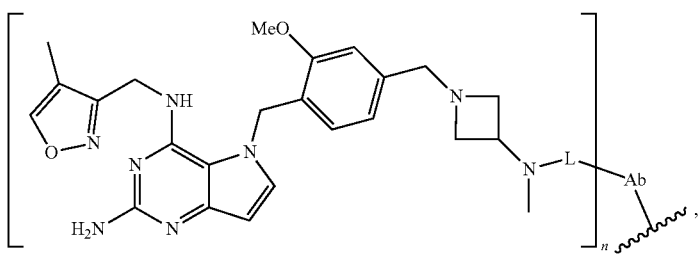
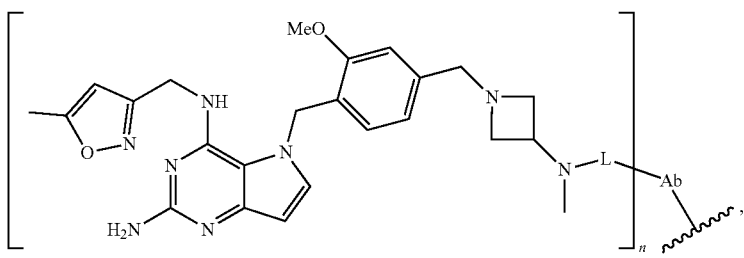
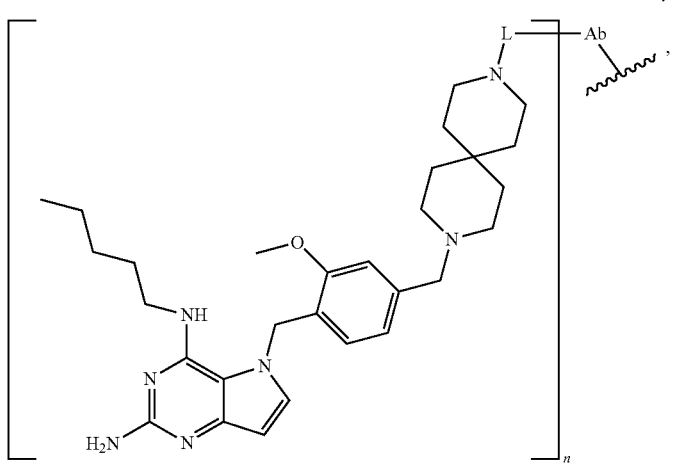

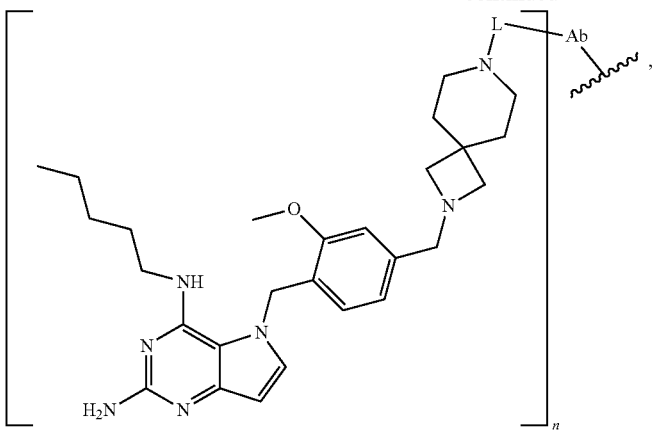
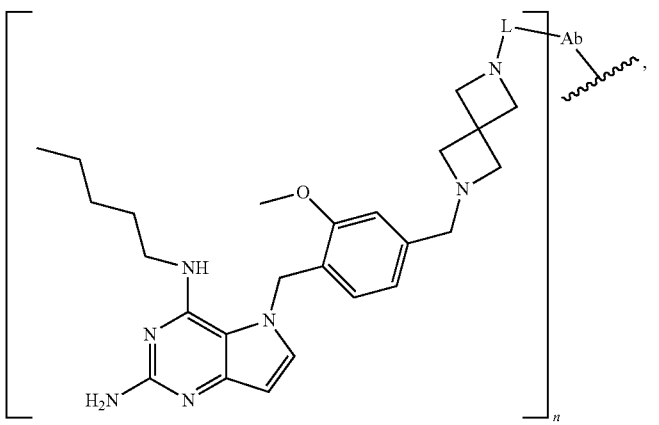
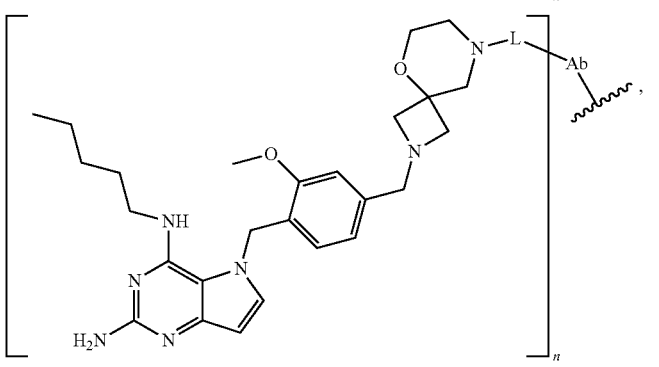
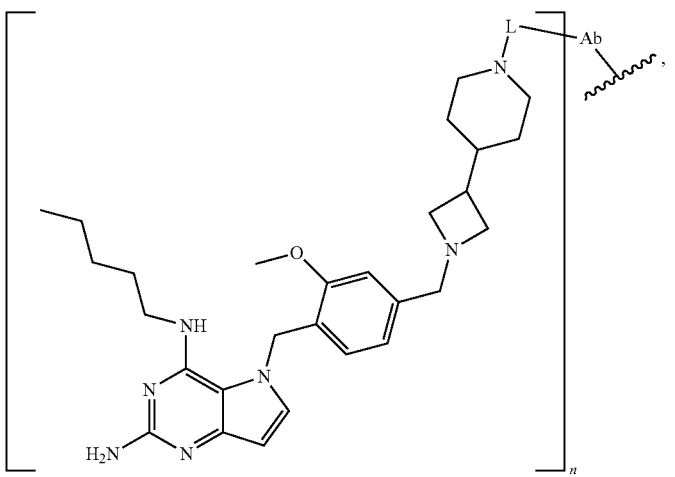

-continued
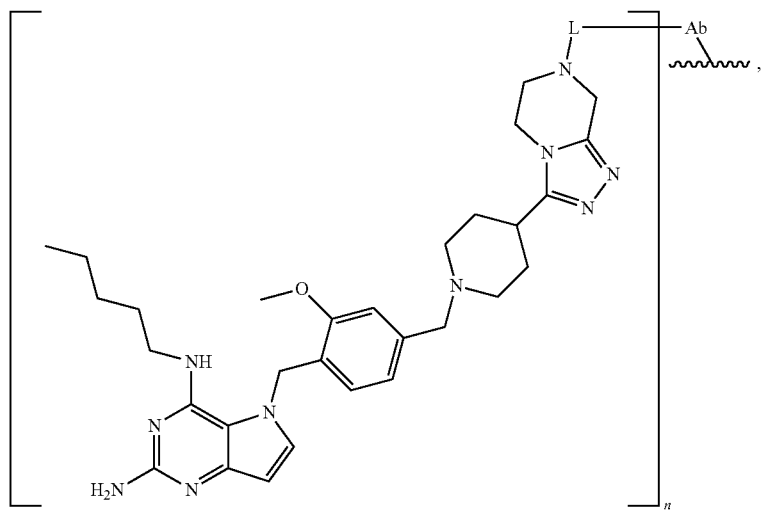
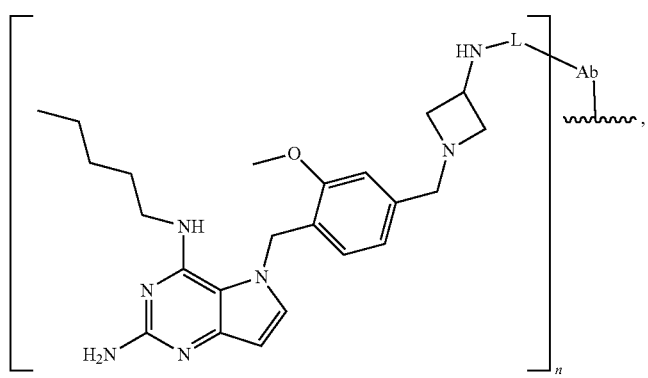
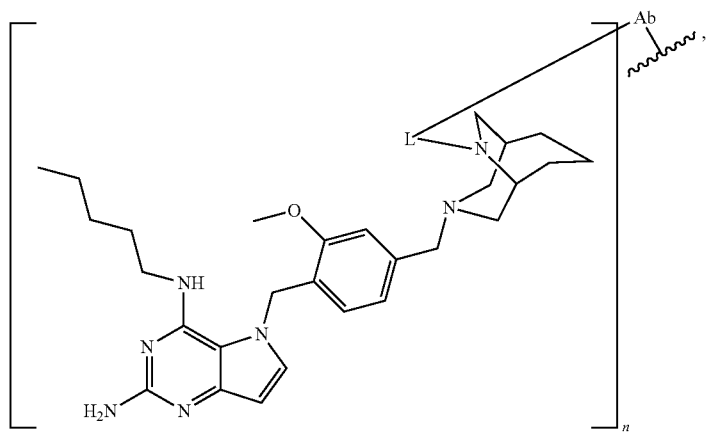
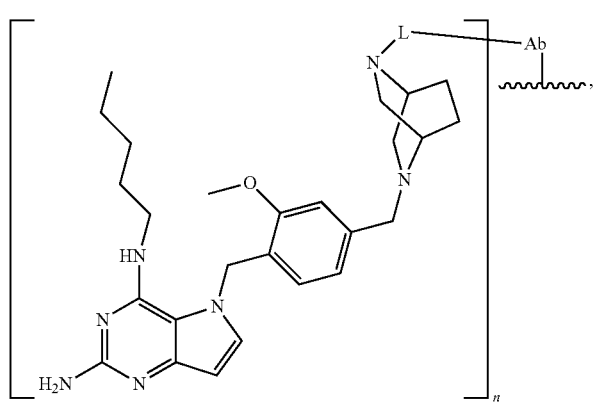

-continued
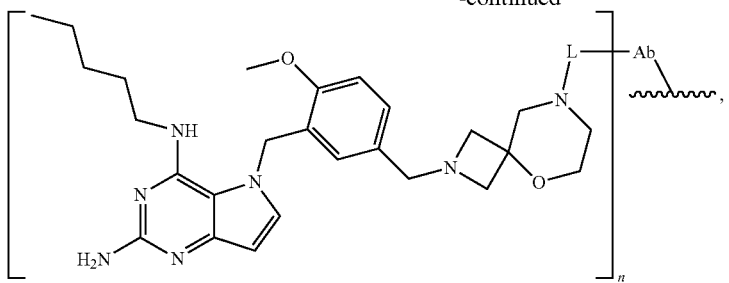
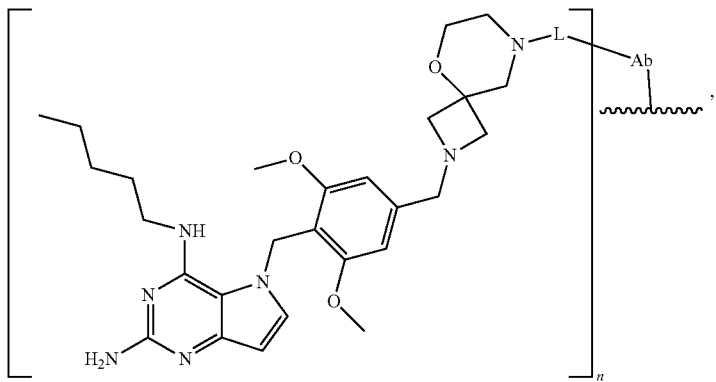
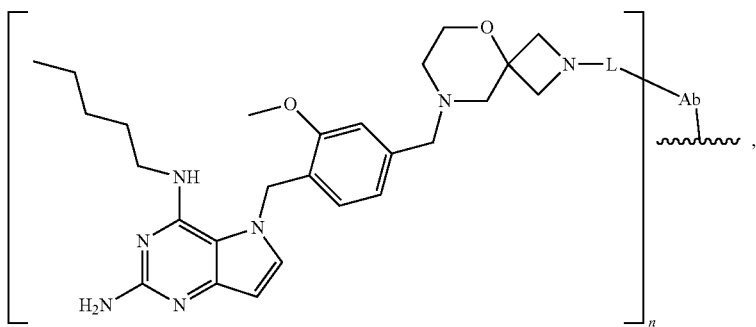
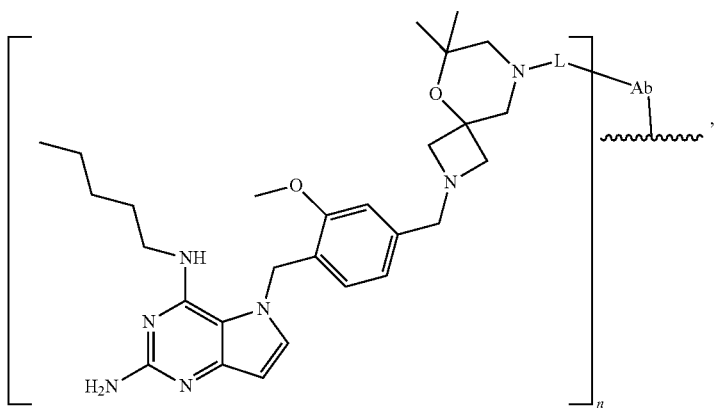

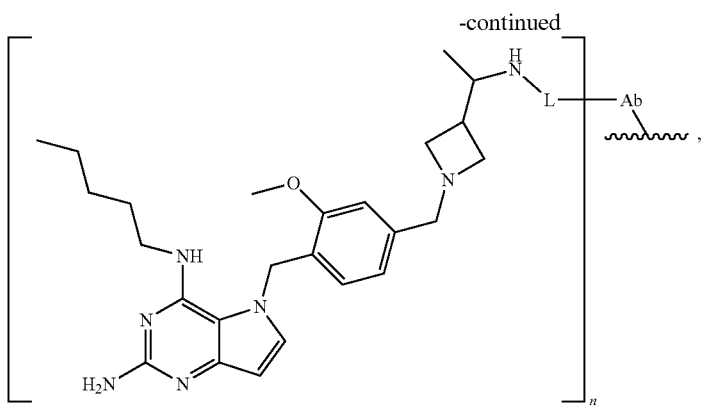
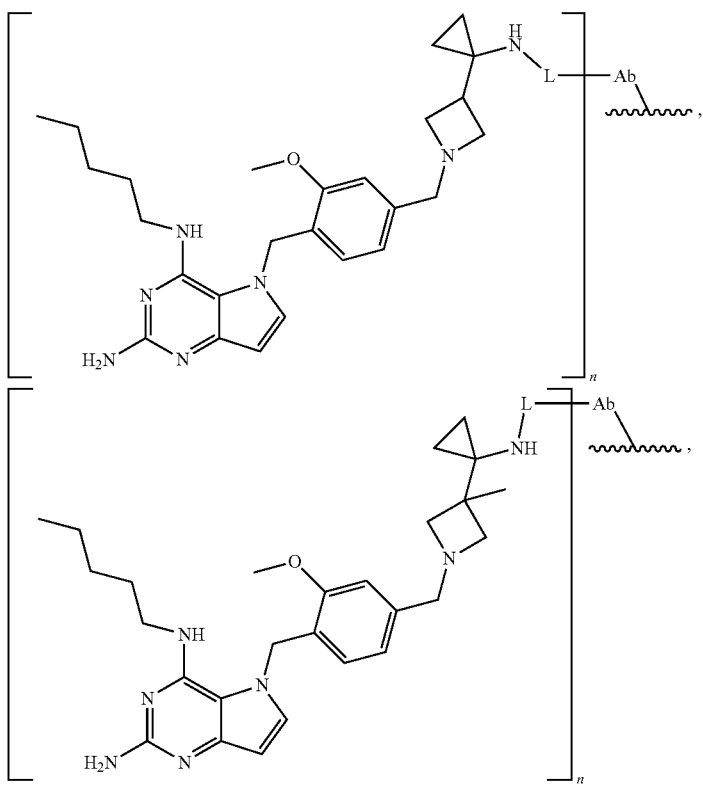
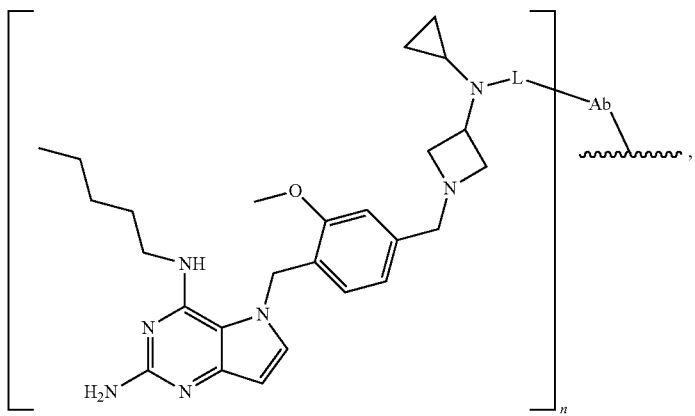

-continued
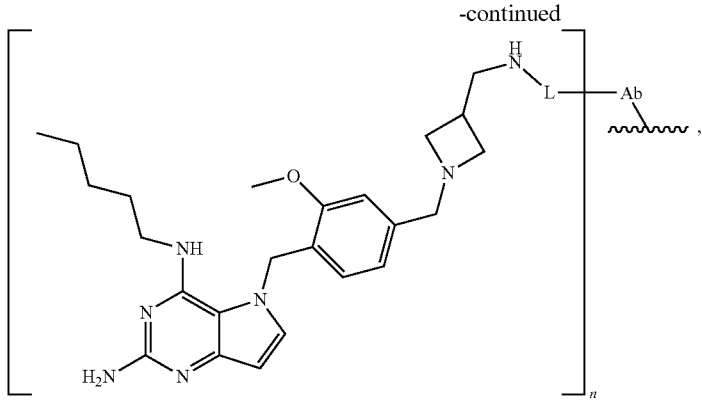
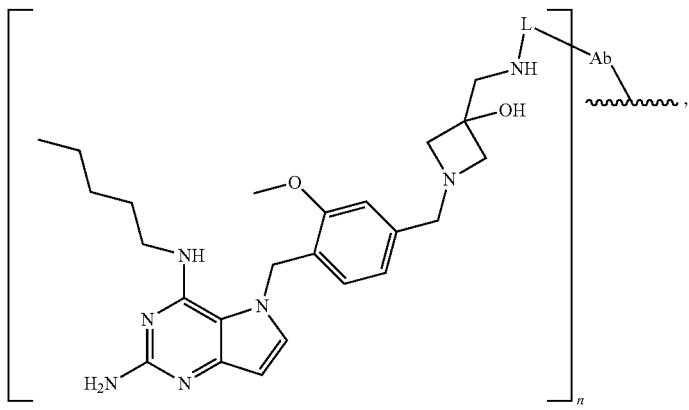
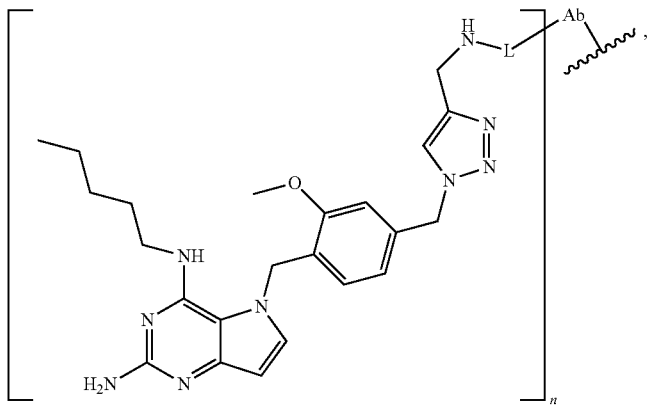
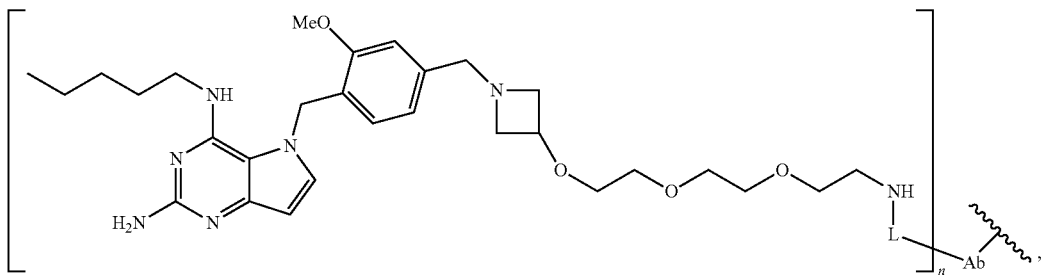

-continued
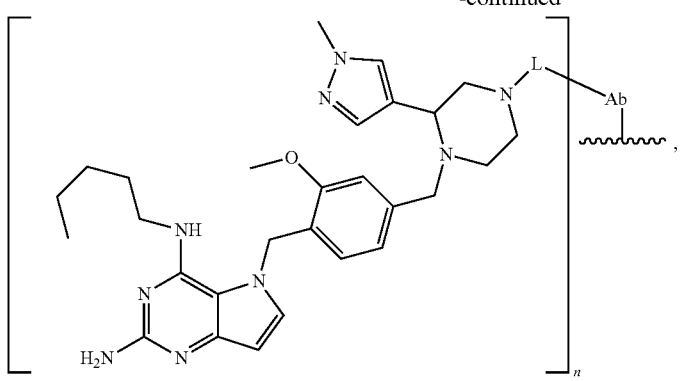
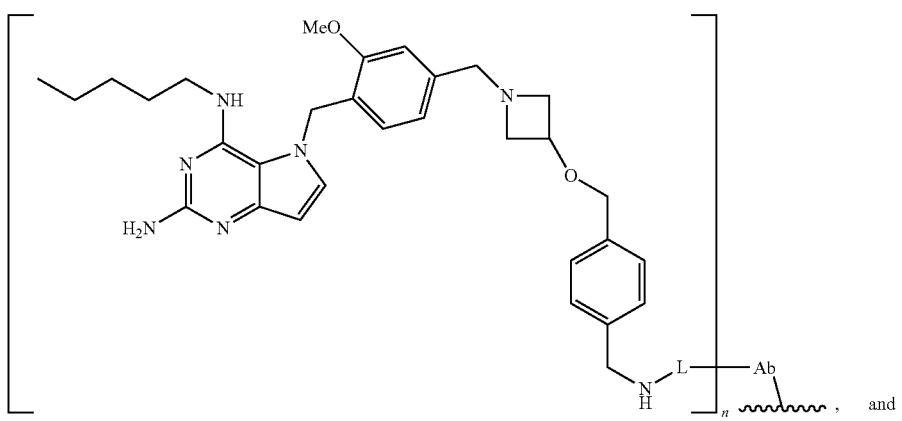
and
Compound 118
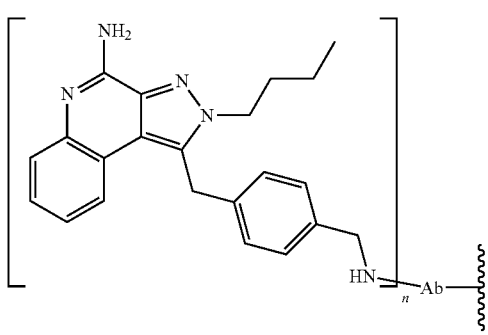

wherein each
indicates a point of attachment to the rest of the formula.
In some embodiments of Formula (I) and/or Formula (II),
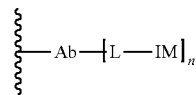
has a structure selected from the group consisting of:
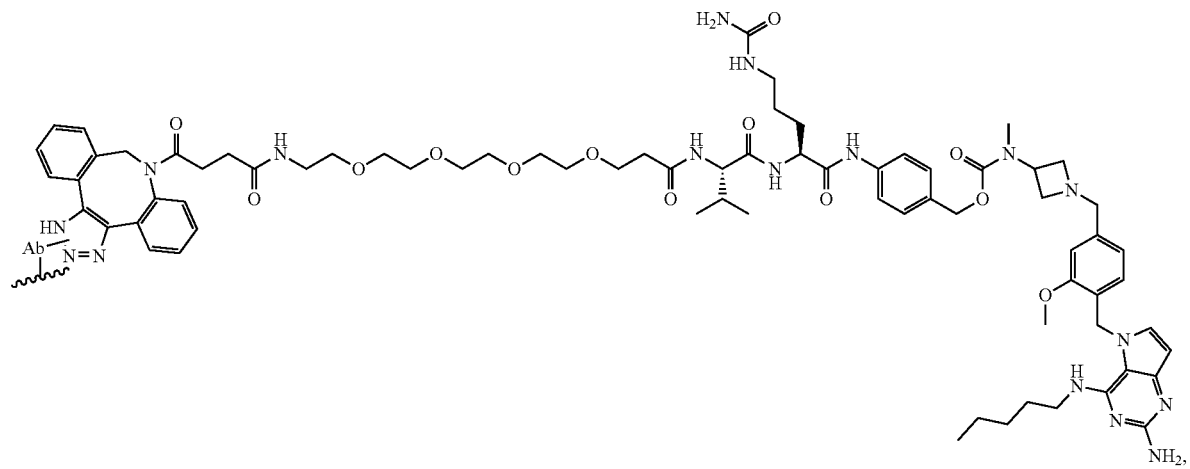
Compound 103
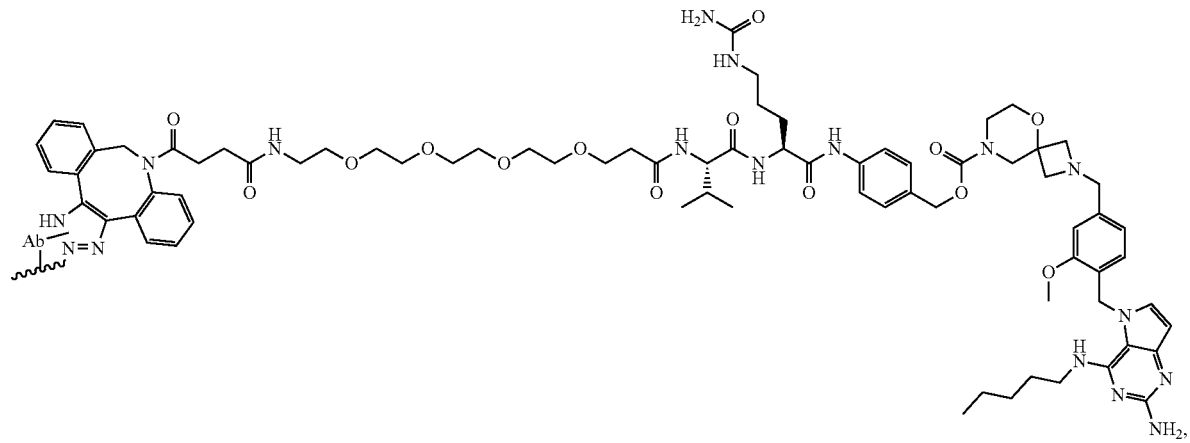
Compound 701

-continued
Compound 601
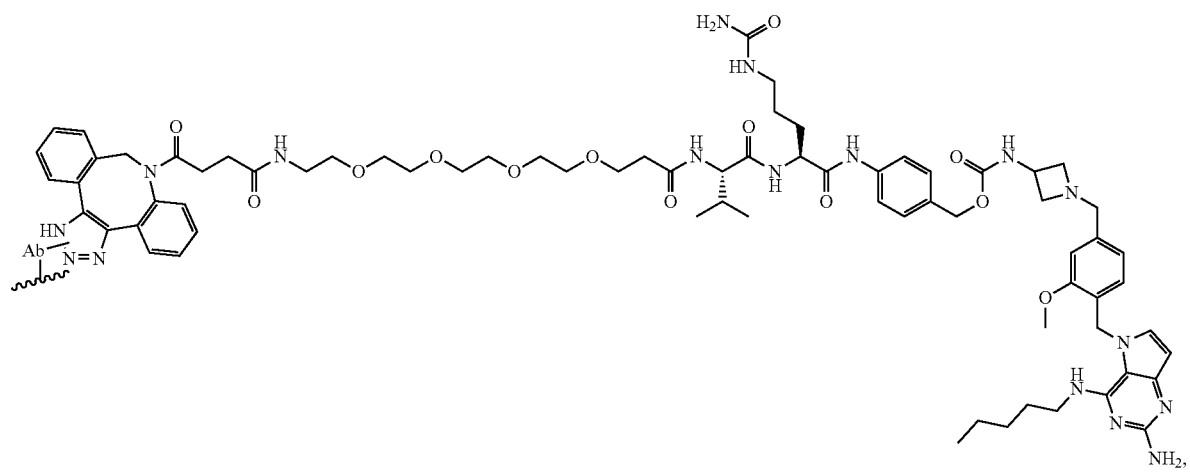
Compound 219
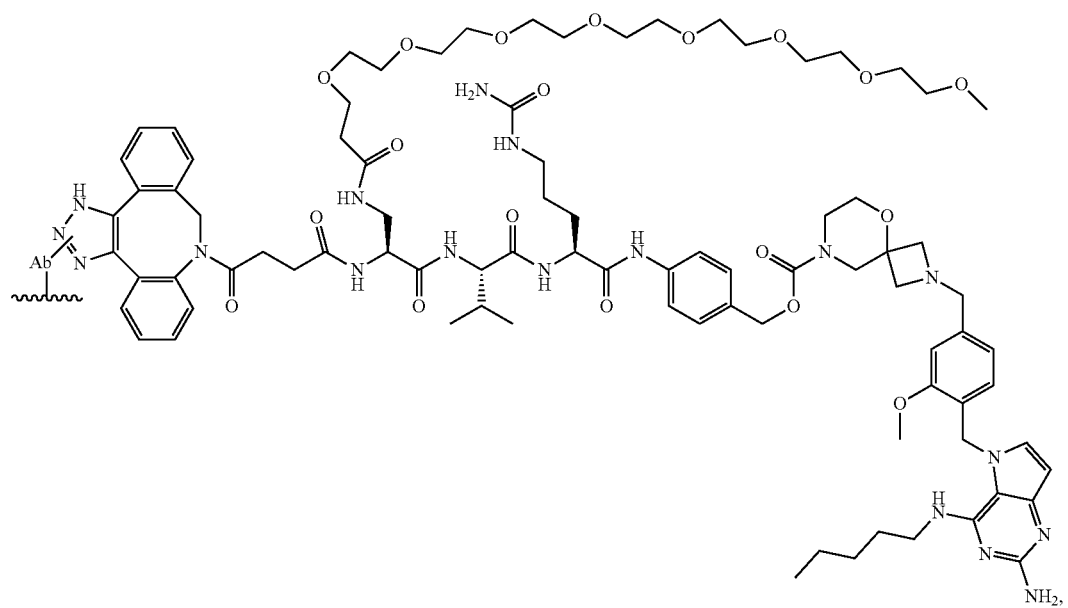
Compound 401
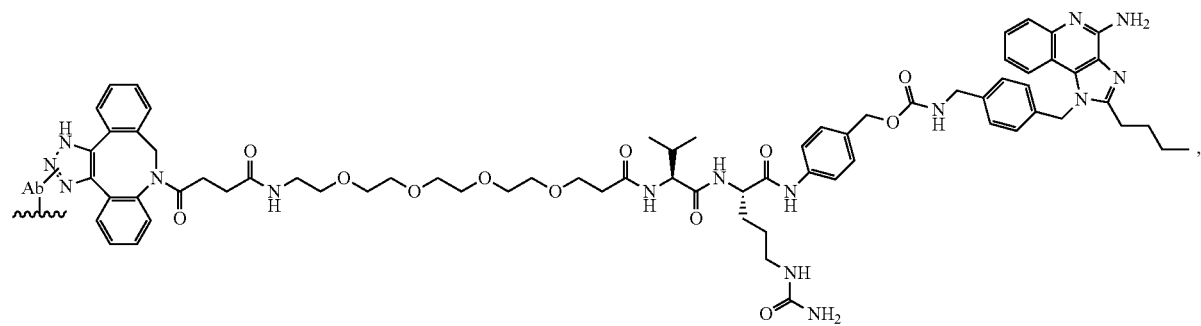

Compound 501
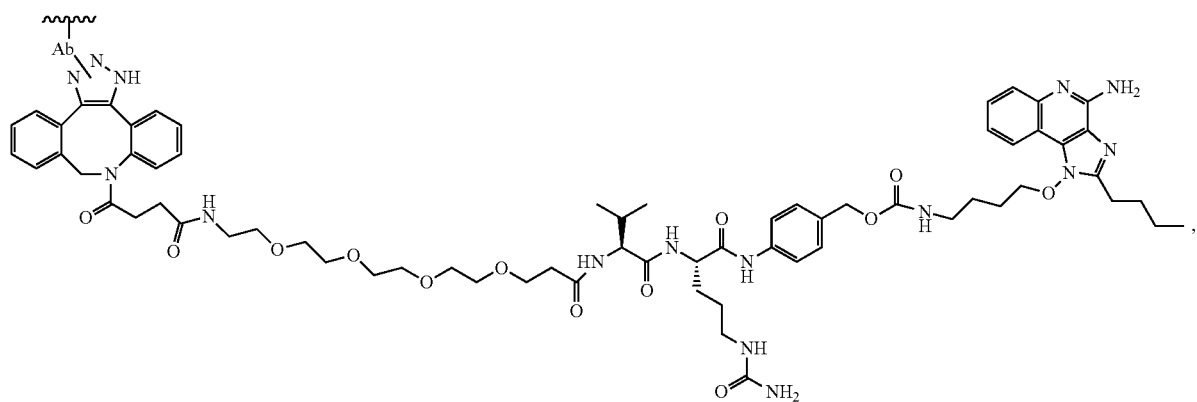
Compound 104
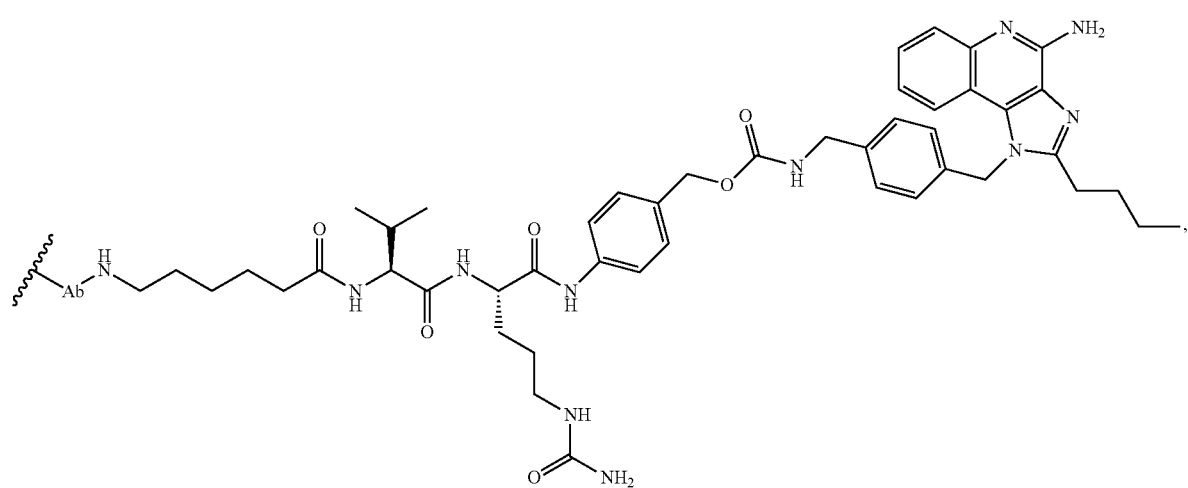
Compound 1001
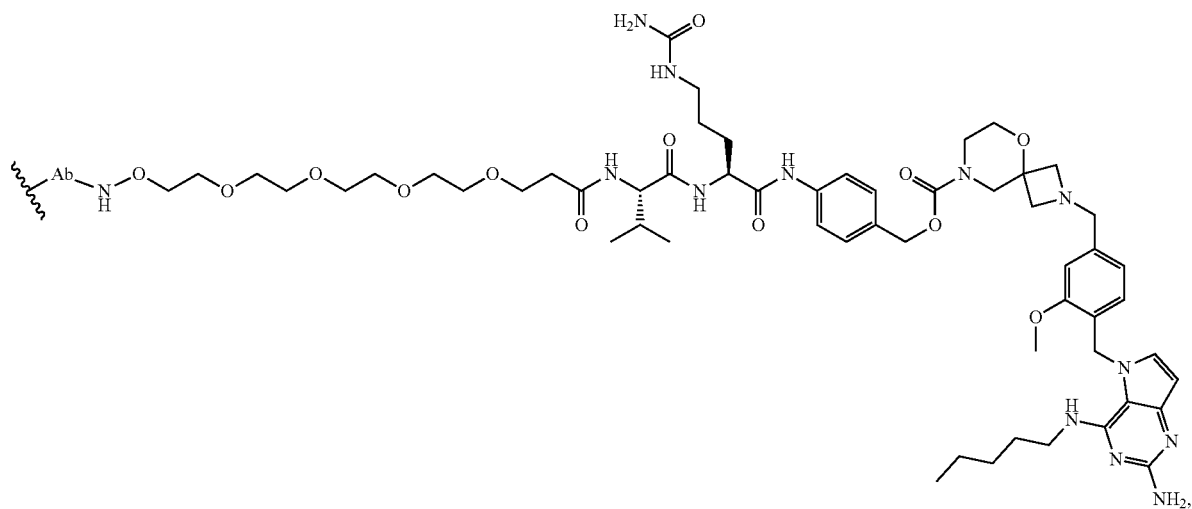

-continued
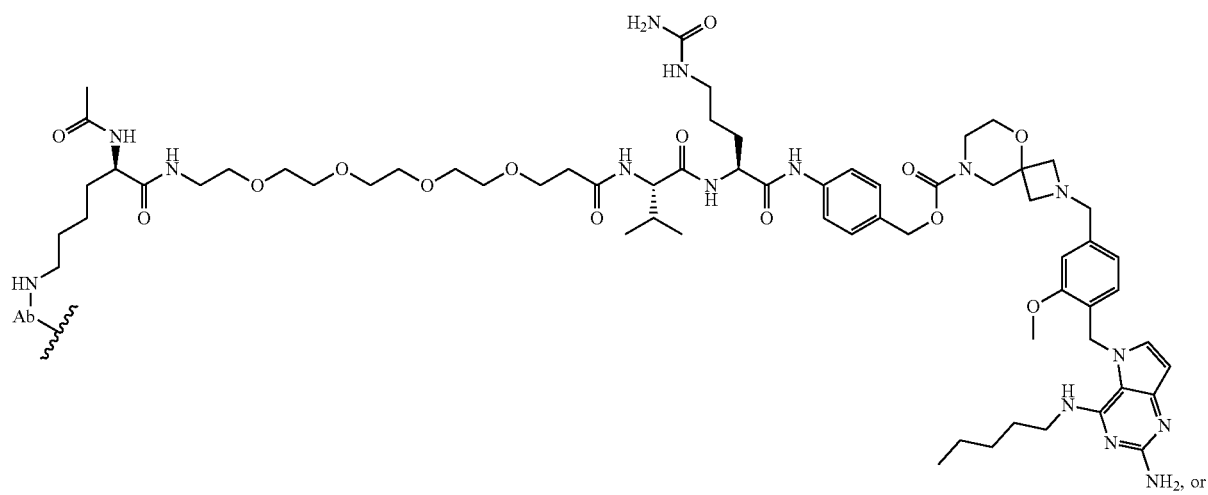
Compound 1002
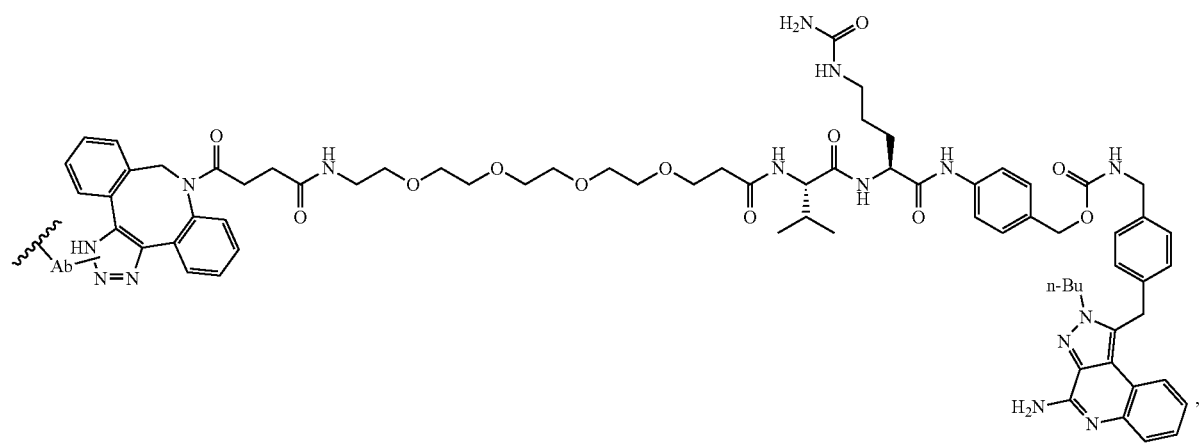
Compound 801
wherein each
indicates a point of attachment to the rest of the formula.
In some embodiments of Formula (I) and/or Formula (II), PA is selected from the group consisting of:
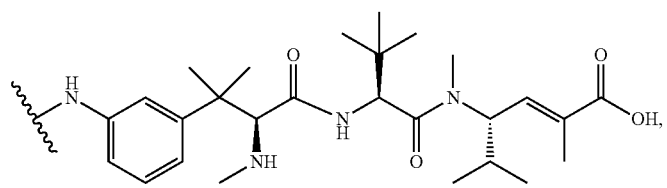
Compound 319

-continued
Compound 320
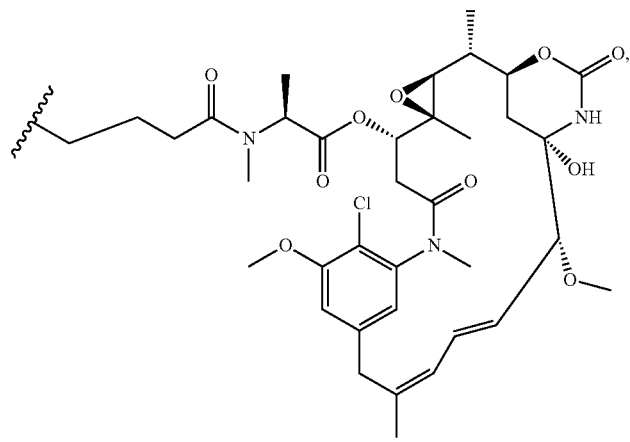
Compound 321
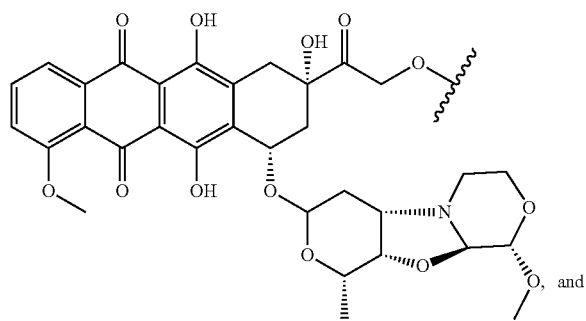
, and
Compound 322
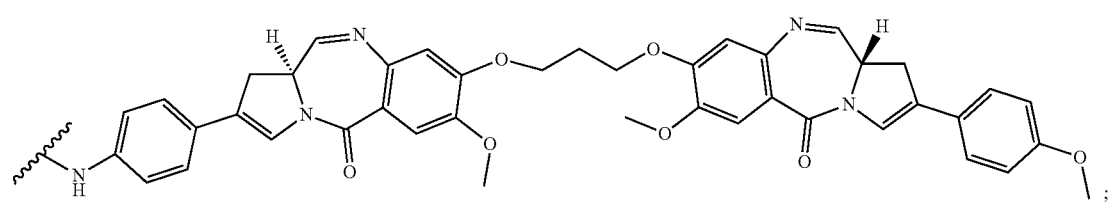
;

wherein each
indicates a point of attachment to the rest of the formula.
In some embodiments of Formula (I) and/or Formula (II),
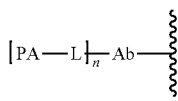
has a structure selected from the group consisting of:
Compound 101
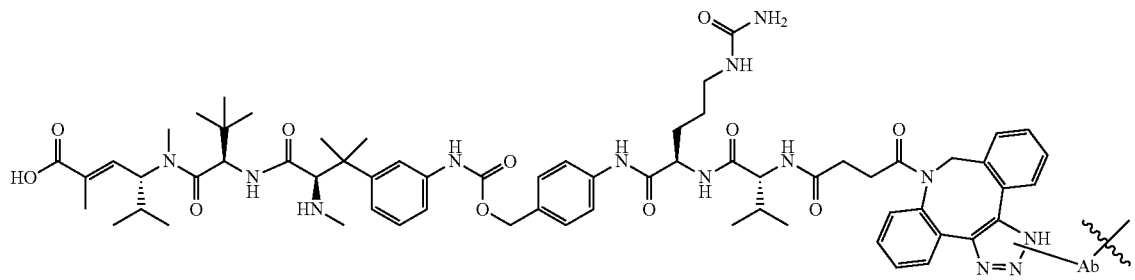
Compound 201
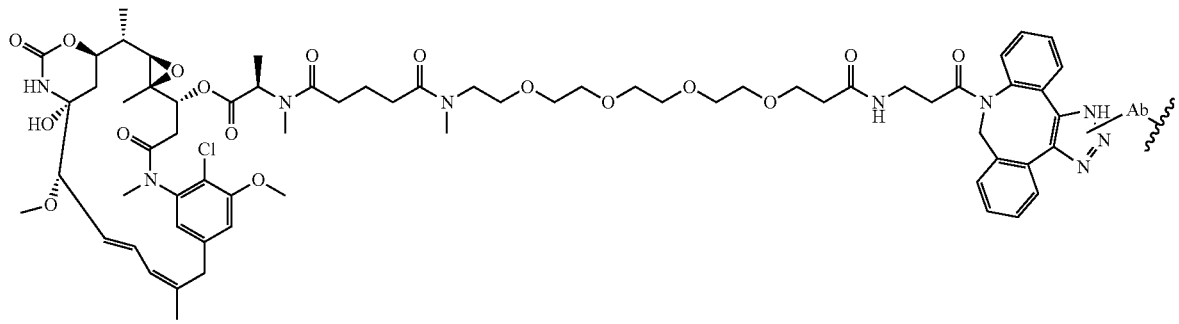
Compound 301
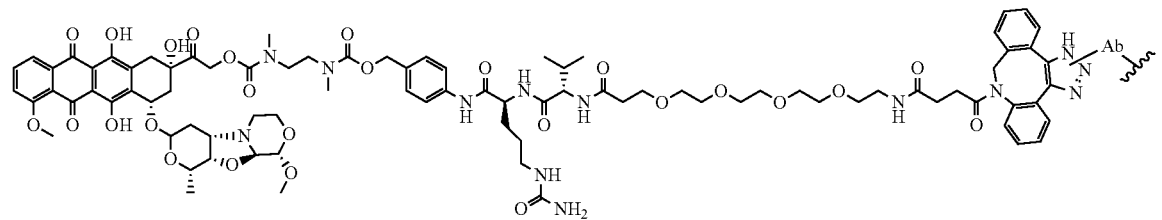
,
Compound 901
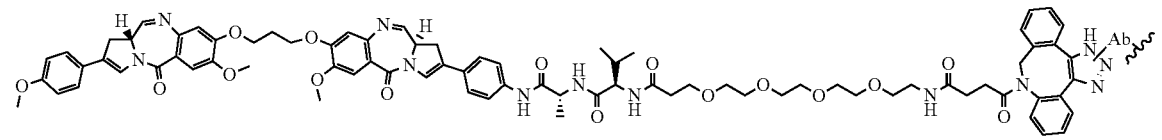
, or a pharmaceutically acceptable salt, solvate, stereoisomer, tautomer or mixture of regioisomers thereof, wherein each
indicates a point of attachment to the rest of the formula.
In some embodiments of Formula (I) and/or Formula (II), the antibody conjugate is selected from the group consisting of:
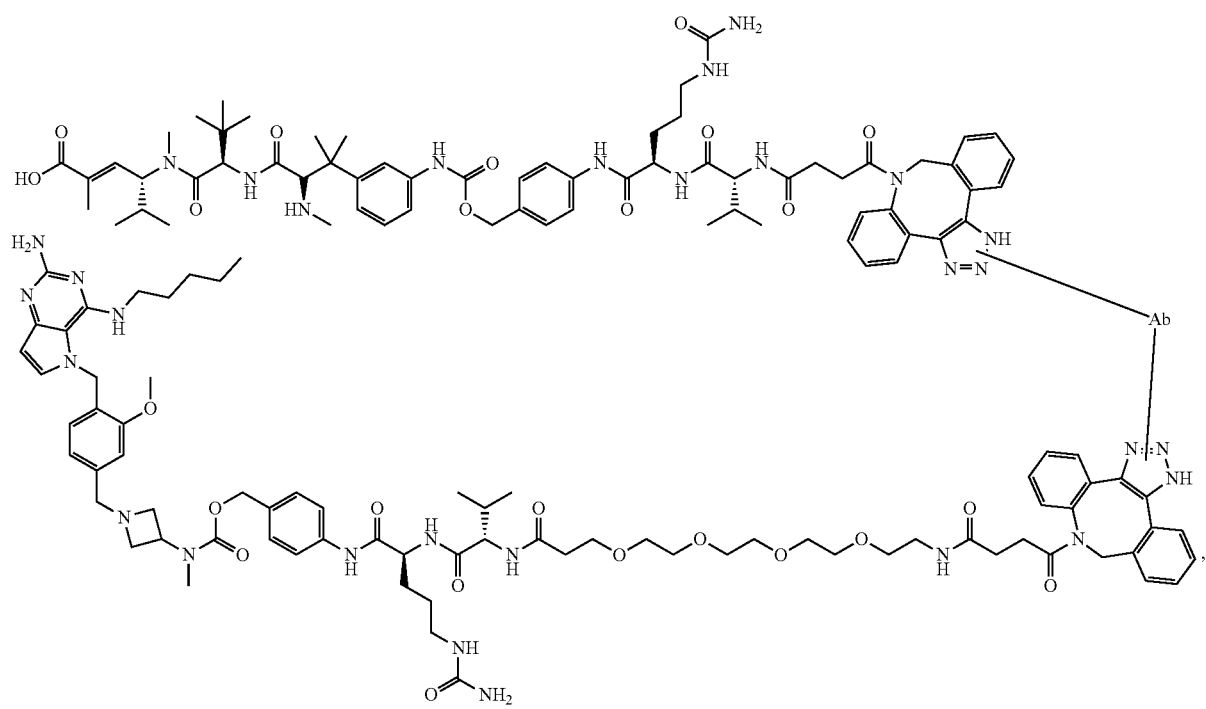
Cmpd. 101/103
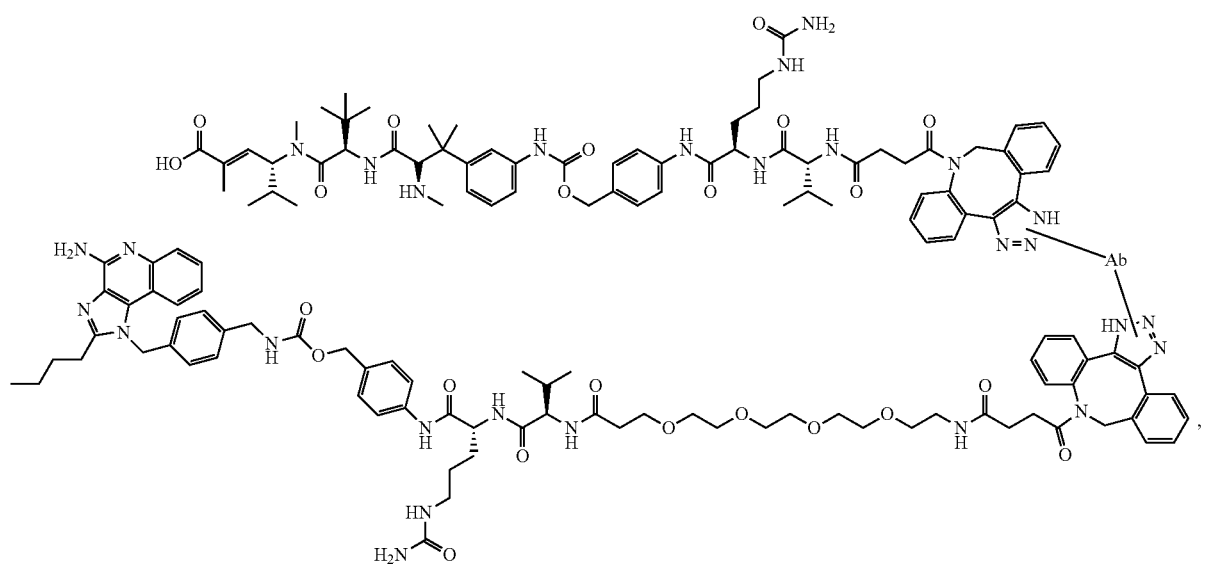
Cmpd. 101/104

-continued
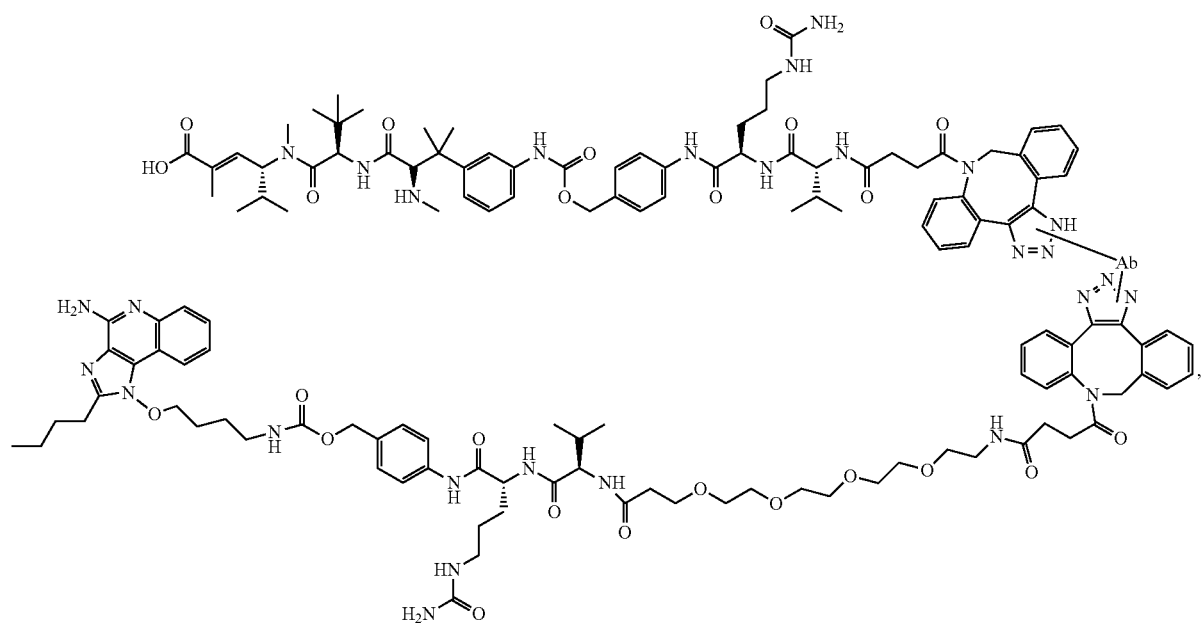
Cmpd. 101/501
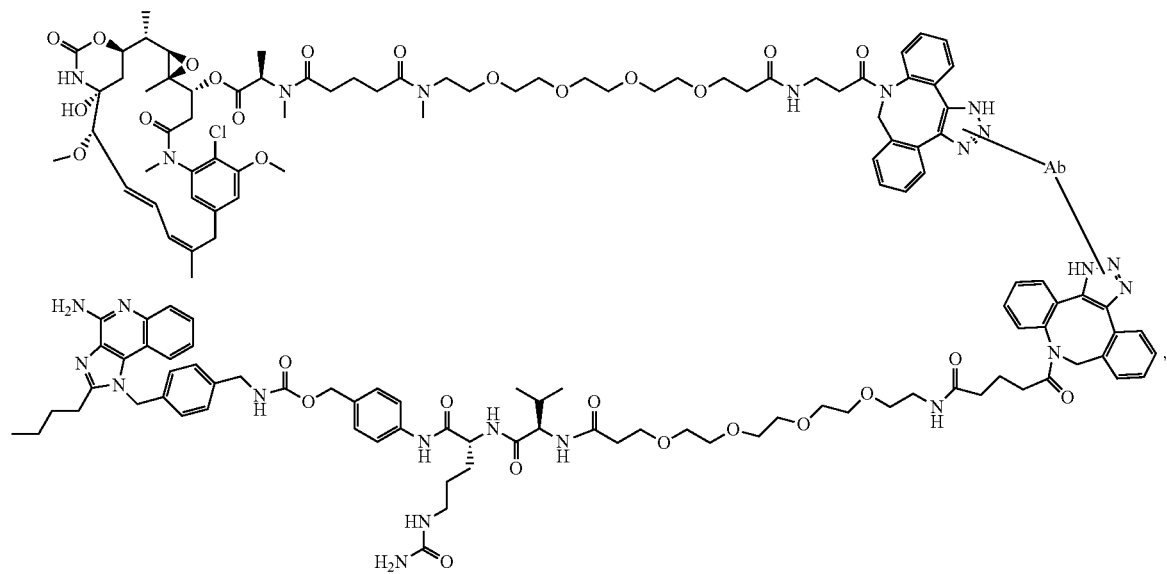
Cmpd. 201/401

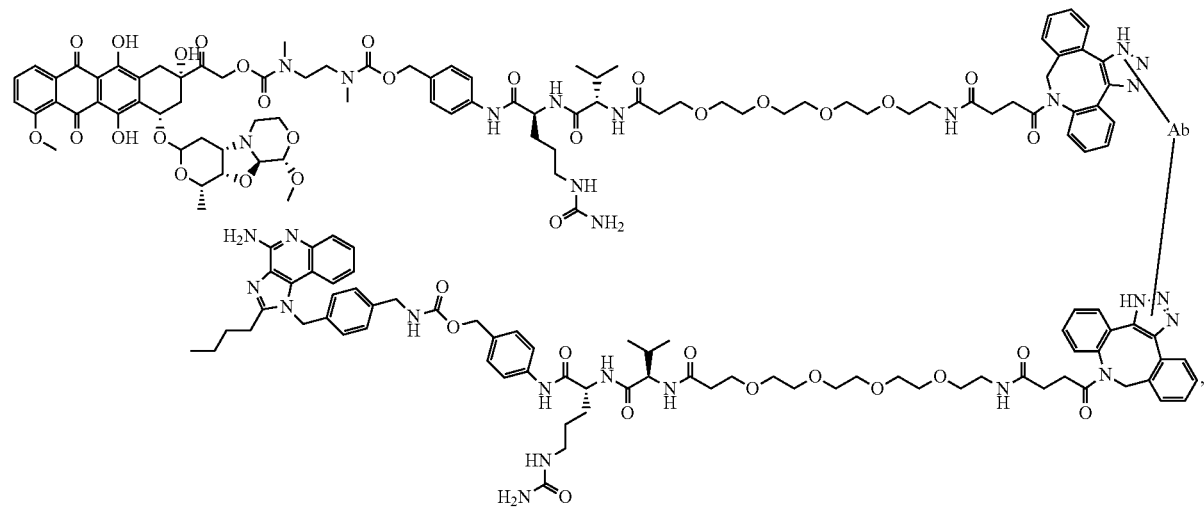
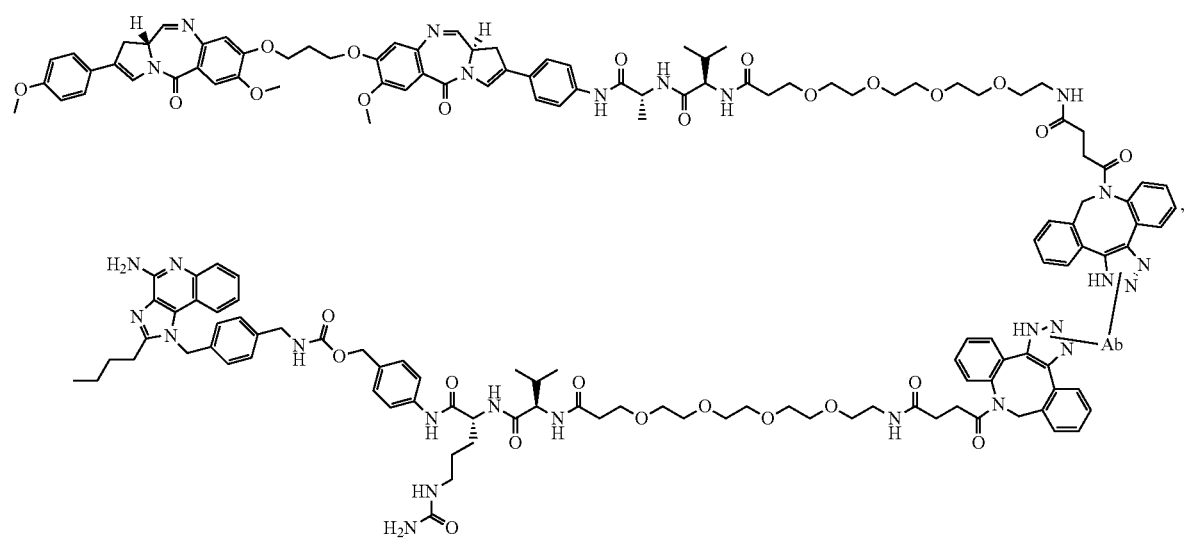
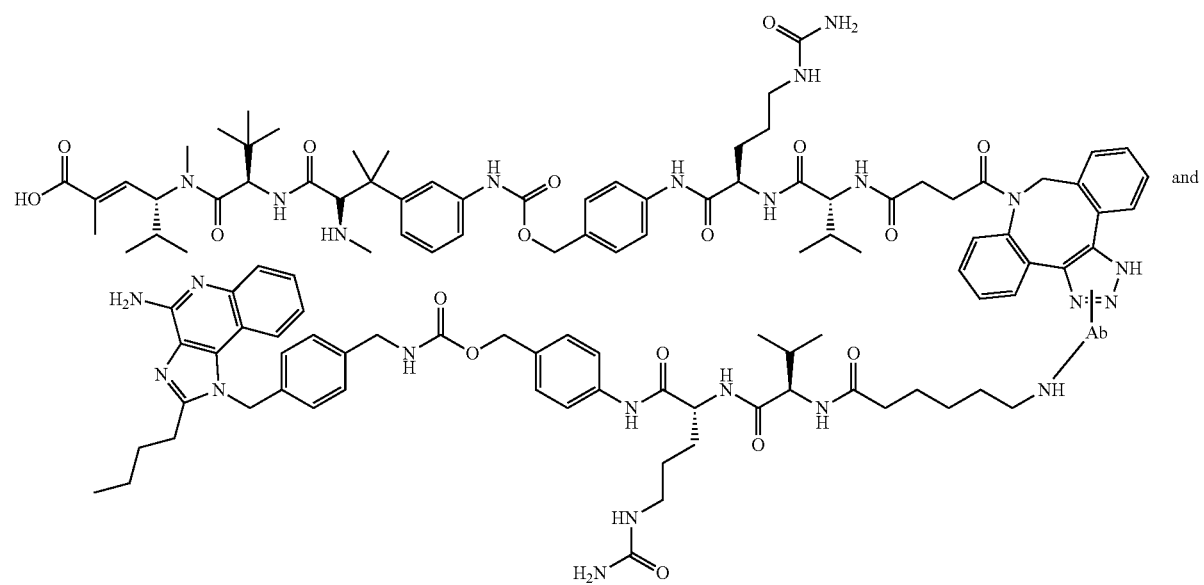

-continued

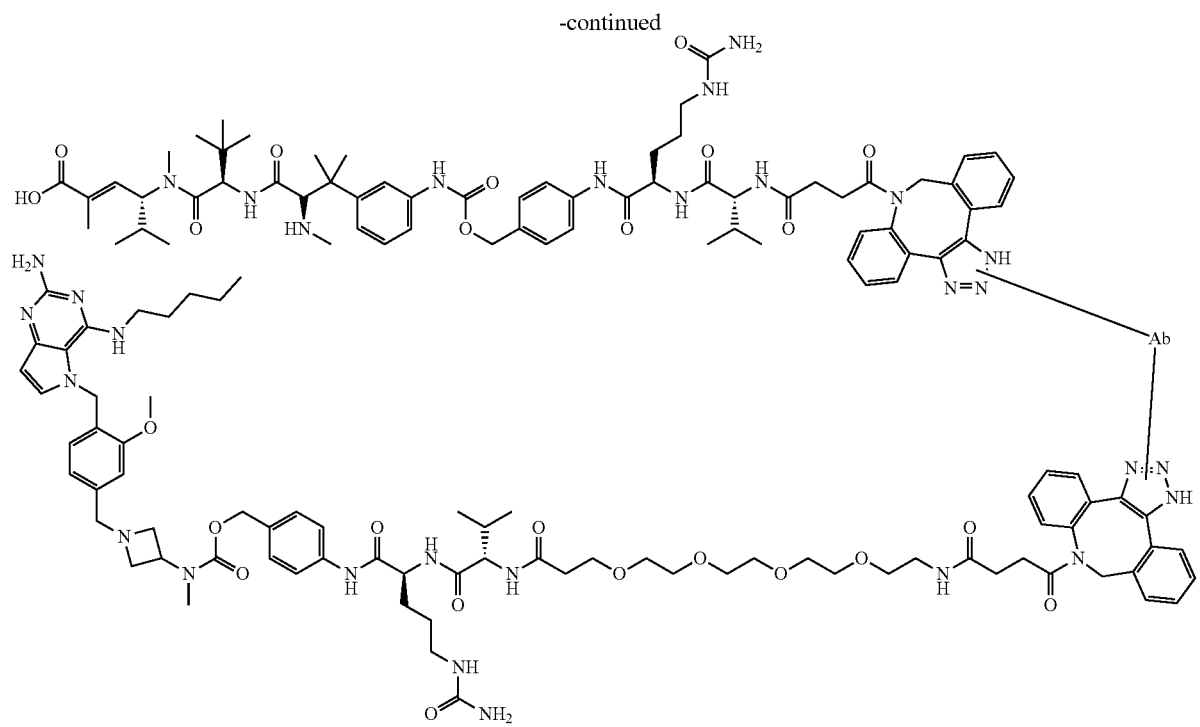

or a pharmaceutically acceptable salt, solvate, stereoisomer, tautomer or mixture of regioisomers thereof.

As used herein, when an antibody is conjugated to a linker precursor, for convenience the conjugate is depicted herein, in some or any embodiments, as follows:

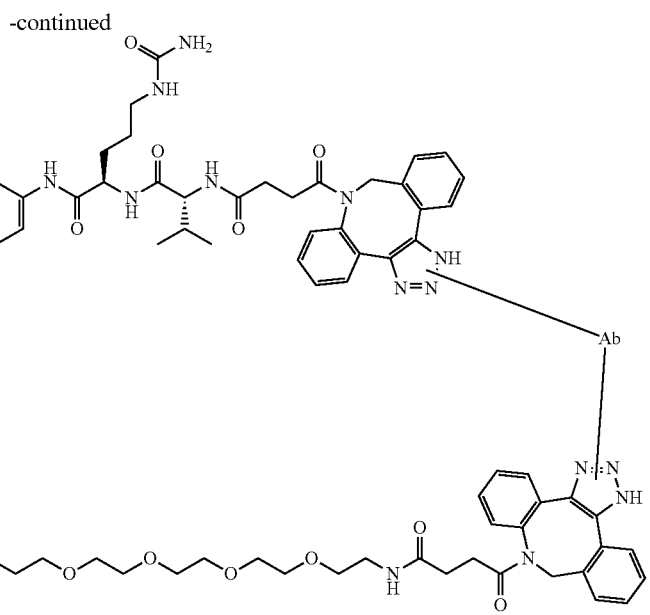

wherein

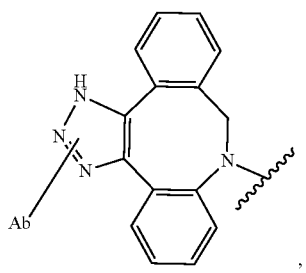

indicates the point of attachment to the rest of the molecule. It will be understood by those of skill in the art that the antibody may be bonded to one of two nitrogens on the triazole, thereby forming two possible regioisomers as shown below:

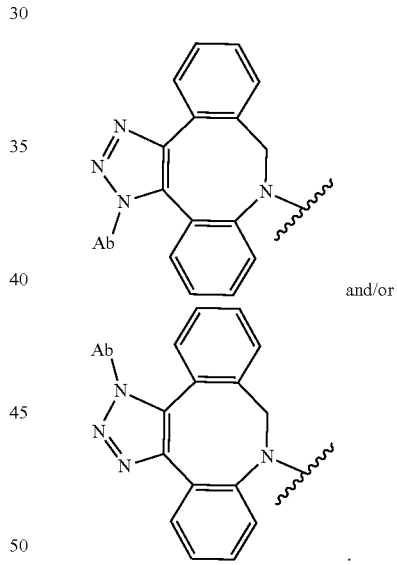

As such, either regioisomer or a mixture of possible regioisomers are provided herein. When more than two regioisomers are possible, all individual regioisomers, and all mixtures thereof, are provided herein.

For any of the preceding embodiments, also contemplated with the scope of embodiments presented herein are antibody drug conjugates where the antibody is selected from various therapeutic antibodies approved for use, in clinical trials, or in development for clinical use. Such therapeutic antibodies include, but are not limited to, rituximab (Rituxan®, IDEC/Genentech/Roche) (see, for example, U.S. Pat. No. 5,736,137), a chimeric anti-CD20 antibody approved to treat Non-Hodgkin's lymphoma; HuMax-CD20, an anti-CD20 currently being developed by Genmab, an anti-CD20 antibody described in U.S. Pat. No. 5,500,362, AME-133 (Applied Molecular Evolution), hA20 (Immunomedics, Inc.), HumaLYM (Intracel), and PR070769 (PCT Application No. PCT/US2003/040426), trastuzumab (Herceptin®, Genentech) (see, for example, U.S. Pat. No. 5,677,171), a humanized anti-Her2/neu antibody approved to treat breast cancer; pertuzumab (rhuMab-2C4, Omnitarg®), currently being developed by Genentech; an anti-Her2 antibody (U.S. Pat. No. 4,753,894); cetuximab (Erbitux®, Imclone) (U.S. Pat. No. 4,943,533; PCT Publication No. WO 96/40210), a chimeric anti-EGFR antibody in clinical trials for a variety of cancers; ABX-EGF (U.S. Pat. No. 6,235,883), currently being developed by Abgenix-Immunex-Amgen; HuMax-EGFr (U.S. Pat. No. 7,247,301), currently being developed by Genmab; 425, EMD55900, EMD62000, and EMD72000 (Merck KGaA) (U.S. Pat. No. 5,558,864; Murthy, et al. (1987) Arch. Biochem. Biophys. 252(2): 549-60; Rodeck, et al. (1987) J. Cell. Biochem. 35(4): 315-20; Kettleborough, et al. (1991) Protein Eng. 4(7): 773-83); ICR62 (Institute of Cancer Research) (PCT Publication No. WO 95/20045; Modjtahedi, et al. (1993) J. Cell. Biophys. 22(I-3): 129-46; Modjtahedi, et al. (1993) Br. J. Cancer 67(2): 247-53; Modjtahedi, et al. (1996) Br. J. Cancer 73(2): 228-35; Modjtahedi, et al. (2003) Int. J. Cancer 105(2): 273-80); TheraCIM hR3 (YM Biosciences, Canada and Centro de Immunologia Molecular, Cuba (U.S. Pat. Nos. 5,891,996; 6,506,883; Mateo, et al. (1997) Immunotechnol. 3(1): 71-81); mAb-806 (Ludwig Institute for Cancer Research, Memorial Sloan-Kettering) (Jungbluth, et al. (2003) Proc. Natl. Acad. Sci. USA. 100(2): 639-44); KSB-102 (KS Biomedix); MR1-1 (IVAX, National Cancer Institute) (PCT Publication No. WO 01/62931A2); and (Scancell) (PCT Publication No. WO 01/88138); alemtuzumab (Campath®, Millenium), a humanized mAb currently approved for treatment of B-cell chronic lymphocytic leukemia; muromonab-CD3 (Orthoclone OKT3®), an anti-CD3 antibody developed by Ortho Biotech/Johnson & Johnson, ibritumomab tiuxetan (Zevalin®), an anti-CD20 antibody developed by IDEC/Schering AG, gemtuzumab ozogamicin (Mylotarg®), an anti-CD33 (p67 protein) antibody developed by Celltech/Wyeth, alefacept (Amevive®), an anti-LFA-3 Fc fusion developed by Biogen), abciximab (ReoPro®), developed by Centocor/Lilly, basiliximab (Simulect®), developed by Novartis, palivizumab (Synagis®), developed by Medimmune, infliximab (Remicade®), an anti-TNFalpha antibody developed by Centocor, adalimumab (Humira®), an anti-TNFalpha antibody developed by Abbott, Humicade®, an anti-TNFalpha antibody developed by Celltech, golimumab (CNTO-148), a fully human TNF antibody developed by Centocor, etanercept (Enbrel®), an p75 TNF receptor Fc fusion developed by Immunex/Amgen, lenercept, an p55TNF receptor Fc fusion previously developed by Roche, ABX-CBL, an anti-CD147 antibody being developed by Abgenix, ABX-IL8, an anti-IL8 antibody being developed by Abgenix, ABX-MA1, an anti-MUC18 antibody being developed by Abgenix, Pemtumomab (R1549, 90Y-muHMFG1), an anti-MUC1 in development by Antisoma, Therex (R1550), an anti-MUC1 antibody being developed by Antisoma, AngioMab (AS1405), being developed by Antisoma, HuBC-1, being developed by Antisoma, Thioplatin (AS1407) being developed by Antisoma, Antegren® (natalizumab), an anti-alpha-4-beta-1 (VLA-4) and alpha-4-beta-7 antibody being developed by Biogen, VLA-1 mAb, an anti-VLA-1 integrin antibody being developed by Biogen, LTBR mAb, an anti-lymphotoxin beta receptor (LTBR) antibody being developed by Biogen, CAT-152, an anti-TGF-0 antibody being developed by Cambridge Antibody Technology, ABT 874 (J695), an anti-IL-12 p40 antibody being developed by Abbott, CAT-192, an anti-TGFβ1 antibody being developed by Cambridge Antibody Technology and Genzyme, CAT-213, an anti-Eotaxin1 antibody being developed by Cambridge Antibody Technology, LymphoStat-B® an anti-Blys antibody being developed by Cambridge Antibody Technology and Human Genome Sciences Inc., TRAIL-R1 mAb, an anti-TRAIL-R1 antibody being developed by Cambridge Antibody Technology and Human Genome Sciences, Inc., Avastin® bevacizumab, rhuMAb-VEGF), an anti-VEGF antibody being developed by Genentech, an anti-HER receptor family antibody being developed by Genentech, Anti-Tissue Factor (ATF), an anti-Tissue Factor antibody being developed by Genentech, Xolair® (Omalizumab), an anti-IgE antibody being developed by Genentech, Raptiva® (Efalizumab), an anti-CD11a antibody being developed by Genentech and Xoma, MLN-02 Antibody (formerly LDP-02), being developed by Genentech and Millenium Pharmaceuticals, HuMax CD4, an anti-CD4 antibody being developed by Genmab, HuMax-IL15, an anti-IL15 antibody being developed by Genmab and Amgen, HuMax-Inflam, being developed by Genmab and Medarex, HuMax-Cancer, an anti-Heparanase I antibody being developed by Genmab and Medarex and Oxford GcoSciences, HuMax-Lymphoma, being developed by Genmab and Amgen, HuMax-TAC, being developed by Genmab, IDEC-131, and anti-CD40L antibody being developed by IDEC Pharmaceuticals, IDEC-151 (Clenoliximab), an anti-CD4 antibody being developed by IDEC Pharmaceuticals, IDEC-114, an anti-CD80 antibody being developed by IDEC Pharmaceuticals, IDEC-152, an anti-CD 23 being developed by IDEC Pharmaceuticals, anti-macrophage migration factor (MIF) antibodies being developed by IDEC Pharmaceuticals, BEC2, an anti-idiotypic antibody being developed by Imclone, IMC-1C11, an anti-KDR antibody being developed by Imclone, DC101, an anti-flk-1 antibody being developed by Imclone, anti-VE cadherin antibodies being developed by Imclone, CEA-Cide® (labetuzumab), an anti-carcinoembryonic antigen (CEA) antibody being developed by Immunomedics, LymphoCide® (Epratuzumab), an anti-CD22 antibody being developed by Immunomedics, AFP-Cide, being developed by Immunomedics, MyelomaCide, being developed by Immunomedics, LkoCide, being developed by Immunomedics, ProstaCide, being developed by Immunomedics, MDX-010, an anti-CTLA4 antibody being developed by Medarex, MDX-060, an anti-CD30 antibody being developed by Medarex, MDX-070 being developed by Medarex, MDX-018 being developed by Medarex, Osidem® (IDM-1), and anti-Her2 antibody being developed by Medarex and Immuno-Designed Molecules, HuMax®-CD4, an anti-CD4 antibody being developed by Medarex and Genmab, HuMax-IL15, an anti-IL15 antibody being developed by Medarex and Genmab, CNTO 148, an anti-TNFα antibody being developed by Medarex and Centocor/J&J, CNTO 1275, an anti-cytokine antibody being developed by Centocor/J&J, MOR101 and MOR102, anti-intercellular adhesion molecule-1 (ICAM-1) (CD54) antibodies being developed by MorphoSys, MOR201, an anti-fibroblast growth factor receptor 3 (FGFR-3) antibody being developed by MorphoSys, Nuvion® (visilizumab), an anti-CD3 antibody being developed by Protein Design Labs, HuZAF®, an anti-gamma interferon antibody being developed by Protein Design Labs, Anti-α5β1 Integrin, being developed by Protein Design Labs, anti-IL-12, being developed by Protein Design Labs, ING-1, an anti-Ep-CAM antibody being developed by Xoma, Xolair® (Omalizumab) a humanized anti-IgE antibody developed by Genentech and Novartis, and MLN01, an anti-Beta2 integrin antibody being developed by Xoma. In another embodiment, the therapeutics include KRN330 (Kirin); huA33 antibody (A33, Ludwig Institute for Cancer Research); CNTO 95 (alpha V integrins, Centocor); MEDI-522 (alpha V03integrin, Medimmune); volociximab (alpha V1 integrin, Biogen/PDL); Human mAb 216 (B cell glycosolated epitope, NCl); BiTE MT103 (bispecific CD19×CD3, Medimmune); 4G7xH22 (Bispecific BcellxFcgammaRl, Medarex/Merck KGa); rM28 (Bispecific CD28xMAPG, EP Patent No. EP1444268); MDX447 (EMD 82633) (Bispecific CD64×EGFR, Medarex); Catumaxomab (removab) (Bispecific EpCAM×anti-CD3, Trion/Fres); Ertumaxomab (bispecific HER2/CD3, Fresenius Biotech); oregovomab (OvaRex) (CA-125, ViRexx); Rencarex® (WX G250) (carbonic anhydrase IX, Wilex); CNTO 888 (CCL2, Centocor); TRC105 (CD105 (endoglin), Tracon); BMS-663513 (CD137 agonist, Bristol Myers Squibb); MDX-1342 (CD19, Medarex); Siplizumab (MEDI-507) (CD2, Medimmune); Ofatumumab (Humax-CD20) (CD20, Genmab); Rituximab (Rituxan) (CD20, Genentech); veltuzumab (hA20) (CD20, Immunomedics); Epratuzumab (CD22, Amgen); lumiliximab (IDEC 152) (CD23, Biogen); muromonab-CD3 (CD3, Ortho); HuM291 (CD3 fc receptor, PDL Biopharma); HeFi-1, CD30, NCl); MDX-060 (CD30, Medarex); MDX-1401 (CD30, Medarex); SGN-30 (CD30, Seattle Genentics); SGN-33 (Lintuzumab) (CD33, Seattle Genentics); Zanolimumab (HuMax-CD4) (CD4, Genmab); HCD122 (CD40, Novartis); SGN-40 (CD40, Seattle Genentics); Campath1h (Alemtuzumab) (CD52, Genzyme); MDX-1411 (CD70, Medarex); hLL1 (EPB-1) (CD74.38, Immunomedics); Galiximab (IDEC-144) (CD80, Biogen); MT293 (TRC093/D93) (cleaved collagen, Tracon); HuLuc63 (CS1, PDL Pharma); ipilimumab (MDX-010) (CTLA4, Bristol Myers Squibb); Tremelimumab (Ticilimumab, Cβ-675,2) (CTLA4, Pfizer); HGS-ETR1 (Mapatumumab) (DR4TRAIL-R1 agonist, Human Genome Science/Glaxo Smith Kline); AMG-655 (DR5, Amgen); Apomab (DR5, Genentech); CS-1008 (DR5, Daiichi Sankyo); HGS-ETR2 (lexatumumab) (DR5TRAIL-R2 agonist, HGS); Cetuximab (Erbitux) (EGFR, Imclone); IMC-11F8, (EGFR, Imclone); Nimotuzumab (EGFR, YM Bio); Panitumumab (Vectabix) (EGFR, Amgen); Zalutumumab (HuMaxEGFr) (EGFR, Genmab); CDX-110 (EGFRvIII, AVANT Immunotherapeutics); adecatumumab (MT201) (Epcam, Merck); edrecolomab (Panorex, 17-1A) (Epcam, Glaxo/Centocor); MORAb-003 (folate receptor a, Morphotech); KW-2871 (ganglioside GD3, Kyowa); MORAb-009 (Gβ-9, Morphotech); CDX-1307 (MDX-1307) (hCGb, Celldex); Trastuzumab (Herceptin) (HER2, Celldex); Pertuzumab (rhuMAb 2C4) (HER2 (DI), Genentech); apolizumab (HLA-DR beta chain, PDL Pharma); AMG-479 (IGF-1R, Amgen); anti-IGF-1R R1507 (IGF1-R, Roche); CP 751871 (IGF1-R, Pfizer); IMC-A12 (IGF1-R, Imclone); BIIB022 (IGF-1R, Biogen); Mik-beta-1 (IL-2Rb (CD122), Hoffman LaRoche); CNTO 328 (IL6, Centocor); Anti-KIR (1-7F9) (Killer cell Ig-like Receptor (KIR), Novo); Hu3S193 (Lewis (y), Wyeth, Ludwig Institute of Cancer Research); hCBE-11 (LTβR, Biogen); HuHMFG1 (MUC1, Antisoma/NCl); RAV12 (N-linked carbohydrate epitope, Raven); CAL (parathyroid hormone-related protein (PTH-rP), University of California); CT-011 (PD1, CureTech); MDX-1106 (ono-4538) (PD1, Medarex/Ono); MAb CT-011 (PD1, Curetech); IMC-3G3 (PDGFRa, Imclone); bavituximab (phosphatidylserine, Peregrine); huJ591 (PSMA, Cornell Research Foundation); muJ591 (PSMA, Cornell Research Foundation); GC1008 (TGFb (pan) inhibitor (IgG4), Genzyme); Infliximab (Remicade) (TNFa, Centocor); A27.15 (transferrin receptor, Salk Institute, INSERN WO 2005/111082); E2.3 (transferrin receptor, Salk Institute); Bevacizumab (Avastin) (VEGF, Genentech); HuMV833 (VEGF, Tsukuba Research Lab, PCT Publication No. WO/2000/034337, University of Texas); IMC-18F1 (VEGFR1, Imclone); IMC-1121 (VEGFR2, Imclone).

Examples of useful bispecific parent antibodies include, but are not limited to, those with one antibody directed against a tumor cell antigen and the other antibody directed against a cytotoxic trigger molecule such as anti-FcγRI/anti-CD 15, anti-p185$^{HER2}$/FcγRIII (CD16), anti-CD3/anti-malignant B-cell (1D10), anti-CD3/anti-p185$^H$R2, anti-CD3/anti-p97, anti-CD3/anti-renal cell carcinoma, anti-CD3/anti-OVCAR-3, anti-CD3/L-D1 (anti-colon carcinoma), anti-CD3/anti-melanocyte stimulating hormone analog, anti-EGF receptor/anti-CD3, anti-CD3/anti-CAMA1, anti-CD3/anti-CD19, anti-CD3/MoV18, anti-neural cell adhesion molecule (NCAM)/anti-CD3, anti-folate binding protein (FBP)/anti-CD3, anti-pan carcinoma associated antigen (AMOC-31)/anti-CD3; bispecific antibodies with one antibody which binds specifically to a tumor antigen and another antibody which binds to a toxin such as anti-saporin/anti-Id-1, anti-CD22/anti-saporin, anti-CD7/anti-saporin, anti-CD38/anti-saporin, anti-CEA/anti-ricin A chain, anti-interferon-α (IFN-α)/anti-hybridoma idiotype, anti-CEA/anti-vinca alkaloid; bispecific antibodies for converting enzyme activated prodrugs such as anti-CD30/anti-alkaline phosphatase (which catalyzes conversion of mitomycin phosphate prodrug to mitomycin alcohol); bispecific antibodies which can be used as fibrinolytic agents such as anti-fibrin/anti-tissue plasminogen activator (tPA), anti-fibrin/anti-urokinase-type plasminogen activator (uPA); bispecific antibodies for targeting immune complexes to cell surface receptors such as anti-low density lipoprotein (LDL)/anti-Fc receptor (e.g. FcγRI, FcγRII or FcγRIII); bispecific antibodies for use in therapy of infectious diseases such as anti-CD3/anti-herpes simplex virus (HSV), anti-T-cell receptor: CD3 complex/anti-influenza, anti-FcγR/anti-HIV; bispecific antibodies for tumor detection in vitro or in vivo such as anti-CEA/anti-EOTUBE, anti-CEA/anti-DPTA, anti-anti-p185$^{HER2}$/anti-hapten; bispecific antibodies as vaccine adjuvants (see Fanger, M W et al., *Crit Rev Immunol.* 1992; 12(34):101-24, which is incorporated by reference herein); and bispecific antibodies as diagnostic tools such as anti-rabbit IgG/anti-ferritin, anti-horse radish peroxidase (HRP)/anti-hormone, anti-somatostatin/anti-substance P, anti-HRP/anti-FITC, anti-CEA/anti-β-galactosidase (see Nolan, O et R. O'Kennedy, Biochim Biophys Acta. 1990 Aug. 1; 1040 (1):1-11, which is incorporated by reference herein). Examples of trispecific antibodies include anti-CD3/anti-CD4/anti-CD37, anti-CD3/anti-CD5/anti-CD37, and anti-CD3/anti-CD8/anti-CD37.

In any of the foregoing embodiments, for instance wherein the antibody conjugate has a structure according to Formulas (I), (II), (Xa-e), and/or (XIa-d), the bracketed structure can be covalently bonded to one or more non-natural amino acids of the antibody, wherein the one or more non-natural amino acids are located at sites independently selected from the group consisting of: HC-F241, HC-F404, HC-Y180, and LC-K42, and combinations thereof, according to the Kabat or EU numbering scheme of Kabat. In some embodiments, the bracketed structure is covalently bonded to one or more non-natural amino acids at site HC-F404 of the antibody. In some embodiments, the bracketed structure is covalently bonded to one or more non-natural amino acids at site HC-Y180 of the antibody. In some embodiments, the bracketed structure is covalently bonded to one or more non-natural amino acids at site HC-F241 of the antibody. In some embodiments, the bracketed structure is covalently bonded to one or more non-natural amino acids at site LC-K42 of the antibody. In some embodiments, the bracketed structure is covalently bonded to one or more non-natural amino acids at sites HC-F404 and HC-Y180 of the antibody. In some embodiments, the bracketed structure is covalently bonded to one or more non-natural amino acids at sites HC-F241, HC-F404, and HC-Y180 of the antibody. In some embodiments, at least one bracketed structure is covalently bonded to a non-natural amino acid at site HC-F404 of the antibody, and at least one bracketed structure is covalently bonded a non-natural amino acid at site HC-Y180 of the antibody. In some embodiments, the bracketed structure is covalently bonded to one or more non-natural amino acids at sites HC-Y180 and LC-K42 of the antibody. In some embodiments, the bracketed structure is covalently bonded to one or more non-natural amino acids at sites HC-F404 and LC-K42 of the antibody. In some embodiments, the bracketed structure is covalently bonded to one or more non-natural amino acids at sites HC-F404, HC-Y180, and LC-K42 of the antibody. In some embodiments, the non-natural amino acid at sites HC-F404, HC-Y180 and LC-K42 are the same non-natural amino acid. In some embodiments, the non-natural amino acid at sites HC-F404, HC-Y180 and LC-K42 are the each independently selected from two different non-natural amino acids. For example, the non-natural amino acid at site HC-F404 and HC-Y180 may be a first non-natural amino acid, while the non-natural amino acid at site LC-K42 may be a different non-natural amino acid. In some embodiments, the non-natural amino acid at site HC-F404 and HC-Y180 is a residue according to Formula (30), while the non-natural amino acid at site LC-K42 is L-para-acetyl-phenylalanine. In particular embodiments, each non-natural amino acid is a residue according to Formula (30).

3. Payloads

In addition to the payloads described above, the molecular payloads can be any molecular entities that one of skill in the art might desire to conjugate to the polypeptide.

In certain embodiments, the payload is a therapeutic moiety (e.g., PA described herein). In other embodiments, the antibody conjugate can be used to deliver an immunomodulator (e.g., IM described herein) to, or in the vicinity of, its molecular target.

In some embodiments, the payload PA is a residue of a cytotoxic compound. Cytotoxic compounds include alkylating agents (e.g., cisplatin, cyclophosphamide), DNA cross-linking agents (e.g., pyrrolobenzodiazepines (PBDs) or dimers thereof), antitumor antibiotics (e.g., doxorubicin, hedamycin, septacidin), microtubule disrupters and/or antimitotic agents (e.g., maytansinoids, hemiasterlins, paclitaxel), anti-metabolites (e.g., 5-fluorouracil, methotrexate), histone-deacetylase (HDAC) inhibitors (e.g., suberanilohydroxamic acid (SAHA), telomerase inhibitors (e.g., BIBR1542) small molecules that target the SF3b subunit of the spliceosomal U2 small nuclear ribonucleoprotein (snRNP) (Spliceostatin A, meayamycin, and pladienolide B) and/or immunogenic cell death inhibitors (e.g., anthracyclines, platinum based chemotherapeutics, cyclophosphamide, mitoxantrone).

In some embodiments of Formula (I) and/or Formula (II), the payload (PA) is a residue of a cytotoxic compound selected from the group consisting of Altretamine, Ansamitocin P3, Auristatins (MMAE, MMAF), Bendamustine hydrochloride, Bleomycin, Bortezomib, Busulfan, Cabazitaxel, Capecitabine, Carboplatin, Carmustine, Chlorambucil, Cisplatin, Cladribine, Clofarabine, Colchicine, Combrestatin-A4, Cytarabine, Cyclophosphamide, Dacarbazine, Dactinomycin, Daunorubicin hydrochloride, Docetaxel, Dolastatin 10, Dolastatin 15, Doxorubicin hydrochloride, Eribulin mesylate, Epirubicin, epothilones A-F, Etoposide, Floxuridine, Fludarabine, 5-Fluorouracil, Gemcitabine, Hedamycin, Hemiasterlins (e.g., HTI-286, E7974), Idarubicin, Ifosfamide, Irinotecan, Ixabepilone, Ixazomib, Leucovorin, Lomustine, Losoxantrone, Maytansinoids (e.g., DM1, DM4), Meayamycin, Mechlorethamine, Melphalan, Mercaptopurine, Methotrexate, Mitomycin, Mitotane, Mitoxantrone, Nelarabine, Nedaplatin, Omacetaxine mepesuccinate, Oxaliplatin, Paclitaxel, Pemetrexed disodium, Pentostatin, Pladienolide B, Pixantrone, Pralatrexate, Procarbazine hydrochloride, pyrrolobenzodiazepines (PBDs, e.g., SG3199), Radium 223 dichloride, Septacidin, Spliceostatin A, Streptozocin, suberanilohydroxamic acid (SAHA), SN-38, Thioguanine, Thiotepa, Temozolomide, Teniposide, Topotecan hydrochloride, Valrubicin, Vincristine sulfate, Vinblastine sulfate, Vinedesine, and Vinorelbine tartrate. In some of such embodiments of Formula (I) and/or Formula (II), the cytotoxic compound is an immunogenic cell death agent. In some of such embodiments, the immunogenic cell death agent is selected from the group consisting of mitoxantrone, oxaliplatin, cyclophosphamide, doxorubicin, daunorubicin, epirubicin, idarubicin, and bortezomib.

In some embodiments, the payload is an antimetabolite. The antimetabolite can be, for example, a purine antagonist (e.g., azothioprine or mycophenolate mofetil), a dihydroBCMA reductase inhibitor (e.g., methotrexate), acyclovir, gangcyclovir, zidovudine, vidarabine, ribavarin, azidothymidine, cytidine arabinoside, amantadine, dideoxyuridine, iododeoxyuridine, poscamet, or trifluridine.

Depending on the initiation stimulus, cancer cell death triggered by cytotoxic compounds can be immunogenic or non-immunogenic. Cytotoxic compounds vary in their ability to induce immunogenic cell death, and consequently anti-cancer immunity. The term "immunogenic cell death" is used to characterize a particular form of cell death that stimulates an immune response to certain antigens released by dying cancer cells (A. Sistigu, et al., *Semin. Immunopathol.* 33 (2011) 369-383). Among a large array of antineoplastic agents, only a few cytotoxic compounds were described to induce ICD. The criteria met by bonafide ICD inducers are that pre-treatment of cancer cells with such compounds, followed by inoculation into immunocompetent mice, will result in tumor rejection upon re-challenge with untreated tumor cells (L. Zitvogel, Immunity 39 (2013) 74-88). These tumor rejections after vaccination of mice with compound-treated tumor cells, are associated with the establishment of immunological memory. Compounds shown to induce high levels of ICD include various anthracyclines such as doxorubicin, epirubicin, and idarubicin, which are commonly used against a variety of malignancies (N. Casares, et al., *J. Exp. Med.* 202 (2005) 1691-1701; M. Obeid, et al., *Nat. Med.* 13 (2007) 54-61; J. Fucikova et al., *Cancer Res.* 71 (2011) 4821-4833). The alkylating agent oxaliplatin, a platinum derivative used in combination regimens to treat advanced colorectal carcinoma, reportedly induces ICD while cisplatin does not (A. Tesniere et al., *Oncogene* 29 (2010) 482-491; I. Martins et al., *Oncogene* 30 (2011) 1147-1158). Other bona fide inducers of ICD are the topoisomerase II inhibitor mitoxantrone and the alkylating agent cyclophosphamide, both are used to treat several cancer types and auto-immune diseases. Bortezomib, a proteasomal inhibitor approved for multiple myeloma and mantle cell lymphoma, also induces ICD (G. Schiavoni et al., *Cancer Res.* 71 (2011) 768-778; A. Sistigu et al., *Semin. Immunopathol.* 33 (2011) 369-383; M. Obeid et al., *Nat. Med.* 13 (2007) 54-61).

These therapeutic agents share in common their ability to induce specific "danger signals" or "damage-associated molecular patterns" (DAMPs) in tumor cells. ICD is characterized by endoplasmic reticulum stress leading to cell surface expression of calreticulin, followed by release of the soluble mediators HMGB1 and ATP (representing DAMPs), and type I interferon. The role of these markers in ICD has been substantiated using RNA interference or neutralizing antibodies to calreticulin or HMGB1, followed by rescue with recombinant calreticulin or HMGB1 protein, respectively (M. Obeid et al., Nat. Med. 13 (2007) 54-61; A. Tesniere et al., *Oncogene* 29 (2010) 482-491). Induction of all four markers appears to be necessary to predict an in vivo ICD response (L. Bezu et al., *Front. Immunol.* 6 (2015) 187). The various redox states of HMGB1 protein may also contribute to different immune functions, including leukocyte recruitment vs. activation (R. Kang et al., *Clin. Cancer Res.* 19 (2013) 4046-4057). The cellular and molecular mechanism involved in sensing of the danger signals involve receptors expressed by dendritic cells, including CD91 (for calreticulin), TLR4 (for HMGB1), and P2RY2/P2RX7 (for ATP) (D. V. Krysko et al., *Nat. Rev. Cancer* 12 (2012) 860-875).

Several tubulin inhibitors used as cytotoxic agents on ADCs have been reported to induce ICD. For example, when auristatin was delivered in the context of an ADC (SGN-35), it was reported to induce markers of ICD in vitro and in vivo including calreticulin, and also to activate dendritic cells (S. J. Gardai et al., *Cancer Res.* 75 (2015) Abstract No. 2469). Anthracyclines are a class of cytotoxic agents used as chemotherapy as well as in ADCs. Doxorubicin is a strong inducer of ICD as a free payload, and an anthracycline conjugated ADC has been shown to have strong ICD activity (D'Amico L et al., *J Immunother Cancer.* 2019 Jan. 21; 7(1):16). Maytansinoids, a commonly used cytotoxic agent on ADCs have also been shown to induce ICD in the context of ADC (Bauzon M, et al., *Oncoimmunology.* 2019 Jan. 22; 8(4):e1565859).

Thus, ICD is a mechanism whereby standard chemotherapy can stimulate the immune system and induces strong inflammatory responses in tumors. Certain cytotoxic agents induce the sequential generation of secreted markers which activate dendritic cell maturation, leading to MHC mediated tumor antigen cross presentation, and ultimately antigen specific CD8+ T-cell recruitment to the tumors. In particular, treatment regimens including anthracyclines (Doxorubicin) and oxaliplatin appear attractive for combination with immuno-oncology compounds, as both compounds were associated with a strong induction of immunogenic tumor cell death, thereby potentially enhancing anti-tumor immune responses (A. Sistigu et al., *Semin. Immunopathol.* 33 (2011) 369-383). Methods for assaying immunogenic cell death are as described herein and in the Examples section.

In a group of embodiments, cytotoxic agents are immunogenic cell death agents. Cytotoxic agents intrinsically endowed with the ability to trigger ICD, include and are not limited to maytansinoids, hemiasterlins, auristatins, mitoxantrone (and/or, e.g., losoxantrone (DuP 941), pixantrone (BBR 2778)), oxaliplatin (and/or other platins e.g., carboplatin, cisplatin, nedaplatin), cyclophosphamide, anthracyclines (e.g., doxorubicin, daunorubicin, epirubicin and idarubicin), and bortezomib (and/or other boronic acid containing agents, e.g., ixazomib).

In certain embodiments, the cytotoxic agent is a maytansinoid, another group of anti-tubulin agents. For example, in specific embodiments, the maytansinoid can be maytansine or DM-1 (ImmunoGen, Inc.; see also Chari et al., 1992, Cancer Res. 52:127-131).

In some embodiments, the payload is an auristatin, such as auristatin E or a derivative thereof. For example, the auristatin E derivative can be an ester formed between auristatin E and a keto acid. For example, auristatin E can be reacted with paraacetyl benzoic acid or benzoylvaleric acid to produce AEB and AEVB, respectively. Other typical auristatin derivatives include AFP (auristatin phenylalanine phenylenediamine), MMAF (monomethyl auristatin F), and MMAE (monomethyl auristatin E). The synthesis and structure of auristatin derivatives are described in U.S. Patent Application Publication Nos. 2003-0083263, 2005-0238649 and 2005-0009751; International Patent Publication No. WO 04/010957, International Patent Publication No. WO 02/088172, and U.S. Pat. Nos. 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414.

In some embodiments, the payload is a hemiasterlin. Hemiasterlins suitable for use in the antibody-drug conjugates described herein are described, for example, in International Patent Publication No. WO 2016/2016/123582, which is incorporated herein by reference in its entirety.

In some embodiments of Formula (I) and/or Formula (II), the cytotoxic compound is a maytansinoid, a hemiasterlin, an anthracycline, and/or a pyrrolobenzodiazepine. In some of such embodiments of Formula (I) and/or Formula (II), the maytansinoid is

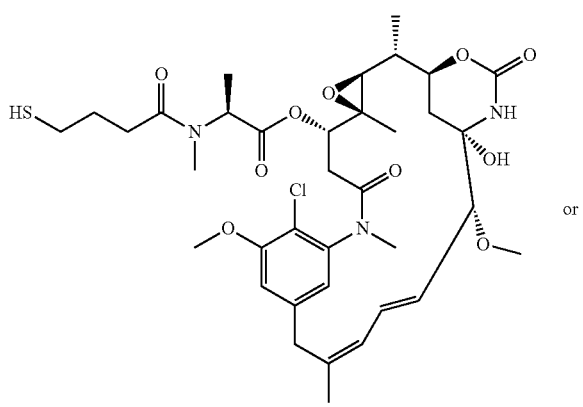

(DM1)

or

-continued
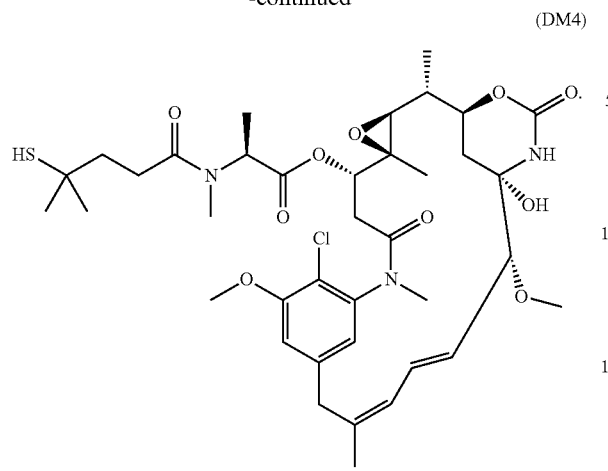
(DM4)
In other such embodiments of Formula (I) and/or Formula (II), the hemiasterlin is
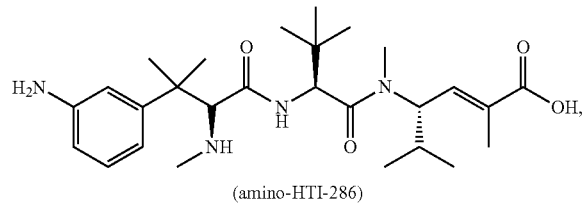
(amino-HTI-286)
-continued
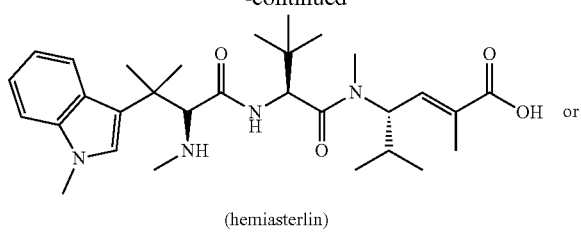
(hemiasterlin)
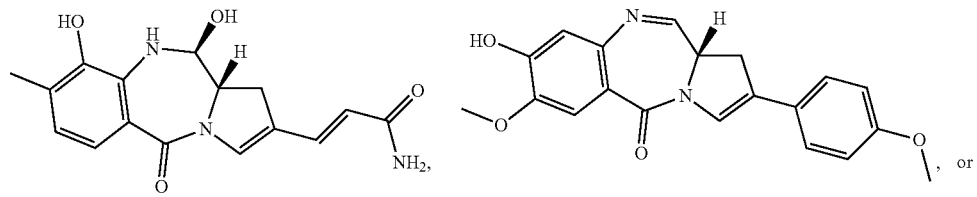
(E7974)
In further such embodiments of Formula (I) and/or Formula (II), the pyrrolobenzodiazepine is a monomer, or a dimeric derivative thereof. In some of such embodiments, the pyrrolobenzodiazepine is
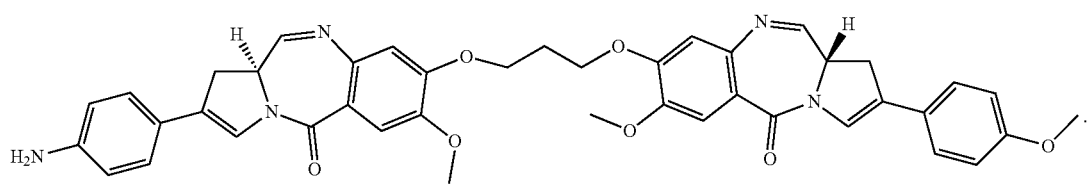

In some embodiments of Formula (I) and/or Formula (II), the immunomodulatory payload (IM) is a residue of an immunomodulatory compound selected from the group consisting of:

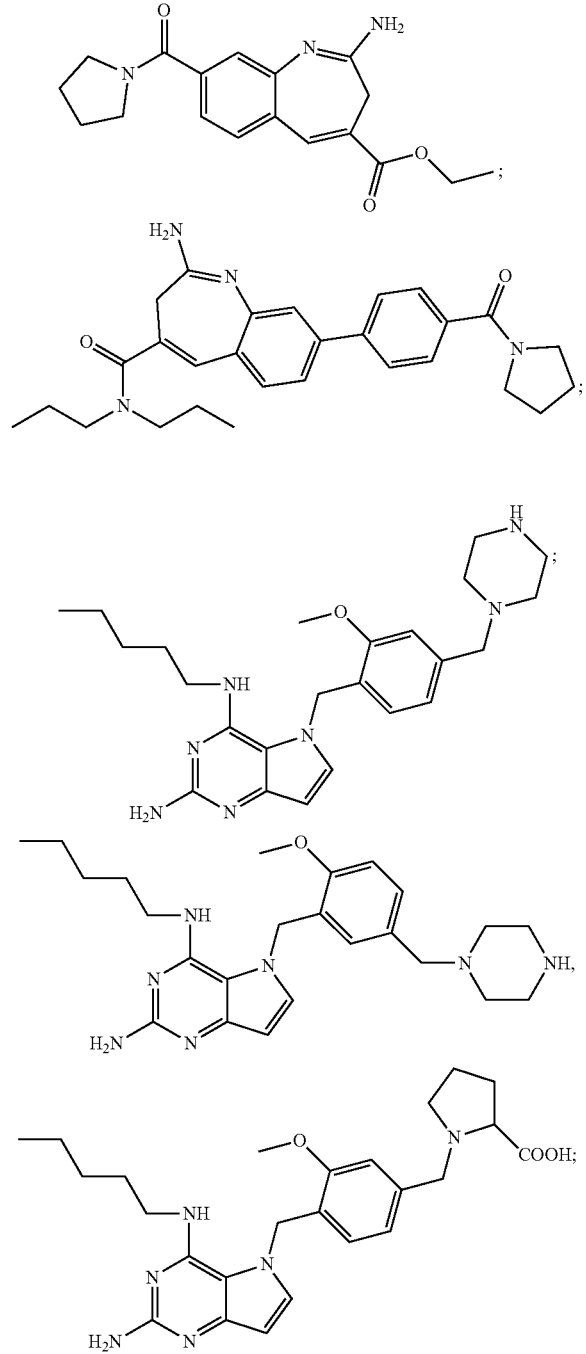

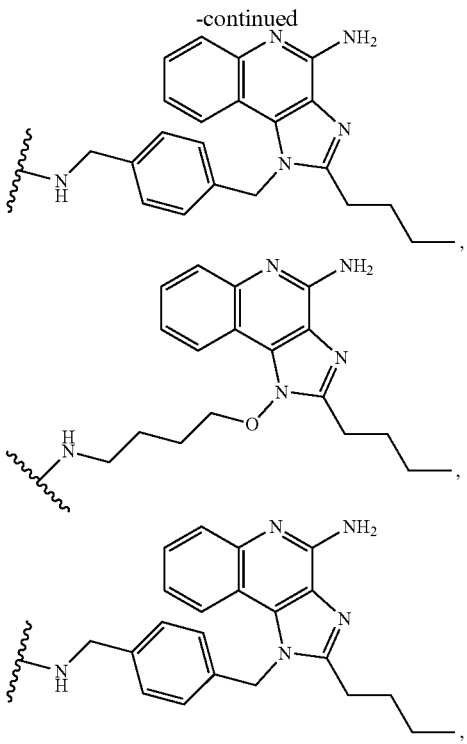

4-amino-2-butoxy-7,8-dihydro-8-[[3-(1-pyrrolidinylmethyl)phenyl]methyl]-6(5H)-pterdinone (vesatolimod, GS9620, CAS No. 1228585-88-3), 1-(2-Methylpropyl)-1H-imidazole[4,5-c]quinoline-4-amine (imiquimod, CAS No. 99011-02-6), 1-(4-amino-2-(ethoxymethyl)-1H-imidazo[4,5-c]quinolin-1-yl)-2-methylpropan-2-ol (resquimod, R848, CAS No. 144875-48-9), 4-amino-2-[(ethylamino)methyl]-α,α-dimethyl-1H-imidazo[4,5-c]quinoline-1-ethanol (gardiquimod, CAS No. 1020412-43-4), N-[4-(4-amino-2-ethyl-1H-imidazo[4,5-c]quinolin-1-yl)butyl]methanesulfonamide (3M-001), 2-propylthiazolo[4,5-c]quinolin-4-amine (3M-002), 4-amino-2-(ethoxymethyl)-α,α-dimethyl-6,7,8,9-tetrahydro-1H-imidazo[4,5-c]quinoline-1-ethanol hydrate (3M-003), N-(1-(4-Amino-2-(ethoxymethyl)-1H-imidazo[4,5-c]quinolin-1-yl)-2-methylpropan-2-yl)methanesulfonamide (CAS No. 642473-62-9, 3M-011, or 854A), and N-(4-(4-amino-2-ethyl-1H-imidazo[4,5-c]quinolin-1-yl)butyl)methanesulfonamide (CAS No. 532959-63-0, 3M-852A, PF-4878691), 2-methyl-1-(2,2,4-trimethylpent-4-en-1-yl)-1H-imidazo[4,5-c]quinolin-4-amine (S-34240), loxoribine, CL264, ssRNA40, and SM-276001.

In some other embodiments of Formula (I) and/or Formula (II), the immunomodulatory payload is a residue of a compound of Formula (III):

Formula (III)

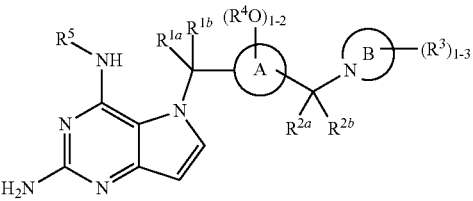

or a pharmaceutically acceptable salt, solvate or N-oxide thereof;
wherein
$R^{1a}$, $R^{1b}$, $R^{2a}$, and $R^{2b}$ are independently, at each occurrence, selected from hydrogen, and $C_{1-6}$alkyl;
ring A is cycloalkyl, heterocycloalkyl, monocyclic aryl, monocyclic heteroaryl, fused bicyclic aryl, or fused bicyclic heteroaryl, where heterocycloalkyl and each heteroaryl comprise 1, 2, 3 or 4 heteroatoms selected from N, S, and O;
ring B is a 4-membered N-linked heterocycloalkyl, which is further substituted with 1-2 $R^3$; wherein $R^3$ is, independently, at each occurrence, —N($R^{3a}$)$_2$, —O$R^{3b}$, —C($R^{3c}$)$_2$NH$_2$, $C_{1-6}$alkyl, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl and partially saturated heteroaryl include 1, 2, 3 or 4 heteroatoms selected from N, S, and O, and are optionally further substituted with 1-2 $C_{1-3}$alkyl;
or
ring B is a 5-6 membered N-linked heterocycloalkyl, which is further substituted with 1-3 $R^3$; wherein $R^3$ is, independently, at each occurrence, —N($R^{3a}$)$_2$, —O$R^{3b}$, —C($R^{3c}$)$_2$NH$_2$, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl and partially saturated heteroaryl include 1, 2, 3 or 4 heteroatoms selected from N, S, and O, and are optionally further substituted with 1-2 $C_{1-3}$alkyl;
or
ring B is a 7-10 membered N-linked heterocycloalkyl, which is further substituted with 1-3 $R^3$, or a 5-10 membered N-linked heteroaryl which is further substituted with 1-3 $R^3$; wherein the heterocycloalkyl and heteroaryl include 1, 2, 3 or 4 heteroatoms selected from N, S, and O; and wherein $R^3$ is, independently, at each occurrence, —N($R^{3a}$)$_2$, —O$R^{3b}$, —C($R^{3'}$)$_2$NH$_2$, $C_{1-6}$alkyl, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl and partially saturated heteroaryl include 1, 2, 3 or 4 heteroatoms selected from N, S, and O, and are optionally further substituted with 1-2 $C_{1-3}$alkyl;
$R^{3a}$ is independently, at each occurrence, selected from hydrogen, $C_{1-6}$alkyl, —C(=O)—CH$_2$NH$_2$, and cycloalkyl;
$R^{3b}$ is independently, at each occurrence, selected from hydrogen,

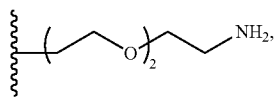

and —CH$_2$-aryl-CH$_2$NH$_2$;
$R^{3c}$ is independently, at each occurrence, selected from hydrogen, and $C_{1-6}$alkyl, or two $R^{3c}$, together with the carbon atom to which they are attached, form a cycloalkyl;

$R^4$ is $C_{1-6}$alkyl; and
$R^5$ is $C_{1-6}$cycloalkyl, or $C_{1-6}$alkyl optionally substituted with halo, hydroxy, alkoxy, amino, $C_{1-6}$alkylamino, $C_{1-6}$dialkylamino, $C_{1-6}$cycloalkyl, aryl or heteroaryl, wherein heteroaryl includes 1, 2, 3 or 4 heteroatoms selected from N, S, and O, and wherein cycloalkyl, aryl and heteroaryl are optionally further substituted with halo, hydroxy, alkyl, or haloalkyl; wherein the immunomodulatory payload (IM) is attached to its linker L via an amino group of R3 or an amino group of ring B.

In some other embodiments of Formula (I) and/or Formula (II), the immunomodulatory payload is a residue of a compound of Formula (III'):

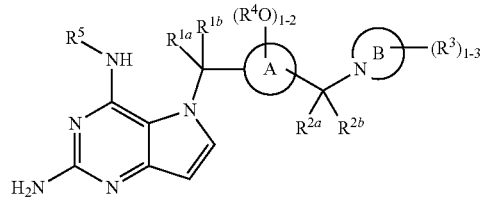

Formula (III')

or a pharmaceutically acceptable salt, solvate or N-oxide thereof;
wherein
$R^{1a}$, $R^{1b}$, $R^{2a}$, and $R^{2b}$ are independently, at each occurrence, selected from hydrogen, and $C_{1-6}$alkyl;
ring A is cycloalkyl, heterocycloalkyl, monocyclic aryl, monocyclic heteroaryl, fused bicyclic aryl, or fused bicyclic heteroaryl, where heterocycloalkyl and each heteroaryl comprise 1, 2, 3 or 4 heteroatoms independently selected from N, S, and O;
ring B is a 4-membered N-linked heterocycloalkyl, which is substituted with 1-2 $R^3$; wherein $R^3$ is, independently, at each occurrence, —N($R^{3a}$)$_2$, —O$R^{3b}$, —C($R^{3c}$)$_2$NH$_2$, $C_1$.6alkyl, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl, and partially saturated heteroaryl in $R^3$ include 1, 2, 3 or 4 heteroatoms independently selected from N, S, and O, and are optionally substituted with 1-2 $C_{1-3}$alkyl;
or
ring B is a 5-6 membered N-linked heterocycloalkyl, which is substituted with 1-3 $R^3$, or a 5-6 membered N-linked heteroaryl, which is substituted with 1-3 $R^3$; wherein $R^3$ is, independently, at each occurrence, —N($R^{3a}$)$_2$, —O$R^{3b}$, —C($R^{3c}$)$_2$NH$_2$, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl, and partially saturated heteroaryl in $R^3$ include 1, 2, 3 or 4 heteroatoms independently selected from N, S, and O, and are optionally substituted with 1-2 $C_{1-3}$alkyl;
or
ring B is a 7-10 membered N-linked heterocycloalkyl, which is substituted with 1-3 $R^3$, or a 5-10 membered N-linked heteroaryl which is substituted with 1-3 $R^3$; wherein $R^3$ is, independently, at each occurrence, —N($R^{3a}$)$_2$, —O$R^{3b}$, —C($R^{3c}$)$_2$NH$_2$, $C_{1-6}$alkyl, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl, and partially saturated heteroaryl in $R^3$ include 1, 2, 3 or 4 heteroatoms independently selected from N, S, and O, and are optionally substituted with 1-2 $C_{1-3}$ alkyl; $R^{3a}$ is independently, at each occurrence, selected from hydrogen, $C_{1-6}$alkyl, —C(=O)—CH$_2$NH$_2$, and cycloalkyl; $R^{3b}$ is independently, at each occurrence, selected from hydrogen,

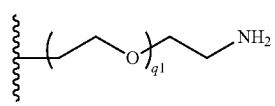

where q1 is 1, 2, or 3, and —CH$_2$-aryl-CH$_2$NH$_2$;
$R^{3c}$ is independently, at each occurrence, selected from hydrogen, and $C_{1-6}$alkyl, or two $R^{3c}$, together with the carbon atom to which they are attached, form a cycloalkyl; $R^4$ is $C_{1-6}$alkyl; and
$R^5$ is $C_{3-6}$cycloalkyl, or $C_{1-6}$alkyl, each of which is optionally substituted with 1, 2, or 3 $R^{5a}$ groups independently selected from halo, hydroxy, alkoxy, amino, $C_{1-6}$alkylamino, $C_{1-6}$dialkylamino, $C_{3-6}$cycloalkyl, aryl, and heteroaryl, wherein heteroaryl includes 1, 2, 3 or 4 heteroatoms independently selected from N, S, and O, and wherein any of the $R^{5a}$ $C_{3-6}$cycloalkyl, aryl, and heteroaryl groups are optionally substituted with 1, 2, or 3 groups independently selected from halo, hydroxy, alkyl, and haloalkyl.

In some embodiments of compounds of Formula (III) and/or Formula (III'),

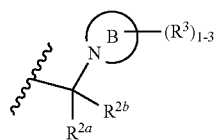

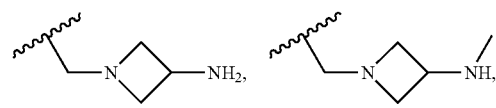

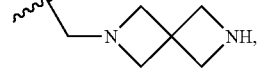

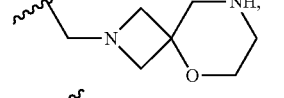

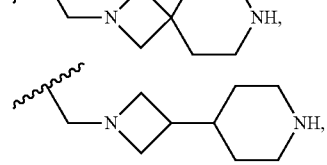

-continued

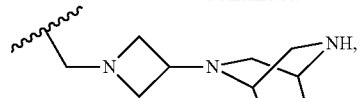

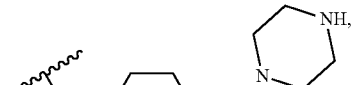

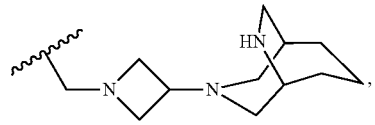

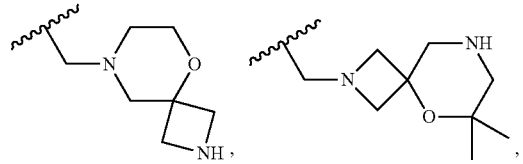

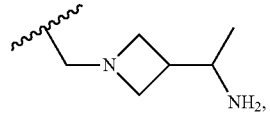

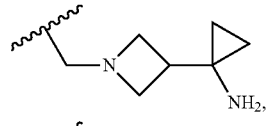

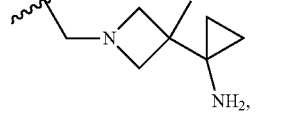

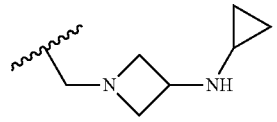

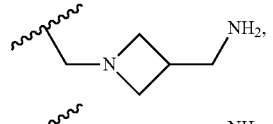

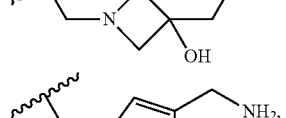

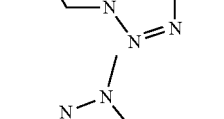

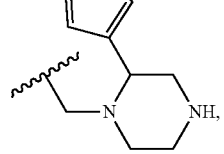

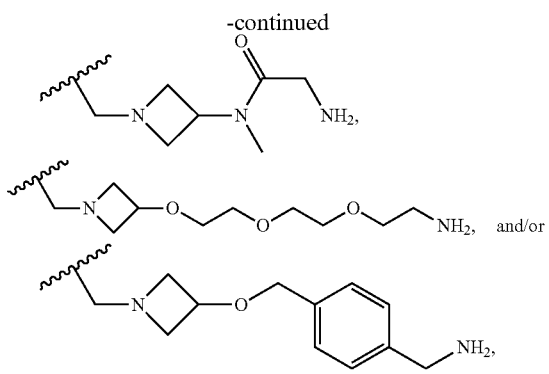

wherein each

indicates a point of attachment to the rest of the formula. In some of such embodiments, in one instance, R⁵ is pentyl and

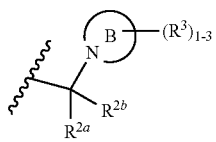

is one or more of the groups indicated above.

In some or any of the preceding embodiments of compounds of Formula (I-P), Formula (I), Formula (II) and/or Formula (III), $R^{1a}$, $R^{1b}$, $R^{2a}$ and $R^{2b}$ are hydrogen, $R^5$ is pentyl, and ring B is an N-linked azetidinyl ring substituted with two $R^3$ which, together with the atom to which they are attached, form a spiro-heterocycloalkyl. In some of such embodiments, the spiro-heterocycloalkyl is selected from spiro-azetidinyl, spiro-morpholinyl, spiro-(gem dimethyl) morpholinyl, or spiro-piperidinyl and is optionally substituted as described herein. In some or any of the preceding embodiments of compounds of Formula (I-P), Formula (I), Formula (II) and/or Formula (III), $R^{1a}$, $R^{1b}$, $R^{2a}$ and $R^{2b}$ are hydrogen, $R^5$ is pentyl, and ring B is an azetidine ring substituted with 1-2 $R^3$ where each is independently selected from —OH, —NH₂, —CH₃,

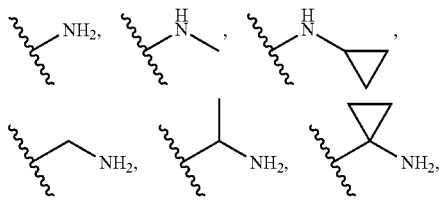

and combinations thereof. In some or any of the preceding embodiments of compounds of Formula (I-P), Formula (I), Formula (II) and/or Formula (III), Ria $R^{1b}$, $R^{2a}$ and $R^{2b}$ are hydrogen, $R^S$ is pentyl, and ring B is an N-linked azetidine substituted with

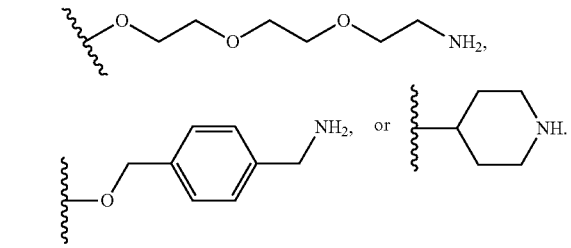

In some or any of the preceding embodiments of compounds of Formula (I-P), Formula (I), Formula (II) and/or Formula (III), $R^{1a}$, $R^{1b}$, $R^{2a}$ and $R^{2b}$ are hydrogen, $R^5$ is pentyl, and ring B is an N-linked azetidine substituted with any combination of $R^3$(s) described herein and/or in this paragraph.

In some or any of the preceding embodiments of compounds of Formula (I-P), Formula (I), Formula (II) and/or Formula (III), $R^{1a}$, $R^{1b}$, $R^{2a}$ and $R^{2b}$ are hydrogen, $R^5$ is pentyl, and ring B is an N-linked morpholinyl or piperidinyl substituted with two $R^3$ which, together with the atom to which they are attached, form a spiro-heterocycloalkyl. In some of such embodiments, the spiro-heterocycloalkyl is an azetidinyl ring, or a piperidinyl ring. In some or any of the preceding embodiments of compounds of Formula (I-P), Formula (I), Formula (II) and/or Formula (III), $R^{1a}$, $R^{1b}$, $R^{2a}$ and $R^{2b}$ are hydrogen, $R^5$ is pentyl, and ring B is an N-linked piperidinyl ring substituted with a partially saturated heteroaryl. In some or any of the preceding embodiments of compounds of Formula (I-P), Formula (I), Formula (II) and/or Formula (III), $R^{1a}$, $R^{1b}$, $R^{2a}$ and $R^{2b}$ are hydrogen, $R^5$ is pentyl, and ring B is a piperazinyl ring substituted with a heteroaryl ring optionally substituted with $C_{1-3}$alkyl. In some or any of the preceding embodiments of compounds of Formula (I-P), Formula (I), Formula (II) and/or Formula (III), $R^{1a}$, $R^{1b}$, $R^{2a}$ and $R^{2b}$ are hydrogen, $R^5$ is pentyl, and ring B is a N-linked heteroaryl substituted with 1-2 $R^3$. In some of such embodiments, ring B is an N-linked triazolyl substituted with 1-2 $R^3$. In some or any of the preceding embodiments of compounds of Formula (I-P), Formula (I), Formula (II), and/or Formula (III), $R^3$ is methyl. In some or any of the preceding embodiments of compounds of Formula (I-P), Formula (I), Formula (II) and/or Formula (III), $R^{1a}$, $R^{1b}$, $R^{2a}$ and $R^{2b}$ are hydrogen, $R^5$ is pentyl, and ring B is an N-linked ring substituted with any combination of $R^3$(s) described herein and/or in this paragraph.

In some or any of the preceding embodiments of compounds of Formula (I-P), Formula (I), Formula (II) and/or Formula (III), $R^{1a}$, $R^{1b}$, $R^{2a}$ and $R^{2b}$ are hydrogen, $R^5$ is pentyl, and ring A is a phenyl ring substituted with one methoxy group at the position ortho to the group

wherein each indicates a point of attachment to the rest of the formula. In some or any of the preceding embodiments of compounds of Formula (I-P), Formula (I), Formula (II) and/or Formula (III), $R^{1a}$, $R^{1b}$, $R^{2a}$ and $R^{2b}$ are hydrogen, $R^5$ is pentyl, and ring A is a phenyl ring substituted with two methoxy groups at the positions ortho to the group

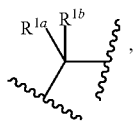, wherein each

indicates a point of attachment to the rest of the formula.

In some embodiments, provided herein are conjugates according to Formula (Xa), (Xb), (Xc), (Xd), or (Xe), wherein L and PA are as described herein:

Formula (Xa)

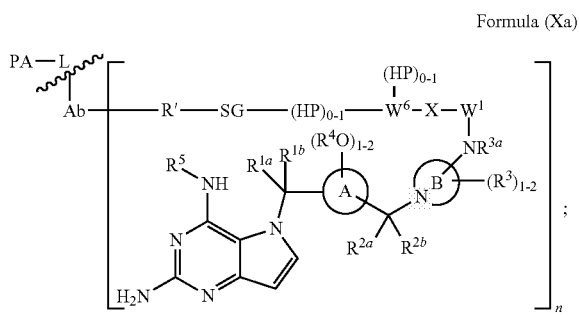

Formula (Xb)

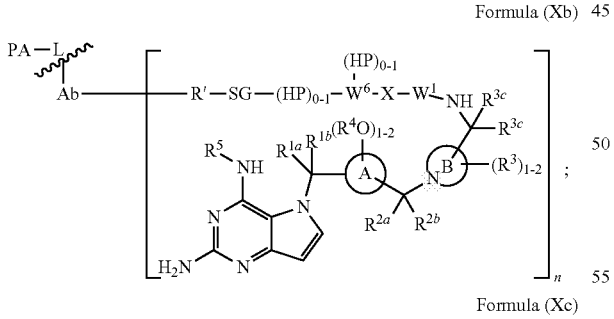

Formula (Xc)

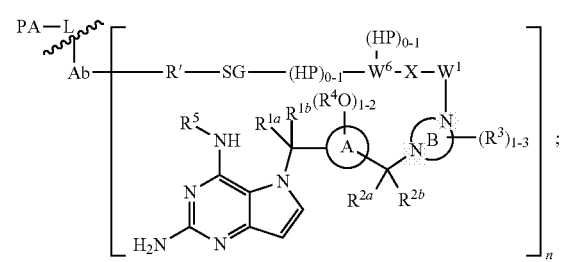

Formula (Xd)

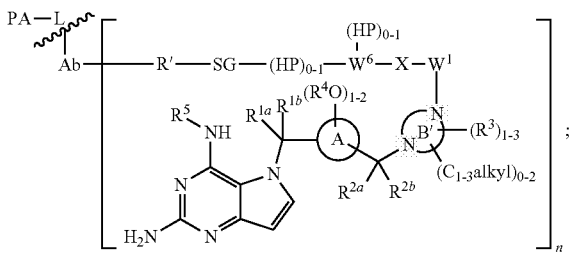

where B' is spiro-heterocycloalkyl which includes 1, 2, 3 or 4 heteroatoms independently selected from N, S, and O; or Formula (Xe)

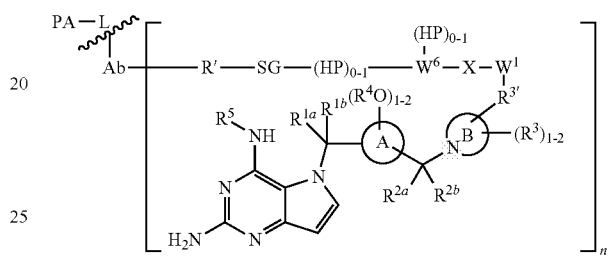

where $R^{3'}$ is heterocycloalkyl or partially saturated heteroaryl, each of which includes 1, 2, 3 or 4 heteroatoms independently selected from N, S, and O, provided that at least one nitrogen is present in the $R^{3'}$ ring and is attached to $W^1$; or $R^{3'}$ is —O—CH$_2$-(phenyl)-CH$_{2-NH}$— where the NH is attached to $W^1$.

In some instances of any of Formulas (Xa), (Xb), (Xc), (Xd), and (Xe), SG is absent,

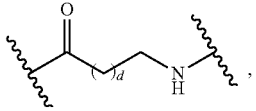,

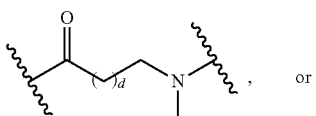, or

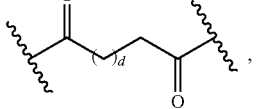, wherein subscript d is an integer selected from 1 to 10, wherein each

indicates a point of attachment to the rest of the formula. In some instances, SG is

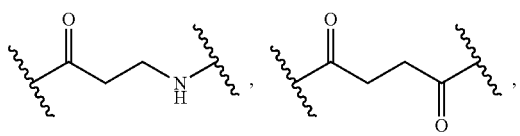

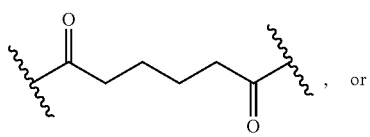, or

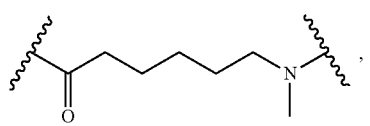

wherein each

indicates a point of attachment to the rest of the formula.
In some instances of Formulas (Xa), (Xb), (Xc), (Xd), and (Xe), W¹, when present, is

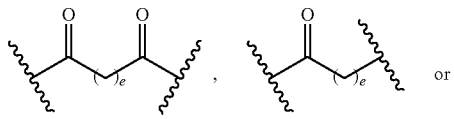, or

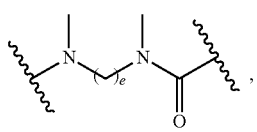, wherein subscript e is an integer selected from 1 to 10, wherein each

indicates a point of attachment to the rest of the formula. In some instances, W¹, when present, is

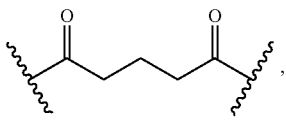,

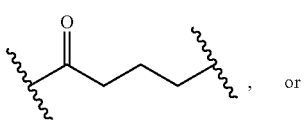, or

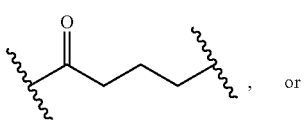

wherein each

indicates a point of attachment to the rest of the formula.

In some instances of Formulas (Xa), (Xb), (Xc), (Xd), and (Xe), when W⁶ is a residue of a peptide, the residue of the peptide may comprise natural and/or non-natural amino acid residues. In some instances of Formulas (Xa), (Xb), (Xc), (Xd), and (Xe), W⁶, when present, is a tripeptide residue. In some of such instances, W⁶ is

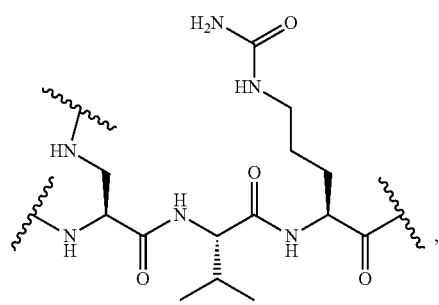,

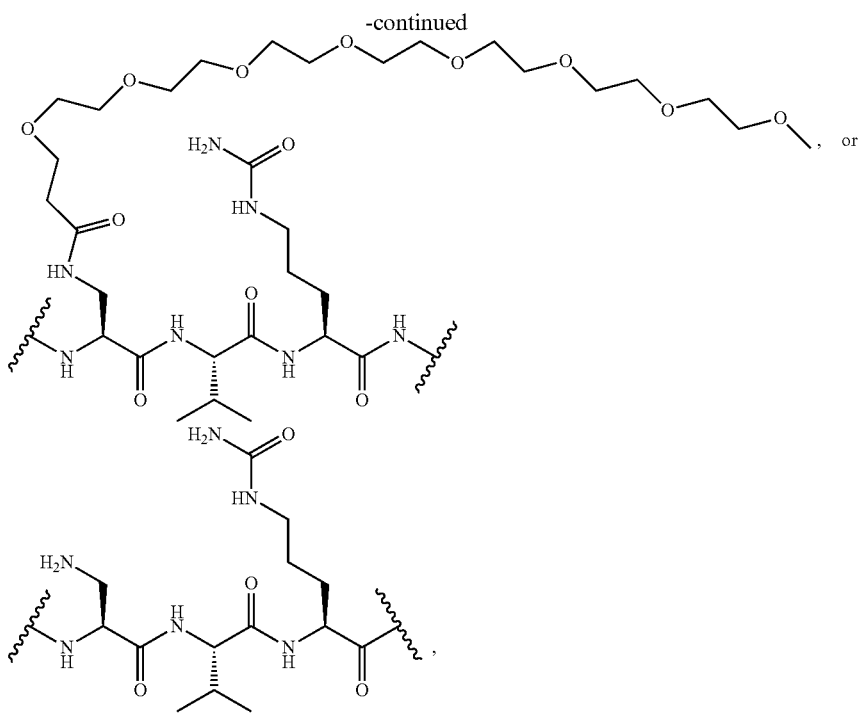
, or wherein each

indicates a point of attachment to the rest of the formula. In some instances of Formulas (Xa), (Xb), (Xc), (Xd), and (Xe), $W^6$, when present, is a dipeptide residue. In some of such instances, $W^6$, when present, is

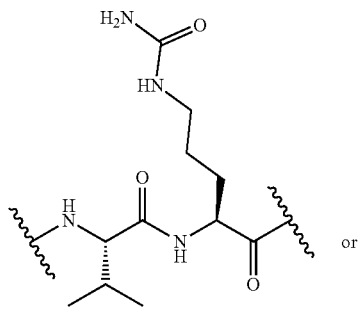

or

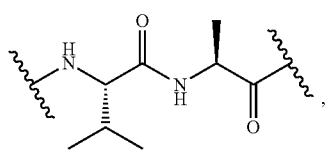

, wherein each

indicates a point of attachment to the rest of the formula.

In some instance of Formulas (Xa), (Xb), (Xc), (Xd), and (Xe), RT is

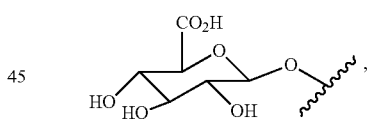

, wherein

indicates a point of attachment to the rest of the formula.

In some instances of Formulas (Xa), (Xb), (Xc), (Xd), and (Xe), HP, when present is a PEG group. In some instances of Formula (VI), HP, when present, is

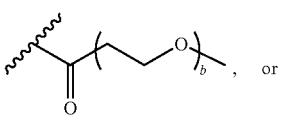

, or

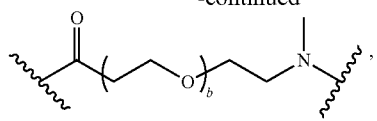

wherein subscript b is an integer selected from 1 to 10, and

indicates a point of attachment to the rest of the formula.

In some instances of Formulas (Xa), (Xb), (Xc), (Xd), and (Xe), R' is.

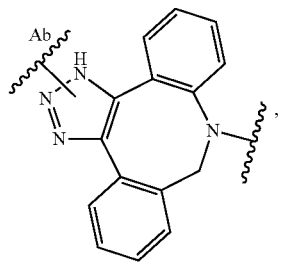

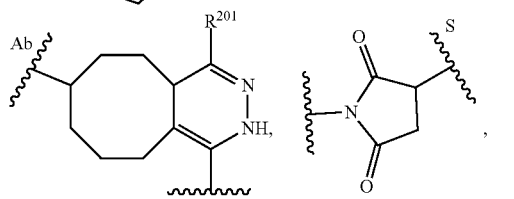

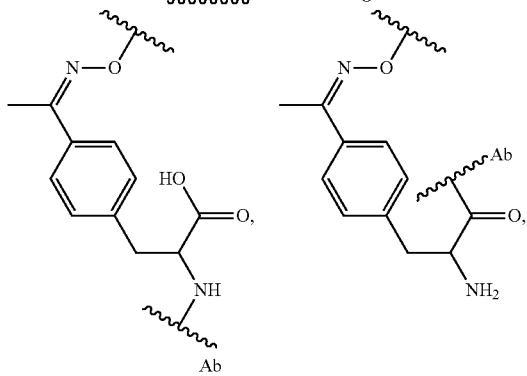

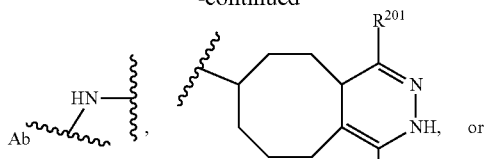

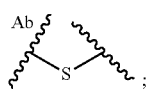

wherein $R^{201}$ is $C_{1-6}$alkyl, wherein each

indicates a point of attachment to the rest of the formula,

indicates a point of attachment to the antibody, or an antigen binding fragment thereof, and

indicates a point of attachment to the antibody, or an antigen binding fragment thereof, via a sulfur atom of a cysteine residue.

In some embodiments, immunomodulatory compounds (IM) suitable for the conjugates described herein, at Toll-like receptor agonists, e.g., TLR7 agonists. In some embodiments of Formula (I) and/or Formula (II), In some embodiments of Formula (I) and/or Formula (II), IM is a compound of Formula (III) or (III') selected from the group consisting of.

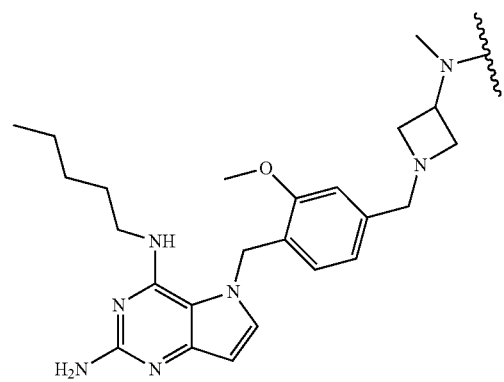

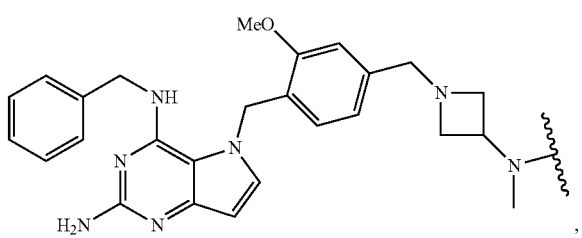

-continued
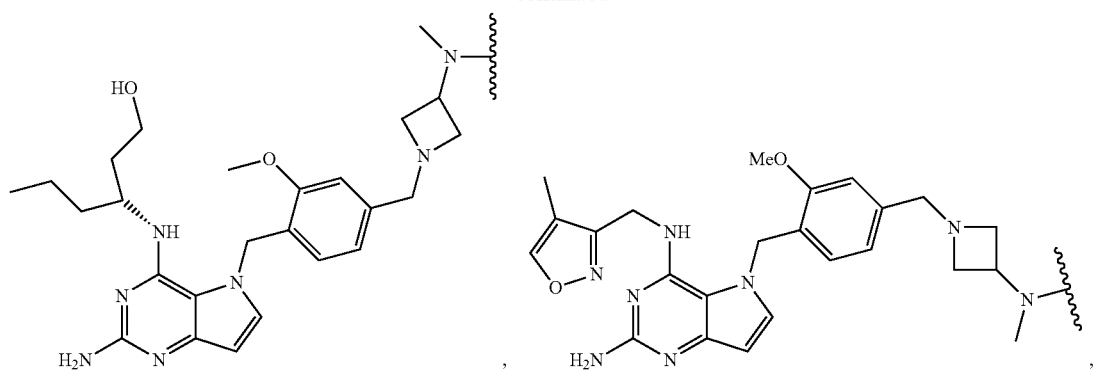
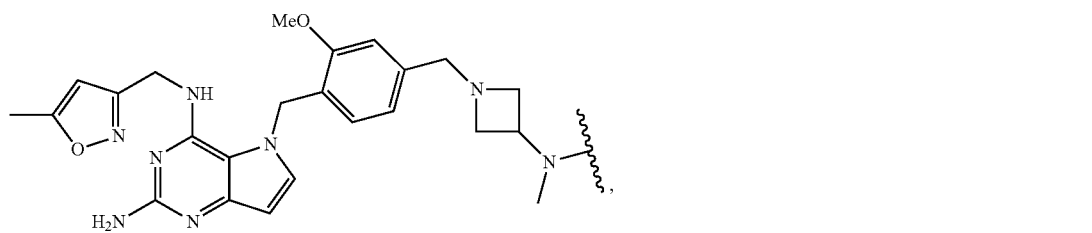
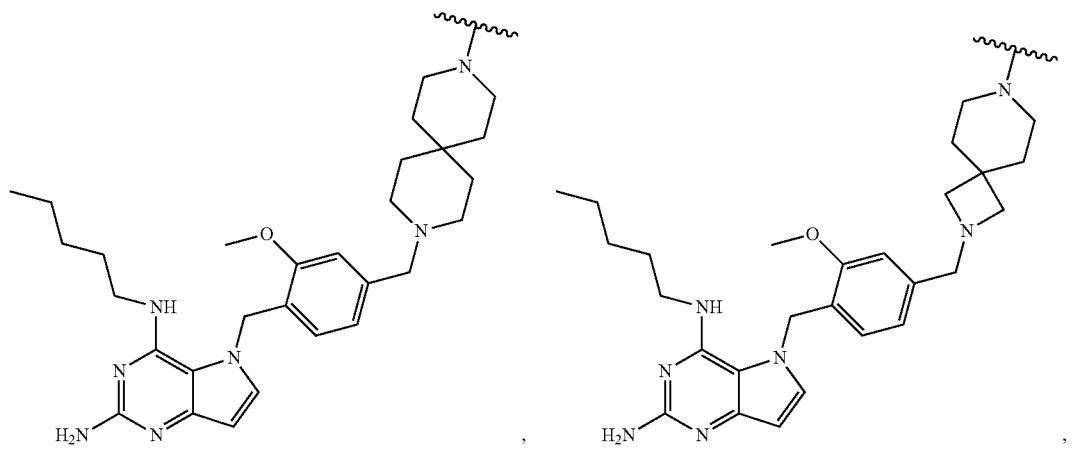
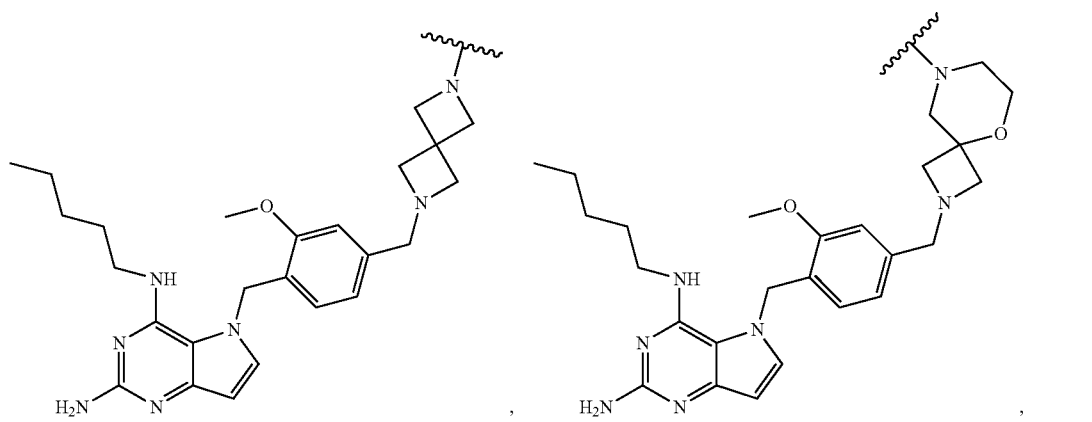

| 149 | 150 |
|---|---|
| 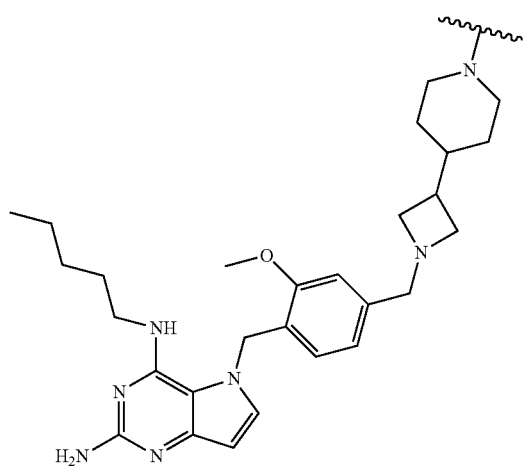 | 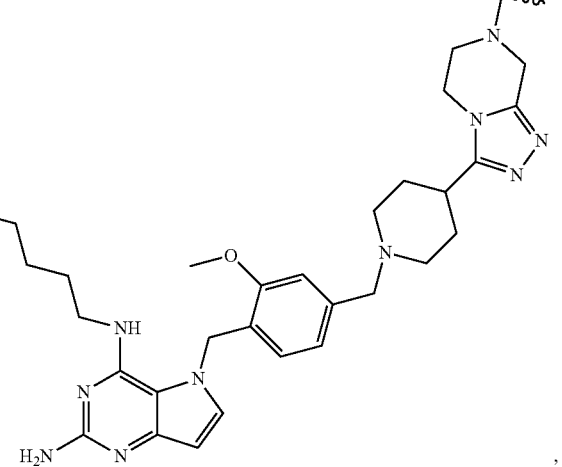 |
| 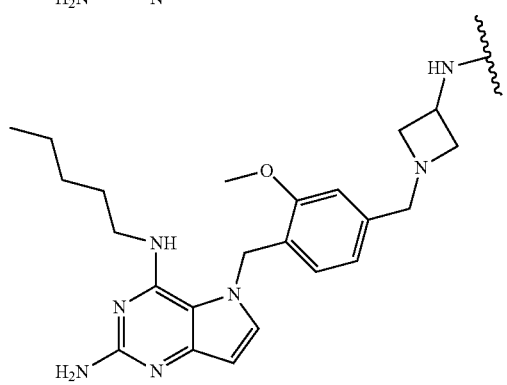 | 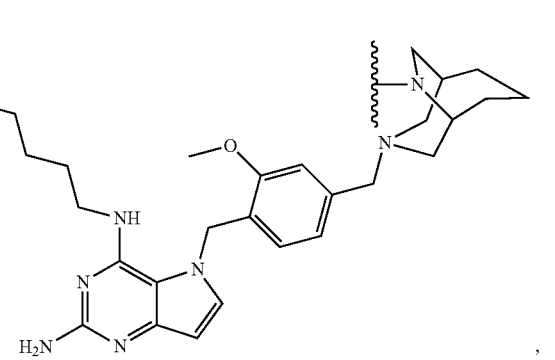 |
| 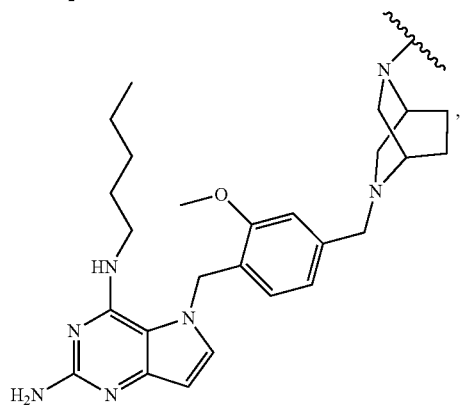 | |
| Compound 131 | Compound 132 |
|---|---|
| 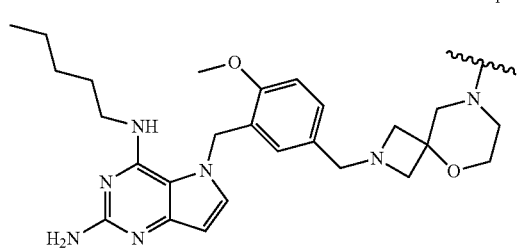 | 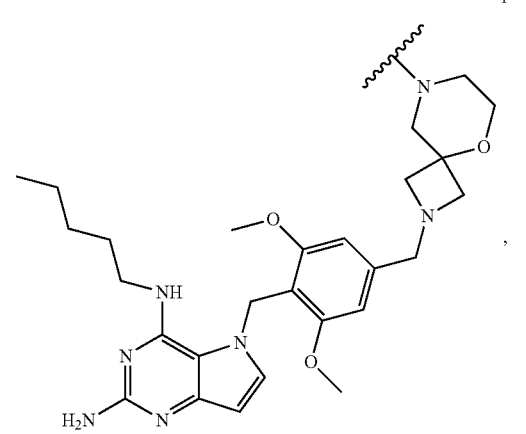 |

-continued
Compound 133
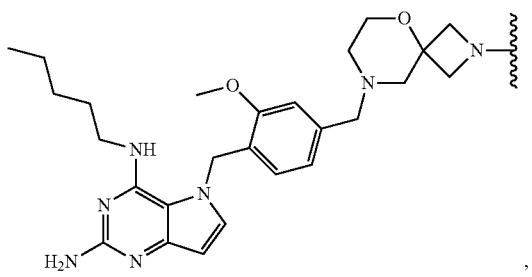
Compound 134
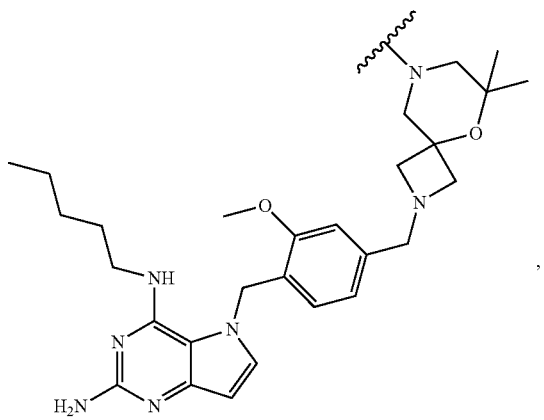
Compound 135
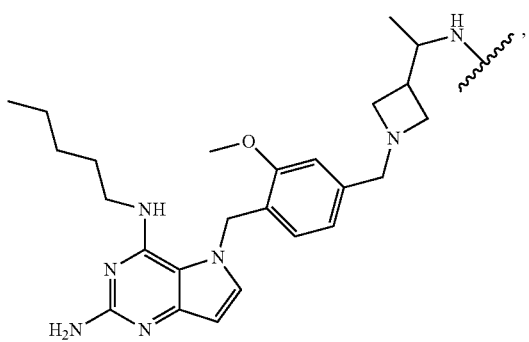
Compound 136
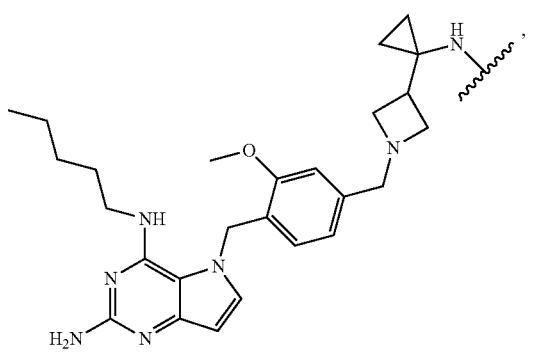
Compound 137
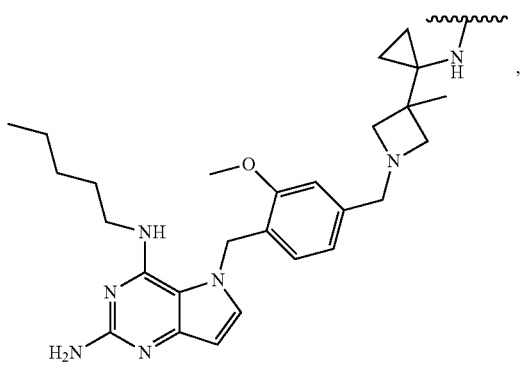
Compound 138
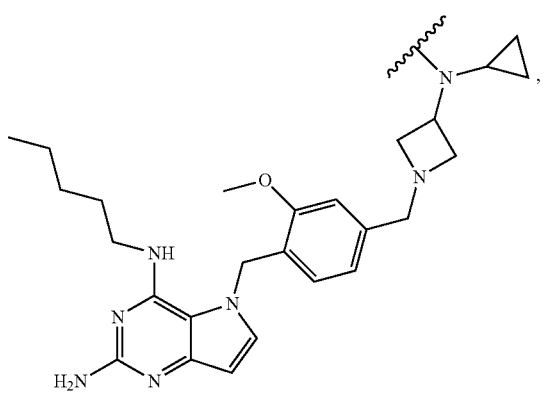
Compound 139
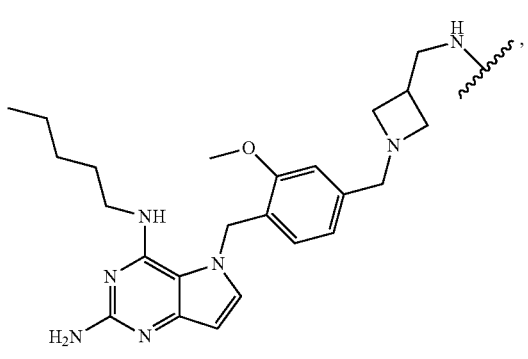
Compound 140
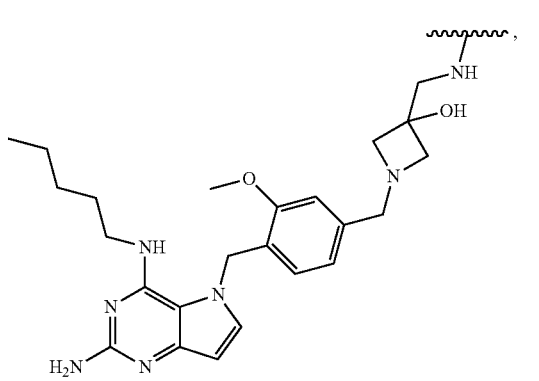

-continued
Compound 141
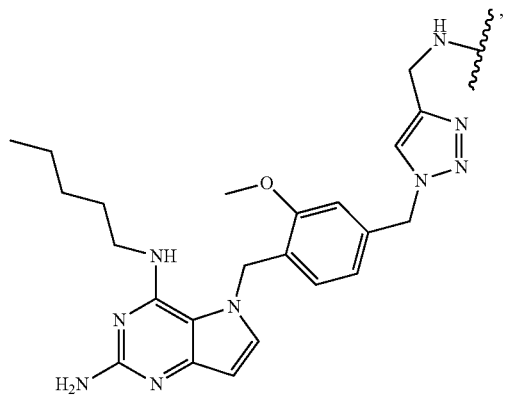
Compound 142
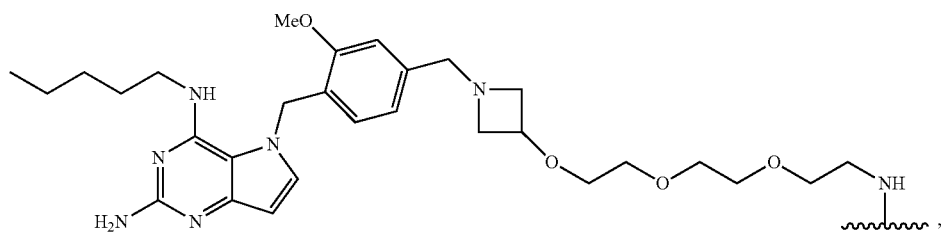
Compound 144
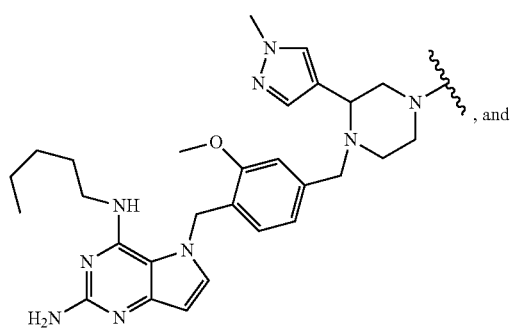
Compound 145
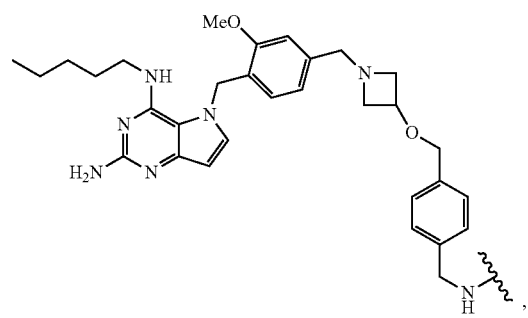

wherein each

indicates a point of attachment to the rest of the formula.

In some other embodiments of Formula (I) and/or Formula (II), the immunomodulatory payload is a residue of a compound of Formula (IV):

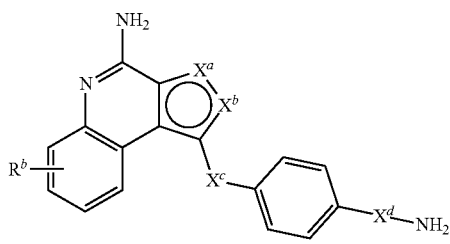

(IV)

or a pharmaceutically acceptable salt, tautomer, stereoisomer, and/or mixture of stereoisomers thereof; wherein one of $X^a$ and $X^b$ is —N= and the other is —N($R^a$)—;

$R^a$ is $C_1$-$C_6$-alkyl, cycloalkyl, or cycloalkyl-alkyl;

$X^c$ and $X^d$ are independently $C_1$-$C_6$-alkylene; and $R^b$ is hydrogen, quinolinyl, or —C(O)OCH$_3$.

In some or any embodiments, the immunostimulatory payload is according to Formula (IV) or a pharmaceutically acceptable salt, tautomer, stereoisomer, and/or mixture of stereoisomers thereof; wherein one of Xa and $X^b$ is —N= and the other is —N($R^a$)—; $X^c$ and $X^d$ are independently C1-$C_6$-alkylene; $R^a$ is $C_1$-$C_6$-alkyl; and $R^b$ is hydrogen.

In some or any embodiments, the immunostimulatory payload of Formula (IV) is according to Formula (IVa) or a pharmaceutically acceptable salt, tautomer, stereoisomer, and/or mixture of stereoisomers thereof:

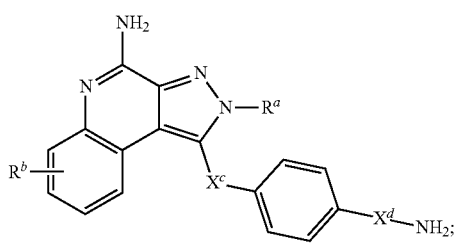

(IVa)

wherein $R^a$, $R^b$, $X^C$, and $X^d$ are as defined in the above, or in any embodiment herein.

In some or any embodiments, the immunostimulatory payload of Formula (IV) is according to Formula (IVb) or a pharmaceutically acceptable salt, tautomer, stereoisomer, and/or mixture of stereoisomers thereof.

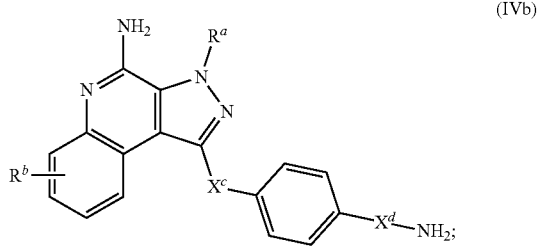

(IVb)

wherein $R^a$, $R^b$, $X^C$, and $X^d$ are as defined in the above, or in any embodiment herein.

In some or any embodiments, provided is an immunostimulatory payload of Formula (IV), (IVa), or (IVb), wherein $R^b$ is hydrogen. In some or any embodiments, provided is an immunostimulatory payload of Formula (IV), (IVa), or (IVb), wherein $X^C$ is CH$_2$. In some or any embodiments, provided is an immunostimulatory payload of Formula (IV), (IVa), or (IVb), wherein $X^d$ is CH$_2$. In some or any embodiments, provided is an immunostimulatory payload of Formula (IV), (IVa), or (IVb), wherein $X^C$ and $X^d$ are each CH$_2$. In some or any embodiments, provided is an immunostimulatory payload of Formula (IV), (IVa), or (IVb), wherein $R^a$ is $C_1$—C-alkyl. In some or any embodiments, provided is an immunostimulatory payload of Formula (IV), (IVa), or (IVb), wherein $R^a$ is methyl, ethyl, n-propyl, isopropyl, n-butyl, isobutyl, sec-butyl, tert-butyl, n-pentyl, sec-pentyl, or iso-pentyl. In some or any embodiments, provided is an immunostimulatory payload of Formula (IV), (IVa), or (IVb), wherein $R^b$ is hydrogen, and $X^C$ is CH$_2$. In some or any embodiments, provided is an immunostimulatory payload of Formula (IV), (IVa), or (IVb), wherein $R^b$ is hydrogen, and $X^d$ is CH$_2$. In some or any embodiments, provided is an immunostimulatory payload of Formula (IV), (IVa), or (IVb), wherein $R^b$ is hydrogen, and $X^C$ and $X^d$ are CH$_2$. In some or any embodiments, provided is an immunostimulatory payload of Formula (IV), (IVa), or (IVb), wherein $R^b$ is hydrogen, $X^C$ and $X^d$ are CH$_2$, and $R^a$ is methyl, ethyl, n-propyl, isopropyl, n-butyl, isobutyl, sec-butyl, tert-butyl, n-pentyl, sec-pentyl, or iso-pentyl. In some or any embodiments, provided is an immunostimulatory payload of Formula (I), (II), or (III), wherein $R^b$ is hydrogen, $X^c$ and $X^d$ are CH$_2$, and $R^a$ is n-propyl, isopropyl, n-butyl, isobutyl, sec-butyl, tert-butyl, n-pentyl, sec-pentyl, or iso-pentyl.

Provided is an immunostimulatory payload of Formula (IVc)

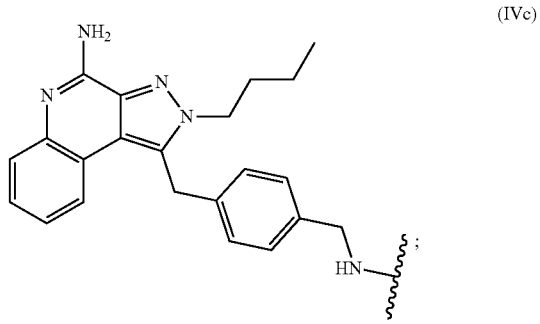 [SMILES: *NCc1ccc(Cc2c3c(nn2CCCC)c(N)nc2ccccc23)cc1]

(IVc)

or a pharmaceutically acceptable salt, tautomer, stereoisomer, and/or mixture of stereoisomers thereof.

In some embodiments, provided herein are conjugates according to Formula (XIa), (XIb), (XIc), or (XId), wherein L and PA are as described herein:

Formula (XIa)

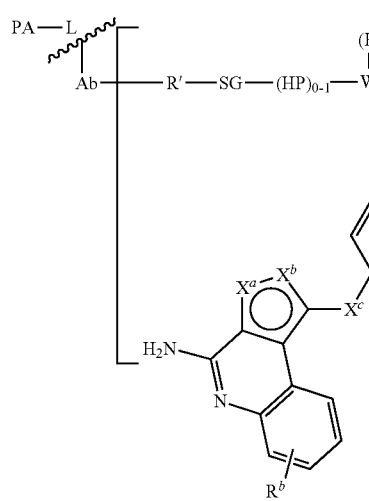

;

Formula (XIb)

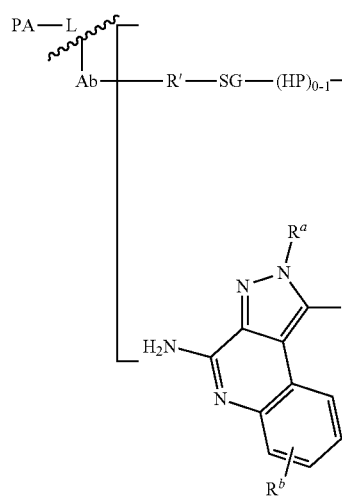

;

Formula (XIc)

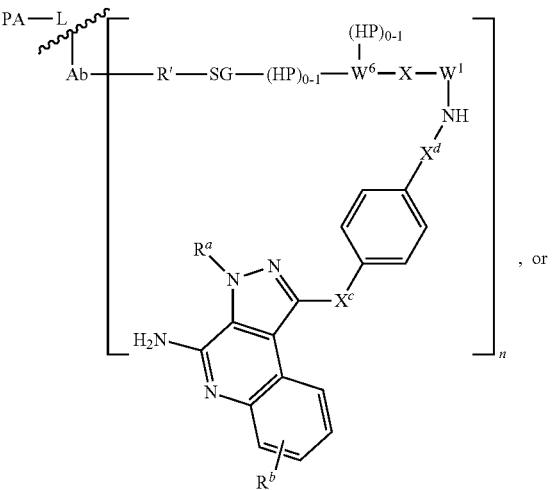

, or

Formula (XId)

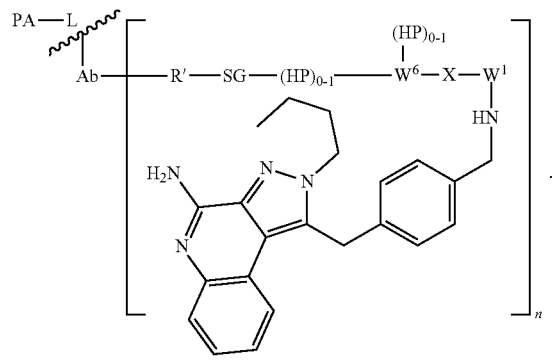

.

In some instances of any of Formulas (XIa), (XIb), (XIc), and (XId), SG is absent,

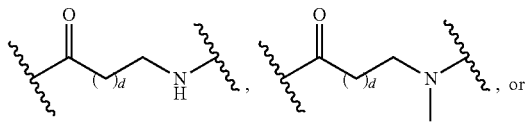, or

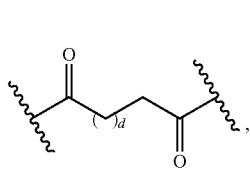, wherein subscript d is an integer selected from 1 to 10, wherein each

indicates a point of attachment to the rest of the formula. In some instances, SG is

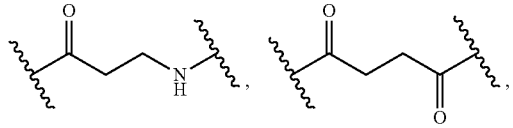

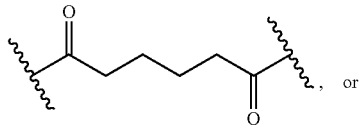, or

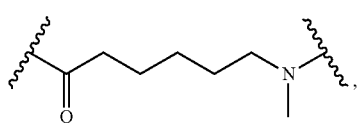, wherein each

indicates a point of attachment to the rest of the formula.

In some instances of Formulas (XIa), (XIb), (XIc), and (XId), W¹, when present,

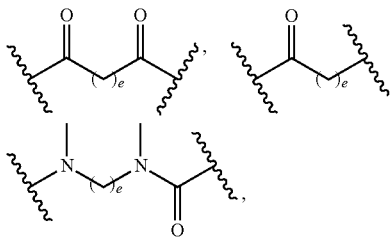

wherein subscript e is an integer selected from 1 to 10, wherein each

indicates a point of attachment to the rest of the formula. In some instances, W¹, when present, is

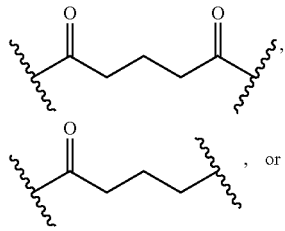

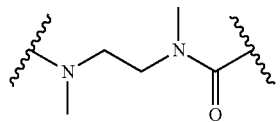

wherein each

indicates a point of attachment to the rest of the formula.

In some instances of Formulas (XIa), (XIb), (XIc), and (XId), when W⁶ is a residue of a peptide, the residue of the peptide may comprise natural and/or non-natural amino acid residues. In some instances of Formulas (XIa), (XIb), (XIc), and (XId), W⁶, when present, is a tripeptide residue. In some of such instances, W⁶ is

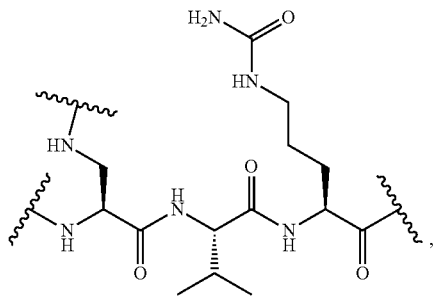

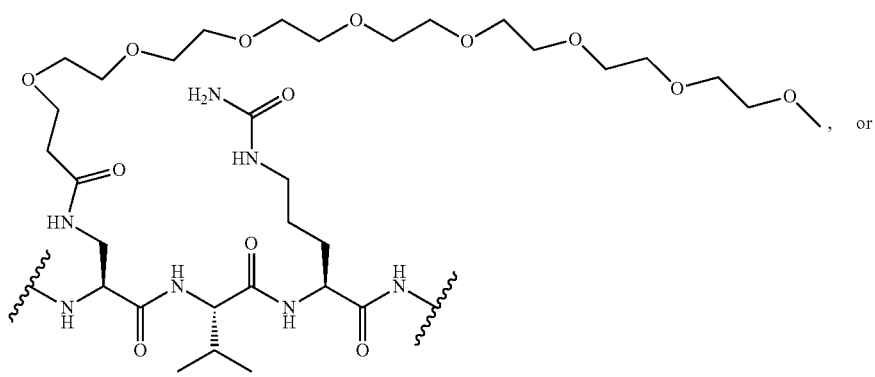

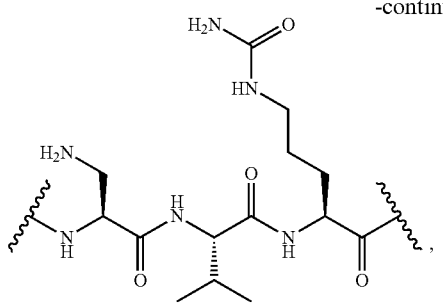

wherein each

indicates a point of attachment to the rest of the formula. In some instances of Formulas (XIa), (XIb), (XIc), and (XId), $W^6$, when present, is a dipeptide residue. In some of such instances, $W^6$, when present, is

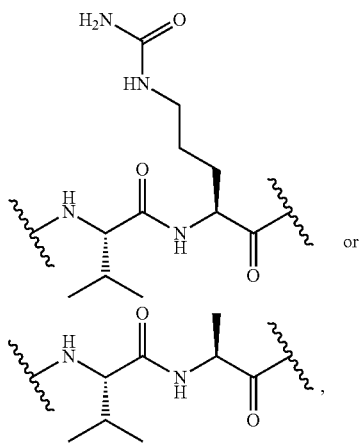

wherein each

indicates a point of attachment to the rest of the formula.

In some instance of Formulas (XIa), (XIb), (XIc), and (XId), RT is

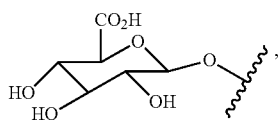 [SMILES: *OC1OC(C(=O)O)C(O)C(O)C1O]

wherein

indicates a point of attachment to the rest of the formula.

In some instances of Formulas (XIa), (XIb), (XIc), and (XId), HP, when present is a PEG group. In some instances of Formula (VI), HP, when present, is

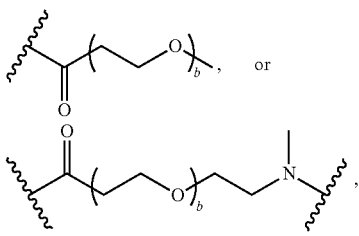

wherein subscript b is an integer selected from 1 to 10, and

indicates a point of attachment to the rest of the formula.

In some instances of Formulas (XIa), (XIb), (XIc), and (XId), R' is:

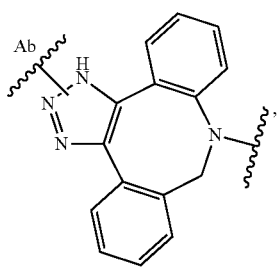

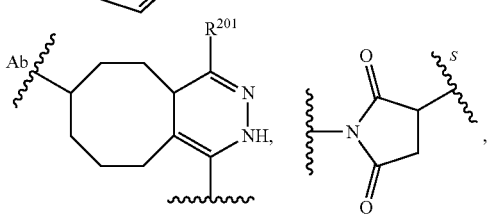

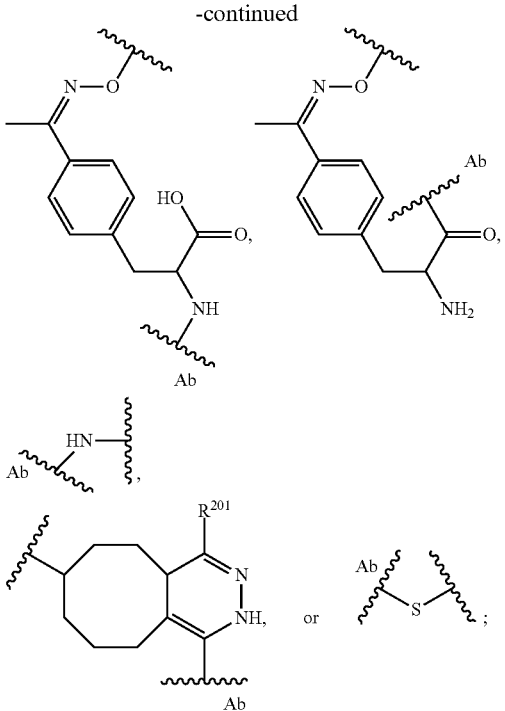

wherein $R^{201}$ is $C_{1-6}$alkyl, wherein each

indicates a point of attachment to the rest of the formula,

indicates a point of attachment to the antibody, or an antigen binding fragment thereof, and

indicates a point of attachment to the antibody, or an antigen binding fragment thereof, via a sulfur atom of a cysteine residue.

Additional examples of immune-modulatory (or immunomodulatory) compounds include and are not limited to kinase inhibitors (e.g., Phosphoinositide 3-kinase (PI3K) inhibitors (e.g., duvelisib, idelalisib), Bruton's tyrosine kinase (BTK) inhibitors (e.g., ibrutinib, acalabrutinib), Janus kinase (JAK) inhibitors (e.g., ruxolitinib, tofacitinib), mitogen-activated protein kinases (MAPK, MEK), originally called extracellular signal-regulated kinases (ERK) inhibitors, c-jun N-terminal kinase (JNK) inhibitors, Anaplastic lymphoma kinase (ALK) inhibitors, mammalian target of rapamycin (mTOR) inhibitors, SRC proto-oncogene, non-receptor tyrosine kinase (Src) inhibitors (e.g., dasatinib, saracatinib, bosutinib, and KX01), Interleukin-1 Receptor-Associated Kinase 4 (IRAK4) inhibitors (e.g., CA-4948), Receptor tyrosine kinase (cKIT) kinase inhibitors, Apoptosis signal-regulating kinase 1 (ASK1, MAP3K5) inhibitors, p38 mitogen-activated protein kinases (p38) inhibitors, Bcr-Abl tyrosine-kinase (TK1) inhibitors (e.g., imitanib), Aurora kinase inhibitors (e.g., barasertib (AZD1152), alisertib (MLN8237), danusertib (PHA-739358)), tyrosine-protein kinase Met or hepatocyte growth factor receptor (HGFR) (c-Met) inhibitors (e.g., sunitinib), cyclin-dependent kinase 4/6 (CDK4/6) inhibitors (e.g., palbociclib (Ibrance®), ribociclib) or other suitable kinase inhibitors), Calcineurin inhibitors, CRAC inhibitors, PARP1 antagonists, PPARγ agonists, Kv1.3 antagonists, PP2A agonists, MYD88 inhibitors, BCL-2 inhibitors (e.g., ABT-199 (venetoclax, RG7601, GDC-0199), Adenosine A2A receptor (A2ar) agonists, (Toll-like receptor 7/8 (TLR7/8) agonists, calcium-activated potassium channel (Kca3.1) agonists, TGF~-R1 inhibitors, TGF-R2 inhibitors, Epidermal growth factor receptor (EGFR) antagonists (e.g., gefitinib, erlotinib, afatinib, brigatinib, icotinib), Platelet derived growth factor (PDGF) inhibitors, Vascular endothelial growth factor (VEGF) inhibitors, GLi 1 inhibitors, tankyrase (TNKS) antagonists, Traf2 and Nck-interacting kinase (TNIK) antagonists, imides (e.g., lenalidomide, thalidomide, and pomalidomide), and vitamin D receptor (VDR) agonists.

In some embodiments, inhibitors of TGFpR1 kinase include those disclosed in US Published Application 2018/0127426, U.S. Pat. No. 8,080,568, WO 2012/002680, WO 2009/009059, WO 2007/076127, WO 2007076086, WO 2006026306, Bioorg. Med. Chem., 2014, 22, 2724-2732 and J. Med. Chem. 2014, 57, 4213-4238, the disclosures of which are incorporated by reference herein.

In some embodiments, inhibitors of the TGFPR2 kinase include those disclosed in WO 2015/136073, Bioorg. Med. Chem. Lett., 2013, 23, 3248-3252, Acta Cryst., 2016, D72, 658-674, WO 2016/020864, US Published Application 2014/0249135, US Published Application 20120225061 and compounds such as 3-amino-6-(4-(aminomethyl)phenyl)—N-(4-morpholinopyridin-3-yl)pyrazine-2-carboxamide, the disclosures of which are incorporated by reference herein.

In some embodiments, inhibitors of TNKS include those disclosed CN 107226808, EP 3313177, U.S. Pat. No. 9,505,749, US Published Application No. 2015/0045368, WO 2014/036022, WO 2017/076484, WO 2018/046933, WO 2018/003962, Eur. J. Med. Chem., 2017, 142, 506-522, the disclosures of which are incorporated by reference herein.

In some embodiments, inhibitors of TNIK include those disclosed US Published Application 2016/0264555, WO 2015/083833, US Published Application 2010/0216795, US Published Application 20100137386, Med. Chem. Commun., 2015, 6, 1564-1572, and Bioorg. Med. Chem. Lett., 2013, 23, 569-573, the disclosures of which are incorporated by reference herein.

Binding of an immune-modulatory compound to its target or protein target can inhibit the function of the protein target expressed in a myofibroblast, an immune cell, or both. Binding of an immune-modulatory compound to its target or target protein can increase the activity of a protein expressed in a myofibroblast, an immune cell, or both.

Some non-limiting examples can include immune-modulatory compounds that are agonists of the adenine-receptor A2R$^a$ such as CGS-21680 or sphingosine-1 analogues that increase activity of the phosphatase PP2A such as FTY720 and derived analogues. Some non-limiting examples of immune-modulatory compounds can include: protein kinase inhibitors for mTOR kinases such as rapamycin, in immune cells; inhibitors of the TGFPR2 kinase such as 3-amino-6-(4-(aminomethyl)phenyl)-N-(4-morpholinopyridin-3-yl) pyrazine-2-carboxamide, in myofibroblasts, immune cells or both; inhibitors of one or both of PI3Kγ and PI3K5 such as Duvelisib, TG 100713, and PF 04691502 in immune cells; and inhibitors of TNIK such as KY-05009 and NCB-0846 [4-((2-((4-(aminomethyl)-1H-benzo[d]imidazol-6-yl) amino)quinazolin-8-yl)oxy)cyclohexan-1-ol] in myofibroblasts, immune cells or both.

In some additional embodiments, the immunomodulatory agent is an agent that modulates components of the immune system such that it would enhance the anti-tumor activity of the conjugate. Such agents would include but are not limited to agonists of Toll-Like receptors (e.g., poly-ICLC (Hiltonol), GLA, MEDI9197, VTX-2337 (Motolimid), CpG (SD-101), and IMO-2125); agonists of the STING (stimulator of interferon genes) pathway (e.g., MK-1454, ADU-S100, and SB11285); activators of RIG-I-Like Receptor (RLR) signaling (e.g., RGT100); inhibitors of adenosinergic signaling (e.g., inhibitors of CD73, CD39 and A2R such as AB680, AB928, A000830, CPI-444), inhibitors of IDO-1 (indoleamine 2,3-dioxygenase 1) (e.g., GDC-0919 (navoximod), BMS-986205, and epacadostat); and small molecule blockers of the PD-1 pathway (e.g., CA-170, BMS-8, BMS-202, and AUNP12).

In some embodiments, the immunomodulatory agent is an anti-multiple myeloma agent. Examples of such immunomodulatory agents include, for example, lenalidomide, pomalidomide, and proteasome inhibitors. Examples of such proteasome inhibitors include, for example, bortezomib, carfilzomib, and ixazomib.

In some embodiments, an immunomodulatory compound is an immunostimulatory compound.

In some embodiments, an immunomodulatory compound is not a cytokine. In some embodiments, an immunomodulatory compound is not an interleukin. In some embodiments, an immunomodulatory compound is not interleukin 2 (IL2). In some embodiments, an immunomodulatory compound may be replaced with a cytokine or an interleukin or IL2.

In additional embodiments, an antibody conjugate can have a payload selected from the group consisting of a label, a dye, a polymer, a water-soluble polymer, polyethylene glycol, a derivative of polyethylene glycol, a photocrosslinker, a cytotoxic compound, a radionuclide, a drug, an affinity label, a photoaffinity label, a reactive compound, a resin, a second protein or polypeptide or polypeptide analog, an antibody or antibody fragment, a metal chelator, a cofactor, a fatty acid, a carbohydrate, a polynucleotide, a DNA, a RNA, an antisense polynucleotide, a peptide, a water-soluble dendrimer, a cyclodextrin, an inhibitory ribonucleic acid, a biomaterial, a nanoparticle, a spin label, a fluorophore, a metal-containing moiety, a radioactive moiety, a novel functional group, a group that covalently or noncovalently interacts with other molecules, a photocaged moiety, a photoisomerizable moiety, biotin, a derivative of biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, a small molecule, or any combination thereof. In an embodiment, the payload is a label, a dye, a polymer, a cytotoxic compound, a radionuclide, a drug, an affinity label, a resin, a protein, a polypeptide, a polypeptide analog, an antibody, antibody fragment, a metal chelator, a cofactor, a fatty acid, a carbohydrate, a polynucleotide, a DNA, a RNA, a peptide, a fluorophore, or a carbon-linked sugar. In another embodiment, the payload is a label, a dye, a polymer, a drug, an antibody, antibody fragment, a DNA, an RNA, or a peptide.

In certain embodiments, the conjugate comprises one or more water soluble polymers. A wide variety of macromolecular polymers and other molecules can be linked to the polypeptides described herein to modulate biological properties of the polypeptide, and/or provide new biological properties to the polypeptide. These macromolecular polymers can be linked to the polypeptide via a naturally encoded amino acid, via a non-naturally encoded amino acid, or any functional substituent of a natural or modified amino acid, or any substituent or functional group added to a natural or modified amino acid. The molecular weight of the polymer may be of a wide range, including but not limited to, between about 100 Da and about 100,000 Da or more.

The polymer selected may be water soluble so that a protein to which it is attached does not precipitate in an aqueous environment, such as a physiological environment. The polymer may be branched or unbranched. Preferably, for therapeutic use of the end-product preparation, the polymer will be pharmaceutically acceptable.

In certain embodiments, the proportion of polyethylene glycol molecules to polypeptide molecules will vary, as will their concentrations in the reaction mixture. In general, the optimum ratio (in terms of efficiency of reaction in that there is minimal excess unreacted protein or polymer) may be determined by the molecular weight of the polyethylene glycol selected and on the number of available reactive groups available. As relates to molecular weight, typically the higher the molecular weight of the polymer, the fewer number of polymer molecules which may be attached to the protein. Similarly, branching of the polymer should be taken into account when optimizing these parameters. Generally, the higher the molecular weight (or the more branches) the higher the polymer:protein ratio.

The water soluble polymer may be any structural form including but not limited to linear, forked, or branched. Typically, the water soluble polymer is a poly(alkylene glycol), such as poly(ethylene glycol) (PEG), but other water soluble polymers can also be employed. By way of example, PEG is used to describe certain embodiments.

PEG is a well-known, water soluble polymer that is commercially available or can be prepared by ring-opening polymerization of ethylene glycol according to methods well known in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented as linked to a polypeptide by the formula: $X'O-(CH_2CH_2O)_n-CH_2CH_2-Y$ where n is 2 to 10,000, X is H or a terminal modification, including but not limited to, a $C_{14}$ alkyl, and Y is the attachment point to the polypeptide.

In some cases, a PEG terminates on one end with hydroxy or methoxy, i.e., $X'$ is H or $CH_3$ ("methoxy PEG"). Alternatively, the PEG can terminate with a reactive group, thereby forming a bifunctional polymer. Typical reactive groups can include those reactive groups that are commonly used to react with the functional groups found in the 20 common amino acids (including but not limited to, maleimide groups, activated carbonates (including but not limited to, p-nitrophenyl ester), activated esters (including but not limited to, N-hydroxysuccinimide, p-nitrophenyl ester, and aldehydes) as well as functional groups that are inert to the 20 common amino acids but that react specifically with complementary functional groups present in non-naturally encoded amino acids (including but not limited to, azide groups, alkyne groups). It is noted that the other end of the PEG, which is shown in the above formula by Y, will attach either directly or indirectly to a polypeptide via a naturally-occurring or non-naturally encoded amino acid. For instance, Y may be an amide, carbamate or urea linkage to an amine group (including but not limited to, the epsilon amine of lysine or the N-terminus) of the polypeptide. Alternatively, Y may be a maleimide linkage to a thiol group (including but not limited to, the thiol group of cysteine). Alternatively, Y may be a linkage to a residue not commonly accessible via the 20 common amino acids. For example, an azide group on the PEG can be reacted with an alkyne group on the polypeptide to form a Huisgen [3+2] cycloaddition product. Alternatively, an alkyne group on the PEG can be reacted with an azide group present in a non-naturally encoded amino acid, such as the modified amino acids described herein, to form a similar product. In some embodiments, a strong nucleophile (including but not limited to, hydrazine, hydrazide, hydroxylamine, semicarbazide) can be reacted with an aldehyde or ketone group present in a non-naturally encoded amino acid to form a hydrazone, oxime, or semicarbazone, as applicable, which in some cases can be further reduced by treatment with an appropriate reducing agent. Alternatively, the strong nucleophile can be incorporated into the polypeptide via a non-naturally encoded amino acid and used to react preferentially with a ketone or aldehyde group present in the water soluble polymer.

Any molecular mass for a PEG can be used as practically desired, including but not limited to, from about 100 Daltons (Da) to 100,000 Da or more as desired (including but not limited to, sometimes 0.1-50 kDa or 10-40 kDa). Branched chain PEGs, including but not limited to, PEG molecules with each chain having a MW ranging from 1-100 kDa (including but not limited to, 1-50 kDa or 5-20 kDa) can also be used. A wide range of PEG molecules are described in, including but not limited to, the Shearwater Polymers, Inc. catalog, and the Nektar Therapeutics catalog, incorporated herein by reference.

Generally, at least one terminus of the PEG molecule is available for reaction with the antibody. For example, PEG derivatives bearing alkyne and azide moieties for reaction with amino acid side chains can be used to attach PEG to non-naturally encoded amino acids as described herein. If the non-naturally encoded amino acid comprises an azide, then the PEG will typically contain either an alkyne moiety to effect formation of the [3+2]cycloaddition product or an activated PEG species (i.e., ester, carbonate) containing a phosphine group to effect formation of the amide linkage. Alternatively, if the non-naturally encoded amino acid comprises an alkyne, then the PEG will typically contain an azide moiety to effect formation of the [3+2] Huisgen cycloaddition product. If the non-naturally encoded amino acid comprises a carbonyl group, the PEG will typically comprise a potent nucleophile (including but not limited to, a hydrazide, hydrazine, hydroxylamine, or semicarbazide functionality) in order to effect formation of corresponding hydrazone, oxime, and semicarbazone linkages, respectively. In other alternatives, a reverse of the orientation of the reactive groups described herein can be used, i.e., an azide moiety in the non-naturally encoded amino acid can be reacted with a PEG derivative containing an alkyne.

In some embodiments, the polypeptide variant with a PEG derivative contains a chemical functionality that is reactive with the chemical functionality present on the side chain of the non-naturally encoded amino acid.

In certain embodiments, the payload is an azide- or acetylene-containing polymer comprising a water soluble polymer backbone having an average molecular weight from about 800 Da to about 100,000 Da. The polymer backbone of the water-soluble polymer can be poly(ethylene glycol). However, it should be understood that a wide variety of water soluble polymers including but not limited to poly (ethylene)glycol and other related polymers, including poly (dextran) and poly(propylene glycol), are also suitable for use and that the use of the term PEG or poly(ethylene glycol) is intended to encompass and include all such molecules. The term PEG includes, but is not limited to, poly(ethylene glycol) in any of its forms, including bifunctional PEG, multiarmed PEG, derivatized PEG, forked PEG, branched PEG, pendent PEG (i.e. PEG or related polymers having one or more functional groups pendent to the polymer backbone), or PEG with degradable linkages therein.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, glycerol oligomers, pentaerythritol, and sorbitol. The central branch moiety can also be derived from several amino acids, such as lysine. The branched poly(ethylene glycol) can be represented in general form as R(-PEG-OH)m in which R is derived from a core moiety, such as glycerol, glycerol oligomers, or pentaerythritol, and m represents the number of arms. Multi-armed PEG molecules, such as those described in U.S. Pat. Nos. 5,932,462 5,643,575; 5,229,490; 4,289,872; U.S. Pat. Appl. 2003/0143596; WO 96/21469; and WO 93/21259, each of which is incorporated by reference herein in its entirety, can also be used as the polymer backbone.

Branched PEG can also be in the form of a forked PEG represented by PEG(-YCHZ$_2$)$_n$, where Y is a linking group and Z is an activated terminal group linked to CH by a chain of atoms of defined length.

Yet another branched form, the pendant PEG, has reactive groups, such as carboxyl, along the PEG backbone rather than at the end of PEG chains.

In addition to these forms of PEG, the polymer can also be prepared with weak or degradable linkages in the backbone. For example, PEG can be prepared with ester linkages in the polymer backbone that are subject to hydrolysis. As shown herein, this hydrolysis results in cleavage of the polymer into fragments of lower molecular weight: -PEG-CO$_2$-PEG-+H$_2$O→PEG-CO$_2$H+HO-PEG- It is understood by those skilled in the art that the term poly(ethylene glycol) or PEG represents or includes all the forms known in the art including but not limited to those disclosed herein.

Many other polymers are also suitable for use. In some embodiments, polymer backbones that are water-soluble, with from 2 to about 300 termini, are particularly suitable. Examples of suitable polymers include, but are not limited to, other poly(alkylene glycols), such as poly(propylene glycol) ("PPG"), copolymers thereof (including but not limited to copolymers of ethylene glycol and propylene glycol), terpolymers thereof, mixtures thereof, and the like. Although the molecular weight of each chain of the polymer backbone can vary, it is typically in the range of from about 800 Da to about 100,000 Da, often from about 6,000 Da to about 80,000 Da.

Those of ordinary skill in the art will recognize that the foregoing list for substantially water soluble backbones is by no means exhaustive and is merely illustrative, and that all polymeric materials having the qualities described herein are contemplated as being suitable for use.

In some embodiments the polymer derivatives are "multifunctional," meaning that the polymer backbone has at least two termini, and possibly as many as about 300 termini, functionalized or activated with a functional group. Multifunctional polymer derivatives include, but are not limited to, linear polymers having two termini, each terminus being bonded to a functional group which may be the same or different.

4. Linkers

In certain embodiments, the antibodies can be linked to the payloads with one or more linkers capable of reacting with an antibody amino acid and with a payload group. The one or more linkers can be any linkers apparent to those of skill in the art.

The term "linker" is used herein to refer to groups or bonds that normally are formed as the result of a chemical reaction and typically are covalent linkages.

Useful linkers include those described herein. In certain embodiments, the linker is any divalent or multivalent linker known to those of skill in the art. Useful divalent linkers include alkylene, substituted alkylene, heteroalkylene, substituted heteroalkylene, arylene, substituted arylene, heteroarylene, and substituted heteroarylene. In certain embodiments, the linker is $C_{1-10}$ alkylene or $C_{1-10}$ heteroalkylene. In some embodiments, the $C_{1-10}$heteoalkylene is PEG.

In certain embodiments, the linker is hydrolytically stable. Hydrolytically stable linkages means that the linkages are substantially stable in water and do not react with water at useful pH values, including but not limited to, under physiological conditions for an extended period of time, perhaps even indefinitely. In certain embodiments, the linker is hydrolytically unstable. Hydrolytically unstable or degradable linkages mean that the linkages are degradable in water or in aqueous solutions, including for example, blood. Enzymatically unstable or degradable linkages mean that the linkage can be degraded by one or more enzymes.

As understood in the art, PEG and related polymers may include degradable linkages in the polymer backbone or in the linker group between the polymer backbone and one or more of the terminal functional groups of the polymer molecule. For example, ester linkages formed by the reaction of PEG carboxylic acids or activated PEG carboxylic acids with alcohol groups on a biologically active agent generally hydrolyze under physiological conditions to release the agent.

Other hydrolytically degradable linkages include, but are not limited to, carbonate linkages; imine linkages resulted from reaction of an amine and an aldehyde; phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide.

A number of different cleavable linkers are known to those of skill in the art. See U.S. Pat. Nos. 4,618,492; 4,542,225, and 4,625,014. The mechanisms for release of an agent from these linker groups include, for example, irradiation of a photolabile bond and acid-catalyzed hydrolysis. U.S. Pat. No. 4,671,958, for example, includes a description of immunoconjugates comprising linkers which are cleaved at the target site in vivo by the proteolytic enzymes of the patient's complement system. The length of the linker may be predetermined or selected depending upon a desired spatial relationship between the polypeptide and the molecule linked to it. In view of the large number of methods that have been reported for attaching a variety of radiodiagnostic compounds, radiotherapeutic compounds, drugs, toxins, and other agents to polypeptides one skilled in the art will be able to determine a suitable method for attaching a given agent to a polypeptide.

The linker may have a wide range of molecular weight or molecular length. Larger or smaller molecular weight linkers may be used to provide a desired spatial relationship or conformation between the polypeptide and the linked entity. Linkers having longer or shorter molecular length may also be used to provide a desired space or flexibility between the polypeptide and the linked entity. Similarly, a linker having a particular shape or conformation may be utilized to impart a particular shape or conformation to the polypeptide or the linked entity, either before or after the polypeptide reaches its target. The functional groups present on each end of the linker may be selected to modulate the release of a polypeptide or a payload under desired conditions. This optimization of the spatial relationship between the polypeptide and the linked entity may provide new, modulated, or desired properties to the molecule.

In some embodiments, provided herein water-soluble bifunctional linkers that have a dumbbell structure that includes: a) an azide, an alkyne, a hydrazine, a hydrazide, a hydroxylamine, or a carbonyl-containing moiety on at least a first end of a polymer backbone; and b) at least a second functional group on a second end of the polymer backbone. The second functional group can be the same or different as the first functional group. The second functional group, in some embodiments, is not reactive with the first functional group. In some embodiments, water-soluble compounds that comprise at least one arm of a branched molecular structure are provided. For example, the branched molecular structure can be a dendritic structure.

In some embodiments, the linker is derived from a linker precursor selected from the group consisting of: N-succinimidyl-3-(2-pyridyldithio)propionate (SPDP), N-succinimidyl 4-(2-pyridyldithio)pentanoate (SPP), N-succinimidyl 4-(2-pyridyldithio)butanoate (SPDB), N-succinimidyl-4-(2-pyridyldithio)-2-sulfo-butanoate (sulfo-SPDB), N-succinimidyl iodoacetate (SIA), N-succinimidyl(4-iodoacetyl) aminobenzoate (SIAB), maleimide PEG NHS, N-succinimidyl 4-(maleimidomethyl)cyclohexanecarboxylate (SMCC), N-sulfosuccinimidyl 4-(maleimidomethyl)cyclohexanecarboxylate (sulfo-SMCC) or 2,5-dioxopyrrolidin-1-yl 17-(2,5-dioxo-2,5-dihydro-1H-pyrrol-1-yl)-5,8,11,14-tetraoxo-4,7,10,13-tetraazaheptadecan-1-oate (CX1-1). In a specific embodiment, the linker is derived from the linker precursor N-succinimidyl 4-(maleimidomethyl)cyclohexanecarboxylate (SMCC).

In some embodiments, the linker is derived from a linker precursor selected from the group consisting of dipeptides, tripeptides, tetrapeptides, and pentapeptides. In such embodiments, the linker can be cleaved by a protease. Exemplary dipeptides include, but are not limited to, valine-citrulline (vc or val-cit), alanine-phenylalanine (AF or ala-phe); phenylalanine-lysine (FK or phe-lys); phenylalanine-homolysine (phe-homolys); and N-methyl-valine-citrulline (Me-val-cit). Exemplary tripeptides include, but are not limited to, glycine-valine-citrulline (gly-val-cit), glycine-glycine-glycine (gly-gly-gly), and glycine-methoxyethoxy-ethyl)serine-valine (gly-val-citalanine OMESerValAla).

In some embodiments, a linker comprises a self-immolative spacer. In certain embodiments, the self-immolative spacer comprises p-aminobenzyl. In some embodiments, a p-aminobenzyl alcohol is attached to an amino acid unit via an amide bond, and a carbamate, methylcarbamate, or carbonate is made between the benzyl alcohol and the payload (Hamann et al. (2005) Expert Opin. Ther. Patents (2005) 15:1087-1103). In some embodiments, the linker comprises p-aminobenzyloxycarbonyl (PAB). Other examples of self-immolative spacers include, but are not limited to, aromatic compounds that are electronically similar to the PAB group, such as 2-aminoimidazol-5-methanol derivatives (U.S. Pat. No. 7,375,078; Hay et al. (1999) Bioorg. Med. Chem. Lett. 9:2237) and ortho- or para-aminobenzylacetals. In some embodiments, spacers can be used that undergo cyclization upon amide bond hydrolysis, such as substituted and unsubstituted 4-aminobutyric acid amides (Rodrigues et al. (1995) Chemistry Biology 2:223), appropriately substituted bicyclo[2.2.1] and bicyclo[2.2.2] ring systems (Storm et al. (1972) J. Amer. Chem. Soc. 94:5815) and 2-aminophenylpropionic acid amides (Amsberry, et al. (1990) J. Org. Chem. 55:5867). Linkage of a drug to the α-carbon of a glycine residue is another example of a self-immolative spacer that may be useful in conjugates (Kingsbury et al. (1984) J. Med. Chem. 27:1447).

In certain embodiments, linker precursors can be combined to form larger linkers. For instance, in certain embodiments, linkers comprise the dipeptide valine-citrulline and p-aminobenzyloxycarbonyl. These are also referenced as citValCit—PAB linkers.

In certain embodiments, the payloads can be linked to the linkers, referred to herein as a linker-payload, with one or more linker groups capable of reacting with an antibody amino acid group. The one or more linkers can be any linkers apparent to those of skill in the art or those set forth herein.

Linker precursors can be prepared as described herein in the Examples section, and/or by standard techniques, or obtained from commercial sources, e.g. WO 2019/055931, WO 2019/055909, WO 2017/132617, and WO 2017/132615, each incorporated by reference in its entirety.

Additional linkers are disclosed herein, such as, for example, the linker precursors (A)-(N) described below.

5. Antibody Specificity

The conjugates comprise antibodies that selectively bind human antigens. In some embodiments, the antibody binds to a homolog of a human antigen. In some aspects, the antibody binds to a homolog of the human antigen from a species selected from monkeys, mice, dogs, cats, rats, cows, horses, goats, and sheep. In some aspects, the homolog is a cynomolgus monkey homolog. In some aspects, the homolog is a mouse or murine homolog.

In some embodiments, the antibody comprises a light chain. In some aspects, the light chain is a kappa light chain. In some aspects, the light chain is a lambda light chain.

In some embodiments, the antibody comprises a heavy chain. In some aspects, the heavy chain is an IgA. In some aspects, the heavy chain is an IgD. In some aspects, the heavy chain is an IgE. In some aspects, the heavy chain is an IgG. In some aspects, the heavy chain is an IgM. In some aspects, the heavy chain is an IgG1. In some aspects, the heavy chain is an IgG2. In some aspects, the heavy chain is an IgG3. In some aspects, the heavy chain is an IgG4. In some aspects, the heavy chain is an IgA1. In some aspects, the heavy chain is an IgA2.

In some embodiments, the antibody is an antibody fragment. In some aspects, the antibody fragment is an Fv fragment. In some aspects, the antibody fragment is a Fab fragment. In some aspects, the antibody fragment is a F(ab')$_2$ fragment. In some aspects, the antibody fragment is a Fab' fragment. In some aspects, the antibody fragment is an scFv (sFv) fragment. In some aspects, the antibody fragment is an scFv-Fc fragment.

In some embodiments, the antibody is a monoclonal antibody. In some embodiments, the antibody is a polyclonal antibody.

In some embodiments, the antibody is a chimeric antibody. In some embodiments, the antibody is a humanized antibody. In some embodiments, the antibody is a human antibody. In some embodiments, the antibody is an affinity matured antibody.

The antibody conjugates provided herein may be useful for the treatment of a variety of diseases and conditions including cancers. In some embodiments, the antibody conjugates provided herein may be useful for the treatment of cancers of solid tumors.

6. Glycosylation Variants

In certain embodiments, an antibody may be altered to increase, decrease, or eliminate the extent to which it is glycosylated. Glycosylation of polypeptides is typically either "N-linked" or "O-linked."

"N-linked" glycosylation refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site.

"O-linked" glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition or deletion of N-linked glycosylation sites to the antibody may be accomplished by altering the amino acid sequence such that one or more of the above-described tripeptide sequences is created or removed. Addition or deletion of O-linked glycosylation sites may be accomplished by addition, deletion, or substitution of one or more serine or threonine residues in or to (as the case may be) the sequence of an antibody.

7. Modified Amino Acids

When the antibody conjugate comprises a modified amino acid, the modified amino acid can be any modified amino acid deemed suitable by the practitioner. In particular embodiments, the modified amino acid comprises a reactive group useful for forming a covalent bond to a linker precursor or to a payload precursor. In certain embodiments, the modified amino acid is a non-natural amino acid. In certain embodiments, the reactive group is selected from the group consisting of amino, carboxy, acetyl, hydrazino, hydrazido, semicarbazido, sulfanyl, azido, and alkynyl. Modified amino acids are also described in, for example, WO 2013/185115 and WO 2015/006555, each of which is incorporated herein by reference in its entirety.

The terms "residue of an amino acid" and "amino acid residue" refer to the product of an amide coupling or peptide coupling of an amino acid to a suitable coupling partner; wherein, for example, a water molecule is expelled after the amide or peptide coupling of the amino acid, resulting in the product having the amino acid residue incorporated therein. In some embodiments, the amino acid residue is according to

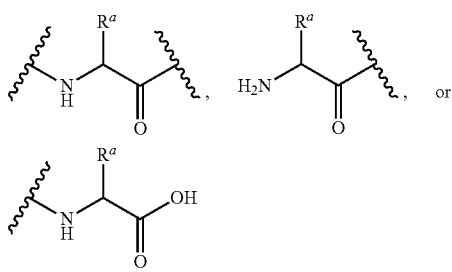

where $R^a$ is the side chain of an amino acid. In some embodiments, the amino acid residue is according to

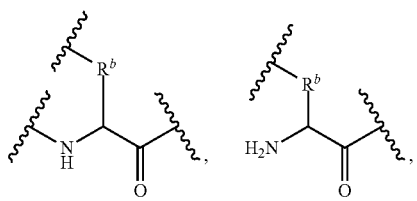

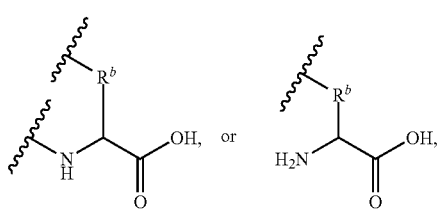

where $R^b$ is a residue of a side chain of an amino acid, e.g. a C(O) residue of C(O)OH in the side chain of an aspartic acid or an NH residue of $NH_2$ in the side chain of a lysine.

The terms "residue of a peptide" and "peptide residue" refer to the product of an amide coupling or peptide coupling of an amino acid to a suitable coupling partner; wherein, for example, a water molecule is expelled after the amide or peptide coupling of the amino acid, resulting in the product having the peptide residue incorporated therein. In some embodiments, the peptide residue is according to

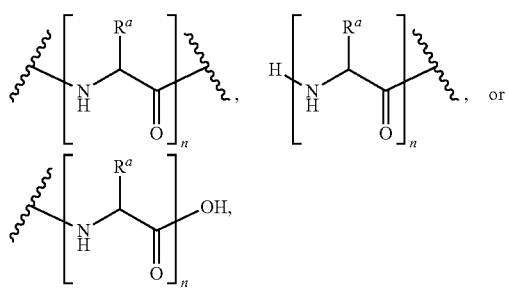

where n is 2 or more and where $R^a$ is the side chain of an amino acid. In some embodiments, the peptide residue is according to

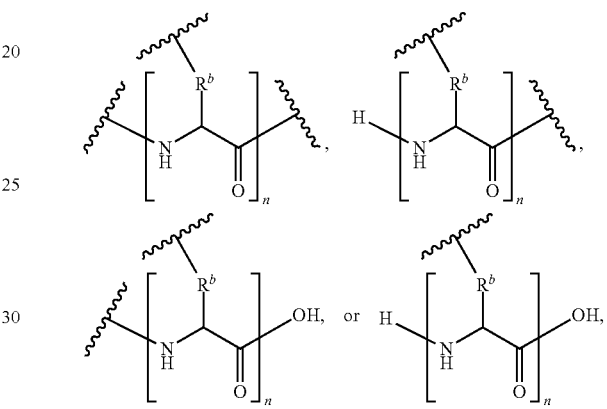

where n is 2 or more and where $R^b$ is a residue of a side chain of an amino acid, e.g. a C(O) residue of C(O)OH in the side chain of an aspartic acid or an NH residue of $NH_2$ in the side chain of a lysine. In some embodiments, n is 2-50, 2-25, 2-10, 1-5, or 2-3. In some embodiments, n is 2. In some embodiments, n is 3.

In certain embodiments, the amino acid residue is according to any of the following formulas:

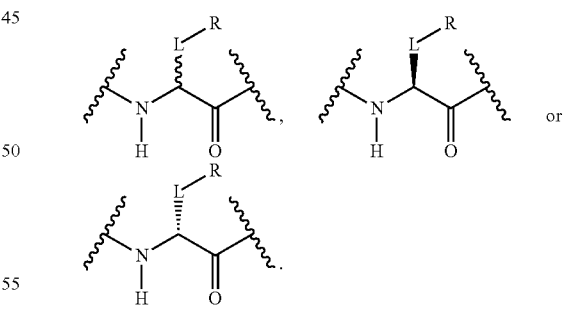

Those of skill in the art will recognize that antibodies are generally comprised of L-amino acids However, with non-natural amino acids, the present methods and compositions provide the practitioner with the ability to use L-, D- or racemic non-natural amino acids at the site-specific positions. In certain embodiments, the non-natural amino acids described herein include D- versions of the natural amino acids and racemic versions of the natural amino acids.

In the above formulas, the wavy lines indicate bonds that connect to the remainder of the polypeptide chains of the antibodies. These non-natural amino acids can be incorporated into polypeptide chains just as natural amino acids are incorporated into the same polypeptide chains. In certain embodiments, the non-natural amino acids are incorporated into the polypeptide chain via amide bonds as indicated in the formulas.

In the above formulas R designates any functional group without limitation, so long as the amino acid residue is not identical to a natural amino acid residue. In certain embodiments, R can be a hydrophobic group, a hydrophilic group, a polar group, an acidic group, a basic group, a chelating group, a reactive group, a therapeutic moiety, or a labeling moiety. In certain embodiments, R is selected from the group consisting of $R^{1z}NR^{2z}R^{3z}$, $R^{1z}C(=O)R^{2z}$, $R^{1z}C(=O)OR^{2z}$, $R^{1z}N_3$, $R^{1z}C(\equiv CH)$. In these embodiments, $R^{1z}$ is selected from the group consisting of a bond, alkylene, heteroalkylene, arylene, heteroarylene. $R^{2z}$ and $R^{3z}$ are each independently selected from the group consisting of hydrogen, alkyl, and heteroalkyl.

In some embodiments, the non-naturally encoded amino acids include side chain functional groups that react efficiently and selectively with functional groups not found in the 20 common amino acids (including but not limited to, azido, ketone, aldehyde and aminooxy groups) to form stable conjugates. For example, antigen-binding polypeptide that includes a non-naturally encoded amino acid containing an azido functional group can be reacted with a polymer (including but not limited to, poly(ethylene glycol) or, alternatively, a second polypeptide containing an alkyne moiety to form a stable conjugate resulting for the selective reaction of the azide and the alkyne functional groups to form a Huisgen [3+2] cycloaddition product.

Exemplary non-naturally encoded amino acids that may be suitable for use in the present invention and that are useful for reactions with water soluble polymers include, but are not limited to, those with carbonyl, aminooxy, hydrazine, hydrazide, semicarbazide, azide and alkyne reactive groups. In some embodiments, non-naturally encoded amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine, and O-mannosaminyl-L-serine. Examples of such amino acids also include examples where the naturally-occurring N- or O-linkage between the amino acid and the saccharide is replaced by a covalent linkage not commonly found in nature-including but not limited to, an alkene, an oxime, a thioether, an amide and the like. Examples of such amino acids also include saccharides that are not commonly found in naturally-occurring proteins such as 2-deoxy-glucose, 2-deoxygalactose, and the like.

Many of the non-naturally encoded amino acids provided herein are commercially available, e.g., from Sigma-Aldrich (St. Louis, Mo., USA), Novabiochem (a division of EMD Biosciences, Darmstadt, Germany), or Peptech (Burlington, Mass., USA). Those that are not commercially available are optionally synthesized as provided herein or using standard methods known to those of skill in the art. For organic synthesis techniques, see, e.g., Organic Chemistry by Fessendon and Fessendon, (1982, Second Edition, Willard Grant Press, Boston Mass.); Advanced Organic Chemistry by March (Third Edition, 1985, Wiley and Sons, New York); and Advanced Organic Chemistry by Carey and Sundberg (Third Edition, Parts A and B, 1990, Plenum Press, New York). See, also, U.S. Patent Application Publications 2003/0082575 and 2003/0108885, which is incorporated by reference herein. In addition to unnatural amino acids that contain unnatural side chains, unnatural amino acids that may be suitable for use in the present invention also optionally comprise modified backbone structures, including but not limited to, as illustrated by the structures of Formula II and III:

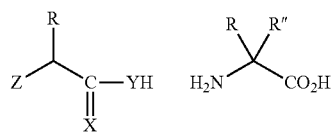

wherein Z typically comprises OH, $NH_2$, SH, NH—R'', or S—R''; X and Y, which can be the same or different, typically comprise S or O, and R and R'', which are optionally the same or different, are typically independently selected from the same list of constituents for the R group described above for the unnatural amino acids having Formula I as well as hydrogen. For example, unnatural amino acids of the invention optionally comprise substitutions in the amino or carboxyl group as illustrated by Formulas II and III. Unnatural amino acids of this type include, but are not limited to, α-hydroxy acids, α-thioacids, α-aminothiocarboxylates, including but not limited to, with side chains corresponding to the common twenty natural amino acids or unnatural side chains. In addition, substitutions at the α-carbon optionally include, but are not limited to, L, D, or α-α-disubstituted amino acids such as D-glutamate, D-alanine, D-methyl-O-tyrosine, aminobutyric acid, and the like. Other structural alternatives include cyclic amino acids, such as proline analogues as well as 3, 4, 6, 7, 8, and 9 membered ring proline analogues, β and γ amino acids such as substituted β-alanine and γ-amino butyric acid.

Many unnatural amino acids are based on natural amino acids, such as tyrosine, glutamine, phenylalanine, and the like, and are suitable for use in the present invention. Tyrosine analogs include, but are not limited to, para-substituted tyrosines, ortho-substituted tyrosines, and meta substituted tyrosines, where the substituted tyrosine comprises, including but not limited to, a keto group (including but not limited to, an acetyl group), a benzoyl group, an amino group, a hydrazine, an hydroxyamine, a thiol group, a carboxy group, an isopropyl group, a methyl group, a $C_6$-$C_{20}$ straight chain or branched hydrocarbon, a saturated or unsaturated hydrocarbon, an O-methyl group, a polyether group, a nitro group, an alkynyl group or the like. In addition, multiply substituted aryl rings are also contemplated. Glutamine analogs that may be suitable for use in the present invention include, but are not limited to, α-hydroxy derivatives, γ-substituted derivatives, cyclic derivatives, and amide substituted glutamine derivatives. Example phenylalanine analogs that may be suitable for use in the present invention include, but are not limited to, para-substituted phenylalanines, ortho-substituted phenylalanines, and meta-substituted phenylalanines, where the substituent comprises, including but not limited to, a hydroxy group, a methoxy group, a methyl group, an allyl group, an aldehyde, an azido, an iodo, a bromo, a keto group (including but not limited to, an acetyl group), a benzoyl, an alkynyl group, or the like. Specific examples of unnatural amino acids that may be suitable for use in the present invention include, but are not limited to, a p-acetyl-L-phenylalanine, an O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-azido-methyl-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, and a p-propargyloxy-phenylalanine, and the like. Examples of structures of a variety of unnatural amino acids that may be suitable for use in the present invention are provided in, for example, WO 2002/085923 entitled "In vivo incorporation of unnatural amino acids." See also Kiick et al., (2002) Incorporation of azides into recombinant proteins for chemoselective modification by the Staudinger ligation, PNAS 99:19-24, for additional methionine analogs.

Many of the unnatural amino acids suitable for use in the present invention are commercially available, e.g., from Sigma (USA) or Aldrich (Milwaukee, Wis., USA). Those that are not commercially available are optionally synthesized as provided herein or as provided in various publications or using standard methods known to those of skill in the art. For organic synthesis techniques, see, e.g., Organic Chemistry by Fessendon and Fessendon, (1982, Second Edition, Willard Grant Press, Boston Mass.); Advanced Organic Chemistry by March (Third Edition, 1985, Wiley and Sons, New York); and Advanced Organic Chemistry by Carey and Sundberg (Third Edition, Parts A and B, 1990, Plenum Press, New York). Additional publications describing the synthesis of unnatural amino acids include, e.g., WO 2002/085923 entitled "In vivo incorporation of Unnatural Amino Acids;" Matsoukas et al., (1995) J. Med. Chem., 38, 4660-4669; King, F. E. & Kidd, D. A. A. (1949) A New Synthesis of Glutamine and of γ-Dipeptides of Glutamic Acid from Phthylated Intermediates. J. Chem. Soc., 3315-3319; Friedman, O. M. & Chatterrji, R. (1959) Synthesis of Derivatives of Glutamine as Model Substrates for Anti-Tumor Agents. *J. Am. Chem. Soc.* 81, 3750-3752; Craig, J. C. et al. (1988) Absolute Configuration of the Enantiomers of 7-Chloro-4 [[4-(diethylamino)-1-methylbutyl]amino]quinoline (Chloroquine). J. Org. Chem. 53, 1167-1170; Azoulay, M., Vilmont, M. & Frappier, F. (1991) Glutamine analogues as Potential Antimalarials, Eur. J. Med. Chem. 26, 201-5; Koskinen, A. M. P. & Rapoport, H. (1989) Synthesis of 4-Substituted Prolines as Conformationally Constrained Amino Acid Analogues. J. Org. Chem. 54, 1859-1866; Christie, B. D. & Rapoport, H. (1985) Synthesis of Optically Pure Pipecolates from L-Asparagine. Application to the Total Synthesis of (+)-Apovincamine through Amino Acid Decarbonylation and Iminium Ion Cyclization. J. Org. Chem. 1989:1859-1866; Barton et al., (1987) Synthesis of Novel a-Amino-Acids and Derivatives Using Radical Chemistry: Synthesis of L- and D-a-Amino-Adipic Acids, L-a-aminopimelic Acid and Appropriate Unsaturated Derivatives. Tetrahedron Lett. 43:4297-4308; and, Subasinghe et al., (1992) Quisqualic acid analogues: synthesis of beta-heterocyclic 2-aminopropanoic acid derivatives and their activity at a novel quisqualate-sensitized site. J. Med. Chem. 35:4602-7. See also, patent applications entitled "Protein Arrays," filed Dec. 22, 2003, Ser. No. 10/744,899, and Ser. No. 60/435,821 filed on Dec. 22, 2002.

Amino acids with a carbonyl reactive group allow for a variety of reactions to link molecules (including but not limited to, PEG or other water soluble molecules) via nucleophilic addition or aldol condensation reactions among others.

Exemplary carbonyl-containing amino acids can be represented as follows:

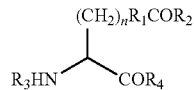

wherein n is 0-10; $R_1$ is an alkyl, aryl, substituted alkyl, or substituted aryl; $R_2$ is H, alkyl, aryl, substituted alkyl, and substituted aryl; and $R_3$ is H, an amino acid, a polypeptide, or an amino terminus modification group, and $R_4$ is H, an amino acid, a polypeptide, or a carboxy terminus modification group. In some embodiments, n is 1, $R_1$ is phenyl and $R_2$ is a simple alkyl (i.e., methyl, ethyl, or propyl) and the ketone moiety is positioned in the para position relative to the alkyl side chain. In some embodiments, n is 1, $R_1$ is phenyl and $R_2$ is a simple alkyl (i.e., methyl, ethyl, or propyl) and the ketone moiety is positioned in the meta position relative to the alkyl side chain.

In some examples, a non-naturally encoded amino acid bearing adjacent hydroxyl and amino groups can be incorporated into the polypeptide as a "masked" aldehyde functionality. For example, 5-hydroxylysine bears a hydroxyl group adjacent to the epsilon amine. Reaction conditions for generating the aldehyde typically involve addition of molar excess of sodium metaperiodate under mild conditions to avoid oxidation at other sites within the polypeptide. The pH of the oxidation reaction is typically about 7.0. A typical reaction involves the addition of about 1.5 molar excess of sodium meta periodate to a buffered solution of the polypeptide, followed by incubation for about 10 minutes in the dark. See, e.g. U.S. Pat. No. 6,423,685, which is incorporated by reference herein.

The carbonyl functionality can be reacted selectively with a hydrazine-, hydrazide-, hydroxylamine-, or semicarbazide-containing reagent under mild conditions in aqueous solution to form the corresponding hydrazone, oxime, or semicarbazone linkages, respectively, that are stable under physiological conditions. See, e.g., Jencks, W. P., J. Am. Chem. Soc. 81, 475-481 (1959); Shao, J. and Tam, J. P., J. Am. Chem. Soc. 117:3893-3899 (1995). Moreover, the unique reactivity of the carbonyl group allows for selective modification in the presence of the other amino acid side chains. See, e.g., Cornish, V. W., et al., J. Am. Chem. Soc. 118:8150-8151 (1996); Geoghegan, K. F. & Stroh, J. G., Bioconjug. Chem. 3:138-146 (1992); Mahal, L. K., et al., Science 276:1125-1128 (1997).

Non-naturally encoded amino acids containing a nucleophilic group, such as a hydrazine, hydrazide or semicarbazide, allow for reaction with a variety of electrophilic groups to form conjugates (including but not limited to, with PEG or other water soluble polymers).

Exemplary hydrazine, hydrazide or semicarbazide-containing amino acids can be represented as follows:

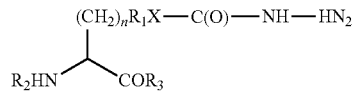

wherein n is 0-10; $R_1$ is an alkyl, aryl, substituted alkyl, or substituted aryl or not present; X, is O, N, or S or not present; $R_2$ is H, an amino acid, a polypeptide, or an amino terminus modification group, and $R_3$ is H, an amino acid, a polypeptide, or a carboxy terminus modification group.

In some embodiments, n is 4, $R_1$ is not present, and X is N. In some embodiments, n is 2, $R_1$ is not present, and X is not present. In some embodiments, n is 1, $R_1$ is phenyl, X is O, and the oxygen atom is positioned para to the aliphatic group on the aryl ring.

Hydrazide-, hydrazine-, and semicarbazide-containing amino acids are available from commercial sources. For instance, L-glutamate-γ-hydrazide is available from Sigma Chemical (St. Louis, Mo.). Other amino acids not available commercially can be prepared by one skilled in the art. See, e.g., U.S. Pat. No. 6,281,211, which is incorporated by reference herein.

Polypeptides containing non-naturally encoded amino acids that bear hydrazide, hydrazine or semicarbazide functionalities can be reacted efficiently and selectively with a variety of molecules that contain aldehydes or other functional groups with similar chemical reactivity. See, e.g., Shao, J. and Tam, J., J. Am. Chem. Soc. 117:3893-3899 (1995). The unique reactivity of hydrazide, hydrazine, and semicarbazide functional groups makes them significantly more reactive toward aldehydes, ketones and other electrophilic groups as compared to the nucleophilic groups present on the 20 common amino acids (including but not limited to, the hydroxyl group of serine or threonine or the amino groups of lysine and the N-terminus).

Non-naturally encoded amino acids containing an aminooxy (also called a hydroxylamine) group allow for reaction with a variety of electrophilic groups to form conjugates (including but not limited to, with PEG or other water soluble polymers). Like hydrazines, hydrazides and semicarbazides, the enhanced nucleophilicity of the aminooxy group permits it to react efficiently and selectively with a variety of molecules that contain aldehydes or other functional groups with similar chemical reactivity. See, e.g., Shao, J. and Tam, J., J. Am. Chem. Soc. 117:3893-3899 (1995); H. Hang and C. Bertozzi, Acc. Chem. Res. 34: 727-736 (2001). Whereas the result of reaction with a hydrazine group is the corresponding hydrazone, however, an oxime results generally from the reaction of an aminooxy group with a carbonyl-containing group such as a ketone.

Exemplary amino acids containing aminooxy groups can be represented as follows:

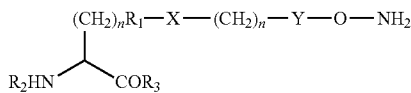

wherein n is 0-10; $R_1$ is an alkyl, aryl, substituted alkyl, or substituted aryl or not present; X is O, N, S or not present; m is 0-10; Y=C(O) or not present; $R_2$ is H, an amino acid, a polypeptide, or an amino terminus modification group, and $R_3$ is H, an amino acid, a polypeptide, or a carboxy terminus modification group. In some embodiments, n is 1, $R_1$ is phenyl, X is O, m is 1, and Y is present. In some embodiments, n is 2, $R_1$ and X are not present, m is O, and Y is not present.

Aminooxy-containing amino acids can be prepared from readily available amino acid precursors (homoserine, serine, and threonine). See, e.g., M. Carrasco and R. Brown, J. Org. Chem. 68: 8853-8858 (2003). Certain aminooxy-containing amino acids, such as L-2-amino-4-(aminooxy)butyric acid), have been isolated from natural sources (Rosenthal, G. et al., Life Sci. 60: 1635-1641 (1997). Other aminooxy-containing amino acids can be prepared by one skilled in the art.

The unique reactivity of azide and alkyne functional groups makes them extremely useful for the selective modification of polypeptides and other biological molecules. Organic azides, particularly aliphatic azides, and alkynes are generally stable toward common reactive chemical conditions. In particular, both the azide and the alkyne functional groups are inert toward the side chains (i.e., R groups) of the 20 common amino acids found in naturally-occurring polypeptides. When brought into close proximity, however, the "spring-loaded" nature of the azide and alkyne groups is revealed and they react selectively and efficiently via Huisgen [3+2] cycloaddition reaction to generate the corresponding triazole. See, e.g., Chin J., et al., Science 301:964-7 (2003); Wang, Q., et al., J. Am. Chem. Soc. 125, 3192-3193 (2003); Chin, J. W., et al., J. Am. Chem. Soc. 124:9026-9027 (2002).

Because the Huisgen cycloaddition reaction involves a selective cycloaddition reaction (see, e.g., Padwa, A., in COMPREHENSIVE ORGANIC SYNTHESIS, Vol. 4, (ed. Trost, B. M., 1991), p. 1069-1109; Huisgen, R. in 1,3-DIPOLAR CYCLOADDITION CHEMISTRY, (ed. Padwa, A., 1984), p. 1-176) rather than a nucleophilic substitution, the incorporation of non-naturally encoded amino acids bearing azide and alkyne-containing side chains permits the resultant polypeptides to be modified selectively at the position of the non-naturally encoded amino acid. Cycloaddition reaction involving azide or alkyne-containing antibody can be carried out at room temperature under aqueous conditions by the addition of Cu(II) (including but not limited to, in the form of a catalytic amount of $CuSO_4$) in the presence of a reducing agent for reducing Cu(II) to Cu(I), in situ, in catalytic amount. See, e.g., Wang, Q., et al., J. Am. Chem. Soc. 125, 3192-3193 (2003); Tomoe, C. W., et al., J. Org. Chem. 67:3057-3064 (2002); Rostovtsev, et al., Angew. Chem. Int. Ed. 41:2596-2599 (2002). Exemplary reducing agents include, including but not limited to, ascorbate, metallic copper, quinine, hydroquinone, vitamin K, glutathione, cysteine, Fe2+, $Co^{2+}$, and an applied electric potential.

In some cases, where a Huisgen [3+2] cycloaddition reaction between an azide and an alkyne is desired, the antigen-binding polypeptide comprises a non-naturally encoded amino acid comprising an alkyne moiety and the water soluble polymer to be attached to the amino acid comprises an azide moiety. Alternatively, the converse reaction (i.e., with the azide moiety on the amino acid and the alkyne moiety present on the water soluble polymer) can also be performed.

The azide functional group can also be reacted selectively with a water soluble polymer containing an aryl ester and appropriately functionalized with an aryl phosphine moiety to generate an amide linkage. The aryl phosphine group reduces the azide in situ and the resulting amine then reacts efficiently with a proximal ester linkage to generate the corresponding amide. See, e.g., E. Saxon and C. Bertozzi, Science 287, 2007-2010 (2000). The azide-containing amino acid can be either an alkyl azide (including but not limited to, 2-amino-6-azido-1-hexanoic acid) or an aryl azide (p-azido-phenylalanine).

Exemplary water soluble polymers containing an aryl ester and a phosphine moiety can be represented as follows:

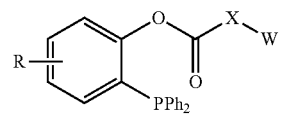

wherein X can be O, N, S or not present, Ph is phenyl, W is a water soluble polymer and R can be H, alkyl, aryl, substituted alkyl and substituted aryl groups. Exemplary R groups include but are not limited to —CH$_2$, —C(CH$_3$)$_3$, —OR', —NR"R'", —SR', -halogen, —C(O)R", —CONR"R'", —S(O)$_2$R", —S(O)$_2$NR"R'", —CN and —NO$_2$. R" and R'" each independently refer to hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R" and R'" groups when more than one of these groups is present. When R" and R'" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (including but not limited to, —CF$_3$ and —CH$_2$CF$_3$) and acyl (including but not limited to, —C(O)CH$_3$, —C(O)CF$_3$, —C(O)CH$_2$OCH$_3$, and the like).

The azide functional group can also be reacted selectively with a water soluble polymer containing a thioester and appropriately functionalized with an aryl phosphine moiety to generate an amide linkage. The aryl phosphine group reduces the azide in situ and the resulting amine then reacts efficiently with the thioester linkage to generate the corresponding amide. Exemplary water soluble polymers containing a thioester and a phosphine moiety can be represented as follows:

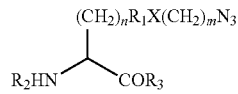

wherein n is 1-10; X can be O, N, S or not present, Ph is phenyl, and W is a water soluble polymer.

Exemplary alkyne-containing amino acids can be represented as follows:

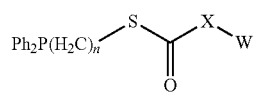

wherein n is 0-10; R$_1$ is an alkyl, aryl, substituted alkyl, or substituted aryl or not present; X is O, N, S or not present; m is 0-10, R$_2$ is H, an amino acid, a polypeptide, or an amino terminus modification group, and R$_3$ is H, an amino acid, a polypeptide, or a carboxy terminus modification group. In some embodiments, n is 1, R$_1$ is phenyl, X is not present, m is 0 and the acetylene moiety is positioned in the para position relative to the alkyl side chain. In some embodiments, n is 1, R$_1$ is phenyl, X is O, m is 1 and the propargyloxy group is positioned in the para position relative to the alkyl side chain (i.e., 0-propargyl-tyrosine). In some embodiments, n is 1, R$_1$ and X are not present and m is O (i.e., propargylglycine).

Alkyne-containing amino acids are commercially available. For example, propargylglycine is commercially available from Peptech (Burlington, Mass.). Alternatively, alkyne-containing amino acids can be prepared according to standard methods. For instance, p-propargyloxyphenylalanine can be synthesized, for example, as described in Deiters, A., et al., J. Am. Chem. Soc. 125: 11782-11783 (2003), and 4-alkynyl-L-phenylalanine can be synthesized as described in Kayser, B., et al., Tetrahedron 53(7): 2475-2484 (1997). Other alkyne-containing amino acids can be prepared by one skilled in the art.

Exemplary azide-containing amino acids can be represented as follows:

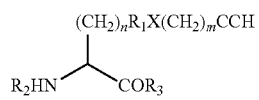

wherein n is 0-10; R$_1$ is an alkyl, aryl, substituted alkyl, substituted aryl or not present; X is O, N, S or not present; m is 0-10; R$_2$ is H, an amino acid, a polypeptide, or an amino terminus modification group, and R$_3$ is H, an amino acid, a polypeptide, or a carboxy terminus modification group. In some embodiments, n is 1, R$_1$ is phenyl, X is not present, m is 0 and the azide moiety is positioned para to the alkyl side chain. In some embodiments, n is 0-4 and R$_1$ and X are not present, and m=0. In some embodiments, n is 1, R$_1$ is phenyl, X is O, m is 2 and the β-azidoethoxy moiety is positioned in the para position relative to the alkyl side chain.

Azide-containing amino acids are available from commercial sources. For instance, 4-azidophenylalanine can be obtained from Chem-Impex International, Inc. (Wood Dale, Ill.). For those azide-containing amino acids that are not commercially available, the azide group can be prepared relatively readily using standard methods known to those of skill in the art, including but not limited to, via displacement of a suitable leaving group (including but not limited to, halide, mesylate, tosylate) or via opening of a suitably protected lactone. See, e.g., Advanced Organic Chemistry by March (Third Edition, 1985, Wiley and Sons, New York).

The unique reactivity of beta-substituted aminothiol functional groups makes them extremely useful for the selective modification of polypeptides and other biological molecules that contain aldehyde groups via formation of the thiazolidine. See, e.g., J. Shao and J. Tam, J. Am. Chem. Soc. 1995, 117 (14) 3893-3899. In some embodiments, beta-substituted aminothiol amino acids can be incorporated into antibodies and then reacted with water soluble polymers comprising an aldehyde functionality. In some embodiments, a water soluble polymer, drug conjugate or other payload can be coupled to an antibody polypeptide comprising a beta-substituted aminothiol amino acid via formation of the thiazolidine.

Particular examples of useful non-natural amino acids include, but are not limited to, p-acetyl-L-phenylalanine, O-methyl-L-tyrosine, L-3-(2-naphthyl)alanine, 3-methyl-phenylalanine, O-4-allyl-L-tyrosine, 4-propyl-L-tyrosine, tri-O-acetyl-GlcNAc b-serine, L-Dopa, fluorinated phenylalanine, isopropyl-L-phenylalanine, p-azido-methyl-L-phenylalanine, p-azido-L-phenylalanine, p-acyl-L-phenylalanine, p-benzoyl-L-phenylalanine, L-phosphoserine, phosphonoserine, phosphonotyrosine, p-iodo-phenylalanine, p-bromophenylalanine, p-amino-L-phenylalanine, isopropyl-L-phenylalanine, and p-propargyloxy-phenylalanine. Further useful examples include N-acetyl-L-glucosaminyl-L-serine, N-acetyl-L-galactosaminyl-L-serine, N-acetyl-L- glucosaminyl-L-threonine, N-acetyl-L-glucosaminyl-L-asparagine, and O-mannosaminyl-L-serine.

In particular embodiments, the non-natural amino acids are selected from p-acetyl-phenylalanine, p-ethynyl-phenylalanine, p-propargyloxyphenylalanine, p-azido-methyl-phenylalanine, and p-azido-phenylalanine. One particularly useful non-natural amino acid is p-azido phenylalanine. This amino acid residue is known to those of skill in the art to facilitate Huisgen [3+2] cyloaddition reactions (so-called "click" chemistry reactions) with, for example, compounds bearing alkynyl groups. This reaction enables one of skill in the art to readily and rapidly conjugate to the antibody at the site-specific location of the non-natural amino acid.

In certain embodiments, the first reactive group is an alkynyl moiety (including but not limited to, in the unnatural amino acid p-propargyloxyphenylalanine, where the propargyl group is also sometimes referred to as an acetylene moiety) and the second reactive group is an azido moiety, and [3+2] cycloaddition chemistry can be used. In certain embodiments, the first reactive group is the azido moiety (including but not limited to, in the unnatural amino acid p-azido-L-phenylalanine) and the second reactive group is the alkynyl moiety.

In the above formulas, each L represents a divalent linker. The divalent linker can be any divalent linker known to those of skill in the art. Generally, the divalent linker is capable of forming covalent bonds to the functional moiety R and the cognate reactive group (e.g., alpha carbon) of the non-natural amino acid. Useful divalent linkers a bond, alkylene, substituted alkylene, heteroalkylene, substituted heteroalkylene, arylene, substituted arylene, heteroarylene, and substituted heteroarylene. In certain embodiments, L is $C_{1-10}$ alkylene or $C_{1-10}$ heteroalkylene.

The non-natural amino acids used in the methods and compositions described herein have at least one of the following four properties: (1) at least one functional group on the sidechain of the non-natural amino acid has at least one characteristics and/or activity and/or reactivity orthogonal to the chemical reactivity of the 20 common, genetically-encoded amino acids (i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine), or at least orthogonal to the chemical reactivity of the naturally occurring amino acids present in the polypeptide that includes the non-natural amino acid; (2) the introduced non-natural amino acids are substantially chemically inert toward the 20 common, genetically-encoded amino acids; (3) the non-natural amino acid can be stably incorporated into a polypeptide, preferably with the stability commensurate with the naturally-occurring amino acids or under typical physiological conditions, and further preferably such incorporation can occur via an in vivo system; and (4) the non-natural amino acid includes an oxime functional group or a functional group that can be transformed into an oxime group by reacting with a reagent, preferably under conditions that do not destroy the biological properties of the polypeptide that includes the non-natural amino acid (unless of course such a destruction of biological properties is the purpose of the modification/transformation), or where the transformation can occur under aqueous conditions at a pH between about 4 and about 8, or where the reactive site on the non-natural amino acid is an electrophilic site. Any number of non-natural amino acids can be introduced into the polypeptide. Non-natural amino acids may also include protected or masked oximes or protected or masked groups that can be transformed into an oxime group after deprotection of the protected group or unmasking of the masked group. Non-natural amino acids may also include protected or masked carbonyl or dicarbonyl groups, which can be transformed into a carbonyl or dicarbonyl group after deprotection of the protected group or unmasking of the masked group and thereby are available to react with hydroxylamines or oximes to form oxime groups.

In further embodiments, non-natural amino acids that may be used in the methods and compositions described herein include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or non-covalently interact with other molecules, photocaged and/or photoisomerizable amino acids, amino acids comprising biotin or a biotin analogue, glycosylated amino acids such as a sugar substituted serine, other carbohydrate modified amino acids, keto-containing amino acids, aldehyde-containing amino acids, amino acids comprising polyethylene glycol or other polyethers, heavy atom substituted amino acids, chemically cleavable and/or photocleavable amino acids, amino acids with an elongated side chains as compared to natural amino acids, including but not limited to, polyethers or long chain hydrocarbons, including but not limited to, greater than about 5 or greater than about 10 carbons, carbon-linked sugar-containing amino acids, redox-active amino acids, amino thioacid containing amino acids, and amino acids comprising one or more toxic moiety.

In some embodiments, non-natural amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine, and O-mannosaminyl-L-serine. Examples of such amino acids also include examples where the naturally-occurring N- or O-linkage between the amino acid and the saccharide is replaced by a covalent linkage not commonly found in nature-including but not limited to, an alkene, an oxime, a thioether, an amide and the like. Examples of such amino acids also include saccharides that are not commonly found in naturally-occurring proteins such as 2-deoxy-glucose, 2-deoxygalactose, and the like.

The chemical moieties incorporated into antibodies via incorporation of non-natural amino acids offer a variety of advantages and manipulations of polypeptides. For example, the unique reactivity of a carbonyl or dicarbonyl functional group (including a keto- or aldehyde-functional group) allows selective modification of antibodies with any of a number of hydrazine- or hydroxylamine-containing reagents in vivo and in vitro. A heavy atom non-natural amino acid, for example, can be useful for phasing x-ray structure data. The site-specific introduction of heavy atoms using non-natural amino acids also provides selectivity and flexibility in choosing positions for heavy atoms. Photoreactive non-natural amino acids (including but not limited to, amino acids with benzophenone and arylazides (including but not limited to, phenylazide) side chains), for example, allow for efficient in vivo and in vitro photocrosslinking of polypeptides. Examples of photoreactive non-natural amino acids include, but are not limited to, p-azido-phenylalanine and p-benzoyl-phenylalanine. The antibodies with the photoreactive non-natural amino acids may then be crosslinked at will by excitation of the photoreactive group-providing temporal control. In a non-limiting example, the methyl group of a non-natural amino can be substituted with an isotopically labeled, including but not limited to, with a methyl group, as a probe of local structure and dynamics, including but not limited to, with the use of nuclear magnetic resonance and vibrational spectroscopy.

Amino acids with an electrophilic reactive group allow for a variety of reactions to link molecules via various chemical reactions, including, but not limited to, nucleophilic addition reactions. Such electrophilic reactive groups include a carbonyl- or dicarbonyl-group (including a keto- or aldehyde group), a carbonyl-like- or dicarbonyl-like-group (which has reactivity similar to a carbonyl- or dicarbonyl-group and is structurally similar to a carbonyl- or dicarbonyl-group), a masked carbonyl- or masked dicarbonyl-group (which can be readily converted into a carbonyl- or dicarbonyl-group), or a protected carbonyl- or protected dicarbonyl-group (which has reactivity similar to a carbonyl- or dicarbonyl-group upon deprotection). Such amino acids include amino acids according to the structure of Formula (AA):

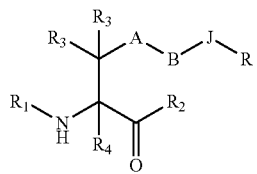

wherein: A is optional, and when present is lower alkylene, substituted lower alkylene, lower cycloalkylene, substituted lower cycloalkylene, lower alkenylene, lower alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene; B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, -S-, —S-(alkylene or substituted alkylene)-, —S(O)k- where k is 1, 2, or 3, —S(O)k(alkylene or substituted alkylene)-, —C(O)—, —NS(O)$_2$—, —OS(O)$_2$—, —C(O)-(alkylene or substituted alkylene)-, —C(S)—, —C(S)-(alkylene or substituted alkylene)-, —N(R")—, —NR"-(alkylene or substituted alkylene)-, —C(O)N(R")—, —CON(R")-(alkylene or substituted alkylene)-, —CSN(R")—, —CSN(R")-(alkylene or substituted alkylene)-, —N(R")CO-(alkylene or substituted alkylene)-, —N(R")C(O)O—, —S(O)kN(R")—, —N(R")C(O)N(R")—, —N(R")C(S)N(R")—, —N(R")S(O)kN(R")—, —N(R")—N═, —C(R")═N—, —C(R")═N—N(R")—, —C(R")═N—N═, —C(R")$_2$—N═N—, and —C(R")$_2$—N(R")—N(R")—, where each R" in B is independently H, alkyl, or substituted alkyl; J is

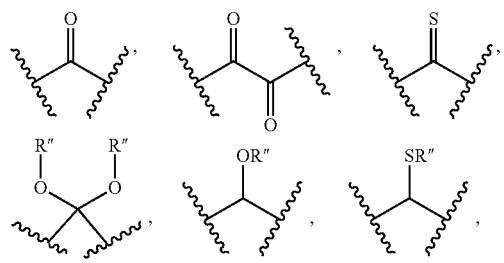

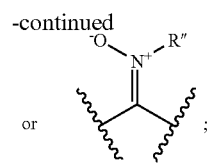

R is H, alkyl, substituted alkyl, cycloalkyl, or substituted cycloalkyl; each R" in J is independently H, alkyl, substituted alkyl, or a protecting group, or when more than one R" group is present, two R" optionally form a heterocycloalkyl; $R_1$ is H, an amino protecting group, resin, amino acid, polypeptide, or polynucleotide; and $R_2$ is OH, an ester protecting group, resin, amino acid, polypeptide, or polynucleotide; each of $R_3$ and $R_4$ is independently H, halogen, lower alkyl, or substituted lower alkyl, or $R_3$ and $R_4$ or two $R_3$ groups optionally form a cycloalkyl or a heterocycloalkyl; or the -A-B-J-R groups together form a bicyclic or tricyclic cycloalkyl or heterocycloalkyl comprising at least one carbonyl group, including a dicarbonyl group, protected carbonyl group, including a protected dicarbonyl group, or masked carbonyl group, including a masked dicarbonyl group; or the -J-R group together forms a monocyclic or bicyclic cycloalkyl or heterocycloalkyl comprising at least one carbonyl group, including a dicarbonyl group, protected carbonyl group, including a protected dicarbonyl group, or masked carbonyl group, including a masked dicarbonyl group; with a proviso that when A is phenylene and each $R_3$ is H, B is present; and that when A is —(CH$_2$)$_4$— and each $R_3$ is H, B is not —NHC(O)(CH$_2$CH$_2$)—; and that when A and B are absent and each $R_3$ is H, R is not methyl. Such non-natural amino acids may be in the form of a salt, or may be incorporated into a non-natural amino acid polypeptide, polymer, polysaccharide, or a polynucleotide and optionally post translationally modified.

In certain embodiments, compounds of Formula (AA) are stable in aqueous solution for at least 1 month under mildly acidic conditions. In certain embodiments, compounds of Formula (AA) are stable for at least 2 weeks under mildly acidic conditions. In certain embodiments, compound of Formula (AA) are stable for at least 5 days under mildly acidic conditions. In certain embodiments, such acidic conditions are pH 2 to 8.

In certain embodiments of compounds of Formula (AA), B is lower alkylene, substituted lower alkylene, —O-(alkylene or substituted alkylene)-, —C(R")═N—N(R")—, —N(R")CO—, —C(O)—, —C(R")═N—, —C(O)-(alkylene or substituted alkylene)-, —CON(R")-(alkylene or substituted alkylene)-, —S(alkylene or substituted alkylene)-, —S(O)(alkylene or substituted alkylene)-, or —S(O)$_2$(alkylene or substituted alkylene)-. In certain embodiments of compounds of Formula (AA), B is —O(CH$_2$)—, —CH═N—, —CH═N—NH—, —NHCH$_2$—, —NHCO—, —C(O)—, —C(O)—(CH$_2$)—, —CONH—(CH$_2$)—, —SCH$_2$—, —S(═O)CH$_2$—, or —S(O)$_2$CH$_2$—. In certain embodiments of compounds of Formula (AA), R is C$_{1-6}$-alkyl or cycloalkyl. In certain embodiments of compounds of Formula (AA) R is —CH$_3$, —CH(CH$_3$)$_2$, or cyclopropyl. In certain embodiments of compounds of Formula (AA), $R_1$ is H, tert-butyloxycarbonyl (Boc), 9-Fluorenylmethoxycarbonyl (Fmoc), N-acetyl, tetrafluoroacetyl (TFA), or benzyloxycarbonyl (Cbz). In certain embodiments of compounds of Formula (AA), $R_1$ is a resin, amino acid, polypeptide, or polynucleotide. In certain embodiments of compounds of Formula (AA), $R_2$ is OH, O-methyl, O-ethyl, or O-t-butyl. In certain embodiments of compounds of Formula (AA), R₂ is a resin, amino acid, polypeptide, or polynucleotide. In certain embodiments of compounds of Formula (AA), R₂ is a polynucleotide. In certain embodiments of compounds of Formula (AA), R₂ is ribonucleic acid (RNA). In certain embodiments of compounds of Formula (AA), R₂ is tRNA. In certain embodiments of compounds of Formula (AA), the tRNA specifically recognizes a selector codon. In certain embodiments of compounds of Formula (AA) the selector codon is selected from the group consisting of an amber codon, ochre codon, opal codon, a unique codon, a rare codon, an unnatural codon, a five-base codon, and a four-base codon. In certain embodiments of compounds of Formula (AA), R₂ is a suppressor tRNA.

In certain embodiments of compounds of Formula (AA),

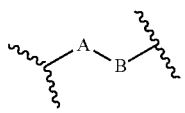

is selected from the group consisting of: (i) A is substituted lower alkylene, C₄-arylene, substituted arylene, heteroarylene, substituted heteroarylene, alkarylene, substituted alkarylene, aralkylene, or substituted aralkylene; B is optional, and when present is a divalent linker selected from the group consisting of lower alkylene, substituted lower alkylene, lower alkenylene, substituted lower alkenylene, —O—, —O-(alkylene or substituted alkylene)-, —S—, —S(O)—, —S(O)₂—, —NS(O)₂—, —OS(0)₂—, —C(O)—, —C(O)-(alkylene or substituted alkylene)-, —C(S)—, —N(R")—, —C(O)N(R")—, —CON(R")-(alkylene or substituted alkylene)-, —CSN(R")—, —N(R")CO-(alkylene or substituted alkylene)-, —N(R")C(O)O—, —N(R")C(S)—, —S(O)N(R"), —S(O)₂N(R"), —N(R')C(O)N(R")—, —N(R")C(S)N(R")—, —N(R")S(O)N(R")—, —N(R")S(O)₂N(R")—, —N(R")—N=, —C(R")=N—N(R")—, —C(R")=N—N=, —C(R")₂—N=N—, and —C(R")₂—N(R")—N(R")—; (ii) A is optional, and when present is substituted lower alkylene, C₄-arylene, substituted arylene, heteroarylene, substituted heteroarylene, alkarylene, substituted alkarylene, aralkylene, or substituted aralkylene; B is a divalent linker selected from the group consisting of lower alkylene, substituted lower alkylene, lower alkenylene, substituted lower alkenylene, —O—, —O-(alkylene or substituted alkylene)-, -5-, —S(O)—, —S(O)₂—, —NS(O)₂—, —OS(O)₂—, —C(O)—, —C(O)-(alkylene or substituted alkylene)-, —C(S)—, —N(R")—, —C(O)N(R")—, —CON(R")-(alkylene or substituted alkylene)-, —CSN(R")—, —N(R")CO-(alkylene or substituted alkylene)-, —N(R")C(O)O—, —N(R")C(S)—, —S(O)N(R"), —S(O)₂N(R"), —N(R")C(O)N(R")—, —N(R')C(S)N(R")—, —N(R')S(O)N(R")—, —N(R")S(O)₂N(R")—, —N(R")—N=, —C(R')=N—N(R")—, —C(R")=N—N=, —C(R")₂—N=N—, and —C(R")₂—N(R")—N(R")—; (iii) A is lower alkylene; B is optional, and when present is a divalent linker selected from the group consisting of lower alkylene, substituted lower alkylene, lower alkenylene, substituted lower alkenylene, —O—, —O-(alkylene or substituted alkylene)-, -5-, —S(O)—, —S(O)₂—, —NS(O)₂—, —OS(O)₂—, —C(O)—, —C(O)-(alkylene or substituted alkylene)-, —C(S)—, —N(R")—, —C(O)N(R")—, —CON(R")-(alkylene or substituted alkylene)-, —N(R")C(O)O—, —N(R")C(S)—, —S(O)N(R"), —S(O)₂N(R"), —N(R")C(O)N(R")—, —N(R")C(S)N(R")—, —N(R")S(O)N(R")—, —N(R")S(O)₂ N(R")—, —N(R")—N=, —C(R")=N—N(R")—, —C(R")=N—N=, —C(R")₂—N=N—, and —C(R")₂—N(R")—N(R")—; and (iv) A is phenylene; B is a divalent linker selected from the group consisting of lower alkylene, substituted lower alkylene, lower alkenylene, substituted lower alkenylene, —O—, —O-(alkylene or substituted alkylene)-, -5-, —S(O)—, —S(O)₂—, —NS(O)₂—, —OS(O)₂—, —C(O)—, —C(O)-(alkylene or substituted alkylene)-, —C(S)—, —N(R")—, —C(O)N(R")—, —CON(R")-(alkylene or substituted alkylene)-, —CSN(R")—, —N(R")CO-(alkylene or substituted alkylene)-, —N(R")C(O)O—, —N(R")C(S)—, —S(O)N(R"), —S(O)₂N(R"), —N(R")C(O)N(R")—, —N(R")C(S)N(R")—, —N(R")S(O)N(R")—, —N(R")S(O)₂N(R")—, —N(R")—N=, —C(R")N—N(R")—, —C(R")=N—N=, —C(R")₂—N=N—, and —C(R")₂—N(R")—N(R")—; J is

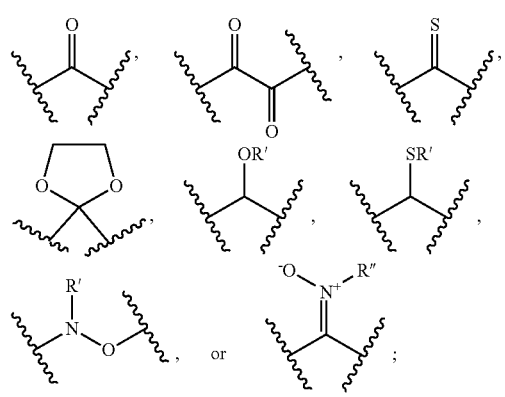

each R' in J is independently H, alkyl, or substituted alkyl; R₁ is optional, and when present, is H, an amino protecting group, resin, amino acid, polypeptide, or polynucleotide; and R₂ is optional, and when present, is OH, an ester protecting group, resin, amino acid, polypeptide, or polynucleotide; and each R₃ and R₄ is independently H, halogen, lower alkyl, or substituted lower alkyl; and R is H, alkyl, substituted alkyl, cycloalkyl, or substituted cycloalkyl.

In certain embodiments, the non-natural amino acid can be according to formula BB:

Formula BB

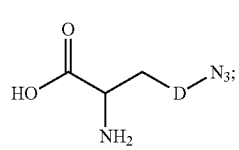

or a salt thereof, wherein: D is —Ar—W₃— or —W₁-Y₁-C(O)—Y₂—W₂—; Ar is

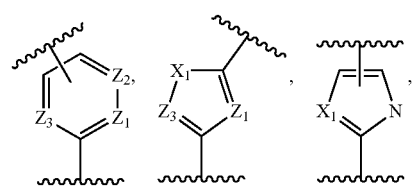

-continued

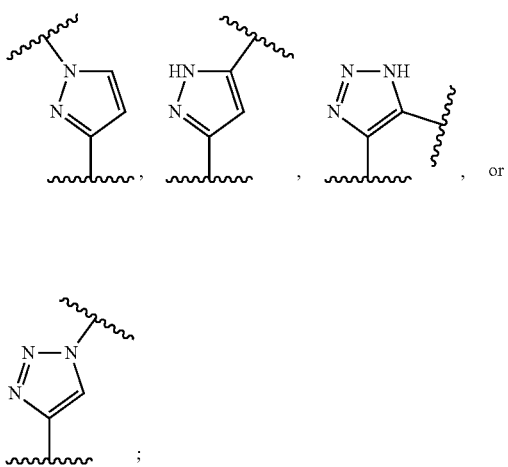

, or

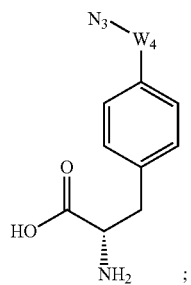

;

each of $W_1$, $W_2$, and $W_3$ is independently a single bond or lower alkylene; each $X_1$ is independently —NH—, —O—, or —S—; each $Y_1$ is independently a single bond, —NH—, or —O—; each $Y_2$ is independently a single bond, —NH—, —O—, or an N-linked or C-linked pyrrolidinylene; and one of $Z_1$, $Z_2$, and $Z_3$ is —N— and the others of $Z_1$, $Z_2$, and $Z_3$ are independently —CH—. In certain embodiments, the non-natural amino acid is according to formula BBa:

Formula BBa

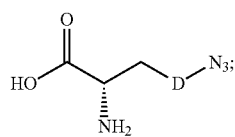

where D is a defined in the context of formula BB. In certain embodiments, the non-natural amino acid is according formula BBb:

Formula BBb

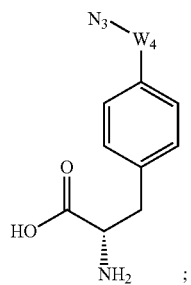

or a salt thereof, wherein $W_4$ is $C_1$-$C_{10}$ alkylene. In a further embodiment, $W_4$ is $C_1$-$C_5$ alkylene. In an embodiment, $W_4$ is $C_1$-$C_3$ alkylene. In an embodiment, $W_4$ is $C_1$ alkylene. In particular embodiments, the non-natural amino acid is selected from the group consisting of:

(1)

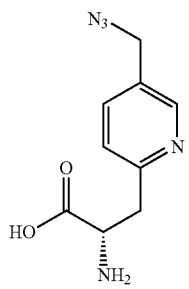

(2)

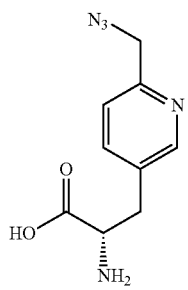

(3)

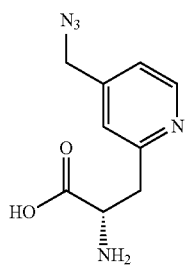

(4)

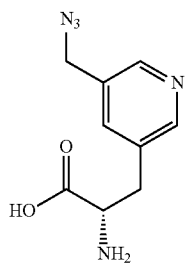

(5)

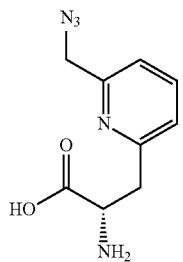

(6)

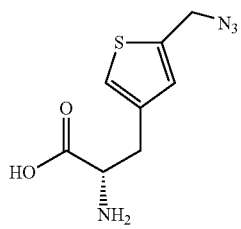

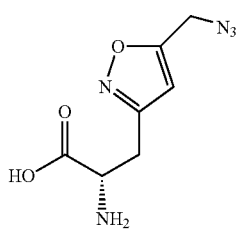 (7)
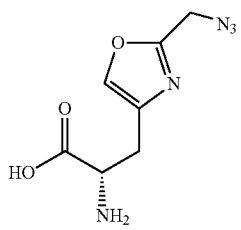 (8)
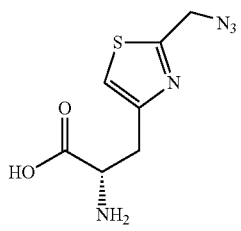 (9)
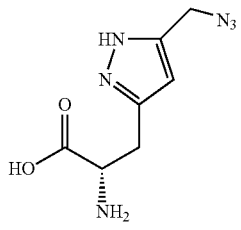 (10)
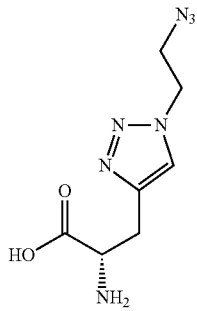 (11)
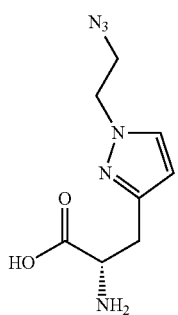 (12)
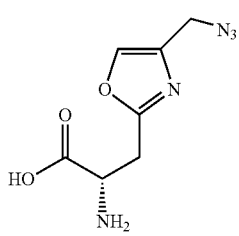 (13)
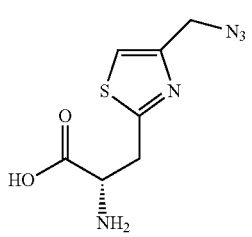 (14)
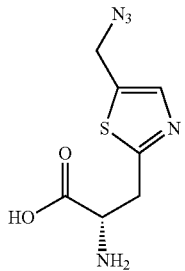 (15)
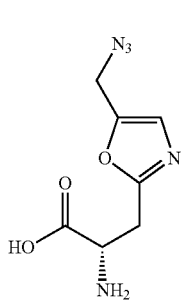 (16)
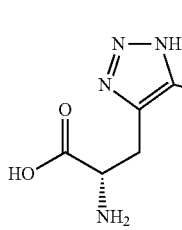 (17)
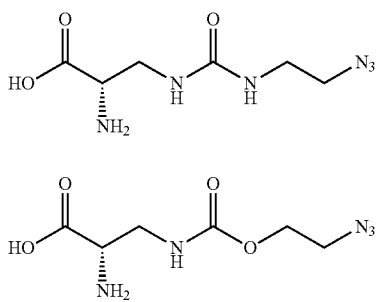 (18)
(19)

-continued

(20) 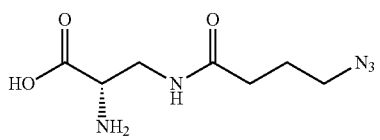

(21) 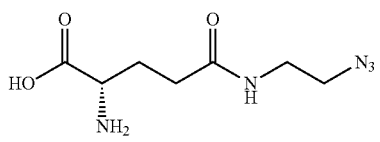

(22) 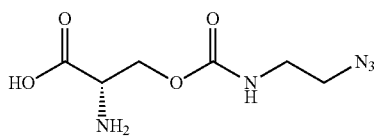

(23) 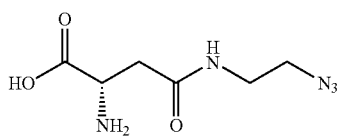

(24) 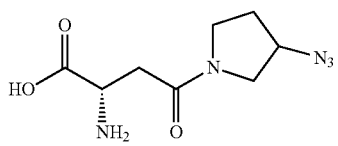

(25) 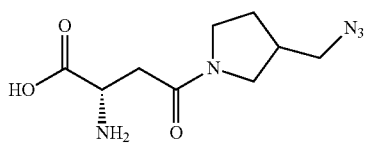

(26) 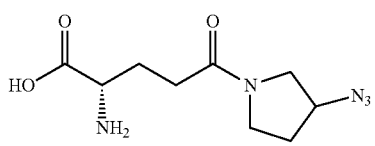

(27) 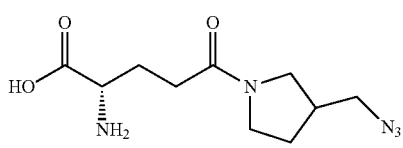

(28) 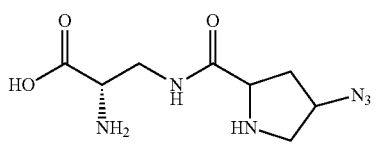

(29) 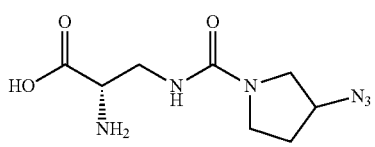

(30) 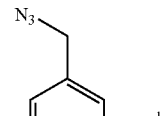

; and

(40) 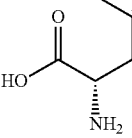

or a salt thereof. Such non-natural amino acids may be in the form of a salt, or may be incorporated into a non-natural amino acid polypeptide, polymer, polysaccharide, or a polynucleotide and optionally post translationally modified.

In certain embodiments, the modified amino acid is according to formula CC:

Formula CC

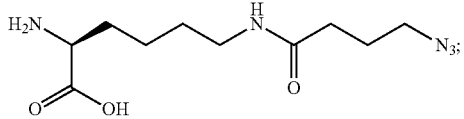

or a salt thereof, wherein Ar is:

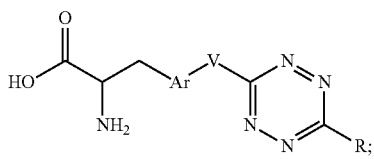

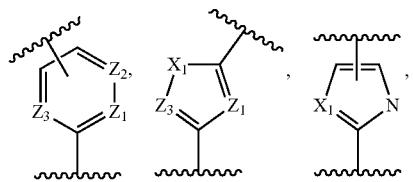

, or

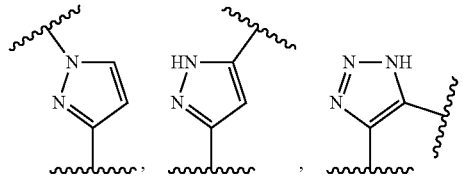

;

V is a single bond, lower alkylene, or —$W_1$—$W_2$—; one of $W_1$ and $W_2$ is absent or lower alkylene, and the other is —NH—, —O—, or —S—; each $X_1$ is independently —NH—, —O—, or —S—; one of $Z_1$, $Z_2$, and $Z_3$ is —CH— or —N— and the others of $Z_1$, $Z_2$, and $Z_3$ are each independently —CH—; and R is lower alkyl. In certain embodiments, when Ar is

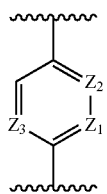

and V is —NH—, then one of $Z_1$, $Z_2$, and $Z_3$ is —N—. In certain embodiments, V is a single bond, —NH—, or —CH$_2$NH—.

In certain embodiments, Ar is

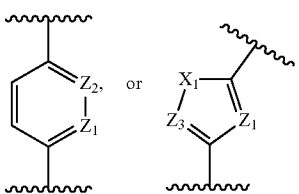

and $Z_1$, $Z_2$, $Z_3$ and $X_1$ are as defined in the context of formula CC. In certain embodiments according to this paragraph, V is —W$_1$—W$_2$—; one of W$_1$ and W$_2$ is absent or —CH$_2$—, and the other is —NH—, —O—, or —S—. In certain embodiments according to this paragraph, V is a single bond, —NH—, or —CH$_2$NH—. In certain embodiments according to this paragraph, $Z_1$ is N. In certain embodiments according to this paragraph, $Z_2$ is N. In certain embodiments according to this paragraph, $Z_3$ is N. In certain embodiments according to this paragraph, $Z_1$ is CH, $Z_3$ is CH and $X_1$ is S.

In certain embodiments, Ar is

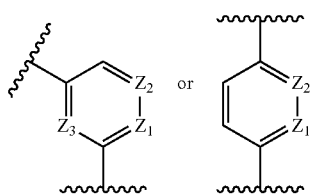

and $Z_1$, $Z_2$, and $Z_3$ are as defined in the context of formula CC. In certain embodiments according to this paragraph, V is —W$_1$—W$_2$—; one of W$_1$ and W$_2$ is absent or —CH$_2$—, and the other is —NH—, —O—, or —S—. In certain embodiments according to this paragraph, V is a single bond, —NH—, or —CH$_2$NH—. In certain embodiments according to this paragraph, $Z_1$ is N. In certain embodiments according to this paragraph, $Z_2$ is N. In certain embodiments according to this paragraph, $Z_3$ is N.

In certain embodiments, Ar is

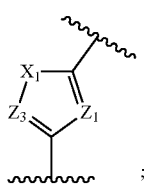

and $Z_1$, $Z_3$ and $X_1$ are as defined in the context of formula CC. In certain embodiments according to this paragraph, V is —W$_1$-W$_2$-; one of W$_1$ and W$_2$ is absent or —CH$_2$—, and the other is —NH—, —O—, or —S—. In certain embodiments according to this paragraph, V is a single bond, —NH—, or —CH$_2$NH—. In certain embodiments according to this paragraph, $Z_1$ is N. In certain embodiments according to this paragraph, $Z_3$ is N. In certain embodiments according to this paragraph, $Z_1$ is CH, $Z_3$ is CH and $X_1$ is S.

In certain embodiments, the modified amino acid is according to Formula CCa:

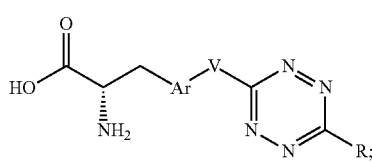

Formula CCa where Ar, V, and R are defined in the context of formula CC.

In an embodiment, compounds of either of formulas CC and CCa are provided wherein V is a single bond. In another embodiment, compounds of either of formulas CC and CCa are provided wherein V is —NH—. In another embodiment, compounds of either of formulas CC and CCa are provided wherein V is —CH$_2$NH—.

In certain embodiments, the modified amino acid is according to Formula DD:

Formula DD or a salt thereof, wherein V and R are as defined in Formula CC. In certain embodiments according to this paragraph, V is —W$_1$—W$_2$—; one of W$_1$ and W$_2$ is absent or —CH$_2$—, and the other is —NH—, —O—, or —S—. In certain embodiments, V is a single bond, —NH—, or —CH$_2$NH—. In certain embodiments, V is a single bond or —CH$_2$NH—; and R is methyl.

In certain embodiments, the modified amino acid is according to Formula EE:

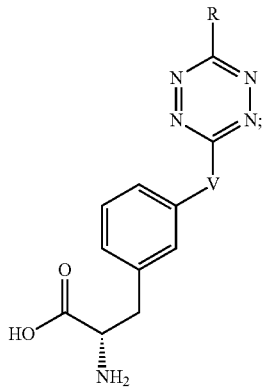

Formula EE or a salt thereof, wherein V and R are as defined in Formula CC. In certain embodiments according to this paragraph, V is —W$_1$—W$_2$—; one of W$_1$ and W$_2$ is absent or —CH$_2$—, and the other is —NH—, —O—, or —S—. In certain embodiments, V is a single bond, —NH—, or —CH$_2$NH—. In certain embodiments, V is a single bond, —NH—, or —CH$_2$NH—; and R is methyl.

In certain embodiments, the modified amino acid is according to Formula FF:

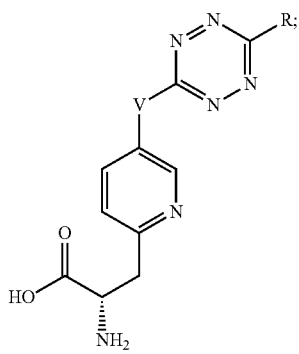

Formula FF or a salt thereof, wherein V and R are as defined in Formula CC. In certain embodiments according to this paragraph, V is —W$_1$—W$_2$—; one of W$_1$ and W$_2$ is absent or —CH$_2$—, and the other is —NH—, —O—, or —S—. In certain embodiments, V is a single bond, —NH—, or —CH$_2$NH—. In certain embodiments, V is a single bond, —NH—, or —CH$_2$NH—; and R is methyl.

In certain embodiments, the modified amino acid is according to Formula GG:

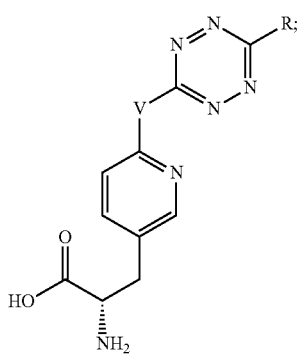

Formula GG or a salt thereof, wherein V and R are as defined in Formula CC. In certain embodiments according to this paragraph, V is —W$_1$—W$_2$—; one of W$_1$ and W$_2$ is absent or —CH$_2$—, and the other is —NH—, —O—, or —S—. In certain embodiments, V is a single bond, —NH—, or —CH$_2$NH—. In certain embodiments, V is a single bond, —NH—, or —CH$_2$NH—; and R is methyl.

In certain embodiments, the modified amino acid is according to Formula HH:

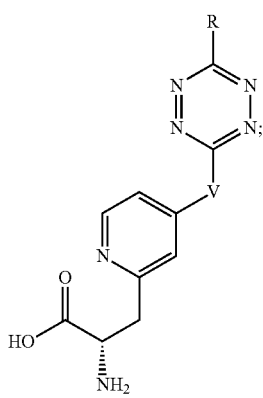

Formula HH or a salt thereof, wherein V and R are as defined in Formula CC. In certain embodiments according to this paragraph, V is —W$_1$—W$_2$—; one of W$_1$ and W$_2$ is absent or —CH$_2$—, and the other is —NH—, —O—, or —S—. In certain embodiments, V is a single bond, —NH—, or —CH$_2$NH—. In certain embodiments, V is a single bond, —NH—, or —CH$_2$NH—; and R is methyl.

In certain embodiments, the modified amino acid is according to Formula JJ:

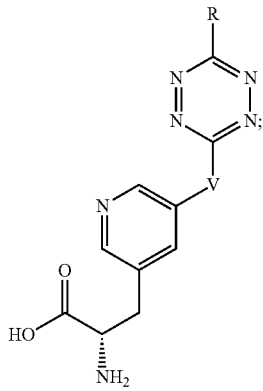

Formula JJ or a salt thereof, wherein V and R are as defined in Formula CC. In certain embodiments according to this paragraph, V is —W$_1$-W$_2$-; one of W$_1$ and W$_2$ is absent or —CH$_2$—, and the other is —NH—, —O—, or —S—. In certain embodiments, V is a single bond, —NH—, or —CH$_2$NH—. In certain embodiments, V is a single bond, —NH—, or —CH$_2$NH—; and R is methyl.

In certain embodiments, the modified amino acid is according to Formula KK:

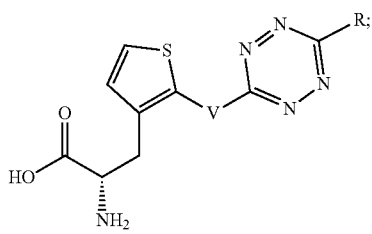

Formula KK or a salt thereof, wherein V and R are as defined in Formula CC. In certain embodiments according to this paragraph, V is —W$_1$-W$_2$-; one of W$_1$ and W$_2$ is absent or —CH$_2$—, and the other is —NH—, —O—, or —S—. In certain embodiments, V is a single bond, —NH—, or —CH$_2$NH—. In certain embodiments, V is a single bond, —NH—, or —CH$_2$NH—; and R is methyl.

In certain embodiments, the modified amino acid is according to Formula LL:

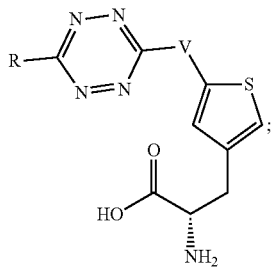

Formula LL or a salt thereof, wherein V and R are as defined in Formula CC. In certain embodiments according to this paragraph, V is —W$_1$—W$_2$—; one of W$_1$ and W$_2$ is absent or —CH$_2$—, and the other is —NH—, —O—, or —S—. In certain embodiments, V is a single bond, —NH—, or —CH$_2$NH—. In certain embodiments, V is a single bond, —NH—, or —CH$_2$NH—; and R is methyl.

In certain embodiments, the modified amino acid is according to any of formulas 51-62:

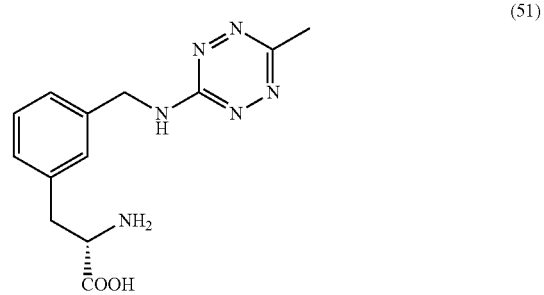

(51)

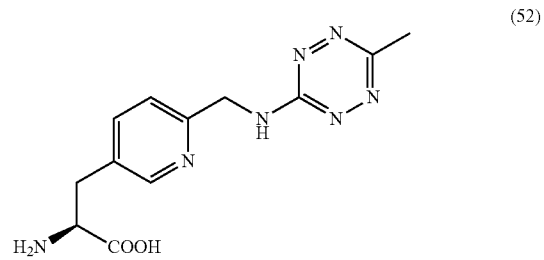

(52)

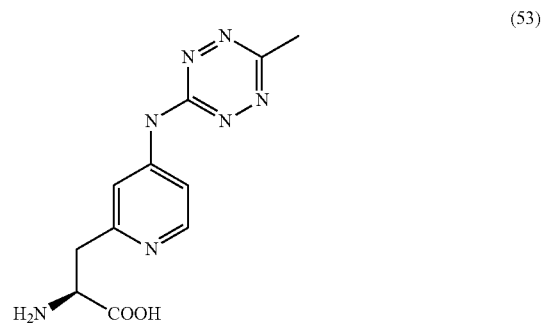

(53)

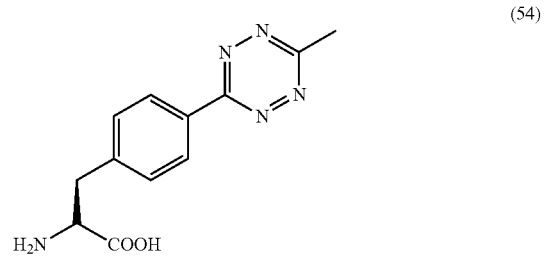

(54)

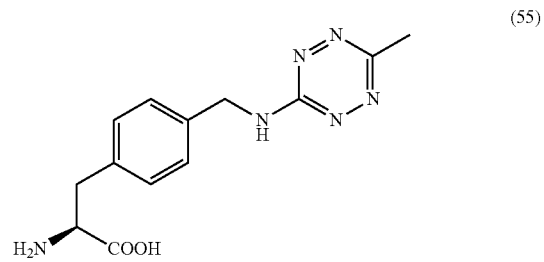

(55)

(56)
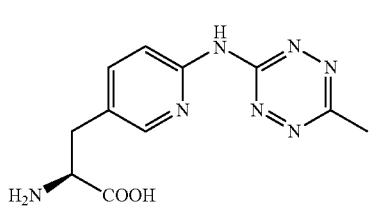

(57)
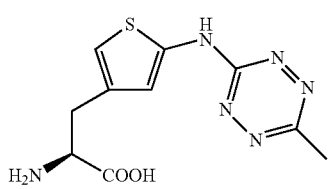

(58)
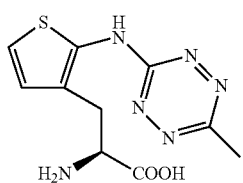

(59)
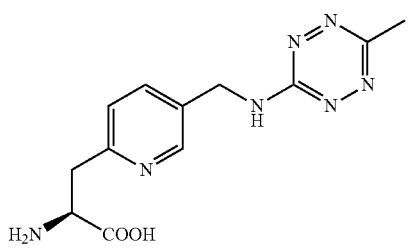

(60)
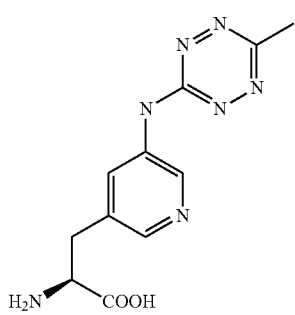

(61)
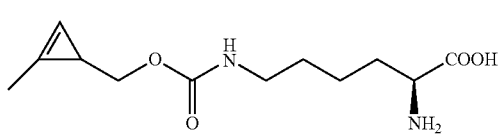

(62)
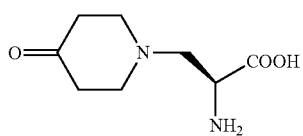

or a salt thereof.

In certain embodiments, the non-natural amino acid is selected from the group consisting of compounds 30, 53, 56, 59, 60, 61, and 62 above. In certain embodiments, the non-natural amino acid is compound 30. In certain embodiments, the non-natural amino acid is compound 56. In some embodiments, the non-natural amino acid is compound 61. In some embodiments, the non-natural amino acid is compound 62.

8. Forms of Compounds of Formula (I) and Subformulae

In some embodiments, provided herein are:
(a) antibody conjugates as described herein, e.g., of Formula I or II, and pharmaceutically acceptable salts and compositions thereof;
(b) antibody conjugates as described herein, e.g., of Formula I or II, and pharmaceutically acceptable salts and compositions thereof for use in the treatment and/or prophylaxis of cancer;
(c) processes for the preparation of antibody conjugates as described herein, e.g., of Formula I or II, as described in more detail elsewhere herein;
(d) pharmaceutical formulations comprising an antibody conjugate as described herein, e.g., of Formula I or II, or a pharmaceutically acceptable salt thereof together with a pharmaceutically acceptable carrier or diluent;
(e) pharmaceutical formulations comprising an antibody conjugate as described herein, e.g., of Formula I or II, or a pharmaceutically acceptable salt thereof together with one or more other effective anti-cancer agents, optionally in a pharmaceutically acceptable carrier or diluent;
(f) use of an antibody conjugate or a composition thereof for the treatment of cancer and/or an inflammatory disease or condition and/or a proliferative disease or condition.

Optically Active Compounds

It is appreciated that antibody conjugates and/or payloads on antibody conjugates provided herein have several chiral centers and may exist in and be isolated in optically active and racemic forms. Some compounds may exhibit polymorphism. It is to be understood that any racemic, optically-active, diastereomeric, polymorphic, or stereoisomeric form, or mixtures thereof, of a compound provided herein, which possess the useful properties described herein is within the scope of the invention. It being well known in the art how to prepare optically active forms (for example, by resolution of the racemic form by recrystallization techniques, by synthesis from optically-active starting materials, by chiral synthesis, or by chromatographic separation using a chiral stationary phase).

Likewise, most amino acids are chiral (designated as L or D, wherein the L enantiomer is the naturally occurring configuration) and can exist as separate enantiomers.

Examples of methods to obtain optically active materials are known in the art, and include at least the following.
i) physical separation of crystals—a technique whereby macroscopic crystals of the individual enantiomers are manually separated. This technique can be used if crystals of the separate enantiomers exist, i.e., the material is a conglomerate, and the crystals are visually distinct;
ii) simultaneous crystallization—a technique whereby the individual enantiomers are separately crystallized from a solution of the racemate, possible only if the latter is a conglomerate in the solid state;
iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step of the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent;

xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

In some embodiments, provided herein are compositions comprising antibody conjugates of Formula (I), (II), (Xa-e), and/or (XIa-d) that are substantially free of a designated enantiomer of that compound. In certain embodiments, in the methods and compositions, the antibody conjugates and/or payloads are substantially free of enantiomers. In some embodiments, the composition includes that includes a compound that is at least 85, 90%, 95%, 98%, 99% to 100% by weight, of the compound, the remainder comprising other chemical species or enantiomers.

Isotopically Enriched Compounds

Also provided herein are isotopically enriched compounds, including but not limited to isotopically enriched antibody conjugates of Formula (I), (II), (Xa-e), and/or (XIa-d).

Isotopic enrichment (for example, deuteration) of pharmaceuticals to improve pharmacokinetics ("PK"), pharmacodynamics ("PD"), and toxicity profiles, has been demonstrated previously with some classes of drugs. See, for example, Lijinsky et. al., Food Cosmet. Toxicol., 20: 393 (1982); Lijinsky et. al., J. Nat. Cancer Inst., 69: 1127 (1982); Mangold et. al., Mutation Res. 308: 33 (1994); Gordon et. al., Drug Metab. Dispos., 15: 589 (1987); Zello et. al., Metabolism, 43: 487 (1994); Gately et. al., J. Nucl. Med., 27: 388 (1986); Wade D, Chem. Biol. Interact. 117: 191 (1999).

Isotopic enrichment of a drug can be used, for example, to (1) reduce or eliminate unwanted metabolites, (2) increase the half-life of the parent drug, (3) decrease the number of doses needed to achieve a desired effect, (4) decrease the amount of a dose necessary to achieve a desired effect, (5) increase the formation of active metabolites, if any are formed, and/or (6) decrees the production of deleterious metabolites in specific tissues and/or create a more effective drug and/or a safer drug for combination therapy, whether the combination therapy is intentional or not.

Replacement of an atom for one of its isotopes often will result in a change in the reaction rate of a chemical reaction. This phenomenon is known as the Kinetic Isotope Effect ("KIE"). For example, if a C—H bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect ("DKIE"). (See, e.g., Foster et al., Adv. Drug Res., vol. 14, pp. 1-36 (1985); Kushner et al., Can. J. Physiol. Pharmacol., vol. 77, pp. 79-88 (1999)).

The magnitude of the DKIE can be expressed as the ratio between the rates of a given reaction in which a C—H bond is broken, and the same reaction where deuterium is substituted for hydrogen. The DKIE can range from about 1 (no isotope effect) to very large numbers, such as 50 or more, meaning that the reaction can be fifty, or more, times slower when deuterium is substituted for hydrogen. High DKIE values may be due in part to a phenomenon known as tunneling, which is a consequence of the uncertainty principle. Tunneling is ascribed to the small mass of a hydrogen atom, and occurs because transition states involving a proton can sometimes form in the absence of the required activation energy. Because deuterium has more mass than hydrogen, it statistically has a much lower probability of undergoing this phenomenon.

Tritium ("T") is a radioactive isotope of hydrogen, used in research, fusion reactors, neutron generators, and radiopharmaceuticals. Tritium is a hydrogen atom that has 2 neutrons in the nucleus and has an atomic weight close to 3. It occurs naturally in the environment in very low concentrations, most commonly found as $T_2O$. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level. Substitution of tritium ("T") for hydrogen results in yet a stronger bond than deuterium and gives numerically larger isotope effects. Similarly, substitution of isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen, may lead to a similar kinetic isotope effect.

For example, the DKIE was used to decrease the hepatotoxicity of halothane by presumably limiting the production of reactive species such as trifluoroacetyl chloride. However, this method may not be applicable to all drug classes. For example, deuterium incorporation can lead to metabolic switching. The concept of metabolic switching asserts that xenogens, when sequestered by Phase I enzymes, may bind transiently and re-bind in a variety of conformations prior to the chemical reaction (e.g., oxidation). This hypothesis is supported by the relatively vast size of binding pockets in many Phase I enzymes and the promiscuous nature of many metabolic reactions. Metabolic switching can potentially lead to different proportions of known metabolites as well as altogether new metabolites. This new metabolic profile may impart more or less toxicity.

The animal body expresses a variety of enzymes for the purpose of eliminating foreign substances, such as therapeutic agents, from its circulation system. Examples of such enzymes include the cytochrome P450 enzymes ("CYPs"), esterases, proteases, reductases, dehydrogenases, and monoamine oxidases, to react with and convert these foreign substances to more polar intermediates or metabolites for renal excretion. Some of the most common metabolic reactions of pharmaceutical compounds involve the oxidation of a carbon-hydrogen (C—H) bond to either a carbon-oxygen (C—O) or carbon-carbon (C—C) pi-bond. The resultant metabolites may be stable or unstable under physiological conditions, and can have substantially different pharmacokinetic, pharmacodynamic, and acute and long-term toxicity profiles relative to the parent compounds. For many drugs, such oxidations are rapid. These drugs therefore often require the administration of multiple or high daily doses.

Therefore, isotopic enrichment at certain positions of a compound provided herein will produce a detectable KIE that will affect the pharmacokinetic, pharmacologic, and/or toxicological profiles of a compound provided herein in comparison with a similar compound having a natural isotopic composition.

9. Preparation of Compounds

The compounds provided herein can be prepared, isolated, or obtained by any method apparent to those of skill in the art. Exemplary methods of preparation are described in detail in the examples below. In some embodiments, a conjugate is prepared by contacting an antibody as disclosed herein with a linker precursor according to a structure described below where the linker precursor may comprise a cytotoxin or an immunomodulator. Any combination of linker and payload is contemplated within the scope of embodiments presented herein.

(A)

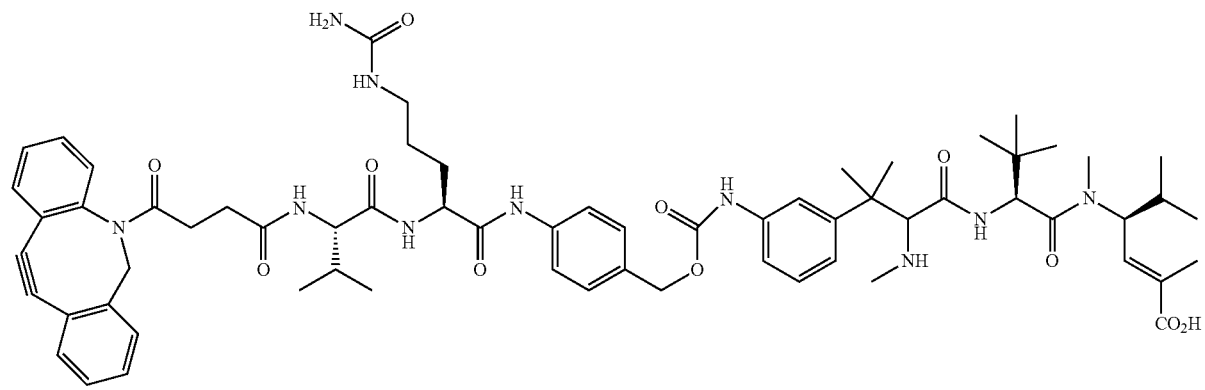

(B)
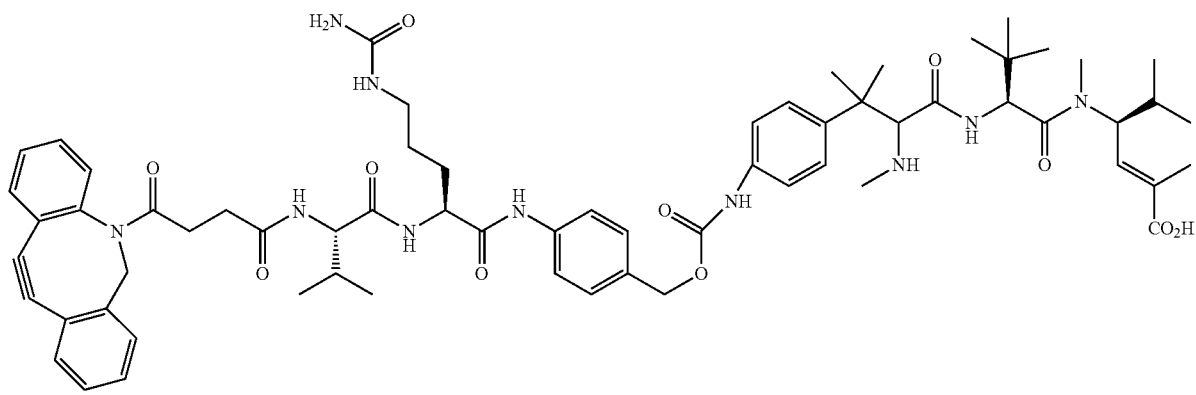
(C)
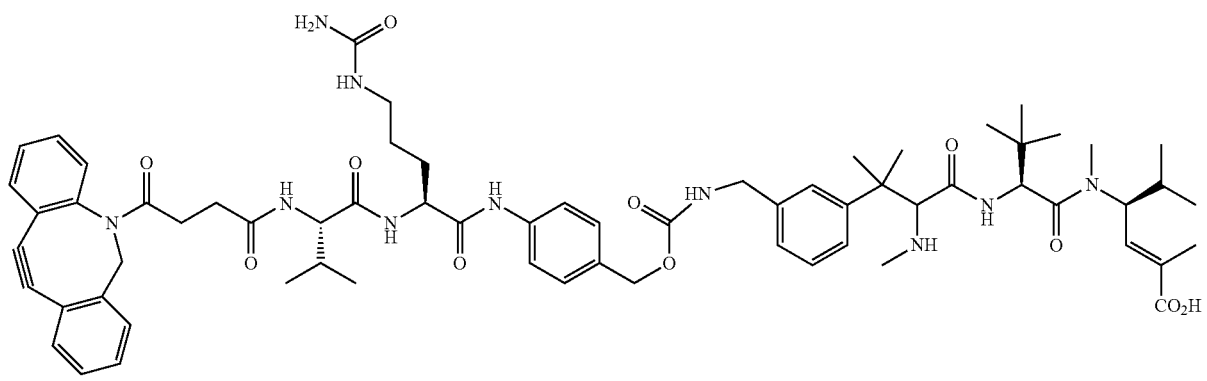
(D)
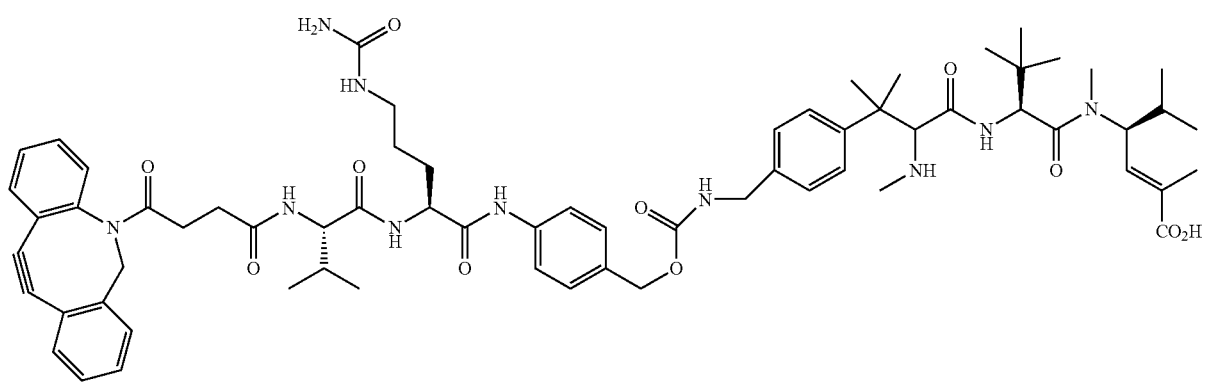
(E)
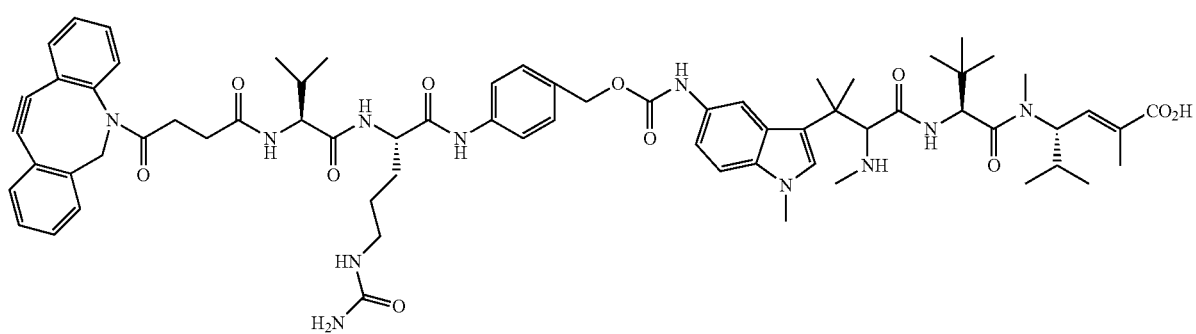

(F)
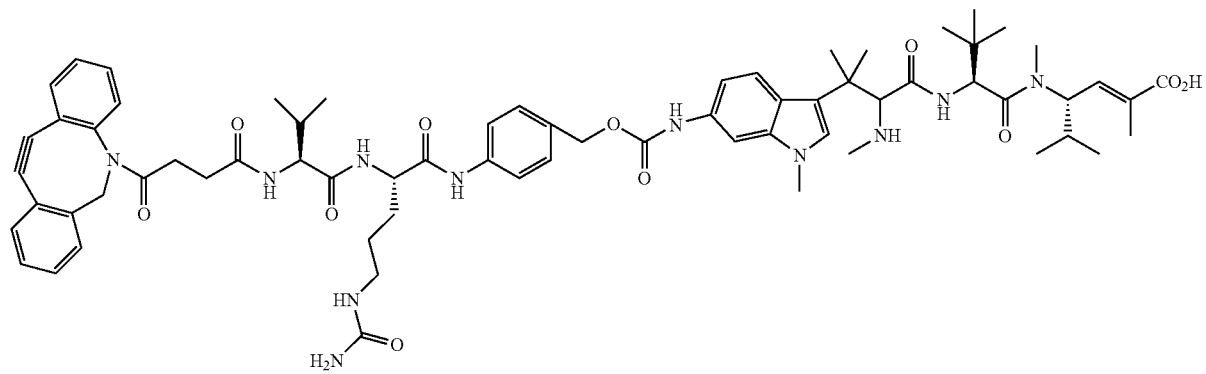
(G)
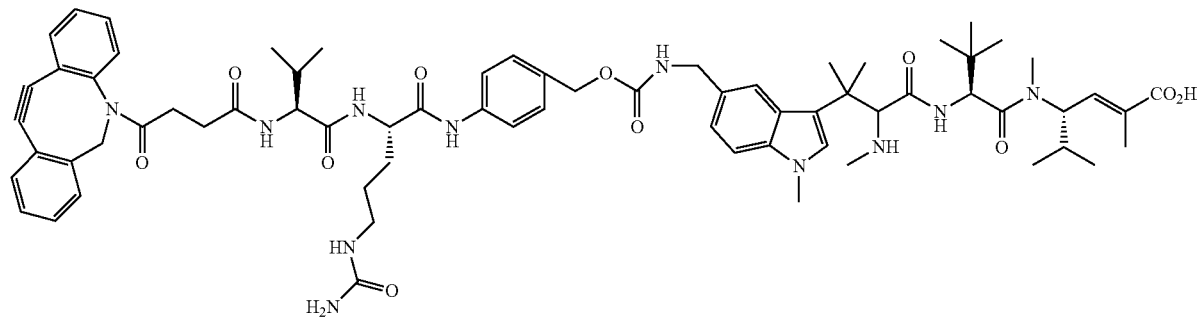
(H)
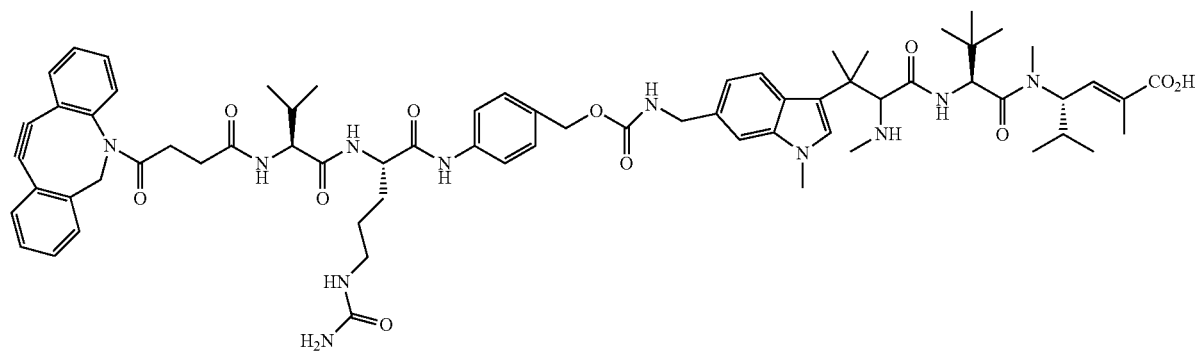
(I)
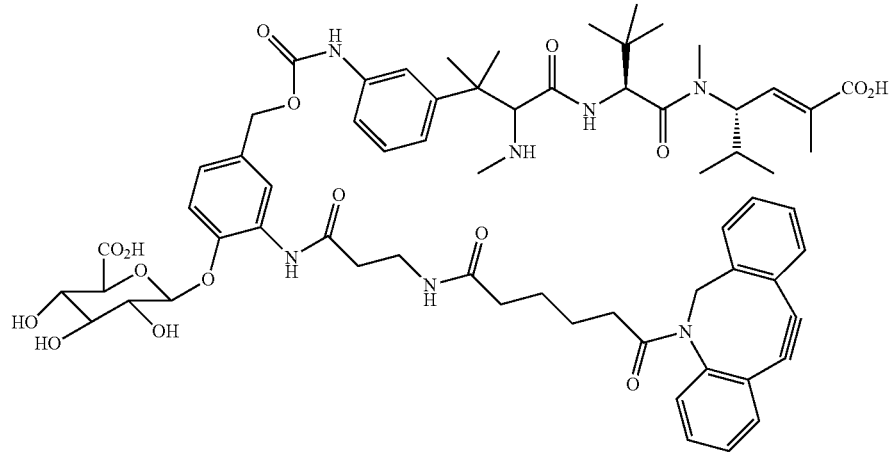

211 212
-continued
(J)
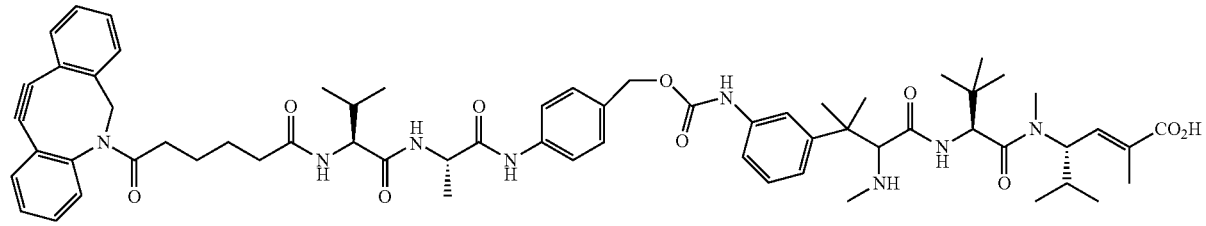
(K)
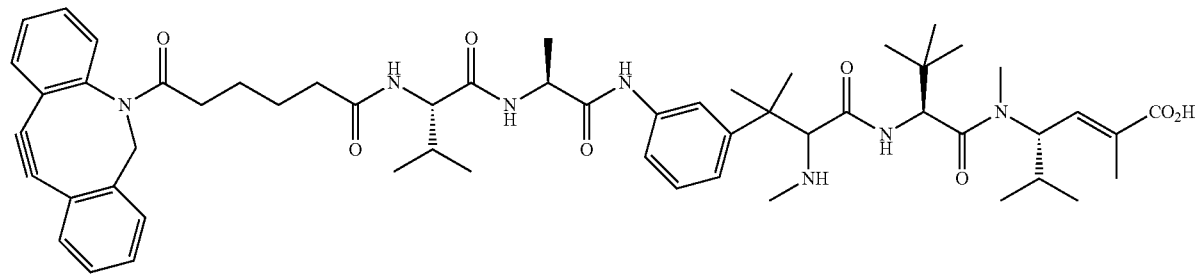
(L)
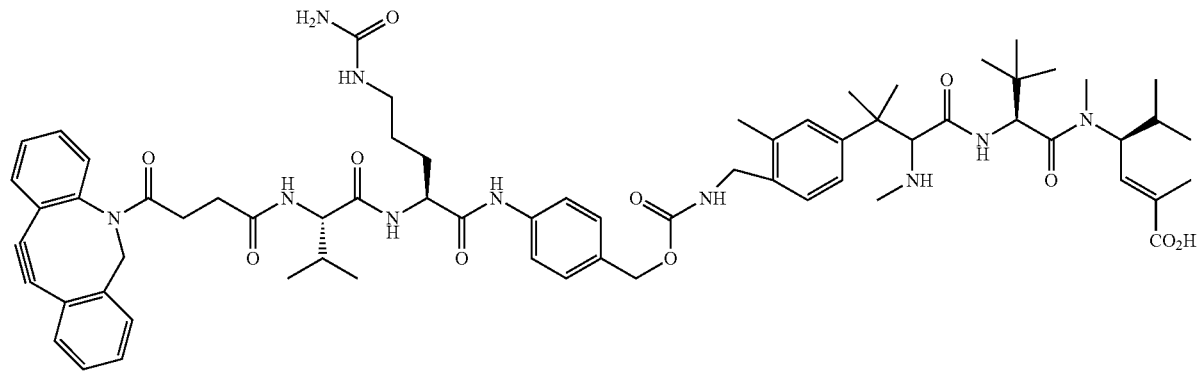
(AAA)
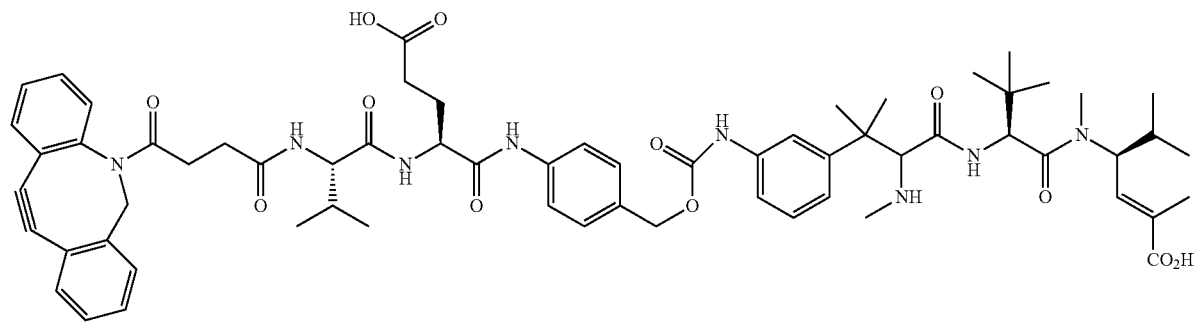

213 214
-continued
(BBB)
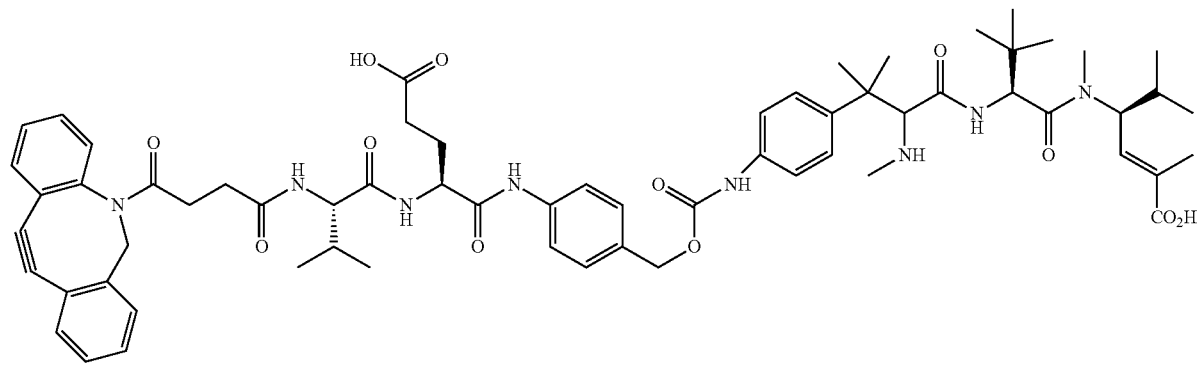
(CCC)
(DDD)
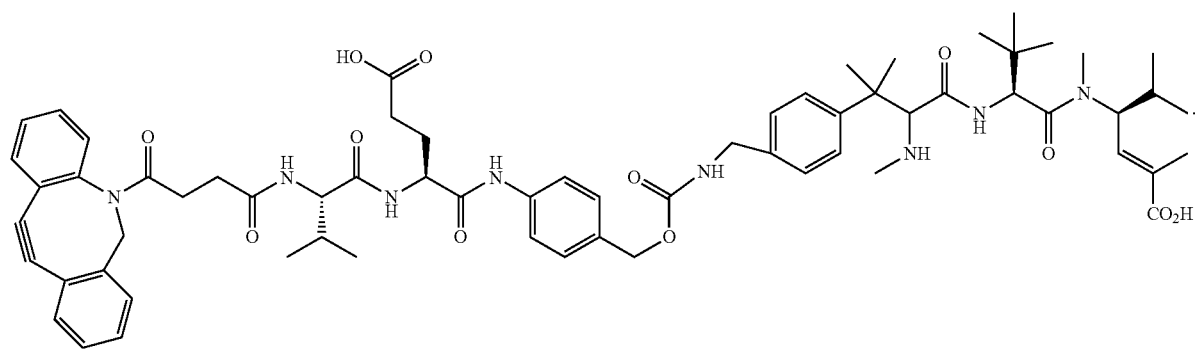
(EEE)
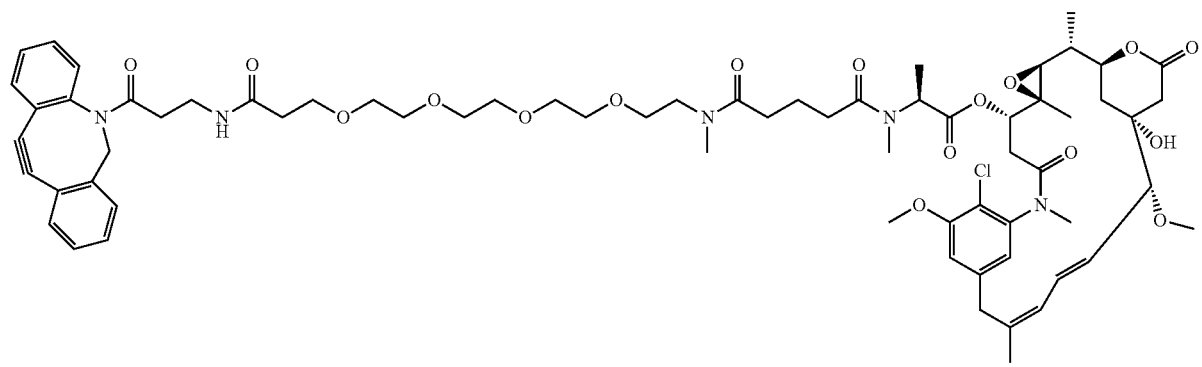

-continued
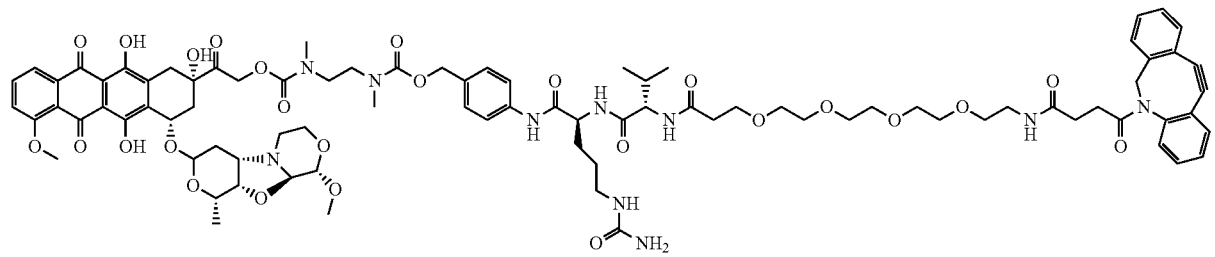
(FFF)
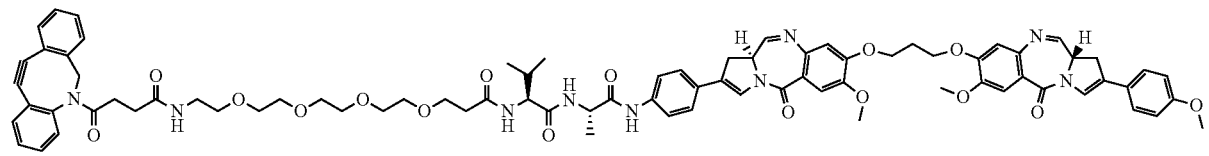
(GGG)
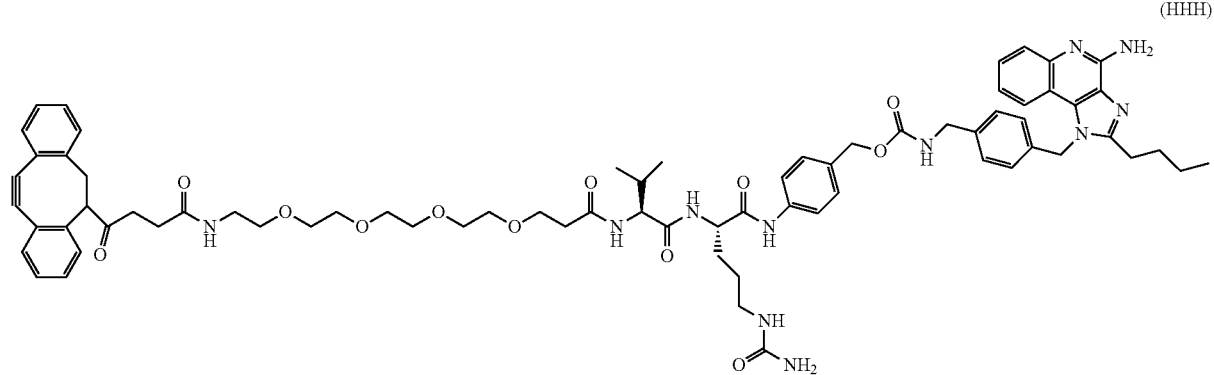
(HHH)
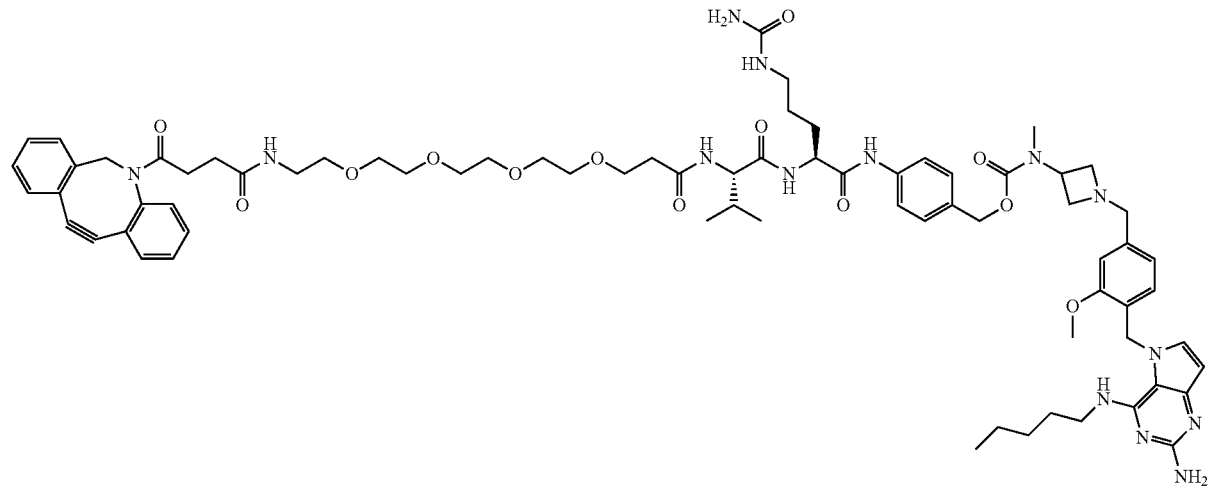
(JJJ)

(KKK)
(LLL)
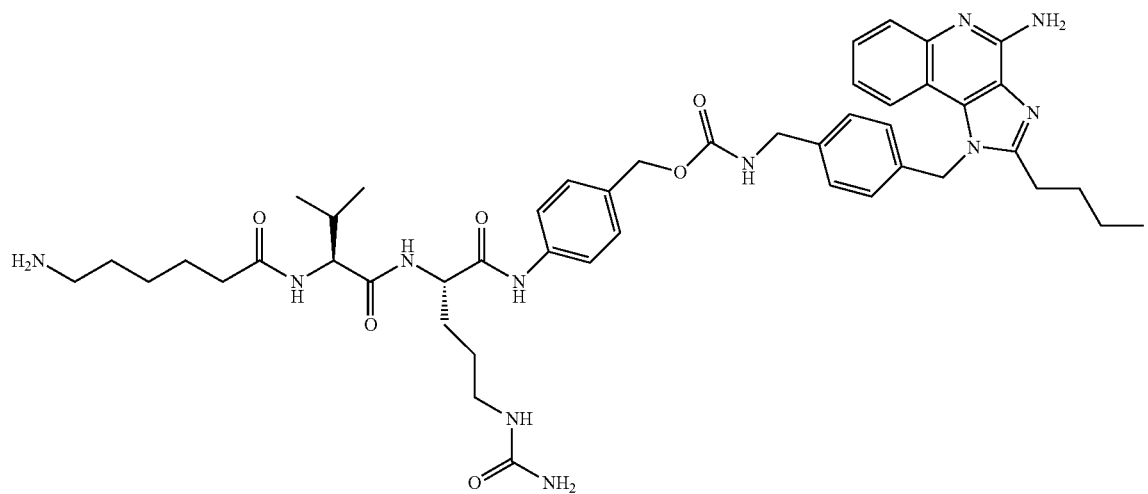
(MMM)
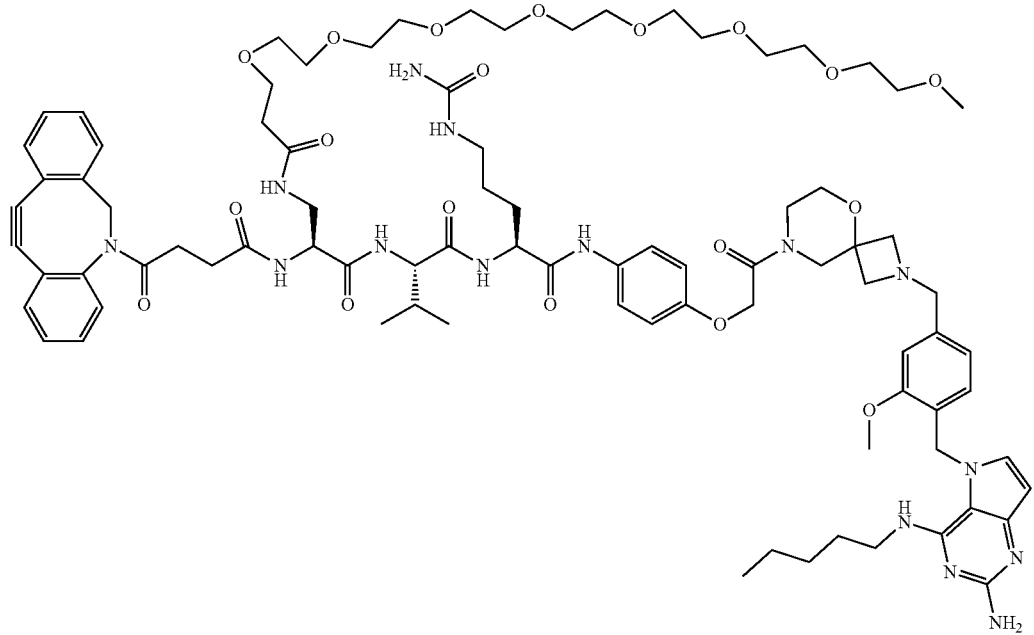

(NNN)
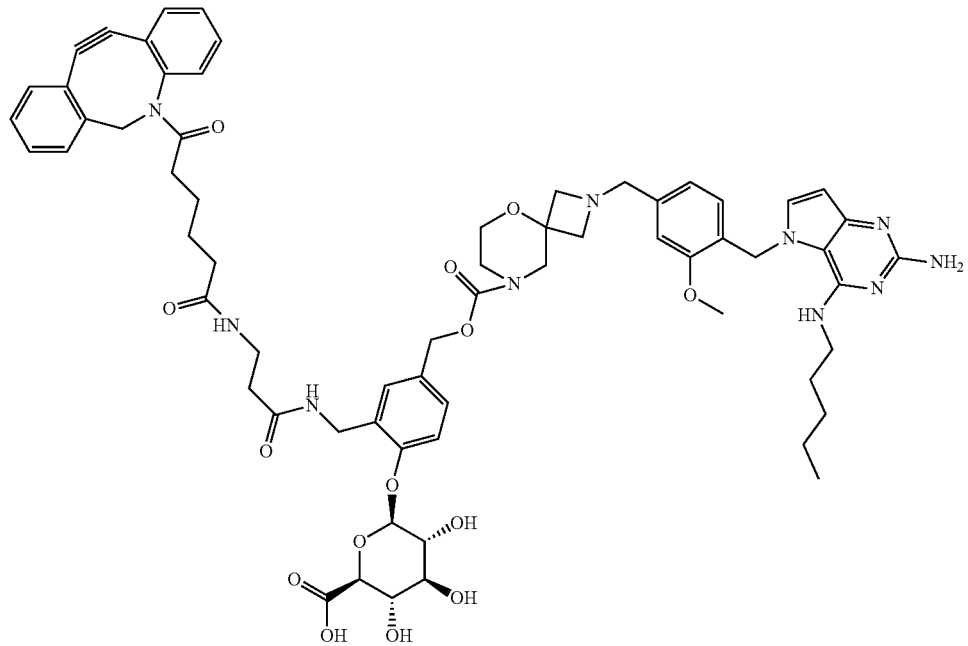
(OOO)

(PPP)
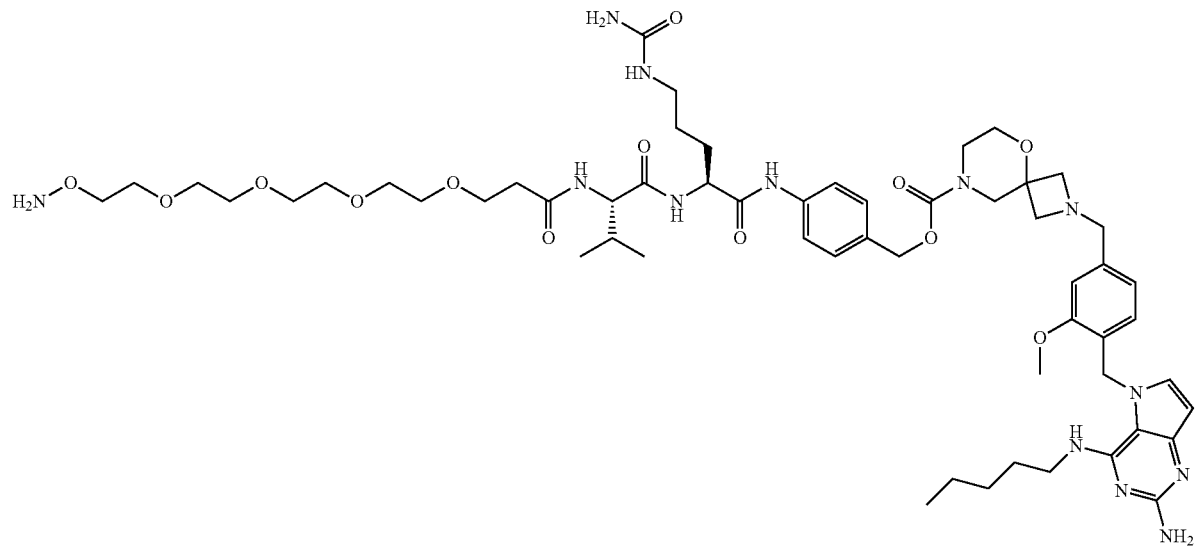
(QQQ)
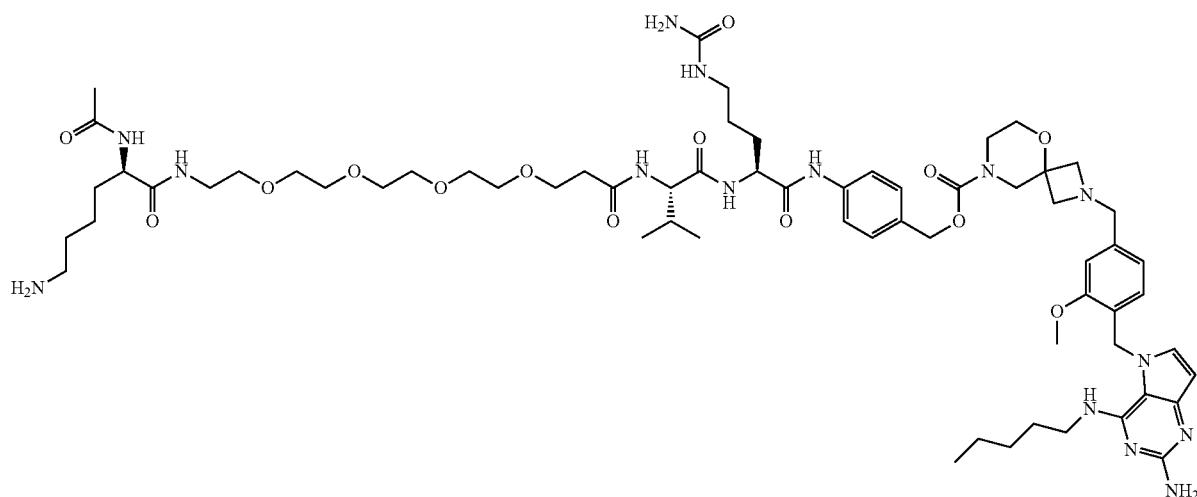
(PPP)
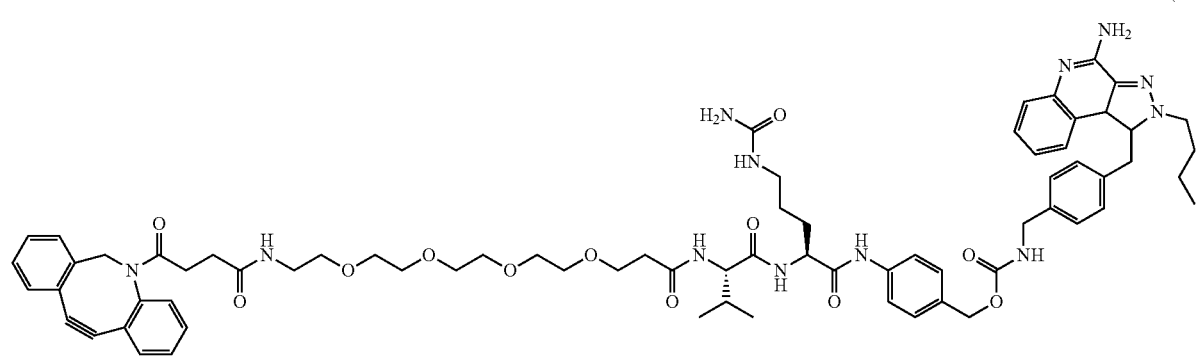

In some embodiments, the stereochemistry of the linker precursors identified above is further identified with R and S notation for each chiral center, from left to right.

In some embodiments, a conjugate is prepared by contacting an antibody as disclosed herein with a linker precursor have a structure of PPP or QQQ above, under conditions suitable for conjugation to one or more glutamine residues or amino termini of the antibody. In certain embodiments, the antibody and linker precursor are contacted in the presence of a sufficient amount of transglutaminase for conjugation. Conjugation at such sites can proceed with the enzyme transglutaminase according to standard techniques. Useful transglutaminase techniques are described in, for instance, Jeger et al., 2010, *Angew. Chem. Int. Ed.* 49:9995-9997, Strop et al., Chemistry & *Biology* 2013:161-167, and the Examples below.

9.1 Preparation of Antibody Conjugates

9.2. Antigen Preparation

The protein to be used for isolation of the antibodies may be intact antigen or a fragment of an antigen. The intact protein, or fragment of the antigen, may be in the form of an isolated protein or protein expressed by a cell. Other forms of antigens useful for generating antibodies will be apparent to those skilled in the art.

9.3. Monoclonal Antibodies

Monoclonal antibodies may be obtained, for example, using the hybridoma method first described by Kohler et al., *Nature*, 1975, 256:495-497 (incorporated by reference in its entirety), and/or by recombinant DNA methods (see e.g., U.S. Pat. No. 4,816,567, incorporated by reference in its entirety). Monoclonal antibodies may also be obtained, for example, using phage or yeast-based libraries. See e.g., U.S. Pat. Nos. 8,258,082 and 8,691,730, each of which is incorporated by reference in its entirety.

In the hybridoma method, a mouse or other appropriate host animal is immunized to elicit lymphocytes that produce or are capable of producing antibodies that will specifically bind to the protein used for immunization. Alternatively, lymphocytes may be immunized in vitro. Lymphocytes are then fused with myeloma cells using a suitable fusing agent, such as polyethylene glycol, to form a hybridoma cell. See Goding J. W., *Monoclonal Antibodies: Principles and Practice* 3$^{rd}$ ed. (1986) Academic Press, San Diego, Calif., incorporated by reference in its entirety.

The hybridoma cells are seeded and grown in a suitable culture medium that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Useful myeloma cells are those that fuse efficiently, support stable high-level production of antibody by the selected antibody-producing cells, and are sensitive media conditions, such as the presence or absence of HAT medium. Among these, preferred myeloma cell lines are murine myeloma lines, such as those derived from MOP-21 and MC-11 mouse tumors (available from the Salk Institute Cell Distribution Center, San Diego, Calif.), and SP-2 or X63-Ag8-653 cells (available from the American Type Culture Collection, Rockville, Md.). Human myeloma and mouse-human heteromyeloma cell lines also have been described for the production of human monoclonal antibodies. See e.g., Kozbor, *J. Immunol.*, 1984, 133:3001, incorporated by reference in its entirety.

After the identification of hybridoma cells that produce antibodies of the desired specificity, affinity, and/or biological activity, selected clones may be subcloned by limiting dilution procedures and grown by standard methods. See Goding, supra. Suitable culture media for this purpose include, for example, D-MEM or RPMI-1640 medium. In addition, the hybridoma cells may be grown in vivo as ascites tumors in an animal.

DNA encoding the monoclonal antibodies may be readily isolated and sequenced using conventional procedures (e.g., by using oligonucleotide probes that are capable of binding specifically to genes encoding the heavy and light chains of the monoclonal antibodies). Thus, the hybridoma cells can serve as a useful source of DNA encoding antibodies with the desired properties. Once isolated, the DNA may be placed into expression vectors, which are then transfected into host cells such as bacteria (e.g., *E. coli*), yeast (e.g., *Saccharomyces* or *Pichia* sp.), COS cells, Chinese hamster ovary (CHO) cells, or myeloma cells that do not otherwise produce antibody, to produce the monoclonal antibodies.

9.4. Humanized Antibodies

Humanized antibodies may be generated by replacing most, or all, of the structural portions of a non-human monoclonal antibody with corresponding human antibody sequences. Consequently, a hybrid molecule is generated in which only the antigen-specific variable, or CDR, is composed of non-human sequence. Methods to obtain humanized antibodies include those described in, for example, Winter and Milstein, *Nature*, 1991, 349:293-299; Rader et al., *Proc. Nat. Acad. Sci. U.S.A.*, 1998, 95:8910-8915; Steinberger et al., *J Biol. Chem.*, 2000, 275:36073-36078; Queen et al., *Proc. Natl. Acad. Sci. U.S.A.*, 1989, 86:10029-10033; and U.S. Pat. Nos. 5,585,089, 5,693,761, 5,693,762, and 6,180,370; each of which is incorporated by reference in its entirety.

9.5. Human Antibodies

Human antibodies can be generated by a variety of techniques known in the art, for example by using transgenic animals (e.g., humanized mice). See, e.g., Jakobovits et al., *Proc. Natl. Acad. Sci. U.S.A.*, 1993, 90:2551; Jakobovits et al., *Nature*, 1993, 362:255-258; Bruggermann et al., *Year in Immuno.*, 1993, 7:33; and U.S. Pat. Nos. 5,591,669, 5,589, 369 and 5,545,807; each of which is incorporated by reference in its entirety. Human antibodies can also be derived from phage-display libraries (see e.g., Hoogenboom et al., *J. Mol. Biol.*, 1991, 227:381-388; Marks et al., *J. Mol. Biol.*, 1991, 222:581-597; and U.S. Pat. Nos. 5,565,332 and 5,573, 905; each of which is incorporated by reference in its entirety). Human antibodies may also be generated by in vitro activated B cells (see e.g., U.S. Pat. Nos. 5,567,610 and 5,229,275, each of which is incorporated by reference in its entirety). Human antibodies may also be derived from yeast-based libraries (see e.g., U.S. Pat. No. 8,691,730, incorporated by reference in its entirety).

9.6. Conjugation

The antibody conjugates can be prepared by standard techniques. In certain embodiments, an antibody is contacted with a payload precursor under conditions suitable for forming a bond from the antibody to the payload to form an antibody-payload conjugate. In certain embodiments, an antibody is contacted with a linker precursor under conditions suitable for forming a bond from the antibody to the linker. The resulting antibody-linker is contacted with a payload precursor under conditions suitable for forming a bond from the antibody-linker to the payload to form an antibody-linker-payload conjugate. In certain embodiments, a payload precursor is contacted with a linker precursor under conditions suitable for forming a bond from the payload to the linker. The resulting payload-linker is contacted with an antibody under conditions suitable for forming a bond from the payload-linker to the antibody to form an antibody-linker-payload conjugate. Suitable linkers for preparing the antibody conjugates are disclosed herein, and exemplary conditions for conjugation are described in the Examples below.

In some embodiments, a conjugate is prepared by contacting an antibody as disclosed herein with a linker precursor according to a structure of any of (M)-(N):

replication, one or more marker genes, an enhancer element, a promoter, and a transcription termination sequence, for example as described in U.S. Pat. No. 5,534,615, incorporated by reference in its entirety.

Illustrative examples of suitable host cells are provided below. These host cells are not meant to be limiting.

Suitable host cells include any prokaryotic (e.g., bacterial), lower eukaryotic (e.g., yeast), or higher eukaryotic (e.g., mammalian) cells. Suitable prokaryotes include eubacteria, such as Gram-negative or Gram-positive organisms, for example, Enterobacteriaceae such as *Escherichia* (*E. coli*), *Enterobacter, Erwinia, Klebsiella, Proteus, Salmonella* (*S. typhimurium*), *Serratia* (*S. marcescans*), *Shigella*, Bacilli (*B. subtilis* and *B. licheniformis*), *Pseudomonas* (*P. aeruginosa*), and *Streptomyces*. One useful *E. coli* cloning host is *E. coli* 294, although other strains such as *E. coli* B, *E. coli* X1776, and *E. coli* $W^{3110}$ are suitable.

In addition to prokaryotes, eukaryotic microbes such as filamentous fungi or yeast are also suitable cloning or expression hosts for antibody-encoding vectors. *Saccharomyces cerevisiae*, or common baker's yeast, is a commonly

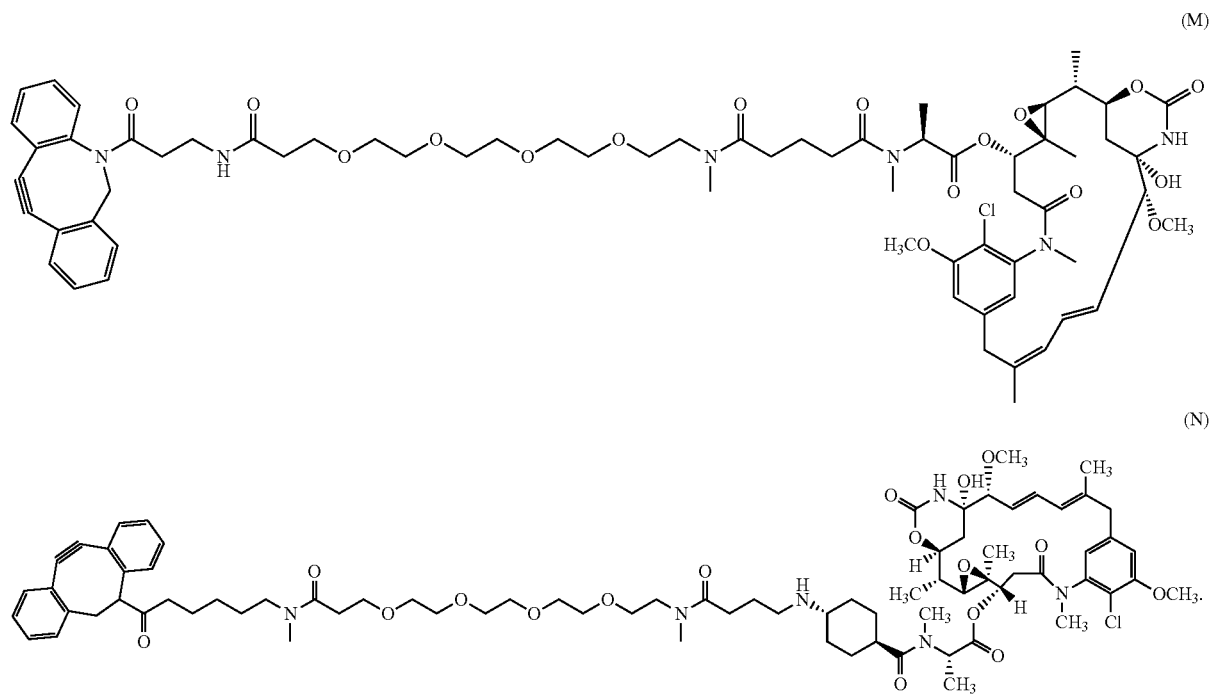

10. Vectors, Host Cells, and Recombinant Methods

Embodiments are also directed to the provision of isolated nucleic acids encoding antibodies, vectors, and host cells comprising the nucleic acids, and recombinant techniques for the production of the antibodies.

For recombinant production of the antibody, the nucleic acid(s) encoding it may be isolated and inserted into a replicable vector for further cloning (i.e., amplification of the DNA) or expression. In some aspects, the nucleic acid may be produced by homologous recombination, for example as described in U.S. Pat. No. 5,204,244, incorporated by reference in its entirety.

Many different vectors are known in the art. The vector components generally include, but are not limited to, one or more of the following: a signal sequence, an origin of used lower eukaryotic host microorganism. However, a number of other genera, species, and strains are available and useful, such as *Spodoptera frugiperda* (e.g., SF9), *Schizosaccharomyces pombe, Kluyveromyces* (*K lactis, K. fragilis, K. bulgaricus* K. wickeramii, *K. waltii, K. drosophilarum, K. thermotolerans*, and *K. marxianus*), *Yarrowia, Pichia pastoris, Candida* (*C. albicans*), *Trichoderma* reesia, *Neurospora crassa, Schwanniomyces* (*S. occidentalis*), and filamentous fungi such as, for example *Penicillium, Tolypocladium*, and *Aspergillus* (*A. nidulans* and *A. niger*).

Useful mammalian host cells include COS-7 cells, HEK293 cells; baby hamster kidney (BHK) cells; Chinese hamster ovary (CHO); mouse sertoli cells; African green monkey kidney cells (VERO-76), and the like.

The host cells used to produce the antibody of this invention may be cultured in a variety of media. Commercially available media such as, for example, Ham's F10, Minimal Essential Medium (MEM), RPMI-1640, and Dulbecco's Modified Eagle's Medium (DMEM) are suitable for culturing the host cells. In addition, any of the media described in Ham et al., *Meth. Enz.,* 1979, 58:44; Barnes et al., *Anal. Biochem.,* 1980, 102:255; and U.S. Pat. Nos. 4,767,704, 4,657,866, 4,927,762, 4,560,655, and 5,122,469, or WO 90/03430 and WO 87/00195 may be used. Each of the foregoing references is incorporated by reference in its entirety.

Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics, trace elements (defined as inorganic compounds usually present at final concentrations in the micromolar range), and glucose or an equivalent energy source. Any other necessary supplements may also be included at appropriate concentrations that would be known to those skilled in the art.

The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. For example, Carter et al. (*Bio Technology,* 1992, 10:163-167) describes a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation.

In some embodiments, the antibody is produced in a cell-free system. In some aspects, the cell-free system is an in vitro transcription and translation system as described in Yin et al., mAbs, 2012, 4:217-225, incorporated by reference in its entirety. In some aspects, the cell-free system utilizes a cell-free extract from a eukaryotic cell or from a prokaryotic cell. In some aspects, the prokaryotic cell is *E. coli*. Cell-free expression of the antibody may be useful, for example, where the antibody accumulates in a cell as an insoluble aggregate, or where yields from periplasmic expression are low. The antibodies produced in a cell-free system may be aglycosylated depending on the source of the cells.

Where the antibody is secreted into the medium, supernatants from such expression systems are generally first concentrated using a commercially available protein concentration filter, for example, an Amicon® or Millipore® Pellcon® ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being a particularly useful purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol.* Meth., 1983, 62:1-13, incorporated by reference in its entirety). Protein G is useful for all mouse isotypes and for human γ3 (Guss et al., *EMBO J,* 1986, 5:1567-1575, incorporated by reference in its entirety).

The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_{H3}$ domain, the BakerBond ABX® resin is useful for purification.

Other techniques for protein purification, such as fractionation on an ion-exchange column, ethanol precipitation, Reverse Phase HPLC, chromatography on silica, chromatography on heparin Sepharose®, chromatofocusing, SDS-PAGE, and ammonium sulfate precipitation are also available, and can be applied by one of skill in the art.

Following any preliminary purification step(s), the mixture comprising the antibody of interest and contaminants may be subjected to low pH hydrophobic interaction chromatography using an elution buffer at a pH between about 2.5 to about 4.5, generally performed at low salt concentrations (e.g., from about 0 to about 0.25 M salt).

11. Pharmaceutical Compositions and Methods of Administration

The antibody conjugates provided herein can be formulated into pharmaceutical compositions using methods available in the art and those disclosed herein. Any of the antibody conjugates provided herein can be provided in the appropriate pharmaceutical composition and be administered by a suitable route of administration.

The methods provided herein encompass administering pharmaceutical compositions comprising at least one antibody conjugate provided herein and one or more compatible and pharmaceutically acceptable carriers. In this context, the term "pharmaceutically acceptable" means approved by a regulatory agency of the Federal or a state government or listed in the U.S. Pharmacopeia or other generally recognized pharmacopeia for use in animals, and more particularly in humans. The term "carrier" includes a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water can be used as a carrier when the pharmaceutical composition is administered intravenously. Saline solutions and aqueous dextrose and glycerol solutions can also be employed as liquid carriers, particularly for injectable solutions. Examples of suitable pharmaceutical carriers are described in Martin, E. W., *Remington's Pharmaceutical Sciences*.

In clinical practice the pharmaceutical compositions or antibody conjugates provided herein may be administered by any route known in the art. Exemplary routes of administration include, but are not limited to, the inhalation, intraarterial, intradermal, intramuscular, intraperitoneal, intravenous, nasal, parenteral, pulmonary, and subcutaneous routes. In some embodiments, a pharmaceutical composition or antibody conjugate provided herein is administered parenterally.

The compositions for parenteral administration can be emulsions or sterile solutions. Parenteral compositions may include, for example, propylene glycol, polyethylene glycol, vegetable oils, and injectable organic esters (e.g., ethyl oleate). These compositions can also contain wetting, isotonizing, emulsifying, dispersing, and stabilizing agents. Sterilization can be carried out in several ways, for example using a bacteriological filter, by radiation or by heating. Parenteral compositions can also be prepared in the form of sterile solid compositions which can be dissolved at the time of use in sterile water or any other injectable sterile medium.

In some embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic antibody conjugates.

The pharmaceutical composition may comprise one or more pharmaceutical excipients. Any suitable pharmaceutical excipient may be used, and one of ordinary skill in the art is capable of selecting suitable pharmaceutical excipients. Non-limiting examples of suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. Whether a particular excipient is suitable for incorporation into a pharmaceutical composition or dosage form depends on a variety of factors well known in the art including, but not limited to, the way in which the dosage form will be administered to a subject and the specific antibody in the dosage form. The composition or single unit dosage form, if desired, can also contain minor amounts of wetting or emulsifying agents, or pH buffering agents. Accordingly, the pharmaceutical excipients provided below are intended to be illustrative, and not limiting. Additional pharmaceutical excipients include, for example, those described in the *Handbook of Pharmaceutical Excipients*, Rowe et al. (*Eds*.) 6th Ed. (2009), incorporated by reference in its entirety.

In some embodiments, the pharmaceutical composition comprises an anti-foaming agent. Any suitable anti-foaming agent may be used. In some aspects, the anti-foaming agent is selected from an alcohol, an ether, an oil, a wax, a silicone, a surfactant, and combinations thereof. In some aspects, the anti-foaming agent is selected from a mineral oil, a vegetable oil, ethylene bis-stearamide, a paraffin wax, an ester wax, a fatty alcohol wax, a long chain fatty alcohol, a fatty acid soap, a fatty acid ester, a silicon glycol, a fluorosilicone, a polyethylene glycol-polypropylene glycol copolymer, polydimethylsiloxane-silicon dioxide, ether, octyl alcohol, capryl alcohol, sorbitan trioleate, ethyl alcohol, 2-ethylhexanol, dimethicone, oleyl alcohol, simethicone, and combinations thereof.

In some embodiments, the pharmaceutical composition comprises a co-solvent. Illustrative examples of co-solvents include ethanol, poly(ethylene) glycol, butylene glycol, dimethylacetamide, glycerin, and propylene glycol.

In some embodiments, the pharmaceutical composition comprises a buffer. Illustrative examples of buffers include acetate, borate, carbonate, lactate, malate, phosphate, citrate, hydroxide, diethanolamine, monoethanolamine, glycine, methionine, guar gum, and monosodium glutamate.

In some embodiments, the pharmaceutical composition comprises a carrier or filler. Illustrative examples of carriers or fillers include lactose, maltodextrin, mannitol, sorbitol, chitosan, stearic acid, xanthan gum, and guar gum.

In some embodiments, the pharmaceutical composition comprises a surfactant. Illustrative examples of surfactants include d-alpha tocopherol, benzalkonium chloride, benzethonium chloride, cetrimide, cetylpyridinium chloride, docusate sodium, glyceryl behenate, glyceryl monooleate, lauric acid, macrogol 15 hydroxystearate, myristyl alcohol, phospholipids, polyoxyethylene alkyl ethers, polyoxyethylene sorbitan fatty acid esters, polyoxyethylene stearates, polyoxylglycerides, sodium lauryl sulfate, sorbitan esters, and vitamin E polyethylene(glycol) succinate.

In some embodiments, the pharmaceutical composition comprises an anti-caking agent. Illustrative examples of anti-caking agents include calcium phosphate (tribasic), hydroxymethyl cellulose, hydroxypropyl cellulose, and magnesium oxide.

Other excipients that may be used with the pharmaceutical compositions include, for example, albumin, antioxidants, antibacterial agents, antifungal agents, bioabsorbable polymers, chelating agents, controlled release agents, diluents, dispersing agents, dissolution enhancers, emulsifying agents, gelling agents, ointment bases, penetration enhancers, preservatives, solubilizing agents, solvents, stabilizing agents, and sugars. Specific examples of each of these agents are described, for example, in the *Handbook of Pharmaceutical Excipients*, Rowe et al. (Eds.) 6th Ed. (2009), The Pharmaceutical Press, incorporated by reference in its entirety.

In some embodiments, the pharmaceutical composition comprises a solvent. In some aspects, the solvent is saline solution, such as a sterile isotonic saline solution or dextrose solution. In some aspects, the solvent is water for injection.

In some embodiments, the pharmaceutical compositions are in a particulate form, such as a microparticle or a nanoparticle. Microparticles and nanoparticles may be formed from any suitable material, such as a polymer or a lipid. In some aspects, the microparticles or nanoparticles are micelles, liposomes, or polymersomes.

Further provided herein are anhydrous pharmaceutical compositions and dosage forms comprising an antibody conjugate, since, in some embodiments, water can facilitate the degradation of some antibodies.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition can be prepared and stored such that its anhydrous nature is maintained. Accordingly, anhydrous compositions can be packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Lactose-free compositions provided herein can comprise excipients that are well known in the art and are listed, for example, in the U.S. Pharmocopeia (USP) SP (XXI)/NF (XVI). In general, lactose-free compositions comprise an active ingredient, a binder/filler, and a lubricant in pharmaceutically compatible and pharmaceutically acceptable amounts. Exemplary lactose-free dosage forms comprise an active ingredient, microcrystalline cellulose, pre gelatinized starch, and magnesium stearate.

Also provided are pharmaceutical compositions and dosage forms that comprise one or more excipients that reduce the rate by which an antibody or antibody-conjugate will decompose. Such excipients, which are referred to herein as "stabilizers," include, but are not limited to, antioxidants such as ascorbic acid, pH buffers, or salt buffers.

11.1. Parenteral Dosage Forms

For therapeutic applications, the antibody conjugates described herein are administered to a mammal, generally a human, in a pharmaceutically acceptable dosage form such as those known in the art and those discussed above. For example, the antibody conjugates of the invention may be administered to a human intravenously as a bolus or by continuous infusion over a period of time, by intramuscular, intraperitoneal, intra-cerebrospinal, subcutaneous, intra-articular, intrasynovial, intrathecal, or intratumoral routes. The antibody conjugates also are suitably administered by peritumoral, intralesional, or perilesional routes, to exert local as well as systemic therapeutic effects. The intraperitoneal route may be particularly useful, for example, in the treatment of ovarian tumors.

In certain embodiments, provided are parenteral dosage forms. Parenteral dosage forms can be administered to subjects by various routes including, but not limited to, subcutaneous, intravenous (including bolus injection), intramuscular, and intraarterial. Because their administration typically bypasses subjects' natural defenses against contaminants, parenteral dosage forms are typically, sterile or capable of being sterilized prior to administration to a subject. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; phosphate buffered saline (PBS), aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Excipients that increase the solubility of one or more of the antibodies disclosed herein can also be incorporated into the parenteral dosage forms.

11.2. Dosage and Unit Dosage Forms

In human therapeutics, the doctor will determine the posology which he considers most appropriate according to a preventive or curative treatment and according to the age, weight, condition and other factors specific to the subject to be treated.

In certain embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic antibodies.

The amount of the antibody conjugate or composition which will be effective in the prevention or treatment of a disorder or one or more symptoms thereof will vary with the nature and severity of the disease or condition, and the route by which the antibody is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

In certain embodiments, exemplary doses of a composition include milligram or microgram amounts of the antibody per kilogram of subject or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram). In certain embodiment, the dosage of the antibody conjugate provided herein, based on weight of the antibody, administered to prevent, treat, manage, or ameliorate a disorder, or one or more symptoms thereof in a subject is 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight. In another embodiment, the dosage of the composition or a composition provided herein administered to prevent, treat, manage, or ameliorate a disorder, or one or more symptoms thereof in a subject is 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 to 15 mg, 0.25 to 12 mg, 0.25 to 10 mg, 0.25 mg to 7.5 mg, 0.25 mg to 5 mg, 0.25 mg to 2.5 mg, 0.5 mg to 20 mg, 0.5 to 15 mg, 0.5 to 12 mg, 0.5 to 10 mg, 0.5 mg to 7.5 mg, 0.5 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg.

The dose can be administered according to a suitable schedule, for example, once, two times, three times, or four times weekly. It may be necessary to use dosages of the antibody conjugate outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the antibodies provided herein are also encompassed by the herein described dosage amounts and dose frequency schedules. Further, when a subject is administered multiple dosages of a composition provided herein, not all of the dosages need be the same. For example, the dosage administered to the subject may be increased to improve the prophylactic or therapeutic effect of the composition or it may be decreased to reduce one or more side effects that a particular subject is experiencing.

In certain embodiments, treatment or prevention can be initiated with one or more loading doses of an antibody conjugate or composition provided herein followed by one or more maintenance doses.

In certain embodiments, a dose of an antibody conjugate or composition provided herein can be administered to achieve a steady-state concentration of the antibody in blood or serum of the subject. The steady-state concentration can be determined by measurement according to techniques available to those of skill or can be based on the physical characteristics of the subject such as height, weight, and age.

In certain embodiments, administration of the same composition may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least 1 day, 2 days, 3 days, 5 days, 10 days, 15 days, 30 days, 45 days, 2 months, 75 days, 3 months, or 6 months.

11.3. Combination Therapies and Formulations

In certain embodiments, provided are compositions, therapeutic formulations, and methods of treatment or uses comprising any of the antibody conjugates provided herein in combination with one or more chemotherapeutic agents disclosed herein, and methods of treatment comprising administering such combinations to subjects in need thereof. Examples of chemotherapeutic agents include, but are not limited to, Bendamustine (TREANDA®, Cephalon), Venetoclax (VENCLEXTA®, Abbvie, Genentech), Denosumab (XGEVA®, Amgen; PROLIA®, Amgen), Carfilzomib (KYPROLIS®, Amgen), Ixazomib (NINLARO®, Takeda), Erlotinib (TARCEVA®, Genentech/OSI Pharm.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (TYKERB®, GSK572016, Glaxo Smith Kline), Lonafamib (SCH 66336), Sorafenib (BAY43-9006, Bayer Labs), and Gefitinib (IRESSA®, AstraZeneca), AG1478, AG1571 (SU 5271; Sugen), alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially uncialamycin, calicheamicin gammaII, and calicheamicin omegaII (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pladienolide B, pteropterin, trimetrexate; purine analogs such as fludarabine, 6-mercaptopurine, thiamniprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (doxetaxel; Rhone-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (Vβ-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

For therapeutic applications, the antibody conjugates of the invention are administered to a mammal, generally a human, in a pharmaceutically acceptable dosage form such as those known in the art and those discussed above. For example, the antibody conjugates of the invention may be administered to a human intravenously as a bolus or by continuous infusion over a period of time, by intramuscular, intraperitoneal, intra-cerebrospinal, subcutaneous, intra-articular, intrasynovial, intrathecal, or intratumoral routes. The antibody conjugates also are suitably administered by peritumoral, intralesional, or perilesional routes, to exert local as well as systemic therapeutic effects. The intraperitoneal route may be particularly useful, for example, in the treatment of ovarian tumors.

The agents administered in combination with the antibody conjugates disclosed herein can be administered just prior to, concurrent with, or shortly after the administration of the antibody conjugates. In certain embodiments, the antibody conjugates provided herein are administered on a first dosing schedule, and the one or more second agents are administered on their own dosing schedules. For purposes of the present disclosure, such administration regimens are considered the administration of an antibody conjugate "in combination with" an additional therapeutically active component. Embodiments include pharmaceutical compositions in which an antibody conjugate disclosed herein is co-formulated with one or more of the chemotherapeutic agents or immunomodulatory agents disclosed herein.

In some embodiments, the immune checkpoint inhibitor is cytotoxic T-lymphocyte antigen 4 (CTLA4, also known as CD 152), T cell immunoreceptor with Ig and ITIM domains (TIGIT), glucocorticoid-induced TNFR-related protein (GITR, also known as TNFRSF18), inducible T cell costimulatory (ICOS, also known as CD278), CD96, poliovirus receptor-related 2 (PVRL2, also known as CD1 12R, programmed cell death protein 1 (PD-1, also known as CD279), programmed cell death 1 ligand 1 (PD-L1, also known as B7-H3 and CD274), programmed cell death ligand 2 (PD-L2, also known as B7-DC and CD273), lymphocyte activation gene-3 (LAG-3, also known as CD223), B7-H4, killer immunoglobulin receptor (KIR), Tumor Necrosis Factor Receptor superfamily member 4 (TNFRSF4, also known as OX40 and CD134) and its ligand OX40L (CD252), indoleamine 2,3-dioxygenase 1 (IDO-1), indoleamine 2,3-dioxygenase 2 (IDO-2), carcinoembryonic antigen-related cell adhesion molecule 1 (CEACAM1), B and T lymphocyte attenuator (BTLA, also known as CD272), T-cell membrane protein 3 (TIM3), the adenosine A2A receptor (A2Ar), and V-domain Ig suppressor of T cell activation (VISTA protein). In some embodiments, the immune checkpoint inhibitor is an inhibitor of CTLA4, PD-1, or PD-L1.

In certain embodiments, provided are compositions, therapeutic formulations, and methods of treatment or uses comprising any of the antibody conjugates provided herein in combination with one or more PD-1 or PD-L1 inhibitors, and methods of treatment comprising administering such combinations to subjects in need thereof. In some embodiments, the one or more PD-1 or PD-L1 inhibitors comprise a small molecule blocker of the PD-1 or PD-L1 pathway. In some embodiments, the one or more PD-1 or PD-L1 inhibitors comprise an antibody that inhibits PD-1 or PD-L1 activity. In some embodiments, the one or more PD-1 or PD-L1 inhibitors are selected from the group consisting of: CA-170, BMS-8, BMS-202, BMS-936558, CK-301, and AUNP12. In some embodiments, the one or more PD-1 or PD-L1 inhibitors are selected from the group consisting of: avelumab, nivolumab, pembrolizumab, atezolizumab, durvalumab, AMβ-224 (GlaxoSmithKline), MEDI0680/AMβ-514 (AstraZeneca), PDR001 (Novartis), cemiplimab, TSR-042 (Tesaro, GlaxoSmithKline), Tizlelizumab/BGB-A317 (Beigene), CK-301 (Checkpoint Therapeutics), BMS-936559 (Bristol-Meyers Squibb), cemiplimab (Regeneron), camrelizumab, sintilimab, toripalimab, genolimzumab, and A167 (Sichuan Kelun-Biotech Biopharmaceutical). In some embodiments, the one or more PD-1 or PD-L1 inhibitors are selected from the group consisting of: MGA012 (Incyte/MacroGenics), PF-06801591 (Pfizer/Merck KGaA), LY3300054 (Eli Lilly), FAZ053 (Novartis), PD-11 (Novartis), CX-072 (CytomX), BGB-A333 (Beigene), BI 754091 (Boehringer Ingelheim), JNJ-63723283 (Johnson and Johnson/Jannsen), AGEN2034 (Agenus), CA-327 (Curis), CX-188 (CytomX), STI-A1110 (Servier), JTX-4014 (Jounce), AM0001 (Armo Biosciences, Eli Lilly), CBT-502 (CBT Pharmaceuticals), FS118 (F-Star/Merck KGaA), XmAb20717 (Xencor), XmAb23104 (Xencor), AB122 (Arcus Biosciences), KY1003 (Kymab), RXI-762 (RXi). In some embodiments, the one or more PD-1 or PD-L1 inhibitors are selected from the group consisting of: PRS-332 (*Pieris* Pharmaceuticals), ALPN-202 (Alpine Immune Science), TSR-075 (Tesaro/Anaptys Bio), MCLA-145 (Merus), MGDO13 (Macrogenics), MGDO19 (Macrogenics), RO7121661 (Hoffman-La Roche), LY3415244 (Eli Lilly). In some embodiments, the one or more PD-1 or PD-L1 inhibitors are selected from an anti-PD1 mono-specific or bi-specific antibody described in, for example, WO 2016/077397, WO 2018/156777, and International Application No. PCT/US2013/034213, filed May 23, 2018.

In certain embodiments, provided are compositions, therapeutic formulations, and methods of treatment or uses comprising any of the antibody conjugates provided herein in combination with one or more LAG3 inhibitors, and methods of treatment comprising administering such combinations to subjects in need thereof. In some embodiments, the one or more LAG3 inhibitors comprise a small molecule blocker of the LAG3 pathway. In some embodiments, the one or more LAG3 inhibitors comprise an antibody that inhibits LAG3 activity. In some embodiments, the one or more LAG3 inhibitors are independently selected from the group consisting of: IMP321 (Eftilagimod alpha, Immutep), relatilimab (Brisol-Myers Squibb), LAG525 (Novartis), MK4280 (Merck), BI 754111 (Boehringer Ingelheim), REGN3767 (Regeneron/Sanofi), Sym022 (Symphogen) and TSR-033 (Tesaro/GSK).

In certain embodiments, provided are compositions, therapeutic formulations, and methods of treatment or uses comprising any of the antibody conjugates provided herein in combination with one or more TIM3 inhibitors, and methods of treatment comprising administering such combinations to subjects in need thereof. In some embodiments, the one or more TIM3 inhibitors comprise a small molecule blocker of the TIM3 pathway. In some embodiments, the one or more TIM3 inhibitors comprise an antibody that inhibits TIM3 activity. In some embodiments, the one or more TIM3 inhibitors are independently selected from the group consisting of: TSR-022 (Tesaro), LY3321367 (Eli Lilly), Sym023 (Symphogen) and MBG453 (Novartis).

In certain embodiments, provided are compositions, therapeutic formulations, and methods of treatment or uses comprising any of the antibody conjugates provided herein in combination with one or more TIGIT inhibitors, and methods of treatment comprising administering such combinations to subjects in need thereof. In some embodiments, the one or more TIGIT inhibitors comprise a small molecule blocker of the TIGIT pathway. In some embodiments, the one or more TIGIT inhibitors comprise an antibody that inhibits TIGIT activity. In some embodiments, the one or more TIGIT inhibitors are independently selected from the group consisting of: BMS-986207 (BMS), tiragolumab (RG6058, Genentech), ASP-8374 (Potenza Therapeutics), etigilimab, AB-154 (Arcus).

In certain embodiments, provided are compositions, therapeutic formulations, and methods of treatment or uses comprising any of the antibody conjugates provided herein in combination with one or more inhibitors of V-domain Ig suppressor of T cell activation (VISTA), and methods of treatment comprising administering such combinations to subjects in need thereof. In some embodiments, the one or more VISTA inhibitors comprise a small molecule blocker of the VISTA pathway. In some embodiments, the one or more VISTA inhibitors comprise an antibody that inhibits VISTA activity. In some embodiments, the one or more VISTA inhibitors are independently selected from the group consisting of: PMC-309 (PharmaAbcine Inc), HMBD-002 (Hummingbird Bioscience Pte Ltd), JNJ-61610588 (Janssen), CA-170 (Aurigene Discovery Technologies Ltd)

In certain embodiments, provided are compositions, therapeutic formulations, and methods of treatment or uses comprising any of the antibody conjugates provided herein in combination with one or more CSF1R inhibitors, and methods of treatment comprising administering such combinations to subjects in need thereof. In some embodiments, the one or more CSF1R inhibitors comprise a small molecule blocker of the CSF1R pathway. In some embodiments, the one or more CSF1R inhibitors comprise an antibody that inhibits CSF1R activity. In some embodiments, the one or more CSF1R inhibitors are independently selected from the group consisting of: AMG 820 (Amgen), Emactuzumab (Roche), IMC-CS4 (LY3022855) (Eli Lilly), MCS110 (Novartis), cabiralizumab (FPA008) (Five Prime Therapeutics), JNJ-40346527 (Johnson and Johnson), BLZ945 (Novartis), ARRY-382 (Array Biopharma), PLX7486 (Plexxicon) and Pexidartinib (Plexxicon).

In certain embodiments, provided are compositions, therapeutic formulations, and methods of treatment or uses comprising any of the antibody conjugates provided herein in combination with one or more CD73 inhibitors, and methods of treatment comprising administering such combinations to subjects in need thereof. In some embodiments, the one or more CD73 inhibitors comprise a small molecule blocker of the CD73 pathway. In some embodiments, the one or more CD73 inhibitors comprise an antibody that inhibits CD73 activity. In some embodiments, the one or more CD73 inhibitors are independently selected from the group consisting of: MED19447 (Medimmune), IPH-5301 (Innate Pharma), AB680 (Arcus), and BMS-986179 (Bristol-Myers Squibb).

In certain embodiments, provided are compositions, therapeutic formulations, and methods of treatment or uses comprising any of the antibody conjugates provided herein in combination with one or more CD39 inhibitors, and methods of treatment comprising administering such combinations to subjects in need thereof. In some embodiments, the one or more CD39 inhibitors comprise a small molecule blocker of the CD39 pathway. In some embodiments, the one or more CD39 inhibitors comprise an antibody that inhibits CD39 activity. In some embodiments, the one or more CD39 inhibitors are independently selected from the group consisting of: CPI-444 (Corvus), PBF-509 (Pablobio, Novartis), MK-3814 (Merck), and AZD4635 (AstraZeneca), TTX-030 (Tizona Therapeutics), IPH-5201 (Innate Pharma), and SRF-617 (Surface Oncology).

In certain embodiments, provided are compositions, therapeutic formulations, and methods of treatment or uses comprising any of the antibody conjugates provided herein in combination with one or more inhibitors of the A2a receptor (A2aR), and methods of treatment comprising administering such combinations to subjects in need thereof. In some embodiments, the one or more A2aR inhibitors comprise a small molecule blocker of the A2aR signaling pathway. In some embodiments, the one or more A2aR inhibitors comprise an antibody that inhibits activity of A2a receptor. In some embodiments, the one or more A2AR inhibitors are independently selected from the group consisting of: CPI-444 (Corvus), PBF-509 (Pablobio, Novartis), MK-3814 (Merck), and AZD4635 (AstraZeneca).

In certain embodiments, provided are compositions, therapeutic formulations, and methods of treatment or uses comprising any of the antibody conjugates provided herein in combination with one or more inhibitors of transforming growth factor-β (TGF-β), and methods of treatment comprising administering such combinations to subjects in need thereof. In some embodiments, the one or more TGF-β inhibitors comprise a small molecule blocker of the TGF-β signaling pathway. In some embodiments, the one or more TGF-β inhibitors comprise an antibody that inhibits activity of TGF-β receptor. In some embodiments, the one or more TGF-β inhibitors are independently selected from the group consisting of: AVID200 (Formation Biologics), LY3200882 (Eli Lilly), M7824 (Merck KGaA).

In certain embodiments, provided are compositions, therapeutic formulations, and methods of treatment or uses comprising any of the antibody conjugates provided herein in combination with one or more B7-H4 inhibitors, and methods of treatment comprising administering such combinations to subjects in need thereof. In some embodiments, the one or more B7-H4 inhibitors comprise a small molecule blocker of the B7-H4 pathway. In some embodiments, the one or more B7-H4 inhibitors comprise an antibody that inhibits B7-H4 activity. In some embodiments, the one or more B7-H4 inhibitors are selected from the group consisting of FPA-150 (Five Prime Therapeutics).

In certain embodiments, provided are compositions, therapeutic formulations, and methods of treatment or uses comprising any of the antibody conjugates provided herein in combination with one or more KIR inhibitors, and methods of treatment comprising administering such combinations to subjects in need thereof. In some embodiments, the one or more KIR inhibitors comprise a small molecule blocker of the KIR pathway. In some embodiments, the one or more KIR inhibitors comprise an antibody that inhibits KIR activity. In some embodiments, the one or more KIR inhibitors are independently selected from the group consisting of Lirilumab (IPH-2102, BMS-986015) (Bristol Myers Squibb), TRL-8605 (Trellis Bioscience Inc.), IPI-41 (IPH 4101) (Innate Pharma S.A.).

In certain embodiments, provided are compositions, therapeutic formulations, and methods of treatment or uses comprising any of the antibody conjugates provided herein in combination with one or more inhibitors of Tumor Necrosis Factor Receptor superfamily member 4 (TNFRSF4, also known as OX40 and CD134) and its ligand OX40L (CD252), and methods of treatment comprising administering such combinations to subjects in need thereof. In some embodiments, the one or more inhibitors of TNFRSF4/OX40 or OX40L comprise a small molecule blocker of the TNFRSF4/OX40 pathway. In some embodiments, the one or more inhibitors of TNFRSF4/OX40 or OX40L comprise an antibody that inhibits TNFRSF4/OX40 activity. In some embodiments, the immune checkpoint inhibitor reduces the interaction between TNFRSF4/OX40 and OX40L. In some embodiments, the one or more inhibitors of TNFRSF4/OX40 or OX40L are independently selected from the group consisting of INCAGN-1949 (Incyte Corp), GSK-3174998 (Glaxo Smith Kline), PF-04518600 (PF-8600) (Pfizer Inc.)

In certain embodiments, provided are compositions, therapeutic formulations, and methods of treatment or uses comprising any of the antibody conjugates provided herein in combination with one or more inhibitors of the indoleamine 2,3-dioxygenase (IDO) pathway, and methods of treatment comprising administering such combinations to subjects in need thereof. In some embodiments, the immune checkpoint inhibitor is an inhibitor of IDO-1. In some embodiments, the immune checkpoint inhibitor is an inhibitor of IDO-2. In some embodiments, the one or more IDO pathway inhibitors comprise a small molecule blocker of the IDO pathway. In some embodiments, the one or more IDO pathway inhibitors comprise an antibody that inhibits IDO-1 or IDO-2. In some embodiments, the one or more IDO1 or IDO-2 inhibitors are independently selected from the group consisting of LY-3381916 (Eli Lilly), BMS-986205 (Bristol-Myers Squibb), KHK2455 (Kyowa Kirin Pharmaceutical Development, Inc.), Indoximod (NewLink Genetics), Epacadostat (INCB24360) (Incyte Corp), GDC-0919 (navoximod) (NewLink Genetics).

In some embodiments, the immune checkpoint inhibitor is an inhibitor of IDO-2. In some embodiments, the immune checkpoint inhibitor is an antibody against IDO-2. In some embodiments, the immune checkpoint inhibitor is a monoclonal antibody against IDO-2. In some embodiments, the immune checkpoint inhibitor is a human or humanized antibody against IDO-2. In some embodiments, the immune checkpoint inhibitor reduces the expression or activity of one or more immune checkpoint proteins, such as IDO-2.

In certain embodiments, provided are compositions, therapeutic formulations, and methods of treatment or uses comprising any of the antibody conjugates provided herein in combination with one or more CEACAM1 inhibitors, and methods of treatment comprising administering such combinations to subjects in need thereof. In some embodiments, the one or more CEACAM1 inhibitors comprise a small molecule blocker of the CEACAM1 pathway. In some embodiments, the one or more CEACAM1 inhibitors comprise an antibody that inhibits CEACAM1. In some embodiments, the one or more CEACAM1 inhibitors are independently selected from the group consisting of PB-04123 (Pangaea Oncology S.A), and CM-24 (MK- 6018) (Merck Sharpe and Dohme).

In certain embodiments, provided are compositions, therapeutic formulations, and methods of treatment or uses comprising any of the antibody conjugates provided herein in combination with one or more activators/agonists of glucocorticoid-induced TNFR-related protein (GITR, also known as TNFRSF18), and methods of treatment comprising administering such combinations to subjects in need thereof. In some embodiments, the one or more GITR agonists comprise a small molecule agonist of the GITR pathway. In some embodiments, the one or more GITR agonists comprise an antibody that activates GITR activity. In some embodiments, the one or more GITR agonists comprise recombinant protein that activates GITR activity. In some embodiments, the one or more GITR agonists are independently selected from the group consisting of BMS- 986156 (Bristol Myers Squibb), TRX-518 (Leap Therapeutics), TNCAGN-1876 (Incyte Corp), MK-1248 (Merck and Co Inc.), MK-4166 (Merck and co), and GWN-323 (Novartis).

In certain embodiments, provided are compositions, therapeutic formulations, and methods of treatment or uses comprising any of the antibody conjugates provided herein in combination with one or more inhibitors of Cluster of Differentiation 47 (CD47, also known as integrin associated protein (IAP)), and methods of treatment comprising administering such combinations to subjects in need thereof. In some embodiments, the one or more CD47 antagonists comprise a small molecule agonist of the CD47 pathway. In some embodiments, the one or more CD47 agonists comprise an antibody that inhibits CD47 activity. In some embodiments, the one or more CD47 agonists comprise recombinant protein that inhibits CD47 activity. In some embodiments, the one or more CD47 antagonists are independently selected from the group consisting of Magrolimab (also known as Hu5F9-G4 (5F9); Gilead), TTI-621 (Trillium Therapeutics), TTI-622 (Trillium Therapeutics), and RRx-001 (EpicentRx).

In certain embodiments, provided are compositions, therapeutic formulations, and methods of treatment or uses comprising any of the antibody conjugates provided herein in combination with one or more activators/agonists of inducible T cell costimulatory (ICOS, also known as CD278), and methods of treatment comprising administering such combinations to subjects in need thereof. In some embodiments, the one or more ICOS agonists comprise a small molecule agonist of the ICOS pathway. In some embodiments, the one or more ICOS agonists comprise an antibody that activates ICOS activity. In some embodiments, the one or more ICOS agonists comprise recombinant protein that activates ICOS activity. In some embodiments, the one or more ICOS agonists are independently selected from the group consisting of Vopratelimab (JTX-2011) (Jounce Therapeutics), GSK-3359609 (GSK), BMS-986226 (BMS), KY-1044 (Kymab Ltd).

In certain embodiments, provided are compositions, therapeutic formulations, and methods of treatment or uses comprising any of the antibody conjugates provided herein in combination with one or more activators/agonists of tumor necrosis factor receptor superfamily member 5 (CD40), and methods of treatment comprising administering such combinations to subjects in need thereof. In some embodiments, the one or more CD40 agonists comprise a small molecule agonist of the CD40 pathway. In some embodiments, the one or more CD40 agonists comprise an antibody that activates CD40 activity. In some embodiments, the one or more CD40 agonists comprise recombinant protein that activates CD40 activity. In some embodiments, the one or more CD40 agonists are independently selected from the group consisting of APX005M (Apexigen), Cβ-870,893 (Pfizer), ABBV-927 (Abbvie), SEA-CD40 (Seattle Genetics).

In certain embodiments, provided are compositions, therapeutic formulations, and methods of treatment or uses comprising any of the antibody conjugates provided herein in combination with one or more activators/agonists of STING (stimulator of interferon genes) pathway, and methods of treatment comprising administering such combinations to subjects in need thereof. In some embodiments, the one or more STING agonists comprise a small molecule agonist of the STING pathway. In some embodiments, the one or more STING agonists comprise an antibody that activates STING activity. In some embodiments, the one or more STING agonists comprise recombinant protein that activates STING activity. In some embodiments, the one or more STING agonists are independently selected from the group consisting of MK-1454 (Merck), ADU-S100 (Aduro), TTI-10001 (Trillium Therapeutics), and SB11285 (Springbank Pharmaceuticals)

In certain embodiments, provided are compositions, therapeutic formulations, and methods of treatment or uses comprising any of the antibody conjugates provided herein in combination with one or more activators/agonists of RIG-I signaling, and methods of treatment comprising administering such combinations to subjects in need thereof. In some embodiments, the one or more RIG-I agonists comprise a small molecule agonist of the RIG-I pathway. In some embodiments, the one or more RIG-I agonists comprise an antibody that activates RIG-I activity. In some embodiments, the one or more RIG-I agonists comprise recombinant protein that activates RIG-I activity. In some embodiments, the one or more RIG-I agonists are independently selected from the group consisting of RGT100 (MK4621, Merck), and KIN 1148 (Kineta Inc.).

In certain embodiments, the antibody conjugates provided herein are administered in combination with VELCADE® (bortezomib), KYPROLIS® (Carfilzomib), and NINLARO® (Ixazomib). In certain embodiments, the antibody conjugates provided herein are administered in combination with FARYDAK® (panobinostat). In certain embodiments, the antibody conjugates provided herein are administered in combination with DARALEX® (daratumumab). In certain embodiments, the antibody conjugates provided herein are administered in combination with EMPLICITI® (elotuzumab). In certain embodiments, the antibody conjugates provided herein are administered in combination with AREDIA® (pamidronate) or ZOMETA® (zolendronic acid). In certain embodiments, the antibody conjugates provided herein are administered in combination with XGEVA® (denosumab) or PROLIA® (denosumab).

In certain embodiments, provided are compositions, therapeutic formulations, and methods of treatment or uses comprising any of the antibody conjugates provided herein in combination with one or more inhibitors of histone deacetylase (HDAC) activity, and methods of treatment comprising administering such combinations to subjects in need thereof. In some embodiments, the one or more HDAC antagonists comprise a small molecule agonist of HDAC activity. In some embodiments, the one or more HDAC antagonists comprise an antibody that inhibits HDAC activity. In some embodiments, the one or more HDAC antagonists comprise recombinant protein that inhibits HDAC activity. In some embodiments, the one or more HDAC antagonists are independently selected from the group consisting of panobinostat (Farydak®, Novartis), Zolinza® (vorinostat, Merck), Istodax® (Romidepsin, Celgene Corporation), Abexinostat (Pharmacyclics), Quisinostat (Janssen Pharmaceuticals) and Beleodaq® (belinostat; TopoTarget)

In certain embodiments, the antibody conjugates provided herein are administered in combination with anti-angiogenic agents. In some embodiments, the one or more inhibitors of angiogenesis comprise a small molecule that inhibits tumor angiogenesis. In some embodiments, the one or more inhibitors of angiogenesis comprise an antibody that inhibits tumor angiogenesis. In some embodiments, the one or more inhibitors of angiogenesis comprise recombinant protein that inhibits tumor angiogenesis. In some embodiments, the one or more inhibitors of angiogenesis are independently selected from the group consisting of such as Avastin® (bevacizumab) (Roche), Zaltrap® (Aflibercept) (Regeneron), and VOTRIENT® (Pazopanib) (Novartis).

In certain embodiments, the antibody conjugates provided herein are administered in combination with inhibitors of enzyme poly ADP ribose polymerase (PARP). In some embodiments, the one or more PARP inhibitors of comprise a small molecule that inhibits tumor PARP. In some embodiments, the one or more PARP inhibitors are independently selected from the group consisting of such as Zejula® (niraparib) (Glaxo Smith Kine), Lynparza® (olaparib) (AstraZeneca), Rubraca® (rucaparib) (Clovis Oncology), veliparib (Abbvie), and Talzenna® (talazoparib) (Pfizer).

In some embodiments, the iADCs described herein are administered in combination with radiotherapy and/or photodynamic therapy (PDT).

12. Therapeutic Applications

For therapeutic applications, the antibody conjugates of the invention are administered to a mammal, generally a human, in a pharmaceutically acceptable dosage form such as those known in the art and those discussed above. For example, the antibody conjugates of the invention may be administered to a human intravenously as a bolus or by continuous infusion over a period of time, by intramuscular, intraperitoneal, intra-cerebrospinal, subcutaneous, intra-articular, intrasynovial, intrathecal, or intratumoral routes. The antibody conjugates also are suitably administered by peritumoral, intralesional, or perilesional routes, to exert local as well as systemic therapeutic effects. The intraperitoneal route may be particularly useful, for example, in the treatment of ovarian tumors.

The antibody conjugates provided herein may be useful for the treatment of any disease or condition described herein (e.g., inflammatory and/or proliferative disease or condition). In some embodiments, the disease or condition is a disease or condition that can be diagnosed by overexpression of an antigen. In some embodiments, the disease or condition is a disease or condition that can benefit from treatment with an antibody. In some embodiments, the disease or condition is a cancer.

Any suitable cancer may be treated with the antibody conjugates provided herein. Illustrative suitable cancers include, for example, acute lymphoblastic leukemia (ALL), acute myeloid leukemia (AML), adrenocortical carcinoma, anal cancer, appendix cancer, astrocytoma, basal cell carcinoma, brain tumor, bile duct cancer, bladder cancer, bone cancer, breast cancer, bronchial tumor, carcinoma of unknown primary origin, cardiac tumor, cervical cancer, chordoma, colon cancer, colorectal cancer, craniopharyngioma, ductal carcinoma, embryonal tumor, endometrial cancer, ependymoma, esophageal cancer, esthesioneuroblastoma, fibrous histiocytoma, Ewing sarcoma, eye cancer, germ cell tumor, gallbladder cancer, gastric cancer, gastrointestinal carcinoid tumor, gastrointestinal stromal tumor, gestational trophoblastic disease, glioma, head and neck cancer, hepatocellular cancer, histiocytosis, Hodgkin lymphoma, hypopharyngeal cancer, intraocular melanoma, islet cell tumor, Kaposi sarcoma, kidney cancer, Langerhans cell histiocytosis, laryngeal cancer, lip and oral cavity cancer, liver cancer, lobular carcinoma in situ, lung cancer, macroglobulinemia, malignant fibrous histiocytoma, melanoma, Merkel cell carcinoma, mesothelioma, metastatic squamous neck cancer with occult primary, midline tract carcinoma involving NUT gene, mouth cancer, multiple endocrine neoplasia syndrome, multiple myeloma, mycosis fungoides, myelodysplastic syndrome, myelodysplastic/myeloproliferative neoplasm, nasal cavity and par nasal sinus cancer, nasopharyngeal cancer, neuroblastoma, non-small cell lung cancer, oropharyngeal cancer, osteosarcoma, ovarian cancer, pancreatic cancer, papillomatosis, paraganglioma, parathyroid cancer, penile cancer, pharyngeal cancer, pheochromocytomas, pituitary tumor, pleuropulmonary blastoma, primary central nervous system lymphoma, prostate cancer, rectal cancer, renal cell cancer, renal pelvis and ureter cancer, retinoblastoma, rhabdoid tumor, salivary gland cancer, Sezary syndrome, skin cancer, small cell lung cancer, small intestine cancer, soft tissue sarcoma, spinal cord tumor, stomach cancer, T-cell lymphoma, teratoid tumor, testicular cancer, throat cancer, thymoma and thymic carcinoma, thyroid cancer, urethral cancer, uterine cancer, vaginal cancer, vulvar cancer, and Wilms tumor.

In some embodiments, the disease to be treated with the antibody conjugates provided herein is gastric cancer, colorectal cancer, renal cell carcinoma, cervical cancer, non-small cell lung carcinoma, ovarian cancer, uterine cancer, endometrial carcinoma, prostate cancer, breast cancer, head and neck cancer, brain carcinoma, liver cancer, pancreatic cancer, mesothelioma, and/or a cancer of epithelial origin. In particular embodiments, the disease is colorectal cancer. In some embodiments, the disease is ovarian cancer. In some embodiments, the disease is breast cancer. In some embodiments, the disease is lung cancer. In some embodiments, the disease is head and neck cancer. In some embodiments, the disease is renal cell carcinoma. In some embodiments, the disease is brain carcinoma. In some embodiments, the disease is endometrial carcinoma. In particular embodiments, the disease is non-hodgkins lymphoma, pancreatic cancer, multiple myeloma, colorectal cancer, renal and mammary carcinomas, skin cancer and/or cervical intraepithelial neoplasia.

In certain embodiments, provided herein are methods for the treatment of cancer that includes the administration of an effective amount of antibody conjugates provided herein, or a pharmaceutically acceptable salt thereof. In certain embodiments, provided herein are methods for treating cancer in a subject. In certain embodiments, the methods encompass the step of administering to the subject in need thereof an amount of an antibody conjugate described herein effective for the treatment of cancer in combination with a second agent effective for the treatment or prevention of the infection. In certain embodiments, the antibody conjugate is in the form of a pharmaceutical composition or dosage form, as described elsewhere herein.

In certain embodiments, the subject is a treatment naïve subject. In further embodiments, the subject has previously received therapy for a cancer. For instance, in certain embodiments, the subject has not responded to a single agent treatment regimen.

In certain embodiments, the subject is a subject that discontinued some other therapy because of one or more adverse events associated with the therapy.

In certain embodiments, the subject has received some other anti-cancer therapy and discontinued that therapy prior to administration of a method provided herein. In further embodiments, the subject has received therapy and continues to receive that therapy along with administration of an antibody conjugate provided herein. The antibody conjugates described herein can be co-administered with other therapy for treatment of cancer according to the judgment of one of skill in the art. In certain embodiments, the methods or compositions provided herein can be co-administered with a reduced dose of the other therapy for the treatment of cancer.

In certain embodiments, provided are methods of treating a subject that is refractory to treatment with some other anti-cancer agent. In some embodiments, the subject can be a subject that has responded poorly to some other anti-cancer treatment.

16 Diagnostic Applications

In some embodiments, the antibody conjugates provided herein are used in diagnostic applications. These assays may be useful, for example, in making a diagnosis and/or prognosis for a disease, such as a cancer.

In some diagnostic and prognostic applications, the antibody conjugate may be labeled with a detectable moiety. Suitable detectable moieties include, but are not limited to radioisotopes, fluorescent labels, and enzyme-substrate labels. In another embodiment, the antibody conjugate need not be labeled, and the presence of the antibody conjugate can be detected using a labeled antibody which specifically binds to the antibody conjugate.

13. Affinity Purification Reagents

The antibody conjugates provided herein may be used as affinity purification agents. In this process, the antibody conjugates may be immobilized on a solid phase such a resin or filter paper, using methods well known in the art. The immobilized antibody conjugate is contacted with a sample containing the antigen (or fragment thereof) to be purified, and thereafter the support is washed with a suitable solvent that will remove substantially all the material in the sample except the protein of interest, which is bound to the immobilized antibody. Finally, the support is washed with another suitable solvent, such as glycine buffer, pH 5.0 that will release the protein from the antibody.

14. Kits

In some embodiments, an antibody conjugate provided herein is provided in the form of a kit, i.e., a packaged combination of reagents in predetermined amounts with instructions for performing a procedure. In some embodiments, the procedure is a diagnostic assay. In other embodiments, the procedure is a therapeutic procedure.

In some embodiments, the kit further comprises a solvent for the reconstitution of the antibody conjugate. In some embodiments, the antibody conjugate is provided in the form of a pharmaceutical composition.

In some embodiments, the kits can include an antibody conjugate or composition provided herein, an optional second agent or composition, and instructions providing information to a health care provider regarding usage for treating the disorder. Instructions may be provided in printed form or in the form of an electronic medium such as a floppy disc, CD, or DVD, or in the form of a website address where such instructions may be obtained. A unit dose of an antibody conjugate or a composition provided herein, or a second agent or composition, can include a dosage such that when administered to a subject, a therapeutically or prophylactically effective plasma level of the compound or composition can be maintained in the subject for at least 1 days. In some embodiments, a compound or composition can be included as a sterile aqueous pharmaceutical composition or dry powder (e.g., lyophilized) composition.

In some embodiments, suitable packaging is provided. As used herein, "packaging" includes a solid matrix or material customarily used in a system and capable of holding within fixed limits a compound provided herein and/or a second agent suitable for administration to a subject. Such materials include glass and plastic (e.g., polyethylene, polypropylene, and polycarbonate) bottles, vials, paper, plastic, and plastic-foil laminated envelopes and the like. If e-beam sterilization techniques are employed, the packaging should have sufficiently low density to permit sterilization of the contents.

Sequences for certain antibodies described herein and in the Examples section are provided below.

| Antibody | Heavy Chain (HC) | Light Chain (LC) |
|---|---|---|
| aFolR1 H01 Y180/F404pAMF | 1848-H01 Y180F404TAG SEQ ID NO: 1 | Trastuzumab LC SEQ ID NO: 2 |
| aFolR1 B10 Y180/F404pAMF | 1848-B10 Y180F404TAG SEQ ID NO: 8 | Trastuzumab LC SEQ ID NO: 2 |

| Antibody | Heavy Chain (HC) | Light Chain (LC) |
|---|---|---|
| aHer2 trastuzumab Y180F404pAMF | Trastuzumab-HC Y180/F404 SEQ ID NO: 3 | Trastuzumab LC SEQ ID NO: 2 |
| aMUC16 sofituzumab Y180F404pAMF | aMUC16-sofituzumab_HC-Y180/F404TAG SEQ ID NO: 4 | aMUC16-sofituzumab_LC SEQ ID NO: 5 |
| aFolR1 B10 Y180pAMF Q295A LC Qtag1 | 1848-B10_Y180TAG_Q295A SEQ ID NO: 6 | trastuzumab-LC-Qtag1 SEQ ID NO: 7 |
| aFolR1-B10 F404TAG Q295A LC Qtag1 | 1848-B10_F404TAG_Q295A SEQ ID NO: 9 | trastuzumab-LC-Qtag1 SEQ ID NO: 7 |

*indicates incorporation of para-azidomethylphenylalanine (pAMF)

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: aq (aqueous); atm (atmospheres); DIBAL (diisobutylaluminium hydride); DIPEA (diisopropylethylamine); kg (kilograms); g (grams); mg (milligrams); mL (milliliters); µL (microliters); mM (millimolar); M (micromolar); Hz (Hertz); MHz (megahertz); mmol (millimoles); h, hr or hrs (hours); min (minutes); MTBE (methyl tert-butyl ether); MS (mass spectrometry); eq (equivalents); NMP (N-methylpyridine); ESI (electrospray ionization); RB (round-bottom); rt (room temperature); TLC (thin layer chromatography); HPLC (high pressure liquid chromatography); LAH (lithium aluminum hydride); LCMS (Liquid chromatography-Mass spectrometry); THF (tetrahydrofuran); CDCl$_3$ (deuterated chloroform); AcOH (acetic acid); DBCO (dibenzocyclooctyne-amine); DCM (dichloromethane); DMSO (dimethylsulfoxide); DMSO-d$_6$ (deuterated dimethylsulfoxide); EtOAc (ethyl acetate); MeOH (methanol); and BOC (t-butyloxycarbonyl).

For all of the following examples, standard work-up and purification methods known to those skilled in the art can be utilized. Unless otherwise indicated, all temperatures are expressed in ° C. (degrees Centigrade). All reactions are conducted at room temperature unless otherwise noted. Synthetic methodologies illustrated herein are intended to exemplify the applicable chemistry through the use of specific examples and are not indicative of the scope of the disclosure.

As used herein, the symbols and conventions used in these processes, schemes and examples, regardless of whether a particular abbreviation is specifically defined, are consistent with those used in the contemporary scientific literature, for example, the Journal of Biological Chemistry and/or the Journal of the American Chemical Society.

For all of the following examples, standard work-up and purification methods known to those skilled in the art can be utilized. Unless otherwise indicated, all temperatures are expressed in ° C. (degrees Celsius). All methods are conducted at room temperature ("rt" or "r.t." or "RT"), unless otherwise noted. FOLR1, as used herein, is also known as FolRa, or FolRa.

Those of skill in the art will recognize that in the examples below, linker-precursors are conjugated to antibodies, and the free compounds are the releasable payloads. For instance, Compound 101 is conjugated to an antibody to form an antibody conjugate, but in certain assays the antibody conjugate may be compared with the free compound, i.e., Compound 1.

Example 1

Synthesis of a Linker Precursor (Compound 101) Comprising a Hemiasterlin Step 1

Compound 1

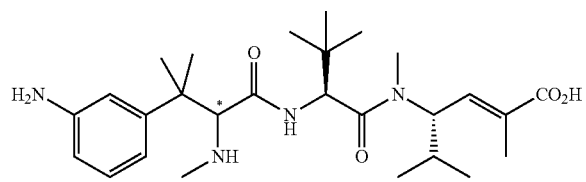

Step 1: Synthesis of Compound 1 (Two Diastereomers)

Scheme 1

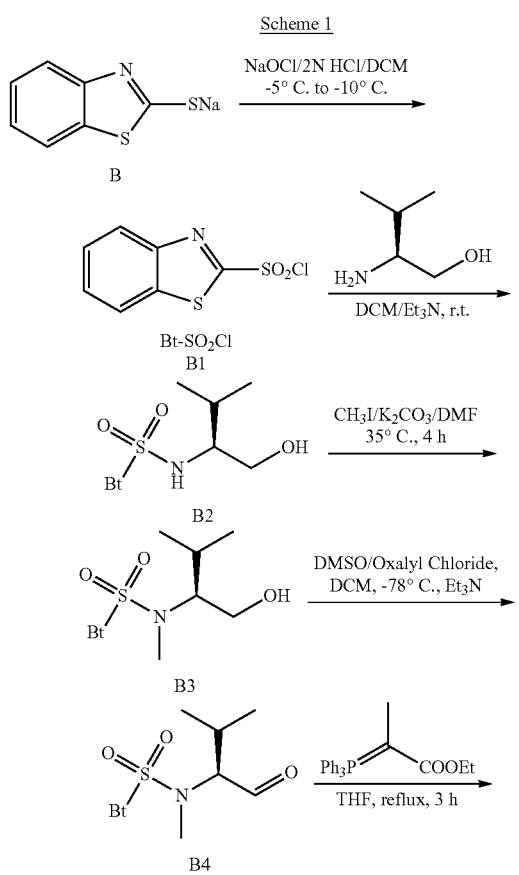

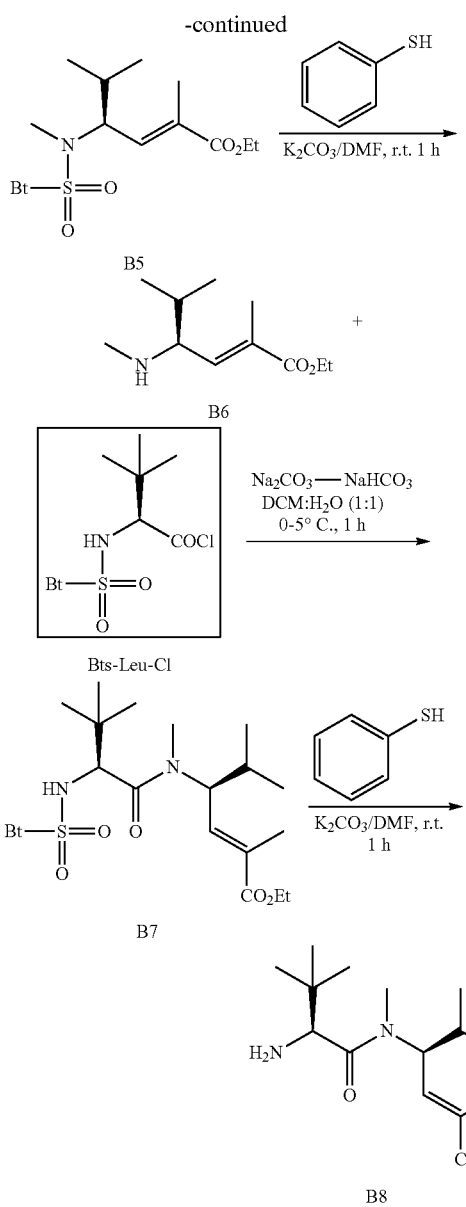

Preparation of Compound B2

To a mixed solvent of dichloromethane (100 mL) and 2N HCl (78 mL, 156 mmol) at −5° C. was added cold bleach (contain 6% NaOCl, 108 mL, 87 mmol) in portions. The mixture was stirred at 0° C. (inside temperature) for 5 min. Sodium 2-mercaptobezothioazole (B, 5 g, 26 mmol) was then added into the mixture in multi-portions. The mixture stirred at −5 to −10° C. for 20 min. The organic layer (B1, major is BtsCl) was collected and mixed with L-valinol (3.2 g, 31.2 mmol) and triethyl amine (8.7 mL, 121 mmol) in dichloromethane at r.t. The mixture allowed stirring at r.t. for 1h. Solvent was removed and product was purified by silica gel column (Hexanes: Ethyl acetate=1:1) to give product B2 (3.1 g, 40%, two steps) as white solid.

LC-MS (ESI): 301 (M+1).

$^1$H NMR (300 MHz, CDCl$_3$) δ 8.08 (dd, J=2.1 and 7.2 Hz, 1H), 7.96 (dd, J=1.8 and 6.9 Hz, 1H), 7.58 (m, 2H), 5.46 (br s, 1H), 3.67 (d, J=4.5 Hz, 2H), 3.54 (br s, 1H), 3.23 (brs, 1H), 1.93 (m, 1H), 0.97 (d, J=6.9 Hz, 6H).

Preparation of Compound B3

To a solution of B2 (3 g, 10 mmol, 1.0 eq) in dimethylformamide (50 mL) was added potassium carbonate (2.77 g, 20 mmol, 2.0 eq) and iodomethane (1.25 mL, 20 mmol, 2.0 eq) at rt. The mixture was heated to 35° C., 4h. The solvent was removed and the residue was worked up with ethyl acetate and water (3×), dried with Na$_2$SO$_4$ and concentrated to give product B3 (3.14 g, 100%) as white solid.

LC-MS (ESI): 315 (M+1).

$^1$H NMR (300 MHz, CDCl$_3$) δ 8.09 (dd, J=1.6 and 7.5 Hz, 1H), 7.95 (dd, J=1.8 and 6.9 Hz, 1H), 7.58 (m, 2H), 4.25 (br s, 1H), 2.90 (s, 3H), 1.93 (m, 1H), 1.02 (dd, J=2.1 and 6.6 Hz, 6H).

Preparation of Compound B4

To a mixed solvent of dichloromethane (50 mL) and DMSO (1.56 mL, 22 mmol, 2.2 eq) at −78° C. was added oxalyl chloride (1.05 mL, 12 mmol, 1.2 eq) slowly under nitrogen and stirred at this temperature for 30 min. B3 (3.14 g, 10 mmol, 1.0 eq) in 20 mL of dichloromethane was then added into this reaction mixture at −78° C. under nitrogen. The reaction mixture allowed stirring at −78° C. for 2h. Triethylamine (7 mL, 50 mmol, 5 eq) was then added into the reaction and stirred at −78° C. for 30 min. and continued to warm up to 0° C. for another 30 min. The reaction mixture was poured into an ice-water and extracted with DCM (3 x). The organic layer was washed with half saturated ammonium chloride (2×) solution, brine and dried with sodium sulfate. It was concentrated at low temperature (below 30° C.) to give product B4 (3.0 g, 96%) as white solid.

$^1$H NMR (300 MHz, CDCl$_3$) δ 9.69 (s, 1H), 8.17 (dd, J=1.5 and 8.1 Hz, 1H), 7.95 (dd, J=2.1 and 6.9 Hz, 1H), 7.58 (m, 2H), 4.30 (d, J=10.2 Hz, 1H), 3.01 (s, 3H), 2.21 (m, 1H), 1.15 (d, J=6.6 Hz, 3H), 0.98 (d, J=6.6 Hz, 3H).

Preparation of Compound B5

Product B4 (3 g, 9.58 mmol, 1.0 eq) and [(1-ethoxycarbonyl)ethylidene]Ph$_3$P (6.95 g, 19.2 mmol, 2 eq) were dissolved in anhydrous tetrahydrofuran (60 mL) and was heated to reflux, 3h. The reaction was cooled to r.t. and poured into ice water. Product was extracted with ethyl acetate (3×). The organic layer was washed with brine, dried with sodium sulfate and then concentrated to give crude product. It was further purified by silica gel column (Hexanes: Ethyl acetate=8:2) to give product B5 (2.9 g, 82%).

$^1$H NMR (300 MHz, CDCl$_3$) δ 8.09 (dd, J=1.2 and 7.2 Hz, 1H), 7.93 (dd, J=1.8 and 8.1 Hz, 1H), 7.53 (m, 2H), 6.39 (dd, J=1.6 and 10.5 Hz, 1H), 4.41 (t, J=10.5 Hz, 1H), 3.87 (q, J=7.2 Hz, 2H), 3.08 (s, 3H), 1.85 (s, 3H), 1.02-1.08 (m, 6H), 0.83 (d, J=6.9 Hz, 3H).

Preparation of Compound B6

To a solution of product B5 (2.9 g, 7.31 mmol, 1.0 eq) in dimethylformamide (30 mL) was added potassium carbonate (4.04 g, 29.2 mmol, 4.0 eq) and thiophenol (2.25 mL, 21.9 mmol, 3.0 eq). The reaction stirred at r.t. for 1 h. It was then worked up with diethyl ether and water (3×). The ether layer was extracted with 1% HCl, the aqueous was washed with ether. The aqueous layer was neutralized with sodium bicarbonate to pH 8 and extracted with dichloromethane (3×). The organic layer was dried with sodium sulfate and concentrated to give pure product B6 (1.2 g, 84%) as yellow oil.

LC-MS (ESI): 200 (M+1).

$^1$H NMR (300 MHz, CDCl$_3$) δ 6.48 (dd, J=1.2 and 10.2 Hz, 1H), 4.18 (q, J=7.2 Hz, 1H), 3.06 (q, J=6.3 Hz, 2H), 2.30 (s, 3H), 1.86 (d, J=1.8 Hz, 2H), 1.72 (m, 1H), 1.28 (t, J=7.2 Hz, 3H), 0.93 (d, J=6.9 Hz, 3H), 0.87 (d, J=6.9 Hz, 3H).

Preparation of Compounds Bts-Leu-Cl and B7

This synthesis is fully described in Vedejs and Kongkittingam, "A Total Synthesis of (−)-Hemiasterlin Using N-Bts Methodology," *J. Org. Chem.* 2001, 66(22), 7355-7364. A summary is provided below.

To a solution of Bts-Leu (2.4 g, 7.3 mmol, 1.0 eq) in anhydrous dichloromethane (30 mL) at 0° C. was added thionyl chloride (1.6 mL, 21.9 mmol, 3.0 eq) under nitrogen. The reaction mixture was refluxed at 42° C. for 2h. It was concentrated and co-evaporated with toluene to give Bt-Leu-Cl as a crude solid and was used in the next step reaction without further purification.

To a solution of product B6 (1.2 g, 6.02 mmol) in a mixed solvent of dichloromethane and water (1:1, 40 mL) at 0° C. was added a solution of sodium carbonate (1.28 g, 12.04 mmol, 2.0 eq) and sodium bicarbonate (1.32 g, 15.7 mmol. 3.2 eq) under nitrogen. The fresh made Bts-Leu-Cl (from above) in dichloromethane (10 mL) was added into this reaction with syringe. The mixture stirred at 0-5° C. for 1 h. Product B7 was extracted with dichloromethane and water (3×), dried with sodium sulfate and concentrated to give crude product B7, which was purified by silica gel column (Hexanes: ethyl acetate=1:1) to give product B7 (1.8 g, 59%) as white solid. LC-MS (ESI): 510 (M+1).

$^1$H NMR (300 MHz, CDCl$_3$) δ 8.11 (dd, J=1.5 Hz, 8.7 Hz, 1H), 7.93 (dd, J=1.2 Hz, 8.7 Hz, 1H), 7.58 (m, 2H), 6.52 (dd, J=1.2 Hz, 9.9 Hz, 1H), 6.10 (d, J=8.7 Hz, 1H), 4.85 (t, J=10.2 Hz, 1H), 4.47 (d, J=8.7 Hz, 1H), 4.16 (m, 2H), 2.94 (s, 3H), 1.82 (d, J=1.2 Hz, 2H), 1.27 (m, 3H), 0.98 (s, 6H), 0.63 (d, J=6.6 Hz, 3H),−0.12 (d, J=6.6 Hz, 3H).

Preparation of Compound B8

To a solution of B7 (200 mg, 0.392 mmol, 1.0 eq) in DMF (2 mL) was added potassium carbonate (217 mg, 1.57 mmol, 4.0 eq) and thiophenol (121 μL, 1.18 mmol, 3.0 eq) under nitrogen at r.t. The reaction mixture was stirred at rt. for 4h and LC-MS showed the reaction completed. The reaction was worked up with water and ether and 10% hydrochloric acid (as the literature described) and pure B8 (100 mg, 82%) obtained. LC-MS (ESI): 313 (M+1). $^1$H NMR (300 MHz, CDCl$_3$) δ 7.99 (s, 1H), 6.63 (dd, J=1.2 Hz, 9.9 Hz, 1H), 5.15 (t, J=9.9 Hz, 1H), 4.19 (m, 2H), 3.45 (s, 1H), 2.86-2.94 (m, 6H), 1.89 (m, 3H), 1.70 (s, bro, 2H), 1.28 (t, J=5.7 Hz, 3H),−0.86-1.01 (m, 12H).

Scheme 2

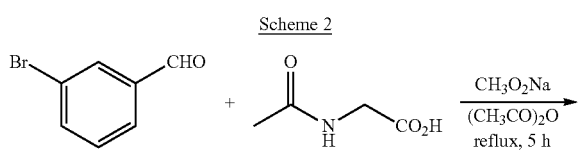

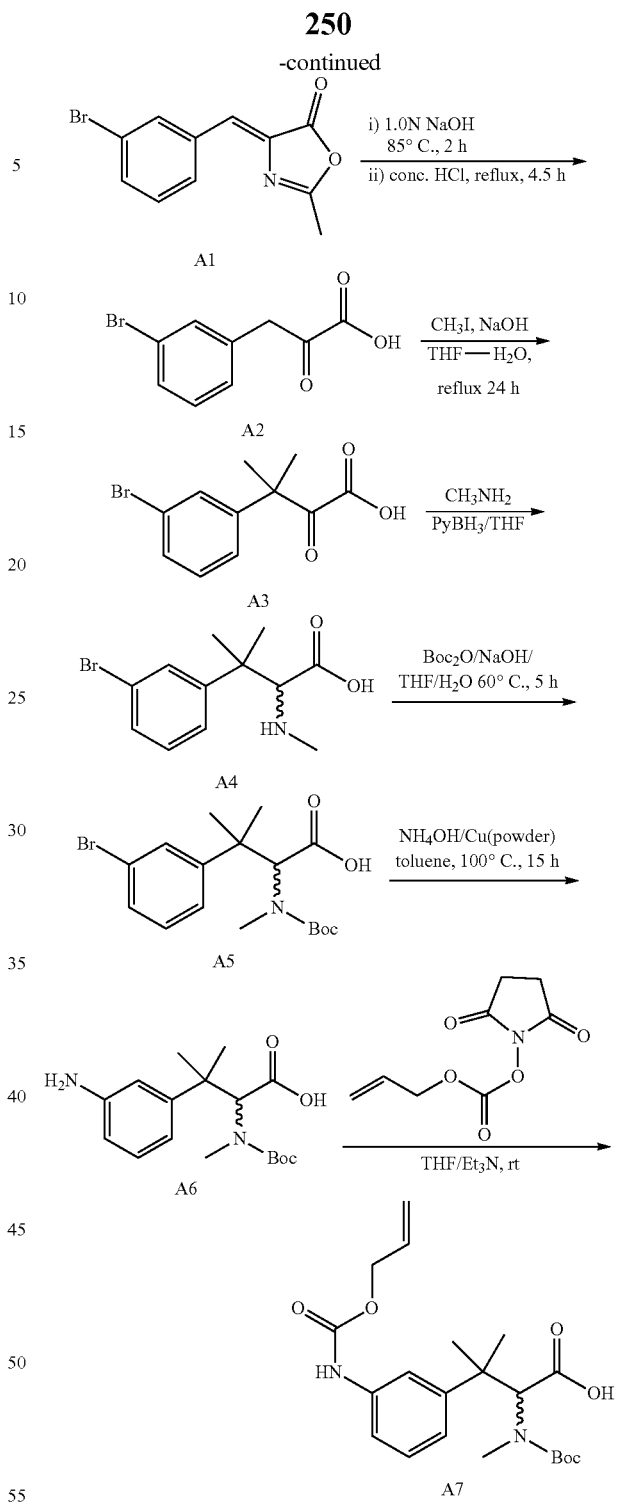

Preparation of Compound A1

A mixture of 3-bromobenzaldehyde (25.0 g, 135 mmol, 1.0 eq), N-acetyl glycine (15.8 g, 135 mmol, 1.0 eq) and sodium acetate (10.6 g, 135 mmol, 1.0 eq) were suspended in acetic anhydride (40 mL) and heated with stirring to reflux under N$_2$ for 5 hr. The resulting solution solidified upon cooling to room temperature and was quenched with ice-cold water and filtered. The solids were washed twice more with water, air dried for 4 h, then further dried in vacuo to give compound A1 (31 g, 86%).

Preparation of Compound A2

Oxazolone A1 (31 g, 117 mmol, 1.0 eq) in 1.0 N NaOH (175 mL, 175 mmol, 1.5 eq) was stirred at 85° C. until a translucent reddish solution was obtained. The reaction was cooled down to room temperature and acidified to pH 1.0 with 5 N HCl to precipitate a brown solid. Concentrated HCl (30 mL) was added to the flask, and the reaction solution diluted to about 500 mL. A reflux was maintained for another 5 hr. The solids were collected by filtration and washed with water twice, and dried under high vacuum to deliver the crude material A2 (23 g, 81%) which was used without further purification.

Preparation of Compound A3

Pyruvic acid A2 (23 g, 94.7 mmol, 1.0 eq) was dissolved in THF (100 mL) and cooled to 0° C. Methyl iodide (36 g, 256 mmol, 2.7 eq) followed by 5 N NaOH (80 mL) were slowly added, and the reaction brought to reflux overnight. The volatiles were stripped off and the residual aqueous solution was extracted with ethyl acetate, and acidified with 10% HCl at 0° C. to pH 1. The resulting aqueous layer was extracted with ethyl acetate (2×). The combined organics were washed with brine, dried over sodium sulfate, and purified by column chromatography (EtOAc/hexanes 1:1) to yield pure compound A3 (11 g, 43%).

Preparation of Compound A4

A 2 N solution of methylamine (14.4 mL, 28.8 mmol, 2.0 eq) was added into a solution of the keto-acid A3 (11 g, 40.6 mmol, 1.0 eq) in THF (100 mL) at room temperature and stirred for 4 hr. An 8 N solution of pyridine-borane complex (5 mL, 40.6 mmol, 1.0 eq) was added, and the mixture heated to 55° C. for 3 hr. The reaction was quenched with methanol, concentrated, and diluted with THF (50 mL) to form a white precipitate. The white solid precipitate was filtered and dried on vacuum to give compound A4 (5 g, 61%).

Preparation of Compound A5

To a solution of compound A4 (1.0 g, 3.5 mmol, 1.0 eq) and (Boc)₂O (1.15 g, 5.24 mmol, 1.5 eq) in THF and water (1:1, 20 mL) was added sodium hydroxide (280 mg, 6.99 mmol, 2.0 eq). The mixture was heated at 60° C. for 5h. The reaction mixture was cooled and concentrated. The residual aqueous solution was acidified with 10% HCl at 0° C. to pH 1, and extracted with ethyl acetate (3×). The combined organic layers were dried over sodium sulfate, and purified with flash column chromatography to give compound A5 (420 mg, 31%).

Preparation of Compound A6

To compound A5 (1.58 g, 4.07 mmol, 1 eq) in toluene (15 mL) in a sealed tube was added ammonium hydroxide (2.7 mL, 40.7 mmol, 10 eq) and copper powder (39 mg, 0.61 mmol, 0.15 eq). The tube was heated to 100° C. overnight and concentrated to give a residue, which was diluted with aqueous NaHCO₃ and n-butanol. The aqueous layer was extracted with n-butanol. The organic layers were concentrated, and purified by silica gel column (DCM: MeOH: Et3N= 9:1:1) to give compound A6 (680 mg, 52%).

Preparation of Compound A7

To a solution of compound A6 (1.42 g, 3.36 mmol, 1 eq) in THF (10 mL) was added Alloc-OSu (1.34 g, 6.72 mmol, 2 eq) and triethylamine (1.4 mL, 10.1 mmol, 3 eq). The mixture was stirred at rt overnight. The solvent was removed and the residue was purified by flash column chromatography (DCM: MeOH=9:1) to give compound A7 (1.01 g, 74%).

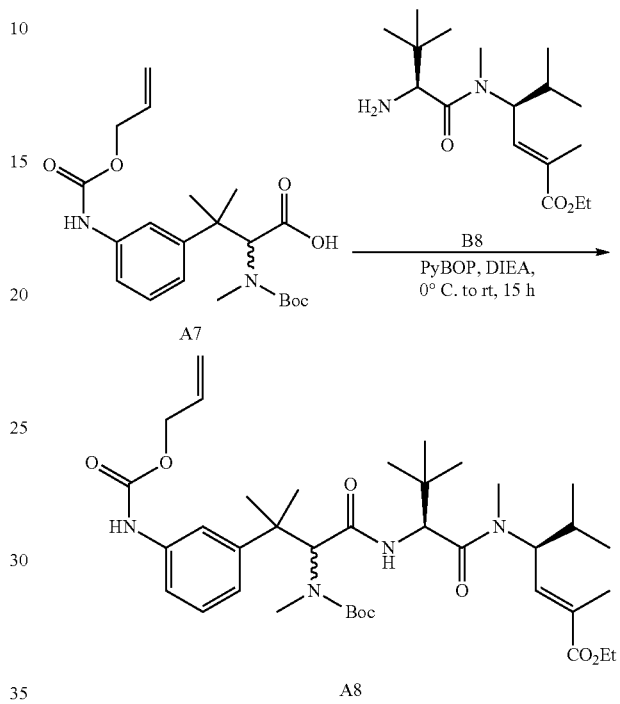

Scheme 3

Preparation of Compound A8

To a solution of compound A7 (41 mg, 0.1 mmol, 1eq) in dry DCM (1.5 mL) was added B8 (31 mg, 0.1 mmol, 1 eq) and PyBOP (57.2 mg, 0.11 mmol, 1.1 eq). The mixture was cooled down to 0° C., and DIEA (49 μL, 0.3 mmol, 3 eq) was added. The reaction was stirred at rt overnight, and diluted with DCM and washed with water. The aqueous was further extracted with DCM (2×). The organic layers were combined, and dried over sodium sulfate, concentrated to dryness to give a crude product. It was purified by pre-HPLC to give A8 (10 mg, 14%) as a mixture of two diastereoisomers (60:40).

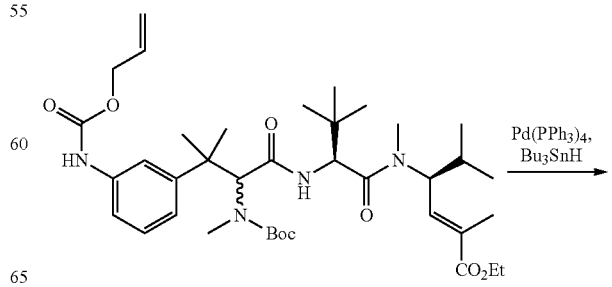

Scheme 4

Preparation of Compound A9

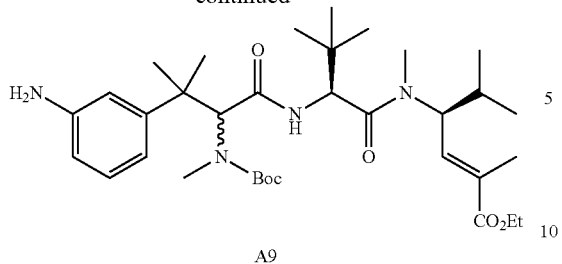

A9

To a solution of compound A8 (150 mg, 0.21 mmol, 1.0 eq) and Pd(PPh₃)₄ (12.4 mg, 0.011 mmol, 0.05 eq) in THF (10 mL) was added tri-n-butyl-tin hydride (113 μL, 0.43 mmol, 2.0 eq). The mixture was degassed and backfilled with nitrogen (3×). The reaction was stirred at rt for 6h. The solvent was removed, and the crude product was purified by silica gel column (DCM: MeOH=9:1) to give A9 (78 mg, 60%) as a mixture of two isomers.

Scheme 5

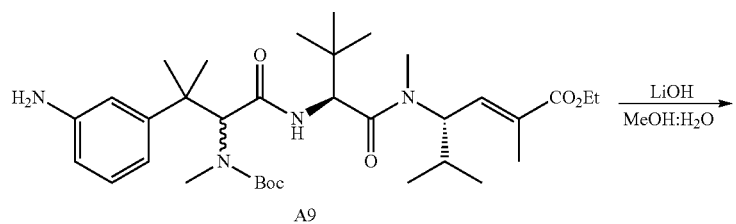

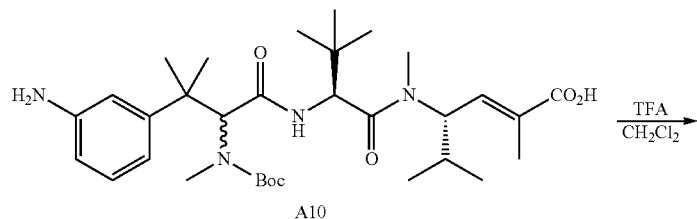

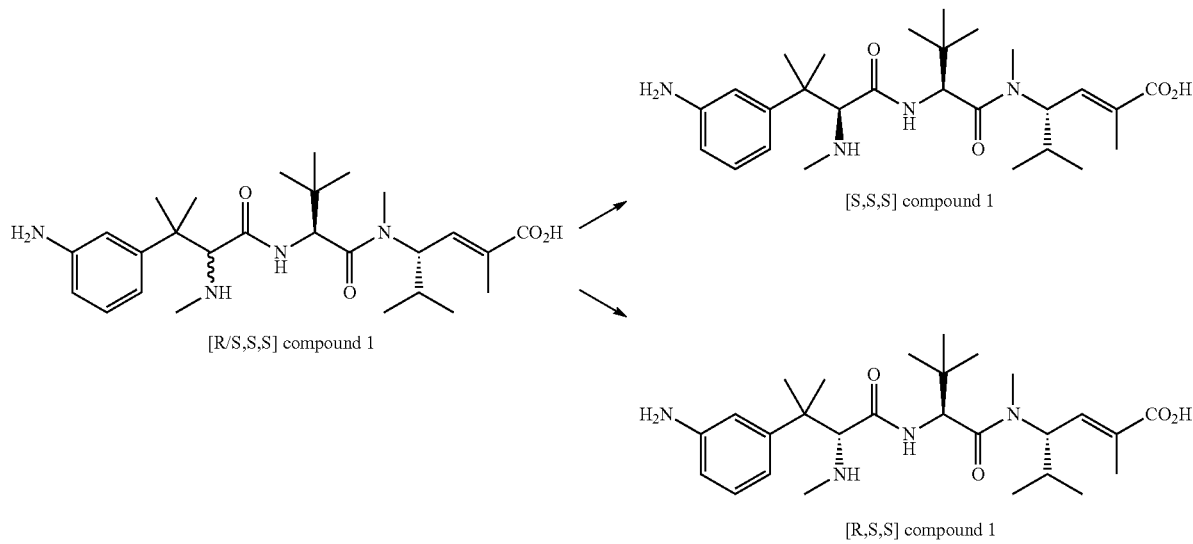

To a solution of compound A9 (28 mg, 0.046 mmol, 1 eq) in MeOH (1 mL) was added LiOH (10 mg, 0.23 mmol, 5 eq) in water (0.5 mL). The mixture was stirred at rt overnight. The product was purified by prep-HPLC to give A12 (23 mg, 85%).

To a solution of A12 (11 mg, 0.0187 mmol, 1 eq) in DCM (1 mL) was added 10% TFA in DCM (1 mL). The mixture stirred at rt for 4h. Solvent was removed and the crude product 1 was purified by preparative RP-HPLC twice to give two isomers 1a (0.8 mg), and 1b (1 mg).

Step 2

Step 2: Synthesis of a Linker Payload Precursor Comprising Compound 1

Synthesis of Compound 101 (Two Diastereomers)

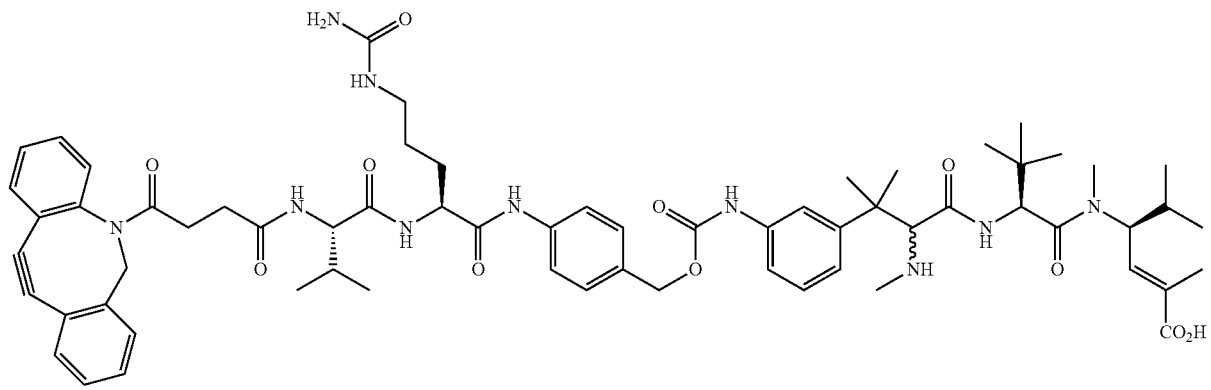

Compound 101

Linkers synthesized from the aryl amine Compound 1 give rise to cleavable Compound 101 which releases the novel aniline parent compounds as a diastereomeric pair.

Scheme 6

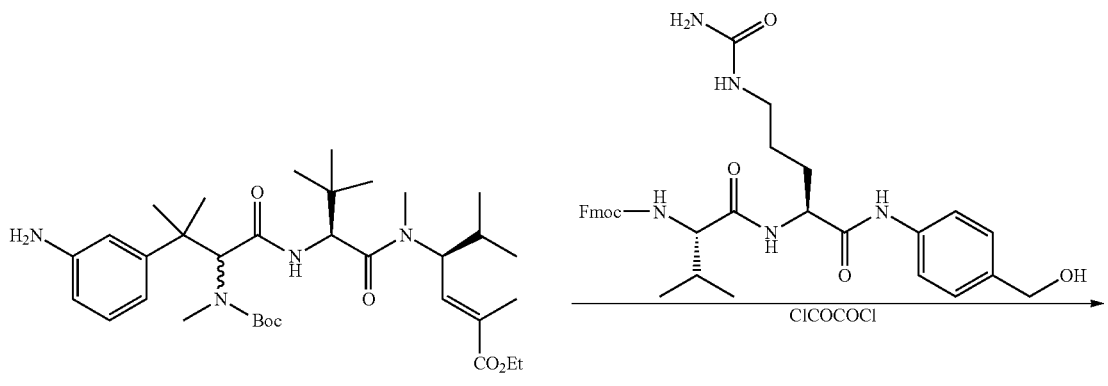

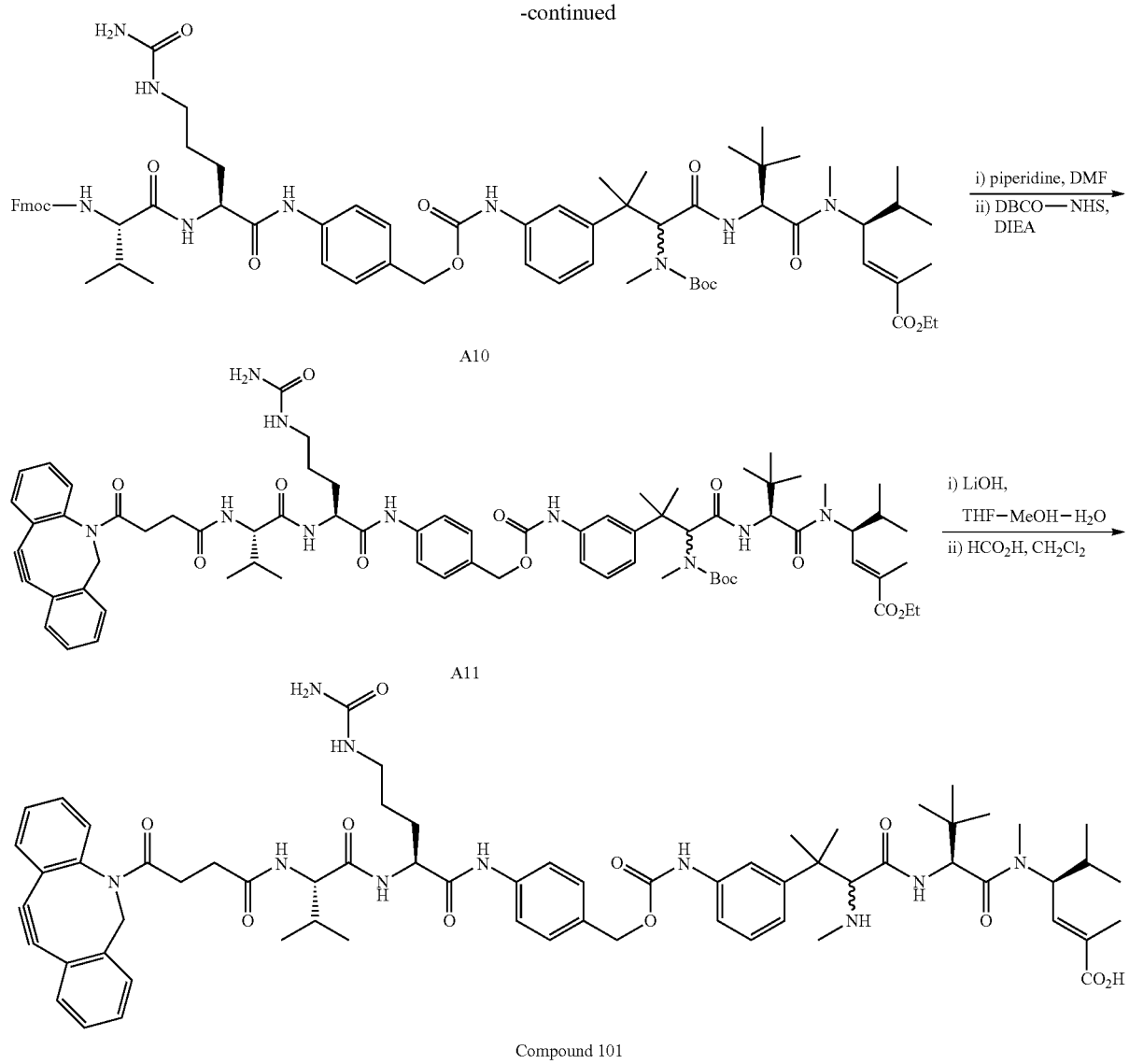

Compound 101

Preparation of Compound A10

To an argon-flushed solution of A9 (27 mg, 0.04 mmol) in 1 mL CH$_2$Cl$_2$ was added 15% w/v phosgene in toluene (0.6 mL, 0.06 mmol). The reaction mixture was heated to 50° C. in a sealed tube for 4h, cooled to ambient temperature, and the volatiles removed in vacuo. To the residue was added a vacuum-dried solution of Fmoc-valine-citruline-p-aminobenzyl alcohol (26 mg, 0.04 mmol) in 1 mL DMF. The reaction mixture was stirred at 45° C. under argon for 6 h, then at ambient temperature for 24 hr. After removal of all volatiles in vacuo the residue was purified on silica gel (90:10 CH$_2$Cl$_2$:MeOH eluent) to give 10 mg (0.008 mmol) A10 as a white solid.

Preparation of A11

To a solution of A10 in CH$_2$Cl$_2$ (1 mL) was added piperidine (0.1 mL) and the reaction mixture was stirred at ambient temperature for 1 hr. After removal of all volatiles in vacuo, to the residue was added DBCO-succinyl N-hydroxysuccinimidyl ester (3.6 mg, 0.009 mmol), DMF (1 mL), and diisopropylethylamine (0.004 mL, 0.02 mmol). The reaction mixture was stirred at ambient temperature for 24 hr. After removal of all volatiles in vacuo the residue was purified on silica gel (90:10 CH$_2$Cl$_2$:MeOH eluent) to give 7 mg (0.005 mmol) A11.

Preparation of Compound 101

Compound A11 (7 mg, 0.005 mmol) was dissolved in 3:1:1 THF:MeOH:H$_2$O (1 mL) and the solution cooled to 0° C. Solid LiOH·H$_2$O (1.7 mg, 0.4 mmol) was added and the reaction mixture stirred at ambient temperature overnight. A few microliters of glacial acetic acid were added, the volatiles removed in vacuo, and the free acid 101 was purified by reverse phase-high performance liquid chromatography (RP-HPLC) using an Ultro 120 (7 μm), 150×20 mm ID column (water-acetonitrile (10 mm NH$_4$OAc) solvent system, gradient mode from 10% ACN to 100% ACN in 50 min, 15 ml/min). LC-MS (ESI): 1282.6 (M+1), 1182.4 (M-Boc+1).

The N-protected acid of A11 (5 mg, 0.004) was dissolved in CH$_2$Cl$_2$ (1 mL) and the solution was cooled to 0° C. To this was added a 0.2 M solution of HCO$_2$H in CH$_2$Cl$_2$ (0.039 mL) and the reaction mixture allowed to stir at ambient temperature overnight. After the volatiles were removed in vacuo, the free amino acid was purified by reverse phase-high performance liquid chromatography (RP-HPLC) using Ultro 120 (7 μm), 150×20 mm ID column (water-acetonitrile (10 mm NH$_4$OAc) solvent system, gradient mode from 10% ACN to 100% ACN in 50 min, 15 ml/min) to give 3 mg (0.0025 mmol, 65%) compound 101 as white solid.

Compound 103

Step 1: Preparation of Compound 103

Compound 103 was prepared according to the scheme shown below.

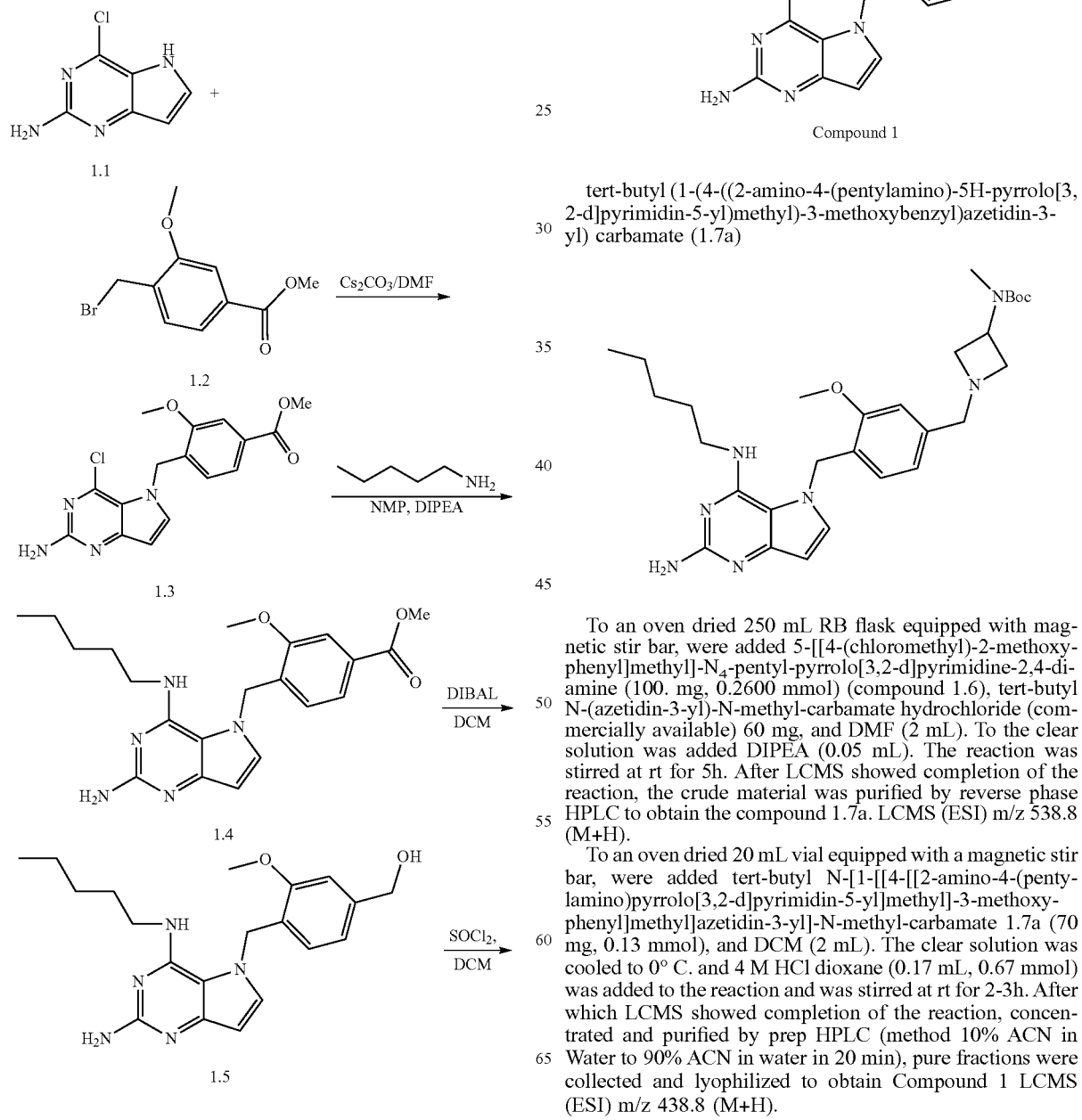

Compound 1 tert-butyl (1-(4-((2-amino-4-(pentylamino)-5H-pyrrolo[3,2-d]pyrimidin-5-yl)methyl)-3-methoxybenzyl)azetidin-3-yl) carbamate (1.7a)

To an oven dried 250 mL RB flask equipped with magnetic stir bar, were added 5-[[4-(chloromethyl)-2-methoxyphenyl]methyl]-N$_4$-pentyl-pyrrolo[3,2-d]pyrimidine-2,4-diamine (100. mg, 0.2600 mmol) (compound 1.6), tert-butyl N-(azetidin-3-yl)-N-methyl-carbamate hydrochloride (commercially available) 60 mg, and DMF (2 mL). To the clear solution was added DIPEA (0.05 mL). The reaction was stirred at rt for 5h. After LCMS showed completion of the reaction, the crude material was purified by reverse phase HPLC to obtain the compound 1.7a. LCMS (ESI) m/z 538.8 (M+H).

To an oven dried 20 mL vial equipped with a magnetic stir bar, were added tert-butyl N-[1-[[4-[[2-amino-4-(pentylamino)pyrrolo[3,2-d]pyrimidin-5-yl]methyl]-3-methoxyphenyl]methyl]azetidin-3-yl]-N-methyl-carbamate 1.7a (70 mg, 0.13 mmol), and DCM (2 mL). The clear solution was cooled to 0° C. and 4 M HCl dioxane (0.17 mL, 0.67 mmol) was added to the reaction and was stirred at rt for 2-3h. After which LCMS showed completion of the reaction, concentrated and purified by prep HPLC (method 10% ACN in Water to 90% ACN in water in 20 min), pure fractions were collected and lyophilized to obtain Compound 1 LCMS (ESI) m/z 438.8 (M+H).

Step 2
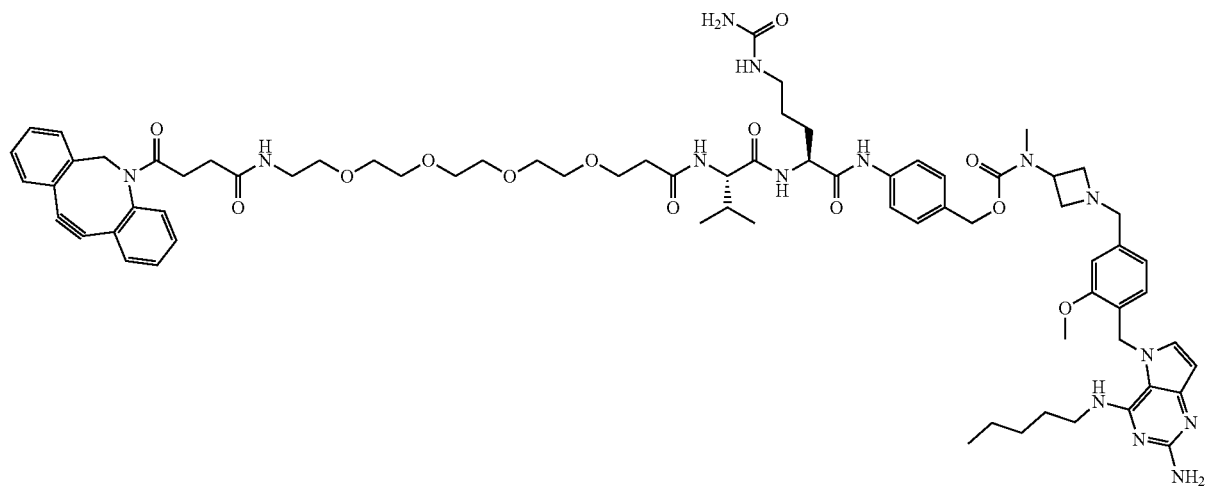
Compound 103
Step 2: Preparation of Compound 103
Compound 103 was prepared according to the Scheme below.
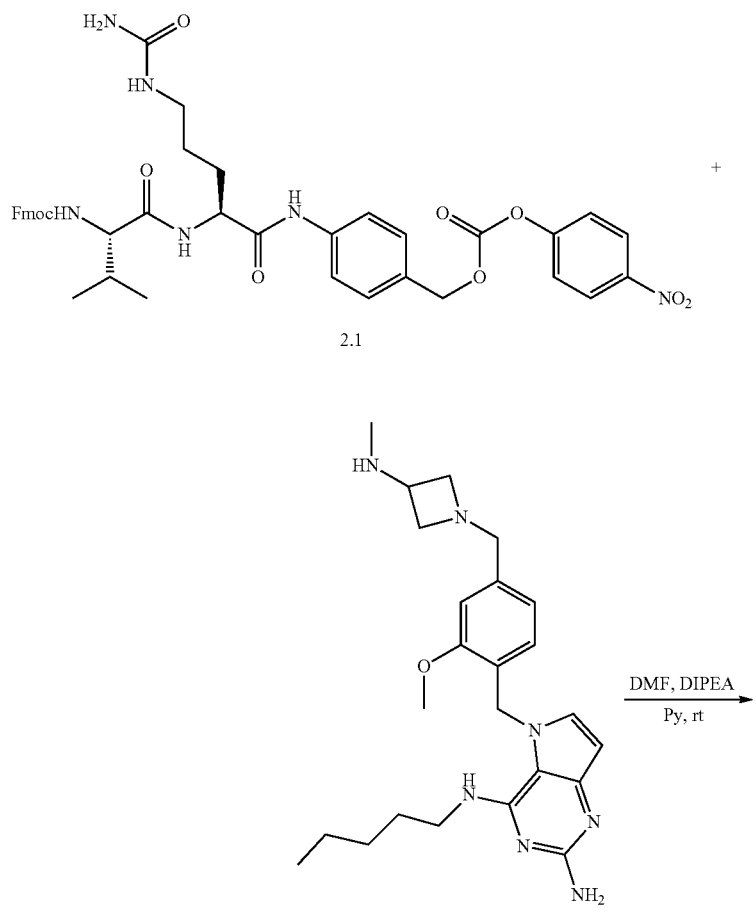

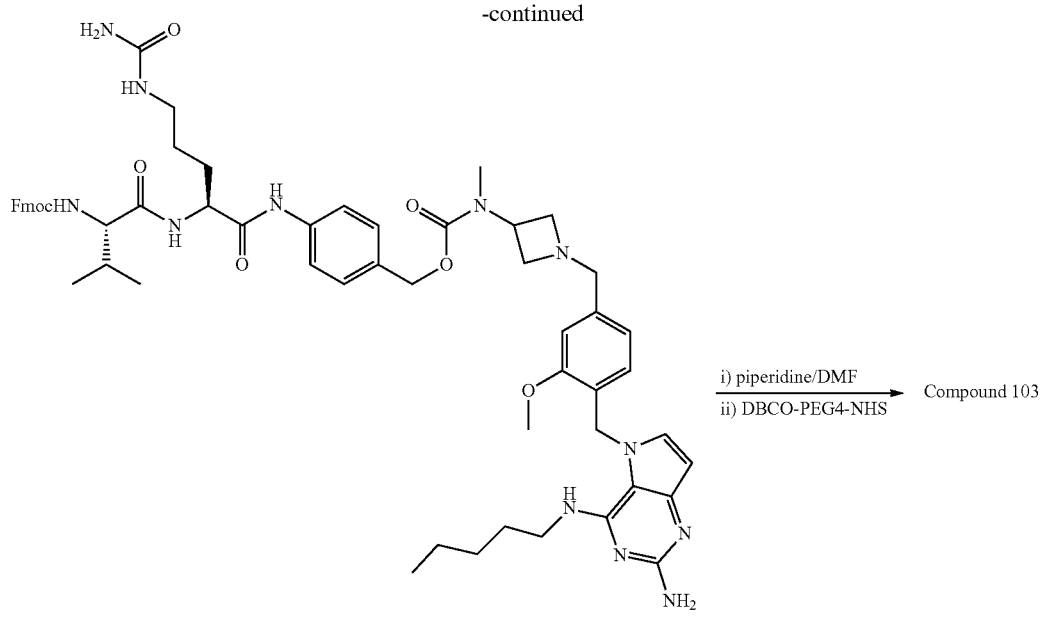

1a i) piperidine/DMF
ii) DBCO-PEG4-NHS
→ Compound 103

To an oven-dried 100 mL flask equipped with a magnetic stir bar, were added 5-(2-methoxy-4-((3-(methylamino)azetidin-1-yl)methyl)benzyl)-N$_4$-pentyl-5H-pyrrolo[3,2-d]pyrimidine-2,4-diamine (compound 1) (200 mg, 0.45 mmol), (4-nitrophenyl) [4-[[rac-(2S)-2-[[rac-(2S)-2-(9H-fluoren-9-ylmethoxycarbonylamino)-3-methyl-butanoyl]amino]-5-ureido-pentanoyl]amino]phenyl]methyl carbonate (2.1) (385 mg, 0.50 mmol), and DMF (2 mL). The clear solution was flushed with argon and then DIPEA (0.2 mL, 1 mmol) was added, and the reaction was stirred at rt for overnight. LCMS showed completion of the reaction. Solvent was removed to dryness and the residue was purified by flash chromatography to obtain compound 1a. LC-MS (ESI) m/z+H 1065.8.

Compound 1a (200 mg, 0.18 mmol) was dissolved in DMF (2 mL), to which was added piperidine (5 eq), and the clear solution was stirred at rt for 30 min. LCMS showed deprotection of Fmoc, and the crude compound tat was purified by preparative HPLC.

To an oven-dried 100 mL flask equipped with magnetic stir bar, were added the above prepared compound tat) (150 mg, 0.17 mmol), DBCO-PEG$_4$-NHS Ester (138 mg, 0.21 mmol), and DMF (2 mL). The clear solution was flushed with argon, and then DIPEA (0.05 mL, 0.31 mmol) was added. The reaction was stirred at rt for 2 h under N$_2$ atm. After LCMS showed completion of the reaction, the material was purified by preparative HPLC (method 10% ACN to 90% ACN in 20 min), and pure fractions were collected and lyophilized to obtain Compound 103. HPLC MS data showed the desired product in 98% purity. LC-MS (ESI) m/z+H 1377.9

Example 2

The following linker-payload precursor comprising a maytansinoid DM1 (Compound 2) is commercially available as DBCO-PEG$_4$-maytansine (ACME Bioscience; Palo Alto, Calif.).

Compound 201

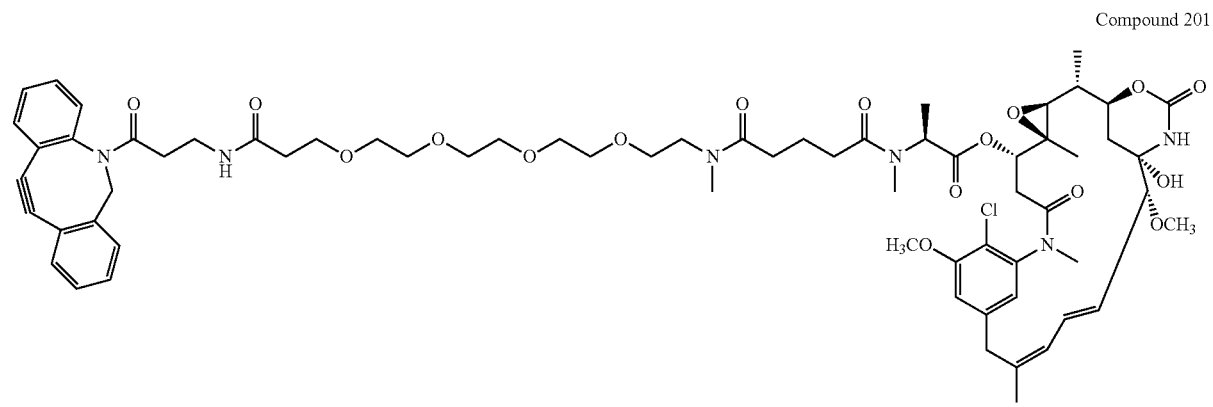 [SMILES: COc1cc2cc(c1Cl)N(C)C(=O)C[C@H](OC(=O)[C@H](C)N(C)C(=O)CCCC(=O)N(C)CCOCCOCCOCCOCCC(=O)NCCC(=O)N1Cc3ccccc3C#Cc3ccccc31)[C@]1(C)O[C@H]1[C@H](C)[C@@H]1C[C@@](O)(NC(=O)O1)[C@H](OC)/C=C/C=C(/C)C2]

Example 3
Synthesis of a Linker Payload Precursor (Compound 301) Comprising an Anthracycline
Step 1
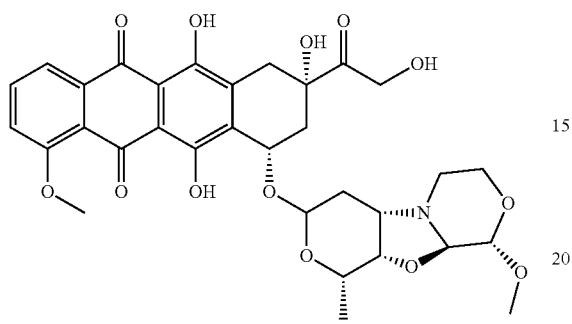
Compound 3
Step 1: Compound 3 is Commercially Available and/or is Prepared Using Published Procedures
Step 2
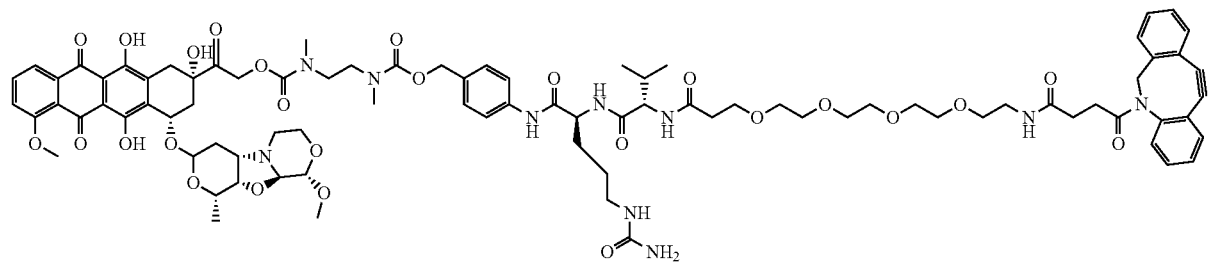
Compound 301
Step 2: Preparation of Compound 301. Compound 301 is Prepared According to the Following Scheme
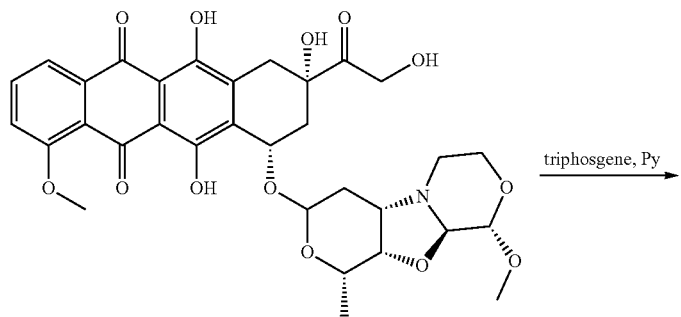
PNU-159682
6.1
triphosgene, Py →

-continued
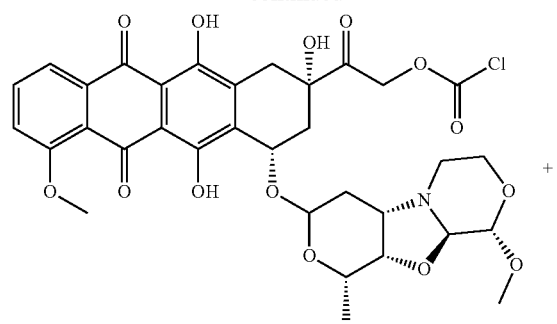
6.2
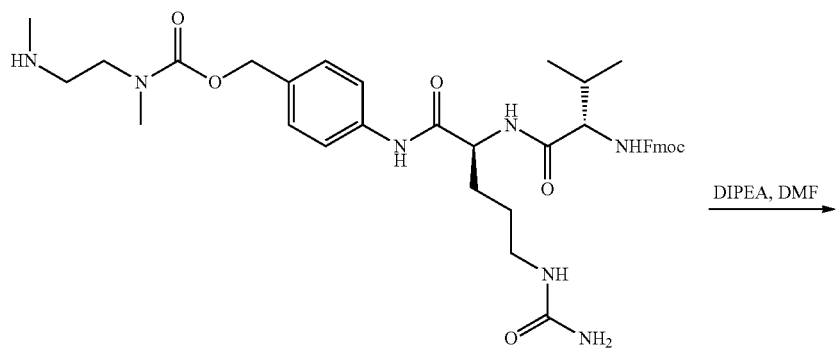
6.3
→ DIPEA, DMF
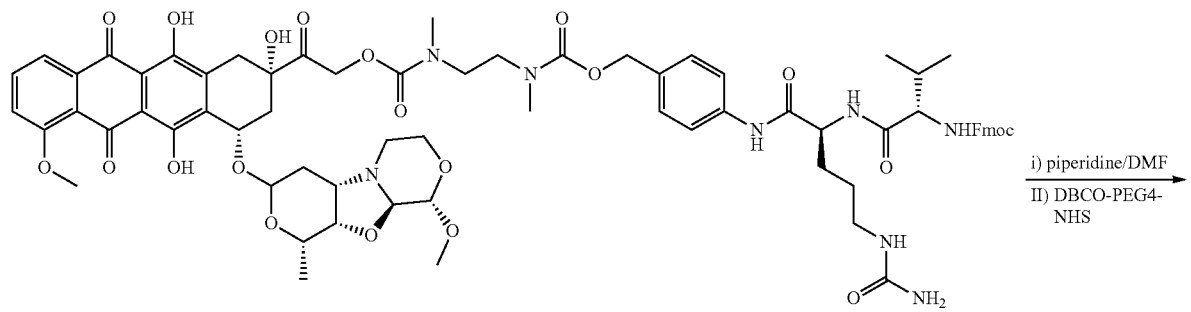
6.4
→ i) piperidine/DMF
II) DBCO-PEG4-NHS
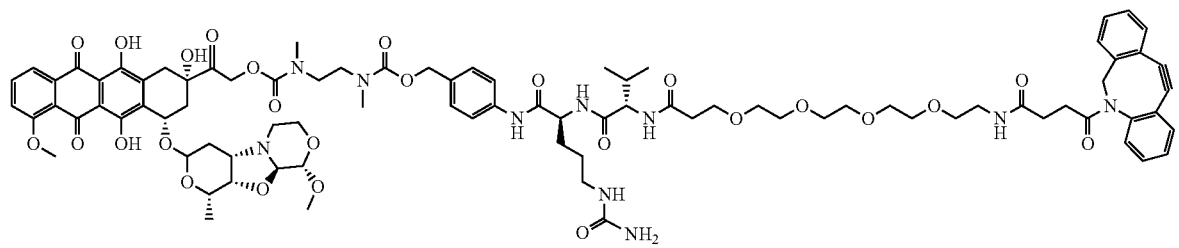
Compound 301

Example 4
Synthesis of a Linker Payload Precursor (Compound 401) Comprising an Immunomodulatory Compound
Step 1
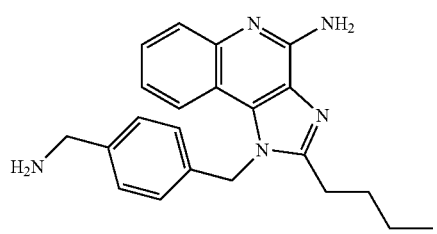
Compound 4
Step 1: Compound 4 is Prepared According to the Following Scheme
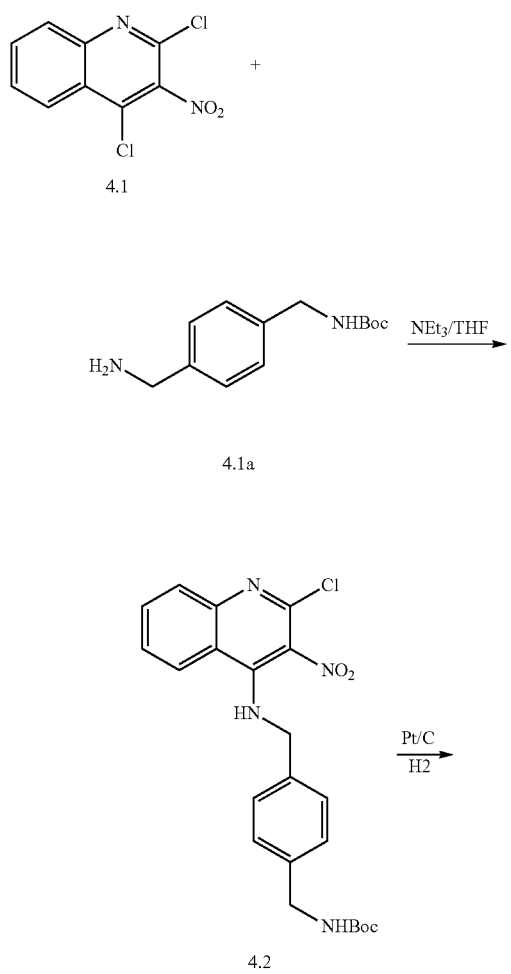
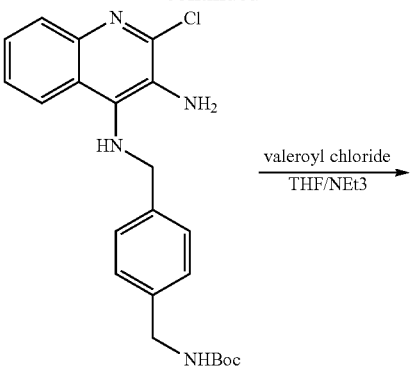
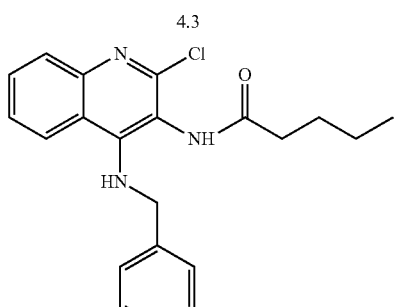
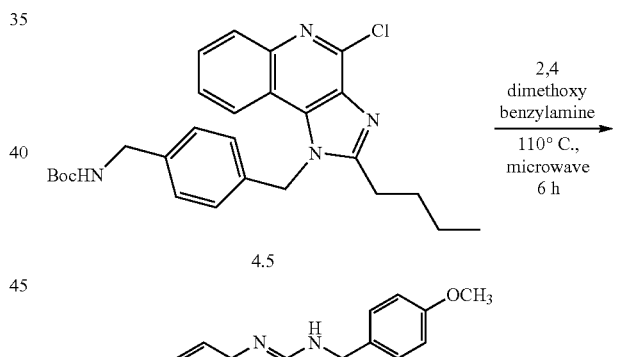
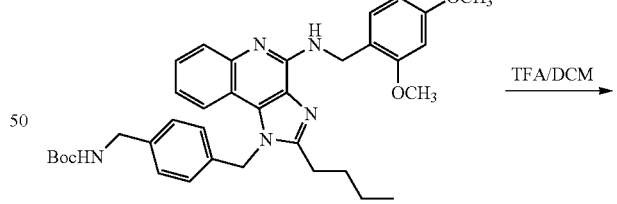
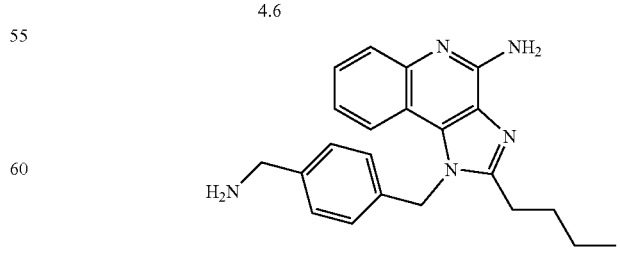
Compound 4

Step 2
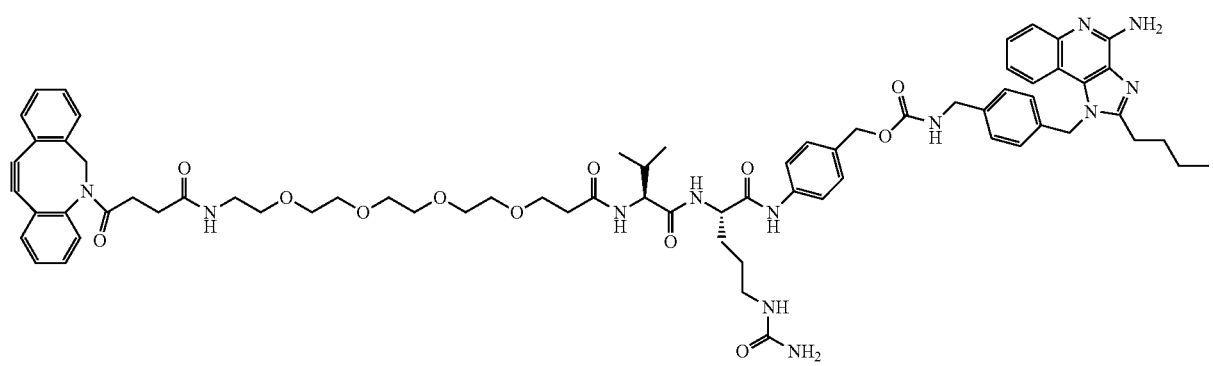
Compound 401
Step 2: Preparation of Compound 401. Compound 401 is Prepared According to the Following Scheme
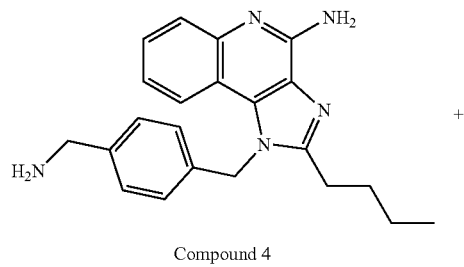
Compound 4
+
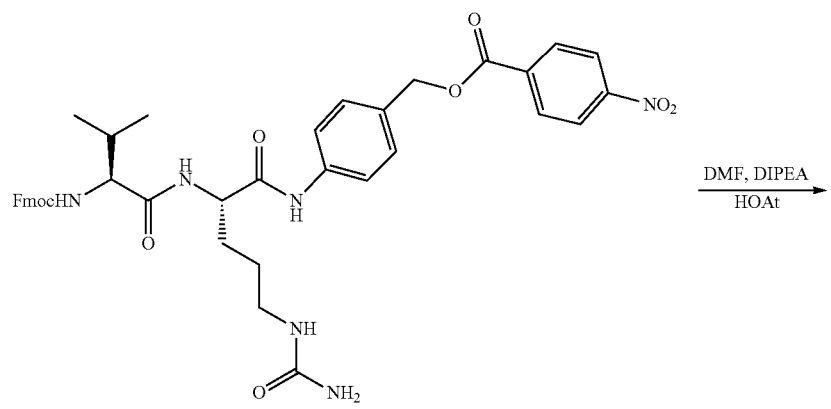
4.7

-continued
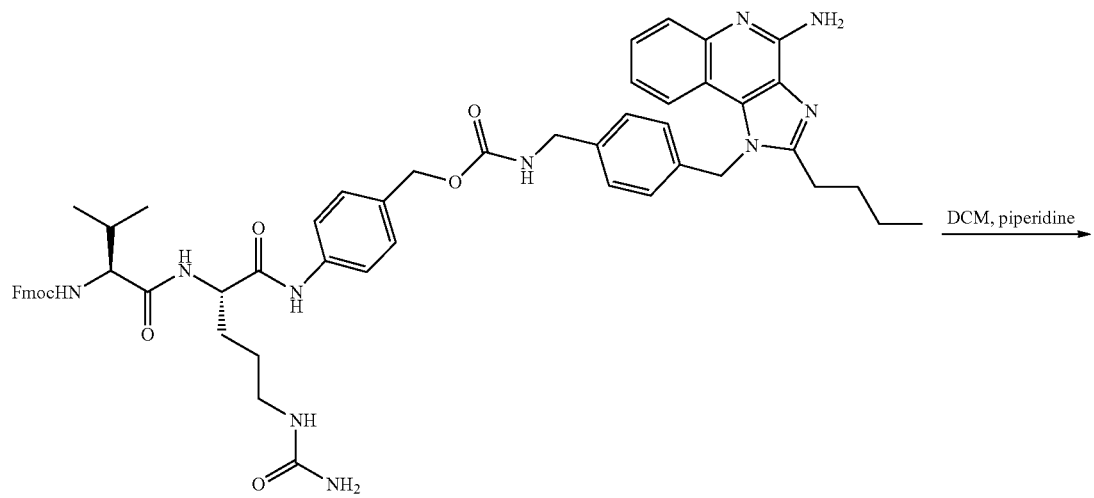
4.8
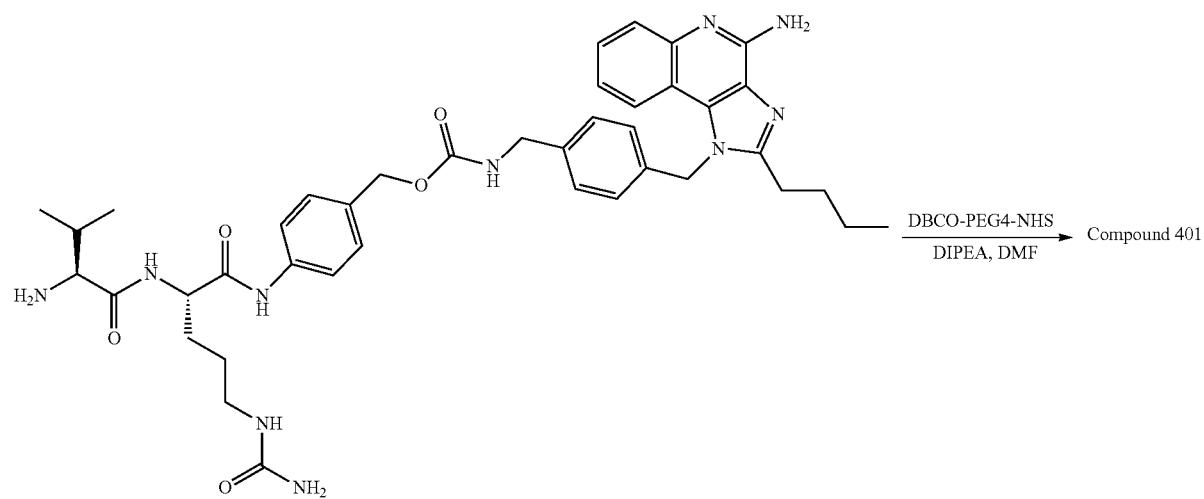
4.9

Example 5
Synthesis of a Linker Payload Compound (Compound 501) Comprising an Immunomodulatory Compound
Step 1
Compound 5
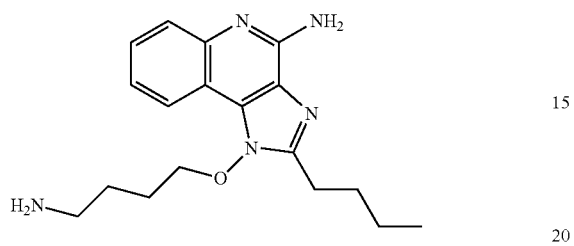
Step 1: Compound 5 is Commercially Available and/or is Prepared According to Published Procedures
Step 2
Compound 501
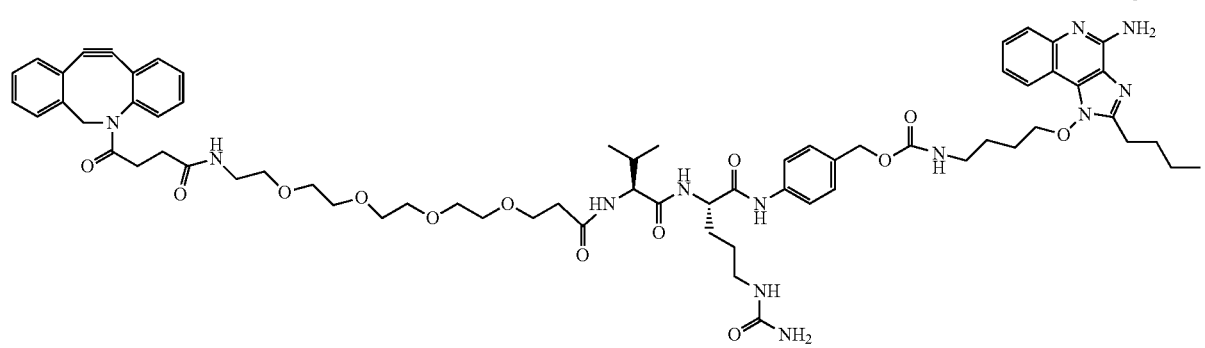
Step 2: Preparation of Compound 501. Compound 501 is Prepared According to the Scheme Below
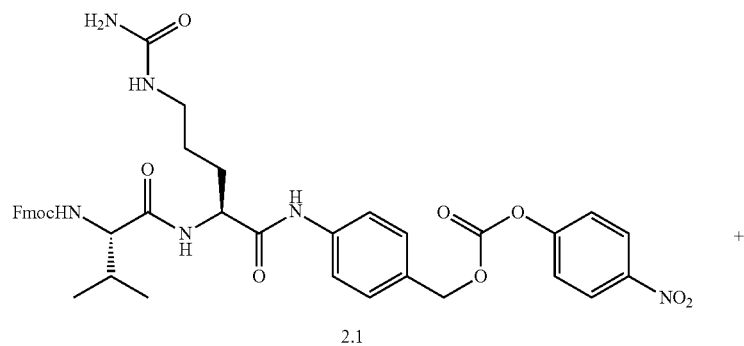
2.1

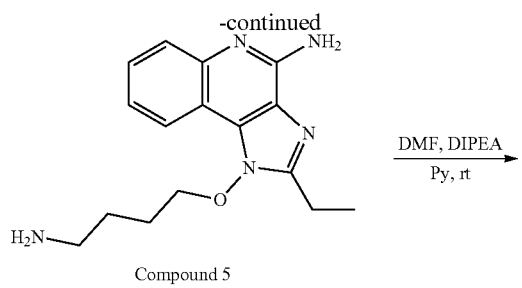
Compound 5
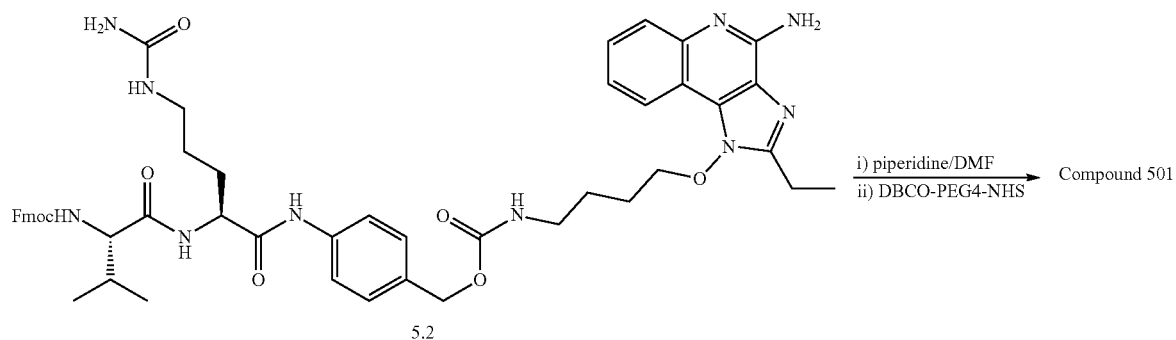
5.2
Example 6
Synthesis of a Linker Payload Compound (Compound 601) Comprising an Immunomodulator Compound
Step 1
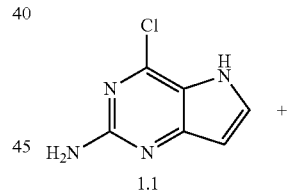
Compound 6
Step 1: Preparation of Compound 6
Compound 6 is Prepared According to the Scheme Below
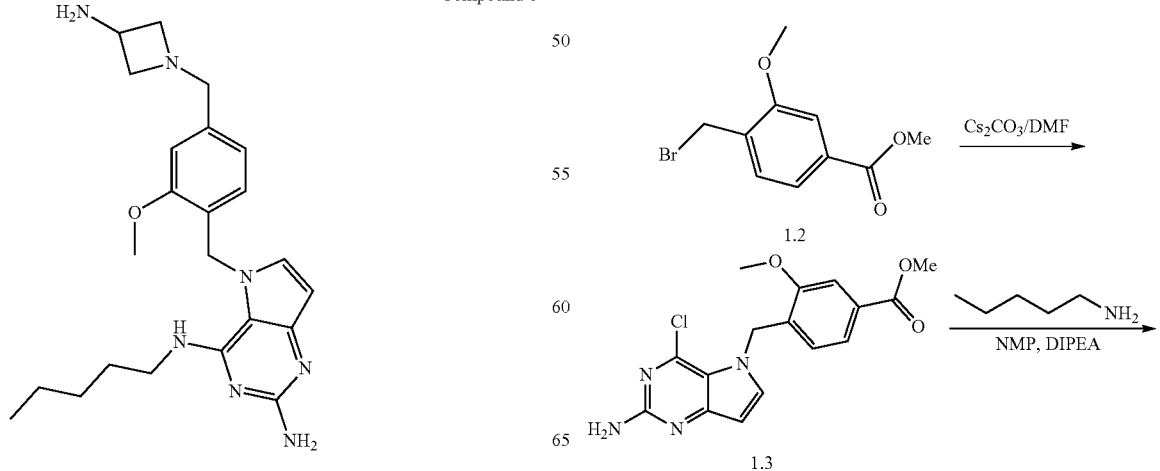

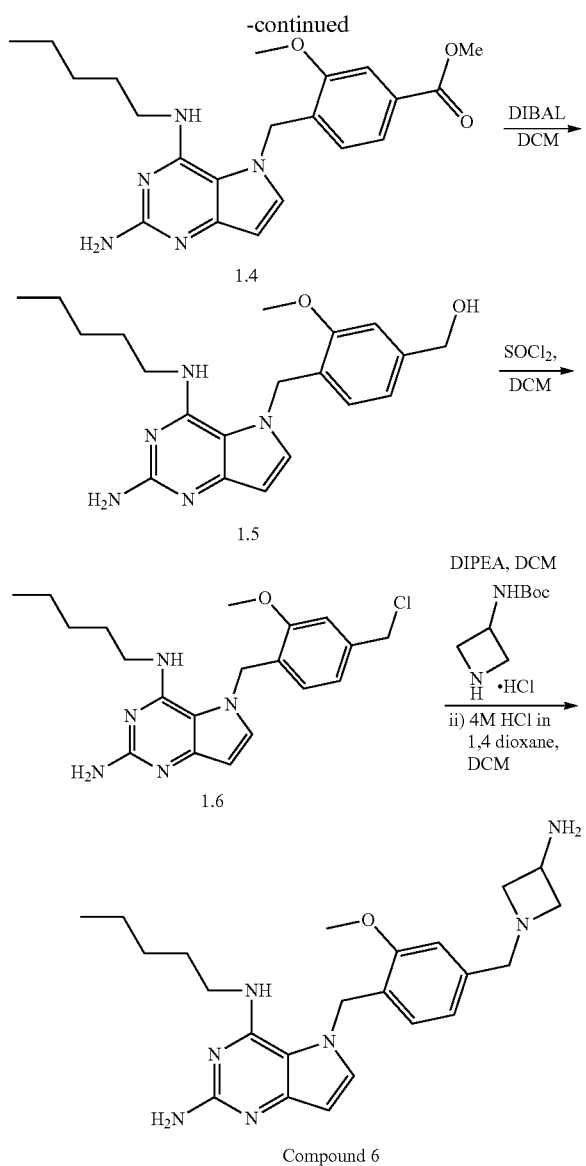

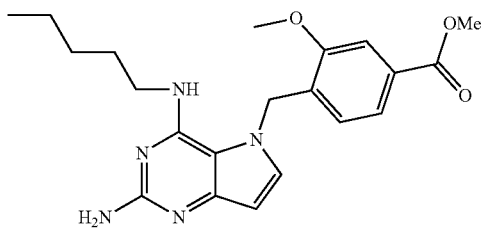

Preparation of methyl 4-((2-amino-4-(pentylamino)-5H-pyrrolo[3,2-d]pyrimidin-5-yl)menthyl)-3-methoxybenzoate (1.4)

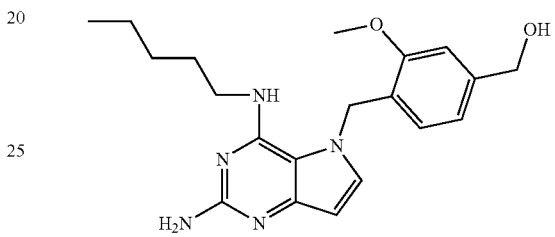

To an oven-dried 250 mL round bottom flask equipped with magnetic stir bar, were added methyl 4-[(2-amino-4-chloro-pyrrolo[3,2-d]pyrimidin-5-yl)methyl]-3-methoxy-benzoate (1.3) (7 g, 20 mmol), anhydrous NMP (20 mL), pentan-1-amine (7.04 mL, 60.5 mmol), and DIPEA (2 eq). The reaction was heated to 50° C. and stirred at that temperature for 2 days under N$_2$ atm. LCMS showed the desired product peak. Solvent was removed to dryness, and the crude material was purified by ISCO (DCM to 10% MeOH/DCM) to obtain methyl 4-[[2-amino-4-(pentylamino)pyrrolo[3,2-d]pyrimidin-5-yl]methyl]-3-methoxybenzoate (1.4b) (6.5 g, 16 mmol, 82% yield). LCMS (ESI) m/z 398.2 (M+H). $^1$HNMR (DMSO-d$_6$): δ 7.53 (d, 1H), 7.51 (d, 1H), 7.48 (dd, 1H), 7.40 (br s, 2H), 7.34 (t, 1H), 6.45 (d, 1H), 6.27 (d, 1H), 5.67 (s, 2H), 3.92 (s, 3H), 3.83 (s, 3H), 3.40 (q, 2H),1.41-1.32 (m, 2H), 1.17-1.07 (m, 2H), 0.97-0.87 (m, 2H), 0.73 (t, 3H).

Preparation of (4-((2-amino-4-(pentylamino)-5H-pyrrolo[3,2-d]pyrimidin-5-yl)methyl)-3-methoxyphenyl)methanol (1.5)

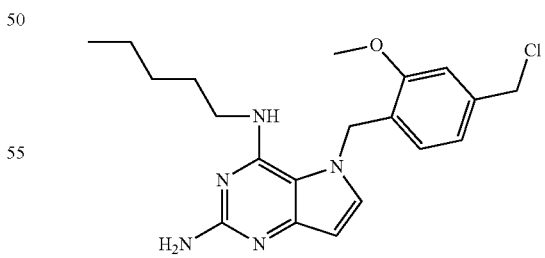

To an oven dried 250 mL round bottom flask equipped with magnetic stir bar, were added methyl 4-[[2-amino-4-(pentylamino)pyrrolo[3,2-d]pyrimidin-5-yl]methyl]-3-methoxy-benzoate (1.4) (3.5 g, 8.8 mmol), and THF (40 mL). The mixture was cooled to 0° C. and then DIBAL (35.22 mL, 1M in THF, 35.22 mmol) was added dropwise under argon atm. The reaction was slowly bought to rt and stirred for 2 h, after which reaction was cooled back to 0° C. and then quenched with saturated aq Na$_2$SO$_4$ until a fine white solid was formed. Excess solid Na$_2$SO$_4$ was added and the reaction mixture was filtered through a pad of celite and washed with DCM/MeOH and few mL of DMF. The filtrate was concentrated under vacuum to afford compound 1.5 (60%) yield. LCMS (ESI) m/z 370.2 (M+H).

Preparation of 5-(4-(chloromethyl)-2-methoxybenzyl)-N$_4$-pentyl-5H-pyrrolo[3,2-d]pyrimidine-2,4-diamine (1.6)

To an oven dried 250 mL round bottom flask equipped with magnetic stir bar, were added [4-[[2-amino-4-(pentylamino)pyrrolo[3,2-d]pyrimidin-5-yl]methyl]-3-methoxy-phenyl]methanol (5) (1.7 g, 4.6 mmol), and anhydrous Chloroform (15 mL). The mixture was cooled to 0° C. and then Thionyl Chloride (2 mL, 28 mmol) was added dropwise under argon atm. The reaction was slowly bought to rt and stirred for 2h. After which, LCMS showed completion of the reaction. The solution was concentrated to remove DCM and SOCl$_2$, and was cooled to 0° C. and then carefully quenched by the addition of sat NaHCO$_3$. The solution was extracted with DCM. The organic layer was washed with brine, and dried over Na$_2$SO$_4$, filtered to remove solids, concentrated, and dried in vacuum to afford compound 1.6. LCMS (ESI) m/z 388.1 (M+H).

tert-butyl (1-(4-((2-amino-4-(pentylamino)-5H-pyrrolo[3,2-d]pyrimidin-5-yl)methyl)-3-methoxybenzyl)azetidin-3-yl)(methyl)carbamate (1.7a)

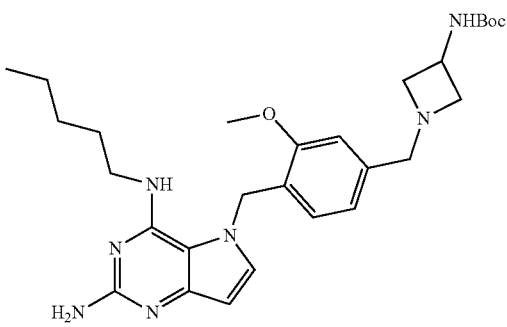 [SMILES: CCCCCNc1nc(N)nc2ccn(Cc3ccc(CN4CC(NC(=O)OC(C)(C)C)C4)cc3OC)c12]

To an oven dried 250 mL RB flask equipped with magnetic stir bar, were added 5-[[4-(chloromethyl)-2-methoxyphenyl]methyl]-N4-pentyl-pyrrolo[3,2-d]pyrimidine-2,4-diamine (100 mg, 0.26 mmol) (compound 1.6), tert-butyl N-(azetidin-3-yl)-carbamate hydrochloride (commercially available) 60 mg, and DMF (2 mL). To the clear solution was added DIPEA (0.05 mL), and the reaction was stirred at rt for 5h. After LCMS showed completion of the reaction, the crude material was purified by reverse phase HPLC to obtain the compound 1.7a. LCMS (ESI) m/z 524.7 (M+H).

To an oven dried 20 mL vial equipped with a magnetic stir bar, were added tert-butyl N-[1-[[4-[[2-amino-4-(pentylamino)pyrrolo[3,2-d]pyrimidin-5-yl]methyl]-3-methoxyphenyl]methyl]azetidin-3-yl] carbamate 7a (70 mg, 0.13 mmol), and DCM (2 mL). The clear solution was cooled to 0° C. and 4 M HCl dioxane (0.17 mL, 0.6700 mmol) was added to the reaction which was stirred at rt for 2-3h. After which LCMS showed completion of the reaction, it was concentrated and purified by prep HPLC (method 10% ACN in Water to 90% ACN in water in 20 min). Pure fractions were collected and lyophilized to obtain Compound 6 LCMS(ESI) m/z 424.78 (M+H).

Step 2

Compound 601

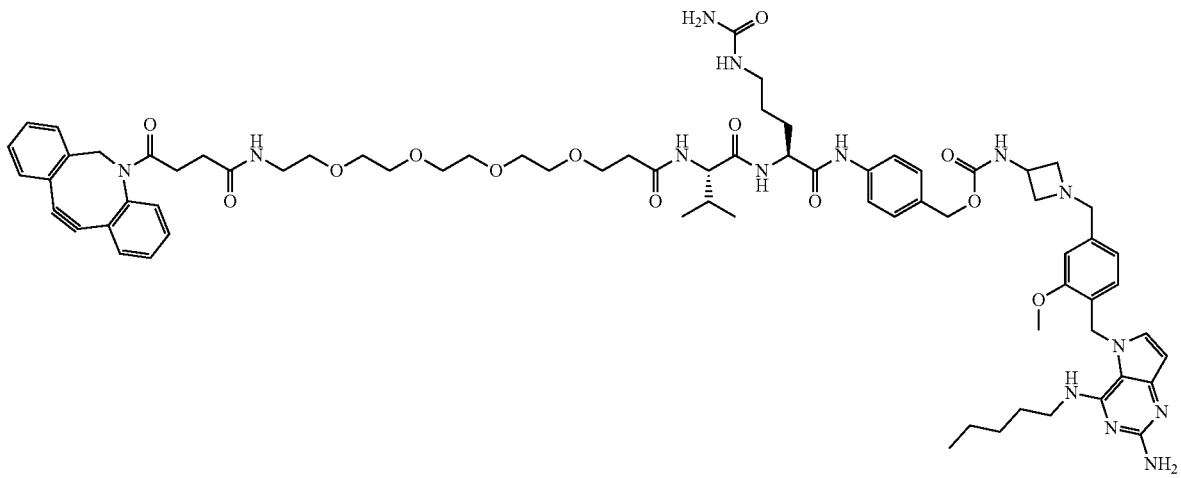

Step 2: Preparation of Compound 601. Compound 601 was Prepared According to the Scheme Below
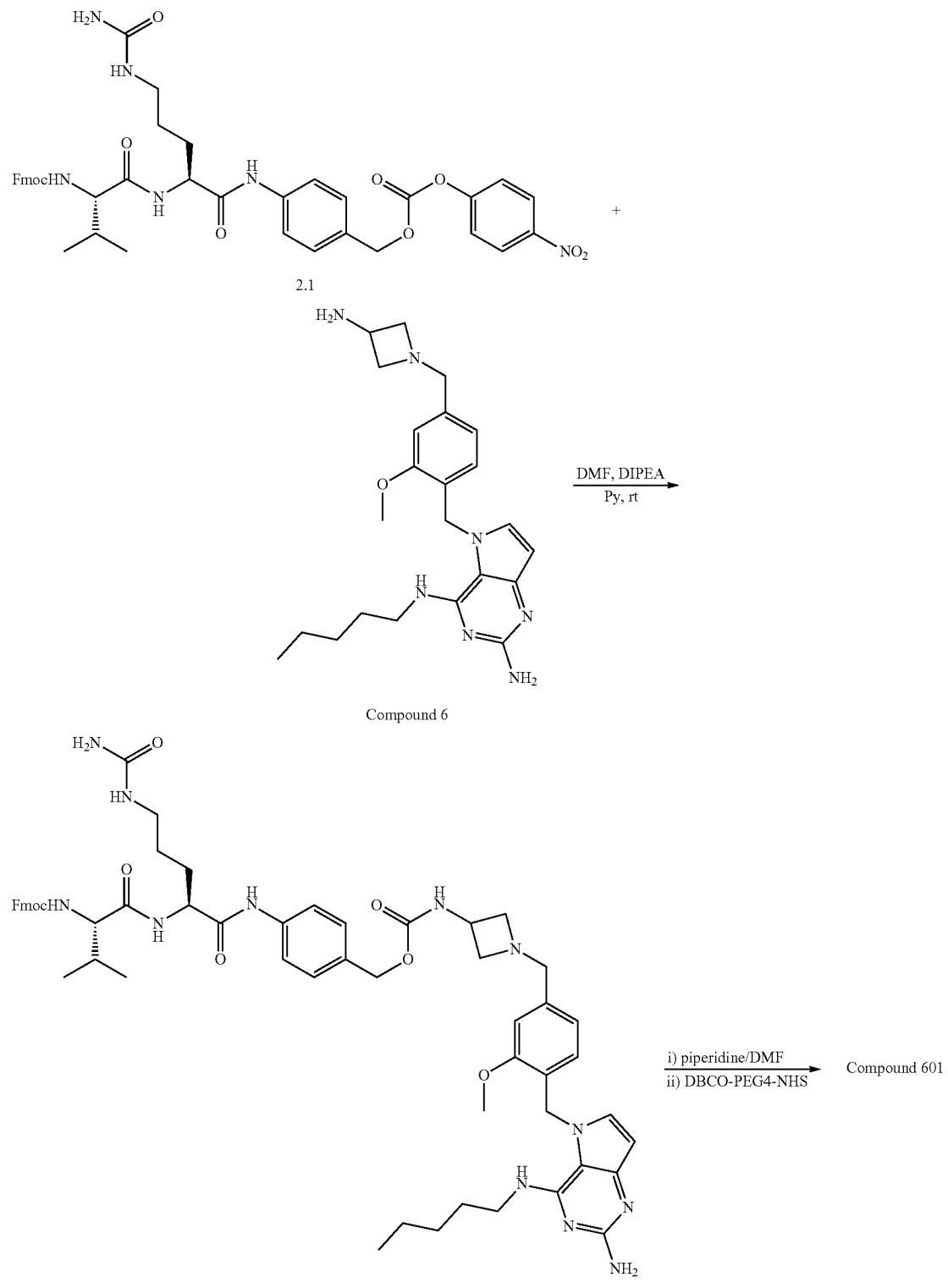

To an oven-dried 100 mL flask equipped with a magnetic stir bar, were added 5-(4-((3-aminoazetidin-1-yl)methyl)-2-methoxybenzyl)-N$_4$-pentyl-5H-pyrrolo[3,2-d]pyrimidine-2,4-diamine (compound 6) (250 mg, 0.59 mmol), (4-nitrophenyl) [4-[[rac-(2S)-2-[[rac-(2S)-2-(9H-fluoren-9-ylmethoxycarbonylamino)-3-methyl-butanoyl]amino]-5-ureido-pentanoyl]amino]phenyl]methyl carbonate (2.1) (497 mg, 0.64 mmol), and DMF (10 mL). The clear solution was flushed with argon and then DIPEA (0.2 mL, 1 mmol) was added, and the reaction was stirred at rt overnight. LCMS showed completion of the reaction. Solvent was removed to dryness and the residue was purified by flash chromatography to obtain compound 6.2. LC-MS (ESI) m/z+H 1051.8.

Compound 6.2 (250 mg, 0.23 mmol) was dissolved in DMF (5 mL), to which was added piperidine (5 eq) and the clear solution was stirred at rt for 30 min, LCMS showed deprotection of Fmoc, and the crude compound 6.2a was purified by preparative HPLC.

To an oven-dried 100 mL flask equipped with magnetic stir bar, were added the above prepared compound (6.2a) (200 mg, 0.24 mmol), DBCO-PEG4-NHS Ester (188 mg, 0.29 mmol), and DMF (5 mL). The clear solution was flushed with argon and then DIPEA (60 μL, 0.31 mmol) was added. The reaction was stirred at rt for 2 h under N$_2$ atm. After LCMS showed completion of the reaction, the material was purified by preparative HPLC (method 10% ACN to 90% ACN in 20 min) and pure fractions were collected and lyophilized to obtain compound 601. HPLC MS data showed the desired product in 98% purity. LC-MS (ESI) m/z+H 1363.9

Example 7

Synthesis of a Linker Payload Compound (Compound 701) Comprising an Immunomodulator Compound Step 1

Compound 7

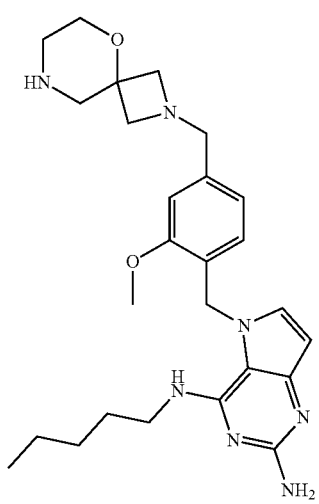

Step 1: Preparation of Compound 7

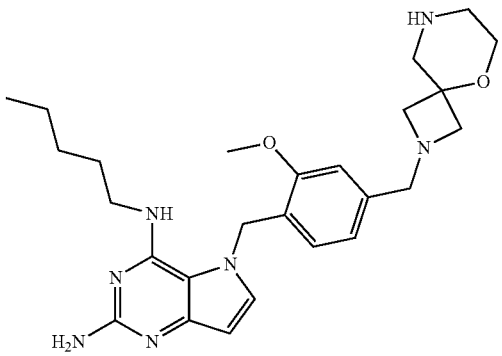 [SMILES: CCCCCNc1nc(N)nc2ccn(Cc3ccc(CN4CC5(CNCCO5)C4)cc3OC)c12]

Compound 7 was prepared according to the Scheme below.

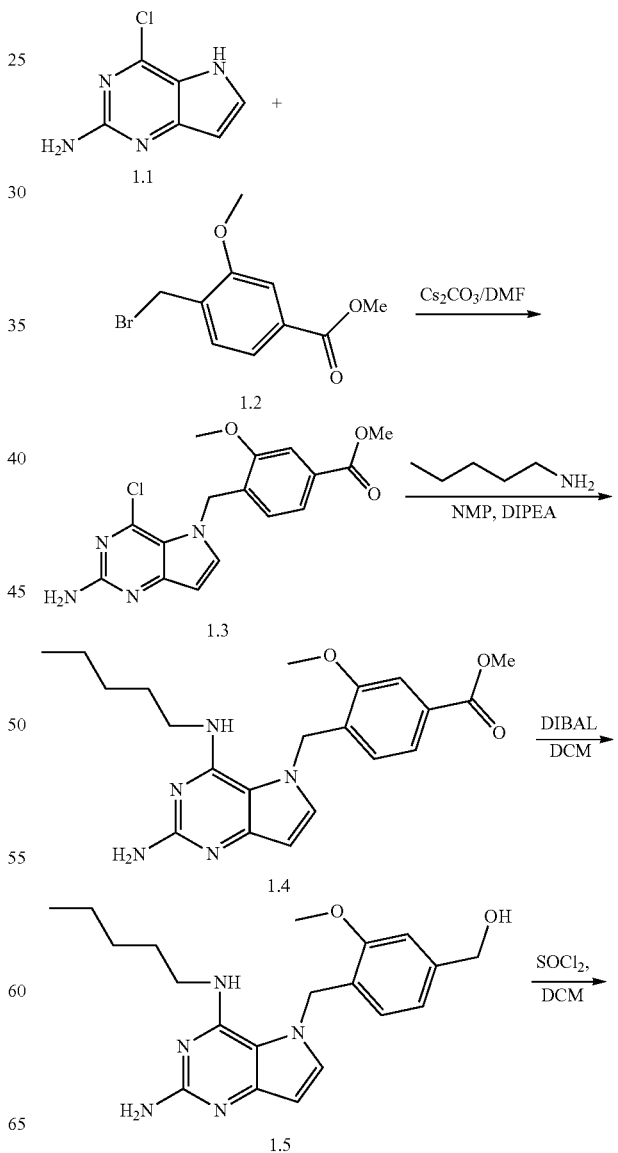

287
-continued

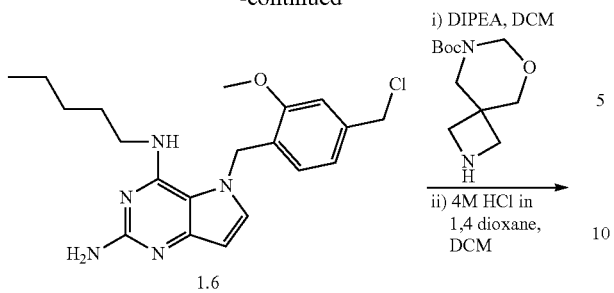

288

Preparation of (4-((2-amino-4-(pentylamino)-5H-pyrrolo[3,2-d]pyrimidin-5-yl)methyl)-3-methoxy-phenyl)methanol (1.5)

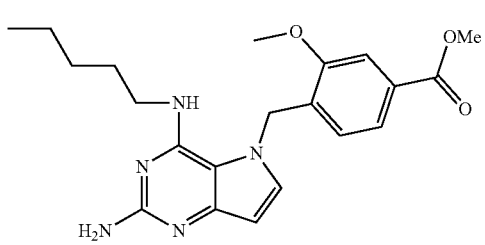 [SMILES: CCCCCNc1nc(N)nc2ccn(Cc3ccc(C(=O)OC)cc3OC)c12]

To an oven dried 250 mL round bottom flask equipped with magnetic stir bar, were added methyl 4-[[2-amino-4-(pentylamino)pyrrolo[3,2-d]pyrimidin-5-yl]methyl]-3-methoxy-benzoate (1.4) (3.5 g, 8.81 mmol), and THF (40 mL). The mixture was cooled to 0° C. and then DIBAL (35.22 mL, 1M in THF, 35.22 mmol) was added dropwise under argon atm. The reaction was slowly bought to rt and stirred for 2 h, after which reaction was cooled back to 0° C. and then quenched with saturated aq Na$_2$SO$_4$ until a fine white solid was formed. Excess solid Na2SO4 was added and the reaction mixture was filtered through a pad of celite and washed with DCM/MeOH and few mL of DMF. The filtrate was concentrated under vacuum to afford a white solid compound 1.5 (60%) yield. LCMS (ESI) m/z 370.2 (M+H).

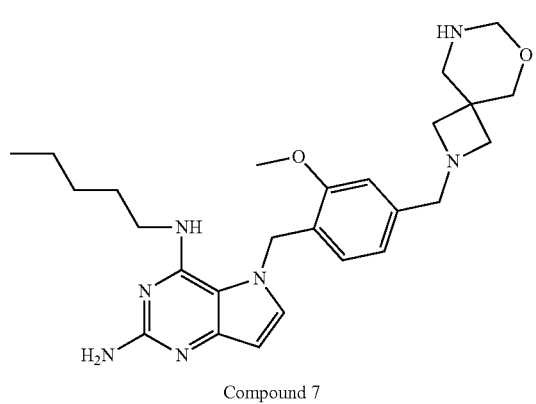

Compound 7

Preparation of methyl 4-((2-amino-4-(pentylamino)-5H-pyrrolo[3,2-d]pyrimidin-5-yl)methyl)-3-methoxybenzoate (1.4)

Preparation of 5-(4-(chloromethyl)-2-methoxybenzyl)-N$_4$-pentyl-5H-pyrrolo[3,2-d]pyrimidine-2,4-diamine (1.6)

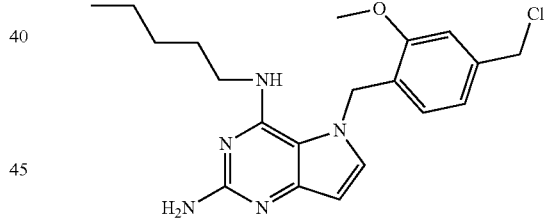

To an oven dried 250 mL round bottom flask equipped with magnetic stir bar, were added methyl 4-[(2-amino-4-chloro-pyrrolo[3,2-d]pyrimidin-5-yl)methyl]-3-methoxy-benzoate (1.3) (7 g, 20.19 mmol), anhydrous NMP (20 mL), pentan-1-amine (7.04 mL, 60.56 mmol), and DIPEA (2 eq). The reaction was heated to 50° C. and stirred at that temperature for 2 days under N$_2$ atm. LCMS showed the desired product peak. Solvent was removed to dryness and the crude purified by ISCO (DCM to 10% MeOH/DCM) to obtain the methyl 4-[[2-amino-4-(pentylamino)pyrrolo[3,2-d]pyrimidin-5-yl]methyl]-3-methoxy-benzoate (1.4) (6.5 g, 16.35 mmol, 82% yield). LCMS (ESI) m/z 398.2 (M+H). $^1$HNMR (DMSO-d$_6$): δ 7.53 (d, 1H), 7.51 (d, 1H), 7.48 (dd, 1H), 7.40 (br s, 2H), 7.34 (t, 1H), 6.45 (d, 1H), 6.27 (d, 1H), 5.67 (s, 2H), 3.92 (s, 3H), 3.83 (s, 3H), 3.40 (q, 2H), 1.41-1.32 (m, 2H), 1.17-1.07 (m, 2H), 0.97-0.87 (m, 2H), 0.73 (t, 3H).

To an oven dried 250 mL round bottom flask equipped with magnetic stir bar, were added [4-[[2-amino-4-(pentylamino)pyrrolo[3,2-d]pyrimidin-5-yl]methyl]-3-methoxy-phenyl]methanol (5) (1.7 g, 4.6 mmol), and anhydrous Chloroform (15 mL). The mixture was cooled to 0° C. and then Thionyl Chloride (2 mL, 27.61 mmol) was added dropwise under argon atm. The reaction was slowly bought to rt and stirred for 2h. After which, LCMS showed completion of the reaction. It was concentrated to remove DCM and SOCl$_2$, and cooled to 0° C. and then carefully quenched by the addition of sat NaHCO$_3$, and extracted with DCM. The organic layer was washed with brine, dried over Na$_2$SO$_4$, filtered and concentrated, and dried in vacuum to afford compound 1.6 as yellow solid. LCMS (ESI) m/z 388.1 (M+H).

General procedure for Boc diamine scaffold coupling to compound 1.6 to prepare Boc-protected compounds:

To an oven dried 25 mL round bottom flask equipped with a magnetic stir bar, were added 5-[[4-(chloromethyl)-2- methoxy-phenyl]methyl]-N₄-pentyl-pyrrolo[3,2-d]pyrimidine-2,4-diamine (1.6) (100 mg, 0.26 mmol), Boc protected diamine scaffold as described above (1 eq), and anhydrous DMF (2 mL). The clear solution was flushed with argon and then DIPEA (3 eq) was added. The reaction was stirred at rt for 5 h under N₂ atm. After LCMS showed completion of the reaction, the crude material was purified by reverse phase HPLC to obtain the Boc protected scaffold.

Deprotection to obtain 5-(4-((5-oxa-2,8-diazaspiro[3.5]nonan-2-yl)methyl)-2-methoxybenzyl)-N₄-pentyl-5H-pyrrolo[3,2-d]pyrimidine-2,4-diamine (Compound 7):

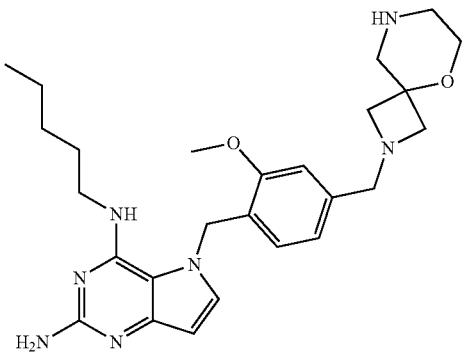 [SMILES: CCCCCNc1nc(N)nc2ccn(Cc3ccc(CN4CC5(CNCCO5)C4)cc3OC)c12]

To an oven dried 250 mL round bottom flask equipped with a magnetic stir bar, were added 5-[[4-(chloromethyl)-2-methoxy-phenyl]methyl]-N₄-pentyl-pyrrolo[3,2-d]pyrimidine-2,4-diamine (100 mg, 0.26 mmol) (compound 1.6), tert-butyl 5-oxa-2,8-diazaspiro[3.5]nonane-8-carboxylate hydrochloride (commercially available) 102.38 mg, and DMF (2 mL). To the clear solution was added DIPEA (0.05 mL). The reaction was stirred ar rt for 5h. After LCMS showed completion of the reaction, the crude material was purified by reverse phase HPLC to obtain the compound 1.7. LCMS (ESI) m/z 580.7 (M+H).

To an oven dried 20 mL vial equipped with a magnetic stir bar, were added tert-butyl 2-[[4-[[2-amino-4-(pentylamino)pyrrolo[3,2-d]pyrimidin-5-yl]methyl]-3-methoxy-phenyl]methyl]-5-oxa-2,8-diazaspiro[3.5]nonane-8-carboxylate (1.7) (70 mg, 0.12 mmol), and DCM (0.94 mL). The clear solution was cooled to 0° C. and then 4M HCl dioxane (0.15 mL, 0.6000 mmol) was added. The reaction was stirred at rt for 2 h. After LCMS showed completion of the reaction, the reaction mixture was concentrated and purified by preparative HPLC (method 10% ACN in Water to 90% ACN in water in 20 min), pure fractions were collected and lyophilized to obtain Compound 7 LCMS(ESI) m/z 480.3 (M+H).

Step 2

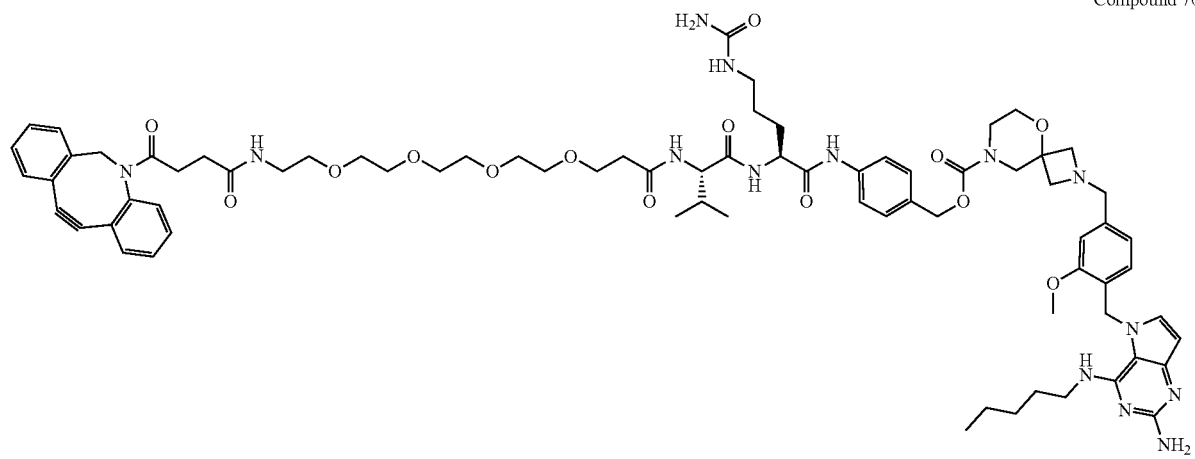

Compound 701

Step 2: Preparation of Compound 701
Compound 701 was prepared according to the scheme shown below.
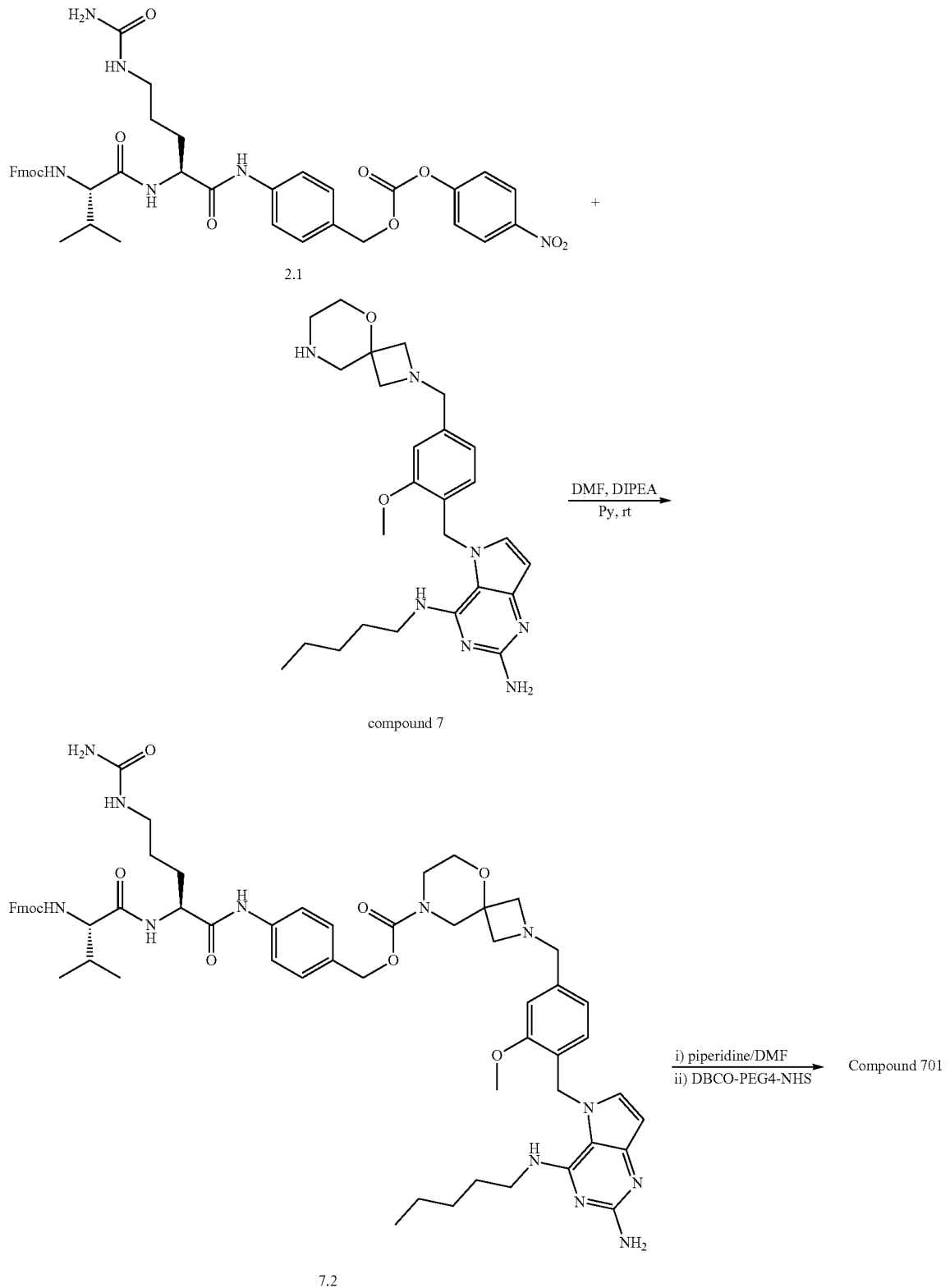

Synthesis of [4-[[rac-(2S)-2-[[rac-(2S)-2-amino-3-methyl-butanoyl]amino]-5-ureido-pentanoyl]amino]phenyl]methyl 2-[[4-[[2-amino-4-(pentylamino)pyrrolo[3,2-d]pyrimidin-5-yl]methyl]-3-methoxy-phenyl]methyl]-5-oxa-2,8-diazaspiro[3.5]nonane-8-carboxylate (2.2)

To an oven dried 100 mL flask equipped with a magnetic stir bar, were added 5-[[2-methoxy-4-(5-oxa-2,8-diazaspiro[3.5]nonan-2-ylmethyl)phenyl]methyl]-N₄-pentyl-pyrrolo[3,2-d]pyrimidine-2,4-diamine (Compound 7) (180 mg, 0.38 mmol), (4-nitrophenyl) [4-[[rac-(2S)-2-[[rac-(2S)-2-(9H-fluoren-9-ylmethoxycarbonylamino)-3-methyl-butanoyl]amino]-5-ureido-pentanoyl]amino]phenyl]methyl carbonate (2.1) (345.3 mg, 0.45 mmol), and DMF (2 mL). The clear solution was flushed with argon and then DIPEA (0.2 mL, 1.13 mmol) was added. The reaction was stirred at rt for overnight. LC-MS showed completion of the reaction, solvent was removed to dryness and purified by ISCO to obtain compound 7.2. LC-MS (ESI) m/z+H 1108.3.

To an oven dried 100 mL flask equipped with magnetic stir bar, were added [4-[[rac-(2S)-2-[[rac-(2S)-2-amino-3-methyl-butanoyl]amino]-5-ureido-pentanoyl]amino]phenyl]methyl 2-[[4-[[2-amino-4-(pentylamino)pyrrolo[3,2-d]pyrimidin-5-yl]methyl]-3-methoxy-phenyl]methyl]-5-oxa-2,8-diazaspiro[3.5]nonane-8-carboxylate (2.2) (200 mg, 0.18 mmol) which was dissolved in DMF (2 mL) and piperidine (5 eq). The clear solution was stirred at rt for 30 min, LCMS showed deprotection of Fmoc, the crude compound 2.2a was purified by prep HPLC.

To an oven-dried 100 mL flask was equipped with magnetic stir bar, were added compound (2.2a) (150 mg, 0.17 mmol) (40 mg, 0.05 mmol), DBCO-PEG4-NHS Ester (122 mg, 0.19 mmol), and DMF (2 mL). The clear solution was flushed with argon and then DIPEA (60 μL, 0.34 mmol) was added. The reaction was stirred at rt for 2h under N₂ atm. After LCMS showed completion of the reaction, purified by preparative HPLC (method 10% ACN to 90% ACN in 20 min) pure fractions were collected and lyophilized to obtain Compound 701. HPLC MS data showed the desired product in 98% purity. LC-MS (ESI) m/z+H 1420.8

Example 8

Synthesis of a Linker Payload Compound (Compound 801) Comprising an Immunomodulator Compound Step 1

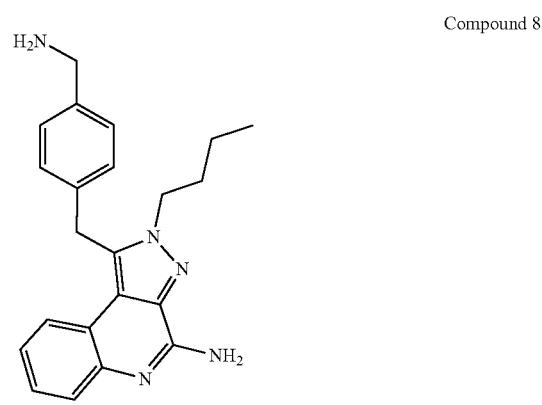 [SMILES: CCCCn1nc2c(N)nc3ccccc3c2c1Cc1ccc(CN)cc1]

Compound 8

Step 1: Preparation of Compound 8. Compound 8 is Commercially Available or is Prepared According to Published Procedures Step 2

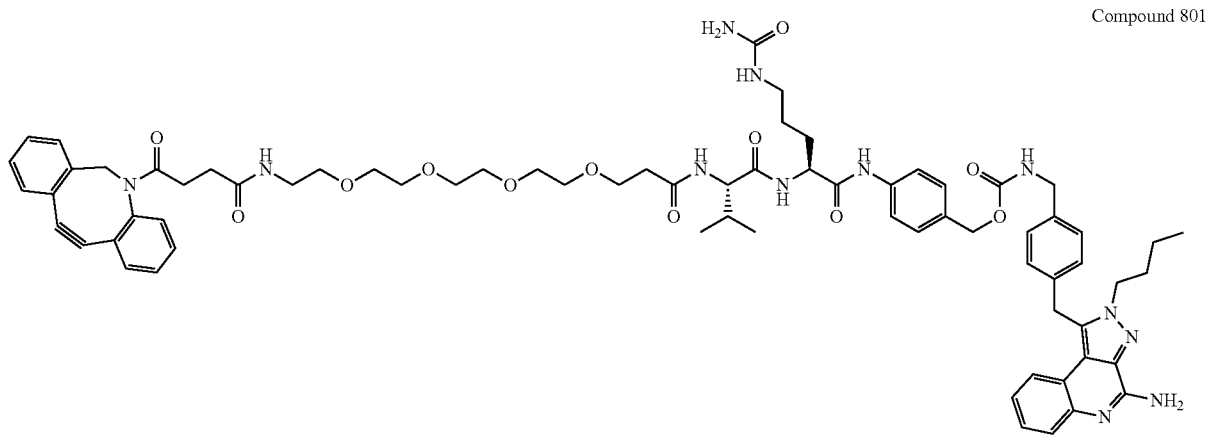

Compound 801

Step 2: Preparation of Compound 801. Compound 801 is Prepared According to the Scheme Below
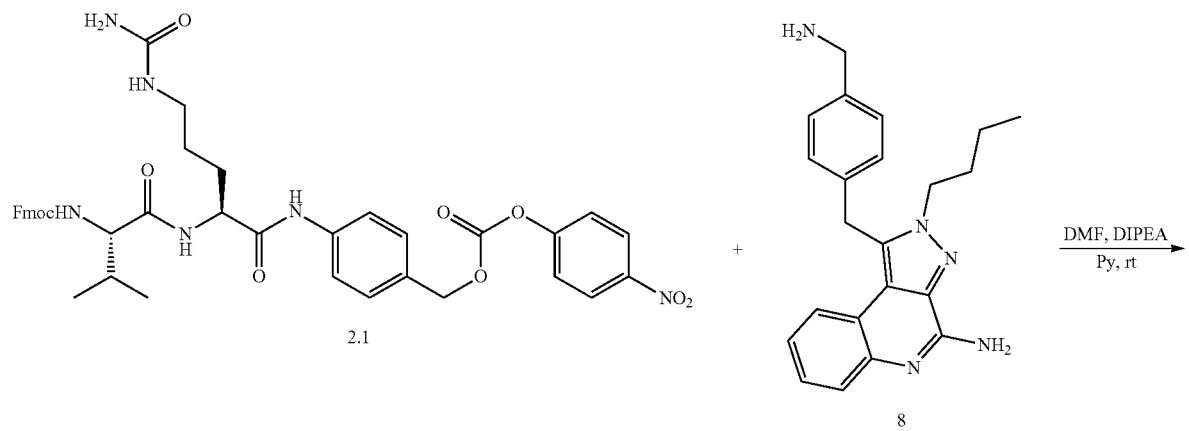
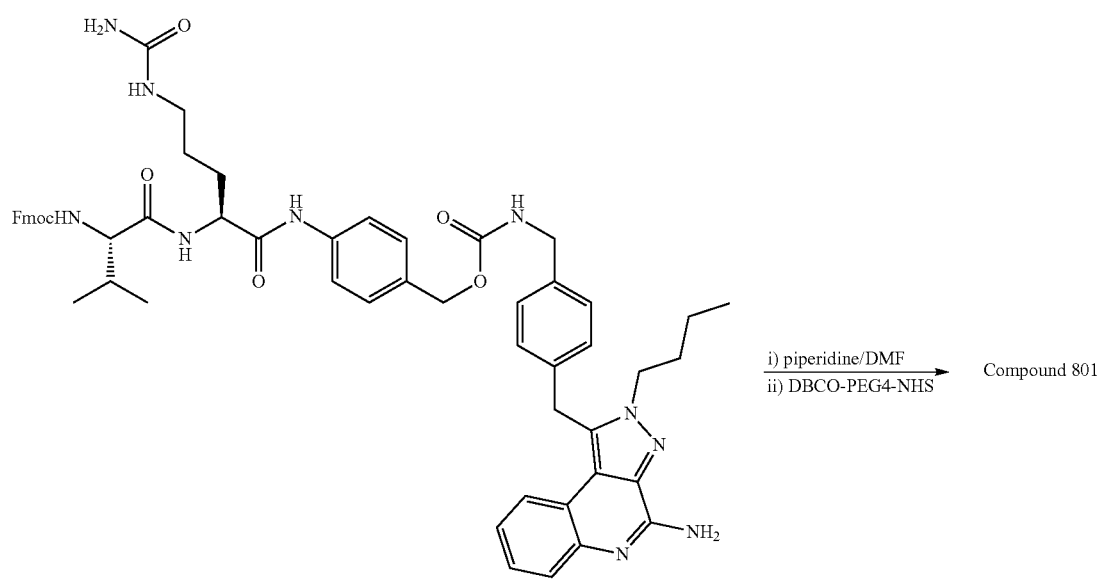

Example 9

Synthesis of a Linker Payload Compound (Compound 102) Comprising an Immunomodulator Compound, Hemiasterlin Cytotoxin Step 1

Step 1: Compound 1 was Prepared as Described in Example 1

Step 2

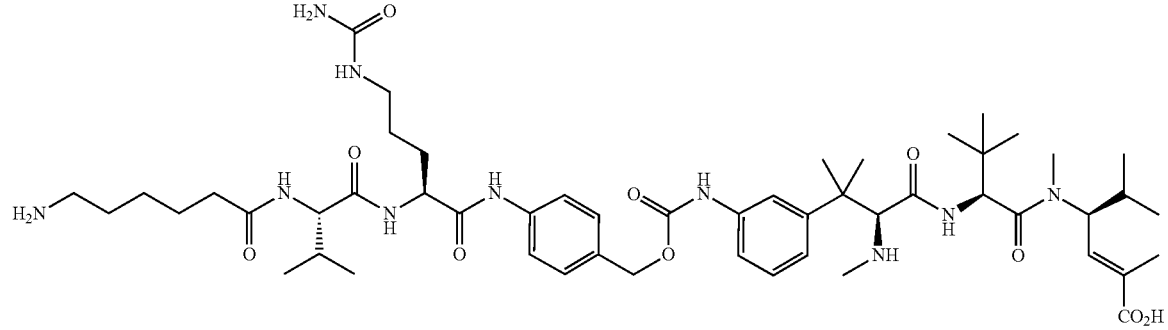

Compound 102

Step 2: Preparation of Compound 102. Compound 102 is Prepared from Compound 1 According to Published Protocols

Example 10

Synthesis of a Linker Payload Compound (Compound 901) Comprising a Cytotoxin Compound Compound 901 is prepared according to the Scheme below.

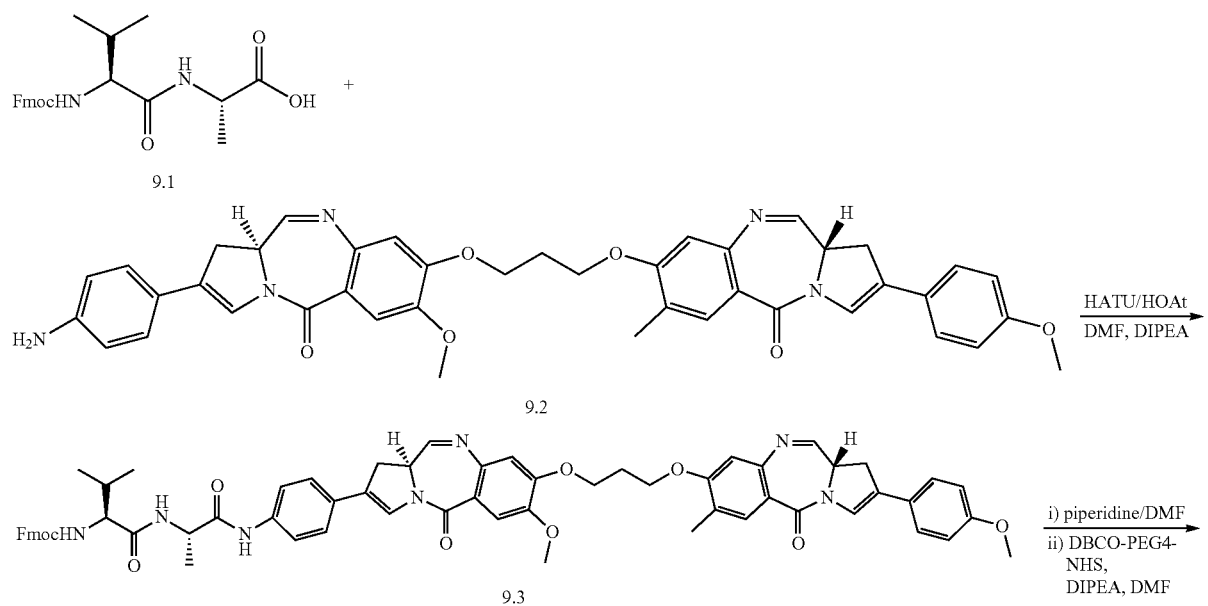

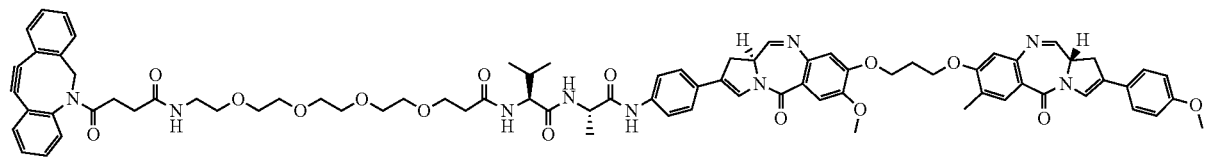
Compound 901
Example 11
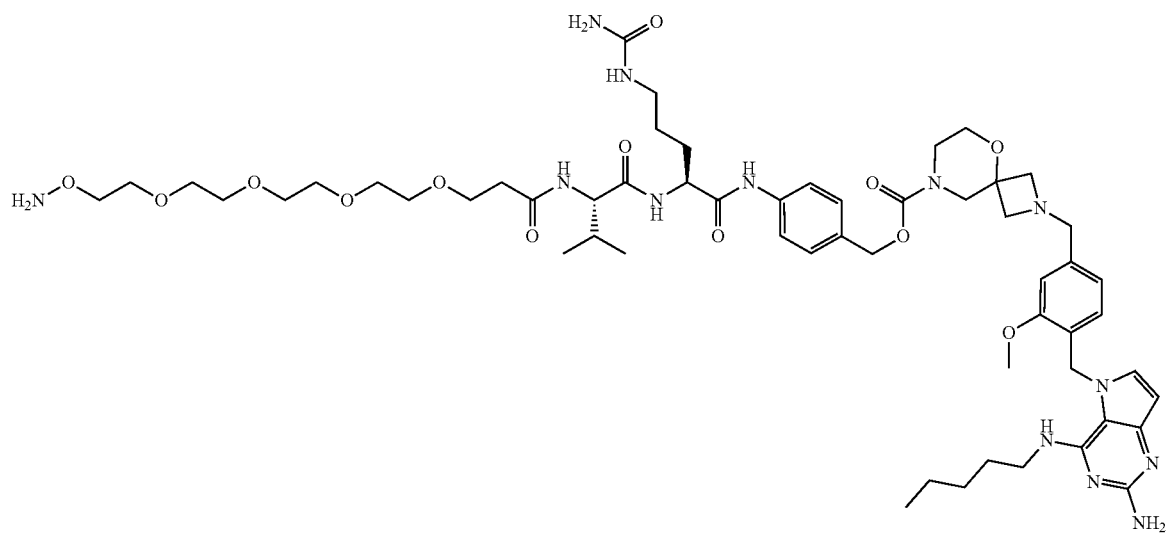
Compound 1001
Step 1: Preparation of Compound 1001
Compound 1001 was prepared according to the scheme shown below.
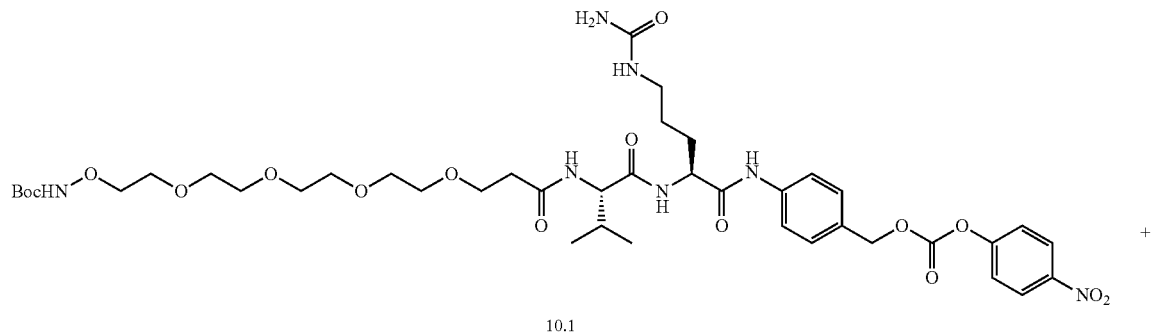
10.1

301 302
-continued
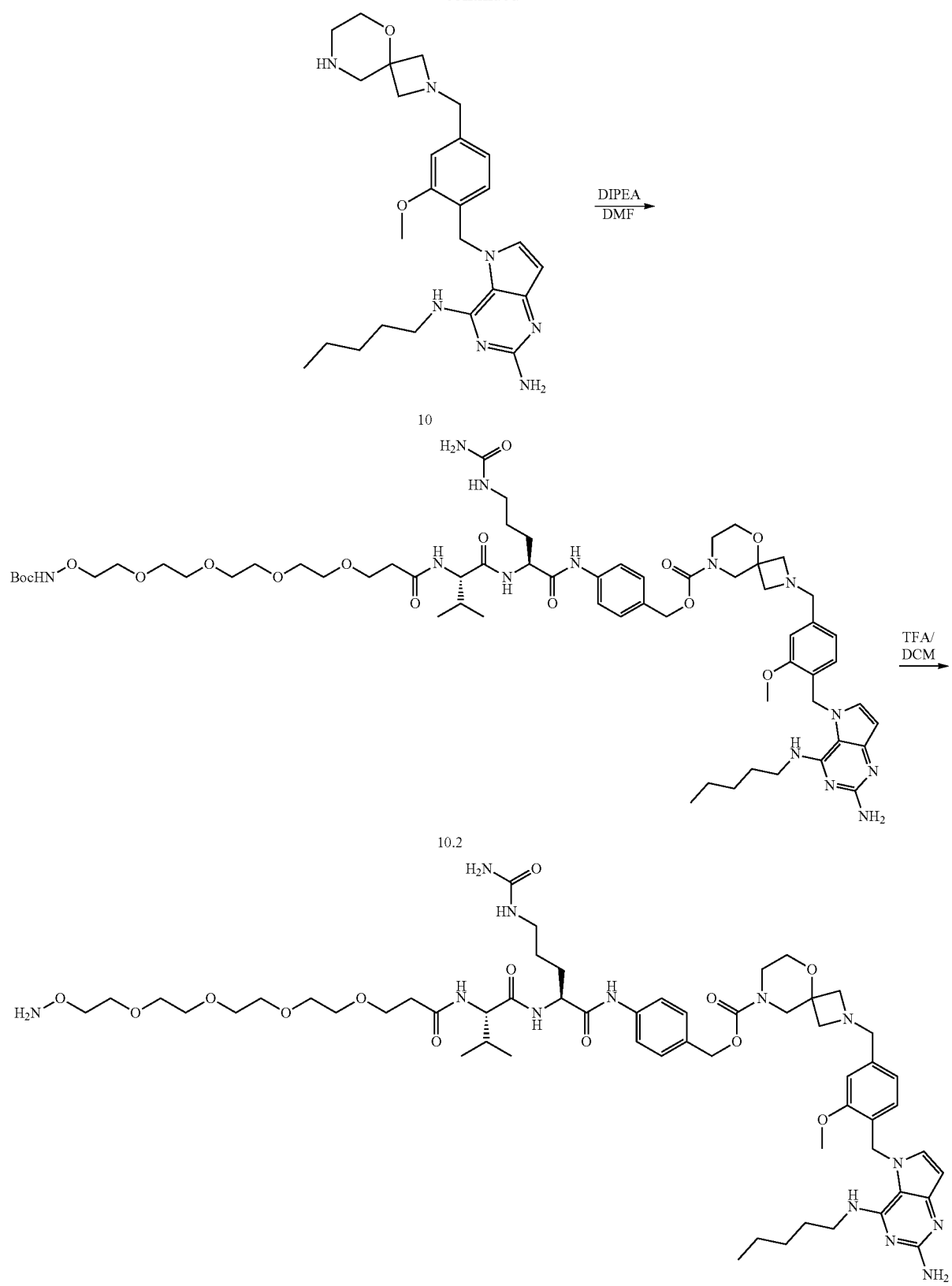

To an oven dried 100 mL RB flask equipped with magnetic stir bar, were added 5-[[2-methoxy-4-(5-oxa-2,8-diazaspiro[3.5]nonan-2-ylmethyl)phenyl]methyl]-N₄-pentyl-pyrrolo[3,2-d]pyrimidine-2,4-diamine Compound 10 (220 mg, 0.46 mmol), (4-nitrophenyl) [4-[[rac-(2S)-2-[[rac-(2S)-2-[3-[2-[2-[2-[2-(tert-butoxycarbonylamino)oxyethoxy]ethoxy]-ethoxy]ethoxy]propanoylamino]-3-methyl-butanoyl]amino]-5-ureido-pentanoyl]amino]phenyl]methyl carbonate compound 10.1 (416.48 mg, 0.46 mmol), and DMF (5 mL). The clear solution was flushed with argon and then DIPEA (0.08 mL, 0.46 mmol) was added. The reaction was stirred at rt for 5 h under N₂ atm. After which, LCMS showed the desired product peak. Solvent was removed to dryness and purified by prep HPLC to obtain compound 10.2 as an off white solid. LC-MS (ESI) m/z+H 1249.5.

To an oven dried 100 mL RB flask equipped with magnetic stir bar, were added compound 10.2 (200 mg, 0.16 mmol) and DCM (5 mL). The clear solution was flushed with argon and then TFA (0.14 mL, 0.8 mmol) was added. The reaction was stirred at rt for 4 h under N₂ atm. LCMS showed completion of the reaction. Solvent was removed to dryness and purified by prep HPLC to obtain Compound 1001 as light brown solid. LC-MS (ESI) m/z+H 1149.5.

Example 12

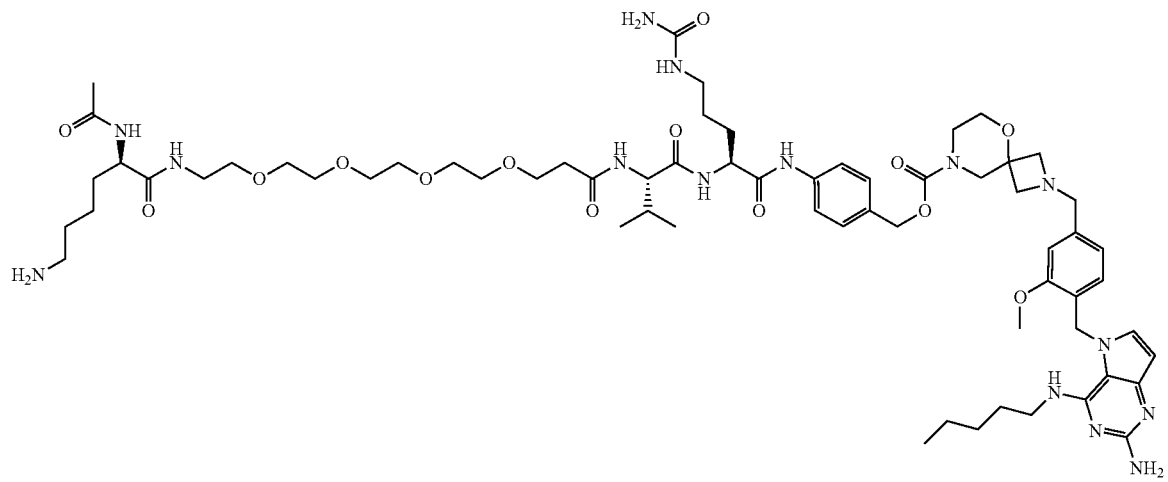

Compound 1002

Step 1: Preparation of Compound 1002

Compound 1002 was prepared according to the scheme shown below.

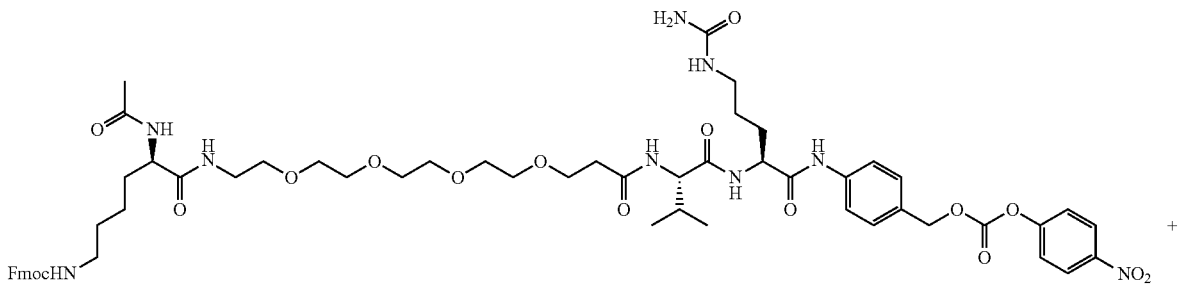

10.3

-continued

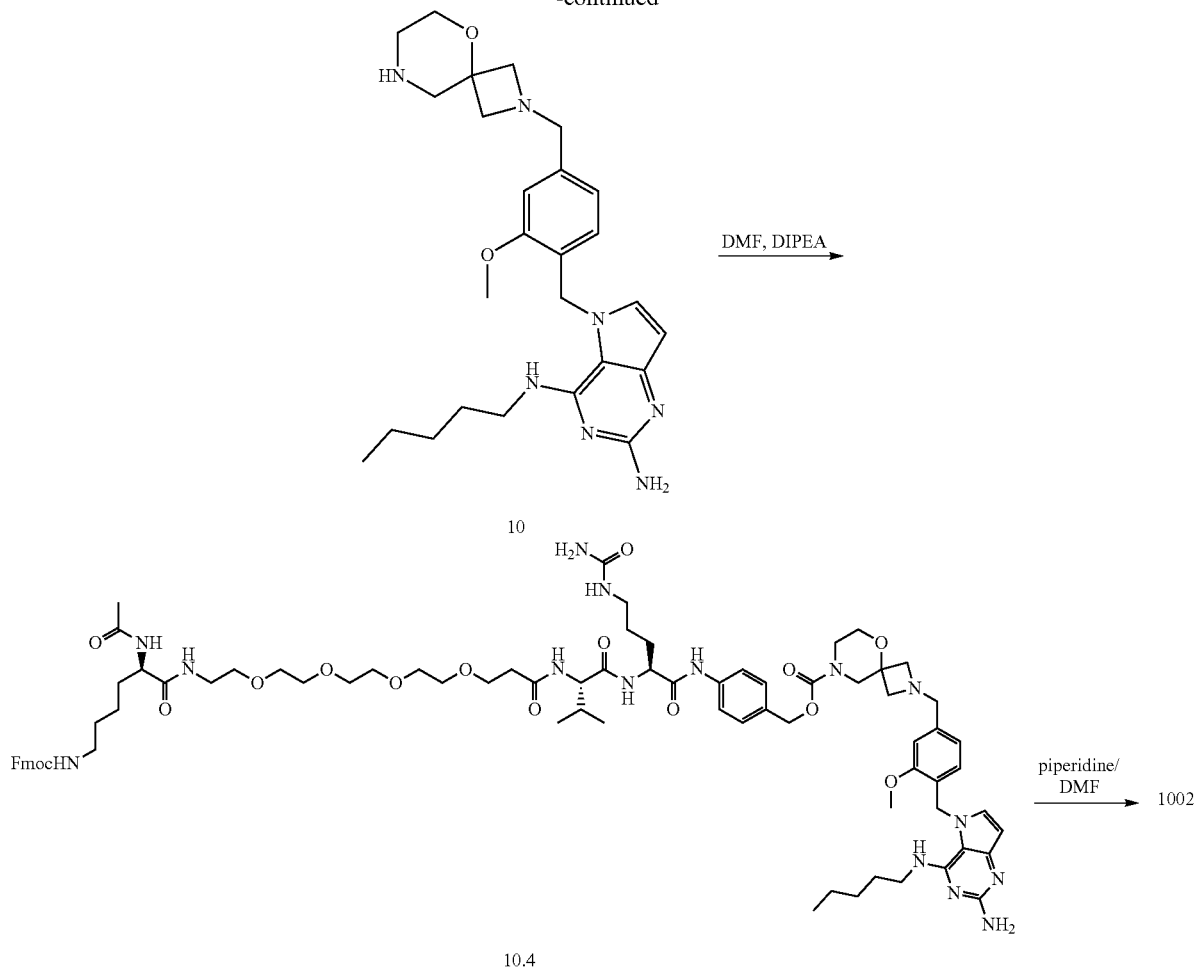

10.4

To an oven dried 100 mL RB flask equipped with magnetic stir bar, were added 5-[[2-methoxy-4-(5-oxa-2,8-diazaspiro[3.5]nonan-2-ylmethyl)phenyl]methyl]-N₄-pentyl-pyrrolo[3,2-d]pyrimidine-2,4-diamine Compound 10 (220 mg, 0.46 mmol), compound 10.3 (544.4 mg, 0.46 mmol), and DMF (5 mL). The clear solution was flushed with argon and then DIPEA (0.08 mL, 0.4600 mmol) was added. The reaction was stirred at rt for 5 h under N₂ atm. After which, LCMS showed completion of the reaction. Solvent was removed to dryness and purified by preparative HPLC to obtain compound 10.4 as an off white solid. LC-MS (ESI) m/z+H 1524.9.

To an oven dried 100 mL RB flask equipped with magnetic stir bar, were added compound 10.4 (200 mg, 0.16 mmol) and DCM (5 mL). The clear solution was flushed with argon and added piperidine (0.1 mL, 0.65 mmol) was added. The reaction was stirred at rt for 4 h under N₂ atm. LCMS showed completion of the reaction. Solvent was removed to dryness and purified by prep HPLC to obtain 1002 as an off white solid. LC-MS (ESI) m/z+H 1302.8.

Example 13

General method for conjugation of compounds to antibodies

Compound 103 conjugation method: Compound 103 was dissolved in DMSO to a final concentration of 5 mM. The conjugation was carried out in 1×PBS at antibody concentration of 1 mg/mL, Compound 103 to pAMF ratio of 3, and with 25% of DMSO. The reaction mixture was incubated at room temperature for overnight. The conjugation efficiency was measured by LC/MS. Unconjugated Compound 103 was removed by cation exchange. The conjugate was formulated in 10 mM Na3PO4 (pH7.4) buffer supplemented with 9% sucrose.

Compound 701 conjugation method: Compound 701 was dissolved in DMSO to a final concentration of 5 mM. The conjugation was carried out in 1×PBS at antibody concentration of 1 mg/mL, Compound 701 to pAMF ratio of 3, and with 25% of DMSO. The reaction mixture was incubated at room temperature for overnight. The conjugation efficiency was measured by LC/MS.

TABLE 1

| Conjugate | | mAbs | | DAR |
|---|---|---|---|---|
| 1 | 70 | aFolR1 H01 Y180F404 | Compd 103 | 3.9 |
| 2 | 67 | aGFP Y180F404 | Compd 103 | 3.8 |
| 3 | 68 | aFolR1 B10 F404 | Compd 103 | 1.9 |
| 4 | 69 | aFolR1 H01 Y180F404 | Compd 701 | 3.9 | iADC with stochastic conjugation method: TLR agonist-PEG-DBCO (Compound 103 and Compound 701) and cytotoxin-linker-DBCO (Compound 101) were dissolved individually in DMSO to a final concentration of 5 mM. Strain-promoted alkyne-azide cycloadditions (SPAAC) conjugation was carried out by adding a mixture of TLR agonist and cytotoxin at a predetermined ratio to antibodies incorporated with 4× pAMF on the heavy chain or 6× pAMF (4× heavy chain+2× Light chain) at a concentration of 1 mg/mL and incubated for 16 hr at room temperature in 1×PBS buffer and 25% DMSO. While the total stoichiometry of 3 moles of DBCO-payload per mole of pAMF in the reaction is held constant, the ratio of TLR agonist-PEG-DBCO to cytotoxin-linker-DBCO in the reaction is adjusted to suit the relative amount of the two payloads desired on the final conjugate. To analyze the ratio of TLR agonist to cytotoxin in the conjugate and conjugation efficiency, samples were digested with IdeS protease and reduced with DTT followed by LC/MS for analysis. Table 2 below shows some data for this experiment.

TABLE 2

| # | Conj. # | mAb | TLR agonist | cytotoxin | % TLR | DAR |
|---|---|---|---|---|---|---|
| 1 | 38 | aFolR HC:4x pAMF | Compd 103 | Compd 101 | 41% | 3.9 |
| 2 | 44 | aGFP HC:4x pAMF | Compd 103 | Compd 101 | 44% | 3.9 |
| 3 | 56 | aFolR HC:4x pAMF, LC:2x pAMF | Compd 701 | Compd 101 | 41% | 5.9 |

Example 14

General method for iADC stochastic conjugation

The following drug linker precursor (L-PA) compounds comprising cytotoxins were used in this experiment:

Compound 101, Compound 201, Compound 301 and Compound 102

The following immunomodulator linker (L-IM) precursor compounds comprising TLR7 agonists were used in this experiment:

Compound 401, Compound 501 and Compound 601, Compound 701, and Compound 801

Compounds 101-801 listed above were dissolved individually in DMSO to a final concentration of 5 mM. Strain-promoted alkyne-azide cycloadditions (SPAAC) conjugation was carried out by adding a mixture of TLR agonist and cytotoxin at a predetermined ratio to antibodies incorporated with 4× pAMF on the heavy chain or 6× pAMF (4× heavy chain+2× Light chain) at a concentration of 1 mg/mL and incubated for 16 hr at room temperature in 1×PBS buffer and 25% DMSO. While the total stoichiometry of 3 moles of DBCO-payload per mole of pAMF in the reaction is held constant, the ratio of TLR agonist-PEG-DBCO to cytotoxin-PEG-DBCO in the reaction is adjusted to suit the relative amount of the two payloads desired on the final conjugate. To analyze the ratio of TLR agonist to cytotoxin in the conjugate and conjugation efficiency, samples were digested with IdeS protease and reduced with DTT followed by LC/MS for analysis.

Because the mass difference between Compound 201 and Compound 401 was too small to be resolved on LC/MS, a stepwise approach was taken to make Compound 401/Compound 201 iADC. In brief, Compound 401 was under conjugated first by reacting with a sub-stoichiometric amount of drug-linker for 16 hrs at room temperature. LC/MS was used to measure conjugation efficiency of the protein after the first half reaction. Compound 201 was then added in excess to drive the conjugation to completion for an additional 16 hrs at room temperature. The ratio of Compound 401 to Compound 201 was calculated assuming all the un-conjugated pAMF site after Compound 401 conjugation was occupied by the Compound 201 payload.

Site specific iADC conjugation method: To enable site specific iADC conjugation, a transglutaminase recognition motif (Qtag) was engineered at the C-terminus of the LC with the amino acid sequence GLLQGA. This Qtag-LC was then paired with a HC containing a non-natural amino acid pAMF. This construct enables true site-specific dual conjugation since the Qtag-LC enables the conjugation of cytotoxin-PEG-primary amine Compound 102 by the enzyme transglutaminase while the pAMF residues in HC enable the conjugation of TLR agonist-PEG-DBCO (Compound 401) by SPAAC. The conjugation reaction carried out at 1 mg/mL protein concentration in 100 mM Tris buffer with 10 mM EDTA at pH 8.0. Compound 102 was added at a molar ratio of 10:1 drug-linker:Qtag and Compound 401 was added at a molar ratio of 3:1 drug-linker:pAMF. A C-term $His_6$ tagged transglutaminase from *Streptomyces hygroscopicus* was expressed recombinantly in *E. coli* and purified by standard IMAC chromatography. The *S. hygroscopicus* transglutaminase was added to the conjugation reaction at a final concentration of 0.2 mg/mL and the reaction was incubated at 37C for 16 hrs. Conjugation efficiency was measured by LC/MS. Table 3 below shows the drug antibody ratio (DAR) obtained for the iADCs. % TLR refers to the percentage of the total conjugated payloads (TLR and cytotoxin) that were TLR agonists (i.e., #TLR/[#TLR+#cytotoxin]).

TABLE 3

| # | mAb | Conjugation type | Conjugated TLR agonist | Conjugated cytotoxin | % TLR | DAR |
|---|---|---|---|---|---|---|
| Conjugate 37 | aFolR HC:4x pAMF | iADC | Compd 401 | Compd 101 | 42% | 3.9 |
| Conjugate 52 | | | Compd 401 | Compd 201 | 87% | 3.9 |
| Conjugate 53 | | | Compd 401 | Compd 201 | 40% | 3.9 |
| Conjugate 38 | | | Compd 103 | Compd 101 | 41% | 3.9 |
| Conjugate 39 | | | Compd 501 | Compd 101 | 57% | 3.9 |
| Conjugate 41 | | | Compd 401 | Compd 301 | 41% | 3.9 |
| Conjugate 43 | aGFP HC:4x pAMF | iADC | Compd 401 | Compd 101 | 52% | 3.9 |
| Conjugate 46 | | | Compd 401 | Compd 201 | 88% | 3.9 |
| Conjugate 54 | | | Compd 401 | Compd 201 | 33% | 3.9 |
| Conjugate 44 | | | Compd 103 | Compd 101 | 44% | 3.9 |
| Conjugate 45 | | | Compd 501 | Compd 101 | 54% | 3.9 |
| Conjugate 47 | | | Compd 401 | Compd 301 | 53% | 3.9 |

TABLE 3-continued

| # | mAb | Conjugation type | Conjugated TLR agonist | Conjugated cytotoxin | % TLR | DAR |
|---|---|---|---|---|---|---|
| Conjugate 49 | sofituzumab HC:4x | iADC | Compd 401 | Compd 101 | 70% | 3.9 |
| Conjugate 55 | pAMF | | Compd 401 | Compd 101 | 43% | 3.9 |
| Conjugate 48 | trastuzmab HC:4x pAMF | iADC | Compd 401 | Compd 101 | 56% | 3.9 |
| Conjugate 56 | aFolR HC:4x | iADC | Compd 701 | Compd 101 | 41% | 5.9 |
| Conjugate 57 | pAMF, LC:2x pAMF | | Compd 801 | Compd 101 | 31% | 5.9 |
| Conjugate 42 | aFolR HC:2x pAMF, LC:2x Qtag | Site-specific iADC | Compd 401 | Compd 102 | 50% | 5.9 |

Example 15

In vitro cytotoxicity of antibody drug conjugate (ADC), immunostimulatory-antibody-conjugate (ISAC), and immunomodulatory antibody drug conjugate (iADC)

ADCs, ISACs and iADCs were tested in cytotoxicity assays on target positive and negative cells.

FOLR1-positive KB or Igrov1 cells, FOLR1-negative A549 cells, Her2 positive SKBR3 cells and Her2 negative MDA-MB-468 cells, Muc16-positive OVCAR3 and Muc16-negative Skov3 were maintained in Ham's F-12: high glucose DMEM (50:50) (Corning) supplemented with 10% heat-inactivated fetal bovine serum (Corning), 1% Penicillin/Streptomycin (Corning) and 2 mmol/L-glutamax (Thermo Fisher Scientific). Adherent cells were washed twice with PBS, harvested with Acutase and counted by the Vi-CELL cell viability analyzer. A total of 625 cells were seeded in each well of a 384-well flat bottom white polystyrene plate. ADC, ISAC, and iADC conjugates were formulated at 2-fold starting concentration in the cell culture medium and filtered through MultiScreenHTS 96-Well Filter Plates (Millipore; Billerica, Mass.). Serial dilutions of test samples (1:3 serial dilution starting from 100 nM) was added into treatment wells. Assay plates were cultured at 37° C. in a CO2 incubator for 120 hrs before assay. For cell viability measurement, 30 µL of Cell Titer-Glo® reagent (Promega Corp. Madison, Wis.) was added into each well, and plates were processed as per product instructions. Relative luminescence was measured on an ENVISION® plate reader (Perkin-Elmer; Waltham, Mass.). Relative luminescence readings were converted to percent viability using untreated cells as controls. Data was fitted with non-linear regression analysis, using a log(inhibitor) vs. response-variable slope, 4-parameter fit with GraphPad Prism (GraphPad v 5.0, Software; San Diego, Calif.). Cell killing activity is reported in Table 2, Table 4 and Table 5 as EC50 (the midpoint of the curve, or concentration at which 50% of the maximum effect was observed) and killing span (the total percentage of cells that are no longer viable relative to an untreated control at the maximum effect level of the test article).

All the Compound 101, Compound 201, and Compound 102 conjugated ADCs and iADCs tested showed potent specific cell killing activity on target positive cells and no cell killing on target negative cells (Tables 4, 5, 6, 7). Anti-GFP antibody conjugated to the same cytotoxic warhead did not show any cell killing on the target positive nor negative cells, indicating that the cell killing is mediated by target binding and there is minimal non-specific killing caused by free toxic warhead release or endocytosis. Unconjugated antibodies, free TLR7 agonist and ISACs did not show any cell killing in this study. Compound 301 conjugated anti-FolR1 ADCs and iADCs showed potent cell killing activity on KB cells, but also showed reduced non-specific cell killing on target negative A549 cells (Table 5). Compound 301 conjugated anti-GFP ADC also showed weak non-specific cell killing on both KB and A549 cells, which may be due to non-specific internalization (endocytosis) of the ADCs (Table 5).

TABLE 4

SUMMARY OF CELL KILLING EC50 AND SPAN FOR EXPERIMENT #1

| | | | | Cell Killing on FolR1 + Igrov1 Cells | |
|---|---|---|---|---|---|
| Conj. | Sample Description | % of Compd 401 | DAR | EC50 (nM) | Span (%) |
| 25 | anti-FolR1 IgG | NA | NA | NK | NK |
| 30 | anti-GFP IgG | NA | NA | NK | NK |
| 1 | anti-FolR1-Compd 101 ADC | NA | 4 | 0.03 | 76 |
| 5 | anti-FolR1- Compd 401 ISAC | 100.0 | 4 | NK | NK |
| 31 | anti-FolR1-Compd 401/Compd 101 iADC | 35.5 | 4 | 0.22 | 57 |
| 32 | anti-Fo1R1-Compd 401/Compd 101 iADC | 46.7 | 4 | 0.89 | 71 |
| 33 | anti-Fo1R1-Compd 401/Compd 101 iADC | 65.4 | 4 | 0.25 | 42 |
| 34 | anti-GFP-Compd 401/Compd 101 iADC | 28.1 | 4 | NK | NK |
| 35 | anti-GFP-Compd 401/Compd 101 iADC | 44.3 | 4 | NK | NK |
| 36 | anti-GFP-Compd 401/Compd 101 iADC | 66.8 | 4 | NK | NK |
| | Compound 4 | NA | NA | NK | NK |
| | Compound 1 | NA | NA | 2.1 | 86 |

NK indicates no cell killing detected
NA indicates not applicable

TABLE 5

SUMMARY OF CELL KILLING EC50 AND SPAN FOR EXPERIMENT #2

| Conj. # | Sample Description | % TLR agonist | DAR | Cell Killing on KB (FolR1+) | | Cell Killing on A549 (FolR1−) | |
|---|---|---|---|---|---|---|---|
| | | | | EC50 (nM) | Span (%) | EC50 (nM) | Span (%) |
| 37 | anti-FolR1 IgG+ Compd 401/Compd 101 | 41.8 | 3.9 | 0.22 | 80.6 | NK | NK |
| 38 | anti-FolR1 IgG+ Compd 103/Compd 101 | 41.4 | 3.9 | 0.29 | 83.9 | NK | NK |
| 39 | anti-FolR1 IgG+ Compd 501/Compd 101 | 56.6 | 3.9 | 0.16 | 103 | NK | NK |
| 52 | anti-FolR1 IgG+ Compd 401/Compd 201 | 86.6 | 3.9 | 0.38 | 91.3 | NK | NK |
| 41 | anti-FolR1 IgG+ Compd 401/Compd 301 | 40.6 | 3.9 | 0.03 | 105 | 8.0 | 102 |
| 42 | anti-FolR1 IgG+ Compd 401/Compd 102 | 50.0 | 3.9 | 0.87 | 78.7 | NK | NK |
| 25 | anti-FolR1 IgG | NA | NA | NK | NK | NK | NK |
| 30 | anti-GFP IgG | NA | NA | NK | NK | NK | NK |
| 43 | anti-GFP IgG+ Compd 401/Compd 101 | 52.4 | 3.9 | NK | NK | NK | NK |
| 44 | anti-GFP IgG+ Compd 103/Compd 101 | 44.1 | 3.9 | NK | NK | NK | NK |
| 45 | anti-GFP IgG+ Compd 501/Compd 101 | 54.4 | 3.9 | NK | NK | NK | NK |
| 46 | anti-GFP IgG+ Compd 401/Compd 201 | 88.3 | 3.9 | NK | NK | NK | NK |
| 47 | anti-GFP IgG+ Compd 401/Compd 301 | 53.0 | 3.9 | 21.8 | 99.8 | 13 | 103 |
| 48 | anti-Her2 trastuzumab+ Compd 401/Compd 101 | 56.0 | 3.9 | NK | NK | NK | NK |
| 49 | anti-MUC16 sofituzumab+ Compd 401/Compd 101 | 70.0 | 3.9 | NK | NK | NK | NK |

NK indicates no cell kill detected
NA indicates not applicable

TABLE 6

SUMMARY OF CELL KILLING EC50 AND SPAN FOR EXPERIMENT #2

| Conj. # | Sample Description | % TLR agonist | % monomer | DAR | Cell Killing on SKBR3 (Her2+) | | Cell Killing on MDA-MB-468 (Her2−) | |
|---|---|---|---|---|---|---|---|---|
| | | | | | EC50 (nM) | Span (%) | EC50 (nM) | Span (%) |
| 43 | anti-GFP - Compd 401/Compd 101 | 52 | 98.0 | 3.9 | NK | NK | NK | NK |
| 48 | anti-Her2 - Compd 401/Compd 101 | 56 | 98.5 | 3.9 | 0.05 | 85.7 | NK | NK |
| 30 | anti-GFP IgG | NA | NA | NA | NK | NK | NK | NK |
| 50 | anti-Her2 IgG | NA | NA | NA | 0.29 | 27.6 | NK | NK |
| NA | Compound 4 | NA | NA | NA | NK | NK | NK | NK |
| NA | Compound 1 | NA | NA | NA | 41.5 | 89.3 | 37.1 | 79.9 |

NK indicates no cell kill detected
NA indicates not applicable

TABLE 7

SUMMARY OF CELL KILLING EC50 AND SPAN FOR EXPERIMENT #2

| Conj. # | Sample Description | % TLR agonist | % monomer | DAR | Cell Killing on OVCAR3 (Muc16+) | | Cell Killing on Skov3 (Muc16−) | |
|---|---|---|---|---|---|---|---|---|
| | | | | | EC50 (%) | Span (%) | EC50 (nM) | Span (%) |
| 43 | anti-GFP - Compd 401/Compd 101 | 52 | 98.0 | 3.9 | NK | NK | NK | NK |
| 49 | anti-Muc16 - Compd 401/Compd 101 | 70 | 99.6 | 3.9 | 0.10 | 33.2 | NK | NK |
| 30 | anti-GFP IgG | NA | NA | NA | NK | NK | NK | NK |
| 51 | anti-Muc 16 IgG | NA | NA | NA | NK | NK | NK | NK |
| NA | Compound 4 | NA | NA | NA | NK | NK | NK | NK |
| NA | Compound 1 | NA | NA | NA | 40.5 | 69.1 | 155.4 | 78.2 |

NK indicates no cell kill detected
NA indicates not applicable

EXAMPLE 16

Anti-FolR1-Compound 101 ADC Induced Immunogenic Cell Death

In this example, the ability of anti-FolR1-Compound 101 ADC to induce immunogenic cell death on FolR1 positive cells was evaluated. Cellular ATP release, expression of Calreticulin on ADC treated FolR1 positive cells and activation of monocyte in PBMCs by ADC treated FolR1 positive cells was used as indicators of immunogenic cell death.

FOLR1-positive KB cells were obtained from ATCC and were maintained in Ham's F-12: high glucose DMEM (50:50) (Corning) supplemented with 10% heat-inactivated fetal bovine serum (Corning), 1% Penicillin/Streptomycin (Corning) and 2 mmol/L-glutamax (Thermo Fisher Scientific).

To measure ATP release and Calreticulin expression on KB cells after ADC treatment, a total of 100,000 KB cells in 250 ul of cell culture medium were seeded in each well of a 12-well flat bottom plate. ADC were formulated at 2-fold starting concentration in the cell culture medium and filtered through Costar Spin-X filter tubes. ADCs were added into treatment wells at a final concentration of 10 nM. Assay plates were cultured at 37° C. in a CO2 incubator for 48 hrs. The condition cell culture medium was collected and the ATP concentration in the medium were measure by ENLITEN ATP assay system from Promega. The calreticulin expression on the KB cell surface was detected by staining the cells with a recombinant anti-calreticulin antibody (EPR3924) from Abcam.

Isolated monocyte or PBMC based assays were set up to evaluate if the anti-FolR1-Compound 101 ADC induced immunogenic cell death would activate antigen presentation by monocytes. PBMCs were isolated from human blood donors by Leukosep tube and Nycoprep 1.077 buffer according to the manufacture's recommendation. CD14+ monocytes were isolated by immunomagnetic negative selection from fresh PBMCs (StemCell #19359—EasySep Human Monocyte Isolation Kit). PBMCs and monocytes were cultured in RPMI supplemented with 10% heat-inactivated fetal bovine serum from Hyclone, 1% Penicillin/Streptomycin and 2 mmol/L-glutamax before the assay. On the day of assay, 300,000 of PBMC or 30,000 of monocytes in 40 ul of culture medium were seeded in 96-well cell culture plates. 40 ul of the test articles (formulated at 3× of starting concentration, 1:10 serial dilution) and 40 ul of 10,000 Oregon green stained target cells were then added into the well. The cell mixtures were co-cultured in the presence of test articles and 10 ug/ml LPS-RS for 48 hr. Cells were collected by 0.25% trypsin and then stained with a-hCD14-APC (BioLegend 301808), a-hCD86-PE/Cy7 (Life Tech 25-0869-42), and a fixable viability dye-eFluor450 (Life Tech 65-0863-18), in the presence of human Fc Block (BD564220). Cells were washed, fixed with 2% PFA overnight, and read on the Attune NxT cytometer (Thermo Fisher). Data is presented as the % of CD86+ cells within the CD14+ population and plotted by log(agonist) vs. response, variable slope, three parameter curve fit (Log transform) using GraphPad Prism software.

Figure 1B:
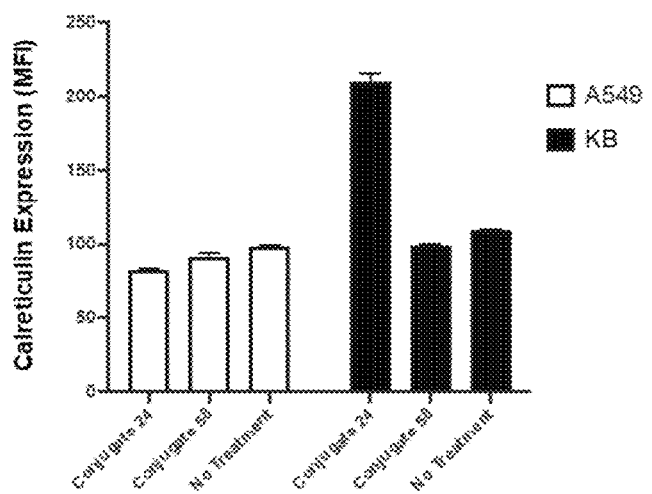
Figure 2A:
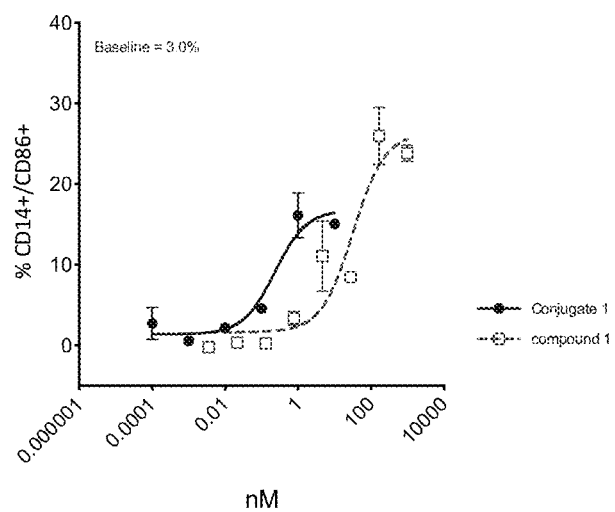
FIGS. 2A-2D, respectively, illustrate monocyte activation induced by immunogenic cell death on FolRα positive KB cells in the presence of certain free compounds and anti-FolR1-ADCs described herein. Data shown is for treated isolated monocytes (two donors, FIG. 2A and FIG. 2B), and treated isolated PBMCs (two donors, FIG. 2C and FIG. 2D).
Figure 2B:
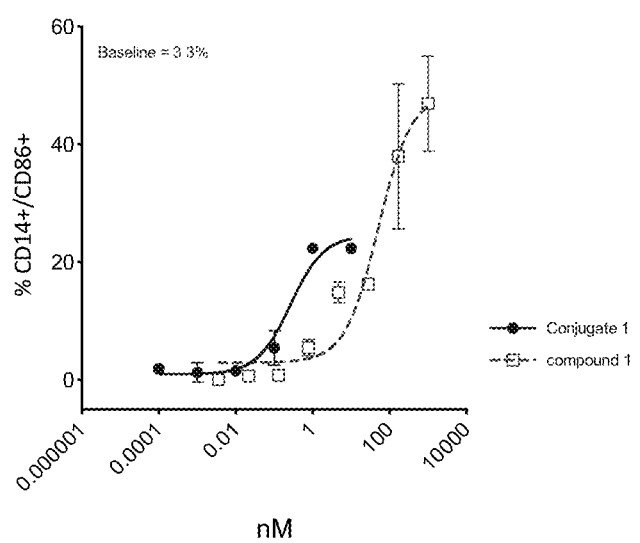
Figure 2C:
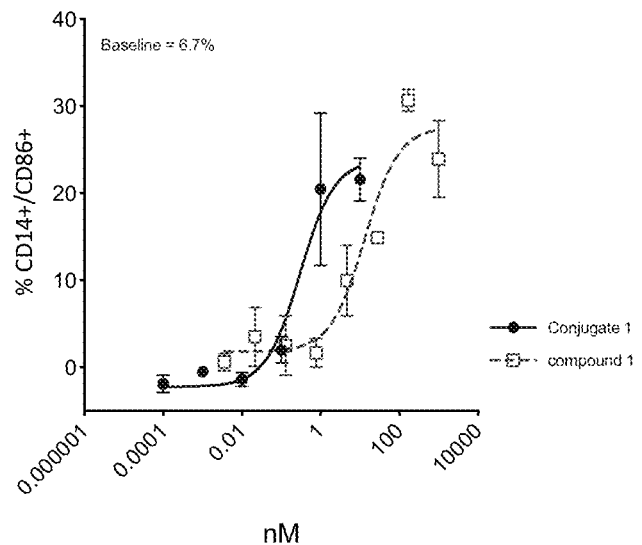
Figure 2D:
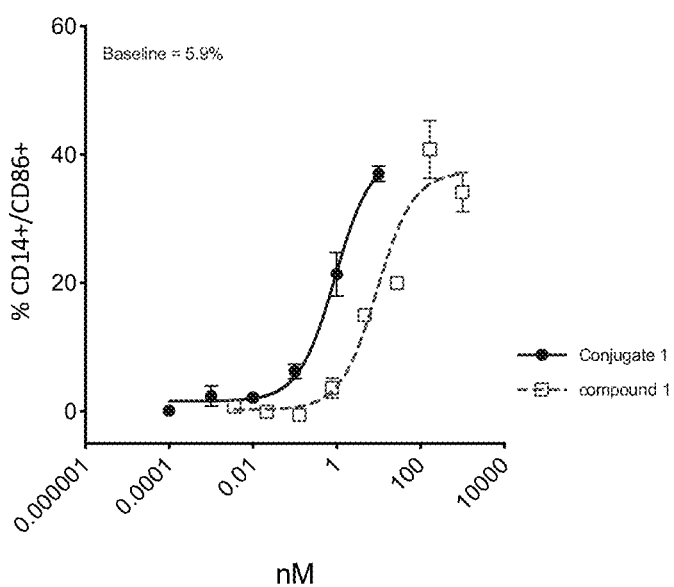
Figure 3A:
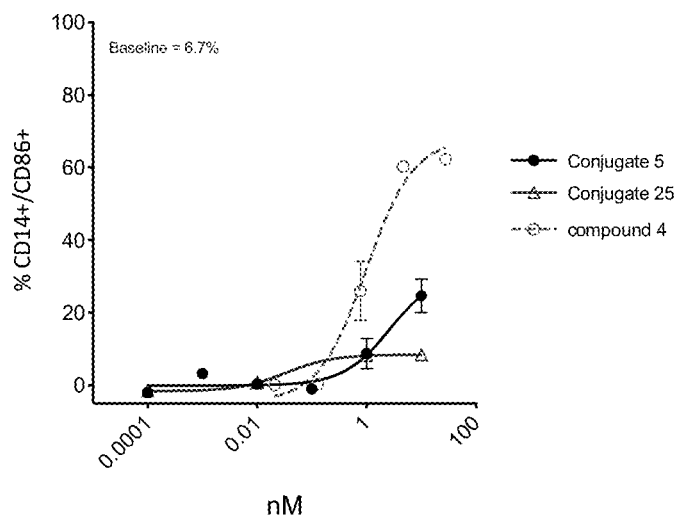
FIGS. 3A-3D, respectively, illustrate monocyte activation in isolated PBMCs (two donors, FIG. 3A and FIG. 3B) treated with free compounds and anti-FolR1-immunostimulatory antibody conjugates (ISACs).
Figure 3B:
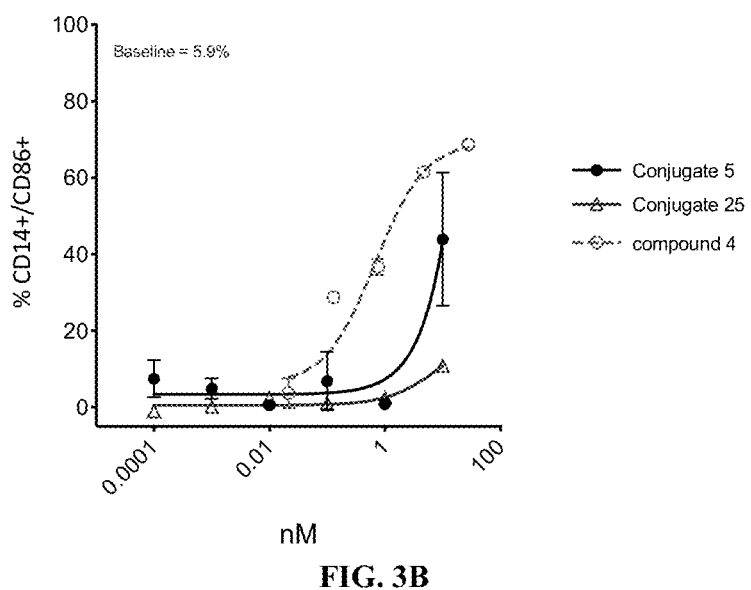
Figure 3C:
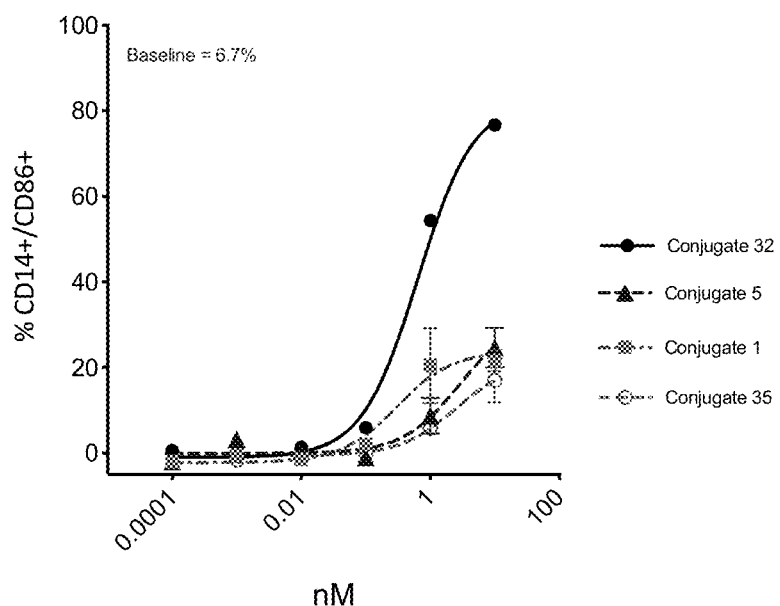
Figure 3D:
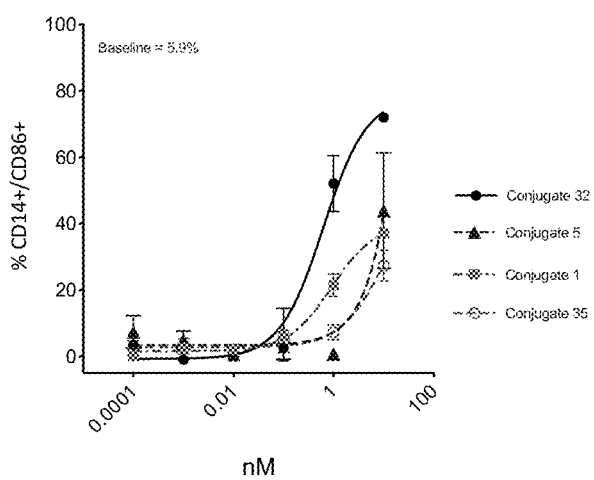
Figure 4A:
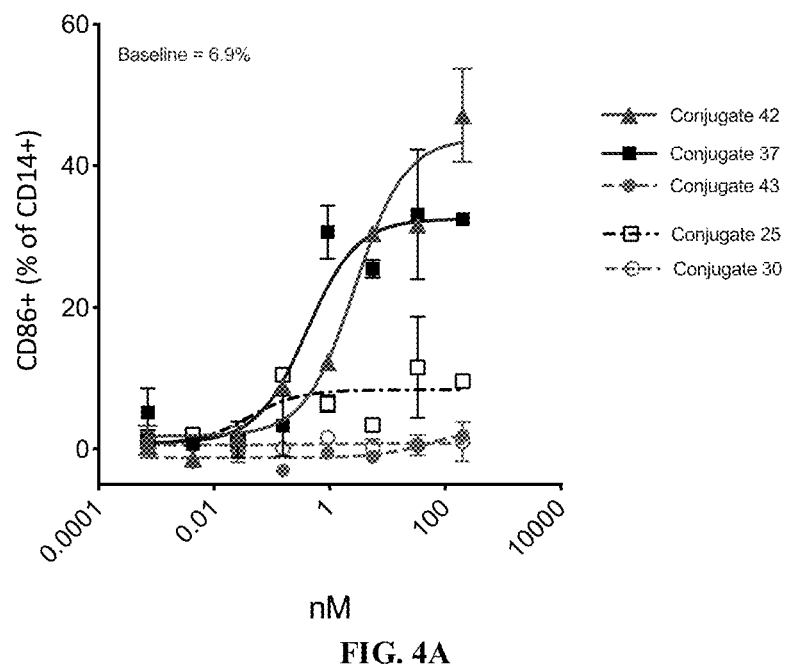
Figure 4B:
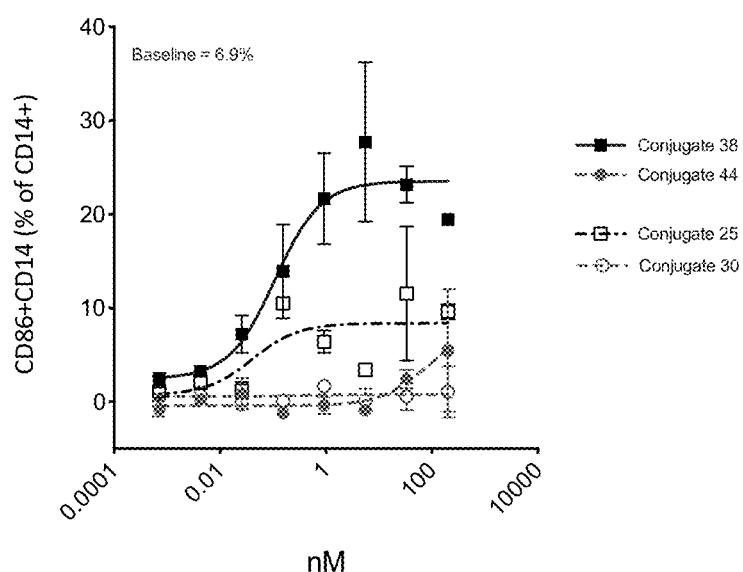
Figure 4C:
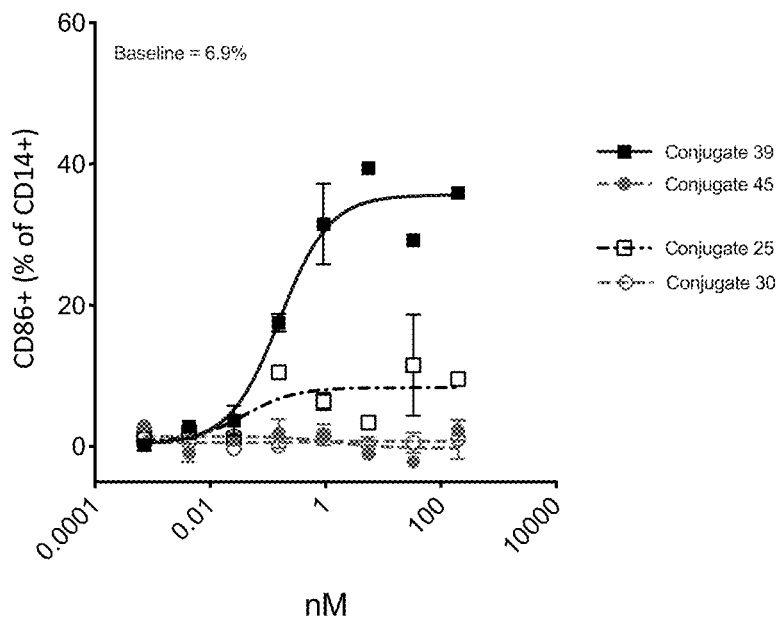
Figure 4D:
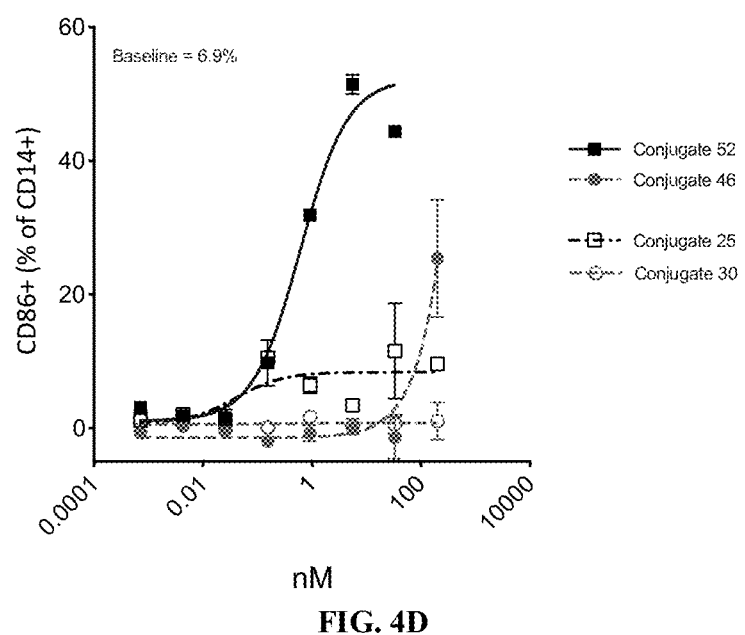

Treating KBs with anti-FolR1-Compound 101 ADC induced immunogenic cell death, indicated by ATP released in the cell culture medium and Calreticulin expression on the cell surface (FIG. 1 A, B). This effect is dependent on FolR1 expression on the KB cells since these markers were not observed on FolR1 negative A549 cells. The induced immunogenic cell death is specific to anti-FolR1-Compound 101 ADC since an anti-GFP antibody conjugated to Compound 101 did not show any sign of immunogenic cell death on KB cells. Immunogenic cell death induced by anti-FolR1-Compound 101 ADC was further confirmed by activation of isolated monocytes (FIG. 2 A, B) and monocytes in the PBMCs by the dying cells (FIG. 2C, D).

Example 17

ISAC and iADC Induced Monocyte Activation

This example evaluates the ability of free TLR7 agonists, immunostimulatory antibody conjugates (ISACs) and immunostimulatory antibody drug conjugates (iADCs) to stimulate monocyte activation. PBMCs were treated with TLR7 agonist, ISAC and iADC in the presence of target positive cells, monocyte activation assay was indicated as percentage of CD14+/CD86+ cells as described in EXAMPLE 12.

TLR7 agonist Compound 401 and anti-FolR1-ISACs tested in this study activated monocyte in the presence of FolR1 positive KB cells. The monocyte activation activity was dependent on the TLR7/8 agonist since the unconjugated antibodies did not exhibit monocyte activity in the same assay (FIG. 3 A, B). Anti-FolR1-iADC induced greater monocyte activation compared to ISAC and ADC alone, indicating that the combination of TLR7/8 agonist and cytotoxic warhead has a synergistic effect on monocyte activation. The monocyte activation effect of anti-FolR1-iADCs is dependent on the anti-FolR1 antibody binding to the FolR1 on the target cells since an anti-GFP antibody conjugated to both Compound 401 and Compound 101 at similar ratio did not activate monocytes in the same assay (FIG. 3 C, D).

Anti-FolR1-iADCs conjugated to other TLR7/8 agonist and other cytotoxic drugs were also tested in the same monocyte activation assays. Potent monocyte activation activity was observed in the presence of FolR1 positive KB cells for all the anti-FolR1 iADCs tested. The monocyte activation effect of anti-FolR1 iADCs is dependent on the anti-FolR1 antibody binding to the FolR1 on the target cells since an anti-GFP antibody conjugated to the same TLR7/8 agonist and the same cytotoxic drug at similar ratio did not activate monocytes in the same assay (FIG. 4A, 4B, 4C, 4D, 4E).

Example 18

In Vivo Efficacy of ADC+ ISAC Combination Treatment

This example evaluates the response of animals bearing MC38-hFolRα tumors treated with an anti FolRa-(Compound 101) ADC (Conjugate 1) in combination with an anti FolRα-(Compound 401) ISAC (Conjugate 2).

Female C57BL/6 mice at 9-10 weeks of age were anesthetized with isoflurane and implanted subcutaneously into the right hind flank with $1\times10^6$ MC38-h FolRα (murine colon adenocarcinoma cells engineered to express human FolRα). Randomization and start of treatment were initiated when the average tumor size was approximately 125 mm$^3$ (designated as Day 0 post-treatment). The test articles and treatment groups for this study are outlined in Table 8 and Table 9, respectively. Historical data was used for Conjugate 1 as a single agent to serve as a reference. All test articles were formulated in 10 mM citrate pH 6.0, 10% sucrose. Body weight and tumor size were monitored 3×/week. Percent body weight change was calculated relative to animal weight on the day treatment was administered. Tumor growth inhibition (TGI) was calculated when the mean of the vehicle control group was >1,200 mm$^3$ and complete response (CR) was defined as the absence of any detectable or palpable tumor after treatment.

TABLE 8

LIST OF TEST ARTICLES

| Conjugate | Description |
|---|---|
| 1 | FolRα antibody 1848-B10 ADC (DAR = 4) comprising an anti-FolRα conjugated to Compound 101 at the Y180 and K42 sites |
| 2 | FolRα antibody 1848-B10 ISAC (DAR = 4) comprising an anti-FolRα conjugated to Compound 401 at the Y180 and F404 sites |

TABLE 9

LIST OF TREATMENT GROUPS

| Group | Treatment | Dose (mg/kg) | Dosing frequency | Route | N |
|---|---|---|---|---|---|
| 1 | Vehicle (PBS) | — | single | IV | 8 |
| 2 | Conjugate 1 (ADC) | 10 | single | IV | 8 |
| 3 | Conjugate 2 (ISAC) | 10 | single | IV | 8 |
| 4 | Conjugate 1 + Conjugate 2 (ADC + ISAC) | 10 + 10 | single | IV | 7 |

In this study, animals bearing established MC38-hFolRα tumors were treated once with the indicated antibody conjugates. FIG. 5A shows that Conjugate 1 was well tolerated and did not exhibit any body weight loss, while Conjugate 2 alone and the combination of Conjugate 1+Conjugate 2 resulted in minimal body weight loss (approximately 4-5%) with recovery within two days.

The effects of treatment on MC38-hFolRα tumor growth is illustrated in FIG. 5B. Treatment with single agents FolRα ADC Conjugate 1 or FolRα ISAC Conjugate 2 exhibited significant efficacy (approximately 50-80% tumor growth inhibition (TGI)) compared to vehicle control on day 11 when the mean of the vehicle control group was >1,200 mm$^3$. The combination of Conjugate 1+Conjugate 2 resulted in added benefit compared to single agents alone as evidenced by 105% TGI indicating tumor regression on day 11 and 5/7 tumor-free animals that showed complete response (CR) at the end of study on day 30. Monotherapy with the Conjugate 1 or Conjugate 2 did not elicit tumor regression or result in animals that achieved CRs.

Results from this study show that Conjugate 1 in combination with Conjugate 2 significantly enhanced anti-tumor efficacy compared to either single agent, suggesting synergy between the cytotoxic agent (ADC) and TLR 7/8 agonist (ISAC).

Example 19

In Vivo Efficacy of a Mixed DAR4 iADC

This example evaluates the activity of a mixed DAR4 iADC FolRα conjugated with a 1:1 ratio of a cytotoxic compound bearing linker precursor (Compound 101) and a TLR 7/8 agonist bearing linker precursor (Compound 401) in MC38-hFolRα tumors.

Female C57BL/6 mice at 8-9 weeks of age were anesthetized with isoflurane and implanted subcutaneously into the right hind flank with $1\times10^6$ MC38-hFolRα. Randomization and start of treatment were initiated when the average tumor size was approximately 125 mm$^3$ (designated as Day 0 post-treatment). The test articles and treatment groups for this study are outlined in Table 10 and Table 11, respectively. All test articles were formulated in 10 mM citrate pH 6.0, 10% sucrose. Body weight and tumor size were monitored 3×/week. Percent body weight change was calculated relative to animal weight on the day treatment was administered. Tumor growth inhibition (TGI) was calculated when the mean of the vehicle control group was >1,200 mm$^3$.

TABLE 10

LIST OF TEST ARTICLES

| Conjugate | Description |
|---|---|
| 3 | Anti-FolRα mixed iADC comprising an anti-FolRα antibody 1848-H01 conjugated at a mixed 1:1 ratio of Compound 101 and Compound 401 at the Y180 and F404 sites resulting in FolRα iADC with DAR = 2 for Compound 101 and DAR of 2 for Compound 401 |
| 1 | FolRα antibody 1848-B10 ADC (DAR = 4) comprised of an anti-FolRα conjugated to Compound 101 at the Y180 and K42 sites |
| 5 | Anti-FolRα ISAC (DAR = 4) comprised of an anti-FolRα antibody 1848-H01 conjugated to Compound 401 at the Y180 and F404 sites |

TABLE 11

LIST OF TREATMENT GROUPS

| Group | Treatment | Dose (mg/kg) | Dosing frequency | Route | N |
|---|---|---|---|---|---|
| 1 | Vehicle (PBS) | — | single | IV | 8 |
| 2 | Conjugate 3 (iADC) | 10 | single | IV | 7 |
| 4 | Conjugate 1 (ADC) + Conjugate 5 (ISAC) | 10 + 10 | single | IV | 8 |

Figure 6A:
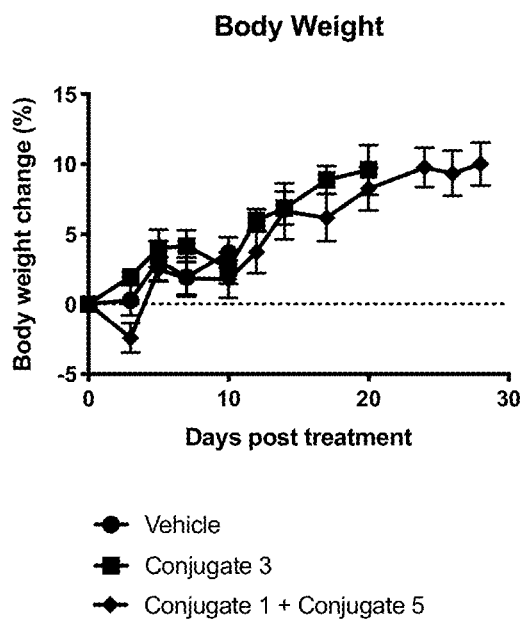
FIGS. 6A-6B illustrate mean percent body weight change and tumor response in animals bearing established MC38-hFolRα tumors treated with Conjugate 3 (mixed DAR4 iADC) or the combination of Conjugate 1 (ADC)+Conjugate 5 (ISAC).

In this study, animals bearing established MC38-hFolRα tumors were treated once with the indicated dose of antibody conjugates. FIG. 6A shows that iADC Conjugate 3 was well tolerated and did not exhibit any body weight loss, while the combination of Conjugate 5+Conjugate 1 resulted in minimal body weight loss (approximately 2%) with recovery within two days.

Figure 6B:
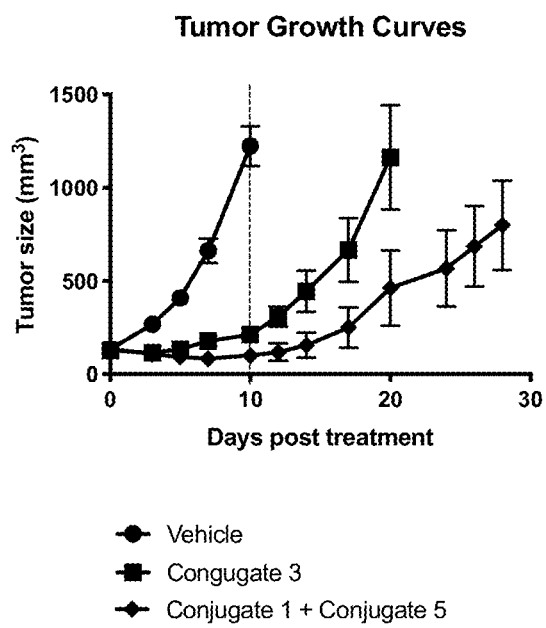

The effects of treatment on MC38-hFolRα tumor growth is illustrated in FIG. 6B. As previously observed, co-administration of a FolRα ADC (Conjugate 1) and FolRα ISAC (Conjugate 5) resulted in significant anti-tumor activity (103% TGI) compared to the vehicle on day 10 when the mean of the vehicle control group was >1,200 mm$^3$.

Conjugate 1 (ADC) and Conjugate 5 (ISAC) each had an approximate DAR of 4. Conjugate 3 (iADC) had an approximate DAR of 2 for the cytotoxin and DAR of 2 for the immunomodulator. Thus, the iADC had a lower effective DAR for each individual payload, namely the cytotoxin and the immunomodulator. The results show that treatment with the FolRα iADC (Conjugate 3) demonstrated comparable activity on day 10 (92% TGI) as the co-administration of Conjugate 1 and Conjugate 5, despite having a lower DAR for the individual payloads, i.e., cytotoxin and immunomodulator. This data demonstrates that the iADCs can provide comparable results even with a lower effective DAR for each individual payload, i.e., cytotoxin and immunomodulator.

In conclusion, results show that Conjugate 3, a DAR4 mixed iADC with an anti-FolRa targeting antibody conjugated with a 1:1 ratio of Compound 101 and Compound 401, exhibited significant efficacy in MC38-hFolRα tumors similar to that observed by co-injection of a DAR4 FolRα ADC+DAR4 FolRα ISAC. The potency or degree of iADC activity may be modulated by utilizing different antibodies, increasing the DAR and/or modifying the ratios of the cytotoxic agent and TLR agonist.

Example 20

In Vitro Cytotoxicity of Cytotoxin-ADC, ISAC and iADC

In this example, anti-FolR1-Compd 103/Compd 101 iADC was tested in cytotoxicity assays on FolR1 positive KB cells and FolR1 negative A549 cells. Un-conjugated anti-FolR1 IgG, anti-GFP-Compd 103/Compd 101 iADC and un-conjugated anti-GFP IgG were used as negative controls in the assay.

KB and A549 cells were obtained from ATCC and were maintained in Ham's F-12: high glucose DMEM (50:50) supplemented with 10% heat-inactivated fetal bovine serum, 1% Penicillin/Streptomycin and 2 mmol/L-glutamax. Adherent cells were harvested with Accutase and counted by the Vi-CELL Cell Viability Analyzers. A total of 625 cells were seeded in each well of a 384-well flat bottom white polystyrene plate. Samples were formulated at 2-fold starting concentration in the cell culture medium and filtered through Costar spin-X 8161 centrifuge filter tubes. Serial dilutions of test antibody (1:3 serial dilution starting from 100 nM) was added into treatment wells. Assay plates were cultured at 37° C. in a $CO_2$ incubator for 120 hrs. For cell viability measurement, 30 µL of Cell Titer-Glo® reagent was added into each well, and plates were processed as per product instructions. Relative luminescence was measured on an ENVISION® plate reader and were converted to percent viability using untreated cells as controls. Data was fitted with non-linear regression analysis, using a log(inhibitor) vs. response-variable slope, 4-parameter fit with GraphPad Prism. Cell killing activity is reported in Table 12 as EC50 (the midpoint of the curve, or concentration at which 50% of the maximum effect was observed) and killing span (the total percentage of cells that are no longer viable relative to an untreated control at the maximum effect level of the test article).

Anti-FolR1-Compd 103/Compd 101 iADC showed potent specific cell killing activity on target positive KB cells and no cell killing on target negative A549 cells. Anti-GFP I-ADC conjugated to the same cytotoxic warhead and TLR7 agonist did not show any cell killing on the target positive nor negative cells, indicating that the cell killing is mediated by target binding and there is minimal non-specific killing caused by free toxic warhead release or endocytosis. Un-conjugated antibodies did not show any cell killing in this study. Table 12 shows data from this experiment.

TABLE 12

SUMMARY OF CELL KILLING EC50 AND SPAN

| Conj. # | Sample Description | % TLR | DAR | Cell Killing on KB (FolR1+) EC50 (nM) | Cell Killing on KB (FolR1+) Span (%) | Cell Killing on A549 (FolR1−) EC50 (nM) | Cell Killing on A549 (FolR1−) Span (%) |
|---|---|---|---|---|---|---|---|
| 38 | anti-FolR1+ Compd 103/Compd 101 | 41.4 | 3.9 | 0.29 | 83.9 | NK | NK |
| 44 | anti-GFP+ Compd 103/Compd 101 | 44.1 | 3.9 | NK | NK | NK | NK |

TABLE 12-continued

SUMMARY OF CELL KILLING EC50 AND SPAN

| Conj. # | Sample Description | % TLR | DAR | Cell Killing on KB (FolR1+) EC50 (nM) | Span (%) | Cell Killing on A549 (FolR1−) EC50 (nM) | Span (%) |
|---|---|---|---|---|---|---|---|
| NA | anti-FolR1 IgG | NA | NA | NK | NK | NK | NK |
| NA | anti-GFP IgG | NA | NA | NK | NK | NK | NK |

NK indicates no killing
NA indicates not tested

Example 21 iADC Induced Monocyte Activation

This example evaluates the ability of anti-FolR1-Compd 601/Compd 101 iADC to stimulate monocyte activation in isolated human PBMCs in the presence of FolR1 positive KB cells.

PBMCs were isolated from human blood donors by Leukosep tube and Nycoprep 1.077 buffer according to the manufacture's recommendation. PBMCs were cultured in RPMI supplemented with 10% heat-inactivated fetal bovine serum from Hyclone, 1% Penicillin/Streptomycin and 2 mmol/L-glutamax before the assay. On the day of assay, 300,000 PBMC in 40 ul of culture medium were seeded in 96-well cell culture plates. 40 ul of the test articles (formulated at 3× of starting concentration) and 40 ul of 10,000 FolR1 positive KB cells were added into the well. The cell mixtures were co-cultured in the presence of test articles and 10 ug/ml LPS-RS for 48 hr and collected by 0.25% trypsin. Cells were then stained with a-hCD14-APC (BioLegend 301808), a-hCD86-PE/Cy7 (Life Tech 25-0869-42), and a fixable viability dye-eFluor450 (Life Tech 65-0863-18), in the presence of human Fc Block (BD564220). Cells were washed, fixed with 2% PFA overnight, and read on the Attune NxT cytometer (Thermo Fisher). Data is presented as the % of CD86+ cells within the CD14+ population and plotted by log(agonist) vs. response, variable slope, three parameter curve fit (Log transform) using GraphPad Prism software.

Figure 7:
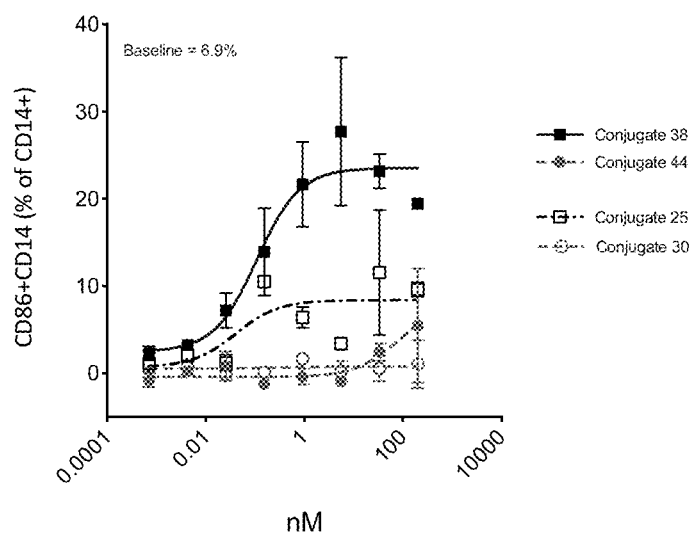
FIG. 7 illustrates iADC induced monocyte activation for certain iADCs described herein.
Figure 8A:
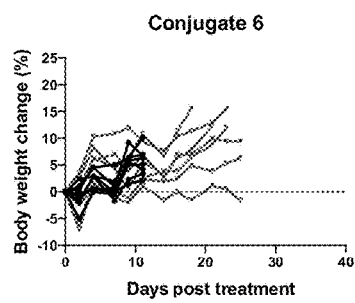
FIGS. 8A-8E illustrate individual percent body weight change for animals bearing established MC38-hFolRα tumors treated with a single 20 mg/kg dose of indicated mixed DAR4 iADC conjugates with 1:1 or 3:1 ratio of cytotoxin to TLR agonist (gray) or vehicle (black).
Figure 8B:
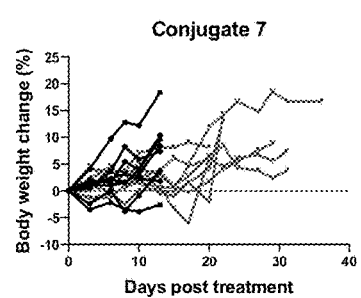
Figure 8C:
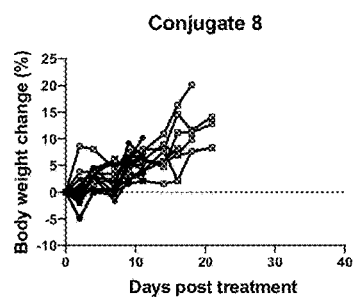
Figure 8D:
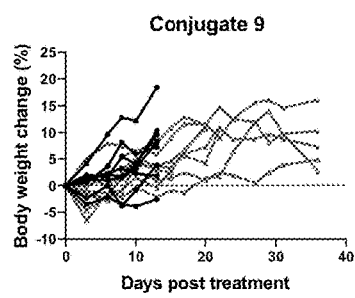
Figure 8E:
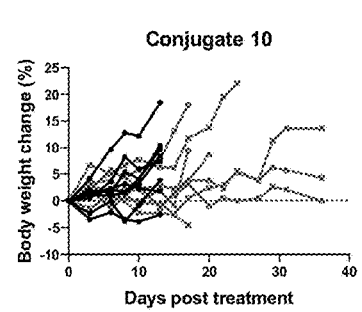
Figure 9A:
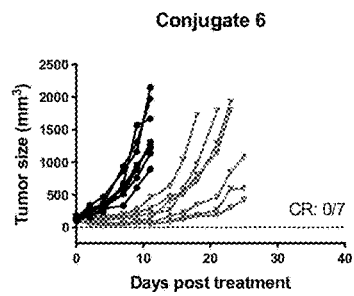
FIGS. 9A-9E illustrate individual tumor growth curves for animals bearing established MC38-hFolRα tumors treated with a single 20 mg/kg dose of indicated mixed DAR4 iADC conjugates with 1:1 or 3:1 ratio of cytotoxin to TLR agonist (gray) or vehicle (black). The number of animals that achieved complete response (CR) is indicated in each figure.
Figure 9B:
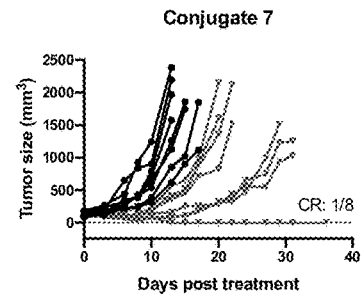
Figure 9C:
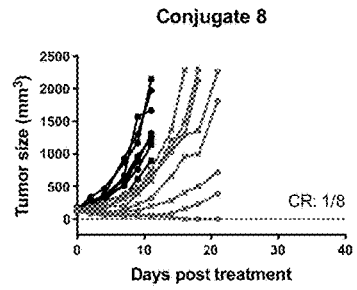
Figure 9D:
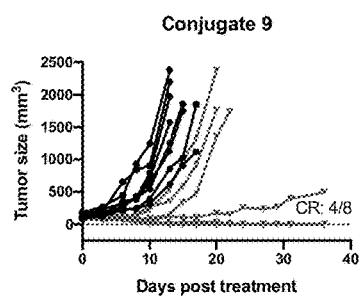
Figure 9E:
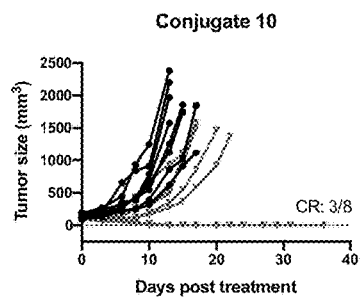

Anti-FolR1-Compd 601/Compd 101 iADC tested in this study activated monocytes in human PBMCs in the presence of FolR1 positive KB cells. The monocyte activation activity was dependent on the TLR7/8 agonist and cytotoxic drug since the un-conjugated antibodies did not show as much monocyte activation activity in the same assay (FIG. 7). The monocyte activation effect of anti-FolR1-iADCs is dependent on the anti-FolR1 antibody binding to the FolR1 on the target cells since an anti-GFP antibody conjugated to Compd 601/Compd 101 at similar ratio did not activate monocytes in the same assay (FIG. 7).

Example 22

In Vivo Efficacy of Mixed DAR4 iADCs with Different Ratios of Cytotoxin and TLR Agonists This example evaluates the activity of a mixed DAR4 FolRα iADC conjugated at a 1:1 or 3:1 ratio of a cytotoxic compound bearing linker precursor (Compound 101) and TLR agonists bearing linker precursors (Compound 601, 701 or 801), respectively, in MC38-hFolRα tumors.

In two independent studies, female C57BL/6 mice at 8-9 weeks of age were anesthetized with isoflurane and implanted subcutaneously into the right hind flank with $1\times10^6$ MC38-hFolRα. Randomization and start of treatment were initiated when the average tumor size was approximately 125 mm$^3$ (designated as Day 0 post-treatment). The test articles are listed in Table 13 and treatment groups are outlined in Tables 14 and 15. All test articles were formulated in 10 mM citrate pH 6.0, 10% sucrose. Body weight and tumor size were monitored 3×/week. Percent body weight change was calculated relative to animal weight on the day treatment was administered. Tumor growth inhibition (TGI) was calculated when the mean of the vehicle control group was >1,200 mm$^3$ and complete response was defined as the absence of any detectable or palpable tumor after treatment. To determine the durability of anti-tumor responses, naïve and tumor-free treated animals were rechallenged with a second implantation of $1\times10^6$ MC38-hFolRα into the contralateral (left hind) flank and monitored for tumor growth.

TABLE 13

LIST OF TEST ARTICLES

| Conjugate | Description |
|---|---|
| 6 | Anti-FolRα mixed iADC comprised of an anti-FolRα antibody 1848-H01 conjugated using pAMF at the Y180 and F404 sites to yield a 1:1 ratio of Compound 101 (49%) and Compound 701 (51%) (DAR 4 total) |
| 7 | Anti-FolRα mixed iADC comprised of an anti-FolRα antibody 1848-H01 conjugated using pAMF at the Y180 and F404 sites to yield a 1:1 ratio of Compound 101 (63%) and Compound 601 (37%) (DAR 4 total) |
| 8 | Anti-FolRα mixed iADC comprised of an anti-FolRα antibody 1848-H01 conjugated using pAMF at the Y180 and F404 sites to yield a 1:1 ratio of Compound 101 (49%) and Compound 801 (51%) (DAR 4 total) |
| 9 | Anti-FolRα mixed iADC comprised of an anti-FolRα antibody 1848-H01 conjugated using pAMF at the Y180 and F404 sites to yield a 3:1 ratio of Compound 101 (78%) and Compound 701 (22%) (DAR 4 total) |
| 10 | Anti-FolRα mixed iADC comprised of an anti-FolRα antibody 1848-H01 conjugated using pAMF at the Y180 and F404 sites to yield a 3:1 ratio of Compound 101 (84%) and Compound 601 (16%) (DAR 4 total) |

TABLE 14

LIST OF TREATMENT GROUPS (STUDY 1)

| Treatment | Dose (mg/kg) | Dosing frequency | Route | N |
|---|---|---|---|---|
| Vehicle (PBS) | — | single | IV | 8 |
| Conjugate 6 (mixed iADC, 1:1 ratio) | 20 | single | IV | 7 |
| Conjugate 8 (mixed iADC, 1:1 ratio) | 20 | single | IV | 8 |

TABLE 15

LIST OF TREATMENT GROUPS (STUDY 2)

| Treatment | Dose (mg/kg) | Dosing frequency | Route | N |
|---|---|---|---|---|
| Vehicle (PBS) | — | single | IV | 8 |
| Conjugate 7 (mixed iADC, 1:1 ratio) | 20 | single | IV | 8 |
| Conjugate 9 (mixed iADC, 3:1 ratio) | 20 | single | IV | 8 |
| Conjugate 10 (mixed iADC, 3:1 ratio) | 20 | single | IV | 8 |

Animals bearing established MC38-hFolRα tumors were administered a single dose of vehicle or 20 mg/kg of the indicated mixed FolRα iADC conjugate. In general, all mixed iADC conjugates were well tolerated with similar trends in body weight changes for vehicle control and iADC treated animals (FIG. 8A-E).

Figure 10:
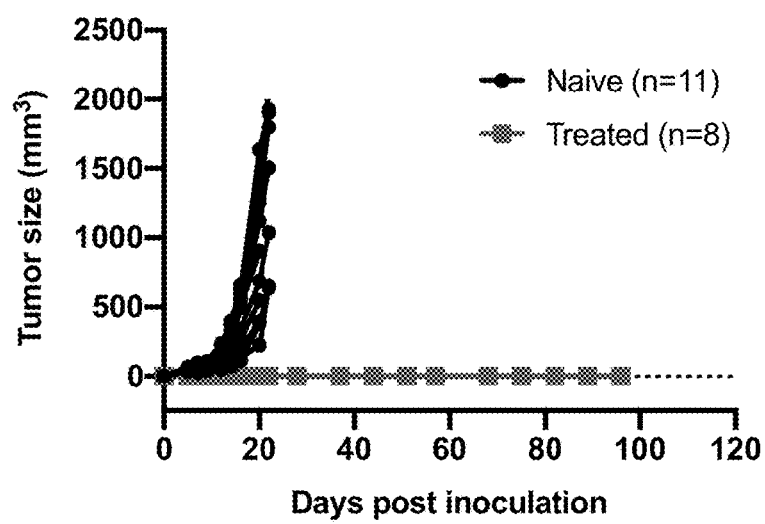
FIG. 10 illustrates individual measurements from rechallenge study where naïve (black) or mixed DAR4 iADC-treated animals with CRs from FIGS. 9B, 9D, and 9E (gray) were re-implanted with MC38-hFolRα cells.

The effects of treatment on MC38-hFolRα tumor growth is illustrated in FIG. 9. Treatment with all iADCs significantly inhibited tumor growth compared to vehicle control and resulted in TGIs ranging from ~80-95%. Continued monitoring showed that FolRa mixed iADCs with a 3:1 ratio of cytotoxin and TLR agonist (Conjugates 9 and 10) resulted in complete tumor regression or complete responses (CR) in ~50% of the animals (FIG. 9D-E). Meanwhile, iADCs with a 1:1 ratio (Conjugates 6-8) induced CR in 0-1 animals (FIG. 9A-C). On day 36 post-treatment for study 2, animals treated with iADC Conjugates 7, 9 and 10 that achieved CR were rechallenged with a second inoculation of MC38-hFolRα cells. As expected, control naïve animals rapidly developed tumors, whereas no tumor recurrence was observed in 8/8 iADC-treated animals in the absence of additional therapy (FIG. 10).

The results show that treatment with FolRα iADCs with different TLR agonists can induce completed tumor eradication and durable anti-tumor immunity, indicating formation of immunological memory. Furthermore, FolRα iADCs with a 3:1 ratio of cytotoxin to TLR agonist demonstrated superior efficacy compared to an iADC with a 1:1 ratio as evidenced by the higher incidence of complete responses. This supports the hypothesis that the potency or degree of iADC activity may be modulated by varying the ratios of cytotoxic agent and TLR agonist.

Example 23

In Vivo Efficacy of a Homogenous DAR6 iADC Using a 6× pAMF Conjugation Strategy

This example evaluates the activity of a homogenous DAR6 FolRα iADC conjugated using six pAMF (6× pAMF) sites at a 4:2 ratio of a cytotoxic compound bearing linker precursor Compound 101 and TLR agonist bearing linker precursor Compound 701, respectively, in MC38-hFolRα tumors. The homogenous 6× pAMF DAR6 FolRα iADC (Conjugate 13) was generated by assembly of a prefabricated light chain conjugated to Compound 701 at the K42 site (DAR 2) and the heavy chain conjugated to Compound 101 at the Y180 and F404 sites (DAR 4).

Female C57BL/6 mice at 8-9 weeks of age were anesthetized with isoflurane and implanted subcutaneously into the right hind flank with 1×10⁶ MC38-hFolRα. Randomization and start of treatment were initiated when the average tumor size was approximately 125 mm³ (designated as Day 0 post-treatment). The test articles and treatment groups are listed in Tables 16 and 17, respectively. All test articles were formulated in 10 mM citrate pH 6.0, 10% sucrose. Body weight and tumor size were monitored 3×/week. Percent body weight change was calculated relative to animal weight on the day treatment was administered. Tumor growth inhibition (TGI) was calculated when the mean of the vehicle control group was >1,200 mm³ and complete response was defined as the absence of any detectable or palpable tumor after treatment. To determine the durability of anti-tumor responses, naïve and tumor-free treated animals were re-challenged with a second implantation of 1×10⁶ MC38-hFolRα into the contralateral (left hind) flank with and monitored for tumor growth.

TABLE 16

List of test articles

| Conjugate | Description |
|---|---|
| 1 | Anti-FolRα DAR4 ADC comprised of an anti-FolRα antibody 1848-B10 conjugated using pAMF at the Y180 and F404 sites with Compound 101 (DAR 4 total) |
| 11 | Anti-FolRα DAR2 ISAC comprised of an anti-FolRα antibody 1848-B10 conjugated using pAMF at the F404 site with Compound 701 (DAR 2 total) |
| 13 | Anti-FolRα homogenous 6× pAMF DAR6 iADC comprised of an anti-FolRα antibody 1848-B10 conjugated using pAMF at the Y180 and F404 sites with Compound 101 and K42 site with Compound 701(DAR 6 [4 + 2] total) |

TABLE 17

List of treatment groups

| Treatment | Dose (mg/kg) | Dosing frequency | Route | N |
|---|---|---|---|---|
| Vehicle (PBS) | — | single | IV | 9 |
| Conjugate 1 (ADC) | 20 | single | IV | 8 |
| Conjugate 11 (ISAC) | 20 | single | IV | 8 |
| Conjugate 13 (iADC) | 20 | single | IV | 7 |

Figure 11:
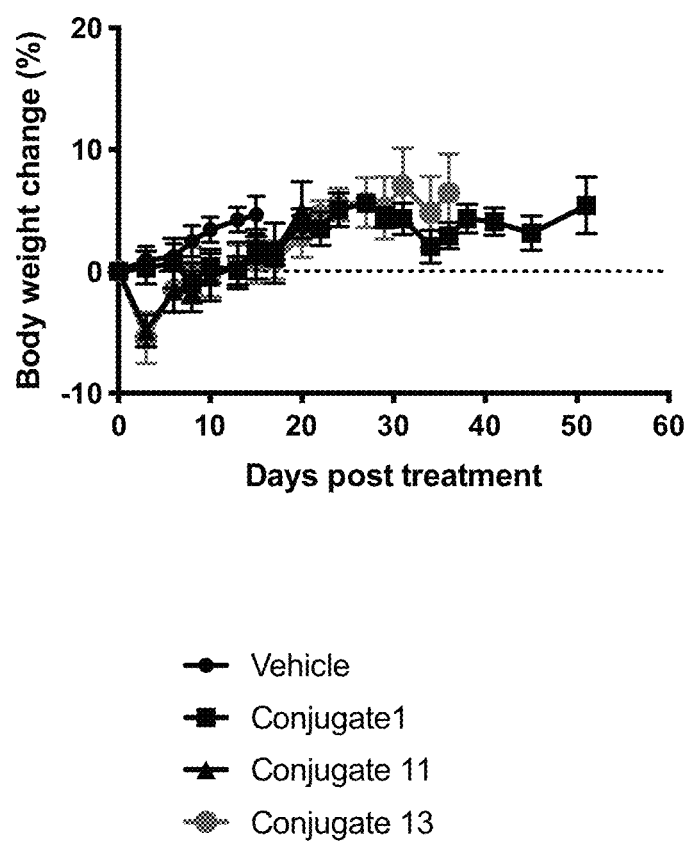
FIG. 11 illustrates mean percent body weight change for animals bearing established MC38-hFolRα tumors treated with a single dose of vehicle, 20 mg/kg Conjugate 1 (DAR4 ADC), 20 mg/kg Conjugate 11 (DAR2 ISAC) or 20 mg/kg Conjugate 13 (homogenous 4+2 iADC). Data are presented as mean±standard error of the mean (SEM).
Figure 12A:
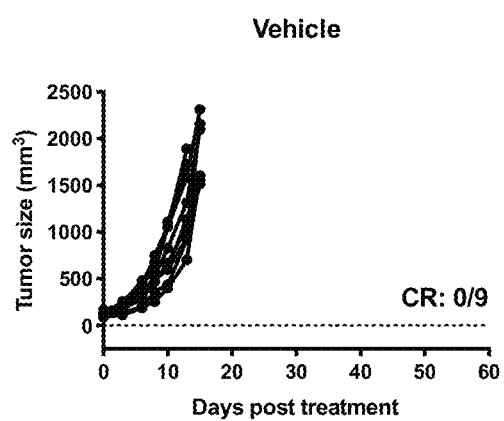
FIG. 12A-12D illustrate individual tumor growth curves for animals bearing established MC38-hFolRα tumors treated with a single dose of vehicle, 20 mg/kg Conjugate 1 (DAR4 ADC), 20 mg/kg Conjugate 11 (DAR2 ISAC) or 20 mg/kg Conjugate 13 (homogenous 4+2 iADC). The number of animals that achieved complete response (CR) is indicated in each figure.
Figure 12B:
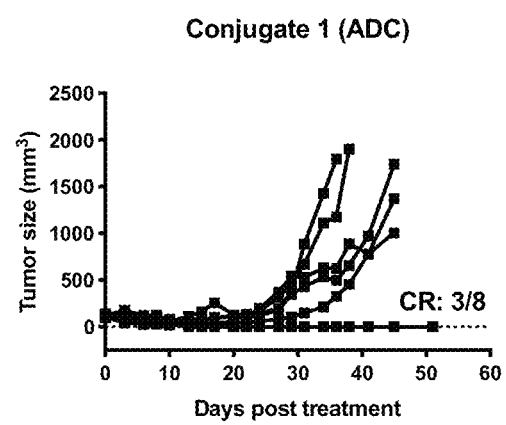
Figure 12C:
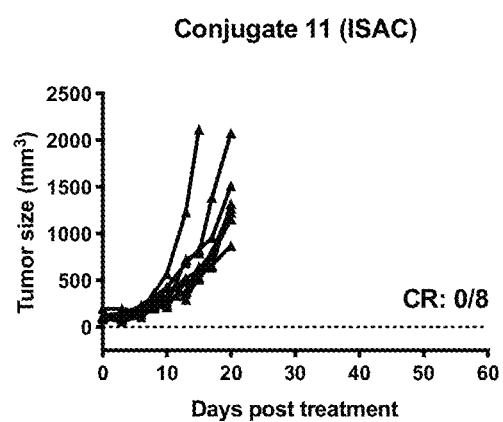
Figure 12D:
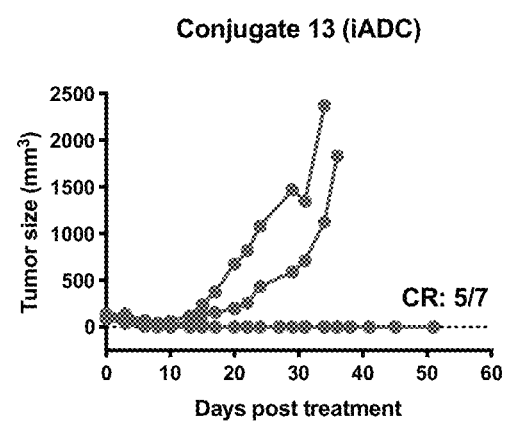

Animals bearing established MC38-hFolRα tumors were administered a single dose of vehicle or 20 mg/kg of the Conjugate 1 (ADC), Conjugate 11 (ISAC), or homogenous Conjugate 13 (iADC). Treatment with Conjugate 11 and Conjugate 13 containing TLR agonist Compound 701 induced a transient 5% body weight loss followed by recovery after approximately 2 days. Otherwise, all treatments were well tolerated showing normal trends in body weight gain (FIG. 11).

Figure 13:
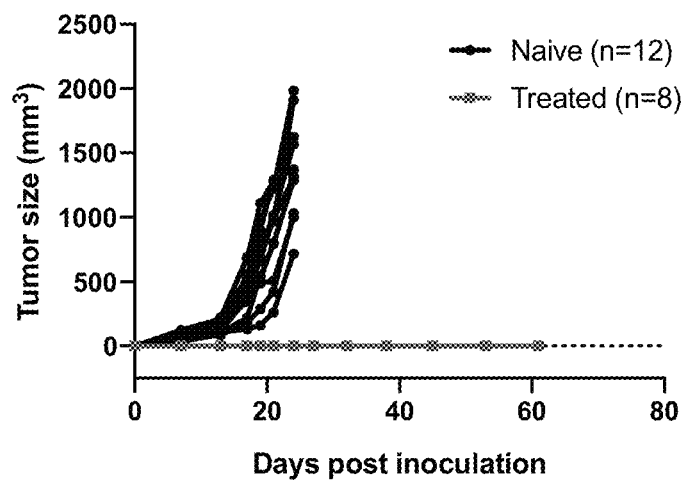
FIG. 13 illustrates individual measurements from rechallenge study where naïve (black) or ADC or homogenous iADC-treated animals with CRs from FIG. 5 (gray) were re-implanted with MC38-hFolRα cells.

The effects of treatment on MC38-hFolRα tumor growth is illustrated in FIG. 12. All treatment groups significantly inhibited tumor growth compared to vehicle control. Conjugate 1 (ADC) and Conjugate 13 (iADC) both induced tumor regression while Conjugate 11 (ISAC) did not. Tumor regrowth was observed the majority of animals (5/8) treated with Conjugate 1 (FIG. 12B). As a result, Conjugate 13 elicited more long-term survivors with CR compared to Conjugate 1 (71% vs 33%, respectively) (FIGS. 12B and 12D). The low frequency of CRs resulting from ADC monotherapy may be due to the immunogenic cell death (ICD) promoting properties of the cytotoxic component (Compound 101) of Conjugate 1. When animals with CRs were re-challenged with MC38-hFolRα cells, all animals treated with either ADC or iADC remained tumor-free without further treatment, while control naïve animals developed tumors (FIG. 13).

In conclusion, the FolRα iADC demonstrated superior activity compared to the FolRα ISAC and FolRα ADC alone as evidenced by a higher percentage of animals with complete remission and protective host immunity against tumor recurrence. These results suggest that the immunostimulatory TLR component of the iADC modality improves potency and anti-tumor activity compared to the ADC.

Example 24

Pharmacokinetics and In Vivo Stability of Homogenous iADCs with Different Conjugation Strategies This example evaluates the pharmacokinetic (PK) profile and drug stability of homogenous FolRα iADC variants conjugated at a 4:2 ratio of a cytotoxic compound bearing linker precursor Compound 101 and TLR agonist bearing linker precursor Compound 701, respectively, in non-tumor bearing mice. The different iADC variants utilized different FolRα antibodies and/or conjugation strategies.

Female non-tumor bearing C57BL/6 mice at 9-10 weeks of age were treated with a single intravenous 10 mg/kg dose of unconjugated antibodies (Conjugates 12, 14 and 16) or homogenous iADCs (Conjugates 13, 15 and 17). All test articles are described in Table 18. Plasma samples were collected at several time points to create a composite PK profile until day 14 for all test articles and determine in vivo stability/DAR until day 7 for all iADC variants (Conjugates 13, 15 and 17).

Figure 14:
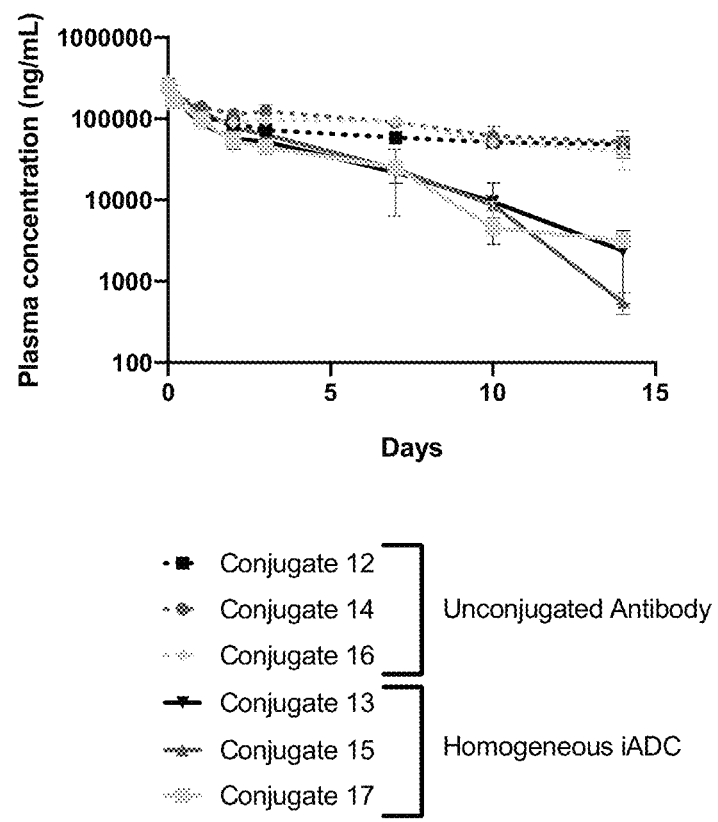
FIG. 14 illustrates the plasma concentration-time profile of unconjugated antibodies or homogenous iADCs until Day 14 in non-tumor bearing C57BL/6 mice following IV bolus administration of a 10 mg/kg dose. Data are presented as mean±standard deviation (SD).

The mean plasma concentration profiles are shown in FIG. 14 and pharmacokinetic parameters are listed in Table 19. Total antibody concentrations were determined by ELISA using an anti-human IgG antibody, and non-compartmental analysis was used to calculate PK parameters. Plasma half-life ($t_{1/2}$) and clearance (CL) for the unconjugated FolRα antibodies, Conjugates 12, 14 and 16, were determined to be ~ 10 days and ~ 5 mL/day/kg, respectively. All homogenous iADCs, Conjugates 13, 15 and 17, exhibited reduced plasma $t_{1/2}$ (approximately 2 days) with increased CL of approximately 18 mL/day/kg compared to their unconjugated counterparts.

Figure 15:
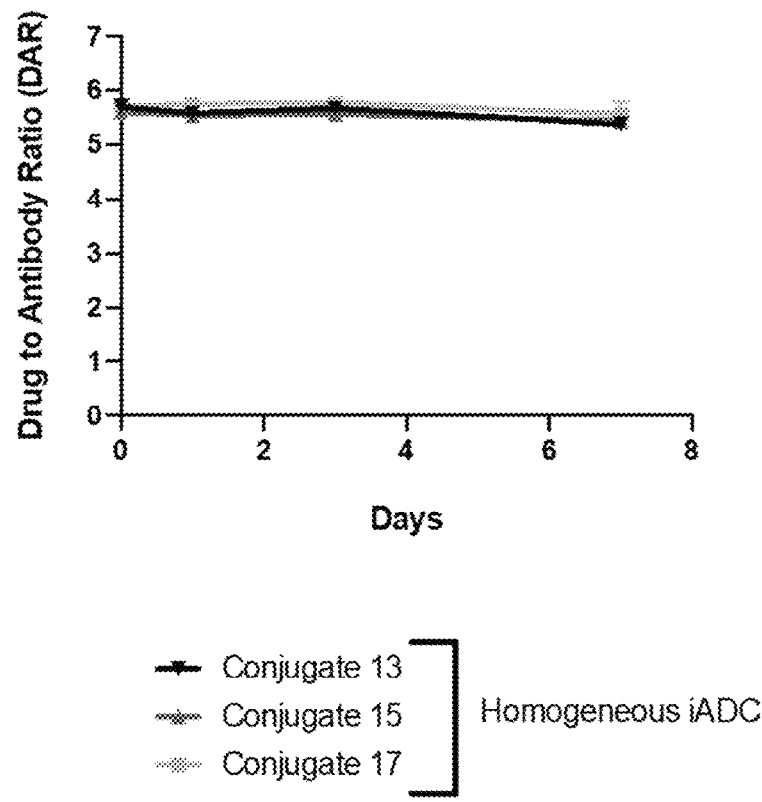
FIG. 15 illustrates homogenous iADCs are stable with no changes in average DAR until Day 7 in non-tumor bearing C57BL/6 mice following IV bolus administration of a 10 mg/kg dose. Data are presented as mean±standard deviation (SD) and corresponds to animals treated with homogeneous iADCs from FIG. 14.

In vivo stability of homogenous iADCs was evaluated by affinity capture LC/MS to determine average DAR values. As expected, Conjugates 13, 15, and 17 showed an average DAR of approximately 5.6 at the earliest time point (15 minutes). Further analysis revealed no changes in DAR, indicating that all iADCs were stable until day 7 (FIG. 15).

Overall, these results demonstrate that all homogenous iADC variants, regardless of the FolRα antibody or conjugation strategy utilized, have similar PK profiles and stability for up to 7 days. In spite of the reduced exposure of iADCs (compared to unconjugated controls), treatment with an iADC (Conjugate 13) induced complete remission and memory response in a greater percentage of animals compared to an ADC (Conjugate 1) (FIGS. 12 and 13).

TABLE 18

LIST OF TEST ARTICLES

| Conjugate | Description |
| --- | --- |
| 12 | Unconjugated anti-FolRα antibody 1848-B10 with pAMF at Y180, F404 and K42 sites |
| 13 | Anti-FolRα homogenous 6x pAMF DAR6 iADC comprised of an anti-FolRα antibody 1848-B10 conjugated using pAMF at the Y180 and F404 sites with Compound 101 and K42 site with Compound 701(DAR 6 [4 +2] total) |
| 14 | Unconjugated anti-FolRα antibody 1848-H01 with pAMF at Y180, F404 and K42 sites |
| 15 | Anti-FolRa homogenous 6x pAMF DAR6 iADC comprised of an anti-FolRα antibody 1848-H01 conjugated using pAMF at the Y180 and F404 sites with Compound 101 and K42 site with Compound 701(DAR 6 [4 +2] total) |
| 16 | Unconjugated anti-FolRα antibody 1848-H01 with pAcF at K42 site and pAMF at Y180 and F404 sites |
| 17 | Anti-FolRα homogenous 4:2 iADC comprised of an anti-FolRα antibody 1848-H01 conjugated via pAMF with Compound 101 at the Y180 and F404 sites and via pAcF with Compound 1001 at the K42 site |

TABLE 19

SUMMARY OF HOMOGENOUS IADC PK PARAMETERS

| Conjugate | Terminal $t_{1/2}$ (day) | $C_0$ (ug/mL) | $C_{max}$ ± S.E. (ug/mL) | $AUC_{0\text{-}last}$ ± S.E. (hr * ug/mL) | $AUC_{0\text{-}inf}$ (hr * ug/mL) | Clearance (mL/day/kg) | $V_{ss}$ (mL/kg) |
| --- | --- | --- | --- | --- | --- | --- | --- |
| Conjugate 12 | 11.8 | 271 | 264 ± 14 | 29,100 ± 1300 | 38,700 | 6.19 | 95.4 |
| Conjugate 14 | 9.33 | 270 | 265 ± 20 | 38,500 ± 3100 | 48,900 | 4.92 | 64.8 |
| Conjugate 16 | 7.79 | 296 | 291 ± 34 | 27,200 ± 1500 | 37,800 | 6.34 | 69.9 |
| Conjugate 13 | 2.63 | 237 | 233 ± 18 | 11,800 ± 700 | 12,000 | 20.0 | 67.9 |
| Conjugate 15 | 1.27 | 305 | 297 ± 6 | 14,300 ± 1100 | 14,300 | 16.8 | 47.8 |
| Conjugate 17 | 2.41 | 250 | 244 ± 10 | 11,200 ± 740 | 11,500 | 20.9 | 69.7 |

Example 25

TGase/PAMF Homogenous iADC Production Method

Dual conjugation of the transglutaminase (TGase) active primary anine-linker-TLR 7 agonist drug (Compound 1002) and DBCO-linker-warhead (Compound 101) were performed in a single-step reaction. The DBCO-Azide SPAAC reaction was performed using the pAMF non-natural amino acid incorporated into the protein at LC position K42 (SEQ ID NO: 2) and HC position Y180 (Kabat numbering) (SEQ ID NO:42) to give an overall drug antibody ratio (DAR) of 4 for Compound 101. The transglutaminase reaction was carried out at HC position Y296 by introducing the mutations Q295L/Y296Q/N297R into the protein sequence to give an overall DAR of 2 for Compound 1002. The conjugation reaction was performed with 1 mg/mL mAb, 0.1 U/mL TGase (Zedira GMbH. T001), 67 uM Compound 1002, 80 µM Compound 101, 10 mM EDTA, and 100 mM Tris HCl, pH 8.0. The conjugation reaction was carried out for 16 hours at 37° C. Unreacted drug and TGase enzyme were removed by preparative SEC (Superdex 200 Increase 10/300 GL, GE Life Sciences, 28990944) and the conjugate was stored in 10 mM Citrate, 9% Sucrose, pH 6.0. DAR analysis was performed by LCMS (Agilent Technologies 6520 Accurate-Mass Q-TOF LC/MS).

Example 26

6xpAMF Homogenous iADC Production

Trastuzumab LC (SEQ ID NO:2) containing pAMF at position K42 conjugated with DBCO-linker-TRL7 agonist drug (Compound 701). The conjugation reaction was performed at a protein concentration of 1 mg/mL and Compound 701 to LC ratio of 3. The reaction was incubated for 16 hr at room temperature in 1×PBS buffer and 25% DMSO. After removal of free Compound 701 by dialysis, the pre-conjugated LC (trastuzumab LC-701) was used as a reagent in cell-free system to produce 1848-H01 iADC intermediate with pAMF incorporated on HC (SEQ ID NO:1) as described in Zimmerman et al., 2014, *Bioconjugate Chem.*, 25 (2), 351-361, with the following modifications. A cell-free extract that has RF1 activity attenuated and chaperones helping IgG folding was treated with 75 µM iodoacetamide for 30 min at RT (20° C.) and added to a premix containing all other components except for IgG heavy chain plasmid and pre-conjugated LC. The final concentration in the protein synthesis reaction was 37% cell extract, 1 mM pAMF, 5 uM pAMF RS, 2 mM GSSG, 2 mM amino acids (except 0.5 mM for Tyrosine and Phenylalanine), 3 µg/mL aFolR heavy chain DNA containing an amber codon at the Y180 and F404 position, 1 mg/mL pre-conjugated trastuzumab LC and incubated at 25° C. for 16 h in a bioreactor at 20% DO and pH of 7.3. The iADC intermediate (Conjugate SP10541) was captured by MabSelect and polished using Capto Adhere Impress. Cytotoxin-linker-DBCO (Compound 101) was then conjugated to Conjugate 26 at drug to pAMF ratio of 3:1, protein concentration of 1 mg/mL in 1×PBS and 10% DMSO to yield Conjugate 15. The reaction mixture was incubated at room temperature for 16 hr. LC/MS was used to measure conjugation efficiency.

Example 27 pAcF/pAMF Homogenous iADC Production

Trastuzumab LC (SEQ ID NO:2) containing pAcF at position K42 was used as a reagent in cell-free system to produce 1848-H01 iADC intermediate with pAMF incorporated on HC (SEQ ID NO: 1). The 1848-H01 antibody containing pAcF on light chain (K42) and pAMF on heavy chain (Conjugate 16) was made the same way as described in Example 27, except that the conjugation of the TLR agonist to the light chain was performed after the synthesis of the heavy chain. Thus, pAcF containing trastuzumab light chain was added to the cell-free protein synthesis reaction at a concentration of 0.5 mg/mL and IgG containing pAcF at light chain residue K42 and pAMF at heavy chain residues Y180 and F404 was produced and purified as described above. The conjugation was carried out in two steps. The TLR agonist with aminooxy functional group (Compound 1001) was added to Conjugate 16 at a drug/pAcF ratio of 6:1, protein concentration of 45 mg/mL in 100 mM acetic acid at pH4.5. The reaction mixture was incubated at 30° C. for 16 hr, it was then neutralized using NaOH to pH 7. DBCO-linker-warhead (Compound 101) was added at a drug to pAMF ratio of 3:1 at protein concentration of 20 mg/mL and 10% DMSO. The reaction was incubated at room temperature for 8 hr with agitation. LC/MS was used to measure conjugation efficiency.

Example 28

In vitro cytotoxicity of homogeneous immunomodulatory antibody drug conjugate (iADC)

FolRα ADCs, ISACs and iADCs were tested in cytotoxicity assays on target positive and negative cells. The cytotoxicity assay conditions were similar to previous examples. The ADCs, ISACs, and iADCs tested in this Example are shown in Table 20.

TABLE 20

Test Articles for Cell Killing Experiment of Example 28

| Conjugate | Description |
|---|---|
| 22 | Anti-FolRα homogenous DAR2 ISAC comprised of an anti-FolRα antibody 1848-H01 with pAMF at the Y180 and K42 sites (both unjconjugated) and with Compound 1002 conjugated to Y296Q (DAR 2) |
| 23 | Anti-FolRα homogenous DAR2 ISAC comprised of an anti-FolRα antibody 1848-H01 with pAMF at the the Y180 and F404 sites (unconjugated) and K42 site conjugated with Compound 1001(DAR 2) |
| 24 | Anti-FolRα homogenous DAR4 ADC comprised of an anti-FolRα antibody 1848-H01 with pAMF at the Y180 and F404 conjugated with Compound 101 (DAR 4) |
| 25 | Anti-FolRα unjonjugated antibody control comprised of an anti-FolRα antibody 1848-H01 with pAMF at the Y180 and F404 (unconjugated) |

TABLE 20-continued

Test Articles for Cell Killing Experiment of Example 28

| Conjugate | Description |
|---|---|
| 26 | Anti-FolRα homogenous 6x pAMF DAR2 iSAC comprised of an anti-FolRα antibody 1848-H01 containing pAMF at the Y180 and F404 sites (unconjugated) and pAMF at the K42 site conjugated with Compound 701 (DAR 2) |
| 27 | Anti-FolRα homogenous DAR4 ADC comprised of an anti-FolRα antibody 1848-H01 with pAMF at the Y180 and K42 sites conjugated with Compound 101 and also containing an unconjugated to Y296Q transglutaminase site (DAR 4) |
| 28 | Anti-FolRα homogenous DAR6 iADC comprised of an anti-FolRα antibody 1848-H01 with pAMF at the Y180 and K42 sites conjugated with Compound 101 and also having Compound 1002 conjugated to Y296Q (DAR 4 + 2) = DAR 6 Total |
| 29 | Isotype control homogenous DAR6 iADC comprised of an anti-GFP antibody with pAMF at the Y180 and F404 sites conjugated with Compound 101 and also having Compound 1002 conjugated to Q295 (DAR 4 + 2) = DAR 6 Total |
| 15 | Anti-FolRα homogenous 6x pAMF DAR6 iADC comprised of an anti-FolRα antibody 1848-H01 conjugated using pAMF at the Y180 and F404 sites with Compound 101 and K42 site with Compound 701(DAR 6 [4 + 2] total) |
| 17 | Anti-FolRα homogenous 4:2 iADC comprised of an anti-FolRα antibody 1848-H01 conjugated via pAMF with Compound 101 at the Y180 and F404 sites and via pAcF with Compound 1001 at the K42 site |

All three homogeneous iADCs tested showed potent specific cell killing activity similar to anti-FolR1 ADCs on target positive cells and no cell killing on target negative cells (Table 21). The cell killing activity of the ADCs and iADCs were more potent than the free warhead Compound 1 on KB cells, which indicated that the ADCs and iADCs were more efficient in bringing the warheads into the cell than the free drug passively crossing the cell membrane. An anti-GFP iADC did not show any cell killing on the target positive nor negative cells, indicating that the cell killing is mediated by target binding and there is minimal non-specific killing caused by free toxic warhead release or endocytosis. Un-conjugated antibodies, free TLR7 agonist and ISACs did not show any cell killing in this study (Table 21).

TABLE 21

Summary of cell killing EC50 and Span

| | | KB | | A549 | |
|---|---|---|---|---|---|
| Sample ID | Sample Information | EC50 (nM) | Span (%) | EC50 (nM) | Span (%) |
| Conjugate 25 | anti-FolRα IgG | NK | NK | NK | NK |
| Conjugate 24 | 4x pAMF ADC | 0.25 | 90 | NK | NK |
| Conjugate 26 | 6x pAMF iSAC | NK | NK | NK | NK |
| Conjugate 15 | 6x pAMF iADC | 0.26 | 94 | NK | NK |
| Conj. 26/24 | 6x pAMF iSAC + 4x pAMF ADC | 0.28 | 57 | NK | NK |
| Conjugate 23 | pAcF/pAMF iSAC | NK | NK | NK | NK |
| Conjugate 17 | pAcF/pAMF iADC | 0.17 | 94 | NK | NK |
| Conjugate 22 | TG/pAMF iSAC | NK | NK | NK | NK |
| Conjugate 27 | TG/pAMF ADC | 0.18 | 91 | NK | NK |
| Conjugate 28 | TG/pAMF iADC | 0.25 | 95 | NK | NK |
| Conjugate 29 | anti-GFP TG/pAMF iADC | NK | NK | NK | NK |
| | Compound 7 | NK | NK | NK | NK |
| | Compound 1 | 1.40 | 96 | 7.7 | 82 |

NK indicates no cell killing detected

Example 29

ISAC and iADC Induced Immune Cell Activation

This example evaluates the ability of three homogeneous iADCs to stimulate the activation of different immune cell populations (monocyte, B cell, and DCs). Free TLR7 agonists, free hemiasterlin warhead, anti-FolRα-ADC, and the corresponding ISACs were used as controls in the experiment. PBMCs from two healthy donors were isolated using similar protocol as descripted in previous examples. PBMCs were treated with three homogeneous iADC and controls in the presence of FolR1 positive KB cells for two days. The immune cells were then stained with different cell population markers and activation markers. Monocyte activation was indicated as increase of CD86 expression on CD14+ cells. B cell activation was indicated as increase of CD86 expression on CD14-/Lin+/HLA-DR+ cells. Dendritic cells (DC) activation was indicated as increase of CD86 expression on CD14-/Lin-/HLA-DR+/CD123+ cells.

Figure 16A:
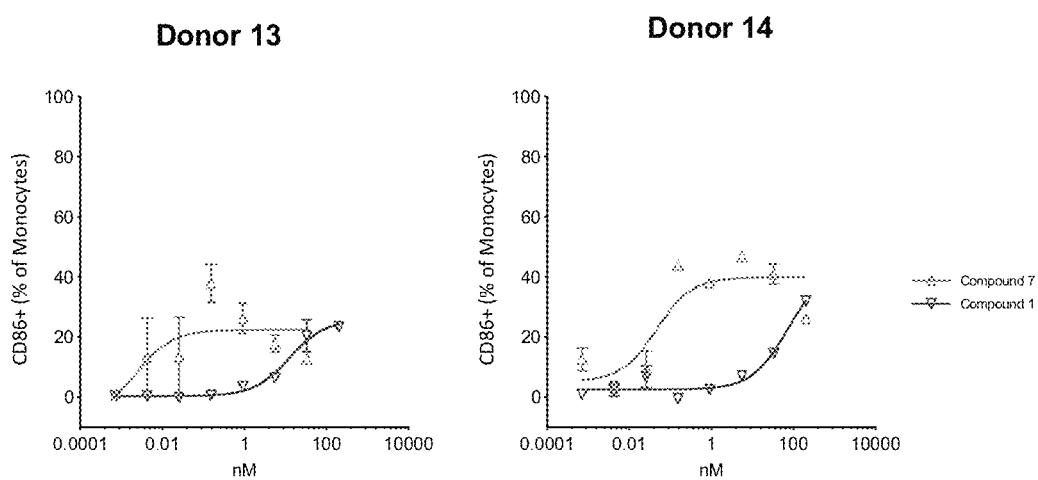
FIGS. 16A-16C illustrate TLR7 agonist-related (Compound 7) activation of monocytes (FIG. 16A), B cells (FIG. 16B) and DCs (FIG. 16C) vs. hemiasterlin warhead (Compound 1).
Figure 16B:
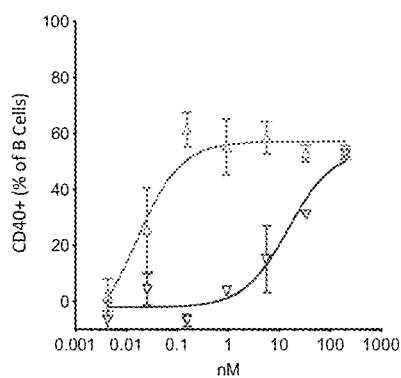
Figure 16B:
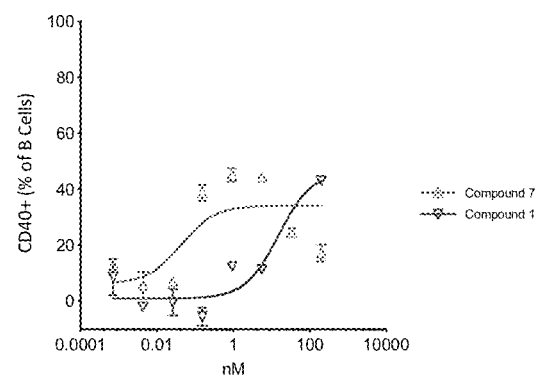
Figure 16C:
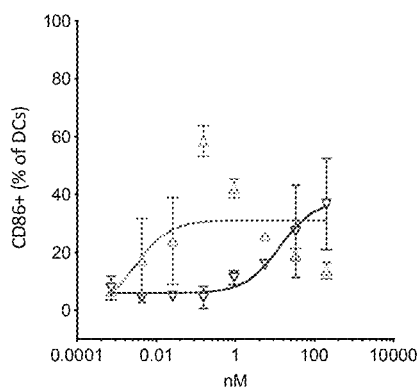
Figure 16C:
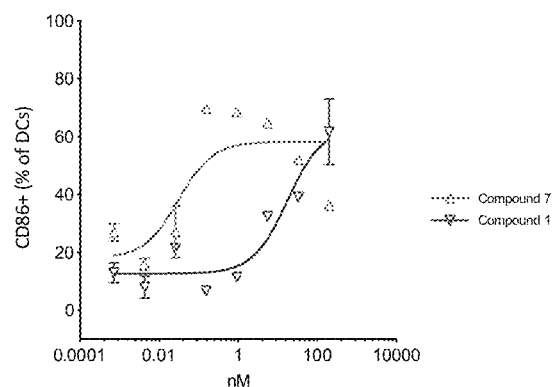
Figure 17A:
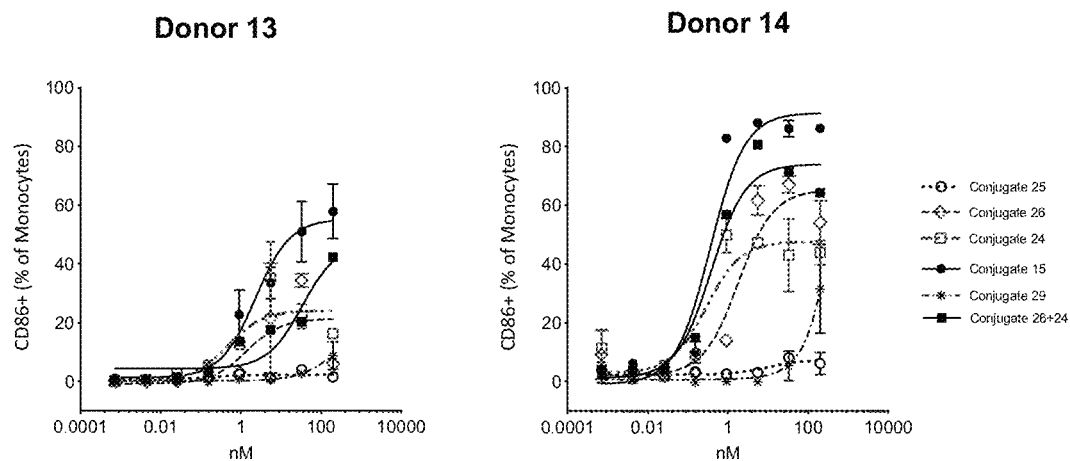
FIGS. 17A-17C illustrate anti-FolR1-iADC (generated by 6× pAMF; Conjugate 15)-related activation on monocytes (FIG. 17A), B cells (FIG. 17B) and DCs (FIG. 17C) compared to ISAC alone, ADC alone, or the combination of ISAC and ADC.
Figure 17B:
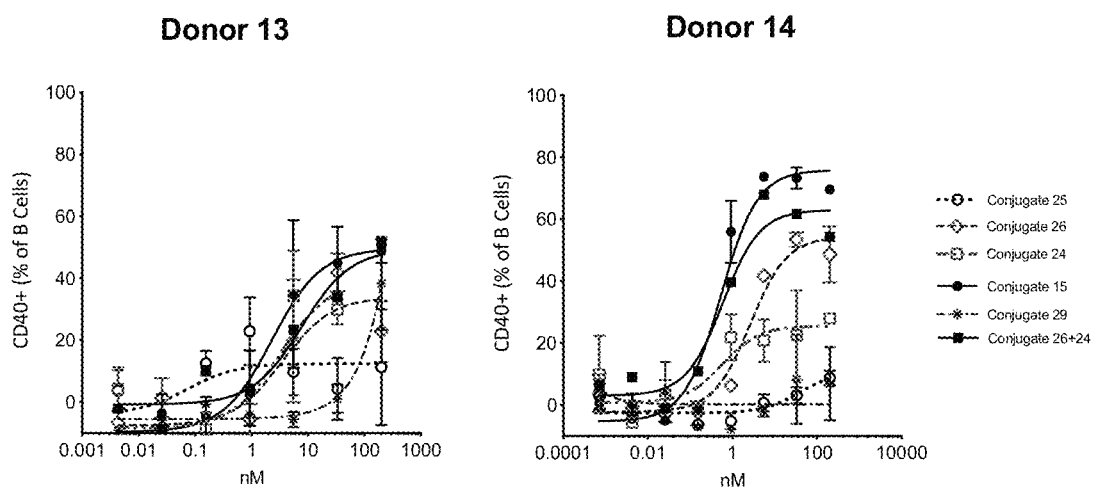
Figure 17C:
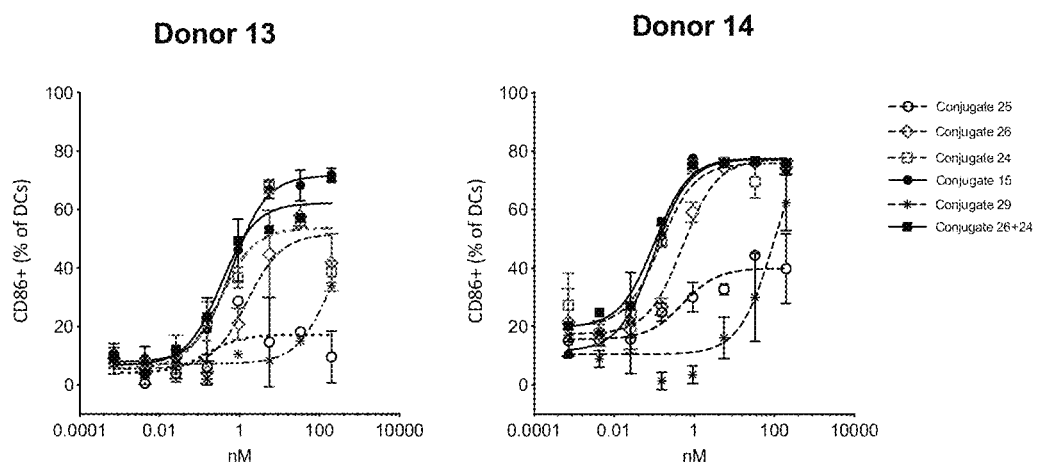
Figure 18A:
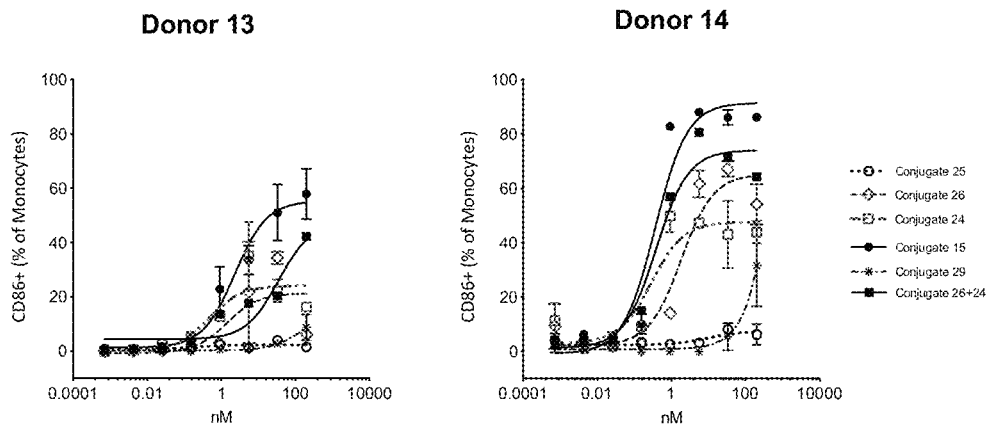
FIGS. 18A-18C illustrate anti-FolR1-iADC (4×pAMF+2xpAcF; Conjugate 17)-related activation on monocytes (FIG. 18A), B cells (FIG. 18B) and DCs (FIG. 18C) vs. anti-FolR1-ISAC (Conjugate 23) and anti-FolR1-ADC (Conjugate 24).
Figure 18B:
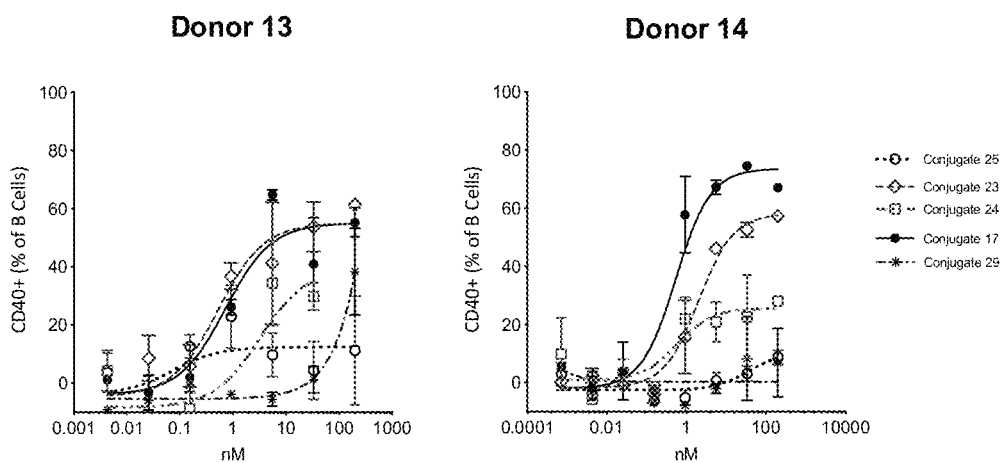
Figure 18C:
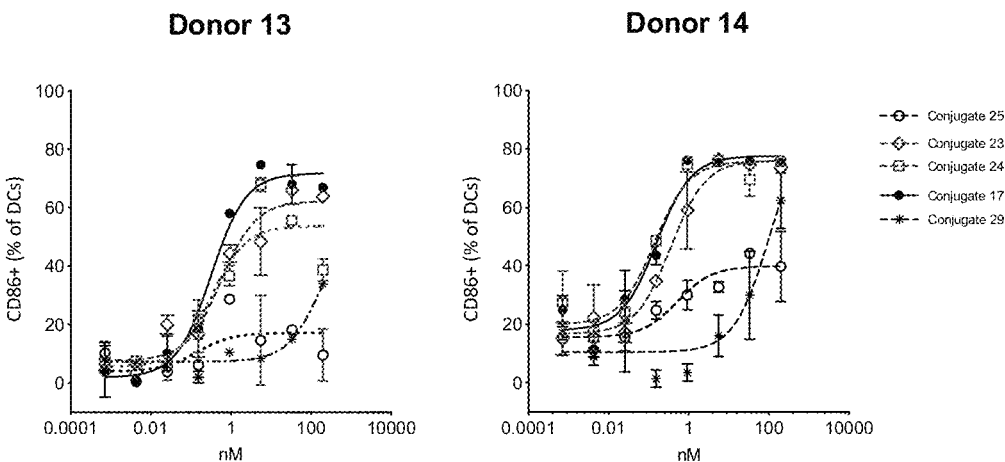
Figure 19A:
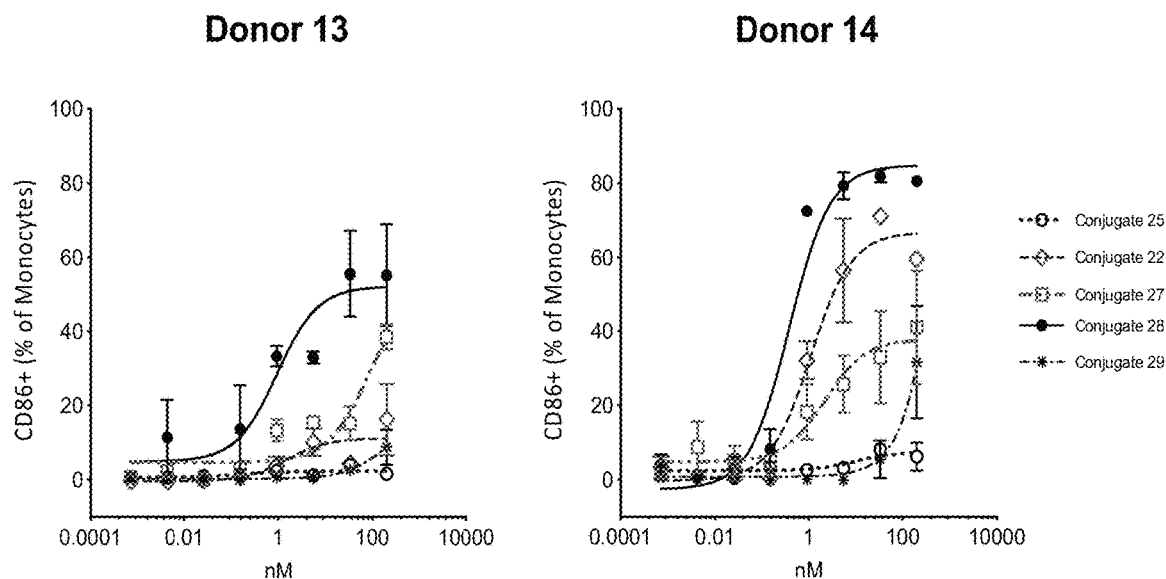
FIGS. 19A-19C illustrate anti-FolR1-iADC (4×pAMF+2xQ-tag; Conjugate 28)-related activation on monocytes (FIG. 19A), B cells (FIG. 19B) and DCs (FIG. 19C) vs. anti-FolR1-ISAC (Conjugate 22) and anti-FolR1-ADC (Conjugate 27).
Figure 19B:
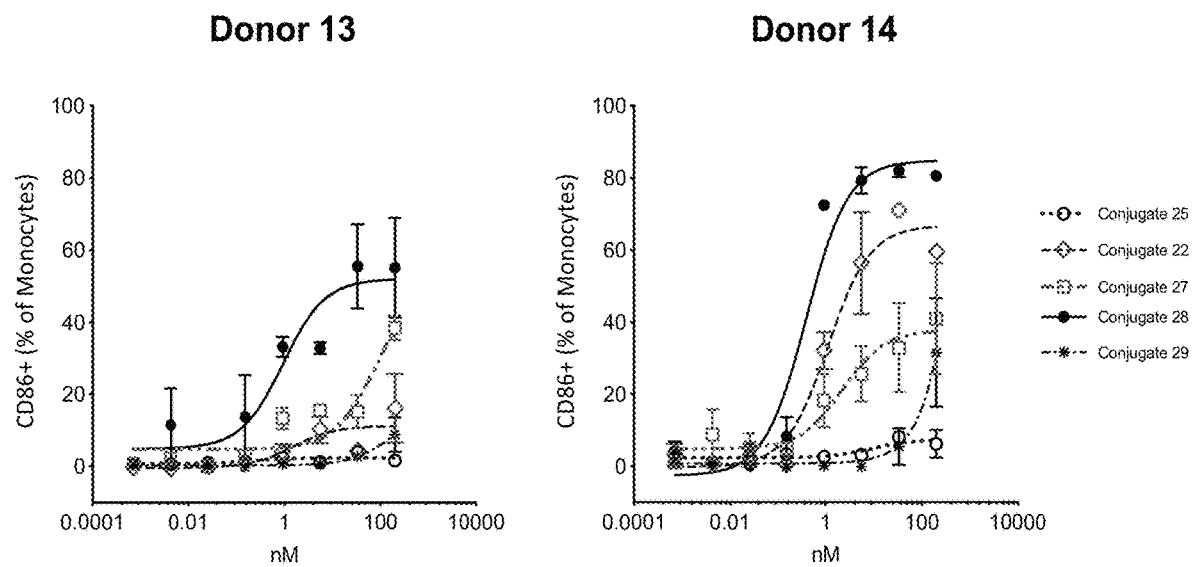
Figure 19C:
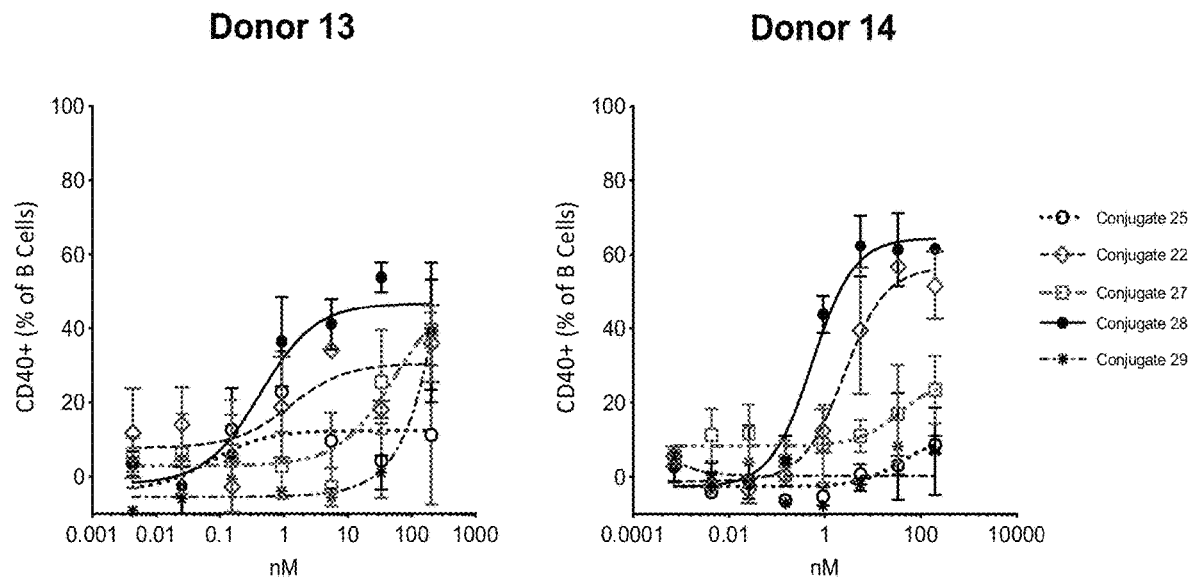
Figure 20A:
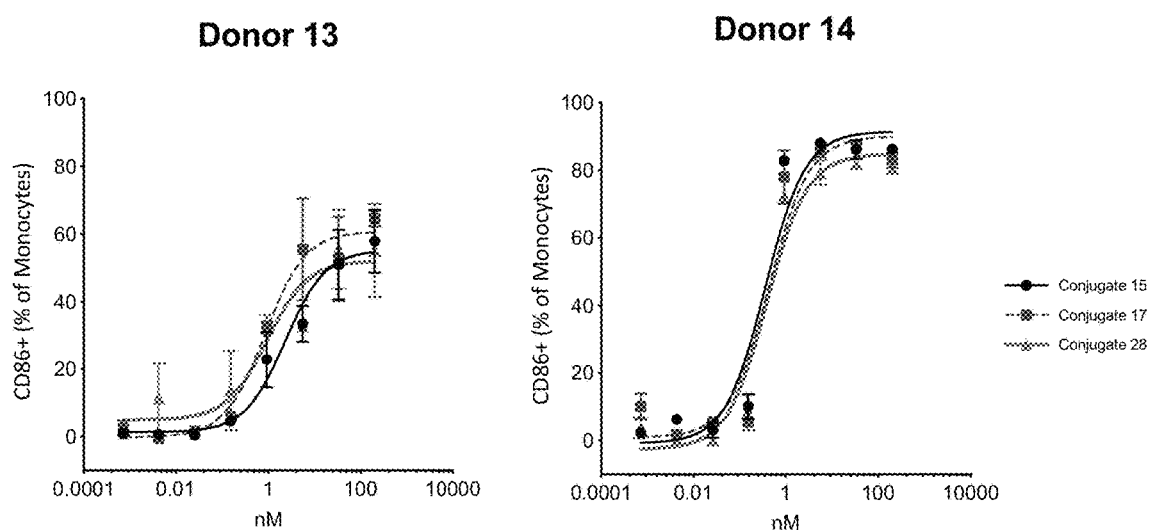
FIGS. 20A-20C illustrate comparable immune cells activation activity of the three homogeneous iADCs (Conjugate 15, Conjugate 17, and Conjugate 28) on monocytes (FIG. 20A), B cells (FIG. 20B) and DCs (FIG. 20C).
Figure 20B:
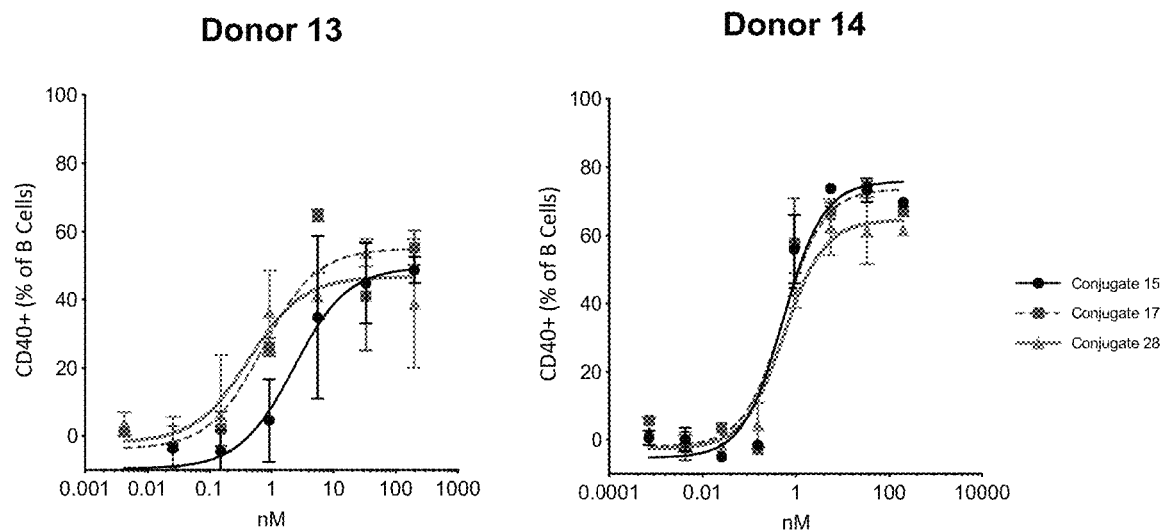
Figure 20C:
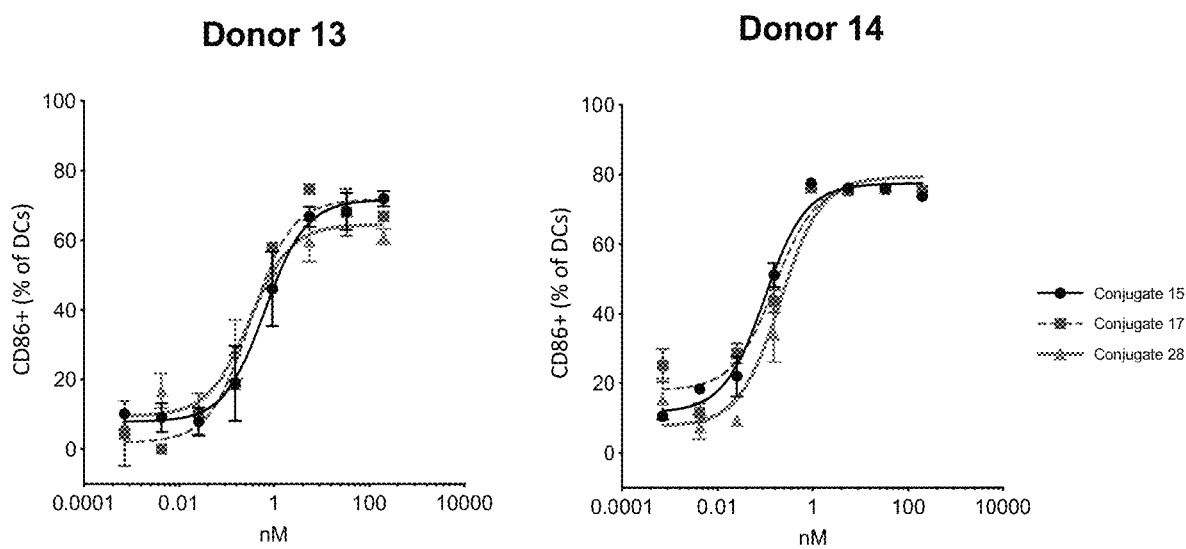

In the presence of FolRα positive KB cells and PBMCs, TLR7 agonist Compound 7 was much more potent in activating monocytes (FIG. 16A), B cells (FIG. 16B) and DCs (FIG. 16C) than hemiasterlin warhead Compound 1. For iADC generated by 6×pAMF, anti-FolR1-iADC (Conjugate 15) induced greater activation on monocytes (FIG. 17A), B cells (FIG. 17B) and DCs (FIG. 17C) compared to ISAC alone or ADC alone or the combination of ISAC and ADC, indicating that the combination of TLR7 agonist and cytotoxicity warhead on the same antibody has a synergistic effect on monocyte activation. Anti-FolR1-iADC generated by 4×pAMF+2xpAcF (Conjugate 17) also showed more potent activation activity on monocytes (FIG. 18A), B cells (FIG. 18B) and DCs (FIG. 18C) than anti-FolR1-ISAC (Conjugate 23) and anti-FolR1-ADC (Conjugate 24). Anti-FolR1-iADC generated by 4×pAMF+2xQ-tag (Conjugate 28) showed more potent activation activity on monocytes (FIG. 19A), B cells (FIG. 19B) and DCs (FIG. 19C) than anti-FolR1-ISAC (Conjugate 22) and anti-FolR1-ADC (Conjugate 27). The immune cells activation activity of the three homogeneous iADCs were very similar to each other on all the cell populations tested (FIG. 20A, 20B, 20C). The immune cells activation activity of the ISACs and iADCs were dependent on the TLR7 agonist and the hemiasterlin warhead since the unconjugated antibodies did not exhibit monocyte activity in the same assay. The monocyte activation effect of anti-FolR1-iADCs is dependent on the anti-FolR1 antibody binding to the FolR1 on the target cells since an anti-GFP antibody conjugated to both Compound 1002 and Compound 101 at similar ratio only activate some immune cells at very high concentrations in the same assay.

EQUIVALENTS

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in this application, in applications claiming priority from this application, or in related applications. Such claims, whether directed to a different invention or to the same invention, and whether broader, narrower, equal, or different in scope in comparison to the original claims, also are regarded as included within the subject matter of the inventions of the present disclosure.

One or more features from any embodiments described herein or in the figures may be combined with one or more features of any other embodiments described herein or in the figures without departing from the scope of the invention.

What is claimed:

1. An antibody conjugate comprising an antibody, or an antigen-binding fragment thereof, covalently linked to a drug payload (PA) and further covalently linked to an immunomodulatory payload (IM) wherein the drug payload is a residue of a cytotoxic compound selected from the group consisting of an alkylating agent, a DNA-crosslinking agent, an anti-tumor antibiotic, an anti-metabolite, an anti-mitotic agent, a histone-deacetylase (HDAC) inhibitor, a telomerase inhibitor, and an immunogenic cell death agent; and the immunomodulatory payload is a residue of an immunomodulatory compound selected from the group consisting of a kinase inhibitor, a growth factor inhibitor, a Calcineurin inhibitor, a CRAC inhibitor, a PARP1 antagonist, a PPARγ agonist, a Kv1.3 antagonist, a PP2A agonist, a MYD88 inhibitor, a BCL-2 inhibitor, an Adenosine A2A receptor (A2ar) agonist, a Toll-like receptor 7/8 (TLR7/8) agonist, a Toll-like receptor 4 (TLR4) agonist, a Toll-like receptor 9 (TLR9) agonist, a calcium-activated potassium channel (Kca3.1) agonist, a TGF-$R_1$ inhibitor, a TGF-$R^2$ inhibitor, a GLi 1 inhibitor, a tankyrase (TNKS) antagonist, a Traf2 and Nck-interacting kinase (TNIK) antagonist, an imide, and a vitamin D receptor (VDR) agonist; and wherein (i) the antibody or antigen-binding fragment thereof comprises a non-natural amino acid at position K42 and at least one non-natural amino acid at position Y180 or F404 that are covalently linked to the immunomodulatory payload or to the drug payload; and/or (ii) the antibody or antigen-binding fragment thereof comprises one or more glutamine (Q) residues that is covalently linked to the immunomodulatory payload or to the drug payload; and/or wherein (iii) the drug payload or the immunomodulatory payload is linked to the antibody, or antigen-binding fragment, via one or more linkers and the one or more linkers comprise a release trigger group, wherein the release trigger group is a β-glucuronidase-cleavable β-glucuronide according to the structure

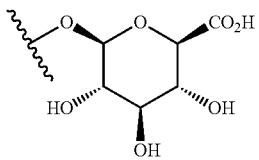

wherein

indicates the atoms in the antibody drug conjugate to which the β-glucuronidase-cleavable β-glucuronide is bonded.

2. The antibody conjugate of claim 1 wherein the drug payload or the immunomodulatory payload is linked to the antibody, or antigen-binding fragment, via one or more linkers and the one or more linkers comprise a release trigger group wherein the release trigger group is a β-glucuronidase-cleavable β-glucuronide according to the structure

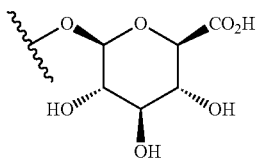 [SMILES: *O[C@H]1O[C@@H](C(=O)O)[C@H](O)[C@@H](O)[C@@H]1O]

wherein

indicates the atoms in the antibody drug conjugate to which the β-glucuronidase-cleavable γ-glucuronide is bonded.

3. The antibody conjugate of claim 1 according to Formula (I):

wherein Ab is the antibody, or antigen-binding fragment thereof;

each L is independently an optional linker;

each PA is independently the cytotoxic compound residue;

each IM is independently the immunomodulatory payload residue;

subscript n is an integer selected from 1 to 30;

subscript m is an integer selected from 1 to 30; and each bracketed group is covalently linked to Ab.

4. The antibody conjugate of claim 3, according to the structure of Formula (II):

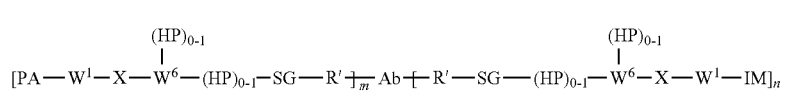

or a pharmaceutically acceptable salt, solvate, stereoisomer, tautomer, or mixture of regioisomers thereof, wherein:

each $W^1$ is independently, at each occurrence, absent or a divalent spacer;

each X is independently, at each occurrence, absent,

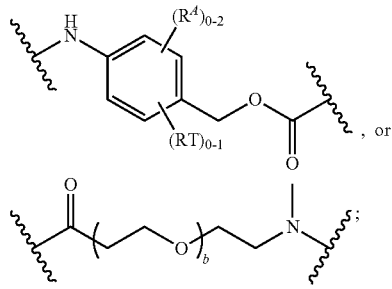, or subscript b is an integer from 1 to 10;
each $R^A$ is independently, at each occurrence, absent or $C_{1-3}$alkyl;
each RT is independently, at each occurrence, absent or a release trigger group;
each HP is independently, at each occurrence, absent or a hydrophilic group;
each $W^6$ is independently, at each occurrence, a peptide residue, or absent;
each SG is independently, at each occurrence, absent, or a divalent spacer group;
each R' is independently, at each occurrence, a divalent residue of a conjugated group;
subscript n is an integer selected from 1 to 30;
subscript m is an integer selected from 1 to 30
Ab is the antibody or the antigen-binding fragment thereof; and
PA is the cytotoxic compound residue; and
IM is the immunomodulatory payload residue, optionally wherein
SG is independently, at each occurrence,

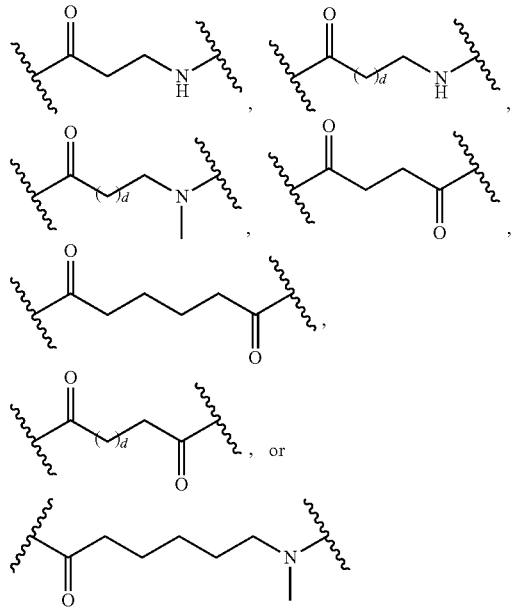

wherein subscript d is an integer selected from 1 to 10, wherein each

indicates a point of attachment to the rest of the formula.

5. The antibody conjugate of claim 4, wherein $W^1$, when present, is

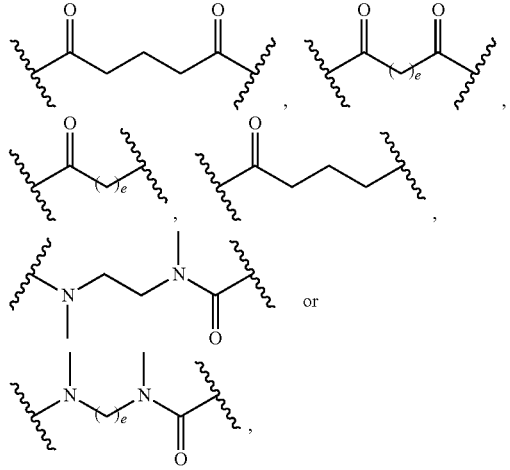

wherein subscript e is an integer selected from 1 to 10, wherein each  indicates a point of attachment to the rest of the formula.

6. The antibody conjugate of claim 4, wherein $W^6$, when present, is independently, at each occurrence, a dipeptide residue, a tripeptide residue,

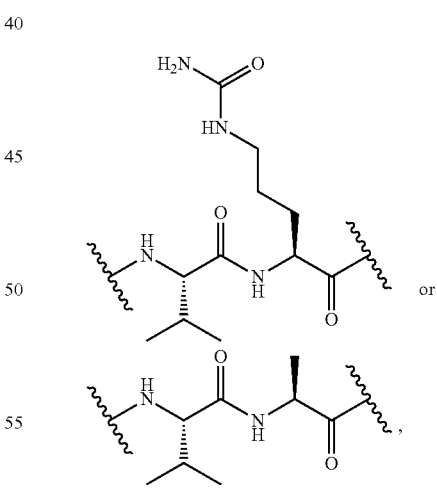

wherein each

indicates a point of attachment to the rest of the formula.

7. The antibody conjugate of claim 4, wherein RT is independently, at each occurrence,

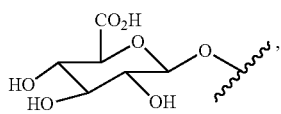

wherein

indicates a point of attachment to the rest of the formula, optionally further wherein HP, when present, is independently, at each occurrence,

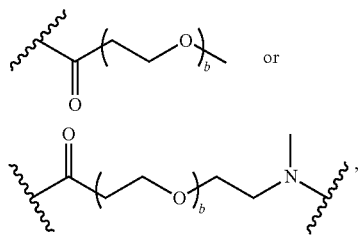

wherein subscript b is an integer from 1 to 10, and

indicates a point of attachment to the rest of the formula.

8. The antibody conjugate of claim 4, wherein R' is independently, at each occurrence:

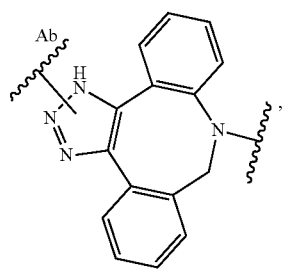

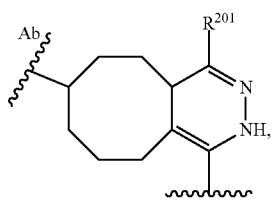

-continued

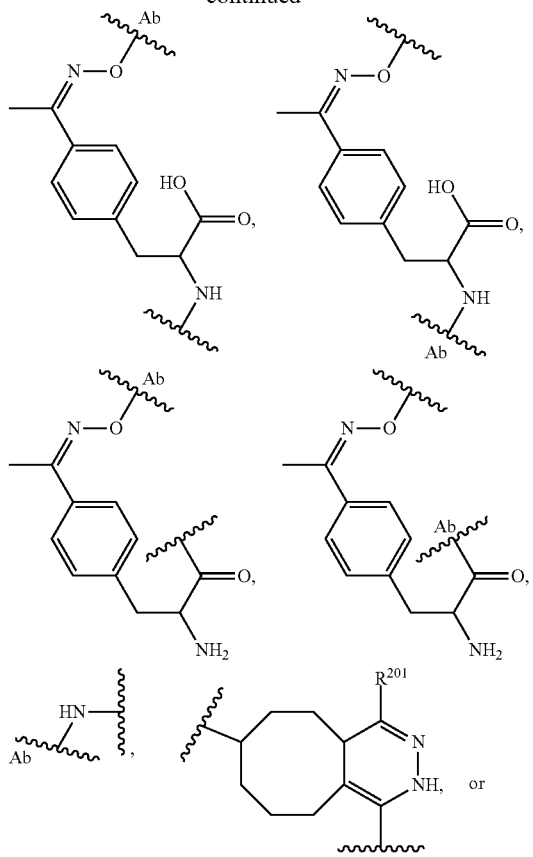

wherein $R^{201}$ is $C_{1-6}$alkyl, wherein each

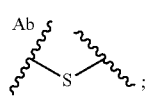

indicates a point of attachment to the rest of the formula,

indicates a point of attachment to the antibody, or the antigen-binding fragment thereof, and

indicates a point of attachment to the antibody, or the antigen-binding fragment thereof, via a sulfur atom of a cysteine residue.

9. The antibody conjugate of claim 4, wherein the antibody, or the antigen-binding thereof, is selected from the group consisting of anti-BCMA, anti-Mucl6, trastuzumab, sofitizumab, anti-GFP, and anti-FolRα, or an antigen-binding fragment thereof.

10. The antibody conjugate of claim 4, wherein the antibody, or the antigen-binding fragment thereof, comprises two or more non-natural amino acids suitable for conjugation, optionally wherein at least one of the two or more non-natural amino acids residues is a pAMF residue.

11. The antibody conjugate of claim 10, wherein the antibody, or the antigen-binding fragment thereof, comprises a Y180 pAMF mutation, a F404 pAMF mutation, or both.

12. The antibody conjugate of claim 1, wherein the antibody, or the antigen-binding fragment thereof, is modified by substituting in or adding one or more glutamine (Q) residues that is compatible with transglutaminase conjugation and is covalently linked to the immunomodulatory payload or drug payload.

13. The antibody conjugate of claim 12, wherein the one or more glutamine residues are in Q tags selected from the group consisting of LLQGA (SEQ ID NO: 44), YAHQAHY (SEQ ID NO: 45), YRYRQ (SEQ ID NO: 46), PNPQLPF (SEQ ID NO: 47), PKPQQFM (SEQ TD NO: 48), GQQQLG (SEQ ID NO: 49), WALQRPH (SEQ ID NO: 50), WELQRPY (SEQ ID NO: 51), YPMQGWF (SEQ TD NO: 52), LSLSQG (SEQ ID NO: 53), GGGLLQGG (SEQ ID NO: 54), GLLQG (SEQ ID NO: 55), GSPLAQSHGG (SEQ ID NO: 56), GLLQGGG (SEQ ID NO: 57), GLLQGG (SEQ ID NO: 58), GLLQ (SEQ ID NO: 59), LLQLLQGA (SEQ ID NO: 60), LLQYQGA (SEQ ID NO: 62), LLQGSG (SEQ ID NO: 63), LLQYQG (SEQ ID NO: 64), LLQLLQG (SEQ ID NO: 65), SLLQG (SEQ ID NO: 66), LLQLQ (SEQ ID NO: 67), LLQLLQ (SEQ ID NO: 68), LLQGR (SEQ ID NO: 69), LLQGPA (SEQ TD NO: 70), LLQGPP (SEQ ID NO: 71) and GGLLQGPP (SEQ ID NO: 72).

14. The antibody conjugate of claim 1, wherein the molar ratio of cytotoxic compound:immunomodulatory payload is about 1-3:1 or greater than 3:1.

15. The antibody conjugate of claim 1, wherein the molar ratio of PA:IM is about 1:1, 2:1, 3:1, or greater than 3:1.

16. The antibody conjugate of claim 1, wherein the payload (PA) is a residue of a cytotoxic compound selected from the group consisting of Altretamine, Ansamitocin P3, Bendamustine hydrochloride, Bleomycin, Bortezomib, Busulfan, Cabazitaxel, Capecitabine, Carboplatin, Carmustine, Chlorambucil, Cisplatin, Cladribine, Clofarabine, Colchicine, Combrestatin-A4, Cytarabine, Cyclophosphamide, Dacarbazine, Dactinomycin, Daunorubicin hydrochloride, Docetaxel, Dolastatin 10, Dolastatin 15, Doxorubicin hydrochloride, Eribulin mesylate, Epirubicin, epothilones A-F, Etoposide, Floxuridine, Fludarabine, 5-Fluorouracil, Gemcitabine, Hemiasterlins, Idarubicin, Ifosfamide, Irinotecan, Ixabepilone, Ixazomib, Leucovorin, Lomustine, Losoxantrone, Maytansinoids, Mechlorethamine, Melphalan, Mercaptopurine, Methotrexate, Mitomycin, Mitotane, Mitoxantrone, Nelarabine, Nedaplatin, Omacetaxine mepesuccinate, Oxaliplatin, Paclitaxel, Pemetrexed disodium, Pentostatin, Pixantrone, Pralatrexate, Procarbazine hydrochloride, pyrrolobenzodiazepines (PBDs), Radium 223 dichloride, Streptozocin, suberanilohydroxamic acid (SAHA), Thioguanine, Thiotepa, Temozolomide, Teniposide, Topotecan hydrochloride, Valrubicin, Vincristine sulfate, Vinblastine sulfate, Vinedesine, and Vinorelbine tartrate.

17. The antibody conjugate of claim 16, wherein the cytotoxic compound is an immunogenic cell death agent residue selected from the group consisting of mitoxantrone, oxaliplatin, cyclophosphamide, doxorubicin, daunorubicin, epirubicin, idarubicin, and bortezomib.

18. The antibody conjugate of claim 16, wherein the maytansinoid is

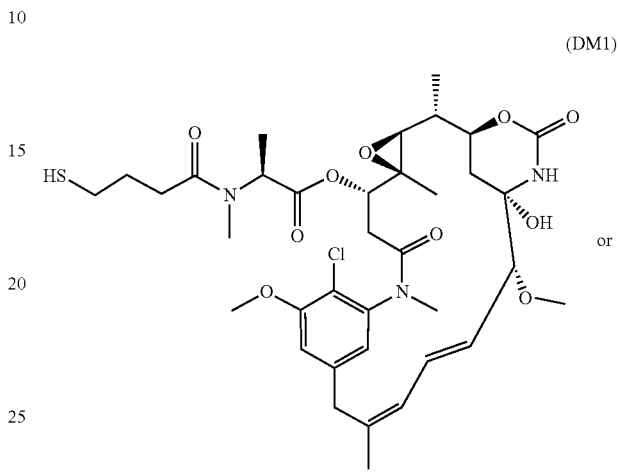

(DM1)

or

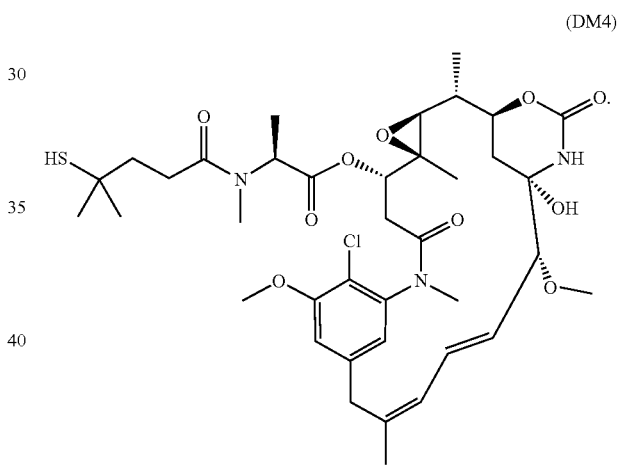

(DM4)

19. The antibody conjugate of claim 16, wherein the hemiasterlin is

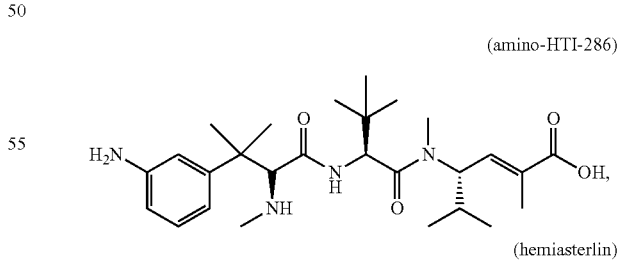

(amino-HTI-286)

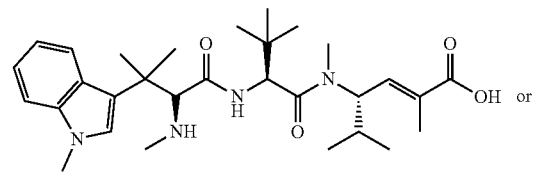

(hemiasterlin)

or

-continued
(E7974)
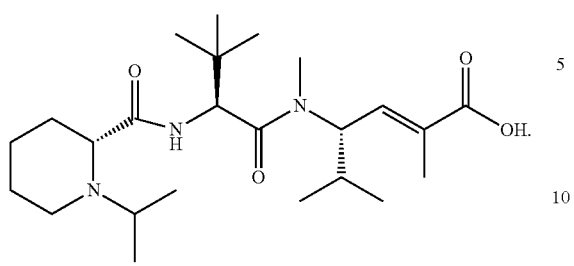
20. The antibody conjugate of claim 16, wherein the pyrrolobenzodiazepine is
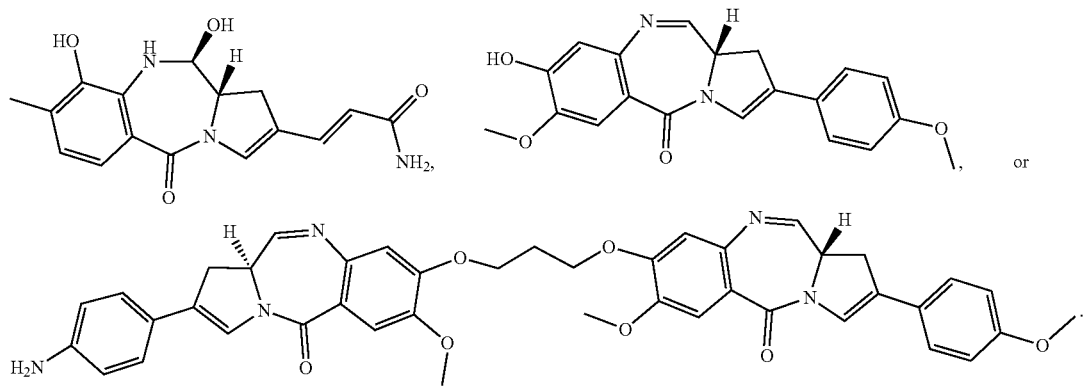
21. The antibody conjugate of claim 1, wherein PA is a residue of:
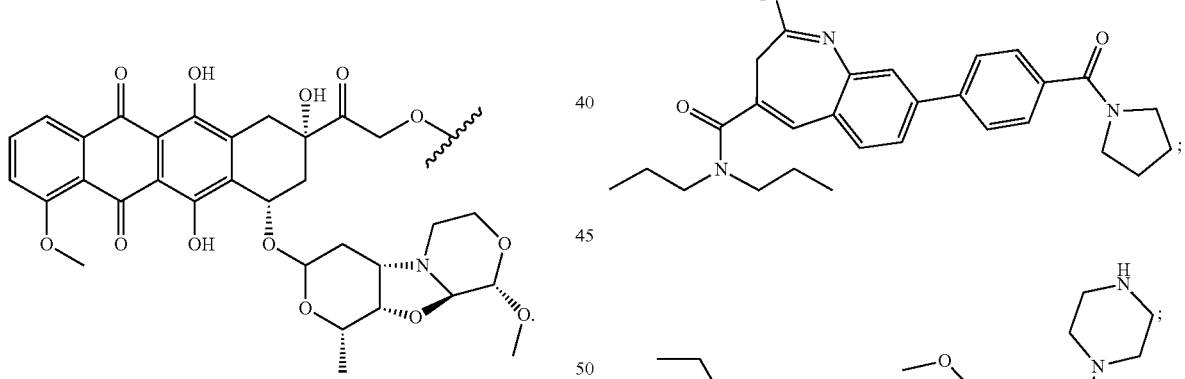
22. The antibody conjugate of claim 1, wherein the immunomodulatory payload (IM) is a residue of an immunomodulatory compound selected from the group consisting of:
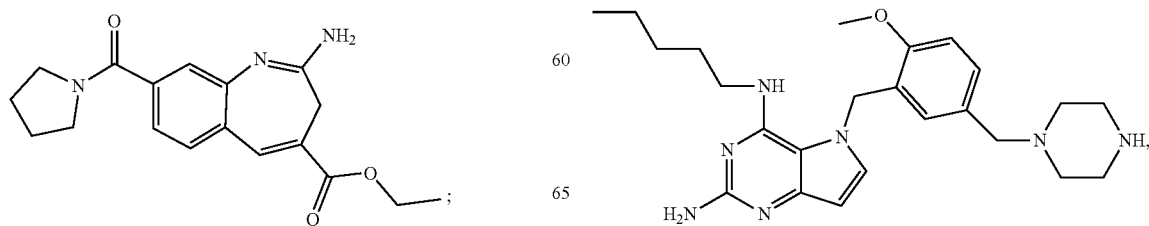

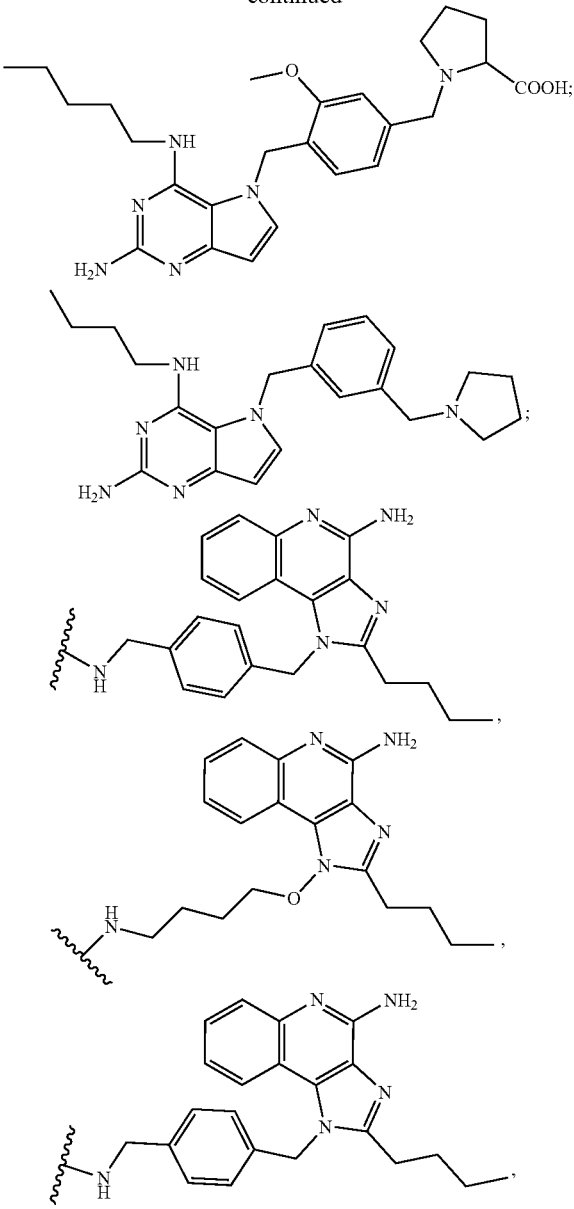

4-amino-2-butoxy-7,8-dihydro-8-[[3-(1-pyrrolidinylmethyl)phenyl]methyl]-6(5H)-pteridinone (vesatolimod, GS9620, CAS No. 1228585-88-3), 1-(2-Methylpropyl)-1H-imidazole[4,5-c]quinoline-4-amine (imiquimod, CAS No. 99011-02-6), 1-(4-amino-2-(ethoxymethyl)-1H-imidazo[4,5-c]quinolin-1-yl)-2-methylpropan-2-ol (resquimod, R848, CAS No. 144875-48-9), 4-amino-2-[(ethylamino)methyl]-α,α-dimethyl-1H-imidazo[4,5-c]quinoline-1-ethanol (gardiquimod, CAS No. 1020412-43-4), N-[4-(4-amino-2-ethyl-1H-imidazo[4,5-c]quinolin-1-yl)butyl]methanesulfonamide (3M-001), 2-propylthiazolo[4,5-c]quinolin-4-amine (3M-002), 4-amino-2-(ethoxymethyl)-α,α-dimethyl-6,7,8,9-tetrahydro-1H-imidazo[4,5-c]quinoline-1-ethanol hydrate (3M-003), N-(1-(4-Amino-2-(ethoxymethyl)-1H-imidazo[4,5-c]quinolin-1-yl)-2-methylpropan-2-yl)methanesulfonamide (CAS No. 642473-62-9, 3M-011, or 854A), N-(4-(4-amino-2-ethyl-1H-imidazo[4,5-c]quinolin-1-yl)butyl)methanesulfonamide (CAS No. 532959-63-0, 3M-852A, PF— 4878691), 2-methyl-1-(2,2,4-trimethylpent-4-en-1-yl)-1H-imidazo[4,5-c]quinolin-4-amine (S-34240), loxoribine, CL264, ssRNA40, and SM-276001.

23. The antibody conjugate of claim 3, wherein the immunomodulatory payload is a residue of a compound of Formula (III):

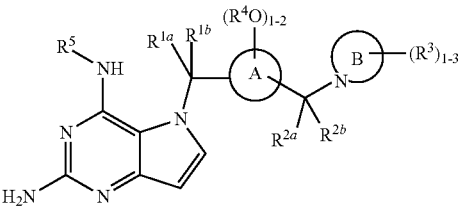

Formula (III)

or a pharmaceutically acceptable salt, solvate or N-oxide thereof;
wherein
$R^{1a}$, $R^{1b}$, $R^{2a}$, and $R^{2b}$ are independently, at each occurrence, selected from hydrogen and $C_{1-6}$alkyl;
ring A is cycloalkyl, heterocycloalkyl, monocyclic aryl, monocyclic heteroaryl, fused bicyclic aryl, or fused bicyclic heteroaryl, where heterocycloalkyl and each heteroaryl comprise 1, 2, 3 or 4 heteroatoms independently selected from N, S, and O;
ring B is a 4-membered N-linked heterocycloalkyl, which is substituted with 1-2 $R^3$; wherein the heterocycloalkyl includes 1 or 2 heteroatoms independently selected from N, S, and O including the N present in Rin2 B shown in Formula (III); and wherein $R^3$ is, independently, at each occurrence, —N($R^{3a}$)$_2$, —OR$^{3b}$, —C($R^{3'}$)$_2$NH$_2$, $C_{1-6}$alkyl, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl and partially saturated heteroaryl in $R^3$ include 1, 2, 3 or 4 heteroatoms independently selected from N, S, and O, and are optionally substituted with 1-2 $C_{1-3}$alkyl;
or
ring B is a 5-6 membered N-linked heterocycloalkyl, which is further substituted with 1-3 $R^3$, or a 5-6 membered N linked heteroaryl, which is substituted with 1-3 $R^3$; wherein the heterocycloalkyl and heteroaryl include 1 or 2 heteroatoms independently selected from N, S, and O including the N present in Ring B shown in Formula (III); wherein $R^3$ is, independently, at each occurrence, —N($R^{3a}$)$_2$, —OR$^{3b}$, —C($R^{3c}$)$_2$NH$_2$, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl and partially saturated heteroaryl in $R^3$ include 1, 2, 3 or 4 heteroatoms independently selected from N, S, and O, and are optionally substituted with 1-2 $C_{1-3}$alkyl;

or ring B is a 7-10 membered N-linked heterocycloalkyl, which is substituted with 1-3 $R^3$, or a 5-10 membered N-linked heteroaryl which is substituted with 1-3 $R^3$; wherein the heterocycloalkyl and heteroaryl include 1, 2, 3 or 4 heteroatoms independently selected from N, S, and O including the N present in Ring B shown in Formula (III); and wherein $R^3$ is, independently, at each occurrence, —N($R^{3a}$)$_2$, —OR$^{3b}$, —C($R^{3c}$)$_2$NH$_2$, C$_{1-6}$alkyl, heterocycloalkyl, heteroaryl, or partially saturated heteroaryl, or two $R^3$ attached to the same carbon, together with the carbon atom to which they are attached, form a spiro-heterocycloalkyl; wherein heterocycloalkyl, spiro-heterocycloalkyl, heteroaryl and partially saturated heteroaryl in $R^3$ include 1, 2, 3 or 4 heteroatoms independently selected from N, S, and O, and are optionally further substituted with 1-2 C$_{1-3}$alkyl;

$R^{3a}$ is independently, at each occurrence, selected from hydrogen, C$_{1-6}$alkyl, —C(=O)—CH$_2$NH$_2$, and cycloalkyl;

$R^{3b}$ is independently, at each occurrence, selected from hydrogen,

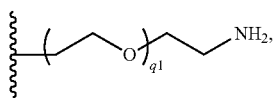

where q1 is 1, 2, or 3, and —CH$_2$-aryl-CH$_2$NH$_2$;

$R^{3c}$ is independently, at each occurrence, selected from hydrogen and C$_{1-6}$alkyl, or two $R^{3c}$, together with the carbon atom to which they are attached, form a cycloalkyl;

$R^4$ is C$_{1-6}$alkyl; and $R^5$ is C$_{3-6}$cycloalkyl or C$_{1-6}$alkyl, each of which is optionally substituted with 1, 2, or 3 $R^{5a}$ groups independently selected from halo, hydroxy, alkoxy, amino, C$_{1-6}$alkylamino, C$_{1-6}$dialkylamino, C$_{3-6}$cycloalkyl, aryl, and heteroaryl, wherein heteroaryl includes 1, 2, 3 or 4 heteroatoms independently selected from N, S, and O, and wherein any of the R" ~ C$_3$0.6 cycloalkyl, aryl, and heteroaryl are optionally substituted with 1, 2, or 3 groups independently selected from halo, hydroxy, alkyl, and haloalkyl;

wherein the immunomodulatory payload (IM) is attached to the linker L via an amino group of $R^3$ or an amino group of ring B.

24. The antibody conjugate of claim 23, wherein IM is selected from the group consisting of:

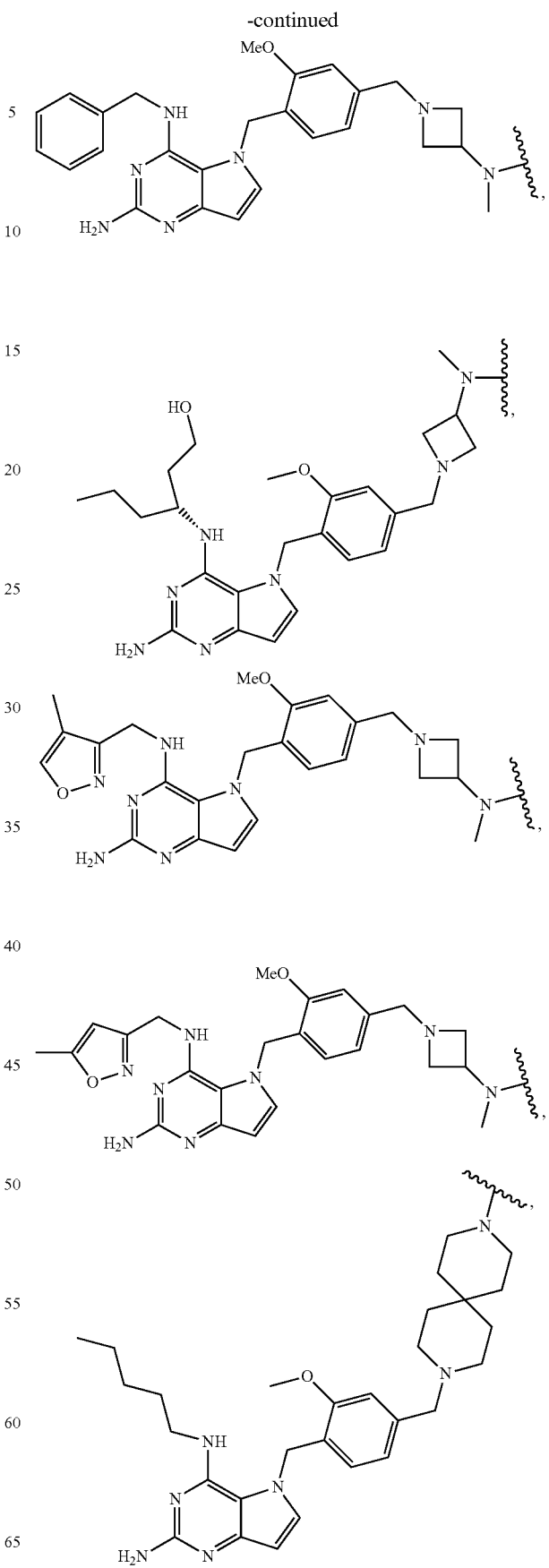

393
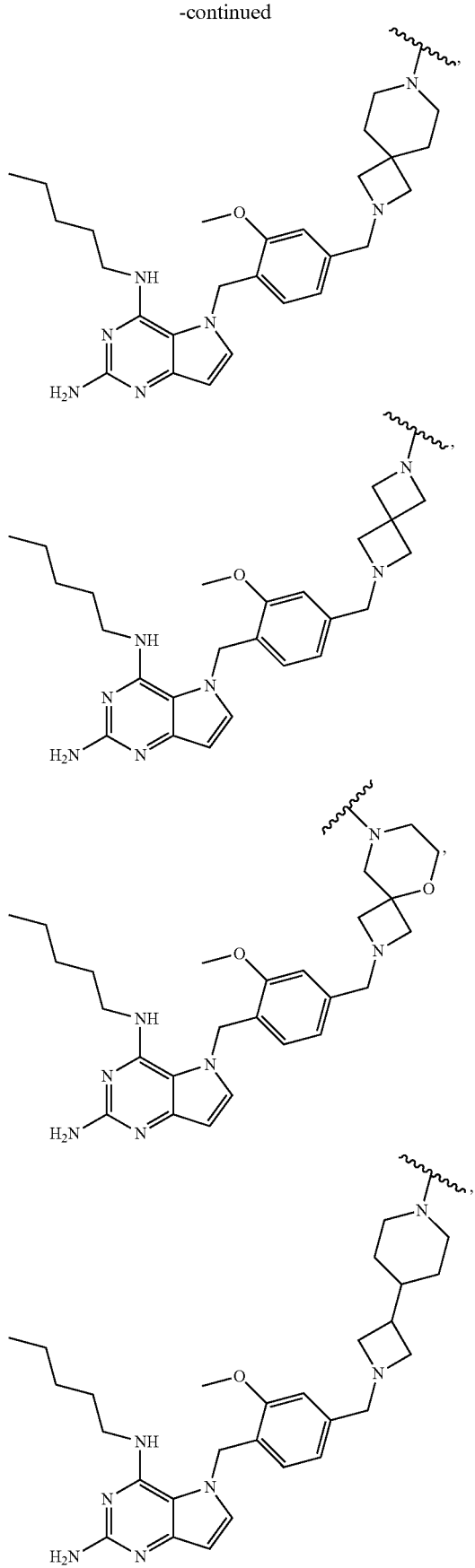
394
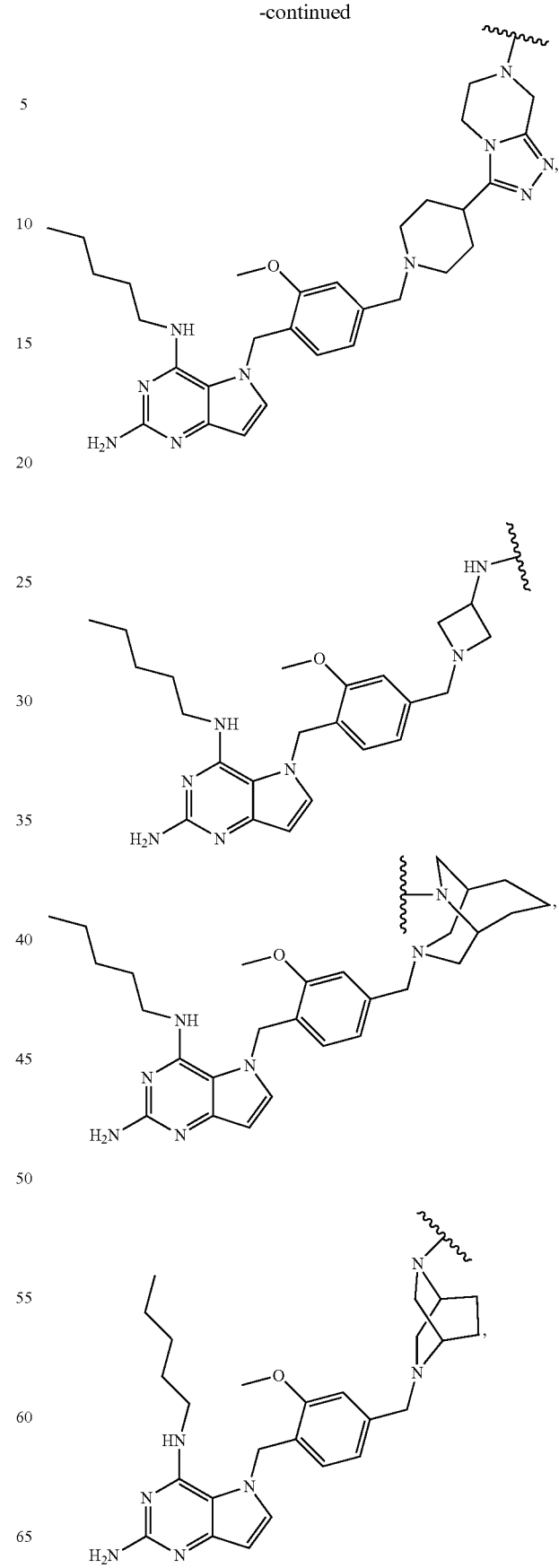

395
-continued
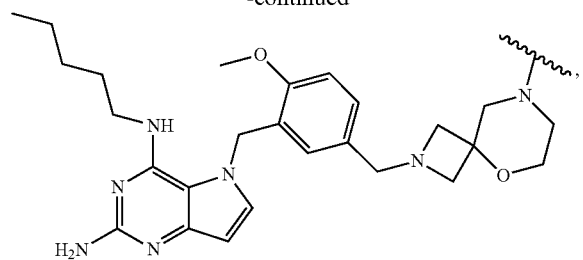
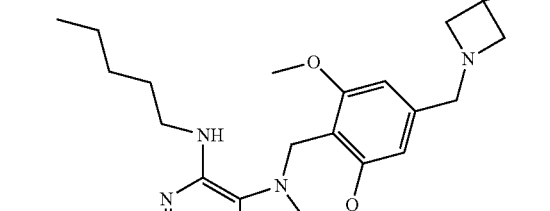
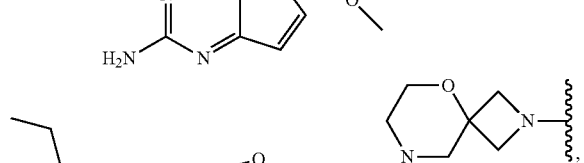
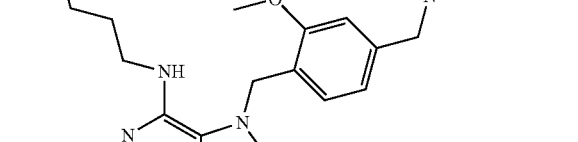
396
-continued
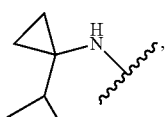
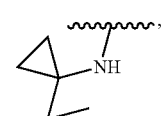
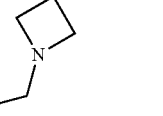

-continued
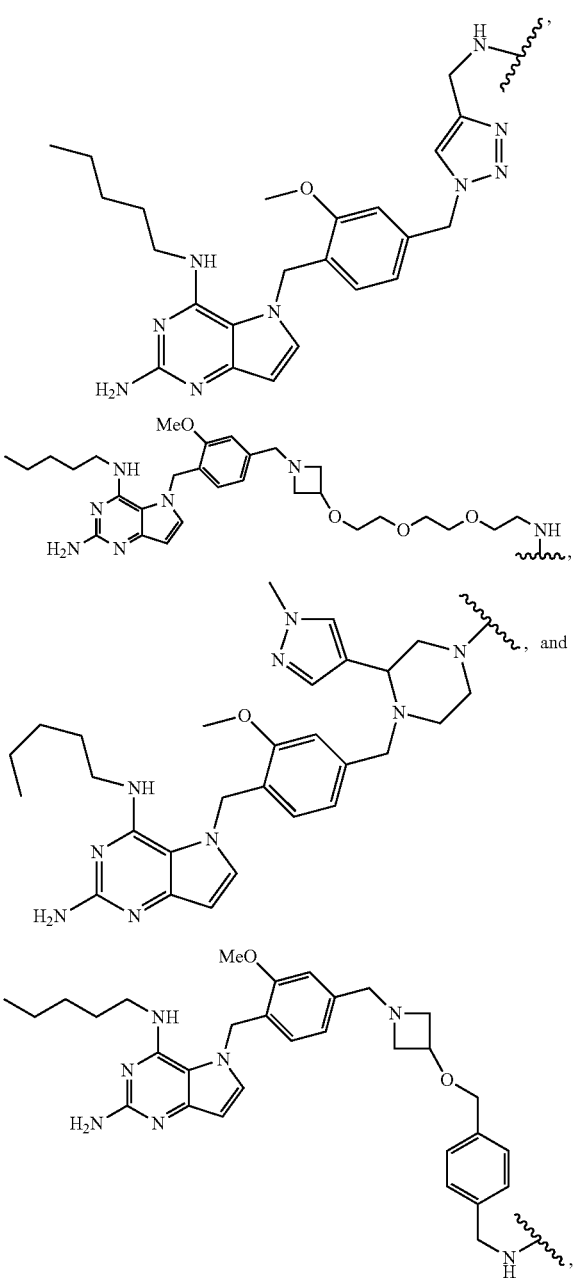
wherein each
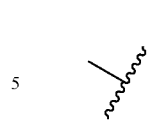
indicates a point of attachment to the rest of the formula.
25. The antibody conjugate of claim 3, wherein
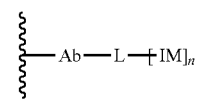
has a structure selected from the group consisting of:
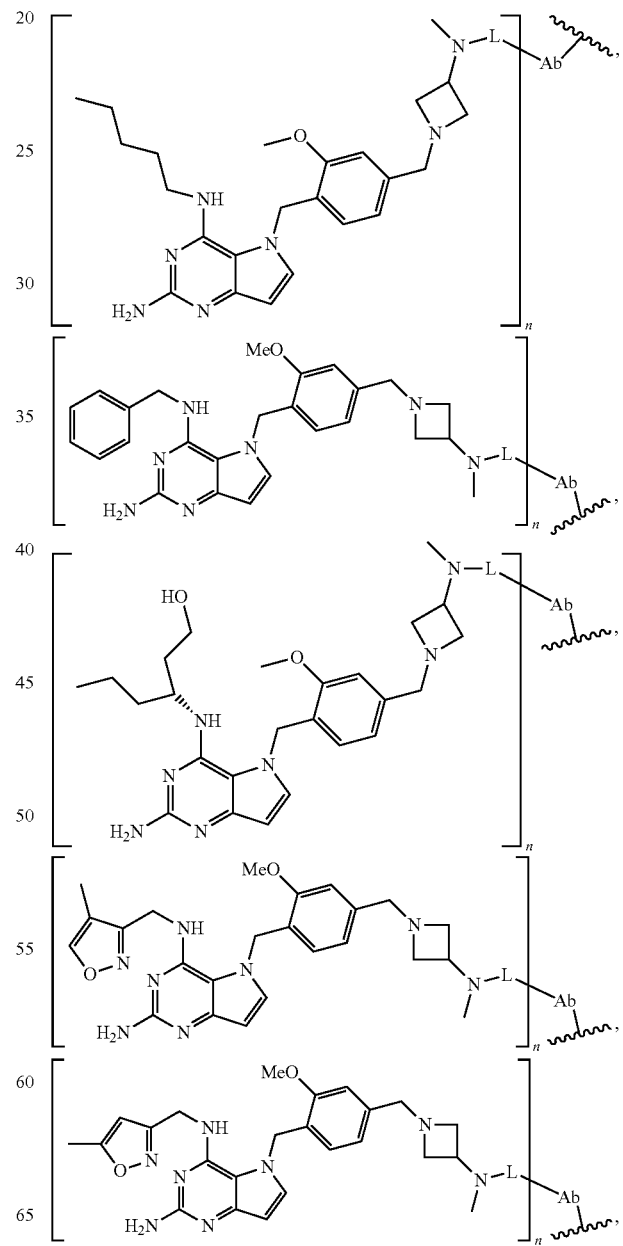

399
-continued
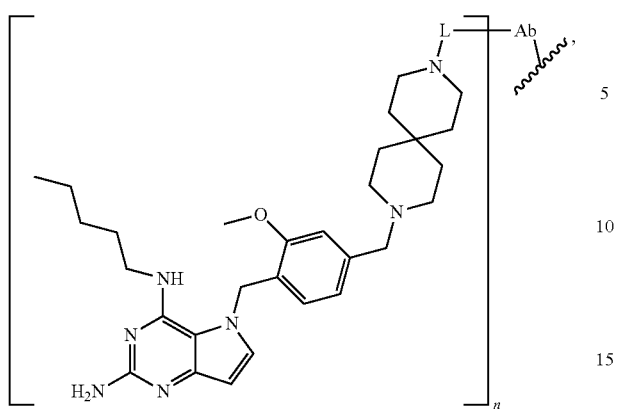
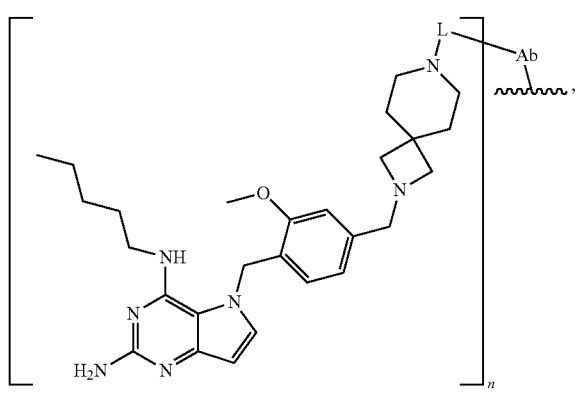
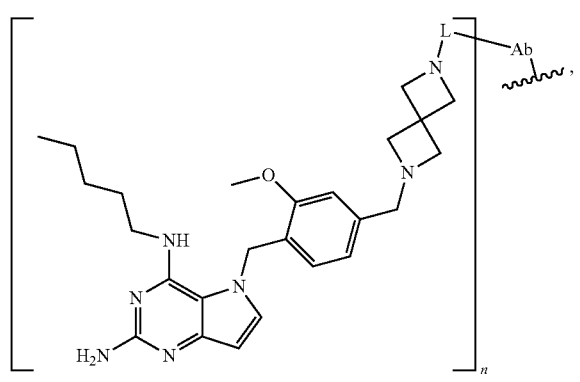
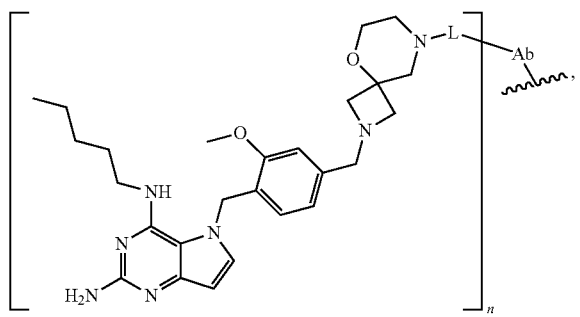
400
-continued
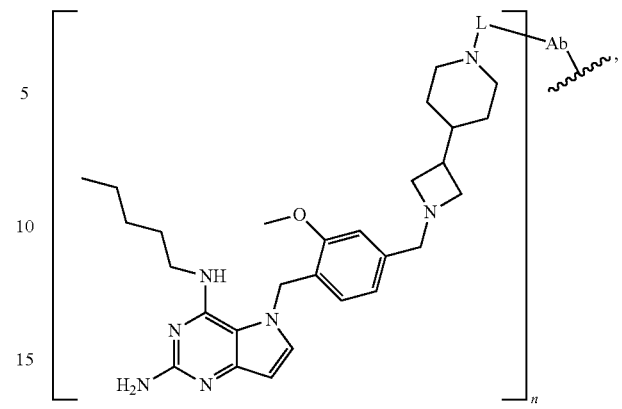
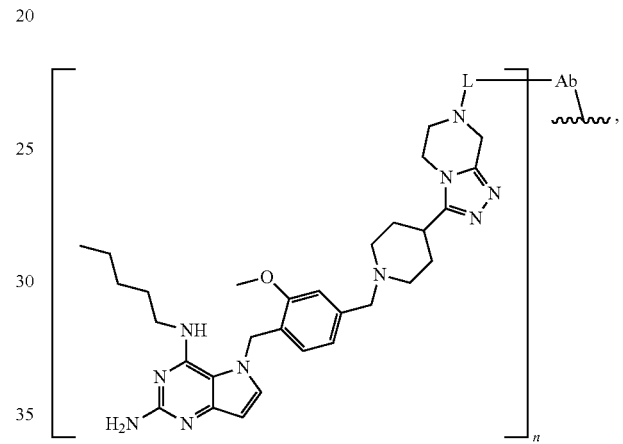
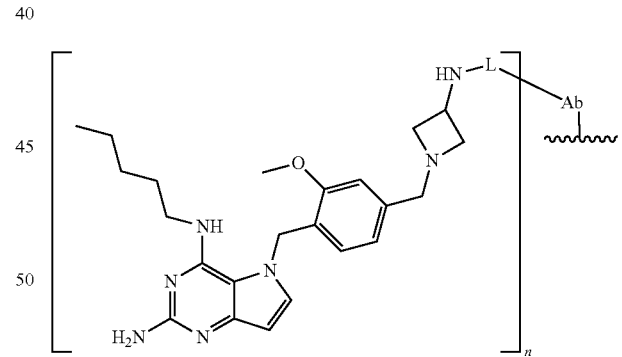
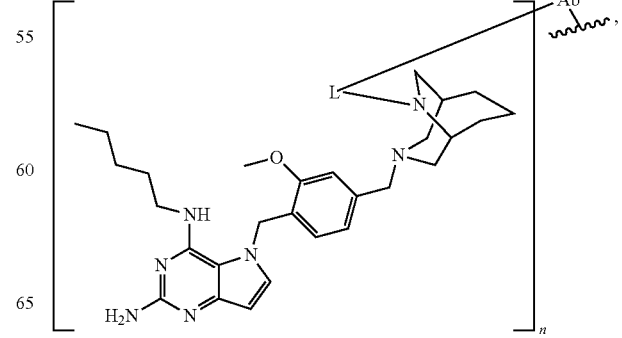

401
-continued
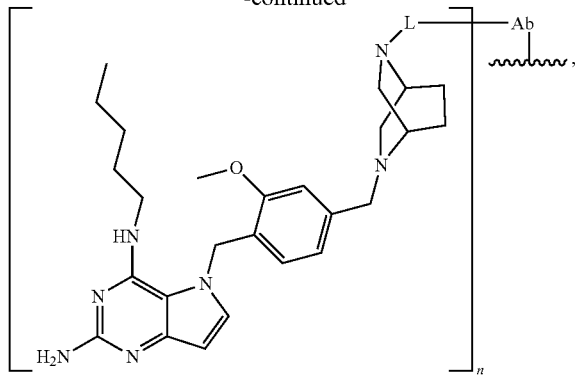
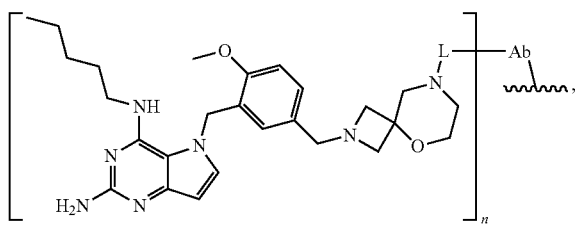
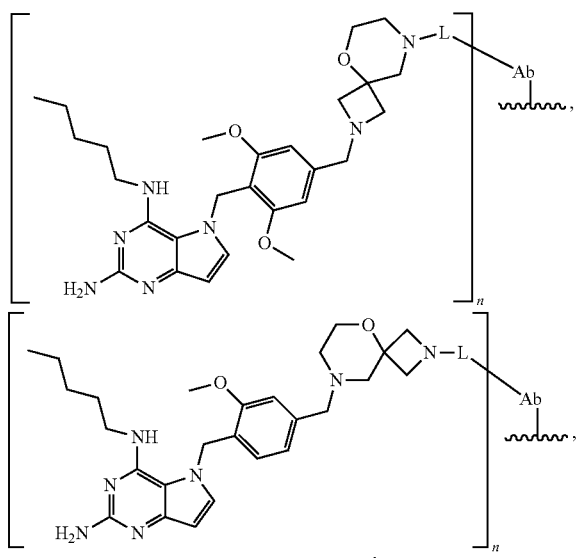
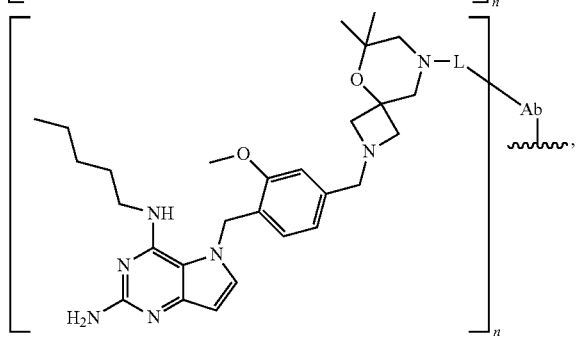
402
-continued
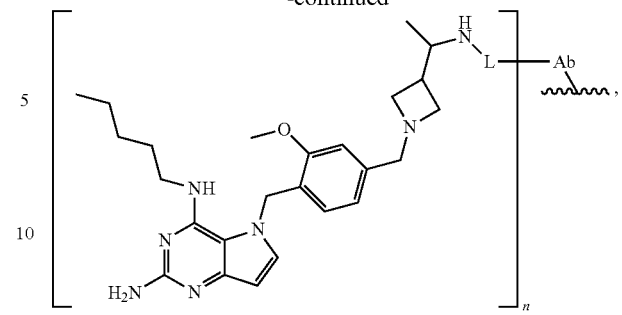
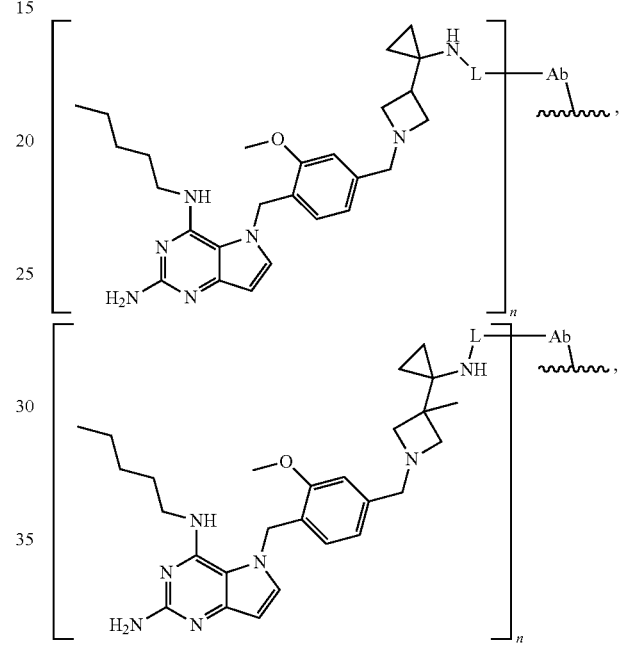
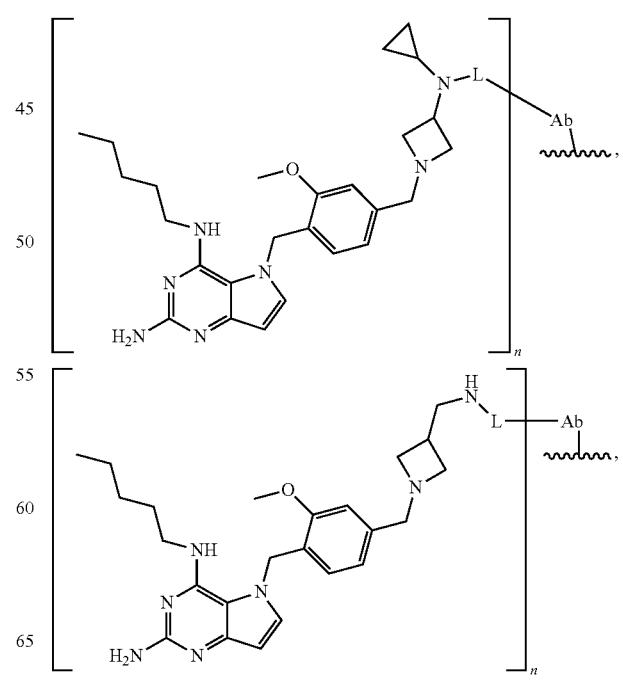

-continued

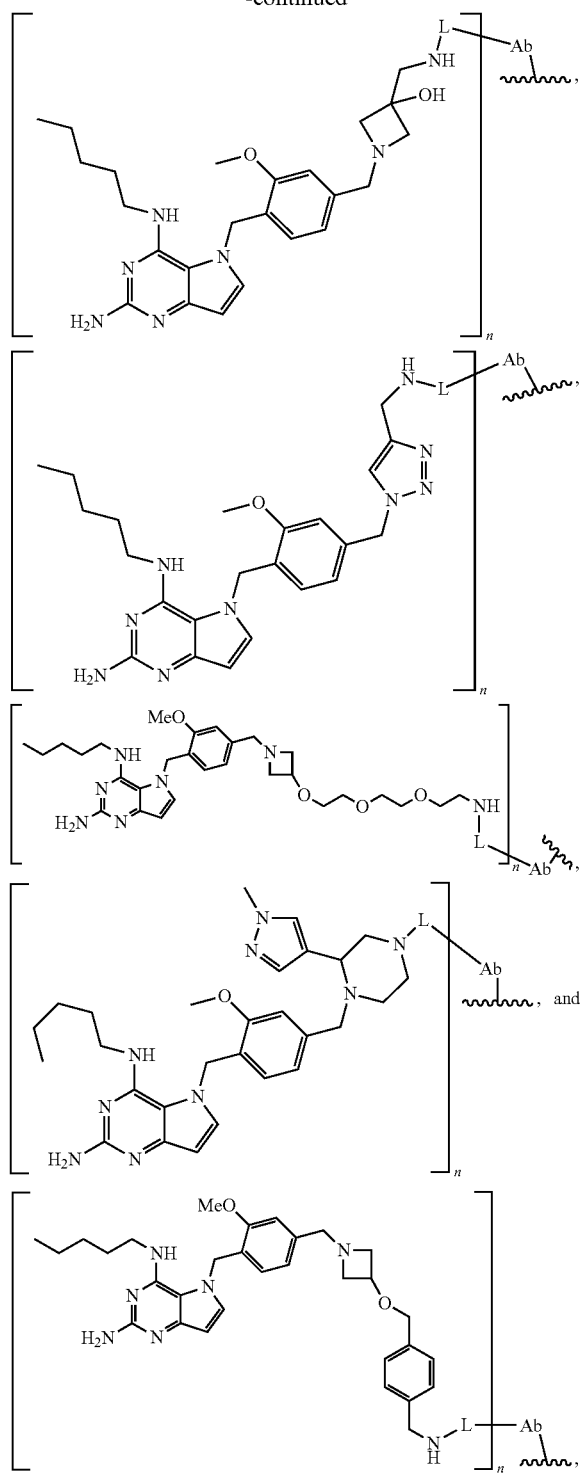

wherein each

![point of attachment symbol]

indicates a point of attachment to the rest of the formula.

26. The antibody conjugate of claim 3, wherein the immunomodulatory payload is a residue of a compound of Formula (IV):

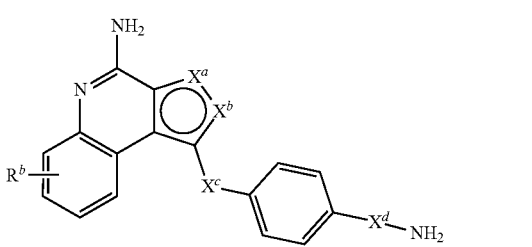

Formula (IV)

or a pharmaceutically acceptable salt, solvate or N-oxide thereof;

wherein one of $X^a$ and $X^b$ is —N= and the other is —N($R^a$)—;

$R^a$ is $C_1$—C-alkyl, cycloalkyl, or cycloalkyl-alkyl;

$X^c$ and $X^d$ are independently $C_1$-$C_6$-alkylene; and $R^b$ is hydrogen, quinolinyl, or —C(O)OCH$_3$.

27. The antibody conjugate of claim 26, wherein the immunomodulatory payload is a residue of a compound of Formula (IVa) or (IVb):

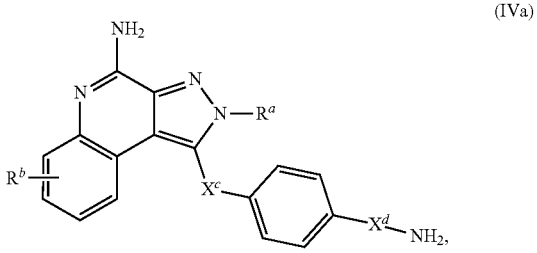
(IVa)

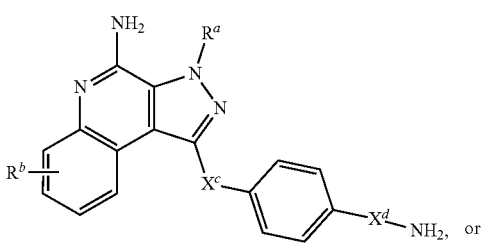
(IVb)

or

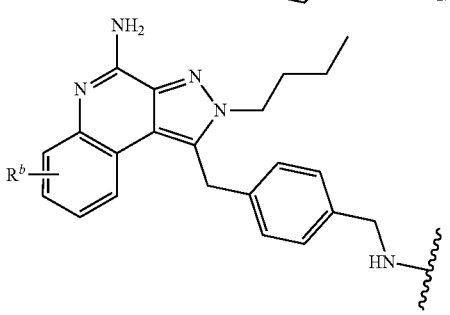

or a pharmaceutically acceptable salt, solvate or N-oxide thereof, wherein
indicates a point of attachment to the rest of the formula.
28. The antibody conjugate of claim 3, wherein
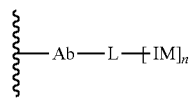
has a structure selected from the group consisting of:
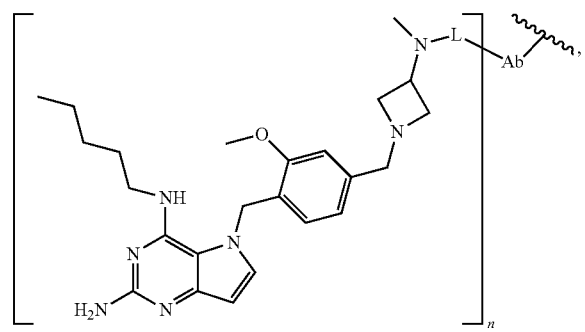
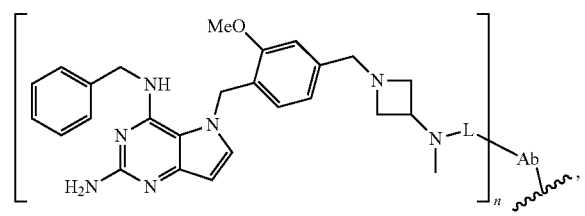
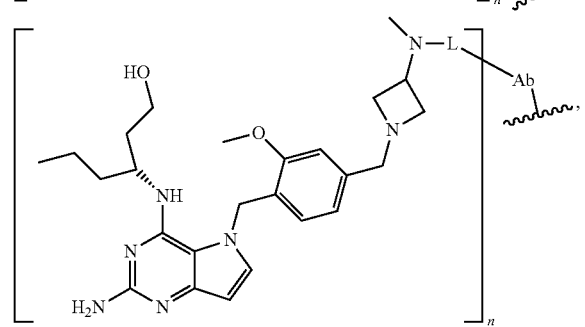
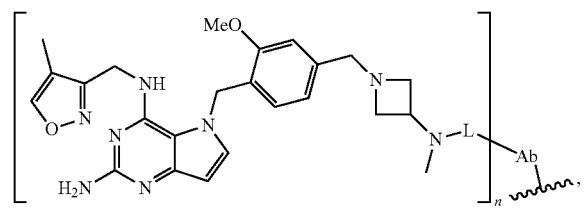
-continued
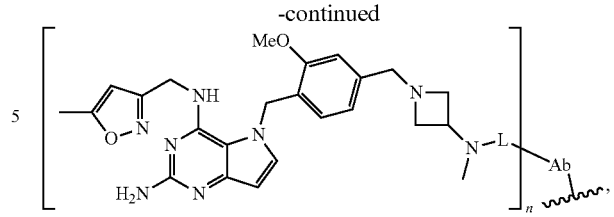
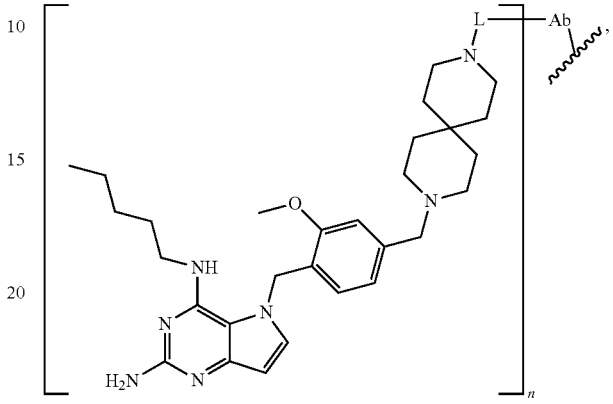
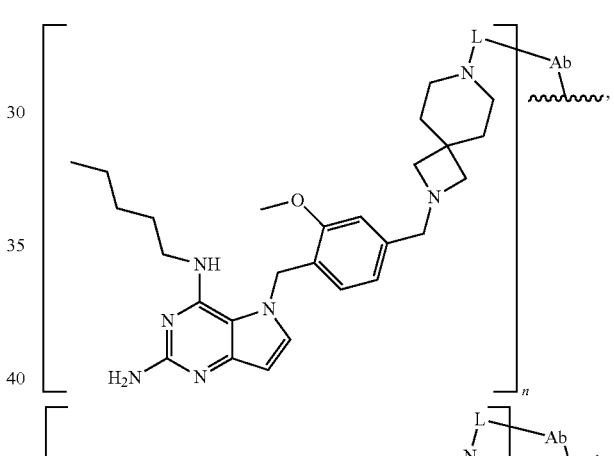
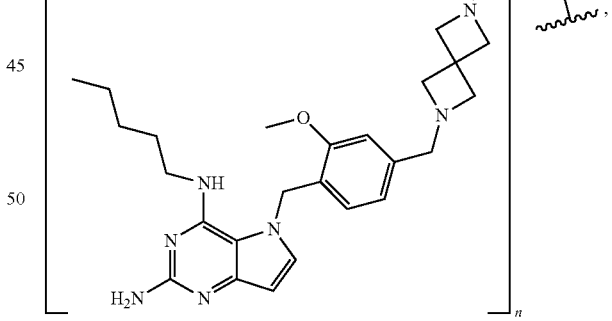
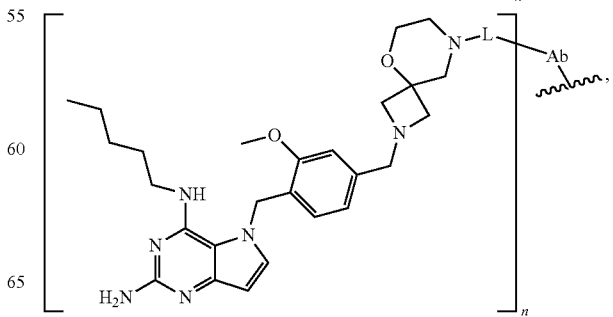

407
-continued
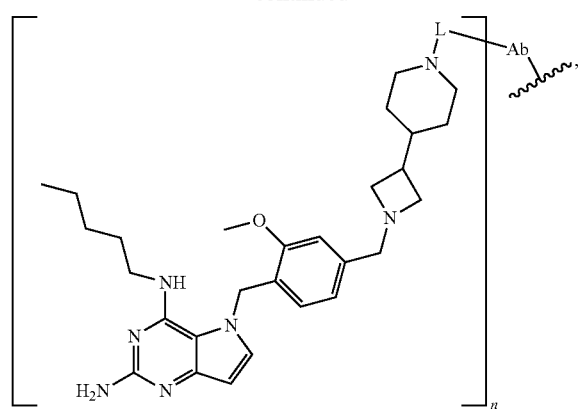
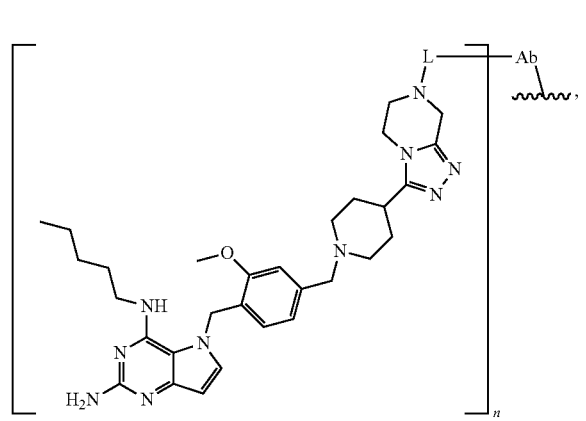
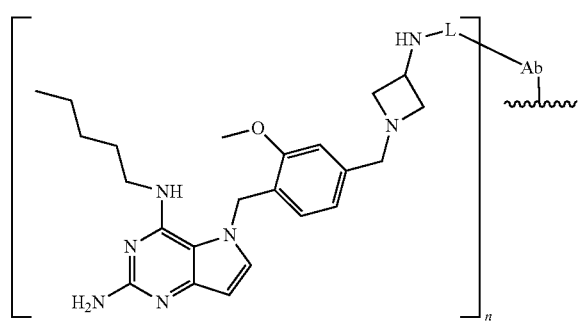
408
-continued
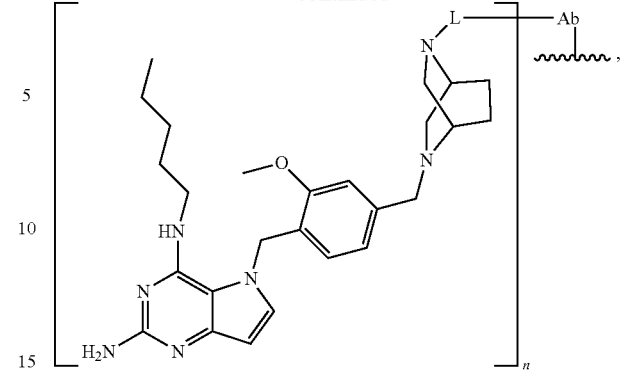
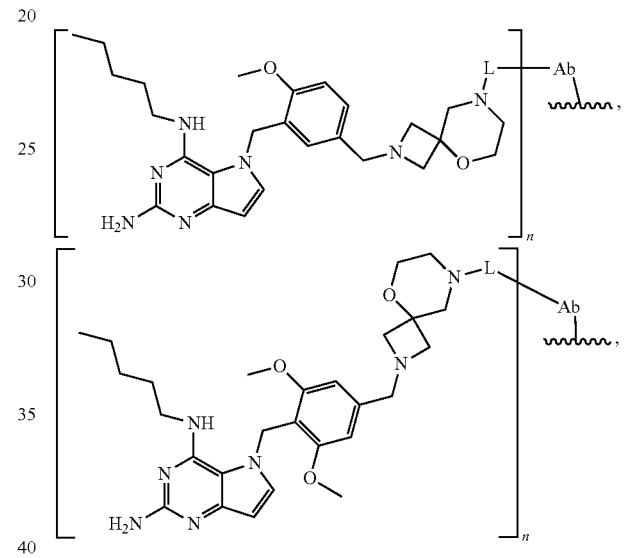
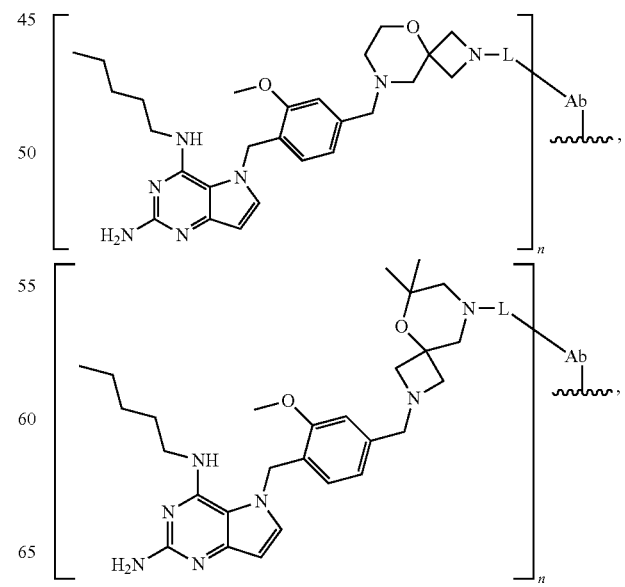

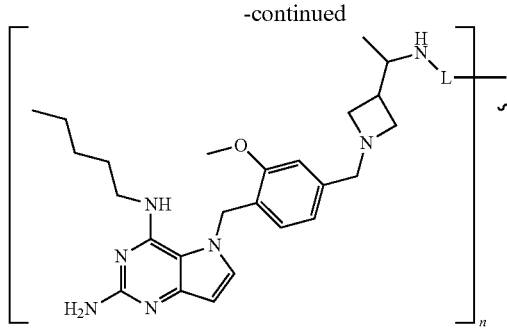
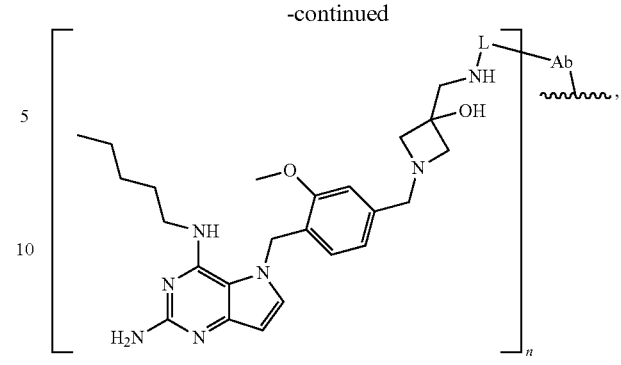
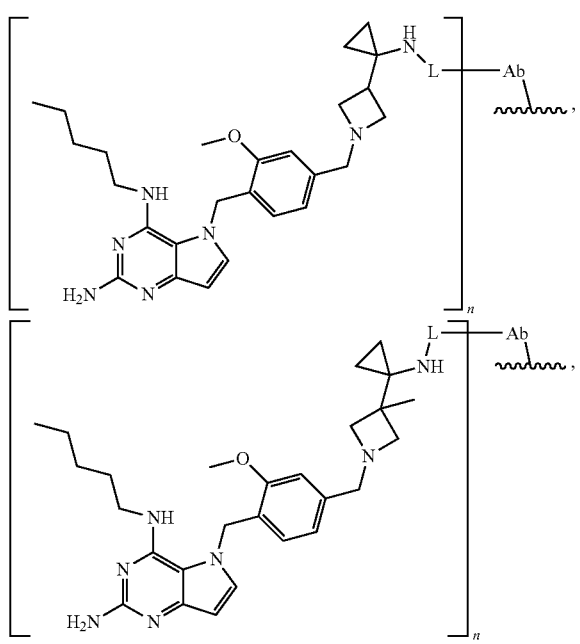
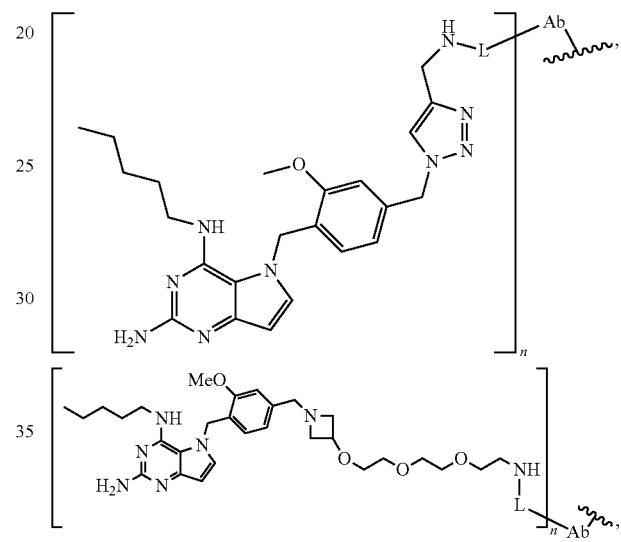
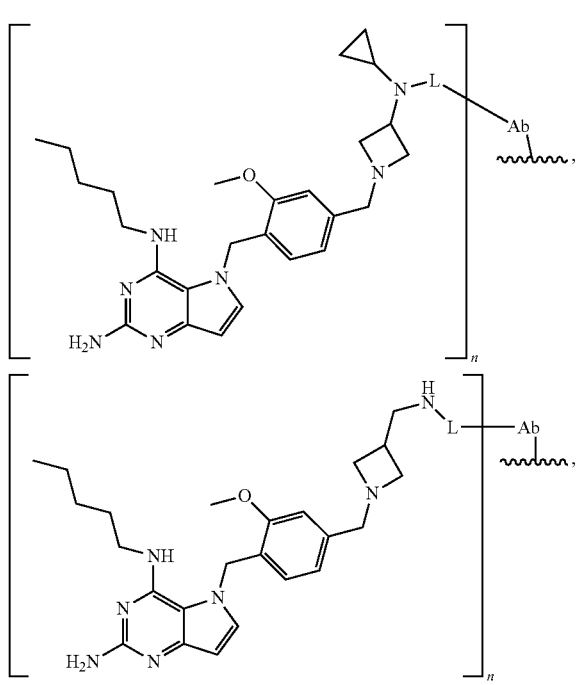
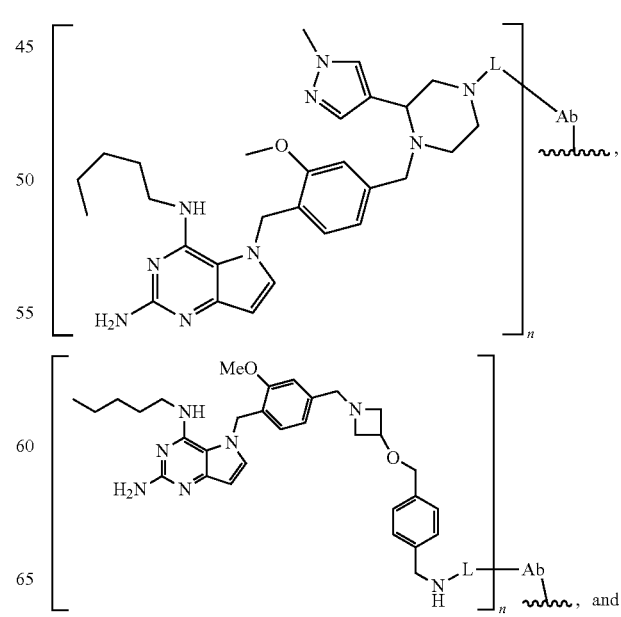

411
-continued
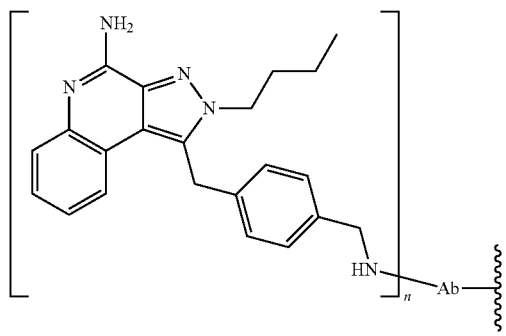
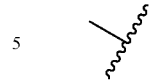
indicates a point of attachment to the rest of the formula.
29. The antibody conjugate of claim 3, wherein
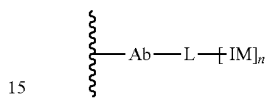
has a structure selected from the group consisting of:
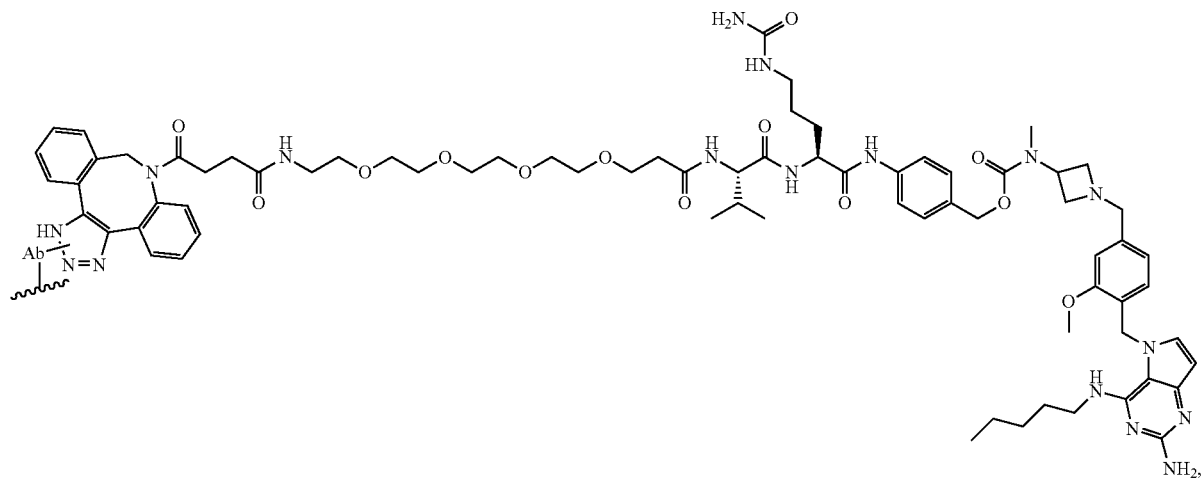
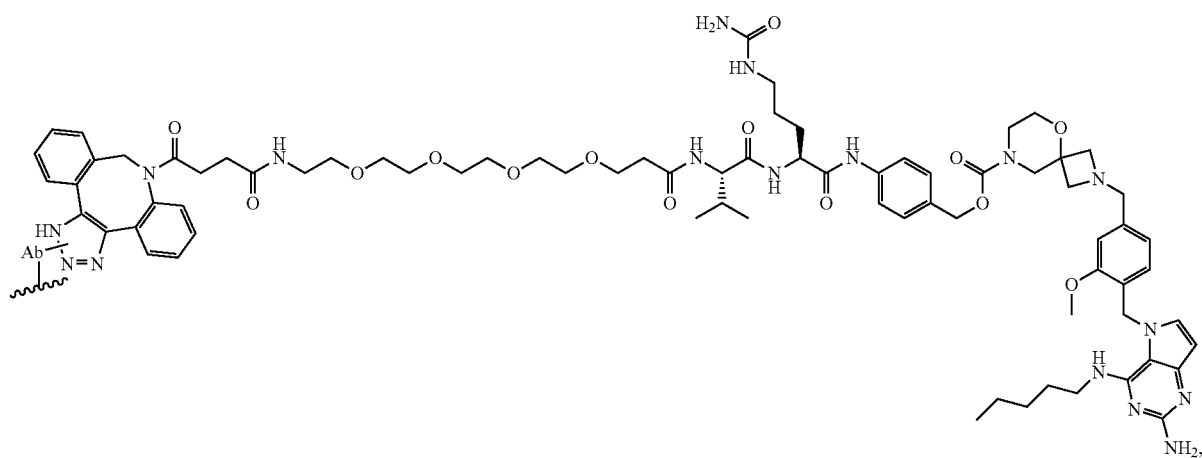

413 414
-continued
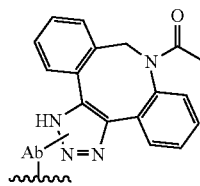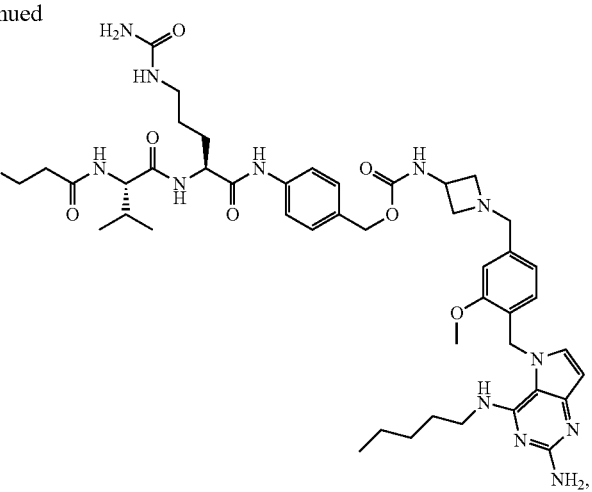
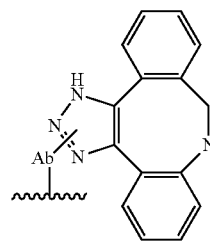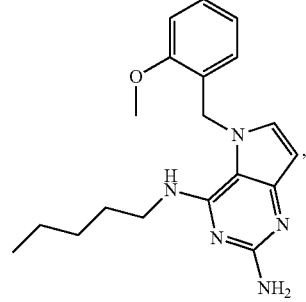
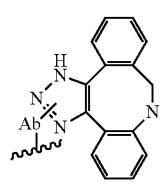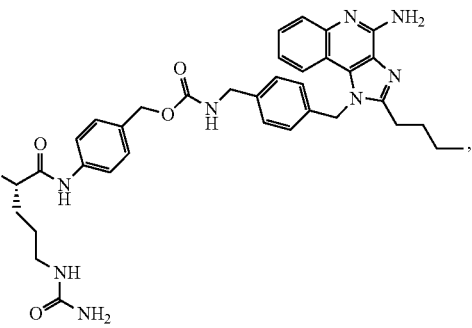

415
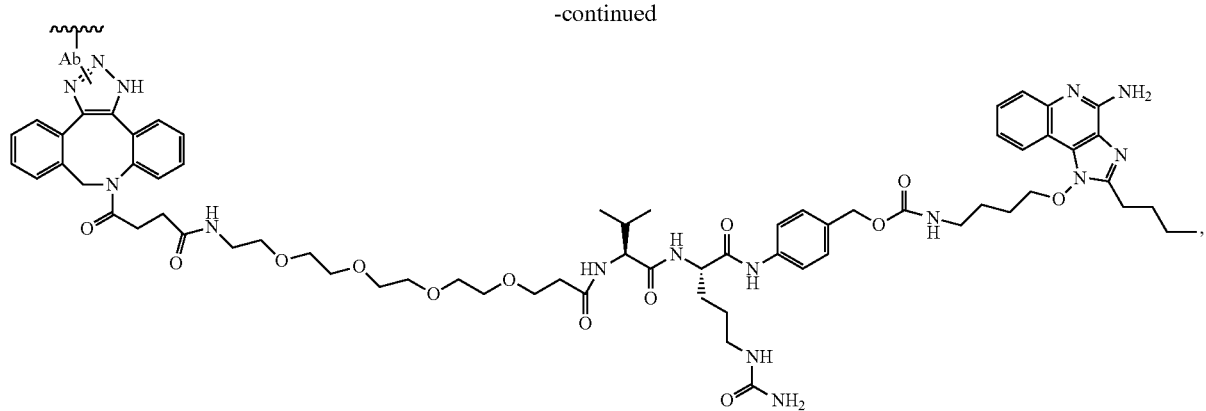
416
-continued
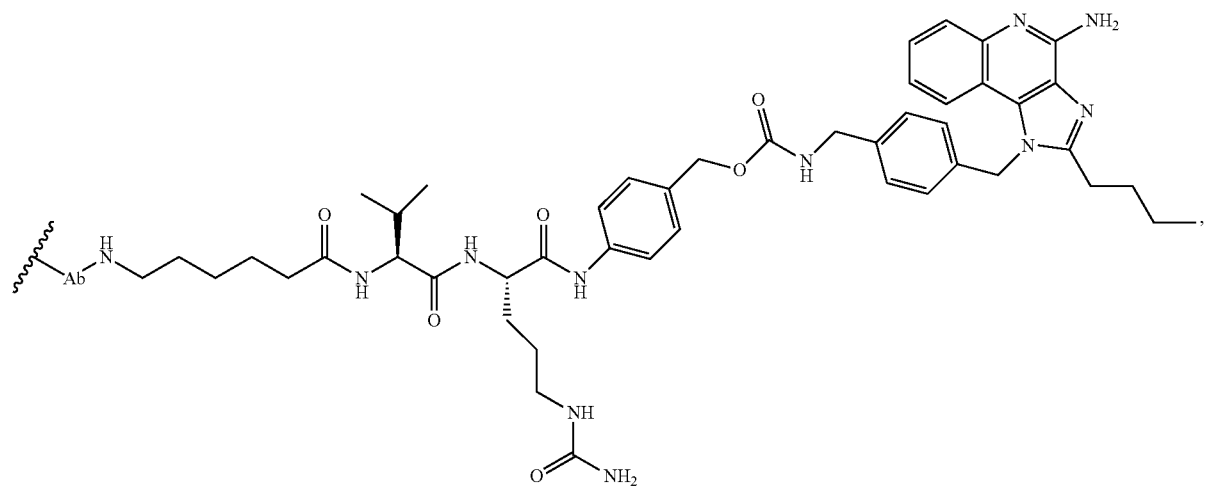
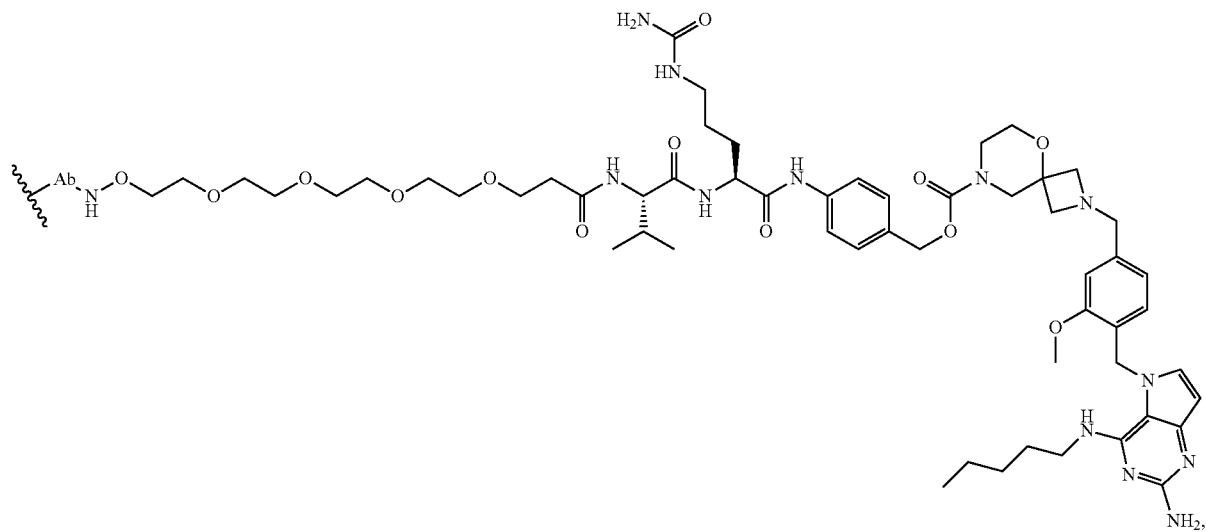

-continued
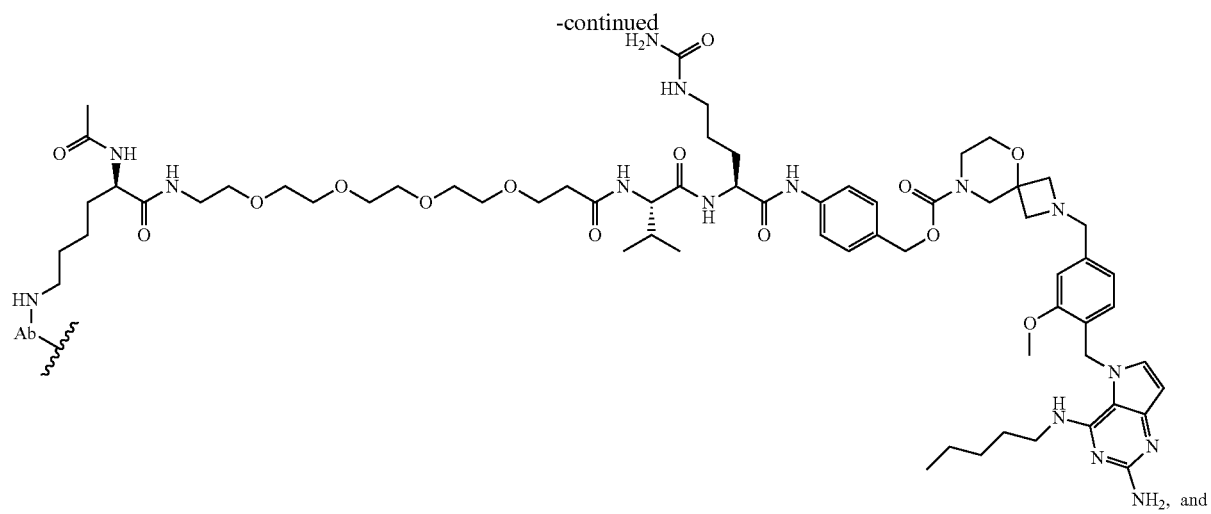
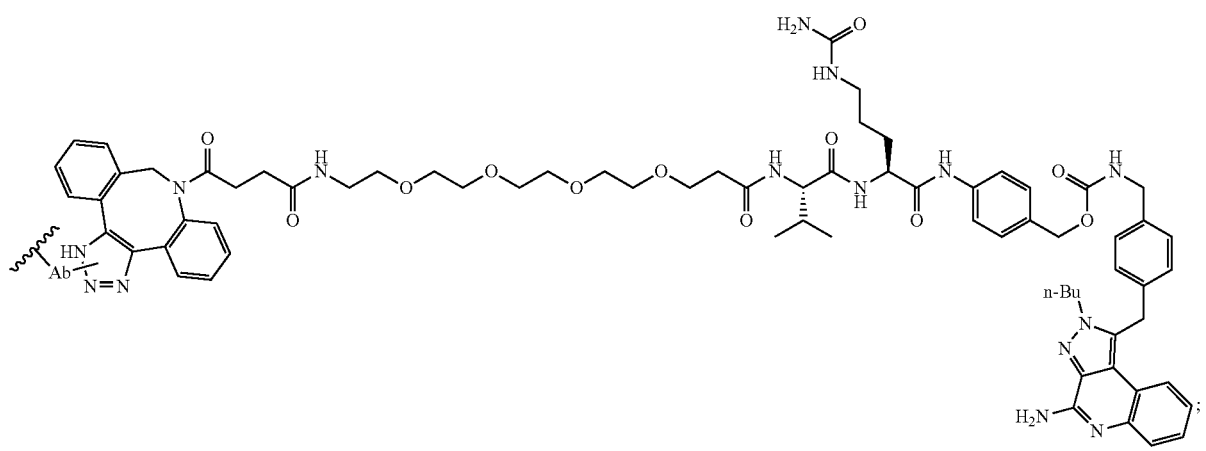
or a pharmaceutically acceptable salt, solvate, stereoisomer, tautomer or mixture of regioisomers thereof, wherein
indicates a point of attachment to the rest of the formula.
30. The antibody conjugate of claim 3, wherein PA is selected from the group consisting of:
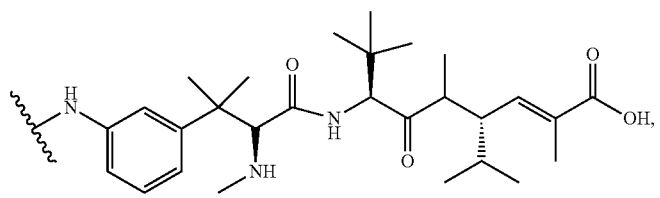

-continued
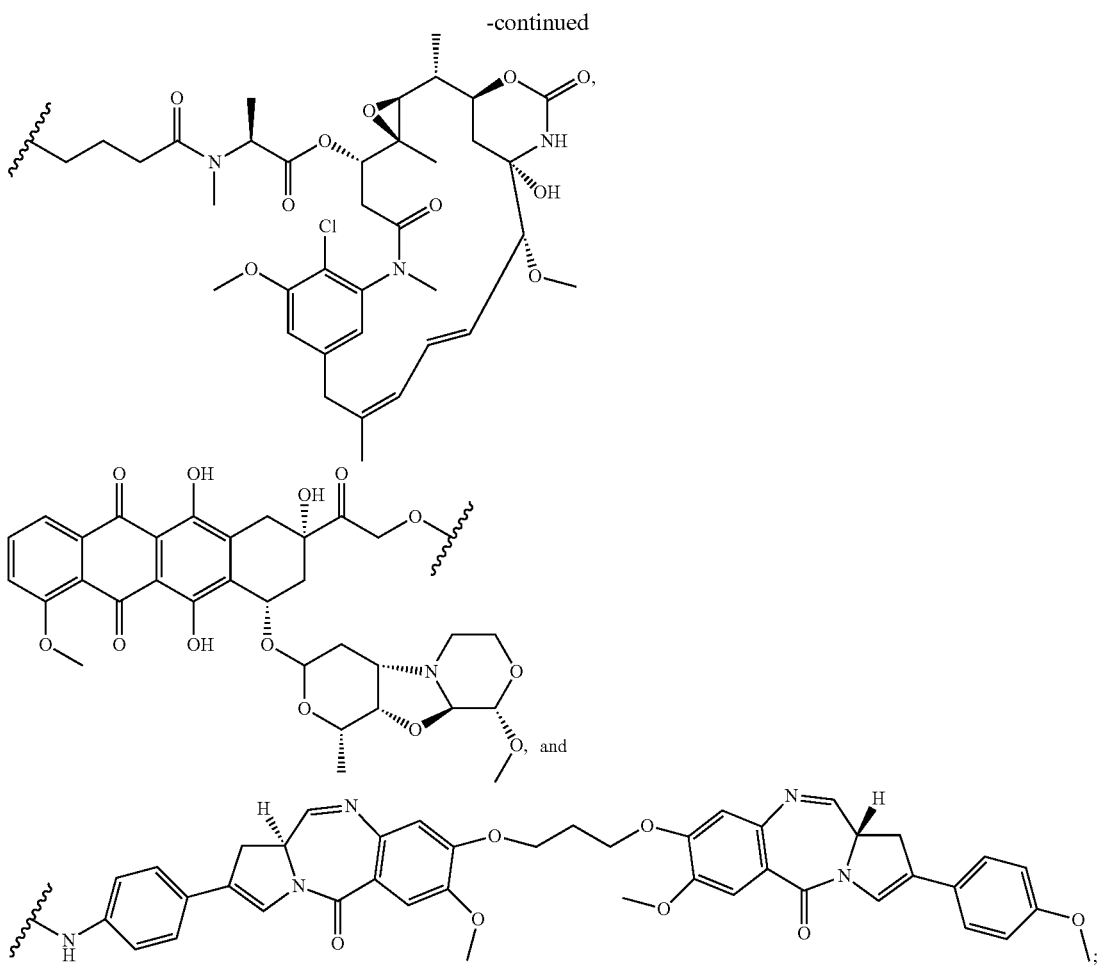
wherein each  indicates a point of attachment to the rest of the formula.
31. The antibody conjugate of claim 3, wherein
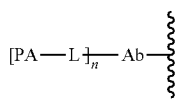
has a structure selected from the group consisting of:
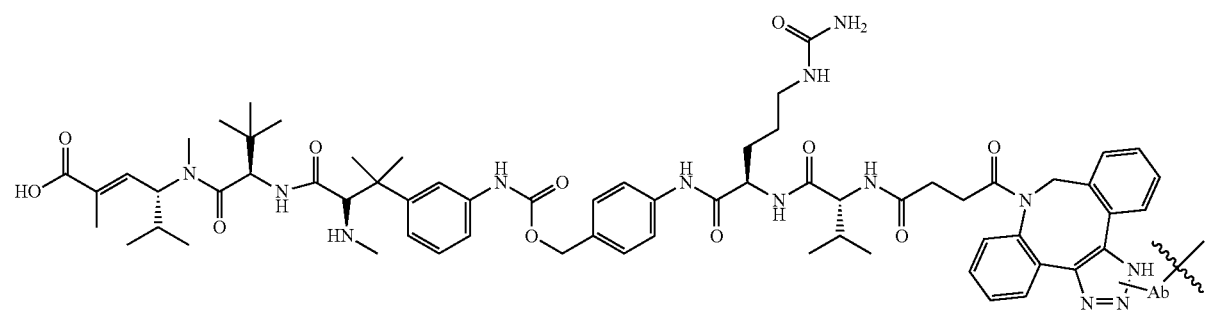

-continued
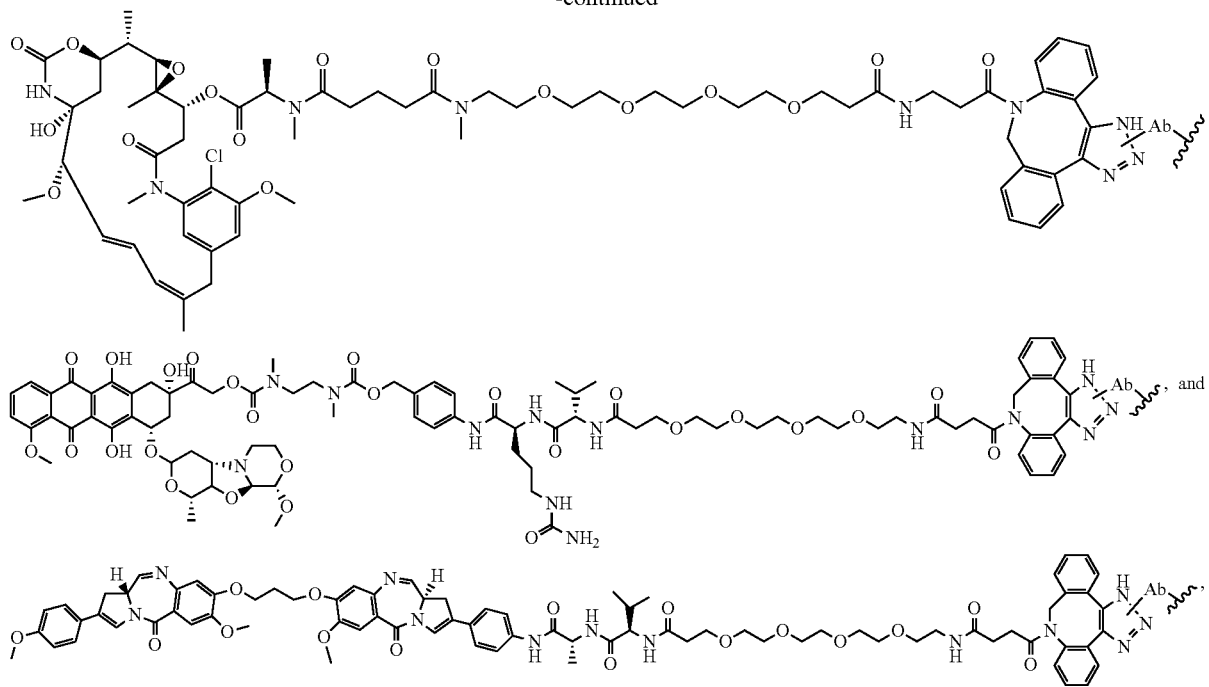
or a pharmaceutically acceptable salt, solvate, stereoisomer, tautomer or mixture of regioisomers thereof, wherein each
indicates a point of attachment to the rest of the formula.
32. The antibody conjugate of claim 1, selected from the group consisting of:
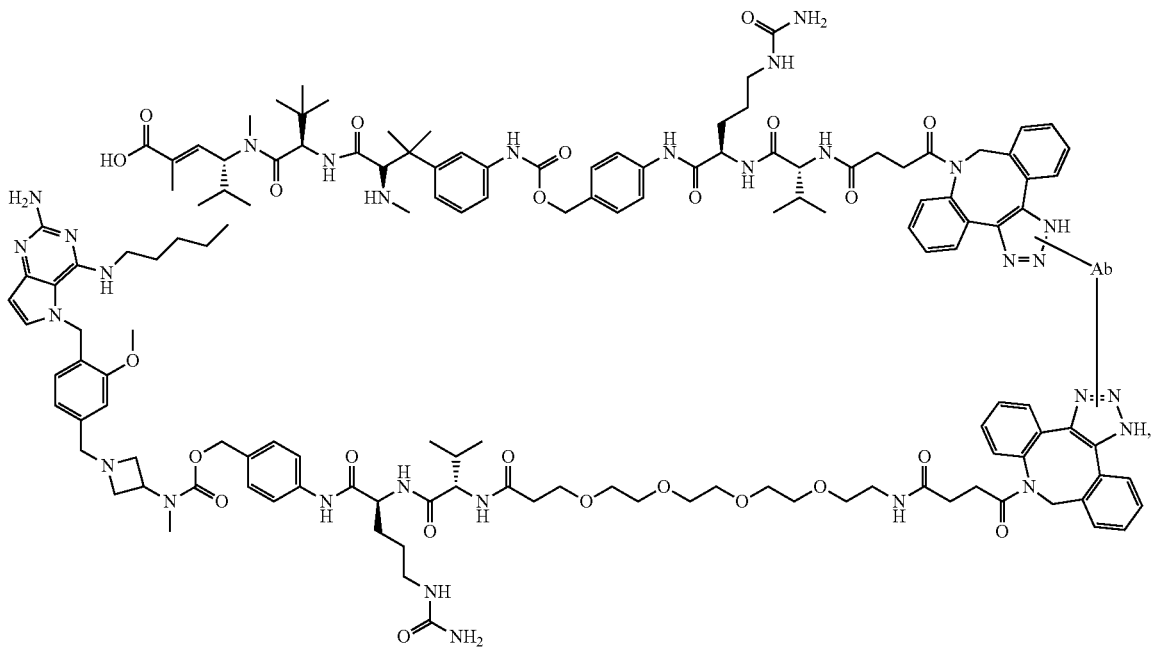

423 424
-continued
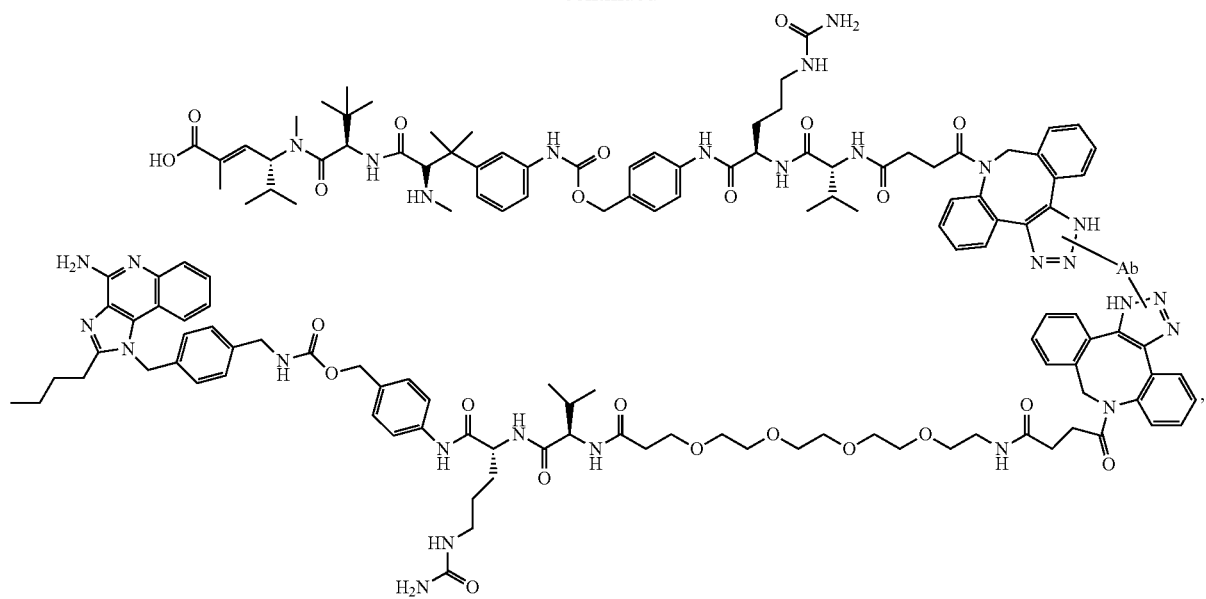
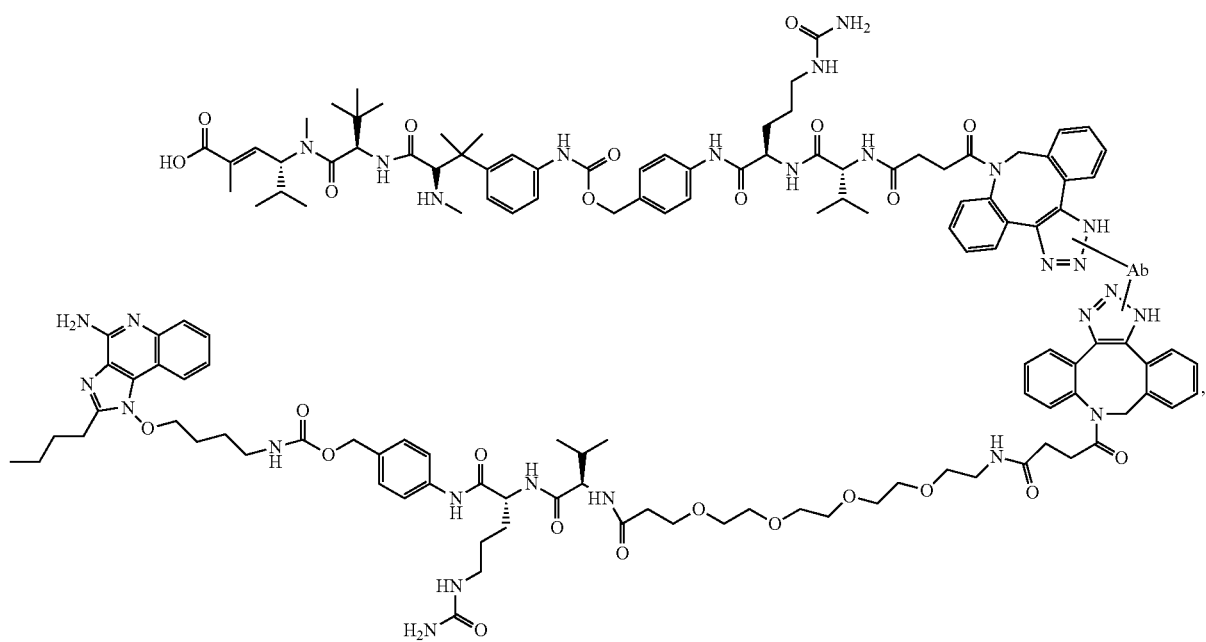

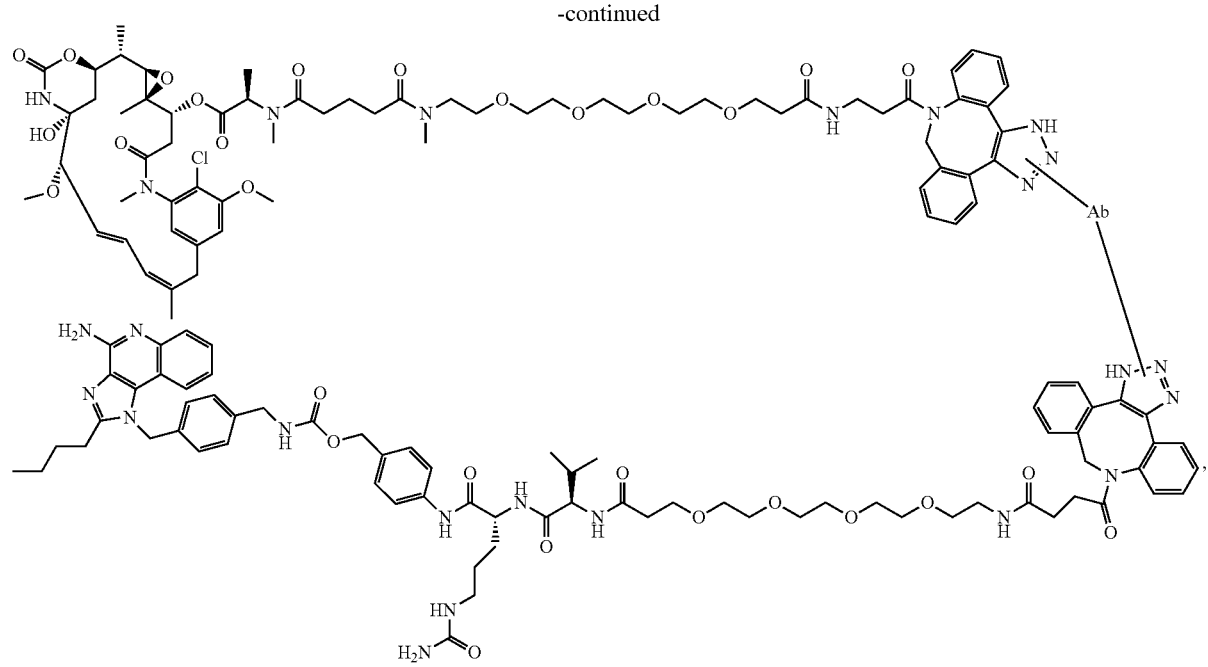
-continued
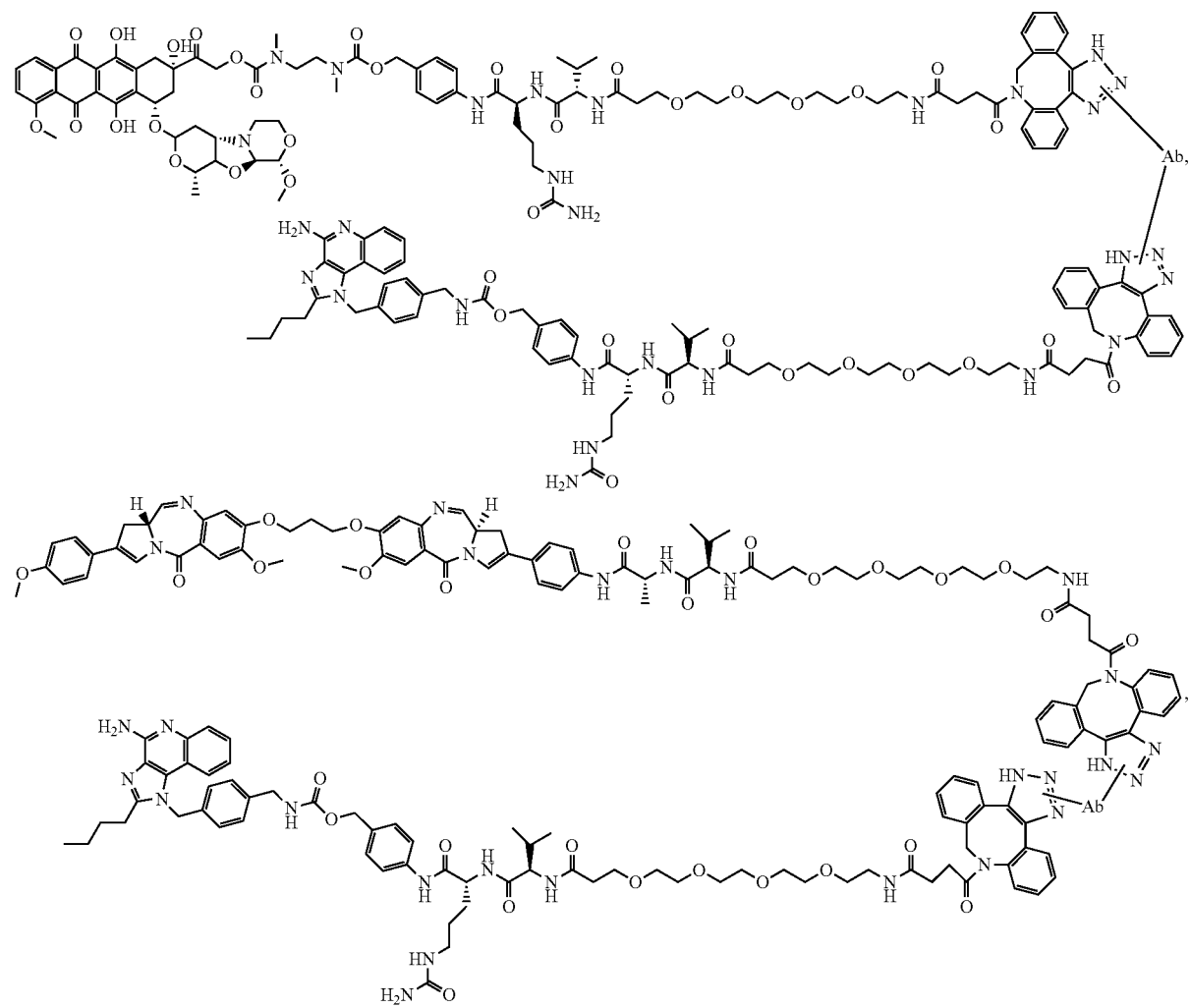

-continued

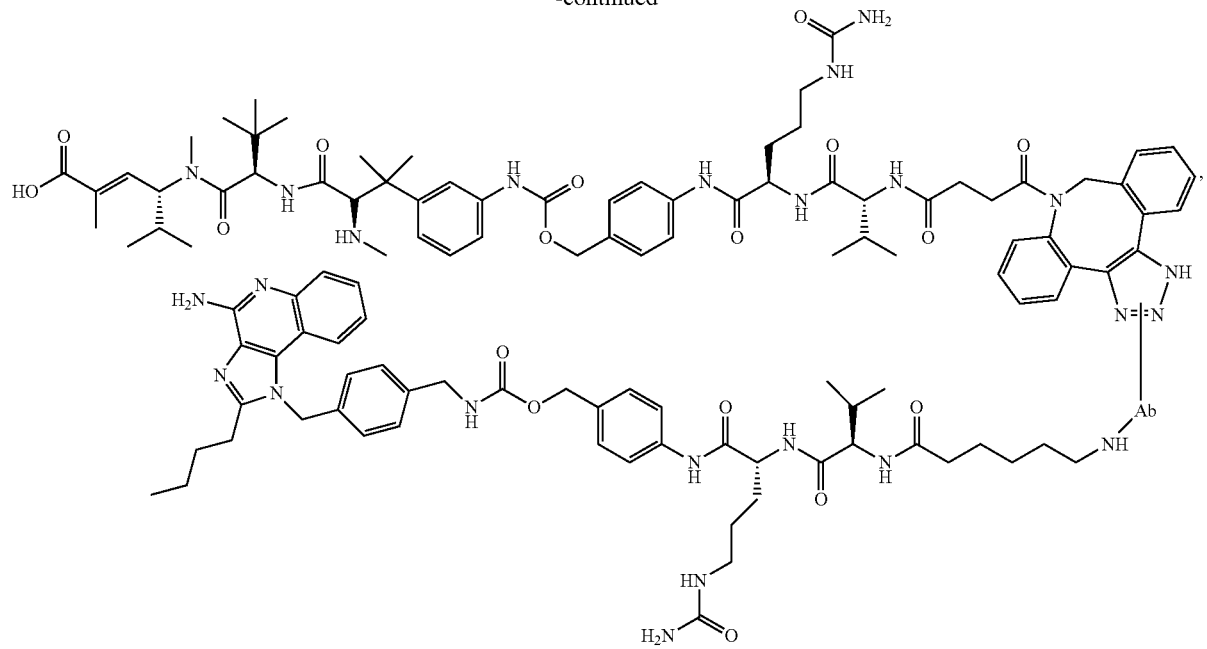

and

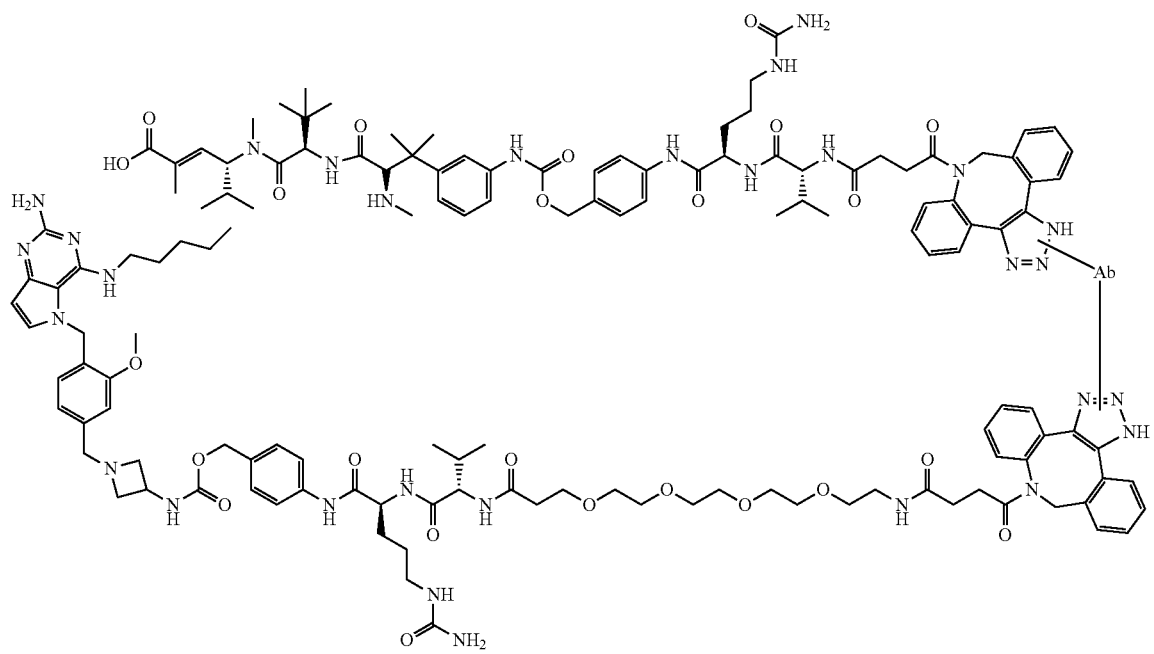

or a pharmaceutically acceptable salt, solvate, stereoisomer, tautomer or mixture of regioisomers thereof.

33. A pharmaceutical composition comprising an antibody conjugate of claim 1, and a pharmaceutically acceptable carrier.

34. A method for treating or preventing a disease or condition in a subject in need thereof comprising administering to the subject an effective amount of an antibody conjugate of claim 1.

35. A method of diagnosing a disease or condition in a subject in need thereof, comprising administering to the subject an effective amount of an antibody conjugate of claim 1.

36. The method of claim 34, wherein the disease or condition is a cancer or inflammatory disease or condition.

37. The method of claim 34, wherein said antibody conjugate is administered in combination or alternation with a second agent.

38. A process for preparing an antibody conjugate of claim 1, the process comprising:
 (i) preparing a conjugate of either the immunomodulatory payload (IM) or drug payload (PA) with the light chain (LC) of the antibody, or antigen-binding fragment thereof,
 (ii) expressing the heavy chain (HC) of the antibody, or antigen-binding fragment thereof, in the presence of the conjugated LC of step (i); and (iii) conjugating the heavy chain of step (ii) to the other of the immunomodulatory payload (IM) or drug payload (PA).

39. The process of claim 38, wherein the payload in step (i) is IM and the payload in step (iii) is PA.

40. The antibody conjugate of claim 1, wherein the drug payload is covalently linked to the heavy chain of the antibody and the immunomodulatory payload is covalently linked to the light chain of the antibody.

41. The antibody conjugate of claim 1, wherein the drug payload is covalently linked to the light chain of the antibody and the immunomodulatory payload is covalently linked to the heavy chain of the antibody.

42. The antibody conjugate of claim 1, wherein the antibody or the antigen binding fragment thereof comprises a non-natural amino acid at Y180 and a non-natural amino acid at K42.

43. The antibody conjugate of claim 1, wherein the antibody or the antigen-binding fragment thereof comprises a non-natural amino acid at F404 and a non-natural amino acid at K42.

44. The antibody conjugate of claim 1, wherein the antibody or the antigen-binding fragment thereof comprises a non-natural amino acid substitution at Y180, a non-natural amino acid at K222, a non-natural amino acid at S7, and a non-natural amino acid at K42.

45. The antibody conjugate of claim 10, wherein the antibody or the antigen-binding fragment thereof comprises a K42 pAcF mutation.

46. The antibody conjugate of claim 1, wherein the antibody or the antigen-binding fragment thereof comprises a K42 pAcF mutation.

47. The antibody conjugate of claim 1, wherein the antibody or the antigen binding fragment thereof comprises a non-natural amino acid at K42 and further comprises a non-natural amino acid substitution at F404 and a non-natural amino acid substitution at Y180.

\* \* \* \* \*